(12) United States Patent
Greene et al.

(10) Patent No.: US 9,322,009 B2
(45) Date of Patent: *Apr. 26, 2016

(54) INNOVATIVE DISCOVERY OF THERAPEUTIC, DIAGNOSTIC, AND ANTIBODY COMPOSITIONS RELATED TO PROTEIN FRAGMENTS OF LYSYL-TRNA SYNTHETASES

(71) Applicants: aTyr Pharma Inc., San Diego, CA (US); Pangu Biopharma Limited, Hong Kong (CN)

(72) Inventors: Leslie Ann Greene, San Diego, CA (US); Kyle P. Chiang, Cardiff, CA (US); Fei Hong, San Diego, CA (US); Alain P. Vasserot, Carlsbad, CA (US); Wing-Sze Lo, Hong Kong (CN); Jeffry D. Watkins, Encinitas, CA (US); Cheryl L. Quinn, Minneapolis, MN (US); John D. Mendlein, Encinitas, CA (US)

(73) Assignees: aTyr Pharma, Inc., San Diego, CA (US); Pangu BioPharma Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,431

(22) Filed: Jan. 8, 2015

(65) Prior Publication Data
US 2015/0252347 A1     Sep. 10, 2015

Related U.S. Application Data

(63) Continuation of application No. 13/700,998, filed as application No. PCT/US2011/038813 on Jun. 1, 2011, now Pat. No. 8,962,560.

(60) Provisional application No. 61/350,242, filed on Jun. 1, 2010, provisional application No. 61/350,411, filed on Jun. 1, 2010, provisional application No. 61/350,409, filed on Jun. 1, 2010, provisional application No. 61/350,407, filed on Jun. 1, 2010, provisional application No. 61/488,619, filed on May 20, 2011, provisional application No. 61/488,528, filed on May 20, 2011, provisional application No. 61/488,514, filed on May 20, 2011, provisional application No. 61/488,503, filed on May 20, 2011.

(51) Int. Cl.
| | | |
|---|---|---|
| *C12N 15/00* | (2006.01) | |
| *C12N 9/00* | (2006.01) | |
| *C07K 16/40* | (2006.01) | |
| *C12N 5/071* | (2010.01) | |
| *C12N 9/96* | (2006.01) | |
| *G01N 33/68* | (2006.01) | |
| *G01N 33/573* | (2006.01) | |
| *A61K 38/00* | (2006.01) | |

(52) U.S. Cl.
CPC . *C12N 9/93* (2013.01); *C07K 16/40* (2013.01); *C12N 5/0602* (2013.01); *C12N 9/96* (2013.01); *G01N 33/573* (2013.01); *G01N 33/68* (2013.01); *A61K 38/00* (2013.01); *C12Y 601/01* (2013.01); *G01N 2333/9015* (2013.01)

(58) Field of Classification Search
None
See application file for complete search history.

(56) References Cited

U.S. PATENT DOCUMENTS

| | | | |
|---|---|---|---|
| 5,370,995 | A | 12/1994 | Hennecke et al. |
| 5,750,387 | A | 5/1998 | Hodgson et al. |
| 5,753,480 | A | 5/1998 | Lawlor |
| 5,756,327 | A | 5/1998 | Sassanfar et al. |
| 5,759,833 | A | 6/1998 | Shiba et al. |
| 5,776,749 | A | 7/1998 | Hodgson et al. |
| 5,795,757 | A | 8/1998 | Hodgson et al. |
| 5,798,240 | A | 8/1998 | Martinis et al. |
| 5,801,013 | A | 9/1998 | Tao et al. |
| 5,866,390 | A | 2/1999 | Lawlor |
| 5,885,815 | A | 3/1999 | Sassanfar et al. |
| 5,928,920 | A | 7/1999 | Hodgson et al. |
| 5,939,298 | A | 8/1999 | Brown et al. |
| 6,225,060 | B1 | 5/2001 | Clark et al. |
| 6,428,960 | B1 | 8/2002 | Clark et al. |
| 6,548,060 | B1 | 4/2003 | Kim |
| 6,696,619 | B1 | 2/2004 | Famodu et al. |
| 6,852,512 | B2 | 2/2005 | Choi et al. |
| 6,903,189 | B2 | 6/2005 | Schimmel et al. |
| 7,067,126 | B2 | 6/2006 | Schimmel et al. |
| 7,144,984 | B2 | 12/2006 | Schimmel et al. |
| 7,196,068 | B2 | 3/2007 | Kim et al. |
| 7,273,844 | B2 | 9/2007 | Schimmel et al. |
| 7,413,885 | B2 | 8/2008 | Schimmel et al. |

(Continued)

FOREIGN PATENT DOCUMENTS

| | | |
|---|---|---|
| CA | 2531146 | 3/2005 |
| CN | 1341725 | 3/2002 |

(Continued)

OTHER PUBLICATIONS

International Preliminary Report on Patentability for International Application No. PCT/US2010/025642, dated Aug. 30, 2011.

(Continued)

*Primary Examiner* — Maryam Monshipouri
(74) *Attorney, Agent, or Firm* — Cooley LLP

(57) ABSTRACT

Provided are compositions comprising newly identified protein fragments of aminoacyl-tRNA synthetases, polynucleotides that encode them and complements thereof, related agents, and methods of use thereof in diagnostic, drug discovery, research, and therapeutic applications.

9 Claims, 9 Drawing Sheets

(56) References Cited

U.S. PATENT DOCUMENTS

| | | |
|---|---|---|
| 7,459,529 B2 | 12/2008 | Kim |
| 7,476,651 B2 | 1/2009 | Schimmel et al. |
| 7,521,215 B2 | 4/2009 | Schimmel et al. |
| 7,528,106 B2 | 5/2009 | Friedlander et al. |
| 7,745,391 B2 | 6/2010 | Mintz et al. |
| 7,901,917 B2 | 3/2011 | Schimmel et al. |
| 7,902,165 B2 | 3/2011 | Kim |
| 8,003,780 B2 | 8/2011 | Kim et al. |
| 8,017,593 B2 | 9/2011 | Schimmel et al. |
| 8,026,088 B2 | 9/2011 | Yang |
| 8,101,566 B2 | 1/2012 | Schimmel et al. |
| 8,148,125 B2 | 4/2012 | Schimmel et al. |
| 8,404,242 B2 | 3/2013 | Zhou et al. |
| 8,404,471 B2 | 3/2013 | Greene et al. |
| 8,481,296 B2 | 7/2013 | Yang |
| 8,962,560 B2 | 2/2015 | Greene et al. |
| 2002/0182666 A1 | 12/2002 | Schimmel et al. |
| 2003/0004309 A1 | 1/2003 | Kim et al. |
| 2003/0017564 A1 | 1/2003 | Schimmel et al. |
| 2003/0018985 A1 | 1/2003 | Falco et al. |
| 2003/0215827 A1 | 11/2003 | Yue et al. |
| 2004/0009163 A1 | 1/2004 | Schimmel et al. |
| 2004/0018505 A1 | 1/2004 | Lee et al. |
| 2004/0048290 A1 | 3/2004 | Lee et al. |
| 2004/0152079 A1 | 8/2004 | Schimmel et al. |
| 2004/0203094 A1 | 10/2004 | Martinis et al. |
| 2004/0214216 A1 | 10/2004 | Famodu et al. |
| 2004/0224981 A1 | 11/2004 | Janjic et al. |
| 2005/0136513 A1 | 6/2005 | Zhang |
| 2005/0208536 A1 | 9/2005 | Schultz et al. |
| 2006/0024288 A1 | 2/2006 | Glidden |
| 2006/0035232 A1 | 2/2006 | McGregor et al. |
| 2006/0046250 A1 | 3/2006 | Kim |
| 2006/0078553 A1 | 4/2006 | Glidden |
| 2006/0160175 A1 | 7/2006 | Anderson et al. |
| 2006/0248617 A1 | 11/2006 | Imanaka et al. |
| 2007/0048322 A1 | 3/2007 | Schimmel et al. |
| 2007/0061916 A1 | 3/2007 | Kovalic et al. |
| 2007/0111238 A1 | 5/2007 | Jamieson et al. |
| 2008/0044854 A1 | 2/2008 | Wang et al. |
| 2008/0113914 A1 | 5/2008 | Hays et al. |
| 2008/0153745 A1 | 6/2008 | Tian |
| 2009/0123971 A1 | 5/2009 | Paulsel et al. |
| 2009/0226966 A1 | 9/2009 | Yokoyama et al. |
| 2009/0227002 A1 | 9/2009 | Schultz et al. |
| 2009/0227662 A1 | 9/2009 | Schimmel et al. |
| 2009/0285792 A1 | 11/2009 | Friedlander et al. |
| 2010/0003230 A1 | 1/2010 | Glidden |
| 2010/0028352 A1 | 2/2010 | Greene et al. |
| 2010/0048413 A1 | 2/2010 | Arcus et al. |
| 2010/0092434 A1 | 4/2010 | Belani et al. |
| 2010/0093082 A1 | 4/2010 | Tian et al. |
| 2010/0297149 A1 | 11/2010 | Zhou et al. |
| 2010/0310576 A1 | 12/2010 | Adams et al. |
| 2011/0104139 A1 | 5/2011 | Faber |
| 2011/0110917 A1 | 5/2011 | Schimmel et al. |
| 2011/0136119 A1 | 6/2011 | Kim et al. |
| 2011/0150885 A1 | 6/2011 | Watkins et al. |
| 2011/0189195 A1 | 8/2011 | Kim et al. |
| 2011/0250701 A1 | 10/2011 | Kim et al. |
| 2011/0256119 A1 | 10/2011 | Kim et al. |
| 2012/0004185 A1 | 1/2012 | Greene |
| 2012/0015383 A1 | 1/2012 | Park et al. |
| 2012/0058133 A1 | 3/2012 | Whitman et al. |
| 2012/0064082 A1 | 3/2012 | Watkins et al. |
| 2013/0052177 A1 | 2/2013 | Schimmel et al. |
| 2013/0108630 A1 | 5/2013 | Watkins et al. |
| 2013/0129703 A1 | 5/2013 | Chiang et al. |
| 2013/0129704 A1 | 5/2013 | Greene et al. |
| 2013/0129705 A1 | 5/2013 | Greene et al. |
| 2013/0142774 A1 | 6/2013 | Greene et al. |
| 2013/0195832 A1 | 8/2013 | Greene et al. |
| 2013/0202574 A1 | 8/2013 | Greene et al. |
| 2013/0202575 A1 | 8/2013 | Greene et al. |
| 2013/0202576 A1 | 8/2013 | Greene et al. |
| 2013/0209434 A1 | 8/2013 | Greene et al. |
| 2013/0209472 A1 | 8/2013 | Greene et al. |
| 2013/0224173 A1 | 8/2013 | Greene et al. |
| 2013/0224174 A1 | 8/2013 | Greene et al. |
| 2013/0230505 A1 | 9/2013 | Greene et al. |
| 2013/0230507 A1 | 9/2013 | Greene et al. |
| 2013/0230508 A1 | 9/2013 | Greene et al. |
| 2013/0236440 A1 | 9/2013 | Greene et al. |
| 2013/0236455 A1 | 9/2013 | Greene et al. |
| 2013/0243766 A1 | 9/2013 | Zhou et al. |
| 2013/0273045 A1 | 10/2013 | Watkins et al. |
| 2013/0280230 A1 | 10/2013 | Greene et al. |
| 2013/0287755 A1 | 10/2013 | Greene et al. |
| 2013/0315887 A1 | 11/2013 | Greene et al. |
| 2013/0330312 A1 | 12/2013 | Greene et al. |
| 2013/0344096 A1 | 12/2013 | Chiang et al. |
| 2014/0066321 A1 | 3/2014 | Xu et al. |

FOREIGN PATENT DOCUMENTS

| | | |
|---|---|---|
| CN | 1341727 | 3/2002 |
| CN | 1352242 | 6/2002 |
| CN | 1352252 | 6/2002 |
| EP | 0893494 | 1/1999 |
| EP | 0893496 | 1/1999 |
| EP | 0897004 | 2/1999 |
| EP | 1275720 | 1/2003 |
| EP | 1300468 | 4/2003 |
| EP | 1377305 | 1/2009 |
| EP | 1776138 | 10/2009 |
| EP | 2177610 | 4/2010 |
| EP | 1274834 | 7/2010 |
| EP | 2084190 | 3/2011 |
| WO | WO 97/25426 | 7/1997 |
| WO | WO 97/26351 | 7/1997 |
| WO | WO 97/39017 | 10/1997 |
| WO | WO 98/14591 | 4/1998 |
| WO | WO 98/50554 | 11/1998 |
| WO | WO 01/07628 | 2/2001 |
| WO | WO 01/19999 | 3/2001 |
| WO | WO 01/64892 | 9/2001 |
| WO | WO 01/75067 | 10/2001 |
| WO | WO 01/75078 | 10/2001 |
| WO | WO 01/88188 | 11/2001 |
| WO | WO 01/90330 | 11/2001 |
| WO | WO 01/94568 | 12/2001 |
| WO | WO 02/44349 | 6/2002 |
| WO | WO 02/059323 | 8/2002 |
| WO | WO 02/067970 | 9/2002 |
| WO | WO 03/009813 | 2/2003 |
| WO | WO 03/094862 | 11/2003 |
| WO | WO 2004/011604 | 2/2004 |
| WO | WO 2004/087875 | 10/2004 |
| WO | WO 2005/019415 | 3/2005 |
| WO | WO 2005/102395 | 11/2005 |
| WO | WO 2005/117954 | 12/2005 |
| WO | WO 2006/016217 | 2/2006 |
| WO | WO 2006/057500 | 6/2006 |
| WO | WO 2007/064941 | 6/2007 |
| WO | WO 2008/016356 | 2/2008 |
| WO | WO 2008/021290 | 2/2008 |
| WO | WO 2008/133359 | 11/2008 |
| WO | WO 2009/059056 | 5/2009 |
| WO | WO 2009/114623 | 9/2009 |
| WO | WO 2009/152247 | 12/2009 |
| WO | WO 2009/158649 | 12/2009 |
| WO | WO 2010/021415 | 2/2010 |
| WO | WO 2010/041892 | 4/2010 |
| WO | WO 2010/041913 | 4/2010 |
| WO | WO 2010/090471 | 8/2010 |
| WO | WO 2010/096170 | 8/2010 |
| WO | WO 2010/099477 | 9/2010 |
| WO | WO 2010/107825 | 9/2010 |
| WO | WO 2010/120509 | 10/2010 |
| WO | WO 2011/072265 | 6/2011 |
| WO | WO 2011/072266 | 6/2011 |
| WO | WO 2011/097031 | 8/2011 |
| WO | WO 2011/139714 | 11/2011 |
| WO | WO 2011/139799 | 11/2011 |

(56) References Cited

FOREIGN PATENT DOCUMENTS

| | | |
|---|---|---|
| WO | WO 2011/139801 | 11/2011 |
| WO | WO 2011/139853 | 11/2011 |
| WO | WO 2011/139854 | 11/2011 |
| WO | WO 2011/139907 | 11/2011 |
| WO | WO 2011/139986 | 11/2011 |
| WO | WO 2011/139988 | 11/2011 |
| WO | WO 2011/140132 | 11/2011 |
| WO | WO 2011/140135 | 11/2011 |
| WO | WO 2011/140266 | 11/2011 |
| WO | WO 2011/140267 | 11/2011 |
| WO | WO 2011/143482 | 11/2011 |
| WO | WO 2011/146410 | 11/2011 |
| WO | WO 2011/150279 | 12/2011 |
| WO | WO 2011/153277 | 12/2011 |
| WO | WO 2012/009289 | 1/2012 |
| WO | WO 2012/021247 | 2/2012 |
| WO | WO 2012/021249 | 2/2012 |
| WO | WO 2012/027611 | 3/2012 |
| WO | WO 2012/048125 | 4/2012 |
| WO | WO 2012/158945 | 11/2012 |
| WO | WO 2013/022982 | 2/2013 |
| WO | WO 2013/086216 | 6/2013 |
| WO | WO 2013/086228 | 6/2013 |
| WO | WO 2013/115926 | 8/2013 |
| WO | WO 2013/123432 | 8/2013 |

OTHER PUBLICATIONS

International Search Report and Written Opinion for International Application No. PCT/US2010/025642, mailed Oct. 29, 2010.
International Search Report and Written Opinion for International Application No. PCT/US2010/059964, mailed Aug. 25, 2011.
International Preliminary Report on Patentability for International Application No. PCT/US2010/059964, dated Jun. 12, 2012.
International Preliminary Report on Patentability for International Application No. PCT/US2010/059963, dated Jun. 12, 2012, 18 pages.
International Search Report and Written Opinion for International Application No. PCT/US2010/059963, mailed May 12, 2011.
International Search Report and Written Opinion for International Application No. PCT/US2011/000210, mailed Aug. 12, 2011.
International Preliminary Report on Patentabiltity for International Application No. PCT/US2011/000210, dated Aug. 7, 2012.
Supplementary European Search Report for European Application No. 11778025.4, mailed Nov. 6, 2013.
International Search Report and Written Opinion for International Application No. PCT/US2011/034387, mailed on Mar. 23, 2012.
International Preliminary Report on Patentability for International Application No. PCT/US2011/034387, dated Oct. 30, 2012.
Supplementary European Search Report for European Application No. 11778026.2, mailed Oct. 22, 2013.
International Search Report and Written Opinion for International Application No. PCT/US2011/034388, mailed on Mar. 23, 2012.
International Preliminary Report on Patentability for International Application No. PCT/US2011/034388, dated Oct. 30, 2012.
International Search Report and Written Opinion for International Application No. PCT/US2011/043596, mailed on Feb. 29, 2012.
International Preliminary Report on Patentability for International Application No. PCT/US2011/043596, dated Jan. 15, 2013.
Supplementary European Search Report for European Application No. 11778118.7, mailed Aug. 19, 2013.
International Search Report and Written Opinion for International Application No. PCT/US2011/034838, mailed Jan. 9, 2012.
International Preliminary Report on Patentability for International Application No. PCT/US2011/034838, dated Nov. 6, 2012.
International Search Report and Written Opinion for International Application No. PCT/US2011/033988, mailed on Feb. 9, 2012.
International Preliminary Report on Patentability for International Application No. PCT/US2011/033988, dated Oct. 30, 2012.
International Search Report and Written Opinion for International Application No. PCT/US2011/038240, mailed on Feb. 9, 2012.
International Preliminary Report on Patentability for International Application No. PCT/US2011/038240, dated Nov. 27, 2012.
Supplementary European Search Report for European Application No. 11778296.1, mailed Nov. 12, 2013.
International Search Report and Written Opinion for International Application No. PCT/US2011/035250, mailed on Jan. 19, 2012.
International Preliminary Report on Patentability for International Application No. PCT/2011/035250, dated Nov. 6, 2012.
International Search Report and Written Opinion for International Application No. PCT/US2011/043756, mailed on Mar. 2, 2012.
International Preliminary Report on Patentability for International Application No. PCT/US2011/043756, dated Jan. 15, 2013.
International Search Report and Written Opinion for International Application No. PCT/US2011/043758, mailed on Mar. 2, 2012.
International Preliminary Report on Patentability for International Application No. PCT/US2011/043758, dated Jan. 15, 2013.
International Search Report and Written Opinion for International Application No. PCT/US2011/034205, mailed on Feb. 8, 2012.
International Preliminary Report on Patentability for International Application No. PCT/US2011/034205, dated Oct. 30, 2012.
International Search Report and Written Opinion for International Application No. PCT/US2011/036684, mailed on Feb. 9, 2012.
International Preliminary Report on Patentability for International Application No. PCT/US2011/036684, dated Nov. 20, 2012.
International Search Report and Written Opinion for International Application No. PCT/US2011/038813, mailed on Mar. 28, 2012.
International Preliminary Report on Patentability for International Application No. PCT/US2011/038813, dated Dec. 4, 2012.
International Search Report and Written Opinion for International Application No. PCT/US2011/035056, mailed on Mar. 23, 2012.
International Preliminary Report on Patentability for International Application No. PCT/US2011/035056, dated Nov. 6, 2012.
International Search Report and Written Opinion for International Application No. PCT/US2011/035053, mailed Mar. 23, 2012.
International Preliminary Report on Patentability for International Application No. PCT/US2011/035053, dated Nov. 6, 2012.
Supplementary European Search Report for European Application No. 11778120.3, mailed Nov. 15, 2013.
International Search Report and Written Opinion for International Application No. PCT/US2011/034840, mailed on Feb. 10, 2012.
International Preliminary Report on Patentability for International Application No. PCT/US2011/034840, dated Nov. 6, 2012.
Supplementary European Search Report for European Application No. 11777984.3, mailed Oct. 18, 2013.
International Search Report and Written Opinion for International Application No. PCT/US2011/034207, mailed Feb. 8, 2012.
International Preliminary Report on Patentability for International Application No. PCT/US2011/034207, dated Oct. 30, 2012.
International Search Report and Written Opinion for International Application No. PCT/US2011/055130, mailed on May 14, 2012.
International Preliminary Report on Patentability for International Application No. PCT/US2011/055130, dated Apr. 9, 2013.
International Search Report and Written Opinion for International Application No. PCT/US2011/049223, mailed Mar. 27, 2012.
International Preliminary Report on Patentability for International Application No. PCT/US2011/049223, dated Feb. 26, 2013.
International Search Report and Written Opinion for International Application No. PCT/US2011/034626, mailed on Jan. 19, 2012.
International Preliminary Report on Patentability for International Application No. PCT/US2011/034626, dated Oct. 30, 2012.
Supplementary European Search Report for European Application No. 11781304.8, mailed Oct. 23, 2013.
International Search Report and Written Opinion for International Application No. PCT/US2011/036326, mailed on Feb. 9, 2012.
International Preliminary Report on Patentability for International Application No. PCT/US2011/036326, dated Nov. 20, 2012.
International Search Report and Written Opinion for International Application No. PCT/US2011/035251, mailed on Feb. 8, 2012.
International Preliminary Report on Patentability for International Application No. PCT/US2011/035251, dated Nov. 6, 2012.
Antonellis, A. et al., "The Role of Aminoacyl-tRNA Synthetases in Genetic Diseases," Annual Review of Genomics and Human Genetics, 9(1):87-107 (2008).

(56) References Cited

OTHER PUBLICATIONS

Brown, M. V. et al., "Mammalian aminoacyl-tRNA synthetases: Cell signaling functions of the protein translation machinery," Vascular Pharmacology, 52(1-2):21-26 (2010).
Carmi-Levy, I. et al., "Importin Beta Plays an Essential Role in the Regulation of the LysRS-Ap$_4$A Pathway in Immunologically Activated Mast Cells," Molecular and Cellular Biology, 31(10):2111-2121 (2011).
Castro de Moura, M. et al., "Entamoeba lysyl-tRNA Synthetase Contains a Cytokine-Like Domain with Chemokine Activity towards Human Endothelial Cells," PLoS Neglected Tropical Diseases, 5(11):e1398 (2011), 13 pages.
Cen, S. et al., "Retrovirus-Specific Packaging of Aminoacyl-tRNA Synthetases with Cognate Primer tRNAs," Journal of Virology, 76(24):13111-13115 (2002).
Chica, R. A. et al., "Semi-rational approaches to engineering enzyme activity: combining the benefits of directed evolution and rational design," Curr. Opin. Biotechnol., 16:378-384 (2005).
Datson, N. A. et al., "Development of the first marmoset-specific DNA microarray (EUMAMA): a new genetic tool for large-scale expression profiling in a non-human primate," BMC Genomics, 8(190):1-9 (2007).
Deiters, A. et al., "Site-specific PEGylation of proteins containing unnatural amino acids," Bioorg Med Chem Lett, 14(23):5743-5745 (2004).
Delgado, C. et al., "The uses and properties of PEG-linked proteins," Critical Reviews in Therapeutic Drug Carrier Systems, 9(3,4):249-304 (1992).
Devos, D. et al., "Practical limits of function prediction," Proteins: Structure, Function, and Genetics, 41:98-107 (2000).
Fang, P. et al., "Structural context for mobilization of a human tRNA synthetase from its cytoplasmic complex," Proc. Natl. Acad. Sci. USA, 108(20):8239-8244 (2011).
Guijarro, J. I. et al., "Structure and Dynamics of the Anticodon Arm Binding Domain of Bacillus stearothermophilus Tyrosyl-tRNA Synthetase," Structure, 10:311-317 (2002).
Guo, M. et al., "Packaging HIV Virion Components through Dynamic Equilibria of a Human tRNA Synthetase," J. Phys. Chem. B, 111(49):16273-16279 (2010).
Guo, M. et al., "Functional expansion of human tRNA synthetases achieved by structural inventions," FEBS Letters, 584(2):434-442 (2010).
Guo, M. et al., "New functions of aminoacyl-tRNA synthetases beyond translation," Nature Reviews Molecular Cell Biology, 11:668-674 (2010).
Halwani, R. et al., "Cellular Distribution of Lysyl-tRNA Synthetase and Its Interaction with Gag during Human Immunodeficiency Virus Type 1 Assembly," Journal of Virology, 78(14):7553-7564 (2004).
Han, J. M. et al., "Hierarchical Network between the Components of the Multi-tRNA Synthetase Complex," Journal of Biological Chemistry, 281(50):38663-38667 (2006).
Hausmann, C. D. et al., "Aminoacyl-tRNA synthetase complexes: molecular multitasking revealed," FEMS Microbiol. Rev., 32(4):705-721 (2008).
Hou, Y-M. et al., "Sequence determination and modeling of structural motifs for the smallest monomeric aminoacyl-tRNA synthetase," Proc. Nat. Acad. Sci., 88(3):976-980 (1991).
Ivakhno, S. S. et al., "Cytokine-Like Activities of Some Aminoacyl-tRNA Synthetases and Auxiliary p43 Cofactor of Aminoacylation Reaction and Their Role in Oncogenesis," Exp. Oncol., 26(4):250-255 (2004).
Ivanov, K. A. et al., "Non-canonical Functions of Aminoacyl-tRNA Synthetases," Biochemistry (Moscow), 65(8):888-897 (2000).
Jura, M. et al., "Comprehensive Insight into human aminoacyl-tRNA synthetases as autoantigens in idiopathic inflammatory myopathies," Critical Reviews in Immunology, 27(6):559-572 (2007).
Kapoor, M. et al., "Mutational separation of aminoacylation and cytokine activities of human tyrosyl-tRNA synthetase," Chemistry & Biology, 16(5):531-539 (2009).

Kepp, O. et al., "Lysyl tRNA synthetase is required for the translocation of calreticulin to the cell surface in immunogenic death," Cell Cycle, 9(15):3072-3077 (2010).
Kim, D. G. et al., "Interaction of two translational components, lysyl-tRNA synthetase and p40/37LRP, in plasma membrane promotes laminin-dependent cell migration," FASEB Journal, 26:1-18 (2012).
Kise, Y. et al., "A short peptide insertion crucial for angiostatic activity of human tryptophanyl-tRNA synthetase," Nature Structural & Molecular Biology, 11(2):149-156 (2004).
Kochendoerfer, G. G., "Site-specific polymer modification of therapeutic proteins," Current Opinion in Chemical Biology, 9:555-560 (2005).
Kovaleski, B. J. et al., "In vitro characterization of the interaction between HIV-1 Gag and human lysyl-tRNA synthetase," J. Bio. Chem., 281(28):19449-19456 (2006).
Levine, S. M. et al., "Anti-aminoacyl tRNA synthetase immune responses: insights into the pathogenesis of the idiopathic inflammatory myopathies," Current Opinion in Rheumatology, 15(6):708-713 (2003).
Link, A. J. et al., "Discovery of aminoacyl-tRNA synthetase activity through cell-surface display of noncanonical amino acids," Proc. Nat. Acad. Sci., 103(27):10180-10185 (2006).
Mukhopadhyay, R. et al., "The GAIT System: a gatekeeper of inflammatory gene expression," Trends in Biochemical Sciences, 34(7):324-331 (2009).
Nechushtan, H. et al., "The Physiological Role of Lysyl tRNA Synthetase in the Immune System," Advances in Immunology, vol. 103, Elsevier Inc. (2009), 27 pages.
Ofir-Birin et al., "Structural Switch of Lysyl-tRNA Synthetase Between Translation and Transcription," Manuscript (2013), 39 pages.
Park, S. G., et al., "Aminoacyl tRNA synthetases and their connections to disease," PNAS, 105(32):11043-11049 (2008).
Park, S. G. et al., "Human lysyl-tRNA syntetase is secreted to trigger proinflammatory response," PNAS, 102(18):6356-6361 (2005).
Park, S. G. et al., "Is there an answer? Do aminoacyl-tRNA synthetases have biological functions other than in protein biosynthesis?" IUBMB Life, 58(9):556-558 (2006).
Sen, S. et al., "Developments in directed evolution for improving enzyme functions," Appl. Biochem. Biotechnol., 143:212-223 (2007).
Veronese, F. M. et al., "Preface: Introduction and overview of peptide and protein pegylation," Advanced Drug Delivery Reviews, 54:453-456 (2002).
Wakasugi, K. et al., "Two distinct cytokines released from a human aminoacyl-tRNA synthetase," Science, 284:147-151 (1999).
Whisstock, J. C. et al., "Prediction of protein function from protein sequence," Q. Rev. Biophysics., 36(3):307-340 (2003).
Wishart, M. J. et al., "A single mutation converts a novel phosphotyrosine binding domain into a dual-specificity phosphatase," J. Biol. Chem., 270(45):26782-26785 (1995).
Witkowski, A. et al., "Conversion of β-ketoacyl synthase to a Malonyl Decarboxylase by replacement of the active cysteine with glutamine," Biochemistry, 38:11643-11650 (1999).
WPI Database Accession No. 2002-090149 (2013).
WPI Database Accession No. 2002-501208 (2013).
WPI Database Accession No. 2002-501210 (2013).
WPI Database Accession No. 2002-692409 (2013).
WPI Database Accession No. 2002-714440 (2013).
Xie, W. et al., "Long-range structural effects of a Charcot-Marie-Tooth disease-causing mutation in human glycyl-tRNA synthetase," PNAS, 104(24):9976-9981 (2007).
Yang, X-L et al., "Crystal structure of a human aminoacyl-tRNA synthetase cytokine," PNAS, 99(24):15369-15374 (2002).
Yang, X-L et al., "Gain-of-Function Mutational Activation of Human tRNA Synthetase Procytokine," Chemistry & Biology, 14(12):1323-1333 (2007).
Yannay-Cohen, N. et al., "LysRS Serves as a Key Signaling Molecule in the Immune Response by Regulating Gene Expression," Molecular Cell, 34:603-611 (2009).

(56) References Cited

OTHER PUBLICATIONS

Yu, Y. et al., "Crystal structure of human tryptophanyl-tRNA synthetase catalytic fragment," The Journal of Biological Chemistry, 279(9):8378-8388 (2004).

Zalipsky, S. et al., "Use of functionalized poly(ethylene glycol)s for modification of polypeptides," Polyethylene glycol chemistry: Biotechnical and Biomedical Applications, pp. 347-370, Plenum Press, New York (1992).

Zhou, Q. et al., "Orthogonal use of a human tRNA synthetase active site to achieve multifunctionality," Nature Structural & Molecular Biology, 17(1):57-62 (2010).

Sambrook, et al., Molecular Cloning: A Laboratory Manual, 3rd. Ed., vol. 2, 10.47 (2001).

Supplementary European Search Report for European Application No. 11790361.7, mailed Dec. 2, 2013.

Kormann, M. S. D. et al., "Expression of therapeutic proteins after delivery of chemically modified mRNA in mice," Nature Biotechnology, 29(2):154-157 (2011).

SEQUENCE LISTING

```
<160> NUMBER OF SEQ ID NOS: 230

<210> SEQ ID NO 1
<211> LENGTH: 77
<212> TYPE: DNA
<213> ORGANISM: Artificial Sequence
<220> FEATURE:
<223> OTHER INFORMATION: Oligonucleotide

<400> SEQUENCE: 1
aggaggtaaa acatatgcat catcatcatc atcacggtaa gcctatccct aacccctttgc     60 tcggtctcga ttctacg                                                    77

<210> SEQ ID NO 2
<211> LENGTH: 12
<212> TYPE: DNA
<213> ORGANISM: Artificial Sequence
<220> FEATURE:
<223> OTHER INFORMATION: Oligonucleotide

<400> SEQUENCE: 2
taatgactcg ag                                                         12
```

```
<210> SEQ ID NO 3
<211> LENGTH: 17
<212> TYPE: DNA
<213> ORGANISM: Artificial Sequence
<220> FEATURE:
<223> OTHER INFORMATION: Oligonucleotide

<400> SEQUENCE: 3
aggagataaa acatatg                                                       17

<210> SEQ ID NO 4
<211> LENGTH: 14
<212> TYPE: DNA
<213> ORGANISM: Artificial Sequence
<220> FEATURE:
<223> OTHER INFORMATION: Oligonucleotide

<400> SEQUENCE: 4
aggaggtaaa acat                                                          14

<210> SEQ ID NO 5
<211> LENGTH: 14
<212> TYPE: DNA
<213> ORGANISM: Artificial Sequence
<220> FEATURE:
<223> OTHER INFORMATION: Oligonucleotide

<400> SEQUENCE: 5
aggagataaa acat                                                          14

<210> SEQ ID NO 6
<211> LENGTH: 15
<212> TYPE: DNA
<213> ORGANISM: Artificial Sequence
<220> FEATURE:
<223> OTHER INFORMATION: Oligonucleotide

<400> SEQUENCE: 6
gaaggagata tacat                                                         15

<210> SEQ ID NO 7
<211> LENGTH: 72
<212> TYPE: DNA
<213> ORGANISM: Artificial Sequence
<220> FEATURE:
<223> OTHER INFORMATION: Oligonucleotide

<400> SEQUENCE: 7
ggtaagccta tccctaaccc tctcctcggt ctcgattcta cgcaccacca tcatcaccat        60
taatgactcg ag                                                            72

<210> SEQ ID NO 8
<211> LENGTH: 72
<212> TYPE: DNA
<213> ORGANISM: Artificial Sequence
<220> FEATURE:
<223> OTHER INFORMATION: Oligonucleotide

<400> SEQUENCE: 8
catatgcatc atcatcatca tcacggtaag cctatcccta accctctcct cggtctcgat        60
tctacgggat cc                                                            72
```

-continued

```
<210> SEQ ID NO 9
<211> LENGTH: 12
<212> TYPE: DNA
<213> ORGANISM: Artificial Sequence
<220> FEATURE:
<223> OTHER INFORMATION: Oligonucleotide

<400> SEQUENCE: 9
ctcgagtaat ga                                                            12

<210> SEQ ID NO 10
<211> LENGTH: 12
<212> TYPE: DNA
<213> ORGANISM: Artificial Sequence
<220> FEATURE:
<223> OTHER INFORMATION: Oligonucleotide

<400> SEQUENCE: 10
catatgggat cc                                                            12

<210> SEQ ID NO 11
<211> LENGTH: 72
<212> TYPE: DNA
<213> ORGANISM: Artificial Sequence
<220> FEATURE:
<223> OTHER INFORMATION: Oligonucleotide

<400> SEQUENCE: 11
ctcgagggta agcctatccc taaccctctc ctcggtctcg attctacgca ccaccaccac         60
caccactaat ga                                                            72

<210> SEQ ID NO 12
<211> LENGTH: 366
<212> TYPE: PRT
<213> ORGANISM: Homo sapiens

<400> SEQUENCE: 12
```

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val
    50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Gly Lys Leu Ile Phe
    130                 135                 140

Tyr Asp Leu Arg Gly Glu Gly Val Lys Leu Gln Val Met Ala Asn Ser
145                 150                 155                 160

Arg Asn Tyr Lys Ser Glu Glu Glu Phe Ile His Ile Asn Asn Lys Leu
                165                 170                 175

Arg Arg Gly Asp Ile Ile Gly Val Gln Gly Asn Pro Gly Lys Thr Lys

```
                 180                 185                 190
Lys Gly Glu Leu Ser Ile Ile Pro Tyr Glu Ile Thr Leu Leu Ser Pro
            195                 200                 205

Cys Leu His Met Leu Pro His Leu His Phe Gly Leu Lys Asp Lys Glu
        210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255

Phe Leu Asp Glu Leu Gly Phe Leu Glu Ile Glu Thr Pro Met Met Asn
                260                 265                 270

Ile Ile Pro Gly Gly Ala Val Ala Lys Pro Phe Ile Thr Tyr His Asn
            275                 280                 285

Glu Leu Asp Met Asn Leu Tyr Met Arg Ile Ala Pro Glu Leu Tyr His
                290                 295                 300

Lys Met Leu Val Val Gly Gly Ile Asp Arg Val Tyr Glu Ile Gly Arg
305                 310                 315                 320

Gln Phe Arg Asn Glu Gly Ile Asp Leu Thr His Asn Pro Glu Phe Thr
                325                 330                 335

Thr Cys Glu Phe Tyr Met Ala Tyr Ala Asp Tyr His Asp Leu Met Glu
                340                 345                 350

Ile Thr Glu Lys Met Val Ser Gly Met Val Lys His Ile Thr
                355                 360                 365

<210> SEQ ID NO 13
<211> LENGTH: 1098
<212> TYPE: DNA
<213> ORGANISM: Homo sapiens

<400> SEQUENCE: 13
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa tcaatactaa caaaatccgc     240
agtcaagcaa ttcatcagct gaaggtcaat ggggaagacc catacccaca caagttccat     300
gtagacatct cactcactga cttcatccaa aaatatagtc acctgcagcc tggggatcac     360
ctgactgaca tcaccttaaa ggtggcaggt aggatccatg ccaaaagagc ttctggggga     420
aagctcatct tctatgatct tcgaggagag ggggtgaagt tgcaagtcat ggccaattcc     480
agaaattata atcagaagaa agaatttatt catattaata caaactgcg tcggggagac     540 ataattggag ttcaggggaa tcctggtaaa accaagaagg gtgagctgag catcattccg     600
tatgagatca cactgctgtc tccctgtttg catatgttac ctcatcttca ctttggcctc     660
aaagacaagg aaacaaggta tcgccagaga tacttggact tgatcctgaa tgactttgtg     720
aggcagaaat ttatcatccg ctctaagatc atcacatata agaagtttt cttagatgag     780 ctgggattcc tagagattga aactcccatg atgaacatca tcccagggg agccgtggcc     840 aagccttttca tcacttatca caacgagctg gacatgaact tatatatgag aattgctcca     900
gaactctatc ataagatgct tgtggttggt ggcatcgacc gggtttatga aattggacgc     960
cagttccgga atgaggggat tgatttgacg cacaatcctg agttcaccac ctgtgagttc    1020
tacatggcct atgcagacta tcacgatctc atggaaatca cggagaagat ggtttcaggg    1080
```

```
atggtgaagc atattaca                                                  1098
```

<210> SEQ ID NO 14
<211> LENGTH: 13
<212> TYPE: PRT
<213> ORGANISM: Mus musculus

<400> SEQUENCE: 14

```
Arg Gly Asp Ile Ile Gly Val Glu Gly Asn Pro Gly Lys
1               5                   10
```

<210> SEQ ID NO 15
<211> LENGTH: 40
<212> TYPE: PRT
<213> ORGANISM: Mus musculus

<400> SEQUENCE: 15

```
Thr Lys Lys Gly Glu Leu Ser Ile Ile Pro Gln Glu Ile Thr Leu Leu
1               5                   10                  15

Ser Pro Cys Leu His Met Leu Pro His Leu His Phe Gly Leu Lys Asp
            20                  25                  30

Lys Glu Thr Arg Tyr Arg Gln Arg
        35                  40
```

<210> SEQ ID NO 16
<211> LENGTH: 11
<212> TYPE: PRT
<213> ORGANISM: Mus musculus

<400> SEQUENCE: 16

```
Tyr Leu Asp Leu Ile Leu Asn Asp Phe Val Arg
1               5                   10
```

<210> SEQ ID NO 17
<211> LENGTH: 64
<212> TYPE: PRT
<213> ORGANISM: Mus musculus

<400> SEQUENCE: 17

```
Arg Gly Asp Ile Ile Gly Val Glu Gly Asn Pro Gly Lys Thr Lys Lys
1               5                   10                  15

Gly Glu Leu Ser Ile Ile Pro Gln Glu Ile Thr Leu Leu Ser Pro Cys
            20                  25                  30

Leu His Met Leu Pro His Leu His Phe Gly Leu Lys Asp Lys Glu Thr
        35                  40                  45

Arg Tyr Arg Gln Arg Tyr Leu Asp Leu Ile Leu Asn Asp Phe Val Arg
    50                  55                  60
```

<210> SEQ ID NO 18
<211> LENGTH: 96
<212> TYPE: PRT
<213> ORGANISM: Homo sapiens

<400> SEQUENCE: 18

```
Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val
```

```
                    50                  55                  60
Gly Pro Glu Glu Glu Ser Val Asp Pro Asn Val Gly Ser Met Pro Lys
65                  70                  75                  80

Glu Leu Leu Gly Glu Ser Ser Ser Met Ile Phe Glu Arg Gly
                85                  90                  95
```

<210> SEQ ID NO 19
<211> LENGTH: 291
<212> TYPE: DNA
<213> ORGANISM: Homo sapiens

<400> SEQUENCE: 19

```
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atgtaggatc catgccaaaa     240
gagcttctgg gggaaagctc atcttctatg atcttcgagg agaggggtg a              291
```

<210> SEQ ID NO 20
<211> LENGTH: 557
<212> TYPE: PRT
<213> ORGANISM: Homo sapiens

<400> SEQUENCE: 20

```
Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
                20                  25                  30

Val Ala Glu Lys Glu Ala Lys Gln Lys Glu Leu Ser Glu Lys Gln Leu
            35                  40                  45

Ser Gln Ala Thr Ala Ala Thr Asn His Thr Thr Asp Asn Gly Val
        50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
            100                 105                 110

Ser His Leu Gln Pro Gly Asp His Leu Thr Ile Thr Leu Lys Val
        115                 120                 125

Ala Gly Arg Ile His Ala Lys Arg Ala Ser Gly Gly Lys Leu Ile Phe
        130                 135                 140

Tyr Asp Leu Arg Gly Glu Gly Val Lys Leu Gln Val Met Ala Asn Ser
145                 150                 155                 160

Arg Asn Tyr Lys Ser Glu Glu Glu Phe Ile His Ile Asn Asn Lys Leu
                165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
        195                 200                 205

Cys Leu His Met Leu Pro His Leu His Phe Gly Leu Lys Asp Lys Glu
        210                 215                 220

Thr Arg Tyr Arg Gln Arg Tyr Leu Asp Leu Ile Leu Asn Asp Phe Val
225                 230                 235                 240
```

```
Arg Gln Lys Phe Ile Ile Arg Ser Lys Ile Ile Thr Tyr Ile Arg Ser
                245                 250                 255
Phe Leu Asp Glu Leu Gly Phe Leu Glu Met Leu Val Val Gly Gly Ile
            260                 265                 270
Asp Arg Val Tyr Glu Ile Gly Arg Gln Phe Arg Asn Glu Gly Ile Asp
        275                 280                 285
Leu Thr His Asn Pro Glu Phe Thr Thr Cys Glu Phe Tyr Met Ala Tyr
    290                 295                 300
Ala Asp Tyr His Asp Leu Met Glu Ile Thr Glu Lys Met Val Ser Gly
305                 310                 315                 320
Met Val Lys His Ile Thr Gly Ser Tyr Lys Val Thr Tyr His Pro Asp
                325                 330                 335
Gly Pro Glu Gly Gln Ala Tyr Asp Val Asp Phe Thr Pro Pro Phe Arg
            340                 345                 350
Arg Ile Asn Met Val Glu Glu Leu Glu Lys Ala Leu Gly Met Lys Leu
        355                 360                 365
Pro Glu Thr Asn Leu Phe Glu Thr Glu Glu Thr Arg Lys Ile Leu Asp
    370                 375                 380
Asp Ile Cys Val Ala Lys Ala Val Glu Cys Pro Pro Pro Arg Thr Thr
385                 390                 395                 400
Ala Arg Leu Leu Asp Lys Leu Val Gly Glu Phe Leu Glu Val Thr Cys
                405                 410                 415
Ile Asn Pro Thr Phe Ile Cys Asp His Pro Gln Ile Met Ser Pro Leu
            420                 425                 430
Ala Lys Trp His Arg Ser Lys Glu Gly Leu Thr Glu Arg Phe Glu Leu
        435                 440                 445
Phe Val Met Lys Lys Glu Ile Cys Asn Ala Tyr Thr Glu Leu Asn Asp
    450                 455                 460
Pro Met Arg Gln Arg Gln Leu Phe Glu Glu Gln Ala Lys Ala Lys Ala
465                 470                 475                 480
Ala Gly Asp Asp Glu Ala Met Phe Ile Asp Glu Asn Phe Cys Thr Ala
                485                 490                 495
Leu Glu Tyr Gly Leu Pro Pro Thr Ala Gly Trp Gly Met Gly Ile Asp
            500                 505                 510
Arg Val Ala Met Phe Leu Thr Asp Ser Asn Asn Ile Lys Glu Val Leu
        515                 520                 525
Leu Phe Pro Ala Met Lys Pro Glu Asp Lys Lys Glu Asn Val Ala Thr
    530                 535                 540
Thr Asp Thr Leu Glu Ser Thr Thr Val Gly Thr Ser Val
545                 550                 555

<210> SEQ ID NO 21
<211> LENGTH: 1674
<212> TYPE: DNA
<213> ORGANISM: Homo sapiens

<400> SEQUENCE: 21
atggcggccg tgcaggcggc cgaggtgaaa gtggatggca gcgagccgaa actgagcaag      60
aatgagctga gagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atcaatacta caaaatccgc     240
agtcaagcaa ttcatcagct gaaggtcaat ggggaagacc catacccaca caagttccat     300
gtagacatct cactcactga cttcatccaa aaatatagtc acctgcagcc tgggatcac     360
```

```
ctgactgaca tcaccttaaa ggtggcaggt aggatccatg ccaaaagagc ttctggggga    420
aagctcatct tctatgatct tcgaggagag ggggtgaagt tgcaagtcat ggccaattcc    480
agaaattata atcagaaga agaatttatt catattaata acaaactgcg tcggggagac    540
ataattggag ttcaggggaa tcctggtaaa accaagaagg gtgagctgag catcattccg    600
tatgagatca cactgctgtc tccctgtttg catatgttac ctcatcttca ctttggcctc    660
aaagacaagg aaacaaggta tcgccagaga tacttggact tgatcctgaa tgactttgtg    720
aggcagaaat ttatcatccg ctctaagatc atcacatata taagaagttt cttagatgag    780
ctgggattcc tagagatgct tgtgttggt ggcatcgacc gggtttatga aattggacgc    840
cagttccgga atgagggat tgatttgacg cacaatcctg agttcaccac ctgtgagttc    900
tacatggcct atgcagacta tcacgatctc atggaaatca cggagaagat ggtttcaggg    960
atggtgaagc atattacagg cagttacaag gtcacctacc acccagatgg cccagagggc   1020
caagcctacg atgttgactt caccccaccc ttccggcgaa tcaacatggt agaagagctt   1080
gagaaagccc tggggatgaa gctgccagaa acgaacctct ttgaaactga agaaactcgc   1140
aaaattcttg atgatatctg tgtggcaaaa gctgttgaat gccctccacc tcggaccaca   1200
gccaggctcc ttgacaagct tgttggggag ttcctggaag tgacttgcat caatcctaca   1260
ttcatctgtg atcacccaca gataatgagc cctttggcta atggcaccg ctctaaagag   1320
ggtctgactg agcgctttga gctgtttgtc atgaagaaag agatatgcaa tgcgtatact   1380
gagctgaatg atcccatgcg gcagcggcag cttttttgaag aacaggccaa ggccaaggct   1440
gcaggtgatg atgaggccat gttcatagat gaaaacttct gtactgccct ggaatatggg   1500
ctgcccccca cagctggctg gggcatgggc attgatcgag tcgccatgtt tctcacggac   1560
tccaacaaca tcaaggaagt acttctgttt cctgccatga aacccgaaga caagaaggag   1620
aatgtagcaa ccactgatac actggaaagc acaacagttg gcacttctgt ctag         1674

<210> SEQ ID NO 22
<211> LENGTH: 406
<212> TYPE: PRT
<213> ORGANISM: Homo sapiens

<400> SEQUENCE: 22

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
                20                  25                  30

Val Ala Glu Lys Glu Ala Lys Gln Lys Glu Leu Ser Glu Lys Gln Leu
            35                  40                  45

Ser Gln Ala Thr Ala Ala Ala Thr Asn His Thr Thr Asp Asn Gly Val
        50                  55                  60

Gly Pro Glu Glu Glu Ser Val Asp Pro Asn Ile Glu Thr Pro Met Met
65                  70                  75                  80

Asn Ile Ile Pro Gly Gly Ala Val Ala Lys Pro Phe Ile Thr Tyr His
                85                  90                  95

Asn Glu Leu Asp Met Asn Leu Tyr Met Arg Ile Ala Pro Glu Leu Tyr
                100                 105                 110

His Lys Met Leu Val Val Gly Gly Ile Asp Arg Val Tyr Glu Ile Gly
            115                 120                 125

Arg Gln Phe Arg Asn Glu Gly Ile Asp Leu Thr His Asn Pro Glu Phe
        130                 135                 140
```

```
Thr Thr Cys Glu Phe Tyr Met Ala Tyr Ala Asp Tyr His Asp Leu Met
145                 150                 155                 160

Glu Ile Thr Glu Lys Met Val Ser Gly Met Val Lys His Ile Thr Gly
                165                 170                 175

Ser Tyr Lys Val Thr Tyr His Pro Asp Gly Pro Glu Gly Gln Ala Tyr
            180                 185                 190

Asp Val Asp Phe Thr Pro Pro Phe Arg Arg Ile Asn Met Val Glu Glu
        195                 200                 205

Leu Glu Lys Ala Leu Gly Met Lys Leu Pro Glu Thr Asn Leu Phe Glu
    210                 215                 220

Thr Glu Glu Thr Arg Lys Ile Leu Asp Asp Ile Cys Val Ala Lys Ala
225                 230                 235                 240

Val Glu Cys Pro Pro Arg Thr Thr Ala Arg Leu Leu Asp Lys Leu
                245                 250                 255

Val Gly Glu Phe Leu Glu Val Thr Cys Ile Asn Pro Thr Phe Ile Cys
            260                 265                 270

Asp His Pro Gln Ile Met Ser Pro Leu Ala Lys Trp His Arg Ser Lys
        275                 280                 285

Glu Gly Leu Thr Glu Arg Phe Glu Leu Phe Val Met Lys Lys Glu Ile
    290                 295                 300

Cys Asn Ala Tyr Thr Glu Leu Asn Asp Pro Met Arg Gln Arg Gln Leu
305                 310                 315                 320

Phe Glu Glu Gln Ala Lys Ala Lys Ala Ala Gly Asp Asp Glu Ala Met
                325                 330                 335

Phe Ile Asp Glu Asn Phe Cys Thr Ala Leu Glu Tyr Gly Leu Pro Pro
            340                 345                 350

Thr Ala Gly Trp Gly Met Gly Ile Asp Arg Val Ala Met Phe Leu Thr
        355                 360                 365

Asp Ser Asn Asn Ile Lys Glu Val Leu Leu Phe Pro Ala Met Lys Pro
370                 375                 380

Glu Asp Lys Lys Glu Asn Val Ala Thr Thr Asp Thr Leu Glu Ser Thr
385                 390                 395                 400

Thr Val Gly Thr Ser Val
                405

<210> SEQ ID NO 23
<211> LENGTH: 1221
<212> TYPE: DNA
<213> ORGANISM: Homo sapiens

<400> SEQUENCE: 23
atggcggccg tgcaggcggc cgaggtgaaa gtggatggca gcgagccgaa actgagcaag      60
aatgagctga gagacgcct  gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atattgaaac tcccatgatg     240
aacatcatcc aggggagc cgtggccaag cctttcatca cttatcacaa cgagctggac      300
atgaacttat atatgagaat tgctccagaa ctctatcata agatgcttgt ggttggtggc     360
atcgaccggg tttatgaaat tggacgccag ttccggaatg aggggattga tttgacgcac     420
aatcctgagt tcaccacctg tgagttctac atggcctatg cagactatca cgatctcatg     480
gaaatcacgg agaagatggt ttcagggatg gtgaagcata ttacaggcag ttacaaggtc     540
acctaccacc cagatggccc agagggccaa gcctacgatg ttgacttcac cccacccttc     600
```

```
cggcgaatca acatggtaga agagcttgag aaagccctgg ggatgaagct gccagaaacg      660
aacctctttg aaactgaaga aactcgcaaa attcttgatg atatctgtgt ggcaaaagct      720
gttgaatgcc ctccacctcg gaccacagcc aggctccttg acaagcttgt tggggagttc      780
ctggaagtga cttgcatcaa tcctacattc atctgtgatc acccacagat aatgagccct      840
ttggctaaat ggcaccgctc taaagagggt ctgactgagc gctttgagct gtttgtcatg      900
aagaaagaga tatgcaatgc gtatactgag ctgaatgatc ccatgcggca gcggcagctt      960
tttgaagaac aggccaaggc caaggctgca ggtgatgatg aggccatgtt catagatgaa     1020
aacttctgta ctgccctgga atatgggctg cccccacag ctggctgggg catgggcatt      1080
gatcgagtcg ccatgtttct cacggactcc aacaacatca aggaagtact tctgtttcct     1140
gccatgaaac ccgaagacaa gaaggagaat gtagcaacca ctgatacact ggaaagcaca     1200
acagttggca cttctgtcta g                                              1221
```

<210> SEQ ID NO 24
<211> LENGTH: 385
<212> TYPE: PRT
<213> ORGANISM: Homo sapiens

<400> SEQUENCE: 24

```
Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Thr Asn His Thr Thr Asp Asn Gly Val
    50                  55                  60

Gly Pro Glu Glu Glu Ser Val Asp Pro Asn Gln Tyr Tyr Lys Ile Arg
65                  70                  75                  80

Ser Gln Ala Ile His Gln Leu Lys Val Asn Gly Glu Asp Pro Tyr Pro
                85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Gly Lys Leu Ile Phe
    130                 135                 140

Tyr Asp Leu Arg Gly Glu Gly Val Lys Leu Gln Val Met Ala Asn Ser
145                 150                 155                 160

Arg Asn Tyr Lys Ser Glu Glu Phe Ile His Ile Asn Asn Lys Leu
                165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
        195                 200                 205

Cys Leu His Met Leu Pro His Leu His Phe Gly Leu Lys Asp Lys Glu
    210                 215                 220

Thr Arg Tyr Arg Gln Arg Tyr Leu Asp Leu Ile Leu Asn Asp Phe Val
225                 230                 235                 240

Arg Gln Lys Phe Ile Ile Arg Ser Lys Ile Ile Thr Tyr Ile Arg Ser
                245                 250                 255
```

Phe Leu Asp Glu Leu Gly Phe Leu Glu Ile Glu Thr Pro Met Met Asn
            260                 265                 270

Ile Ile Pro Gly Gly Ala Val Ala Lys Pro Phe Ile Thr Tyr His Asn
            275                 280                 285

Glu Leu Asp Met Asn Leu Tyr Met Arg Ile Ala Pro Glu Leu Tyr His
            290                 295                 300

Lys Ala Lys Ala Ala Gly Asp Asp Glu Ala Met Phe Ile Asp Glu Asn
305                 310                 315                 320

Phe Cys Thr Ala Leu Glu Tyr Gly Leu Pro Pro Thr Ala Gly Trp Gly
                325                 330                 335

Met Gly Ile Asp Arg Val Ala Met Phe Leu Thr Asp Ser Asn Asn Ile
            340                 345                 350

Lys Glu Val Leu Leu Phe Pro Ala Met Lys Pro Glu Asp Lys Lys Glu
            355                 360                 365

Asn Val Ala Thr Thr Asp Thr Leu Glu Ser Thr Thr Val Gly Thr Ser
            370                 375                 380

Val
385

<210> SEQ ID NO 25
<211> LENGTH: 1158
<212> TYPE: DNA
<213> ORGANISM: Homo sapiens

<400> SEQUENCE: 25
atggcggccg tgcaggcggc cgaggtgaaa gtggatggca gcgagccgaa actgagcaag       60
aatgagctga agagacgcct gaaagctgag aagaaagtag cagagaagga ggccaaacag      120
aaagagctca gtgagaaaca gctaagccaa gccactgctg ctgccaccaa ccacaccact      180
gataatggtg tgggtcctga ggaagagagc gtggacccaa atcaatacta caaaatccgc      240
agtcaagcaa ttcatcagct gaaggtcaat ggggaagacc catacccaca caagttccat      300
gtagacatct cactcactga cttcatccaa aaatatagtc acctgcagcc tggggatcac      360
ctgactgaca tcaccttaaa ggtggcaggt aggatccatg ccaaaagagc ttctggggga      420
aagctcatct tctatgatct tcgaggagag ggggtgaagt tgcaagtcat ggccaattcc      480
agaaattata atcagaagaa gaatttattt catattaata caaactgcg tcggggagac      540 ataattggag ttcagggaa tcctggtaaa accaagaagg gtgagctgag catcattccg      600
tatgagatca cactgctgtc tccctgtttg catatgttac ctcatcttca ctttggcctc      660
aaagacaagg aaacaaggta tcgccagaga tacttggact tgatcctgaa tgactttgtg      720
aggcagaaat ttatcatccg ctctaagatc atcacatata taagaagttt cttagatgag      780
ctgggattcc tagagattga aactcccatg atgaacatca tcccaggggg agccgtggcc      840
aagcctttca tcacttatca caacgagctg gacatgaact tatatatgag aattgctcca      900
gaactctatc ataaggccaa ggctgcaggt gatgatgagg ccatgttcat agatgaaaac      960
ttctgtactg ccctggaata tgggctgccc cccacagctg gctgggcat gggcattgat     1020 cgagtcgcca tgtttctcac ggactccaac aacatcaagg aagtacttct gtttcctgcc     1080
atgaaacccg aagacaagaa ggagaatgta gcaaccactg atacactgga aagcacaaca     1140
gttggcactt ctgtctag                                                    1158

<210> SEQ ID NO 26
<211> LENGTH: 76
<212> TYPE: PRT

<213> ORGANISM: Homo sapiens

<400> SEQUENCE: 26

Met Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val
    50                  55                  60

Gly Pro Glu Glu Glu Ser Val Asp Pro Asn Lys Leu
65                  70                  75

<210> SEQ ID NO 27
<211> LENGTH: 231
<212> TYPE: DNA
<213> ORGANISM: Homo sapiens

<400> SEQUENCE: 27
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa ataaattata a              231

<210> SEQ ID NO 28
<211> LENGTH: 21
<212> TYPE: PRT
<213> ORGANISM: Homo sapiens

<400> SEQUENCE: 28

Met Ala Ala Val Gln Ala Ala Glu Val Lys Val Asp Gly Ser Glu Pro
1               5                   10                  15

Lys Leu Ser Lys Lys
            20

<210> SEQ ID NO 29
<211> LENGTH: 66
<212> TYPE: DNA
<213> ORGANISM: Homo sapiens

<400> SEQUENCE: 29
atggcggccg tgcaggcggc cgaggtgaaa gtggatggca gcgagccgaa actgagcaag      60
aagtag                                                                66

<210> SEQ ID NO 30
<211> LENGTH: 149
<212> TYPE: PRT
<213> ORGANISM: Homo sapiens

<400> SEQUENCE: 30

Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
            20                  25                  30

Val Ala Glu Lys Glu Ala Lys Gln Lys Glu Leu Ser Glu Lys Gln Leu
        35                  40                  45

Ser Gln Ala Thr Ala Ala Ala Thr Asn His Thr Thr Asp Asn Gly Val

```
            50                  55                  60
Gly Pro Glu Glu Glu Ser Val Asp Pro Asn Gln Tyr Tyr Lys Ile Arg
 65                  70                  75                  80

Ser Gln Ala Ile His Gln Leu Lys Val Asn Gly Glu Asp Pro Tyr Pro
                 85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Glu Ile Ile Asn Gln Lys Lys Asn Leu Phe Ile Leu Ile Thr Asn
    130                 135                 140

Cys Val Gly Glu Thr
145

<210> SEQ ID NO 31
<211> LENGTH: 450
<212> TYPE: DNA
<213> ORGANISM: Homo sapiens

<400> SEQUENCE: 31
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atcaatacta caaaatccgc     240
agtcaagcaa ttcatcagct gaaggtcaat ggggaagacc catacccaca caagttccat     300
gtagacatct cactcactga cttcatccaa aaatatagtc acctgcagcc tggggatcac     360
ctgactgaca tcaccttaaa ggtggcagaa attataaatc agaagaagaa tttattcata     420
ttaataacaa actgcgtcgg ggagacataa                                      450

<210> SEQ ID NO 32
<211> LENGTH: 259
<212> TYPE: PRT
<213> ORGANISM: Homo sapiens

<400> SEQUENCE: 32

Met Ala Ala Val Gln Ala Ala Glu Val Lys Val Asp Gly Ser Glu Pro
 1               5                  10                  15

Lys Leu Ser Lys Asn Glu Leu Lys Arg Arg Leu Lys Ala Glu Lys Lys
             20                  25                  30

Val Ala Glu Lys Glu Ala Lys Gln Lys Glu Leu Ser Glu Lys Gln Leu
         35                  40                  45

Ser Gln Ala Thr Ala Ala Thr Asn His Thr Thr Asp Asn Gly Val
     50                  55                  60

Gly Pro Glu Glu Glu Ser Val Asp Pro Asn Gln Tyr Tyr Lys Ile Arg
 65                  70                  75                  80

Ser Gln Ala Ile His Gln Leu Lys Val Asn Gly Glu Asp Pro Tyr Pro
                 85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Gly Lys Leu Ile Phe
    130                 135                 140
```

```
Tyr Asp Leu Arg Gly Glu Gly Val Lys Leu Gln Val Met Ala Asn Ser
145                 150                 155                 160
Arg Asn Tyr Lys Ser Glu Glu Glu Phe Ile His Ile Asn Asn Lys Leu
                165                 170                 175
Arg Arg Gly Asp Ile Ile Gly Val Gln Gly Asn Pro Gly Lys Thr Lys
            180                 185                 190
Lys Gly Glu Leu Ser Ile Ile Pro Tyr Glu Ile Thr Leu Leu Ser Pro
        195                 200                 205
Cys Leu His Met Leu Pro His Leu His Phe Gly Leu Lys Asp Lys Lys
        210                 215                 220
Leu Ala Lys Phe Leu Met Ile Ser Val Trp Gln Lys Leu Leu Asn Ala
225                 230                 235                 240
Leu His Leu Gly Pro Gln Pro Gly Ser Leu Thr Ser Leu Leu Gly Ser
                245                 250                 255
Ser Trp Lys

<210> SEQ ID NO 33
<211> LENGTH: 780
<212> TYPE: DNA
<213> ORGANISM: Homo sapiens

<400> SEQUENCE: 33
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atcaatacta caaaatccgc     240
agtcaagcaa ttcatcagct gaaggtcaat ggggaagacc catacccaca caagttccat     300
gtagacatct cactcactga cttcatccaa aaatatagtc acctgcagcc tggggatcac     360
ctgactgaca tcaccttaaa ggtggcaggt aggatccatg ccaaaagagc ttctggggga     420
aagctcatct tctatgatct tcgaggagag ggggtgaagt tgcaagtcat ggccaattcc     480
agaaattata atcagaaga agaatttatt catattaata caaaactgcg tcggggagac     540
ataattggag ttcaggggaa tcctggtaaa ccaagaaagg gtgagctgag catcattccg     600
tatgagatca cactgctgtc tccctgtttg catatgttac ctcatcttca ctttggcctc     660
aaagacaaga aactcgcaaa attcttgatg atatctgtgt ggcaaaagct gttgaatgcc     720
ctccacctcg gaccacagcc aggctccttg acaagcttgt tggggagttc ctggaagtga     780

<210> SEQ ID NO 34
<211> LENGTH: 50
<212> TYPE: DNA
<213> ORGANISM: Homo sapiens

<400> SEQUENCE: 34
tgaggaagag agcgtggacc caaatgtagg atccatgcca aaagagcttc                  50

<210> SEQ ID NO 35
<211> LENGTH: 16
<212> TYPE: PRT
<213> ORGANISM: Homo sapiens

<400> SEQUENCE: 35

Glu Glu Glu Ser Val Asp Pro Asn Val Gly Ser Met Pro Lys Glu Leu
1               5                   10                  15
```

```
<210> SEQ ID NO 36
<211> LENGTH: 50
<212> TYPE: DNA
<213> ORGANISM: Homo sapiens

<400> SEQUENCE: 36
cttagatgag ctgggattcc tagagatgct tgtggttggt ggcatcgacc          50

<210> SEQ ID NO 37
<211> LENGTH: 16
<212> TYPE: PRT
<213> ORGANISM: Homo sapiens

<400> SEQUENCE: 37

Leu Asp Glu Leu Gly Phe Leu Glu Met Leu Val Val Gly Gly Ile Asp
1               5                   10                  15

<210> SEQ ID NO 38
<211> LENGTH: 50
<212> TYPE: DNA
<213> ORGANISM: Homo sapiens

<400> SEQUENCE: 38
tgaggaagag agcgtggacc caaatattga aactcccatg atgaacatca          50

<210> SEQ ID NO 39
<211> LENGTH: 16
<212> TYPE: PRT
<213> ORGANISM: Homo sapiens

<400> SEQUENCE: 39

Glu Glu Glu Ser Val Asp Pro Asn Ile Glu Thr Pro Met Met Asn Ile
1               5                   10                  15

<210> SEQ ID NO 40
<211> LENGTH: 50
<212> TYPE: DNA
<213> ORGANISM: Homo sapiens

<400> SEQUENCE: 40
aattgctcca gaactctatc ataaggccaa ggctgcaggt gatgatgagg          50

<210> SEQ ID NO 41
<211> LENGTH: 16
<212> TYPE: PRT
<213> ORGANISM: Homo sapiens

<400> SEQUENCE: 41

Ile Ala Pro Glu Leu Tyr His Lys Ala Lys Ala Ala Gly Asp Asp Glu
1               5                   10                  15

<210> SEQ ID NO 42
<211> LENGTH: 50
<212> TYPE: DNA
<213> ORGANISM: Homo sapiens

<400> SEQUENCE: 42
tgaggaagag agcgtggacc caaataaatt ataaatcaga agaagaattt          50

<210> SEQ ID NO 43
<211> LENGTH: 10
<212> TYPE: PRT
<213> ORGANISM: Homo sapiens

<400> SEQUENCE: 43
```

```
Glu Glu Glu Ser Val Asp Pro Asn Lys Leu
1               5                   10
```

<210> SEQ ID NO 44
<211> LENGTH: 50
<212> TYPE: DNA
<213> ORGANISM: Homo sapiens

<400> SEQUENCE: 44

```
gcagcgagcc gaaactgagc aagaagtagg atccatgcca aaagagcttc                50
```

<210> SEQ ID NO 45
<211> LENGTH: 8
<212> TYPE: PRT
<213> ORGANISM: Homo sapiens

<400> SEQUENCE: 45

```
Ser Glu Pro Lys Leu Ser Lys Lys
1               5
```

<210> SEQ ID NO 46
<211> LENGTH: 50
<212> TYPE: DNA
<213> ORGANISM: Homo sapiens

<400> SEQUENCE: 46

```
actgacatca ccttaaaggt ggcagaaatt ataaatcaga agaagaattt                50
```

<210> SEQ ID NO 47
<211> LENGTH: 16
<212> TYPE: PRT
<213> ORGANISM: Homo sapiens

<400> SEQUENCE: 47

```
Thr Asp Ile Thr Leu Lys Val Ala Glu Ile Ile Asn Gln Lys Lys Asn
1               5                   10                  15
```

<210> SEQ ID NO 48
<211> LENGTH: 50
<212> TYPE: DNA
<213> ORGANISM: Homo sapiens

<400> SEQUENCE: 48

```
tcttcacttt ggcctcaaag acaagaaact cgcaaaattc ttgatgatat                50
```

<210> SEQ ID NO 49
<211> LENGTH: 16
<212> TYPE: PRT
<213> ORGANISM: Homo sapiens

<400> SEQUENCE: 49

```
Leu His Phe Gly Leu Lys Asp Lys Lys Leu Ala Lys Phe Leu Met Ile
1               5                   10                  15
```

<210> SEQ ID NO 50
<211> LENGTH: 76
<212> TYPE: PRT
<213> ORGANISM: Homo sapiens

<400> SEQUENCE: 50

```
Met Ala Ala Val Gln Ala Ala Glu Val Lys Val Asp Gly Ser Glu Pro
1               5                   10                  15

Lys Leu Ser Lys Asn Glu Leu Lys Arg Arg Leu Lys Ala Glu Lys Lys
```

| | | | | 20 | | | | 25 | | | | 30 | | |

Val Ala Glu Lys Glu Ala Lys Gln Lys Glu Leu Ser Glu Lys Gln Leu
               35                     40                   45

Ser Gln Ala Thr Ala Ala Ala Thr Asn His Thr Thr Asp Asn Gly Val
 50                       55                      60

Gly Pro Glu Glu Glu Ser Val Asp Pro Asn Gln Tyr
65                   70                     75

<210> SEQ ID NO 51
<211> LENGTH: 228
<212> TYPE: DNA
<213> ORGANISM: Homo sapiens

<400> SEQUENCE: 51

| | | | |
|---|---|---|---|
| atggcggccg tgcaggcggc cgaggtgaaa gtggatggca gcgagccgaa actgagcaag | | | 60 |
| aatgagctga agagacgcct gaaagctgag aagaaagtag cagagaagga ggccaaacag | | | 120 |
| aaagagctca gtgagaaaca gctaagccaa gccactgctg ctgccaccaa ccacaccact | | | 180 |
| gataatggtg tgggtcctga ggaagagagc gtggacccaa atcaatac | | | 228 |

<210> SEQ ID NO 52
<211> LENGTH: 194
<212> TYPE: PRT
<213> ORGANISM: Homo sapiens

<400> SEQUENCE: 52

Met Ala Ala Val Gln Ala Ala Glu Val Lys Val Asp Gly Ser Glu Pro
1                5                   10               15

Lys Leu Ser Lys Asn Glu Leu Lys Arg Arg Leu Lys Ala Glu Lys Lys
               20                     25                     30

Val Ala Glu Lys Glu Ala Lys Gln Lys Glu Leu Ser Glu Lys Gln Leu
               35                     40                   45

Ser Gln Ala Thr Ala Ala Ala Thr Asn His Thr Thr Asp Asn Gly Val
 50                      55                      60

Gly Pro Glu Glu Glu Ser Val Asp Pro Asn Gln Tyr Tyr Lys Ile Arg
65                   70                     75                   80

Ser Gln Ala Ile His Gln Leu Lys Val Asn Gly Glu Asp Pro Tyr Pro
               85                     90                     95

His Lys Phe His Val Asp Ile Ser Leu Thr Asp Phe Ile Gln Lys Tyr
              100                  105                 110

Ser His Leu Gln Pro Gly Asp His Leu Thr Asp Ile Thr Leu Lys Val
            115                  120                125

Ala Gly Arg Ile His Ala Lys Arg Ala Ser Gly Gly Lys Leu Ile Phe
 130                   135                  140

Tyr Asp Leu Arg Gly Glu Gly Val Lys Leu Gln Val Met Ala Asn Ser
145                  150                   155               160

Arg Asn Tyr Lys Ser Glu Glu Glu Phe Ile His Ile Asn Asn Lys Leu
              165                  170                 175

Arg Arg Gly Asp Ile Ile Gly Val Gln Gly Asn Pro Gly Lys Thr Lys
            180                  185                 190

Lys Gly

<210> SEQ ID NO 53
<211> LENGTH: 582
<212> TYPE: DNA
<213> ORGANISM: Homo sapiens -continued

<400> SEQUENCE: 53

```
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atcaatacta caaaatccgc     240
agtcaagcaa ttcatcagct gaaggtcaat ggggaagacc catacccaca caagttccat     300
gtagacatct cactcactga cttcatccaa aaatatagtc acctgcagcc tggggatcac     360
ctgactgaca tcaccttaaa ggtggcaggt aggatccatg ccaaaagagc ttctggggga     420
aagctcatct tctatgatct tcgaggagag ggggtgaagt tgcaagtcat ggccaattcc     480
agaaattata atcagaaga agaatttatt catattaata caaaactgcg tcggggagac     540
ataattggag ttcaggggaa tcctggtaaa accaagaagg gt                        582
```

<210> SEQ ID NO 54
<211> LENGTH: 65
<212> TYPE: PRT
<213> ORGANISM: Homo sapiens

<400> SEQUENCE: 54

```
Met Ala Ala Val Gln Ala Ala Glu Val Lys Val Asp Gly Ser Glu Pro
1               5                   10                  15
Lys Leu Ser Lys Asn Glu Leu Lys Arg Arg Leu Lys Ala Glu Lys Lys
            20                  25                  30
Val Ala Glu Lys Glu Ala Lys Gln Lys Glu Leu Ser Glu Lys Gln Leu
        35                  40                  45
Ser Gln Ala Thr Ala Ala Ala Thr Asn His Thr Thr Asp Asn Gly Val
    50                  55                  60
Gly
65
```

<210> SEQ ID NO 55
<211> LENGTH: 195
<212> TYPE: DNA
<213> ORGANISM: Homo sapiens

<400> SEQUENCE: 55

```
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggt                                                      195
```

<210> SEQ ID NO 56
<211> LENGTH: 214
<212> TYPE: PRT
<213> ORGANISM: Homo sapiens

<400> SEQUENCE: 56

```
Met Ala Ala Val Gln Ala Ala Glu Val Lys Val Asp Gly Ser Glu Pro
1               5                   10                  15
Lys Leu Ser Lys Asn Glu Leu Lys Arg Arg Leu Lys Ala Glu Lys Lys
            20                  25                  30
Val Ala Glu Lys Glu Ala Lys Gln Lys Glu Leu Ser Glu Lys Gln Leu
        35                  40                  45
Ser Gln Ala Thr Ala Ala Ala Thr Asn His Thr Thr Asp Asn Gly Val
```

```
Gly Pro Glu Glu Glu Ser Val Asp Pro Asn Gln Tyr Tyr Lys Ile Arg
 65                  70                  75                  80

Ser Gln Ala Ile His Gln Leu Lys Val Asn Gly Glu Asp Pro Tyr Pro
                 85                  90                  95

His Lys Phe His Val Asp Ile Ser Leu Thr Asp Phe Ile Gln Lys Tyr
            100                 105                 110

Ser His Leu Gln Pro Gly Asp His Leu Thr Asp Ile Thr Leu Lys Val
        115                 120                 125

Ala Gly Arg Ile His Ala Lys Arg Ala Ser Gly Gly Lys Leu Ile Phe
    130                 135                 140

Tyr Asp Leu Arg Gly Glu Gly Val Lys Leu Gln Val Met Ala Asn Ser
145                 150                 155                 160

Arg Asn Tyr Lys Ser Glu Glu Phe Ile His Ile Asn Asn Lys Leu
                165                 170                 175

Arg Arg Gly Asp Ile Ile Gly Val Gln Gly Asn Pro Gly Lys Thr Lys
            180                 185                 190

Lys Gly Glu Leu Ser Ile Ile Pro Tyr Glu Ile Thr Leu Leu Ser Pro
        195                 200                 205

Cys Leu His Met Leu Pro
    210
```

```
<210> SEQ ID NO 57
<211> LENGTH: 642
<212> TYPE: DNA
<213> ORGANISM: Homo sapiens

<400> SEQUENCE: 57
atggcggccg tgcaggcggc cgaggtgaaa gtggatggca gcgagccgaa actgagcaag      60
aatgagctga agagacgcct gaaagctgag aagaaagtag cagagaagga ggccaaacag     120
aaagagctca gtgagaaaca gctaagccaa gccactgctg ctgccaccaa ccacaccact     180
gataatggtg tgggtcctga ggaagagagc gtggacccaa atcaatacta caaaatccgc     240
agtcaagcaa ttcatcagct gaaggtcaat ggggaagacc catacccaca caagttccat     300
gtagacatct cactcactga cttcatccaa aaatatagtc acctgcagcc tggggatcac     360
ctgactgaca tcaccttaaa ggtggcaggt aggatccatg ccaaaagagc ttctggggga     420
aagctcatct ctatgatctc gaggagaggg gggtgaagt tgcaagtcat ggccaattcc     480
agaaattata atcagaaga agaatttatt catattaata caaaactgcg tcggggagac     540
ataattggag ttcaggggaa tcctggtaaa accaagaagg gtgagctgag catcattccg     600
tatgagatca cactgctgtc tccctgtttg catatgttac ct                        642

<210> SEQ ID NO 58
<211> LENGTH: 390
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 58

Met His His His His His His Gly Lys Pro Ile Pro Asn Pro Leu Leu
  1               5                  10                  15

Gly Leu Asp Ser Thr Gly Ser Ala Ala Val Gln Ala Ala Glu Val Lys
             20                  25                  30
```

Val Asp Gly Ser Glu Pro Lys Leu Ser Lys Asn Glu Leu Lys Arg Arg
         35                  40                  45

Leu Lys Ala Glu Lys Val Ala Glu Lys Ala Lys Gln Lys Glu
 50                  55                  60

Leu Ser Glu Lys Gln Leu Ser Gln Ala Thr Ala Ala Thr Asn His
 65                  70                  75                  80

Thr Thr Asp Asn Gly Val Gly Pro Glu Glu Ser Val Asp Pro Asn
                 85                  90                  95

Gln Tyr Tyr Lys Ile Arg Ser Gln Ala Ile His Gln Leu Lys Val Asn
            100                 105                 110

Gly Glu Asp Pro Tyr Pro His Lys Phe His Val Asp Ile Ser Leu Thr
            115                 120                 125

Asp Phe Ile Gln Lys Tyr Ser His Leu Gln Pro Gly Asp His Leu Thr
130                 135                 140

Asp Ile Thr Leu Lys Val Ala Gly Arg Ile His Ala Lys Arg Ala Ser
145                 150                 155                 160

Gly Gly Lys Leu Ile Phe Tyr Asp Leu Arg Gly Glu Gly Val Lys Leu
                165                 170                 175

Gln Val Met Ala Asn Ser Arg Asn Tyr Lys Ser Glu Glu Phe Ile
            180                 185                 190

His Ile Asn Asn Lys Leu Arg Arg Gly Asp Ile Ile Gly Val Gln Gly
            195                 200                 205

Asn Pro Gly Lys Thr Lys Lys Gly Glu Leu Ser Ile Ile Pro Tyr Glu
            210                 215                 220

Ile Thr Leu Leu Ser Pro Cys Leu His Met Leu Pro His Leu His Phe
225                 230                 235                 240

Gly Leu Lys Asp Lys Glu Thr Arg Tyr Arg Gln Arg Tyr Leu Asp Leu
                245                 250                 255

Ile Leu Asn Asp Phe Val Arg Gln Lys Phe Ile Ile Arg Ser Lys Ile
            260                 265                 270

Ile Thr Tyr Ile Arg Ser Phe Leu Asp Glu Leu Gly Phe Leu Glu Ile
            275                 280                 285

Glu Thr Pro Met Met Asn Ile Ile Pro Gly Gly Ala Val Ala Lys Pro
290                 295                 300

Phe Ile Thr Tyr His Asn Glu Leu Asp Met Asn Leu Tyr Met Arg Ile
305                 310                 315                 320

Ala Pro Glu Leu Tyr His Lys Met Leu Val Val Gly Gly Ile Asp Arg
                325                 330                 335

Val Tyr Glu Ile Gly Arg Gln Phe Arg Asn Glu Gly Ile Asp Leu Thr
            340                 345                 350

His Asn Pro Glu Phe Thr Thr Cys Glu Phe Tyr Met Ala Tyr Ala Asp
            355                 360                 365

Tyr His Asp Leu Met Glu Ile Thr Glu Lys Met Val Ser Gly Met Val
370                 375                 380

Lys His Ile Thr Leu Glu
385                 390

<210> SEQ ID NO 59
<211> LENGTH: 390
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 59

```
Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
            20                  25                  30

Lys Lys Val Ala Glu Lys Glu Ala Lys Gln Lys Glu Leu Ser Glu Lys
        35                  40                  45

Gln Leu Ser Gln Ala Thr Ala Ala Thr Asn His Thr Thr Asp Asn
50                  55                  60

Gly Val Gly Pro Glu Glu Ser Val Asp Pro Asn Gln Tyr Tyr Lys
65              70                  75                  80

Ile Arg Ser Gln Ala Ile His Gln Leu Lys Val Asn Gly Glu Asp Pro
                85                  90                  95

Tyr Pro His Lys Phe His Val Asp Ile Ser Leu Thr Asp Phe Ile Gln
            100                 105                 110

Lys Tyr Ser His Leu Gln Pro Gly Asp His Leu Thr Asp Ile Thr Leu
        115                 120                 125

Lys Val Ala Gly Arg Ile His Ala Lys Arg Ala Ser Gly Gly Lys Leu
130                 135                 140

Ile Phe Tyr Asp Leu Arg Gly Glu Gly Val Lys Leu Gln Val Met Ala
145                 150                 155                 160

Asn Ser Arg Asn Tyr Lys Ser Glu Glu Glu Phe Ile His Ile Asn Asn
                165                 170                 175

Lys Leu Arg Arg Gly Asp Ile Ile Gly Val Gln Gly Asn Pro Gly Lys
            180                 185                 190

Thr Lys Lys Gly Glu Leu Ser Ile Ile Pro Tyr Glu Ile Thr Leu Leu
        195                 200                 205

Ser Pro Cys Leu His Met Leu Pro His Leu His Phe Gly Leu Lys Asp
210                 215                 220

Lys Glu Thr Arg Tyr Arg Gln Arg Tyr Leu Asp Leu Ile Leu Asn Asp
225                 230                 235                 240

Phe Val Arg Gln Lys Phe Ile Ile Arg Ser Lys Ile Ile Thr Tyr Ile
                245                 250                 255

Arg Ser Phe Leu Asp Glu Leu Gly Phe Leu Glu Ile Glu Thr Pro Met
            260                 265                 270

Met Asn Ile Ile Pro Gly Gly Ala Val Ala Lys Pro Phe Ile Thr Tyr
        275                 280                 285

His Asn Glu Leu Asp Met Asn Leu Tyr Met Arg Ile Ala Pro Glu Leu
290                 295                 300

Tyr His Lys Met Leu Val Val Gly Gly Ile Asp Arg Val Tyr Glu Ile
305                 310                 315                 320

Gly Arg Gln Phe Arg Asn Glu Gly Ile Asp Leu Thr His Asn Pro Glu
                325                 330                 335

Phe Thr Thr Cys Glu Phe Tyr Met Ala Tyr Ala Asp Tyr His Asp Leu
            340                 345                 350

Met Glu Ile Thr Glu Lys Met Val Ser Gly Met Val Lys His Ile Thr
        355                 360                 365

Leu Glu Gly Lys Pro Ile Pro Asn Pro Leu Leu Gly Leu Asp Ser Thr
370                 375                 380

His His His His His
385             390

<210> SEQ ID NO 60
<211> LENGTH: 100
```

<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 60

Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
            20                  25                  30

Val Asp Gly Ser Glu Pro Lys Leu Ser Lys Asn Glu Leu Lys Arg Arg
        35                  40                  45

Leu Lys Ala Glu Lys Lys Val Ala Glu Lys Glu Ala Lys Gln Lys Glu
    50                  55                  60

Leu Ser Glu Lys Gln Leu Ser Gln Ala Thr Ala Ala Thr Asn His
65                  70                  75                  80

Thr Thr Asp Asn Gly Val Gly Pro Glu Glu Ser Val Asp Pro Asn
                85                  90                  95

Gln Tyr Leu Glu
            100

<210> SEQ ID NO 61
<211> LENGTH: 100
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 61

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
            20                  25                  30

Lys Lys Val Ala Glu Lys Glu Ala Lys Gln Lys Glu Leu Ser Glu Lys
        35                  40                  45

Gln Leu Ser Gln Ala Thr Ala Ala Thr Asn His Thr Thr Asp Asn
    50                  55                  60

Gly Val Gly Pro Glu Glu Ser Val Asp Pro Asn Gln Tyr Leu Glu
65                  70                  75                  80

Gly Lys Pro Ile Pro Asn Pro Leu Leu Gly Leu Asp Ser Thr His His
                85                  90                  95

His His His His
            100

<210> SEQ ID NO 62
<211> LENGTH: 218
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 62

Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
            20                  25                  30

Val Asp Gly Ser Glu Pro Lys Leu Ser Lys Asn Glu Leu Lys Arg Arg

```
            35                  40                  45
Leu Lys Ala Glu Lys Val Ala Glu Lys Ala Lys Gln Lys Glu
 50                  55                  60

Leu Ser Glu Lys Gln Leu Ser Gln Ala Thr Ala Ala Thr Asn His
 65                  70                  75                  80

Thr Thr Asp Asn Gly Val Gly Pro Glu Glu Ser Val Asp Pro Asn
                 85                  90                  95

Gln Tyr Tyr Lys Ile Arg Ser Gln Ala Ile His Gln Leu Lys Val Asn
                100                 105                 110

Gly Glu Asp Pro Tyr Pro His Lys Phe His Val Asp Ile Ser Leu Thr
                115                 120                 125

Asp Phe Ile Gln Lys Tyr Ser His Leu Gln Pro Gly Asp His Leu Thr
                130                 135                 140

Asp Ile Thr Leu Lys Val Ala Gly Arg Ile His Ala Lys Arg Ala Ser
145                 150                 155                 160

Gly Gly Lys Leu Ile Phe Tyr Asp Leu Arg Gly Glu Gly Val Lys Leu
                165                 170                 175

Gln Val Met Ala Asn Ser Arg Asn Tyr Lys Ser Glu Glu Glu Phe Ile
                180                 185                 190

His Ile Asn Asn Lys Leu Arg Arg Gly Asp Ile Ile Gly Val Gln Gly
                195                 200                 205

Asn Pro Gly Lys Thr Lys Lys Gly Leu Glu
                210                 215

<210> SEQ ID NO 63
<211> LENGTH: 218
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 63

Met Gly Ser Ala Ala Val Gln Ala Ala Glu Val Lys Val Asp Gly Ser
 1               5                  10                  15

Glu Pro Lys Leu Ser Lys Asn Glu Leu Lys Arg Arg Leu Lys Ala Glu
                 20                  25                  30

Lys Lys Val Ala Glu Lys Glu Ala Lys Gln Lys Glu Leu Ser Glu Lys
             35                  40                  45

Gln Leu Ser Gln Ala Thr Ala Ala Thr Asn His Thr Thr Asp Asn
 50                  55                  60

Gly Val Gly Pro Glu Glu Ser Val Asp Pro Asn Gln Tyr Tyr Lys
 65                  70                  75                  80

Ile Arg Ser Gln Ala Ile His Gln Leu Lys Val Asn Gly Glu Asp Pro
                 85                  90                  95

Tyr Pro His Lys Phe His Val Asp Ile Ser Leu Thr Asp Phe Ile Gln
                100                 105                 110

Lys Tyr Ser His Leu Gln Pro Gly Asp His Leu Thr Asp Ile Thr Leu
                115                 120                 125

Lys Val Ala Gly Arg Ile His Ala Lys Arg Ala Ser Gly Gly Lys Leu
            130                 135                 140

Ile Phe Tyr Asp Leu Arg Gly Glu Gly Val Lys Leu Gln Val Met Ala
145                 150                 155                 160

Asn Ser Arg Asn Tyr Lys Ser Glu Glu Glu Phe Ile His Ile Asn Asn
                165                 170                 175
```

Lys Leu Arg Arg Gly Asp Ile Ile Gly Val Gln Gly Asn Pro Gly Lys
                180                 185                 190

Thr Lys Lys Gly Leu Glu Gly Lys Pro Ile Pro Asn Pro Leu Leu Gly
            195                 200                 205

Leu Asp Ser Thr His His His His His His
    210                 215

<210> SEQ ID NO 64
<211> LENGTH: 89
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 64

Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
                20                  25                  30

Val Asp Gly Ser Glu Pro Lys Leu Ser Lys Asn Glu Leu Lys Arg Arg
            35                  40                  45

Leu Lys Ala Glu Lys Lys Val Ala Glu Lys Glu Ala Lys Gln Lys Glu
    50                  55                  60

Leu Ser Glu Lys Gln Leu Ser Gln Ala Thr Ala Ala Thr Asn His
65                  70                  75                  80

Thr Thr Asp Asn Gly Val Gly Leu Glu
                85

<210> SEQ ID NO 65
<211> LENGTH: 89
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 65

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
                20                  25                  30

Lys Lys Val Ala Glu Lys Glu Ala Lys Gln Lys Glu Leu Ser Glu Lys
            35                  40                  45

Gln Leu Ser Gln Ala Thr Ala Ala Thr Asn His Thr Thr Asp Asn
    50                  55                  60

Gly Val Gly Leu Glu Gly Lys Pro Ile Pro Asn Pro Leu Leu Gly Leu
65                  70                  75                  80

Asp Ser Thr His His His His His His
                85

<210> SEQ ID NO 66
<211> LENGTH: 238
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 66

Met His His His His His His Gly Lys Pro Ile Pro Asn Pro Leu Leu

```
                1               5              10              15
            Gly Leu Asp Ser Thr Gly Ser Ala Ala Val Gln Ala Ala Glu Val Lys
                            20                  25                  30

Val Asp Gly Ser Glu Pro Lys Leu Ser Lys Asn Glu Leu Lys Arg Arg
                            35                  40                  45

Leu Lys Ala Glu Lys Lys Val Ala Glu Lys Glu Ala Lys Gln Lys Glu
                    50                  55                  60

Leu Ser Glu Lys Gln Leu Ser Gln Ala Thr Ala Ala Thr Asn His
            65                  70                  75                  80

Thr Thr Asp Asn Gly Val Gly Pro Glu Glu Ser Val Asp Pro Asn
                                85                  90                  95

Gln Tyr Tyr Lys Ile Arg Ser Gln Ala Ile His Gln Leu Lys Val Asn
                            100                 105                 110

Gly Glu Asp Pro Tyr Pro His Lys Phe His Val Asp Ile Ser Leu Thr
                            115                 120                 125

Asp Phe Ile Gln Lys Tyr Ser His Leu Gln Pro Gly Asp His Leu Thr
                        130                 135                 140

Asp Ile Thr Leu Lys Val Ala Gly Arg Ile His Ala Lys Arg Ala Ser
            145                 150                 155                 160

Gly Gly Lys Leu Ile Phe Tyr Asp Leu Arg Gly Glu Gly Val Lys Leu
                            165                 170                 175

Gln Val Met Ala Asn Ser Arg Asn Tyr Lys Ser Glu Glu Phe Ile
                        180                 185                 190

His Ile Asn Asn Lys Leu Arg Arg Gly Asp Ile Ile Gly Val Gln Gly
                        195                 200                 205

Asn Pro Gly Lys Thr Lys Lys Gly Glu Leu Ser Ile Ile Pro Tyr Glu
                        210                 215                 220

Ile Thr Leu Leu Ser Pro Cys Leu His Met Leu Pro Leu Glu
            225                 230                 235

<210> SEQ ID NO 67
            <211> LENGTH: 238
            <212> TYPE: PRT
            <213> ORGANISM: Artificial Sequence
            <220> FEATURE:
            <223> OTHER INFORMATION: Lysyl tRNA Synthetase polypeptide with
                  C-terminal 6xHis affinity tag

<400> SEQUENCE: 67

Met Gly Ser Ala Ala Val Gln Ala Ala Glu Val Lys Val Asp Gly Ser
            1               5                   10                  15

Glu Pro Lys Leu Ser Lys Asn Glu Leu Lys Arg Arg Leu Lys Ala Glu
                            20                  25                  30

Lys Lys Val Ala Glu Lys Glu Ala Lys Gln Lys Glu Leu Ser Glu Lys
                        35                  40                  45

Gln Leu Ser Gln Ala Thr Ala Ala Thr Asn His Thr Thr Asp Asn
                    50                  55                  60

Gly Val Gly Pro Glu Glu Ser Val Asp Pro Asn Gln Tyr Tyr Lys
            65                  70                  75                  80

Ile Arg Ser Gln Ala Ile His Gln Leu Lys Val Asn Gly Glu Asp Pro
                            85                  90                  95

Tyr Pro His Lys Phe His Val Asp Ile Ser Leu Thr Asp Phe Ile Gln
                        100                 105                 110

Lys Tyr Ser His Leu Gln Pro Gly Asp His Leu Thr Asp Ile Thr Leu
                        115                 120                 125
```

```
Lys Val Ala Gly Arg Ile His Ala Lys Arg Ala Ser Gly Gly Lys Leu
130                 135                 140

Ile Phe Tyr Asp Leu Arg Gly Glu Gly Val Lys Leu Gln Val Met Ala
145                 150                 155                 160

Asn Ser Arg Asn Tyr Lys Ser Glu Glu Glu Phe Ile His Ile Asn Asn
                165                 170                 175

Lys Leu Arg Arg Gly Asp Ile Ile Gly Val Gln Gly Asn Pro Gly Lys
                180                 185                 190

Thr Lys Lys Gly Glu Leu Ser Ile Ile Pro Tyr Glu Ile Thr Leu Leu
                195                 200                 205

Ser Pro Cys Leu His Met Leu Pro Leu Glu Gly Lys Pro Ile Pro Asn
210                 215                 220

Pro Leu Leu Gly Leu Asp Ser Thr His His His His His His
225                 230                 235
```

<210> SEQ ID NO 68
<211> LENGTH: 120
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 68

```
Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
                20                  25                  30

Val Asp Gly Ser Glu Pro Lys Leu Ser Lys Asn Glu Leu Lys Arg Arg
            35                  40                  45

Leu Lys Ala Glu Lys Lys Val Ala Glu Lys Glu Ala Lys Gln Lys Glu
50                  55                  60

Leu Ser Glu Lys Gln Leu Ser Gln Ala Thr Ala Ala Thr Asn His
65                  70                  75                  80

Thr Thr Asp Asn Gly Val Gly Pro Glu Glu Glu Ser Val Asp Pro Asn
                85                  90                  95

Val Gly Ser Met Pro Lys Glu Leu Leu Gly Glu Ser Ser Ser Ser Met
                100                 105                 110

Ile Phe Glu Glu Arg Gly Leu Glu
            115                 120
```

<210> SEQ ID NO 69
<211> LENGTH: 120
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 69

```
Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
                20                  25                  30

Lys Lys Val Ala Glu Lys Glu Ala Lys Gln Lys Glu Leu Ser Glu Lys
            35                  40                  45

Gln Leu Ser Gln Ala Thr Ala Ala Thr Asn His Thr Thr Asp Asn
50                  55                  60
```

```
Gly Val Gly Pro Glu Glu Ser Val Asp Pro Asn Val Gly Ser Met
 65                  70                  75                  80

Pro Lys Glu Leu Leu Gly Glu Ser Ser Ser Met Ile Phe Glu Glu
                 85                  90                  95

Arg Gly Leu Glu Gly Lys Pro Ile Pro Asn Pro Leu Leu Gly Leu Asp
            100                 105                 110

Ser Thr His His His His His
            115                 120
```

<210> SEQ ID NO 70
<211> LENGTH: 430
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 70

```
Met His His His His His His Gly Lys Pro Ile Pro Asn Pro Leu Leu
  1               5                  10                  15

Gly Leu Asp Ser Thr Gly Ser Ala Ala Val Gln Ala Ala Glu Val Lys
             20                  25                  30

Val Asp Gly Ser Glu Pro Lys Leu Ser Lys Asn Glu Leu Lys Arg Arg
         35                  40                  45

Leu Lys Ala Glu Lys Lys Val Ala Glu Lys Glu Ala Lys Gln Lys Glu
 50                  55                  60

Leu Ser Glu Lys Gln Leu Ser Gln Ala Thr Ala Ala Thr Asn His
 65                  70                  75                  80

Thr Thr Asp Asn Gly Val Gly Pro Glu Glu Ser Val Asp Pro Asn
                 85                  90                  95

Ile Glu Thr Pro Met Met Asn Ile Ile Pro Gly Gly Ala Val Ala Lys
            100                 105                 110

Pro Phe Ile Thr Tyr His Asn Glu Leu Asp Met Asn Leu Tyr Met Arg
            115                 120                 125

Ile Ala Pro Glu Leu Tyr His Lys Met Leu Val Val Gly Gly Ile Asp
130                 135                 140

Arg Val Tyr Glu Ile Gly Arg Gln Phe Arg Asn Glu Gly Ile Asp Leu
145                 150                 155                 160

Thr His Asn Pro Glu Phe Thr Thr Cys Glu Phe Tyr Met Ala Tyr Ala
                165                 170                 175

Asp Tyr His Asp Leu Met Glu Ile Thr Glu Lys Met Val Ser Gly Met
            180                 185                 190

Val Lys His Ile Thr Gly Ser Tyr Lys Val Thr Tyr His Pro Asp Gly
            195                 200                 205

Pro Glu Gly Gln Ala Tyr Asp Val Asp Phe Thr Pro Pro Phe Arg Arg
            210                 215                 220

Ile Asn Met Val Glu Glu Leu Glu Lys Ala Leu Gly Met Lys Leu Pro
225                 230                 235                 240

Glu Thr Asn Leu Phe Glu Thr Glu Glu Thr Arg Lys Ile Leu Asp Asp
                245                 250                 255

Ile Cys Val Ala Lys Ala Val Glu Cys Pro Pro Pro Arg Thr Thr Ala
            260                 265                 270

Arg Leu Leu Asp Lys Leu Val Gly Glu Phe Leu Glu Val Thr Cys Ile
            275                 280                 285

Asn Pro Thr Phe Ile Cys Asp His Pro Gln Ile Met Ser Pro Leu Ala
            290                 295                 300
```

```
Lys Trp His Arg Ser Lys Glu Gly Leu Thr Glu Arg Phe Glu Leu Phe
305                 310                 315                 320

Val Met Lys Lys Glu Ile Cys Asn Ala Tyr Thr Glu Leu Asn Asp Pro
                325                 330                 335

Met Arg Gln Arg Gln Leu Phe Glu Glu Gln Ala Lys Ala Lys Ala Ala
            340                 345                 350

Gly Asp Asp Glu Ala Met Phe Ile Asp Glu Asn Phe Cys Thr Ala Leu
                355                 360                 365

Glu Tyr Gly Leu Pro Pro Thr Ala Gly Trp Gly Met Gly Ile Asp Arg
    370                 375                 380

Val Ala Met Phe Leu Thr Asp Ser Asn Asn Ile Lys Glu Val Leu Leu
385                 390                 395                 400

Phe Pro Ala Met Lys Pro Glu Asp Lys Lys Glu Asn Val Ala Thr Thr
                405                 410                 415

Asp Thr Leu Glu Ser Thr Thr Val Gly Thr Ser Val Leu Glu
                420                 425                 430

<210> SEQ ID NO 71
<211> LENGTH: 430
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 71

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
                20                  25                  30

Lys Lys Val Ala Glu Lys Glu Ala Lys Gln Lys Glu Leu Ser Glu Lys
            35                  40                  45

Gln Leu Ser Gln Ala Thr Ala Ala Thr Asn His Thr Thr Asp Asn
    50                  55                  60

Gly Val Gly Pro Glu Glu Glu Ser Val Asp Pro Asn Ile Glu Thr Pro
65                  70                  75                  80

Met Met Asn Ile Ile Pro Gly Gly Ala Val Ala Lys Pro Phe Ile Thr
                85                  90                  95

Tyr His Asn Glu Leu Asp Met Asn Leu Tyr Met Arg Ile Ala Pro Glu
                100                 105                 110

Leu Tyr His Lys Met Leu Val Val Gly Gly Ile Asp Arg Val Tyr Glu
            115                 120                 125

Ile Gly Arg Gln Phe Arg Asn Glu Gly Ile Asp Leu Thr His Asn Pro
    130                 135                 140

Glu Phe Thr Thr Cys Glu Phe Tyr Met Ala Tyr Ala Asp Tyr His Asp
145                 150                 155                 160

Leu Met Glu Ile Thr Glu Lys Met Val Ser Gly Met Val Lys His Ile
                165                 170                 175

Thr Gly Ser Tyr Lys Val Thr Tyr His Pro Asp Gly Pro Glu Gly Gln
            180                 185                 190

Ala Tyr Asp Val Asp Phe Thr Pro Pro Phe Arg Arg Ile Asn Met Val
    195                 200                 205

Glu Glu Leu Glu Lys Ala Leu Gly Met Lys Leu Pro Glu Thr Asn Leu
210                 215                 220

Phe Glu Thr Glu Glu Thr Arg Lys Ile Leu Asp Asp Ile Cys Val Ala
```

```
                   225                 230                 235                 240
    Lys Ala Val Glu Cys Pro Pro Arg Thr Thr Ala Arg Leu Leu Asp
                        245                 250                 255

Lys Leu Val Gly Glu Phe Leu Glu Val Thr Cys Ile Asn Pro Thr Phe
                        260                 265                 270

Ile Cys Asp His Pro Gln Ile Met Ser Pro Leu Ala Lys Trp His Arg
                        275                 280                 285

Ser Lys Glu Gly Leu Thr Glu Arg Phe Glu Leu Phe Val Met Lys Lys
                        290                 295                 300

Glu Ile Cys Asn Ala Tyr Thr Glu Leu Asn Asp Pro Met Arg Gln Arg
    305                 310                 315                 320

Gln Leu Phe Glu Glu Gln Ala Lys Ala Lys Ala Gly Asp Asp Glu
                        325                 330                 335

Ala Met Phe Ile Asp Glu Asn Phe Cys Thr Ala Leu Glu Tyr Gly Leu
                        340                 345                 350

Pro Pro Thr Ala Gly Trp Gly Met Gly Ile Asp Arg Val Ala Met Phe
                        355                 360                 365

Leu Thr Asp Ser Asn Asn Ile Lys Glu Val Leu Leu Phe Pro Ala Met
                        370                 375                 380

Lys Pro Glu Asp Lys Lys Glu Asn Val Ala Thr Thr Asp Thr Leu Glu
    385                 390                 395                 400

Ser Thr Thr Val Gly Thr Ser Val Leu Glu Gly Lys Pro Ile Pro Asn
                        405                 410                 415

Pro Leu Leu Gly Leu Asp Ser Thr His His His His His His
                        420                 425                 430

<210> SEQ ID NO 72
<211> LENGTH: 409
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 72

Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
                20                  25                  30

Val Asp Gly Ser Glu Pro Lys Leu Ser Lys Asn Glu Leu Lys Arg Arg
            35                  40                  45

Leu Lys Ala Glu Lys Lys Val Ala Lys Glu Ala Lys Gln Lys Glu
    50                  55                  60

Leu Ser Glu Lys Gln Leu Ser Gln Ala Thr Ala Ala Thr Asn His
65                  70                  75                  80

Thr Thr Asp Asn Gly Val Gly Pro Glu Glu Ser Val Asp Pro Asn
                85                  90                  95

Gln Tyr Tyr Lys Ile Arg Ser Gln Ala Ile His Gln Leu Lys Val Asn
                100                 105                 110

Gly Glu Asp Pro Tyr Pro His Lys Phe His Val Asp Ile Ser Leu Thr
                115                 120                 125

Asp Phe Ile Gln Lys Tyr Ser His Leu Gln Pro Gly Asp His Leu Thr
    130                 135                 140

Asp Ile Thr Leu Lys Val Ala Gly Arg Ile His Ala Lys Arg Ala Ser
145                 150                 155                 160
```

Gly Gly Lys Leu Ile Phe Tyr Asp Leu Arg Gly Glu Gly Val Lys Leu
            165                 170                 175

Gln Val Met Ala Asn Ser Arg Asn Tyr Lys Ser Glu Glu Glu Phe Ile
        180                 185                 190

His Ile Asn Asn Lys Leu Arg Arg Gly Asp Ile Ile Gly Val Gln Gly
        195                 200                 205

Asn Pro Gly Lys Thr Lys Lys Gly Glu Leu Ser Ile Ile Pro Tyr Glu
    210                 215                 220

Ile Thr Leu Leu Ser Pro Cys Leu His Met Leu Pro His Leu His Phe
225                 230                 235                 240

Gly Leu Lys Asp Lys Glu Thr Arg Tyr Arg Gln Arg Tyr Leu Asp Leu
                245                 250                 255

Ile Leu Asn Asp Phe Val Arg Gln Lys Phe Ile Ile Arg Ser Lys Ile
            260                 265                 270

Ile Thr Tyr Ile Arg Ser Phe Leu Asp Glu Leu Gly Phe Leu Glu Ile
        275                 280                 285

Glu Thr Pro Met Met Asn Ile Ile Pro Gly Gly Ala Val Ala Lys Pro
    290                 295                 300

Phe Ile Thr Tyr His Asn Glu Leu Asp Met Asn Leu Tyr Met Arg Ile
305                 310                 315                 320

Ala Pro Glu Leu Tyr His Lys Ala Lys Ala Ala Gly Asp Asp Glu Ala
                325                 330                 335

Met Phe Ile Asp Glu Asn Phe Cys Thr Ala Leu Glu Tyr Gly Leu Pro
            340                 345                 350

Pro Thr Ala Gly Trp Gly Met Gly Ile Asp Arg Val Ala Met Phe Leu
        355                 360                 365

Thr Asp Ser Asn Asn Ile Lys Glu Val Leu Leu Phe Pro Ala Met Lys
    370                 375                 380

Pro Glu Asp Lys Lys Glu Asn Val Ala Thr Thr Asp Thr Leu Glu Ser
385                 390                 395                 400

Thr Thr Val Gly Thr Ser Val Leu Glu
                405

<210> SEQ ID NO 73
<211> LENGTH: 409
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 73

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
            20                  25                  30

Lys Lys Val Ala Glu Lys Glu Ala Lys Gln Lys Glu Leu Ser Glu Lys
        35                  40                  45

Gln Leu Ser Gln Ala Thr Ala Ala Ala Thr Asn His Thr Thr Asp Asn
    50                  55                  60

Gly Val Gly Pro Glu Glu Glu Ser Val Asp Pro Asn Gln Tyr Tyr Lys
65                  70                  75                  80

Ile Arg Ser Gln Ala Ile His Gln Leu Lys Val Asn Gly Glu Asp Pro
                85                  90                  95

Tyr Pro His Lys Phe His Val Asp Ile Ser Leu Thr Asp Phe Ile Gln
            100                 105                 110

```
Lys Tyr Ser His Leu Gln Pro Gly Asp His Leu Thr Asp Ile Thr Leu
            115                 120                 125
Lys Val Ala Gly Arg Ile His Ala Lys Arg Ala Ser Gly Gly Lys Leu
        130                 135                 140
Ile Phe Tyr Asp Leu Arg Gly Glu Gly Val Lys Leu Gln Val Met Ala
145                 150                 155                 160
Asn Ser Arg Asn Tyr Lys Ser Glu Glu Phe Ile His Ile Asn Asn
                165                 170                 175
Lys Leu Arg Arg Gly Asp Ile Ile Gly Val Gln Gly Asn Pro Gly Lys
            180                 185                 190
Thr Lys Lys Gly Glu Leu Ser Ile Ile Pro Tyr Glu Ile Thr Leu Leu
        195                 200                 205
Ser Pro Cys Leu His Met Leu Pro His Leu His Phe Gly Leu Lys Asp
        210                 215                 220
Lys Glu Thr Arg Tyr Arg Gln Arg Tyr Leu Asp Leu Ile Leu Asn Asp
225                 230                 235                 240
Phe Val Arg Gln Lys Phe Ile Ile Arg Ser Lys Ile Ile Thr Tyr Ile
                245                 250                 255
Arg Ser Phe Leu Asp Glu Leu Gly Phe Leu Glu Ile Glu Thr Pro Met
            260                 265                 270
Met Asn Ile Ile Pro Gly Gly Ala Val Ala Lys Pro Phe Ile Thr Tyr
        275                 280                 285
His Asn Glu Leu Asp Met Asn Leu Tyr Met Arg Ile Ala Pro Glu Leu
        290                 295                 300
Tyr His Lys Ala Lys Ala Gly Asp Asp Glu Ala Met Phe Ile Asp
305                 310                 315                 320
Glu Asn Phe Cys Thr Ala Leu Glu Tyr Gly Leu Pro Pro Thr Ala Gly
                325                 330                 335
Trp Gly Met Gly Ile Asp Arg Val Ala Met Phe Leu Thr Asp Ser Asn
            340                 345                 350
Asn Ile Lys Glu Val Leu Leu Phe Pro Ala Met Lys Pro Glu Asp Lys
        355                 360                 365
Lys Glu Asn Val Ala Thr Thr Asp Thr Leu Glu Ser Thr Thr Val Gly
        370                 375                 380
Thr Ser Val Leu Glu Gly Lys Pro Ile Pro Asn Pro Leu Leu Gly Leu
385                 390                 395                 400
Asp Ser Thr His His His His His His
                405

<210> SEQ ID NO 74
<211> LENGTH: 100
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 74

Met His His His His His His Gly Lys Pro Ile Pro Asn Pro Leu Leu
1               5                   10                  15
Gly Leu Asp Ser Thr Gly Ser Ala Ala Val Gln Ala Ala Glu Val Lys
            20                  25                  30
Val Asp Gly Ser Glu Pro Lys Leu Ser Lys Asn Glu Leu Lys Arg Arg
        35                  40                  45
Leu Lys Ala Glu Lys Lys Val Ala Glu Lys Glu Ala Lys Gln Lys Glu
```

```
Leu Ser Glu Lys Gln Leu Ser Gln Ala Thr Ala Ala Thr Asn His
65                  70                  75                  80

Thr Thr Asp Asn Gly Val Gly Pro Glu Glu Ser Val Asp Pro Asn
                85                  90                  95

Lys Leu Leu Glu
            100

<210> SEQ ID NO 75
<211> LENGTH: 100
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 75

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
            20                  25                  30

Lys Lys Val Ala Glu Lys Glu Ala Lys Gln Lys Glu Leu Ser Glu Lys
        35                  40                  45

Gln Leu Ser Gln Ala Thr Ala Ala Ala Thr Asn His Thr Thr Asp Asn
    50                  55                  60

Gly Val Gly Pro Glu Glu Ser Val Asp Pro Asn Lys Leu Leu Glu
65                  70                  75                  80

Gly Lys Pro Ile Pro Asn Pro Leu Leu Gly Leu Asp Ser Thr His His
                85                  90                  95

His His His His
            100

<210> SEQ ID NO 76
<211> LENGTH: 45
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 76

Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
            20                  25                  30

Val Asp Gly Ser Glu Pro Lys Leu Ser Lys Lys Leu Glu
        35                  40                  45

<210> SEQ ID NO 77
<211> LENGTH: 45
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 77

Met Gly Ser Ala Ala Val Gln Ala Ala Glu Val Lys Val Asp Gly Ser
1               5                   10                  15

Glu Pro Lys Leu Ser Lys Lys Leu Glu Gly Lys Pro Ile Pro Asn Pro
            20                  25                  30
```

Leu Leu Gly Leu Asp Ser Thr His His His His His
        35                  40                  45

<210> SEQ ID NO 78
<211> LENGTH: 173
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 78

Met His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
            20                  25                  30

Val Asp Gly Ser Glu Pro Lys Leu Ser Lys Asn Glu Leu Lys Arg Arg
        35                  40                  45

Leu Lys Ala Glu Lys Lys Val Ala Glu Lys Glu Ala Lys Gln Lys Glu
    50                  55                  60

Leu Ser Glu Lys Gln Leu Ser Gln Ala Thr Ala Ala Thr Asn His
65                  70                  75                  80

Thr Thr Asp Asn Gly Val Gly Pro Glu Glu Glu Ser Val Asp Pro Asn
                85                  90                  95

Gln Tyr Tyr Lys Ile Arg Ser Gln Ala Ile His Gln Leu Lys Val Asn
            100                 105                 110

Gly Glu Asp Pro Tyr Pro His Lys Phe His Val Asp Ile Ser Leu Thr
        115                 120                 125

Asp Phe Ile Gln Lys Tyr Ser His Leu Gln Pro Gly Asp His Leu Thr
    130                 135                 140

Asp Ile Thr Leu Lys Val Ala Glu Ile Ile Asn Gln Lys Lys Asn Leu
145                 150                 155                 160

Phe Ile Leu Ile Thr Asn Cys Val Gly Glu Thr Leu Glu
                165                 170

<210> SEQ ID NO 79
<211> LENGTH: 173
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 79

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
            20                  25                  30

Lys Lys Val Ala Glu Lys Glu Ala Lys Gln Lys Glu Leu Ser Glu Lys
        35                  40                  45

Gln Leu Ser Gln Ala Thr Ala Ala Ala Thr Asn His Thr Thr Asp Asn
    50                  55                  60

Gly Val Gly Pro Glu Glu Glu Ser Val Asp Pro Asn Gln Tyr Tyr Lys
65                  70                  75                  80

Ile Arg Ser Gln Ala Ile His Gln Leu Lys Val Asn Gly Glu Asp Pro
                85                  90                  95

Tyr Pro His Lys Phe His Val Asp Ile Ser Leu Thr Asp Phe Ile Gln
            100                 105                 110

```
Lys Tyr Ser His Leu Gln Pro Gly Asp His Leu Thr Asp Ile Thr Leu
        115                 120                 125

Lys Val Ala Glu Ile Ile Asn Gln Lys Lys Asn Leu Phe Ile Leu Ile
    130                 135                 140

Thr Asn Cys Val Gly Glu Thr Leu Glu Gly Lys Pro Ile Pro Asn Pro
145                 150                 155                 160

Leu Leu Gly Leu Asp Ser Thr His His His His His
                165                 170

<210> SEQ ID NO 80
<211> LENGTH: 283
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 80

Met His His His His His His Gly Lys Pro Ile Pro Asn Pro Leu Leu
1               5                   10                  15

Gly Leu Asp Ser Thr Gly Ser Ala Ala Val Gln Ala Ala Glu Val Lys
            20                  25                  30

Val Asp Gly Ser Glu Pro Lys Leu Ser Lys Asn Glu Leu Lys Arg Arg
        35                  40                  45

Leu Lys Ala Glu Lys Lys Val Ala Lys Glu Ala Lys Gln Lys Glu
    50                  55                  60

Leu Ser Glu Lys Gln Leu Ser Gln Ala Thr Ala Ala Thr Asn His
65                  70                  75                  80

Thr Thr Asp Asn Gly Val Gly Pro Glu Glu Ser Val Asp Pro Asn
                85                  90                  95

Gln Tyr Tyr Lys Ile Arg Ser Gln Ala Ile His Gln Leu Lys Val Asn
            100                 105                 110

Gly Glu Asp Pro Tyr Pro His Lys Phe His Val Asp Ile Ser Leu Thr
        115                 120                 125

Asp Phe Ile Gln Lys Tyr Ser His Leu Gln Pro Gly Asp His Leu Thr
    130                 135                 140

Asp Ile Thr Leu Lys Val Ala Gly Arg Ile His Ala Lys Arg Ala Ser
145                 150                 155                 160

Gly Gly Lys Leu Ile Phe Tyr Asp Leu Arg Gly Glu Gly Val Lys Leu
                165                 170                 175

Gln Val Met Ala Asn Ser Arg Asn Tyr Lys Ser Glu Glu Phe Ile
            180                 185                 190

His Ile Asn Asn Lys Leu Arg Arg Gly Asp Ile Ile Gly Val Gln Gly
        195                 200                 205

Asn Pro Gly Lys Thr Lys Lys Gly Glu Leu Ser Ile Ile Pro Tyr Glu
    210                 215                 220

Ile Thr Leu Leu Ser Pro Cys Leu His Met Leu Pro His Leu His Phe
225                 230                 235                 240

Gly Leu Lys Asp Lys Lys Leu Ala Lys Phe Leu Met Ile Ser Val Trp
                245                 250                 255

Gln Lys Leu Leu Asn Ala Leu His Leu Gly Pro Gln Pro Gly Ser Leu
            260                 265                 270

Thr Ser Leu Leu Gly Ser Ser Trp Lys Leu Glu
        275                 280
```

<210> SEQ ID NO 81
<211> LENGTH: 283
<212> TYPE: PRT
<213> ORGANISM: Artificial Sequence
<220> FEATURE:
<223> OTHER INFORMATION: Lysyl tRNA Synthetase polypeptide with
     C-terminal 6xHis affinity tag

<400> SEQUENCE: 81

Met Gly Ser Ala Ala Val Gln Ala Ala Glu Val Lys Val Asp Gly Ser
1               5                   10                  15

Glu Pro Lys Leu Ser Lys Asn Glu Leu Lys Arg Arg Leu Lys Ala Glu
            20                  25                  30

Lys Lys Val Ala Glu Lys Glu Ala Lys Gln Lys Glu Leu Ser Glu Lys
        35                  40                  45

Gln Leu Ser Gln Ala Thr Ala Ala Ala Thr Asn His Thr Thr Asp Asn
    50                  55                  60

Gly Val Gly Pro Glu Glu Ser Val Asp Pro Asn Gln Tyr Tyr Lys
65                  70                  75                  80

Ile Arg Ser Gln Ala Ile His Gln Leu Lys Val Asn Gly Glu Asp Pro
                85                  90                  95

Tyr Pro His Lys Phe His Val Asp Ile Ser Leu Thr Asp Phe Ile Gln
            100                 105                 110

Lys Tyr Ser His Leu Gln Pro Gly Asp His Leu Thr Asp Ile Thr Leu
        115                 120                 125

Lys Val Ala Gly Arg Ile His Ala Lys Arg Ala Ser Gly Gly Lys Leu
    130                 135                 140

Ile Phe Tyr Asp Leu Arg Gly Glu Gly Val Lys Leu Gln Val Met Ala
145                 150                 155                 160

Asn Ser Arg Asn Tyr Lys Ser Glu Glu Glu Phe Ile His Ile Asn Asn
                165                 170                 175

Lys Leu Arg Arg Gly Asp Ile Ile Gly Val Gln Gly Asn Pro Gly Lys
            180                 185                 190

Thr Lys Lys Gly Glu Leu Ser Ile Ile Pro Tyr Glu Ile Thr Leu Leu
        195                 200                 205

Ser Pro Cys Leu His Met Leu Pro His Leu His Phe Gly Leu Lys Asp
    210                 215                 220

Lys Lys Leu Ala Lys Phe Leu Met Ile Ser Val Trp Gln Lys Leu Leu
225                 230                 235                 240

Asn Ala Leu His Leu Gly Pro Gln Pro Gly Ser Leu Thr Ser Leu Leu
                245                 250                 255

Gly Ser Ser Trp Lys Leu Glu Gly Lys Pro Ile Pro Asn Pro Leu Leu
            260                 265                 270

Gly Leu Asp Ser Thr His His His His His His
        275                 280

<210> SEQ ID NO 82
<211> LENGTH: 1107
<212> TYPE: DNA
<213> ORGANISM: Artificial Sequence
<220> FEATURE:
<223> OTHER INFORMATION: Codon optimized lysyl tRNA Synthetase
     polynucleotide

<400> SEQUENCE: 82
ggatccgcag cggtacaagc ggcggaagtg aaagtggatg gctctgaacc aaaactgtcg       60
aaaaacgaac tgaaacgtcg cctgaaagcc gagaaaaaag ttgctgagaa agaggccaaa      120

| | |
|---|---|
| caaaaagaac tgtccgagaa acagctgtca caggcaacag cagcagccac aaatcatacc | 180 |
| accgataacg gggttggacc tgaagaagaa agcgttgatc cgaaccaata ctataagatt | 240 |
| cgtagccagg ctattcatca gctgaaagtg aacggcgaag atccgtatcc tcacaaattc | 300 |
| catgtcgata ttagtctgac cgactttatc cagaaatatt cccacctgca accgggtgat | 360 |
| catctgactg acatcacact gaaagtggca ggccgtattc atgctaaacg tgcctcaggg | 420 |
| ggtaaactga tcttttatga cctgcgcggt gaaggtgtta aactgcaagt gatggccaat | 480 |
| tcccgtaact ataaaagtga ggaggagttc atccacatca caacaaaact gcgtcgtggc | 540 |
| gatatcattg tgtccaggg taatccgggc aaaacgaaaa aaggtgaact gagcatcatc | 600 |
| ccgtatgaaa tcactctgct gagtccgtgt ctgcatatgc tgcctcacct gcattttggg | 660 |
| ctgaaagaca agaaactcg ctatcgccag cgttatctgg acctgattct gaacgatttc | 720 |
| gtccgccaga aattcattat ccgctcgaaa atcatcacct atatccgttc ctttctggat | 780 |
| gaactgggct tcctggaaat tgaaaccct atgatgaaca tcattccggg tggtgctgtt | 840 |
| gctaaacctt ttatcacgta tcacaacgag ctggacatga acctgtatat gcgcattgcc | 900 |
| cctgagctgt atcataaaat gctggtcgtg gcggtattg atcgtgtgta tgagattgga | 960 |
| cgtcagttcc gtaacgaggg cattgatctg acccataatc cggagtttac cacctgtgag | 1020 |
| ttctatatgg cctatgccga ctatcatgac ctgatggaga ttaccgagaa aatggtgagc | 1080 |
| gggatggtga aacacatcac actcgag | 1107 |

<210> SEQ ID NO 83
<211> LENGTH: 237
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 83

| | |
|---|---|
| ggatccgcag cggtacaagc ggcggaagtg aaagtggatg ctctgaacc aaaactgtcg | 60 |
| aaaaacgaac tgaaacgtcg cctgaaagcc gagaaaaaag ttgctgagaa agaggccaaa | 120 |
| caaaaagaac tgtccgagaa acagctgtca caggcaacag cagcagccac aaatcatacc | 180 |
| accgataacg gggttggacc tgaagaagaa agcgttgatc cgaaccaata cctcgag | 237 |

<210> SEQ ID NO 84
<211> LENGTH: 591
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 84

| | |
|---|---|
| ggatccgcag cggtacaagc ggcggaagtg aaagtggatg ctctgaacc aaaactgtcg | 60 |
| aaaaacgaac tgaaacgtcg cctgaaagcc gagaaaaaag ttgctgagaa agaggccaaa | 120 |
| caaaaagaac tgtccgagaa acagctgtca caggcaacag cagcagccac aaatcatacc | 180 |
| accgataacg gggttggacc tgaagaagaa agcgttgatc cgaaccaata ctataagatt | 240 |
| cgtagccagg ctattcatca gctgaaagtg aacggcgaag atccgtatcc tcacaaattc | 300 |
| catgtcgata ttagtctgac cgactttatc cagaaatatt cccacctgca accgggtgat | 360 |
| catctgactg acatcacact gaaagtggca ggccgtattc atgctaaacg tgcctcaggg | 420 |
| ggtaaactga tcttttatga cctgcgcggt gaaggtgtta aactgcaagt gatggccaat | 480 |

```
tcccgtaact ataaaagtga ggaggagttc atccacatca acaacaaact gcgtcgtggc    540
gatatcattg gtgtccaggg taatccgggc aaaacgaaaa aaggtctcga g             591
```

<210> SEQ ID NO 85
<211> LENGTH: 204
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 85

```
ggatccgcag cggtacaagc ggcggaagtg aaagtggatg gctctgaacc aaaactgtcg    60
aaaaacgaac tgaaacgtcg cctgaaagcc gagaaaaaag ttgctgagaa agaggccaaa   120 caaaagaac tgtccgagaa acagctgtca caggcaacag cagcagccac aaatcatacc   180
accgataacg gggttggact cgag                                          204
```

<210> SEQ ID NO 86
<211> LENGTH: 651
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 86

```
ggatccgcag cggtacaagc ggcggaagtg aaagtggatg gctctgaacc aaaactgtcg    60
aaaaacgaac tgaaacgtcg cctgaaagcc gagaaaaaag ttgctgagaa agaggccaaa   120 caaaagaac tgtccgagaa acagctgtca caggcaacag cagcagccac aaatcatacc   180
accgataacg gggttggacc tgaagaagaa agcgttgatc cgaaccaata ctataagatt   240
cgtagccagg ctattcatca gctgaaagtg aacggcgaag atccgtatcc tcacaaattc   300
catgtcgata ttagtctgac cgactttatc cagaaatatt cccacctgca accgggtgat   360
catctgactg acatcacact gaaagtggca ggccgtattc atgctaaacg tgcctcaggg   420
ggtaaactga tcttttatga cctgcgcggt gaaggtgtta aactgcaagt gatggccaat   480
tcccgtaact ataaaagtga ggaggagttc atccacatca acaacaaact gcgtcgtggc   540
gatatcattg gtgtccaggg taatccgggc aaaacgaaaa aaggtgaact gagcatcatc   600
ccgtatgaaa tcactctgct gagtccgtgt ctgcatatgc tgcctctcga g            651
```

<210> SEQ ID NO 87
<211> LENGTH: 297
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 87

```
ggatccgcag cggtacaagc ggcggaagtg aaagtggatg gctctgaacc aaaactgtcg    60
aaaaacgaac tgaaacgtcg cctgaaagcc gagaaaaaag ttgctgagaa agaggccaaa   120 caaaagaac tgtccgagaa acagctgtca caggcaacag cagcagccac aaatcatacc   180
accgataacg gggttggacc tgaagaagaa agcgttgatc cgaacgtggg ctctatgccg   240
aaagaactgc tgggtgaaag ctcttctagc atgattttcg aggaacgtgg cctcgag      297
```

```
<210> SEQ ID NO 88
<211> LENGTH: 1227
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 88
ggatccgcag cggtacaagc ggcggaagtg aaagtggatg gctctgaacc aaaactgtcg      60
aaaaacgaac tgaaacgtcg cctgaaagcc gagaaaaaag ttgctgagaa agaggccaaa     120
caaaaagaac tgtccgagaa acagctgtca caggcaacag cagcagccac aaatcatacc     180
accgataacg gggttggacc tgaagaagaa agcgttgatc cgaacattga acaccgatg      240 atgaatatta tcccggggtgg tgctgtagcc aaaccgttta tcacatatca caacgaactg     300
gacatgaatc tgtatatgcg cattgctccg gaactgtatc ataaaatgct ggtcgtgggc     360
ggtattgatc gtgtgtatga aattggccgt caattccgta acgagggtat cgacctgacc     420
cataatccag aattcacaac ctgtgagttt tatatggcct atgccgacta tcatgacctg     480
atggagatca ccgagaaaat ggttagcggc atggtgaaac acattaccgg ctcctataaa     540
gtgacctatc accctgacgg tcctgaaggt caagcatatg acgtggactt acaccgcct      600 tttcgtcgta tcaacatggt tgaggaactg gaaaaagcac tgggtatgaa actgccggaa     660
accaacctgt tgaaaccgga gaaacccgt aaaatcctgg acgacatctg tgtggcaaaa     720
gccgttgagt gtcctccgcc tcgtacaact gctcgtctgc tggacaaaact ggtaggggaa     780 tttctggagg tcacctgtat taatccgacc ttcatctgtg atcatcctca gattatgagc     840
cctctggcga atggcatcg tagcaaagaa ggcctgactg aacgcttcga actgttcgtg      900
atgaaaaaag agatctgtaa cgcctatact gagctgaatg accctatgcg tcaacgccaa     960
ctgtttgagg agcaggcgaa agcgaaagca gctggggacg atgaggcaat gtttatcgat    1020
gagaacttct gtactgccct ggaatatggt ctgcctccta ctgctggttg gggtatgggg    1080
atcgaccgtg ttgccatgtt tctgaccgat ccaacaaca tcaaagaagt gctgctgttc     1140
cctgccatga accggagga taaaaaagaa acgtggcga ccaccgatac actggagtct      1200
accactgttg gcaccagcgt gctcgag                                        1227

<210> SEQ ID NO 89
<211> LENGTH: 1164
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 89
ggatccgcag cggtacaagc ggcggaagtg aaagtggatg gctctgaacc aaaactgtcg      60
aaaaacgaac tgaaacgtcg cctgaaagcc gagaaaaaag ttgctgagaa agaggccaaa     120
caaaaagaac tgtccgagaa acagctgtca caggcaacag cagcagccac aaatcatacc     180
accgataacg gggttggacc tgaagaagaa agcgttgatc cgaaccaata ctataagatt     240
cgtagccagg ctattcatca gctgaaagtg aacggcgaag atccgtatcc tcacaaattc     300
catgtcgata ttagtctgac cgactttatc cagaaatatt cccacctgca accgggtgat     360
catctgactg acatcacact gaaagtggca ggccgtattc atgctaaacg tgcctcaggg     420
ggtaaactga tctttttatga cctgcgcggt gaaggtgtta aactgcaagt gatggccaat     480
```

```
tcccgtaact ataaaagtga ggaggagttc atccacatca acaacaaact gcgtcgtggc      540
gatatcattg gtgtccaggg taatccgggc aaaacgaaaa aaggtgaact gagcatcatc      600
ccgtatgaaa tcactctgct gagtccgtgt ctgcatatgc tgcctcacct gcattttggg      660
ctgaaagaca agaaactcg ctatcgccag cgttatctgg acctgattct gaacgatttc       720
gtccgccaga aattcattat ccgctcgaaa atcatcacct atatccgttc ctttctggat      780
gaactgggct tcctggaaat tgaaacccct atgatgaaca tcattccggg tggtgctgtt      840
gctaaacctt ttatcacgta tcacaacgag ctggacatga acctgtatat gcgcattgcc      900
cctgagctgt atcataaagc caaagcagca ggtgatgatg aagctatgtt tatcgacgag      960
aacttctgta cagcactgga gtatggtctg ccaccaacag ctggatgggg aatgggtatt     1020
gatcgtgtcg ccatgtttct gactgatagc aacaacatca aagaggttct gctgttccca     1080
gcaatgaaac cggaggacaa aaaagaaaat gtggccacga ctgacacact ggaatcaacc     1140
acagttggca ccagcgttct cgag                                            1164
```

<210> SEQ ID NO 90
<211> LENGTH: 237
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 90

```
ggatccgcag cggtacaagc ggcggaagtg aaagtggatg gctctgaacc aaaactgtcg       60
aaaaacgaac tgaaacgtcg cctgaaagcc gagaaaaaag ttgctgagaa agaggccaaa      120
caaaaagaac tgtccgagaa acagctgtca caggcaacag cagcagccac aaatcatacc      180
accgataacg gggttggacc tgaagaagaa agcgttgatc cgaaccaaact gctcgag       237
```

<210> SEQ ID NO 91
<211> LENGTH: 72
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 91

```
ggatccgcag cggtacaagc ggcggaagtg aaagtggatg gctctgaacc aaaactgtcg       60
aaaaagctcg ag                                                          72
```

<210> SEQ ID NO 92
<211> LENGTH: 456
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 92

```
ggatccgcag cggtacaagc ggcggaagtg aaagtggatg gctctgaacc aaaactgtcg       60
aaaaacgaac tgaaacgtcg cctgaaagcc gagaaaaaag ttgctgagaa agaggccaaa      120
caaaaagaac tgtccgagaa acagctgtca caggcaacag cagcagccac aaatcatacc      180
accgataacg gggttggacc tgaagaagaa agcgttgatc cgaaccaata ctataagatt      240
cgtagccagg ctattcatca gctgaaagtg aacggcgaag atccgtatcc tcacaaattc      300
```

```
catgtcgata ttagtctgac cgactttatc cagaaatatt cccacctgca accgggtgat    360
catctgactg acatcacact gaaagtggca gagatcatta accagaaaaa aaacctgttc    420
atcctgatta ccaactgtgt gggcgaaact ctcgag                              456
```

<210> SEQ ID NO 93
<211> LENGTH: 786
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 93

```
ggatccgcag cggtacaagc ggcggaagtg aaagtggatg gctctgaacc aaaactgtcg     60
aaaaacgaac tgaaacgtcg cctgaaagcc gagaaaaaag ttgctgagaa agaggccaaa    120 caaaagaac tgtccgagaa acagctgtca caggcaacag cagcagccac aaatcatacc    180
accgataacg gggttggacc tgaagaagaa agcgttgatc cgaaccaata ctataagatt    240
cgtagccagg ctattcatca gctgaaagtg aacggcgaag atccgtatcc tcacaaattc    300
catgtcgata ttagtctgac cgactttatc cagaaatatt cccacctgca accgggtgat    360
catctgactg acatcacact gaaagtggca ggccgtattc atgctaaacg tgcctcaggg    420
ggtaaactga tctttatga cctgcgcggt gaaggtgtta aactgcaagt gatggccaat    480
tcccgtaact ataaaagtga ggaggagttc atccacatca caacaaact gcgtcgtggc    540 gatatcattg gtgtccaggg taatccgggc aaaacgaaaa aaggtgaact gagcatcatc    600
ccgtatgaaa tcactctgct gagtccgtgt ctgcatatgc tgcctcacct gcatttgggg    660
ctgaaagaca aaaaactggc caaatttctg atgatcagcg tgtggcagaa actgctgaat    720
gcactgcatc tgggtcctca acctggttca ctgacctcgc tgctgggttc ttcttggaaa    780
ctcgag                                                              786
```

<210> SEQ ID NO 94
<211> LENGTH: 541
<212> TYPE: PRT
<213> ORGANISM: Homo sapiens

<400> SEQUENCE: 94

```
Asn His Thr Thr Asp Asn Gly Val Gly Pro Glu Glu Ser Val Asp
1               5                  10                  15

Pro Asn Gln Tyr Tyr Lys Ile Arg Ser Gln Ala Ile His Gln Leu Lys
            20                  25                  30

Val Asn Gly Glu Asp Pro Tyr Pro His Lys Phe His Val Asp Ile Ser
        35                  40                  45

Leu Thr Asp Phe Ile Gln Lys Tyr Ser His Leu Gln Pro Gly Asp His
    50                  55                  60

Leu Thr Asp Ile Thr Leu Lys Val Ala Gly Arg Ile His Ala Lys Arg
65                  70                  75                  80

Ala Ser Gly Gly Lys Leu Ile Phe Tyr Asp Leu Arg Gly Glu Gly Val
                85                  90                  95

Lys Leu Gln Val Met Ala Asn Ser Arg Asn Tyr Lys Ser Glu Glu Glu
            100                 105                 110

Phe Ile His Ile Asn Asn Lys Leu Arg Arg Gly Asp Ile Ile Gly Val
        115                 120                 125

Gln Gly Asn Pro Gly Lys Thr Lys Lys Gly Glu Leu Ser Ile Ile Pro
    130                 135                 140
```

| | | | | | | | | | | | |
|---|---|---|---|---|---|---|---|---|---|---|---|
|Tyr|Glu|Ile|Thr|Leu|Leu|Ser|Pro|Cys|Leu|His|Met|Leu|Pro|His|Leu|
|145| | | | |150| | | | |155| | | | |160|

Tyr Glu Ile Thr Leu Leu Ser Pro Cys Leu His Met Leu Pro His Leu
145                 150                 155                 160

His Phe Gly Leu Lys Asp Lys Glu Thr Arg Tyr Arg Gln Arg Tyr Leu
            165                 170                 175

Asp Leu Ile Leu Asn Asp Phe Val Arg Gln Lys Phe Ile Ile Arg Ser
        180                 185                 190

Lys Ile Ile Thr Tyr Ile Arg Ser Phe Leu Asp Glu Leu Gly Phe Leu
    195                 200                 205

Glu Ile Glu Thr Pro Met Met Asn Ile Ile Pro Gly Gly Ala Val Ala
210                 215                 220

Lys Pro Phe Ile Thr Tyr His Asn Glu Leu Asp Met Asn Leu Tyr Met
225                 230                 235                 240

Arg Ile Ala Pro Glu Leu Tyr His Lys Met Leu Val Val Gly Gly Ile
            245                 250                 255

Asp Arg Val Tyr Glu Ile Gly Arg Gln Phe Arg Asn Glu Gly Ile Asp
        260                 265                 270

Leu Thr His Asn Pro Glu Phe Thr Thr Cys Glu Phe Tyr Met Ala Tyr
    275                 280                 285

Ala Asp Tyr His Asp Leu Met Glu Ile Thr Glu Lys Met Val Ser Gly
290                 295                 300

Met Val Lys His Ile Thr Gly Ser Tyr Lys Val Thr Tyr His Pro Asp
305                 310                 315                 320

Gly Pro Glu Gly Gln Ala Tyr Asp Val Asp Phe Thr Pro Pro Phe Arg
            325                 330                 335

Arg Ile Asn Met Val Glu Glu Leu Glu Lys Ala Leu Gly Met Lys Leu
        340                 345                 350

Pro Glu Thr Asn Leu Phe Glu Thr Glu Glu Thr Arg Lys Ile Leu Asp
    355                 360                 365

Asp Ile Cys Val Ala Lys Ala Val Glu Cys Pro Pro Pro Arg Thr Thr
370                 375                 380

Ala Arg Leu Leu Asp Lys Leu Val Gly Glu Phe Leu Glu Val Thr Cys
385                 390                 395                 400

Ile Asn Pro Thr Phe Ile Cys Asp His Pro Gln Ile Met Ser Pro Leu
            405                 410                 415

Ala Lys Trp His Arg Ser Lys Glu Gly Leu Thr Glu Arg Phe Glu Leu
        420                 425                 430

Phe Val Met Lys Lys Glu Ile Cys Asn Ala Tyr Thr Glu Leu Asn Asp
    435                 440                 445

Pro Met Arg Gln Arg Gln Leu Phe Glu Glu Gln Ala Lys Ala Lys Ala
450                 455                 460

Ala Gly Asp Asp Glu Ala Met Phe Ile Asp Glu Asn Phe Cys Thr Ala
465                 470                 475                 480

Leu Glu Tyr Gly Leu Pro Pro Thr Ala Gly Trp Gly Met Gly Ile Asp
            485                 490                 495

Arg Val Ala Met Phe Leu Thr Asp Ser Asn Asn Ile Lys Glu Val Leu
        500                 505                 510

Leu Phe Pro Ala Met Lys Pro Glu Asp Lys Lys Glu Asn Val Ala Thr
    515                 520                 525

Thr Asp Thr Leu Glu Ser Thr Thr Val Gly Thr Ser Val
530                 535                 540

<210> SEQ ID NO 95
<211> LENGTH: 1626

<212> TYPE: DNA
<213> ORGANISM: Homo sapiens

<400> SEQUENCE: 95

```
aaccacacca ctgataatgg tgtgggtcct gaggaagaga gcgtggaccc aaatcaatac    60
tacaaaatcc gcagtcaagc aattcatcag ctgaaggtca atggggaaga cccatacccca  120
cacaagttcc atgtagacat ctcactcact gacttcatcc aaaaatatag tcacctgcag  180
cctggggatc acctgactga catcacctta aggtggcag gtaggatcca tgccaaaaga   240
gcttctgggg gaaagctcat cttctatgat cttcgaggag aggggtgaa gttgcaagtc   300
atggccaatt ccagaaatta taaatcagaa gaagaattta ttcatattaa taacaaactg   360
cgtcggggag acataattgg agttcagggg aatcctggta aaaccaagaa gggtgagctg   420
agcatcattc cgtatgagat cacactgctg tctccctgtt tgcatatgtt acctcatctt   480
cactttggcc tcaaagacaa ggaaacaagg tatcgccaga gatacttgga cttgatcctg   540
aatgactttg tgaggcagaa atttatcatc cgctctaaga tcatcacata tataagaagt   600
ttcttagatg agctgggatt cctagagatt gaaactccca tgatgaacat catcccaggg   660
ggagccgtgg ccaagccttt catcacttat acaacgagc tggacatgaa cttatatatg    720
agaattgctc cagaactcta tcataagatg cttgtggttg gtggcatcga ccgggtttat   780
gaaattggac gccagttccg gaatgagggg attgatttga cgcacaatcc tgagttcacc   840
acctgtgagt tctacatggc ctatgcagac tatcacgatc tcatggaaat cacggagaag   900
atggtttcag ggatggtgaa gcatattaca ggcagttaca aggtcaccta ccacccagat   960
ggcccagagg gccaagccta cgatgttgac ttcacccccac ccttccggcg aatcaacatg  1020
gtagaagagc ttgagaaagc cctggggatg aagctgccag aaacgaacct ctttgaaact  1080
gaagaaactc gcaaaattct tgatgatatc tgtgtggcaa aagctgttga atgccctcca  1140
cctcggacca cagccaggct ccttgacaag cttgttgggg agttcctgga agtgacttgc  1200
atcaatccta cattcatctg tgatcaccca cagataatga gcccttttggc taaatggcac  1260
cgctctaaag agggtctgac tgagcgctttt gagctgtttg tcatgaagaa agagatatgc  1320
aatgcgtata ctgagctgaa tgatcccatg cggcagcggc agcttttttga agaacaggcc  1380
aaggccaagg ctgcaggtga tgatgaggcc atgttcatag atgaaaactt ctgtactgcc  1440
ctggaatatg ggctgccccc cacagctggc tggggcatgg gcattgatcg agtcgccatg  1500
tttctcacgg actccaacaa catcaaggaa gtacttctgt ttcctgccat gaaacccgaa  1560
gacaagaagg agaatgtagc aaccactgat acactggaaa gcacaacagt tggcacttct  1620
gtctag                                                             1626
```

<210> SEQ ID NO 96
<211> LENGTH: 16
<212> TYPE: PRT
<213> ORGANISM: Mus musculus

<400> SEQUENCE: 96

Gly Val Gly Ala Glu Glu Glu Thr Leu Asp Pro Asn Gln Tyr Tyr Lys
1               5                   10                  15

<210> SEQ ID NO 97
<211> LENGTH: 10
<212> TYPE: PRT
<213> ORGANISM: Mus musculus

<400> SEQUENCE: 97

```
Ile Arg Ser Gln Ala Val Gln Leu Lys
1               5                   10
```

<210> SEQ ID NO 98
<211> LENGTH: 10
<212> TYPE: PRT
<213> ORGANISM: Mus musculus

<400> SEQUENCE: 98

```
Val Thr Gly Glu Asp Pro Tyr Pro His Lys
1               5                   10
```

<210> SEQ ID NO 99
<211> LENGTH: 132
<212> TYPE: PRT
<213> ORGANISM: Mus musculus

<400> SEQUENCE: 99

```
Phe His Val Asp Ile Ser Leu Thr Gln Phe Ile Gln Glu Tyr Ser His
1               5                   10                  15

Leu Gln Pro Gly Asp His Leu Thr Asp Val Thr Leu Lys Val Ala Gly
                20                  25                  30

Arg Ile His Ala Lys Arg Ala Ser Gly Gly Lys Leu Ile Phe Tyr Asp
            35                  40                  45

Leu Arg Gly Glu Gly Val Lys Leu Gln Val Met Ala Asn Ser Arg Asn
50                  55                  60

Tyr Lys Ser Glu Glu Phe Val His Ile Asn Asn Lys Leu Arg Arg
65                  70                  75                  80

Gly Asp Ile Ile Gly Val Glu Gly Asn Pro Gly Lys Thr Lys Lys Gly
                85                  90                  95

Glu Leu Ser Ile Ile Pro Gln Glu Ile Thr Leu Leu Ser Pro Cys Leu
            100                 105                 110

His Met Leu Pro His Leu His Phe Gly Leu Lys Asp Lys Glu Thr Arg
        115                 120                 125

Tyr Arg Gln Arg
        130
```

<210> SEQ ID NO 100
<211> LENGTH: 11
<212> TYPE: PRT
<213> ORGANISM: Mus musculus

<400> SEQUENCE: 100

```
Tyr Leu Asp Leu Ile Leu Asn Asp Phe Val Arg
1               5                   10
```

<210> SEQ ID NO 101
<211> LENGTH: 166
<212> TYPE: PRT
<213> ORGANISM: Mus musculus

<400> SEQUENCE: 101

```
Gln Lys Phe Ile Val Arg Ser Lys Ile Ile Thr Tyr Ile Arg Ser Phe
1               5                   10                  15

Leu Asp Glu Leu Gly Phe Leu Glu Ile Glu Thr Pro Met Met Asn Ile
                20                  25                  30

Ile Pro Gly Gly Ala Val Ala Lys Pro Phe Ile Thr Tyr His Asn Glu
            35                  40                  45

Leu Asp Met Asn Leu Tyr Met Arg Ile Ala Pro Glu Leu Tyr His Lys
```

```
                50             55             60
Met Leu Val Val Gly Gly Ile Asp Arg Val Tyr Glu Ile Gly Arg Gln
 65                  70                  75                  80

Phe Arg Asn Glu Gly Ile Asp Leu Thr His Asn Pro Glu Phe Thr Thr
                 85                  90                  95

Cys Glu Phe Tyr Met Ala Tyr Ala Asp Tyr His Asp Leu Met Glu Ile
                100                 105                 110

Thr Glu Lys Met Leu Ser Gly Met Val Lys Ser Ile Thr Gly Ser Tyr
            115                 120                 125

Lys Ile Thr Tyr His Pro Asp Gly Pro Glu Gly Gln Ala Tyr Glu Val
        130                 135                 140

Asp Phe Thr Pro Pro Phe Arg Arg Ile Ser Met Val Glu Glu Leu Glu
145                 150                 155                 160

Lys Ala Leu Gly Val Lys
                165
```

<210> SEQ ID NO 102
<211> LENGTH: 13
<212> TYPE: PRT
<213> ORGANISM: Mus musculus

<400> SEQUENCE: 102

```
Leu Pro Glu Thr Ser Leu Phe Glu Thr Glu Thr Arg
 1               5                  10
```

<210> SEQ ID NO 103
<211> LENGTH: 26
<212> TYPE: PRT
<213> ORGANISM: Mus musculus

<400> SEQUENCE: 103

```
Lys Ile Leu Asp Asp Ile Cys Val Ala Lys Ala Val Glu Cys Pro Pro
 1               5                  10                  15

Pro Arg Thr Thr Ala Arg Leu Leu Asp Lys
            20                  25
```

<210> SEQ ID NO 104
<211> LENGTH: 28
<212> TYPE: PRT
<213> ORGANISM: Mus musculus

<400> SEQUENCE: 104

```
Leu Val Gly Glu Phe Leu Glu Val Thr Cys Ile Ser Pro Thr Phe Ile
 1               5                  10                  15

Cys Asp His Pro Gln Ile Met Ser Pro Leu Ala Lys
            20                  25
```

<210> SEQ ID NO 105
<211> LENGTH: 19
<212> TYPE: PRT
<213> ORGANISM: Mus musculus

<400> SEQUENCE: 105

```
Trp His Arg Ser Lys Glu Gly Leu Thr Glu Arg Phe Glu Leu Phe Val
 1               5                  10                  15

Met Lys Lys
```

<210> SEQ ID NO 106
<211> LENGTH: 14
<212> TYPE: PRT

<213> ORGANISM: Mus musculus

<400> SEQUENCE: 106

Glu Ile Cys Asn Ala Tyr Thr Glu Leu Asn Asp Pro Val Arg
1               5                   10

<210> SEQ ID NO 107
<211> LENGTH: 46
<212> TYPE: PRT
<213> ORGANISM: Mus musculus

<400> SEQUENCE: 107

Gln Arg Gln Leu Phe Glu Gln Ala Lys Ala Lys Ala Ala Gly Asp
1               5                   10                  15

Asp Glu Ala Met Phe Ile Asp Glu Asn Phe Cys Thr Ala Leu Glu Tyr
                20                  25                  30

Gly Leu Pro Pro Thr Ala Gly Trp Gly Met Gly Ile Asp Arg
            35                  40                  45

<210> SEQ ID NO 108
<211> LENGTH: 12
<212> TYPE: PRT
<213> ORGANISM: Mus musculus

<400> SEQUENCE: 108

Leu Thr Met Phe Leu Thr Asp Ser Asn Asn Ile Lys
1               5                   10

<210> SEQ ID NO 109
<211> LENGTH: 13
<212> TYPE: PRT
<213> ORGANISM: Mus musculus

<400> SEQUENCE: 109

Glu Val Leu Leu Phe Pro Ala Met Lys Pro Glu Asp Lys
1               5                   10

<210> SEQ ID NO 110
<211> LENGTH: 19
<212> TYPE: PRT
<213> ORGANISM: Mus musculus

<400> SEQUENCE: 110

Lys Glu Thr Ala Ala Thr Thr Glu Thr Pro Glu Ser Thr Glu Ala Ser
1               5                   10                  15

Pro Ser Val

<210> SEQ ID NO 111
<211> LENGTH: 535
<212> TYPE: PRT
<213> ORGANISM: Mus musculus

<400> SEQUENCE: 111

Gly Val Gly Ala Glu Glu Glu Thr Leu Asp Pro Asn Gln Tyr Tyr Lys
1               5                   10                  15

Ile Arg Ser Gln Ala Val Gln Gln Leu Lys Val Thr Gly Glu Asp Pro
                20                  25                  30

Tyr Pro His Lys Phe His Val Asp Ile Ser Leu Thr Gln Phe Ile Gln
            35                  40                  45

Glu Tyr Ser His Leu Gln Pro Gly Asp His Leu Thr Asp Val Thr Leu
        50                  55                  60

```
Lys Val Ala Gly Arg Ile His Ala Lys Arg Ala Ser Gly Gly Lys Leu
 65                  70                  75                  80

Ile Phe Tyr Asp Leu Arg Gly Glu Gly Val Lys Leu Gln Val Met Ala
                 85                  90                  95

Asn Ser Arg Asn Tyr Lys Ser Glu Glu Glu Phe Val His Ile Asn Asn
                100                 105                 110

Lys Leu Arg Arg Gly Asp Ile Ile Gly Val Glu Gly Asn Pro Gly Lys
                115                 120                 125

Thr Lys Lys Gly Glu Leu Ser Ile Ile Pro Gln Glu Ile Thr Leu Leu
130                 135                 140

Ser Pro Cys Leu His Met Leu Pro His Leu His Phe Gly Leu Lys Asp
145                 150                 155                 160

Lys Glu Thr Arg Tyr Arg Gln Arg Tyr Leu Asp Leu Ile Leu Asn Asp
                165                 170                 175

Phe Val Arg Gln Lys Phe Ile Val Arg Ser Lys Ile Ile Thr Tyr Ile
                180                 185                 190

Arg Ser Phe Leu Asp Glu Leu Gly Phe Leu Glu Ile Glu Thr Pro Met
                195                 200                 205

Met Asn Ile Ile Pro Gly Gly Ala Val Ala Lys Pro Phe Ile Thr Tyr
210                 215                 220

His Asn Glu Leu Asp Met Asn Leu Tyr Met Arg Ile Ala Pro Glu Leu
225                 230                 235                 240

Tyr His Lys Met Leu Val Val Gly Gly Ile Asp Arg Val Tyr Glu Ile
                245                 250                 255

Gly Arg Gln Phe Arg Asn Glu Gly Ile Asp Leu Thr His Asn Pro Glu
                260                 265                 270

Phe Thr Thr Cys Glu Phe Tyr Met Ala Tyr Ala Asp Tyr His Asp Leu
                275                 280                 285

Met Glu Ile Thr Glu Lys Met Leu Ser Gly Met Val Lys Ser Ile Thr
                290                 295                 300

Gly Ser Tyr Lys Ile Thr Tyr His Pro Asp Gly Pro Glu Gly Gln Ala
305                 310                 315                 320

Tyr Glu Val Asp Phe Thr Pro Pro Phe Arg Arg Ile Ser Met Val Glu
                325                 330                 335

Glu Leu Glu Lys Ala Leu Gly Val Lys Leu Pro Glu Thr Ser Leu Phe
                340                 345                 350

Glu Thr Glu Glu Thr Arg Lys Ile Leu Asp Asp Ile Cys Val Ala Lys
                355                 360                 365

Ala Val Glu Cys Pro Pro Pro Arg Thr Thr Ala Arg Leu Leu Asp Lys
                370                 375                 380

Leu Val Gly Glu Phe Leu Glu Val Thr Cys Ile Ser Pro Thr Phe Ile
385                 390                 395                 400

Cys Asp His Pro Gln Ile Met Ser Pro Leu Ala Lys Trp His Arg Ser
                405                 410                 415

Lys Glu Gly Leu Thr Glu Arg Phe Glu Leu Phe Val Met Lys Lys Glu
                420                 425                 430

Ile Cys Asn Ala Tyr Thr Glu Leu Asn Asp Pro Val Arg Gln Arg Gln
                435                 440                 445

Leu Phe Glu Glu Gln Ala Lys Ala Lys Ala Ala Gly Asp Asp Glu Ala
                450                 455                 460

Met Phe Ile Asp Glu Asn Phe Cys Thr Ala Leu Glu Tyr Gly Leu Pro
465                 470                 475                 480

Pro Thr Ala Gly Trp Gly Met Gly Ile Asp Arg Leu Thr Met Phe Leu
```

```
                  485                 490                 495
Thr Asp Ser Asn Asn Ile Lys Glu Val Leu Leu Phe Pro Ala Met Lys
                500                 505                 510

Pro Glu Asp Lys Lys Glu Thr Ala Ala Thr Thr Glu Thr Pro Glu Ser
                515                 520                 525

Thr Glu Ala Ser Pro Ser Val
                530                 535

<210> SEQ ID NO 112
<211> LENGTH: 441
<212> TYPE: PRT
<213> ORGANISM: Homo sapiens

<400> SEQUENCE: 112

Met Ala Asn Ser Arg Asn Tyr Lys Ser Glu Glu Phe Ile His Ile
1               5                   10                  15

Asn Asn Lys Leu Arg Arg Gly Asp Ile Ile Gly Val Gln Gly Asn Pro
                20                  25                  30

Gly Lys Thr Lys Lys Gly Glu Leu Ser Ile Ile Pro Tyr Glu Ile Thr
            35                  40                  45

Leu Leu Ser Pro Cys Leu His Met Leu Pro His Leu His Phe Gly Leu
        50                  55                  60

Lys Asp Lys Glu Thr Arg Tyr Arg Gln Arg Tyr Leu Asp Leu Ile Leu
65                  70                  75                  80

Asn Asp Phe Val Arg Gln Lys Phe Ile Ile Arg Ser Lys Ile Ile Thr
                85                  90                  95

Tyr Ile Arg Ser Phe Leu Asp Glu Leu Gly Phe Leu Glu Ile Glu Thr
                100                 105                 110

Pro Met Met Asn Ile Ile Pro Gly Gly Ala Val Ala Lys Pro Phe Ile
                115                 120                 125

Thr Tyr His Asn Glu Leu Asp Met Asn Leu Tyr Met Arg Ile Ala Pro
            130                 135                 140

Glu Leu Tyr His Lys Met Leu Val Val Gly Gly Ile Asp Arg Val Tyr
145                 150                 155                 160

Glu Ile Gly Arg Gln Phe Arg Asn Glu Gly Ile Asp Leu Thr His Asn
                165                 170                 175

Pro Glu Phe Thr Thr Cys Glu Phe Tyr Met Ala Tyr Ala Asp Tyr His
                180                 185                 190

Asp Leu Met Glu Ile Thr Glu Lys Met Val Ser Gly Met Val Lys His
            195                 200                 205

Ile Thr Gly Ser Tyr Lys Val Thr Tyr His Pro Asp Gly Pro Glu Gly
        210                 215                 220

Gln Ala Tyr Asp Val Asp Phe Thr Pro Pro Phe Arg Arg Ile Asn Met
225                 230                 235                 240

Val Glu Glu Leu Glu Lys Ala Leu Gly Met Lys Leu Pro Glu Thr Asn
                245                 250                 255

Leu Phe Glu Thr Glu Glu Thr Arg Lys Ile Leu Asp Asp Ile Cys Val
                260                 265                 270

Ala Lys Ala Val Glu Cys Pro Pro Pro Arg Thr Thr Ala Arg Leu Leu
            275                 280                 285

Asp Lys Leu Val Gly Glu Phe Leu Glu Val Thr Cys Ile Asn Pro Thr
        290                 295                 300

Phe Ile Cys Asp His Pro Gln Ile Met Ser Pro Leu Ala Lys Trp His
305                 310                 315                 320
```

```
Arg Ser Lys Glu Gly Leu Thr Glu Arg Phe Glu Leu Phe Val Met Lys
            325                 330                 335

Lys Glu Ile Cys Asn Ala Tyr Thr Glu Leu Asn Asp Pro Met Arg Gln
        340                 345                 350

Arg Gln Leu Phe Glu Glu Gln Ala Lys Ala Lys Ala Ala Gly Asp Asp
            355                 360                 365

Glu Ala Met Phe Ile Asp Glu Asn Phe Cys Thr Ala Leu Glu Tyr Gly
        370                 375                 380

Leu Pro Pro Thr Ala Gly Trp Gly Met Gly Ile Asp Arg Val Ala Met
385                 390                 395                 400

Phe Leu Thr Asp Ser Asn Asn Ile Lys Glu Val Leu Leu Phe Pro Ala
                405                 410                 415

Met Lys Pro Glu Asp Lys Lys Glu Asn Val Ala Thr Thr Asp Thr Leu
            420                 425                 430

Glu Ser Thr Thr Val Gly Thr Ser Val
            435                 440

<210> SEQ ID NO 113
<211> LENGTH: 1326
<212> TYPE: DNA
<213> ORGANISM: Homo sapiens

<400> SEQUENCE: 113
atggccaatt ccagaaatta taaatcagaa gaagaattta ttcatattaa taacaaactg      60
cgtcggggag acataattgg agttcagggg aatcctggta aaaccaagaa gggtgagctg     120
agcatcattc cgtatgagat cacactgctg tctccctgtt tgcatatgtt acctcatctt     180
cactttggcc tcaaagacaa ggaaacaagg tatcgccaga gatacttgga cttgatcctg     240
aatgactttg tgaggcagaa atttatcatc cgctctaaga tcatcacata taagaagt      300 ttcttagatg agctgggatt cctagagatt gaaactccca tgatgaacat catcccaggg     360
ggagccgtgg ccaagccttt catcacttat cacaacgagc tggacatgaa cttatatatg     420
agaattgctc agaactcta tcataagatg cttgtggttg gtggcatcga ccgggtttat     480
gaaattggac gccagttccg gaatgagggg attgatttga cgcacaatcc tgagttcacc     540
acctgtgagt tctacatggc ctatgcagac tatcacgatc tcatggaaat cacggagaag     600
atggtttcag ggatggtgaa gcatattaca ggcagttaca aggtcaccta ccacccagat     660
ggcccagagg gccaagccta cgatgttgac ttcaccccac ccttccggcg aatcaacatg     720
gtagaagagc ttgagaaagc cctggggatg aagctgccag aaacgaacct ctttgaaact     780
gaagaaactc gcaaaattct tgatgatatc tgtgtggcaa aagctgttga atgccctcca     840
cctcggacca cagccaggct ccttgacaag cttgttgggg agttcctgga agtgacttgc     900
atcaatccta cattcatctg tgatcaccca cagataatga gccctttggc taaatggcac    960
cgctctaaag agggtctgac tgagcgcttt gagctgtttg tcatgaagaa agagatatgc   1020
aatgcgtata ctgagctgaa tgatcccatg cggcagcggc agcttttga agaacaggcc    1080 aaggccaagg ctgcaggtga tgatgaggcc atgttcatag atgaaaactt ctgtactgcc   1140
ctggaatatg gctgcccccc cacagctggc tggggcatgg gcattgatcg agtcgccatg   1200
tttctcacgg actccaacaa catcaaggaa gtacttctgt ttcctgccat gaaacccgaa   1260
gacaagaagg agaatgtagc aaccactgat acactggaaa gcacaacagt tggcacttct   1320
gtctag                                                               1326
```

<210> SEQ ID NO 114
<211> LENGTH: 449
<212> TYPE: PRT
<213> ORGANISM: Homo sapiens

<400> SEQUENCE: 114

| Met | Val | Trp | Val | Leu | Arg | Lys | Arg | Ala | Trp | Thr | Gln | Ile | Asn | Tyr | Lys |
|---|---|---|---|---|---|---|---|---|---|---|---|---|---|---|---|
| 1 | | | | 5 | | | | | 10 | | | | | 15 | |

| Ser | Glu | Glu | Glu | Phe | Ile | His | Ile | Asn | Asn | Lys | Leu | Arg | Arg | Gly | Asp |
|---|---|---|---|---|---|---|---|---|---|---|---|---|---|---|---|
| | | | 20 | | | | | 25 | | | | | 30 | | |

| Ile | Ile | Gly | Val | Gln | Gly | Asn | Pro | Gly | Lys | Thr | Lys | Lys | Gly | Glu | Leu |
|---|---|---|---|---|---|---|---|---|---|---|---|---|---|---|---|
| | | | 35 | | | | | 40 | | | | | 45 | | |

| Ser | Ile | Ile | Pro | Tyr | Glu | Ile | Thr | Leu | Leu | Ser | Pro | Cys | Leu | His | Met |
|---|---|---|---|---|---|---|---|---|---|---|---|---|---|---|---|
| | 50 | | | | | 55 | | | | | 60 | | | | |

| Leu | Pro | His | Leu | His | Phe | Gly | Leu | Lys | Asp | Lys | Glu | Thr | Arg | Tyr | Arg |
|---|---|---|---|---|---|---|---|---|---|---|---|---|---|---|---|
| 65 | | | | | 70 | | | | | 75 | | | | | 80 |

| Gln | Arg | Tyr | Leu | Asp | Leu | Ile | Leu | Asn | Asp | Phe | Val | Arg | Gln | Lys | Phe |
|---|---|---|---|---|---|---|---|---|---|---|---|---|---|---|---|
| | | | | 85 | | | | | 90 | | | | | 95 | |

| Ile | Ile | Arg | Ser | Lys | Ile | Ile | Thr | Tyr | Ile | Arg | Ser | Phe | Leu | Asp | Glu |
|---|---|---|---|---|---|---|---|---|---|---|---|---|---|---|---|
| | | | 100 | | | | | 105 | | | | | 110 | | |

| Leu | Gly | Phe | Leu | Glu | Ile | Glu | Thr | Pro | Met | Met | Asn | Ile | Ile | Pro | Gly |
|---|---|---|---|---|---|---|---|---|---|---|---|---|---|---|---|
| | | | 115 | | | | | 120 | | | | | 125 | | |

| Gly | Ala | Val | Ala | Lys | Pro | Phe | Ile | Thr | Tyr | His | Asn | Glu | Leu | Asp | Met |
|---|---|---|---|---|---|---|---|---|---|---|---|---|---|---|---|
| | 130 | | | | | 135 | | | | | 140 | | | | |

| Asn | Leu | Tyr | Met | Arg | Ile | Ala | Pro | Glu | Leu | Tyr | His | Lys | Met | Leu | Val |
|---|---|---|---|---|---|---|---|---|---|---|---|---|---|---|---|
| 145 | | | | | 150 | | | | | 155 | | | | | 160 |

| Val | Gly | Gly | Ile | Asp | Arg | Val | Tyr | Glu | Ile | Gly | Arg | Gln | Phe | Arg | Asn |
|---|---|---|---|---|---|---|---|---|---|---|---|---|---|---|---|
| | | | | 165 | | | | | 170 | | | | | 175 | |

| Glu | Gly | Ile | Asp | Leu | Thr | His | Asn | Pro | Glu | Phe | Thr | Thr | Cys | Glu | Phe |
|---|---|---|---|---|---|---|---|---|---|---|---|---|---|---|---|
| | | | 180 | | | | | 185 | | | | | 190 | | |

| Tyr | Met | Ala | Tyr | Ala | Asp | Tyr | His | Asp | Leu | Met | Glu | Ile | Thr | Glu | Lys |
|---|---|---|---|---|---|---|---|---|---|---|---|---|---|---|---|
| | | | 195 | | | | | 200 | | | | | 205 | | |

| Met | Val | Ser | Gly | Met | Val | Lys | His | Ile | Thr | Gly | Ser | Tyr | Lys | Val | Thr |
|---|---|---|---|---|---|---|---|---|---|---|---|---|---|---|---|
| | 210 | | | | | 215 | | | | | 220 | | | | |

| Tyr | His | Pro | Asp | Gly | Pro | Glu | Gly | Gln | Ala | Tyr | Asp | Val | Asp | Phe | Thr |
|---|---|---|---|---|---|---|---|---|---|---|---|---|---|---|---|
| 225 | | | | | 230 | | | | | 235 | | | | | 240 |

| Pro | Pro | Phe | Arg | Arg | Ile | Asn | Met | Val | Glu | Glu | Leu | Glu | Lys | Ala | Leu |
|---|---|---|---|---|---|---|---|---|---|---|---|---|---|---|---|
| | | | | 245 | | | | | 250 | | | | | 255 | |

| Gly | Met | Lys | Leu | Pro | Glu | Thr | Asn | Leu | Phe | Glu | Thr | Glu | Glu | Thr | Arg |
|---|---|---|---|---|---|---|---|---|---|---|---|---|---|---|---|
| | | | 260 | | | | | 265 | | | | | 270 | | |

| Lys | Ile | Leu | Asp | Asp | Ile | Cys | Val | Ala | Lys | Ala | Val | Glu | Cys | Pro | Pro |
|---|---|---|---|---|---|---|---|---|---|---|---|---|---|---|---|
| | | | 275 | | | | | 280 | | | | | 285 | | |

| Pro | Arg | Thr | Thr | Ala | Arg | Leu | Leu | Asp | Lys | Leu | Val | Gly | Glu | Phe | Leu |
|---|---|---|---|---|---|---|---|---|---|---|---|---|---|---|---|
| | 290 | | | | | 295 | | | | | 300 | | | | |

| Glu | Val | Thr | Cys | Ile | Asn | Pro | Thr | Phe | Ile | Cys | Asp | His | Pro | Gln | Ile |
|---|---|---|---|---|---|---|---|---|---|---|---|---|---|---|---|
| 305 | | | | | 310 | | | | | 315 | | | | | 320 |

| Met | Ser | Pro | Leu | Ala | Lys | Trp | His | Arg | Ser | Lys | Glu | Gly | Leu | Thr | Glu |
|---|---|---|---|---|---|---|---|---|---|---|---|---|---|---|---|
| | | | | 325 | | | | | 330 | | | | | 335 | |

| Arg | Phe | Glu | Leu | Phe | Val | Met | Lys | Lys | Glu | Ile | Cys | Asn | Ala | Tyr | Thr |
|---|---|---|---|---|---|---|---|---|---|---|---|---|---|---|---|
| | | | 340 | | | | | 345 | | | | | 350 | | |

| Glu | Leu | Asn | Asp | Pro | Met | Arg | Gln | Arg | Gln | Leu | Phe | Glu | Glu | Gln | Ala |
|---|---|---|---|---|---|---|---|---|---|---|---|---|---|---|---|
| | | 355 | | | | | 360 | | | | | 365 | | | |

| Lys | Ala | Lys | Ala | Ala | Gly | Asp | Asp | Glu | Ala | Met | Phe | Ile | Asp | Glu | Asn |
|---|---|---|---|---|---|---|---|---|---|---|---|---|---|---|---|
| | 370 | | | | | 375 | | | | | 380 | | | | |

Phe Cys Thr Ala Leu Glu Tyr Gly Leu Pro Pro Thr Ala Gly Trp Gly
385                 390                 395                 400

Met Gly Ile Asp Arg Val Ala Met Phe Leu Thr Asp Ser Asn Asn Ile
            405                 410                 415

Lys Glu Val Leu Leu Phe Pro Ala Met Lys Pro Glu Asp Lys Lys Glu
        420                 425                 430

Asn Val Ala Thr Thr Asp Thr Leu Glu Ser Thr Val Gly Thr Ser
        435                 440                 445

Val

<210> SEQ ID NO 115
<211> LENGTH: 1350
<212> TYPE: DNA
<213> ORGANISM: Homo sapiens

<400> SEQUENCE: 115

```
atggtgtggg tcctgaggaa gagagcgtgg acccaaataa attataaatc agaagaagaa      60
tttattcata ttaataacaa actgcgtcgg ggagacataa ttggagttca ggggaatcct     120
ggtaaaacca agaagggtga gctgagcatc attccgtatg agatcacact gctgtctccc     180
tgtttgcata tgttacctca tcttcacttt ggcctcaaag acaaggaaac aaggtatcgc     240
cagagatact tggacttgat cctgaatgac tttgtgaggc agaaatttat catccgctct     300
aagatcatca catatataag aagtttctta gatgagctgg gattcctaga gattgaaact     360
cccatgatga acatcatccc aggggagcc gtggccaagc ctttcatcac ttatcacaac     420
gagctggaca tgaacttata tatgagaatt gctccagaac tctatcataa gatgcttgtg     480
gttggtggca tcgaccgggt ttatgaaatt ggacgccagt tccggaatga ggggattgat     540
ttgacgcaca atcctgagtt caccacctgt gagttctaca tggcctatgc agactatcac     600
gatctcatgg aaatcacgga agatggtt tcagggatgg tgaagcatat acaggcagt      660
tacaaggtca cctaccaccc agatgggcca gagggccaag cctacgatgt tgacttcacc     720
ccacccttcc ggcgaatcaa catggtagaa gagcttgaga aagccctggg gatgaagctg     780
ccagaaacga acctctttga aactgaagaa actcgcaaaa ttcttgatga tatctgtgtg     840
gcaaaagctg ttgaatgccc tccacctcgg accacagcca ggctccttga caagcttgtt     900
ggggagttcc tggaagtgac ttgcatcaat cctacattca tctgtgatca cccacagata     960
atgagccctt tggctaaatg gcaccgctct aaagagggtc tgactgagcg ctttgagctg    1020
tttgtcatga gaaagagat atgcaatgcg tatactgagc tgaatgatcc catgcggcag    1080
cggcagcttt ttgaagaaca ggccaaggcc aaggctgcag gtgatgatga ggccatgttc    1140
atagatgaaa acttctgtac tgccctggaa tatgggctgc cccccacagc tggctggggc    1200
atgggcattg atcgagtcgc catgtttctc acggactcca acaacatcaa ggaagtactt    1260
ctgtttcctg ccatgaaacc cgaagacaag aaggagaatg tagcaaccac tgatacactg    1320
gaaagcacaa cagttggcac ttctgtctag                                   1350
```

<210> SEQ ID NO 116
<211> LENGTH: 386
<212> TYPE: PRT
<213> ORGANISM: Homo sapiens

<400> SEQUENCE: 116

Met Leu Pro His Leu His Phe Gly Leu Lys Asp Lys Glu Thr Arg Tyr
1               5                   10                  15

```
Arg Gln Arg Tyr Leu Asp Leu Ile Leu Asn Asp Phe Val Arg Gln Lys
                 20                  25                  30

Phe Ile Ile Arg Ser Lys Ile Ile Thr Tyr Ile Arg Ser Phe Leu Asp
         35                  40                  45

Glu Leu Gly Phe Leu Glu Ile Glu Thr Pro Met Met Asn Ile Ile Pro
 50                  55                  60

Gly Gly Ala Val Ala Lys Pro Phe Ile Thr Tyr His Asn Glu Leu Asp
 65                  70                  75                  80

Met Asn Leu Tyr Met Arg Ile Ala Pro Glu Leu Tyr His Lys Met Leu
                 85                  90                  95

Val Val Gly Gly Ile Asp Arg Val Tyr Glu Ile Gly Arg Gln Phe Arg
                100                 105                 110

Asn Glu Gly Ile Asp Leu Thr His Asn Pro Glu Phe Thr Thr Cys Glu
                115                 120                 125

Phe Tyr Met Ala Tyr Ala Asp Tyr His Asp Leu Met Glu Ile Thr Glu
130                 135                 140

Lys Met Val Ser Gly Met Val Lys His Ile Thr Gly Ser Tyr Lys Val
145                 150                 155                 160

Thr Tyr His Pro Asp Gly Pro Glu Gly Gln Ala Tyr Asp Val Asp Phe
                165                 170                 175

Thr Pro Pro Phe Arg Arg Ile Asn Met Val Glu Glu Leu Glu Lys Ala
                180                 185                 190

Leu Gly Met Lys Leu Pro Glu Thr Asn Leu Phe Glu Thr Glu Glu Thr
                195                 200                 205

Arg Lys Ile Leu Asp Asp Ile Cys Val Ala Lys Ala Val Glu Cys Pro
210                 215                 220

Pro Pro Arg Thr Thr Ala Arg Leu Leu Asp Lys Leu Val Gly Glu Phe
225                 230                 235                 240

Leu Glu Val Thr Cys Ile Asn Pro Thr Phe Ile Cys Asp His Pro Gln
                245                 250                 255

Ile Met Ser Pro Leu Ala Lys Trp His Arg Ser Lys Glu Gly Leu Thr
                260                 265                 270

Glu Arg Phe Glu Leu Phe Val Met Lys Lys Glu Ile Cys Asn Ala Tyr
                275                 280                 285

Thr Glu Leu Asn Asp Pro Met Arg Gln Arg Gln Leu Phe Glu Glu Gln
290                 295                 300

Ala Lys Ala Lys Ala Ala Gly Asp Asp Glu Ala Met Phe Ile Asp Glu
305                 310                 315                 320

Asn Phe Cys Thr Ala Leu Glu Tyr Gly Leu Pro Pro Thr Ala Gly Trp
                325                 330                 335

Gly Met Gly Ile Asp Arg Val Ala Met Phe Leu Thr Asp Ser Asn Asn
                340                 345                 350

Ile Lys Glu Val Leu Leu Phe Pro Ala Met Lys Pro Glu Asp Lys Lys
                355                 360                 365

Glu Asn Val Ala Thr Thr Asp Thr Leu Glu Ser Thr Thr Val Gly Thr
                370                 375                 380

Ser Val
385

<210> SEQ ID NO 117
<211> LENGTH: 1161
<212> TYPE: DNA
<213> ORGANISM: Homo sapiens

<400> SEQUENCE: 117
```

```
atgttacctc atcttcactt tggcctcaaa gacaaggaaa caaggtatcg ccagagatac    60
ttggacttga tcctgaatga ctttgtgagg cagaaattta tcatccgctc taagatcatc   120
acatatataa gaagtttctt agatgagctg ggattcctag agattgaaac tcccatgatg   180
aacatcatcc aggggggagc cgtggccaag cctttcatca cttatcacaa cgagctggac   240
atgaacttat atatgagaat tgctccagaa ctctatcata agatgcttgt ggttggtggc   300
atcgaccggg tttatgaaat tggacgccag ttccggaatg aggggattga tttgacgcac   360
aatcctgagt tcaccacctg tgagttctac atggcctatg cagactatca cgatctcatg   420
gaaatcacgg agaagatggt ttcagggatg gtgaagcata ttacaggcag ttacaaggtc   480
acctaccacc cagatggccc agagggccaa gcctacgatg ttgacttcac cccacccttc   540
cggcgaatca acatggtaga agagcttgag aaagccctgg ggatgaagct gccagaaacg   600
aacctctttg aaactgaaga aactcgcaaa attcttgatg atatctgtgt ggcaaaagct   660
gttgaatgcc ctccacctcg gaccacagcc aggctccttg acaagcttgt tggggagttc   720
ctggaagtga cttgcatcaa tcctacattc atctgtgatc acccacagat aatgagccct   780
ttggctaaat ggcaccgctc taaagagggt ctgactgagc gctttgagct gtttgtcatg   840
aagaaagaga tatgcaatgc gtatactgag ctgaatgatc ccatgcggca gcggcagctt   900
tttgaagaac aggccaaggc caaggctgca ggtgatgatg aggccatgtt catagatgaa   960
aacttctgta ctgccctgga atatgggctg ccccccacag ctggctgggg catgggcatt  1020
gatcgagtcg ccatgtttct cacggactcc aacaacatca aggaagtact tctgtttcct  1080
gccatgaaac ccgaagacaa gaaggagaat gtagcaacca ctgatacact ggaaagcaca  1140
acagttggca cttctgtcta g                                            1161
```

<210> SEQ ID NO 118
<211> LENGTH: 129
<212> TYPE: PRT
<213> ORGANISM: Homo sapiens

<400> SEQUENCE: 118

Met Ser Pro Leu Ala Lys Trp His Arg Ser Lys Glu Gly Leu Thr Glu
1               5                   10                  15

Arg Phe Glu Leu Phe Val Met Lys Lys Glu Ile Cys Asn Ala Tyr Thr
            20                  25                  30

Glu Leu Asn Asp Pro Met Arg Gln Arg Gln Leu Phe Glu Glu Gln Ala
        35                  40                  45

Lys Ala Lys Ala Ala Gly Asp Asp Glu Ala Met Phe Ile Asp Glu Asn
    50                  55                  60

Phe Cys Thr Ala Leu Glu Tyr Gly Leu Pro Pro Thr Ala Gly Trp Gly
65                  70                  75                  80

Met Gly Ile Asp Arg Val Ala Met Phe Leu Thr Asp Ser Asn Asn Ile
                85                  90                  95

Lys Glu Val Leu Leu Phe Pro Ala Met Lys Pro Glu Asp Lys Lys Glu
            100                 105                 110

Asn Val Ala Thr Thr Asp Thr Leu Glu Ser Thr Thr Val Gly Thr Ser
        115                 120                 125

Val

<210> SEQ ID NO 119
<211> LENGTH: 390
<212> TYPE: DNA

<213> ORGANISM: Homo sapiens

<400> SEQUENCE: 119

```
atgagccctt tggctaaatg caccgctct aaagagggtc tgactgagcg ctttgagctg      60
tttgtcatga agaaagagat atgcaatgcg tatactgagc tgaatgatcc catgcggcag     120
cggcagcttt ttgaagaaca ggccaaggcc aaggctgcag gtgatgatga ggccatgttc    180
atagatgaaa acttctgtac tgccctggaa tatgggctgc ccccacagc tggctggggc     240
atgggcattg atcgagtcgc catgtttctc acggactcca acaacatcaa ggaagtactt    300
ctgtttcctg ccatgaaacc cgaagacaag aaggagaatg tagcaaccac tgatacactg    360
gaaagcacaa cagttggcac ttctgtctag                                     390
```

<210> SEQ ID NO 120
<211> LENGTH: 50
<212> TYPE: DNA
<213> ORGANISM: Homo sapiens

<400> SEQUENCE: 120

```
acaagtcatt ttctgatcaa agaagcaata ctacaaaatc cgcagtcaag              50
```

<210> SEQ ID NO 121
<211> LENGTH: 50
<212> TYPE: DNA
<213> ORGANISM: Homo sapiens

<400> SEQUENCE: 121

```
tgaggaagag agcgtggacc caaataaatt ataaatcaga agaagaattt              50
```

<210> SEQ ID NO 122
<211> LENGTH: 16
<212> TYPE: PRT
<213> ORGANISM: Homo sapiens

<400> SEQUENCE: 122

```
Arg Lys Arg Ala Trp Thr Gln Ile Asn Tyr Lys Ser Glu Glu Glu Phe
1               5                   10                  15
```

<210> SEQ ID NO 123
<211> LENGTH: 50
<212> TYPE: DNA
<213> ORGANISM: Homo sapiens

<400> SEQUENCE: 123

```
actgacatca ccttaaaggt ggcagaaatt ataaatcaga agaagaattt              50
```

<210> SEQ ID NO 124
<211> LENGTH: 50
<212> TYPE: DNA
<213> ORGANISM: Homo sapiens

<400> SEQUENCE: 124

```
tcttcacttt ggcctcaaag acaagaaact cgcaaaattc ttgatgatat              50
```

<210> SEQ ID NO 125
<211> LENGTH: 465
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 125

```
Met His His His His His Gly Lys Pro Ile Pro Asn Pro Leu Leu
1               5                   10                  15

Gly Leu Asp Ser Thr Gly Ser Ala Asn Ser Arg Asn Tyr Lys Ser Glu
            20                  25                  30

Glu Glu Phe Ile His Ile Asn Asn Lys Leu Arg Arg Gly Asp Ile Ile
                35                  40                  45

Gly Val Gln Gly Asn Pro Gly Lys Thr Lys Lys Gly Glu Leu Ser Ile
    50                  55                  60

Ile Pro Tyr Glu Ile Thr Leu Leu Ser Pro Cys Leu His Met Leu Pro
65                  70                  75                  80

His Leu His Phe Gly Leu Lys Asp Lys Glu Thr Arg Tyr Arg Gln Arg
                85                  90                  95

Tyr Leu Asp Leu Ile Leu Asn Asp Phe Val Arg Gln Lys Phe Ile Ile
            100                 105                 110

Arg Ser Lys Ile Ile Thr Tyr Ile Arg Ser Phe Leu Asp Glu Leu Gly
        115                 120                 125

Phe Leu Glu Ile Glu Thr Pro Met Met Asn Ile Ile Pro Gly Gly Ala
    130                 135                 140

Val Ala Lys Pro Phe Ile Thr Tyr His Asn Glu Leu Asp Met Asn Leu
145                 150                 155                 160

Tyr Met Arg Ile Ala Pro Glu Leu Tyr His Lys Met Leu Val Val Gly
                165                 170                 175

Gly Ile Asp Arg Val Tyr Glu Ile Gly Arg Gln Phe Arg Asn Glu Gly
            180                 185                 190

Ile Asp Leu Thr His Asn Pro Glu Phe Thr Thr Cys Glu Phe Tyr Met
        195                 200                 205

Ala Tyr Ala Asp Tyr His Asp Leu Met Glu Ile Thr Glu Lys Met Val
    210                 215                 220

Ser Gly Met Val Lys His Ile Thr Gly Ser Tyr Lys Val Thr Tyr His
225                 230                 235                 240

Pro Asp Gly Pro Glu Gly Gln Ala Tyr Asp Val Asp Phe Thr Pro Pro
                245                 250                 255

Phe Arg Arg Ile Asn Met Val Glu Glu Leu Glu Lys Ala Leu Gly Met
            260                 265                 270

Lys Leu Pro Glu Thr Asn Leu Phe Glu Thr Glu Glu Thr Arg Lys Ile
        275                 280                 285

Leu Asp Asp Ile Cys Val Ala Lys Ala Val Glu Cys Pro Pro Pro Arg
    290                 295                 300

Thr Thr Ala Arg Leu Leu Asp Lys Leu Val Gly Glu Phe Leu Glu Val
305                 310                 315                 320

Thr Cys Ile Asn Pro Thr Phe Ile Cys Asp His Pro Gln Ile Met Ser
                325                 330                 335

Pro Leu Ala Lys Trp His Arg Ser Lys Glu Gly Leu Thr Glu Arg Phe
            340                 345                 350

Glu Leu Phe Val Met Lys Lys Glu Ile Cys Asn Ala Tyr Thr Glu Leu
        355                 360                 365

Asn Asp Pro Met Arg Gln Arg Gln Leu Phe Glu Glu Gln Ala Lys Ala
    370                 375                 380

Lys Ala Ala Gly Asp Asp Glu Ala Met Phe Ile Asp Glu Asn Phe Cys
385                 390                 395                 400

Thr Ala Leu Glu Tyr Gly Leu Pro Pro Thr Ala Gly Trp Gly Met Gly
                405                 410                 415
```

```
Ile Asp Arg Val Ala Met Phe Leu Thr Asp Ser Asn Asn Ile Lys Glu
            420                 425                 430

Val Leu Leu Phe Pro Ala Met Lys Pro Glu Asp Lys Lys Glu Asn Val
        435                 440                 445

Ala Thr Thr Asp Thr Leu Glu Ser Thr Val Gly Thr Ser Val Leu
    450                 455                 460

Glu
465

<210> SEQ ID NO 126
<211> LENGTH: 465
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 126

Met Gly Ser Ala Asn Ser Arg Asn Tyr Lys Ser Glu Glu Phe Ile
1               5                   10                  15

His Ile Asn Asn Lys Leu Arg Arg Gly Asp Ile Ile Gly Val Gln Gly
            20                  25                  30

Asn Pro Gly Lys Thr Lys Lys Gly Glu Leu Ser Ile Ile Pro Tyr Glu
        35                  40                  45

Ile Thr Leu Leu Ser Pro Cys Leu His Met Leu Pro His Leu His Phe
    50                  55                  60

Gly Leu Lys Asp Lys Glu Thr Arg Tyr Arg Gln Arg Tyr Leu Asp Leu
65                  70                  75                  80

Ile Leu Asn Asp Phe Val Arg Gln Lys Phe Ile Ile Arg Ser Lys Ile
                85                  90                  95

Ile Thr Tyr Ile Arg Ser Phe Leu Asp Glu Leu Gly Phe Leu Glu Ile
            100                 105                 110

Glu Thr Pro Met Met Asn Ile Ile Pro Gly Gly Ala Val Ala Lys Pro
        115                 120                 125

Phe Ile Thr Tyr His Asn Glu Leu Asp Met Asn Leu Tyr Met Arg Ile
    130                 135                 140

Ala Pro Glu Leu Tyr His Lys Met Leu Val Val Gly Gly Ile Asp Arg
145                 150                 155                 160

Val Tyr Glu Ile Gly Arg Gln Phe Arg Asn Glu Gly Ile Asp Leu Thr
                165                 170                 175

His Asn Pro Glu Phe Thr Thr Cys Glu Phe Tyr Met Ala Tyr Ala Asp
            180                 185                 190

Tyr His Asp Leu Met Glu Ile Thr Glu Lys Met Val Ser Gly Met Val
        195                 200                 205

Lys His Ile Thr Gly Ser Tyr Lys Val Thr Tyr His Pro Asp Gly Pro
    210                 215                 220

Glu Gly Gln Ala Tyr Asp Val Asp Phe Thr Pro Pro Phe Arg Arg Ile
225                 230                 235                 240

Asn Met Val Glu Glu Leu Glu Lys Ala Leu Gly Met Lys Leu Pro Glu
                245                 250                 255

Thr Asn Leu Phe Glu Thr Glu Glu Thr Arg Lys Ile Leu Asp Asp Ile
            260                 265                 270

Cys Val Ala Lys Ala Val Glu Cys Pro Pro Pro Arg Thr Thr Ala Arg
        275                 280                 285

Leu Leu Asp Lys Leu Val Gly Glu Phe Leu Glu Val Thr Cys Ile Asn
    290                 295                 300
```

```
Pro Thr Phe Ile Cys Asp His Pro Gln Ile Met Ser Pro Leu Ala Lys
305                 310                 315                 320

Trp His Arg Ser Lys Glu Gly Leu Thr Glu Arg Phe Glu Leu Phe Val
            325                 330                 335

Met Lys Lys Glu Ile Cys Asn Ala Tyr Thr Glu Leu Asn Asp Pro Met
        340                 345                 350

Arg Gln Arg Gln Leu Phe Glu Glu Gln Ala Lys Ala Lys Ala Ala Gly
    355                 360                 365

Asp Asp Glu Ala Met Phe Ile Asp Glu Asn Phe Cys Thr Ala Leu Glu
    370                 375                 380

Tyr Gly Leu Pro Pro Thr Ala Gly Trp Gly Met Gly Ile Asp Arg Val
385                 390                 395                 400

Ala Met Phe Leu Thr Asp Ser Asn Asn Ile Lys Glu Val Leu Leu Phe
                405                 410                 415

Pro Ala Met Lys Pro Glu Asp Lys Lys Glu Asn Val Ala Thr Thr Asp
            420                 425                 430

Thr Leu Glu Ser Thr Thr Val Gly Thr Ser Val Leu Glu Gly Lys Pro
        435                 440                 445

Ile Pro Asn Pro Leu Leu Gly Leu Asp Ser Thr His His His His His
    450                 455                 460

His
465

<210> SEQ ID NO 127
<211> LENGTH: 473
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 127

Met His His His His His Gly Lys Pro Ile Pro Asn Pro Leu Leu
1               5                   10                  15

Gly Leu Asp Ser Thr Gly Ser Val Trp Val Leu Arg Lys Arg Ala Trp
            20                  25                  30

Thr Gln Ile Asn Tyr Lys Ser Glu Glu Phe Ile His Ile Asn Asn
        35                  40                  45

Lys Leu Arg Arg Gly Asp Ile Ile Gly Val Gln Gly Asn Pro Gly Lys
    50                  55                  60

Thr Lys Lys Gly Glu Leu Ser Ile Ile Pro Tyr Glu Ile Thr Leu Leu
65                  70                  75                  80

Ser Pro Cys Leu His Met Leu Pro His Leu His Phe Gly Leu Lys Asp
                85                  90                  95

Lys Glu Thr Arg Tyr Arg Gln Arg Tyr Leu Asp Leu Ile Leu Asn Asp
            100                 105                 110

Phe Val Arg Gln Lys Phe Ile Ile Arg Ser Lys Ile Ile Thr Tyr Ile
        115                 120                 125

Arg Ser Phe Leu Asp Glu Leu Gly Phe Leu Glu Ile Glu Thr Pro Met
    130                 135                 140

Met Asn Ile Ile Pro Gly Gly Ala Val Ala Lys Pro Phe Ile Thr Tyr
145                 150                 155                 160

His Asn Glu Leu Asp Met Asn Leu Tyr Met Arg Ile Ala Pro Glu Leu
                165                 170                 175

Tyr His Lys Met Leu Val Val Gly Gly Ile Asp Arg Val Tyr Glu Ile
```

```
            180                 185                 190
Gly Arg Gln Phe Arg Asn Glu Gly Ile Asp Leu Thr His Asn Pro Glu
        195                 200                 205

Phe Thr Thr Cys Glu Phe Tyr Met Ala Tyr Ala Asp Tyr His Asp Leu
    210                 215                 220

Met Glu Ile Thr Glu Lys Met Val Ser Gly Met Val Lys His Ile Thr
225                 230                 235                 240

Gly Ser Tyr Lys Val Thr Tyr His Pro Asp Gly Pro Glu Gly Gln Ala
                245                 250                 255

Tyr Asp Val Asp Phe Thr Pro Pro Phe Arg Arg Ile Asn Met Val Glu
            260                 265                 270

Glu Leu Glu Lys Ala Leu Gly Met Lys Leu Pro Glu Thr Asn Leu Phe
        275                 280                 285

Glu Thr Glu Glu Thr Arg Lys Ile Leu Asp Asp Ile Cys Val Ala Lys
    290                 295                 300

Ala Val Glu Cys Pro Pro Arg Thr Ala Arg Leu Leu Asp Lys
305                 310                 315                 320

Leu Val Gly Glu Phe Leu Glu Val Thr Cys Ile Asn Pro Thr Phe Ile
                325                 330                 335

Cys Asp His Pro Gln Ile Met Ser Pro Leu Ala Lys Trp His Arg Ser
            340                 345                 350

Lys Glu Gly Leu Thr Glu Arg Phe Glu Leu Phe Val Met Lys Lys Glu
        355                 360                 365

Ile Cys Asn Ala Tyr Thr Glu Leu Asn Asp Pro Met Arg Gln Arg Gln
    370                 375                 380

Leu Phe Glu Glu Gln Ala Lys Ala Lys Ala Ala Gly Asp Asp Glu Ala
385                 390                 395                 400

Met Phe Ile Asp Glu Asn Phe Cys Thr Ala Leu Glu Tyr Gly Leu Pro
                405                 410                 415

Pro Thr Ala Gly Trp Gly Met Gly Ile Asp Arg Val Ala Met Phe Leu
            420                 425                 430

Thr Asp Ser Asn Asn Ile Lys Glu Val Leu Leu Phe Pro Ala Met Lys
        435                 440                 445

Pro Glu Asp Lys Lys Glu Asn Val Ala Thr Thr Asp Thr Leu Glu Ser
    450                 455                 460

Thr Thr Val Gly Thr Ser Val Leu Glu
465                 470

<210> SEQ ID NO 128
<211> LENGTH: 473
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 128

Met Gly Ser Val Trp Val Leu Arg Lys Arg Ala Trp Thr Gln Ile Asn
1               5                   10                  15

Tyr Lys Ser Glu Glu Glu Phe Ile His Ile Asn Asn Lys Leu Arg Arg
            20                  25                  30

Gly Asp Ile Ile Gly Val Gln Gly Asn Pro Gly Lys Thr Lys Lys Gly
        35                  40                  45

Glu Leu Ser Ile Ile Pro Tyr Glu Ile Thr Leu Leu Ser Pro Cys Leu
    50                  55                  60
```

```
His Met Leu Pro His Leu His Phe Gly Leu Lys Asp Lys Glu Thr Arg
 65                  70                  75                  80

Tyr Arg Gln Arg Tyr Leu Asp Leu Ile Leu Asn Asp Phe Val Arg Gln
                 85                  90                  95

Lys Phe Ile Ile Arg Ser Lys Ile Ile Thr Tyr Ile Arg Ser Phe Leu
            100                 105                 110

Asp Glu Leu Gly Phe Leu Glu Ile Glu Thr Pro Met Met Asn Ile Ile
            115                 120                 125

Pro Gly Gly Ala Val Ala Lys Pro Phe Ile Thr Tyr His Asn Glu Leu
        130                 135                 140

Asp Met Asn Leu Tyr Met Arg Ile Ala Pro Glu Leu Tyr His Lys Met
145                 150                 155                 160

Leu Val Val Gly Gly Ile Asp Arg Val Tyr Glu Ile Gly Arg Gln Phe
                165                 170                 175

Arg Asn Glu Gly Ile Asp Leu Thr His Asn Pro Glu Phe Thr Thr Cys
            180                 185                 190

Glu Phe Tyr Met Ala Tyr Ala Asp Tyr His Asp Leu Met Glu Ile Thr
            195                 200                 205

Glu Lys Met Val Ser Gly Met Val Lys His Ile Thr Gly Ser Tyr Lys
        210                 215                 220

Val Thr Tyr His Pro Asp Gly Pro Glu Gly Gln Ala Tyr Asp Val Asp
225                 230                 235                 240

Phe Thr Pro Pro Phe Arg Arg Ile Asn Met Val Glu Glu Leu Glu Lys
                245                 250                 255

Ala Leu Gly Met Lys Leu Pro Glu Thr Asn Leu Phe Gly Thr Glu Glu
            260                 265                 270

Thr Arg Lys Ile Leu Asp Asp Ile Cys Val Ala Lys Ala Val Glu Cys
            275                 280                 285

Pro Pro Pro Arg Thr Thr Ala Arg Leu Leu Asp Lys Leu Val Gly Glu
        290                 295                 300

Phe Leu Glu Val Thr Cys Ile Asn Pro Thr Phe Ile Cys Asp His Pro
305                 310                 315                 320

Gln Ile Met Ser Pro Leu Ala Lys Trp His Arg Ser Lys Glu Gly Leu
                325                 330                 335

Thr Glu Arg Phe Glu Leu Phe Val Met Lys Lys Glu Ile Cys Asn Ala
            340                 345                 350

Tyr Thr Glu Leu Asn Asp Pro Met Arg Gln Arg Gln Leu Phe Glu Glu
            355                 360                 365

Gln Ala Lys Ala Lys Ala Ala Gly Asp Asp Glu Ala Met Phe Ile Asp
        370                 375                 380

Glu Asn Phe Cys Thr Ala Leu Glu Tyr Gly Leu Pro Pro Thr Ala Gly
385                 390                 395                 400

Trp Gly Met Gly Ile Asp Arg Val Ala Met Phe Leu Thr Asp Ser Asn
                405                 410                 415

Asn Ile Lys Glu Val Leu Leu Phe Pro Ala Met Lys Pro Glu Asp Lys
            420                 425                 430

Lys Glu Asn Val Ala Thr Thr Asp Thr Leu Glu Ser Thr Thr Val Gly
            435                 440                 445

Thr Ser Val Leu Glu Gly Lys Pro Ile Pro Asn Pro Leu Leu Gly Leu
        450                 455                 460

Asp Ser Thr His His His His His His
465                 470
```

```
<210> SEQ ID NO 129
<211> LENGTH: 410
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 129

Met His His His His His Gly Lys Pro Ile Pro Asn Pro Leu Leu
1               5                   10                  15

Gly Leu Asp Ser Thr Gly Ser Leu Pro His Leu His Phe Gly Leu Lys
            20                  25                  30

Asp Lys Glu Thr Arg Tyr Arg Gln Arg Tyr Leu Asp Leu Ile Leu Asn
        35                  40                  45

Asp Phe Val Arg Gln Lys Phe Ile Ile Arg Ser Lys Ile Ile Thr Tyr
50                  55                  60

Ile Arg Ser Phe Leu Asp Glu Leu Gly Phe Leu Glu Ile Glu Thr Pro
65                  70                  75                  80

Met Met Asn Ile Ile Pro Gly Gly Ala Val Ala Lys Pro Phe Ile Thr
                85                  90                  95

Tyr His Asn Glu Leu Asp Met Asn Leu Tyr Met Arg Ile Ala Pro Glu
            100                 105                 110

Leu Tyr His Lys Met Leu Val Val Gly Gly Ile Asp Arg Val Tyr Glu
        115                 120                 125

Ile Gly Arg Gln Phe Arg Asn Glu Gly Ile Asp Leu Thr His Asn Pro
130                 135                 140

Glu Phe Thr Thr Cys Glu Phe Tyr Met Ala Tyr Ala Asp Tyr His Asp
145                 150                 155                 160

Leu Met Glu Ile Thr Glu Lys Met Val Ser Gly Met Val Lys His Ile
                165                 170                 175

Thr Gly Ser Tyr Lys Val Thr Tyr His Pro Asp Gly Pro Glu Gly Gln
            180                 185                 190

Ala Tyr Asp Val Asp Phe Thr Pro Pro Phe Arg Arg Ile Asn Met Val
        195                 200                 205

Glu Glu Leu Glu Lys Ala Leu Gly Met Lys Leu Pro Glu Thr Asn Leu
210                 215                 220

Phe Glu Thr Glu Glu Thr Arg Lys Ile Leu Asp Asp Ile Cys Val Ala
225                 230                 235                 240

Lys Ala Val Glu Cys Pro Pro Pro Arg Thr Thr Ala Arg Leu Leu Asp
                245                 250                 255

Lys Leu Val Gly Glu Phe Leu Glu Val Thr Cys Ile Asn Pro Thr Phe
            260                 265                 270

Ile Cys Asp His Pro Gln Ile Met Ser Pro Leu Ala Lys Trp His Arg
        275                 280                 285

Ser Lys Glu Gly Leu Thr Glu Arg Phe Glu Leu Phe Val Met Lys Lys
290                 295                 300

Glu Ile Cys Asn Ala Tyr Thr Glu Leu Asn Asp Pro Met Arg Gln Arg
305                 310                 315                 320

Gln Leu Phe Glu Glu Gln Ala Lys Ala Lys Ala Ala Gly Asp Asp Glu
                325                 330                 335

Ala Met Phe Ile Asp Glu Asn Phe Cys Thr Ala Leu Glu Tyr Gly Leu
            340                 345                 350

Pro Pro Thr Ala Gly Trp Gly Met Gly Ile Asp Arg Val Ala Met Phe
        355                 360                 365
```

```
Leu Thr Asp Ser Asn Asn Ile Lys Glu Val Leu Leu Phe Pro Ala Met
    370                 375                 380
Lys Pro Glu Asp Lys Lys Glu Asn Val Ala Thr Thr Asp Thr Leu Glu
385                 390                 395                 400
Ser Thr Thr Val Gly Thr Ser Val Leu Glu
                405                 410

<210> SEQ ID NO 130
<211> LENGTH: 410
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 130

Met Gly Ser Leu Pro His Leu His Phe Gly Leu Lys Asp Lys Glu Thr
1               5                   10                  15
Arg Tyr Arg Gln Arg Tyr Leu Asp Leu Ile Leu Asn Asp Phe Val Arg
            20                  25                  30
Gln Lys Phe Ile Ile Arg Ser Lys Ile Ile Thr Tyr Ile Arg Ser Phe
        35                  40                  45
Leu Asp Glu Leu Gly Phe Leu Glu Ile Glu Thr Pro Met Met Asn Ile
    50                  55                  60
Ile Pro Gly Gly Ala Val Ala Lys Pro Phe Ile Thr Tyr His Asn Glu
65                  70                  75                  80
Leu Asp Met Asn Leu Tyr Met Arg Ile Ala Pro Glu Leu Tyr His Lys
                85                  90                  95
Met Leu Val Val Gly Gly Ile Asp Arg Val Tyr Glu Ile Gly Arg Gln
            100                 105                 110
Phe Arg Asn Glu Gly Ile Asp Leu Thr His Asn Pro Glu Phe Thr Thr
        115                 120                 125
Cys Glu Phe Tyr Met Ala Tyr Ala Asp Tyr His Asp Leu Met Glu Ile
    130                 135                 140
Thr Glu Lys Met Val Ser Gly Met Val Lys His Ile Thr Gly Ser Tyr
145                 150                 155                 160
Lys Val Thr Tyr His Pro Asp Gly Pro Glu Gly Gln Ala Tyr Asp Val
                165                 170                 175
Asp Phe Thr Pro Pro Phe Arg Arg Ile Asn Met Val Glu Glu Leu Glu
            180                 185                 190
Lys Ala Leu Gly Met Lys Leu Pro Glu Thr Asn Leu Phe Glu Thr Glu
        195                 200                 205
Glu Thr Arg Lys Ile Leu Asp Asp Ile Cys Val Ala Lys Ala Val Glu
    210                 215                 220
Cys Pro Pro Pro Arg Thr Thr Ala Arg Leu Leu Asp Lys Leu Val Gly
225                 230                 235                 240
Glu Phe Leu Glu Val Thr Cys Ile Asn Pro Thr Phe Ile Cys Asp His
                245                 250                 255
Pro Gln Ile Met Ser Pro Leu Ala Lys Trp His Arg Ser Lys Glu Gly
            260                 265                 270
Leu Thr Glu Arg Phe Glu Leu Phe Val Met Lys Lys Glu Ile Cys Asn
        275                 280                 285
Ala Tyr Thr Glu Leu Asn Asp Pro Met Arg Gln Arg Gln Leu Phe Glu
    290                 295                 300
Glu Gln Ala Lys Ala Lys Ala Ala Gly Asp Asp Glu Ala Met Phe Ile
305                 310                 315                 320
```

```
Asp Glu Asn Phe Cys Thr Ala Leu Glu Tyr Gly Leu Pro Pro Thr Ala
                325                 330                 335

Gly Trp Gly Met Gly Ile Asp Arg Val Ala Met Phe Leu Thr Asp Ser
            340                 345                 350

Asn Asn Ile Lys Glu Val Leu Leu Phe Pro Ala Met Lys Pro Glu Asp
        355                 360                 365

Lys Lys Glu Asn Val Ala Thr Thr Asp Thr Leu Glu Ser Thr Thr Val
370                 375                 380

Gly Thr Ser Val Leu Glu Gly Lys Pro Ile Pro Asn Pro Leu Leu Gly
385                 390                 395                 400

Leu Asp Ser Thr His His His His His His
                405                 410

<210> SEQ ID NO 131
<211> LENGTH: 153
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 131

Met His His His His His His Gly Lys Pro Ile Pro Asn Pro Leu Leu
1               5                   10                  15

Gly Leu Asp Ser Thr Gly Ser Ser Pro Leu Ala Lys Trp His Arg Ser
            20                  25                  30

Lys Glu Gly Leu Thr Glu Arg Phe Glu Leu Phe Val Met Lys Lys Glu
        35                  40                  45

Ile Cys Asn Ala Tyr Thr Glu Leu Asn Asp Pro Met Arg Gln Arg Gln
    50                  55                  60

Leu Phe Glu Glu Gln Ala Lys Ala Lys Ala Ala Gly Asp Asp Glu Ala
65                  70                  75                  80

Met Phe Ile Asp Glu Asn Phe Cys Thr Ala Leu Glu Tyr Gly Leu Pro
                85                  90                  95

Pro Thr Ala Gly Trp Gly Met Gly Ile Asp Arg Val Ala Met Phe Leu
            100                 105                 110

Thr Asp Ser Asn Asn Ile Lys Glu Val Leu Leu Phe Pro Ala Met Lys
        115                 120                 125

Pro Glu Asp Lys Lys Glu Asn Val Ala Thr Thr Asp Thr Leu Glu Ser
    130                 135                 140

Thr Thr Val Gly Thr Ser Val Leu Glu
145                 150

<210> SEQ ID NO 132
<211> LENGTH: 153
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 132

Met Gly Ser Ser Pro Leu Ala Lys Trp His Arg Ser Lys Glu Gly Leu
1               5                   10                  15

Thr Glu Arg Phe Glu Leu Phe Val Met Lys Lys Glu Ile Cys Asn Ala
            20                  25                  30

Tyr Thr Glu Leu Asn Asp Pro Met Arg Gln Arg Gln Leu Phe Glu Glu
        35                  40                  45
```

```
Gln Ala Lys Ala Lys Ala Ala Gly Asp Asp Glu Ala Met Phe Ile Asp
    50                  55                  60
Glu Asn Phe Cys Thr Ala Leu Glu Tyr Gly Leu Pro Pro Thr Ala Gly
 65                  70                  75                  80
Trp Gly Met Gly Ile Asp Arg Val Ala Met Phe Leu Thr Asp Ser Asn
                 85                  90                  95
Asn Ile Lys Glu Val Leu Leu Phe Pro Ala Met Lys Pro Glu Asp Lys
            100                 105                 110
Lys Glu Asn Val Ala Thr Thr Asp Thr Leu Glu Ser Thr Thr Val Gly
        115                 120                 125
Thr Ser Val Leu Glu Gly Lys Pro Ile Pro Asn Pro Leu Leu Gly Leu
    130                 135                 140
Asp Ser Thr His His His His His His
145                 150

<210> SEQ ID NO 133
<211> LENGTH: 1332
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 133
ggatccgcta atagccgcaa ctataaaagc gaagaggaat tcatccatat caataataaa      60
ctgcggcgcg cgatattat cggtgttcag gggaatcctg gtaaaacgaa aaaaggcgaa      120
ctgagcatta tcccgtatga gatcacactg ctgtcacctt gtctgcatat gctgcctcat     180
ctgcactttg gtctgaaaga caaagaaacc cgctatcgtc agcgttatct ggacctgatt     240
ctgaatgatt ttgtacgcca aaaattcatc atccgctcga aaatcatcac ctatatccgt     300
tcctttctgg acgaactggg cttcctggaa attgaaacgc ctatgatgaa catcattccg     360
ggtggtgctg ttgctaaacc gtttatcacg tatcacaacg agctggacat gaacctgtat     420
atgcgcattg ctccggaact gtatcataaa atgctggtcg tgggcggaat cgatcgtgtg     480
tatgaaattg gtcgccagtt tcgtaatgaa ggcatcgatc tgacccataa tccagagttc     540
accacgtgtg agttctatat ggcttatgcc gactatcatg acctgatgga gattaccgag     600
aaaatggtgt ctggtatggt caaacacatc acgggctcgt ataaagtgac ctatcaccct     660
gacggacctg aaggtcaggc ttatgacgtg gattttacac cgccattccg tcgtattaac     720
atggtggagg agctggaaaa agcgctgggt atgaaactgc cggaaccaa cctgttcgaa     780 accgaagaaa ctcgtaaaat tctggatgac atttgtgtgg caaaagcggt tgaatgtccg     840
cctcctcgta ctaccgctcg tctgctggac aaactggtgg tgaatttct ggaagtgacg     900 tgtattaacc cgaccttcat ctgtgatcat cctcagatta tgagccctct ggcgaaatgg     960
catcgtagca agaaggtct gaccgaacgc tttgaactgt tcgttatgaa aaagagatt    1020 tgtaacgcct ataccgagct gaacgatcct atgcgtcaac gccagctgtt cgaggaacaa    1080
gcaaaagcga aagcagcagg cgacgacgaa gcaatgttta tcgacgagaa cttctgtact    1140
gccctggagt atggactgcc tcctaccgct ggttgggta tgggcattga ccgtgttgcc    1200
atgtttctga cagactccaa caacatcaaa gaggttctgc tgttccctgc catgaaacct    1260
gaggacaaaa agaaaaacgt ggccactact gataccctgg aatcaaccac cgttggtaca    1320
agcgtactcg ag                                                        1332
```

<210> SEQ ID NO 134
<211> LENGTH: 1356
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 134

```
ggatccgttt gggttctgcg taaacgtgct tggacacaga tcaactataa aagcgaagag    60
gaattcatcc atatcaataa taaactgcgg cgcggcgata ttatcggtgt tcaggggaat   120
cctggtaaaa cgaaaaaagg cgaactgagc attatcccgt atgagatcac actgctgtca   180
ccttgtctgc atatgctgcc tcatctgcac tttggtctga agacaaaga aacccgctat    240
cgtcagcgtt atctggacct gattctgaat gattttgtac gccaaaaatt catcatccgc   300
tcgaaaatca tcacctatat ccgttccttt ctggacgaac tgggcttcct ggaaattgaa   360
acgcctatga tgaacatcat tccgggtggt gctgttgcta accgtttat cacgtatcac    420
aacgagctgg acatgaacct gtatatgcgc attgctccgg aactgtatca taaaatgctg   480
gtcgtgggcg aatcgatcg tgtgtatgaa attggtcgcc agtttcgtaa tgaaggcatc    540
gatctgaccc ataatccaga gttcaccacg tgtgagttct atatggctta tgccgactat   600
catgacctga tggagattac cgagaaaatg gtgtctggta tggtcaaaca catcacgggc   660
tcgtataaag tgacctatca ccctgacgga cctgaaggtc aggcttatga cgtggatttt   720
acaccgccat tccgtcgtat taacatggtg gaggagctgg aaaaagcgct gggtatgaaa   780
ctgccggaaa ccaacctgtt cgaaaccgaa gaaactcgta aaattctgga tgacatttgt   840
gtggcaaaag cggttgaatg tccgcctcct cgtactaccg ctcgtctgct ggacaaactg   900
gtgggtgaat ttctggaagt gacgtgtatt aacccgacct catctgtga tcatcctcag   960
attatgagcc ctctggcgaa atggcatcgt agcaaagaag gtctgaccga acgctttgaa   1020
ctgttcgtta tgaaaaaaga gatttgtaac gcctataccg agctgaacga tcctatgcgt   1080
caacgccagc tgttcgagga acaagcaaaa gcgaaagcag caggcgacga cgaagcaatg   1140
tttatcgacg agaacttctg tactgccctg gagtatggac tgcctcctac cgctggttgg   1200
ggtatgggca ttgaccgtgt tgccatgttt ctgacagact ccaacaacat caaagaggtt   1260
ctgctgttcc ctgccatgaa acctgaggac aaaaaagaaa acgtggccac tactgatacc   1320
ctggaatcaa ccaccgttgg tacaagcgta ctcgag                            1356
```

<210> SEQ ID NO 135
<211> LENGTH: 1167
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 135

```
ggatccctgc tcatctgca ctttggtctg aaagacaaag aaacccgcta tcgtcagcgt     60
tatctggacc tgattctgaa tgattttgta cgccaaaaat tcatcatccg ctcgaaaatc    120
atcacctata tccgttcctt tctggacgaa ctgggcttcc tggaaattga aacgcctatg   180
atgaacatca ttccgggtgg tgctgttgct aaccgtttta tcacgtatca caacgagctg   240
gacatgaacc tgtatatgcg cattgctccg gaactgtatc ataaaatgct ggtcgtgggc   300
gaatcgatcg tgtgtatga aattggtcgc cagtttcgta tgaaggcat cgatctgacc     360
```

```
cataatccag agttcaccac gtgtgagttc tatatggctt atgccgacta tcatgacctg      420
atggagatta ccgagaaaat ggtgtctggt atggtcaaac acatcacggg ctcgtataaa      480
gtgacctatc accctgacgg acctgaaggt caggcttatg acgtggattt tacaccgcca      540
ttccgtcgta ttaacatggt ggaggagctg aaaaagcgc tgggtatgaa actgccggaa       600
accaacctgt tcgaaaccga agaaactcgt aaaattctgg atgacatttg tgtggcaaaa      660
gcggttgaat gtccgcctcc tcgtactacc gctcgtctgc tggacaaact ggtgggtgaa      720
tttctggaag tgacgtgtat taacccgacc ttcatctgtg atcatcctca gattatgagc      780
cctctggcga atggcatcg tagcaaagaa ggtctgaccg aacgctttga actgttcgtt       840
atgaaaaaag agatttgtaa cgcctatacc gagctgaacg atcctatgcg tcaacgccag      900
ctgttcgagg aacaagcaaa agcgaaagca gcaggcgacg acgaagcaat gtttatcgac      960
gagaacttct gtactgccct ggagtatgga ctgcctccta ccgctggttg gggtatgggc     1020
attgaccgtg ttgccatgtt tctgacagac tccaacaaca tcaaagaggt tctgctgttc     1080
cctgccatga aacctgagga caaaaaagaa acgtggcca ctactgatac cctggaatca      1140
accaccgttg gtacaagcgt actcgag                                          1167

<210> SEQ ID NO 136
<211> LENGTH: 396
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 136
ggatccagcc ctctggcgaa atggcatcgt agcaaagaag gtctgaccga acgctttgaa       60
ctgttcgtta tgaaaaaaga gatttgtaac gcctataccg agctgaacga tcctatgcgt      120
caacgccagc tgttcgagga acaagcaaaa gcgaaagcag caggcgacga cgaagcaatg      180
tttatcgacg agaacttctg tactgccctg gagtatggac tgcctcctac cgctggttgg      240
ggtatgggca ttgaccgtgt tgccatgttt ctgacagact ccaacaacat caaagaggtt      300
ctgctgttcc ctgccatgaa acctgaggac aaaaaagaaa acgtggccac tactgatacc      360
ctggaatcaa ccaccgttgg tacaagcgta ctcgag                                396

<210> SEQ ID NO 137
<211> LENGTH: 150
<212> TYPE: PRT
<213> ORGANISM: Homo sapiens

<400> SEQUENCE: 137

Gly Pro Glu Glu Glu Ser Val Asp Pro Asn Gln Tyr Tyr Lys Ile Arg
1               5                   10                  15

Ser Gln Ala Ile His Gln Leu Lys Val Asn Gly Glu Asp Pro Tyr Pro
            20                  25                  30

His Lys Phe His Val Asp Ile Ser Leu Thr Asp Phe Ile Gln Lys Tyr
        35                  40                  45

Ser His Leu Gln Pro Gly Asp His Leu Thr Asp Ile Thr Leu Lys Val
    50                  55                  60

Ala Gly Arg Ile His Ala Lys Arg Ala Ser Gly Gly Lys Leu Ile Phe
65                  70                  75                  80

Tyr Asp Leu Arg Gly Glu Gly Val Lys Leu Gln Val Met Ala Asn Ser
                85                  90                  95
```

```
Arg Asn Tyr Lys Ser Glu Glu Phe Ile His Ile Asn Asn Lys Leu
                100                 105                 110

Arg Arg Gly Asp Ile Ile Gly Val Gln Gly Asn Pro Gly Lys Thr Lys
            115                 120                 125

Lys Gly Glu Leu Ser Ile Ile Pro Tyr Glu Ile Thr Leu Leu Ser Pro
130                 135                 140

Cys Leu His Met Leu Pro
145                 150

<210> SEQ ID NO 138
<211> LENGTH: 450
<212> TYPE: DNA
<213> ORGANISM: Homo sapiens

<400> SEQUENCE: 138
ggtcctgagg aagagagcgt ggacccaaat caatactaca aaatccgcag tcaagcaatt      60
catcagctga aggtcaatgg ggaagaccca tacccacaca gttccatgt agacatctca     120 ctcactgact tcatccaaaa atatagtcac ctgcagcctg ggatcacct gactgacatc     180 accttaaagg tggcaggtag gatccatgcc aaaagagctt ctgggggaaa gctcatcttc     240
tatgatcttc gaggagaggg ggtgaagttg caagtcatgg ccaattccag aaattataaa     300
tcagaagaag aatttattca tattaataac aaactgcgtc ggggagacat aattggagtt     360
caggggaatc ctggtaaaac caagaagggt gagctgagca tcattccgta tgagatcaca     420
ctgctgtctc cctgtttgca tatgttacct                                     450

<210> SEQ ID NO 139
<211> LENGTH: 175
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 139

Met His His His His His His Gly Lys Pro Ile Pro Asn Pro Leu Leu
1               5                   10                  15

Gly Leu Asp Ser Thr Gly Ser Gly Pro Glu Glu Glu Ser Val Asp Pro
            20                  25                  30

Asn Gln Tyr Tyr Lys Ile Arg Ser Gln Ala Ile His Gln Leu Lys Val
        35                  40                  45

Asn Gly Glu Asp Pro Tyr Pro His Lys Phe His Val Asp Ile Ser Leu
    50                  55                  60

Thr Asp Phe Ile Gln Lys Tyr Ser His Leu Gln Pro Gly Asp His Leu
65                  70                  75                  80

Thr Asp Ile Thr Leu Lys Val Ala Gly Arg Ile His Ala Lys Arg Ala
                85                  90                  95

Ser Gly Gly Lys Leu Ile Phe Tyr Asp Leu Arg Gly Glu Gly Val Lys
            100                 105                 110

Leu Gln Val Met Ala Asn Ser Arg Asn Tyr Lys Ser Glu Glu Glu Phe
        115                 120                 125

Ile His Ile Asn Asn Lys Leu Arg Arg Gly Asp Ile Ile Gly Val Gln
    130                 135                 140

Gly Asn Pro Gly Lys Thr Lys Lys Gly Glu Leu Ser Ile Ile Pro Tyr
145                 150                 155                 160

Glu Ile Thr Leu Leu Ser Pro Cys Leu His Met Leu Pro Leu Glu
```

<210> SEQ ID NO 140
<211> LENGTH: 175
<212> TYPE: PRT
<213> ORGANISM: Artificial Sequence
<220> FEATURE:
<223> OTHER INFORMATION: Lysyl tRNA Synthetase polypeptide with
    C-terminal 6xHis affinity tag

<400> SEQUENCE: 140

Met Gly Ser Gly Pro Glu Glu Ser Val Asp Pro Asn Gln Tyr Tyr
1               5                   10                  15

Lys Ile Arg Ser Gln Ala Ile His Gln Leu Lys Val Asn Gly Glu Asp
            20                  25                  30

Pro Tyr Pro His Lys Phe His Val Asp Ile Ser Leu Thr Asp Phe Ile
        35                  40                  45

Gln Lys Tyr Ser His Leu Gln Pro Gly Asp His Leu Thr Asp Ile Thr
    50                  55                  60

Leu Lys Val Ala Gly Arg Ile His Ala Lys Arg Ala Ser Gly Gly Lys
65                  70                  75                  80

Leu Ile Phe Tyr Asp Leu Arg Gly Glu Gly Val Lys Leu Gln Val Met
                85                  90                  95

Ala Asn Ser Arg Asn Tyr Lys Ser Glu Glu Phe Ile His Ile Asn
            100                 105                 110

Asn Lys Leu Arg Arg Gly Asp Ile Ile Gly Val Gln Gly Asn Pro Gly
        115                 120                 125

Lys Thr Lys Lys Gly Glu Leu Ser Ile Ile Pro Tyr Glu Ile Thr Leu
    130                 135                 140

Leu Ser Pro Cys Leu His Met Leu Pro Leu Glu Gly Lys Pro Ile Pro
145                 150                 155                 160

Asn Pro Leu Leu Gly Leu Asp Ser Thr His His His His His His
                165                 170                 175

<210> SEQ ID NO 141
<211> LENGTH: 462
<212> TYPE: DNA
<213> ORGANISM: Artificial Sequence
<220> FEATURE:
<223> OTHER INFORMATION: Codon optimized lysyl tRNA Synthetase
    polynucleotide

<400> SEQUENCE: 141
ggatccggtc cagaagaaga aagcgttgat ccgaaccagt attataaaat ccgtagccag    60
gccattcacc aactgaaagt gaacggtgag gaccettatc cacacaaatt ccacgtcgac   120
attagtctga ccgacttcat ccaaaaatat tcccacctgc agccgggcga ccatctgact   180
gatatcacac tgaaagtggc gggtcgtatt catgctaaac gtgcctctgg tggtaaactg   240
atcttctatg acctgcgcgg tgaaggtgta aaactgcaag tcatggccaa tagccgtaac   300
tataaaagtg aggaggagtt cattcacatt aacaacaaac tgcgtcgcgg agacattatc   360
ggtgttcagg gtaatccagg gaaaacgaaa aaaggcgagc tgtccattat tccgtatgag   420
atcacgctgc tgtcaccttg tctgcatatg ctgcctctcg ag                      462

<210> SEQ ID NO 142
<211> LENGTH: 394
<212> TYPE: PRT
<213> ORGANISM: Homo sapiens

<400> SEQUENCE: 142

```
Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Gln Tyr Tyr Lys Ile Arg Ser Gln Ala Ile
            100                 105                 110

His Gln Leu Lys Val Asn Gly Glu Asp Pro Tyr Pro His Lys Phe His
        115                 120                 125

Val Asp Ile Ser Leu Thr Asp Phe Ile Gln Lys Tyr Ser His Leu Gln
130                 135                 140

Pro Gly Asp His Leu Thr Asp Ile Thr Leu Lys Val Ala Gly Arg Ile
145                 150                 155                 160

His Ala Lys Arg Ala Ser Gly Gly Lys Leu Ile Phe Tyr Asp Leu Arg
                165                 170                 175

Gly Glu Gly Val Lys Leu Gln Val Met Ala Asn Ser Arg Asn Tyr Lys
            180                 185                 190

Ser Glu Glu Glu Phe Ile His Ile Asn Asn Lys Leu Arg Arg Gly Asp
        195                 200                 205

Ile Ile Gly Val Gln Gly Asn Pro Gly Lys Thr Lys Lys Gly Glu Leu
    210                 215                 220

Ser Ile Ile Pro Tyr Glu Ile Thr Leu Leu Ser Pro Cys Leu His Met
225                 230                 235                 240

Leu Pro His Leu His Phe Gly Leu Lys Asp Lys Glu Thr Arg Tyr Arg
                245                 250                 255

Gln Arg Tyr Leu Asp Leu Ile Leu Asn Asp Phe Val Arg Gln Lys Phe
            260                 265                 270

Ile Ile Arg Ser Lys Ile Ile Thr Tyr Ile Arg Ser Phe Leu Asp Glu
        275                 280                 285

Leu Gly Phe Leu Glu Ile Glu Thr Pro Met Met Asn Ile Ile Pro Gly
    290                 295                 300

Gly Ala Val Ala Lys Pro Phe Ile Thr Tyr His Asn Glu Leu Asp Met
305                 310                 315                 320

Asn Leu Tyr Met Arg Ile Ala Pro Glu Leu Tyr His Lys Met Leu Val
                325                 330                 335

Val Gly Gly Ile Asp Arg Val Tyr Glu Ile Gly Arg Gln Phe Arg Asn
            340                 345                 350

Glu Gly Ile Asp Leu Thr His Asn Pro Glu Phe Thr Thr Cys Glu Phe
        355                 360                 365

Tyr Met Ala Tyr Ala Asp Tyr His Asp Leu Met Glu Ile Thr Glu Lys
    370                 375                 380

Met Val Ser Gly Met Val Lys His Ile Thr
385                 390
```

<210> SEQ ID NO 143

<211> LENGTH: 1182
<212> TYPE: DNA
<213> ORGANISM: Homo sapiens

<400> SEQUENCE: 143

```
atgttgacgc aagctgctgt aaggcttgtt aggggggtccc tgcgcaaaac ctcctgggca      60
gagtgggggtc acagggaact gcgactgggt caacttgctc ctttcacagc gcctcacaag     120
gacaagtcat tttctgatca agaagtgag ctgaagagac gcctgaaagc tgagaagaaa      180
gtagcagaga aggaggccaa acagaaagag ctcagtgaga aacagctaag ccaagccact      240
gctgctgcca ccaaccacac cactgataat ggtgtgggtc ctgaggaaga gagcgtggac      300
ccaaatcaat actacaaaat ccgcagtcaa gcaattcatc agctgaaggt caatggggaa      360
gacccatacc cacacaagtt ccatgtagac atctcactca ctgacttcat ccaaaaatat      420
agtcacctgc agcctgggga tcacctgact gacatcacct taaaggtggc aggtaggatc      480
catgccaaaa gagcttctgg gggaaagctc atcttctatg atcttcgagg agaggggtg      540
aagttgcaag tcatggccaa ttccagaaat tataaatcag aagaagaatt tattcatatt      600
aataacaaac tgcgtcgggg agacataatt ggagttcagg ggaatcctgg taaaaccaag      660
aagggtgagc tgagcatcat tccgtatgag atcacactgc tgtctccctg tttgcatatg      720
ttacctcatc ttcactttgg cctcaaagac aaggaaacaa ggtatcgcca gagatacttg      780
gacttgatcc tgaatgactt tgtgaggcag aaatttatca tccgctctaa gatcatcaca      840
tatataagaa gtttcttaga tgagctggga ttcctagaga ttgaaactcc catgatgaac      900
atcatcccag ggggagccgt ggccaagcct ttcatcactt atcacaacga gctggacatg      960
aacttatata tgagaattgc tccagaactc tatcataaga tgcttgtggt tggtggcatc     1020
gaccgggttt atgaaattgg acgccagttc cggaatgagg ggattgattt gacgcacaat     1080
cctgagttca ccacctgtga gttctacatg gcctatgcag actatcacga tctcatggaa     1140
atcacggaga gatggtttc agggatggtg aagcatatta ca                       1182
```

<210> SEQ ID NO 144
<211> LENGTH: 13
<212> TYPE: PRT
<213> ORGANISM: Mus musculus

<400> SEQUENCE: 144

Arg Gly Asp Ile Ile Gly Val Glu Gly Asn Pro Gly Lys
1               5                   10

<210> SEQ ID NO 145
<211> LENGTH: 40
<212> TYPE: PRT
<213> ORGANISM: Mus musculus

<400> SEQUENCE: 145

Thr Lys Lys Gly Glu Leu Ser Ile Ile Pro Gln Glu Ile Thr Leu Leu
1               5                   10                  15

Ser Pro Cys Leu His Met Leu Pro His Leu His Phe Gly Leu Lys Asp
                20                  25                  30

Lys Glu Thr Arg Tyr Arg Gln Arg
            35                  40

<210> SEQ ID NO 146
<211> LENGTH: 11
<212> TYPE: PRT
<213> ORGANISM: Mus musculus

<400> SEQUENCE: 146

Tyr Leu Asp Leu Ile Leu Asn Asp Phe Val Arg
1               5                   10

<210> SEQ ID NO 147
<211> LENGTH: 64
<212> TYPE: PRT
<213> ORGANISM: mUS MUSCULUS

<400> SEQUENCE: 147

Arg Gly Asp Ile Ile Gly Val Glu Gly Asn Pro Gly Lys Thr Lys Lys
1               5                   10                  15

Gly Glu Leu Ser Ile Ile Pro Gln Glu Ile Thr Leu Leu Ser Pro Cys
            20                  25                  30

Leu His Met Leu Pro His Leu His Phe Gly Leu Lys Asp Lys Glu Thr
        35                  40                  45

Arg Tyr Arg Gln Arg Tyr Leu Asp Leu Ile Leu Asn Asp Phe Val Arg
    50                  55                  60

<210> SEQ ID NO 148
<211> LENGTH: 61
<212> TYPE: PRT
<213> ORGANISM: Homo sapiens

<400> SEQUENCE: 148

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Asn Thr Thr Lys Ser Ala Val Lys Gln Phe Ile Ser
    50                  55                  60

<210> SEQ ID NO 149
<211> LENGTH: 186
<212> TYPE: DNA
<213> ORGANISM: Homo sapiens

<400> SEQUENCE: 149
atgttgacgc aagctgctgt aaggcttgtt agggggtccc tgcgcaaaac ctcctgggca      60
gagtggggtc acagggaact gcgactgggt caacttgctc ctttcacagc gcctcacaag     120
gacaagtcat tttctgatca agaagcaat actacaaaat ccgcagtcaa gcaattcatc      180
agctga                                                                186

<210> SEQ ID NO 150
<211> LENGTH: 124
<212> TYPE: PRT
<213> ORGANISM: Homo sapiens

<400> SEQUENCE: 150

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

```
Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Val Gly Ser Met Pro Lys Glu Leu Leu Gly
            100                 105                 110

Glu Ser Ser Ser Met Ile Phe Glu Glu Arg Gly
            115                 120

<210> SEQ ID NO 151
<211> LENGTH: 375
<212> TYPE: DNA
<213> ORGANISM: Homo sapiens

<400> SEQUENCE: 151
atgttgacgc aagctgctgt aaggcttgtt aggggtccc tgcgcaaaac ctcctgggca     60
gagtggggtc acagggaact gcgactgggt caacttgctc ctttcacagc gcctcacaag   120
gacaagtcat tttctgatca agaagtgag ctgaagagac gcctgaaagc tgagaagaaa    180
gtagcagaga aggaggccaa acagaaagag ctcagtgaga aacagctaag ccaagccact   240
gctgctgcca ccaaccacac cactgataat ggtgtgggtc ctgaggaaga gagcgtggac   300
ccaaatgtag gatccatgcc aaaagagctt ctgggggaaa gctcatcttc tatgatcttc   360
gaggagaggg ggtga                                                    375

<210> SEQ ID NO 152
<211> LENGTH: 585
<212> TYPE: PRT
<213> ORGANISM: Homo sapiens

<400> SEQUENCE: 152

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Gln Tyr Tyr Lys Ile Arg Ser Gln Ala Ile
            100                 105                 110

His Gln Leu Lys Val Asn Gly Glu Asp Pro Tyr Pro His Lys Phe His
            115                 120                 125

Val Asp Ile Ser Leu Thr Asp Phe Ile Gln Lys Tyr Ser His Leu Gln
        130                 135                 140

Pro Gly Asp His Leu Thr Asp Ile Thr Leu Lys Val Ala Gly Arg Ile
145                 150                 155                 160

His Ala Lys Arg Ala Ser Gly Gly Lys Leu Ile Phe Tyr Asp Leu Arg
                165                 170                 175

Gly Glu Gly Val Lys Leu Gln Val Met Ala Asn Ser Arg Asn Tyr Lys
```

```
            180                 185                 190
Ser Glu Glu Glu Phe Ile His Ile Asn Asn Lys Leu Arg Arg Gly Asp
        195                 200                 205
Ile Ile Gly Val Gln Gly Asn Pro Gly Lys Thr Lys Lys Gly Glu Leu
        210                 215                 220
Ser Ile Ile Pro Tyr Glu Ile Thr Leu Leu Ser Pro Cys Leu His Met
225                 230                 235                 240
Leu Pro His Leu His Phe Gly Leu Lys Asp Lys Glu Thr Arg Tyr Arg
                245                 250                 255
Gln Arg Tyr Leu Asp Leu Ile Leu Asn Asp Phe Val Arg Gln Lys Phe
            260                 265                 270
Ile Ile Arg Ser Lys Ile Ile Thr Tyr Ile Arg Ser Phe Leu Asp Glu
            275                 280                 285
Leu Gly Phe Leu Glu Met Leu Val Val Gly Gly Ile Asp Arg Val Tyr
        290                 295                 300
Glu Ile Gly Arg Gln Phe Arg Asn Glu Gly Ile Asp Leu Thr His Asn
305                 310                 315                 320
Pro Glu Phe Thr Thr Cys Glu Phe Tyr Met Ala Tyr Ala Asp Tyr His
                325                 330                 335
Asp Leu Met Glu Ile Thr Glu Lys Met Val Ser Gly Met Val Lys His
                340                 345                 350
Ile Thr Gly Ser Tyr Lys Val Thr Tyr His Pro Asp Gly Pro Glu Gly
            355                 360                 365
Gln Ala Tyr Asp Val Asp Phe Thr Pro Pro Phe Arg Arg Ile Asn Met
        370                 375                 380
Val Glu Glu Leu Glu Lys Ala Leu Gly Met Lys Leu Pro Glu Thr Asn
385                 390                 395                 400
Leu Phe Glu Thr Glu Thr Arg Lys Ile Leu Asp Asp Ile Cys Val
                405                 410                 415
Ala Lys Ala Val Glu Cys Pro Pro Arg Thr Thr Ala Arg Leu Leu
                420                 425                 430
Asp Lys Leu Val Gly Glu Phe Leu Glu Val Thr Cys Ile Asn Pro Thr
        435                 440                 445
Phe Ile Cys Asp His Pro Gln Ile Met Ser Pro Leu Ala Lys Trp His
        450                 455                 460
Arg Ser Lys Glu Gly Leu Thr Glu Arg Phe Glu Leu Phe Val Met Lys
465                 470                 475                 480
Lys Glu Ile Cys Asn Ala Tyr Thr Glu Leu Asn Asp Pro Met Arg Gln
                485                 490                 495
Arg Gln Leu Phe Glu Glu Gln Ala Lys Ala Lys Ala Ala Gly Asp Asp
                500                 505                 510
Glu Ala Met Phe Ile Asp Glu Asn Phe Cys Thr Ala Leu Glu Tyr Gly
            515                 520                 525
Leu Pro Pro Thr Ala Gly Trp Gly Met Gly Ile Asp Arg Val Ala Met
        530                 535                 540
Phe Leu Thr Asp Ser Asn Asn Ile Lys Glu Val Leu Leu Phe Pro Ala
545                 550                 555                 560
Met Lys Pro Glu Asp Lys Lys Glu Asn Val Ala Thr Thr Asp Thr Leu
                565                 570                 575
Glu Ser Thr Thr Val Gly Thr Ser Val
            580                 585

<210> SEQ ID NO 153
```

<211> LENGTH: 1758
<212> TYPE: DNA
<213> ORGANISM: Homo sapiens

<400> SEQUENCE: 153

```
atgttgacgc aagctgctgt aaggcttgtt aggggtccc tgcgcaaaac ctcctgggca      60
gagtggggtc acagggaact gcgactgggt caacttgctc ctttcacagc gcctcacaag    120
gacaagtcat tttctgatca agaagtgag ctgaagagac gcctgaaagc tgagaagaaa    180
gtagcagaga aggaggccaa acagaaagag ctcagtgaga aacagctaag ccaagccact    240
gctgctgcca ccaaccacac cactgataat ggtgtgggtc ctgaggaaga gagcgtggac    300
ccaaatcaat actacaaaat ccgcagtcaa gcaattcatc agctgaaggt caatggggaa    360
gacccatacc cacacaagtt ccatgtagac atctcactca ctgacttcat ccaaaaatat    420
agtcacctgc agcctgggga tcacctgact gacatcacct taaaggtggc aggtaggatc    480
catgccaaaa gagcttctgg gggaaagctc atcttctatg atcttcgagg agaggggtg     540
aagttgcaag tcatggccaa ttccagaaat tataaatcag aagaagaatt tattcatatt    600
aataacaaac tgcgtcgggg agacataatt ggagttcagg ggaatcctgg taaaaccaag    660
aagggtgagc tgagcatcat tccgtatgag atcacactgc tgtctccctg tttgcatatg    720
ttacctcatc ttcactttgg cctcaaagac aaggaaacaa ggtatcgcca gagatacttg    780
gacttgatcc tgaatgactt tgtgaggcag aaatttatca tccgctctaa gatcatcaca    840
tatataagaa gtttcttaga tgagctggga ttcctagaga tgcttgtggt tggtggcatc    900
gaccgggttt atgaaattgg acgccagttc cggaatgagg ggattgattt gacgcacaat    960
cctgagttca ccacctgtga gttctacatg gcctatgcag actatcacga tctcatggaa   1020
atcacggaga gatggtttc agggatggtg aagcatatta caggcagtta caggtcacc    1080
taccacccag atggcccaga gggccaagcc tacgatgttg acttcacccc acccttccgg   1140
cgaatcaaca tggtagaaga gcttgagaaa gccctgggga tgaagctgcc agaaacgaac   1200
ctctttgaaa ctgaagaaac tcgcaaaatt cttgatgata tctgtgtggc aaaagctgtt   1260
gaatgccctc cacctcggac cacagccagg ctccttgaca gcttgttgg ggagttcctg   1320
gaagtgactt gcatcaatcc tacattcatc tgtgatcacc cacagataat gagcccttg    1380
gctaaatggc accgctctaa agagggtctg actgagcgct ttgagctgtt tgtcatgaag   1440
aaagagatat gcaatgcgta tactgagctg aatgatccca tgcggcagcg gcagcttttt   1500
gaagaacagg ccaaggccaa ggctgcaggt gatgatgagg ccatgttcat agatgaaaac   1560
ttctgtactg ccctggaata tgggctgccc cccacagctg gctggggcat gggcattgat   1620
cgagtcgcca tgtttctcac ggactccaac aacatcaagg aagtacttct gtttcctgcc   1680
atgaaacccg aagacaagaa ggagaatgta gcaaccactg atacactgga aagcacaaca   1740
gttggcactt ctgtctag                                                  1758
```

<210> SEQ ID NO 154
<211> LENGTH: 434
<212> TYPE: PRT
<213> ORGANISM: Homo sapiens

<400> SEQUENCE: 154

```
Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30
```

```
Ala Pro Phe Thr Ala Pro His Lys Asp Lys Ser Phe Ser Asp Gln Arg
         35                  40                  45

Ser Glu Leu Lys Arg Arg Leu Lys Ala Glu Lys Lys Val Ala Glu Lys
 50                  55                  60

Glu Ala Lys Gln Lys Glu Leu Ser Glu Lys Gln Leu Ser Gln Ala Thr
 65                  70                  75                  80

Ala Ala Ala Thr Asn His Thr Thr Asp Asn Gly Val Gly Pro Glu Glu
                 85                  90                  95

Glu Ser Val Asp Pro Asn Ile Glu Thr Pro Met Met Asn Ile Ile Pro
                100                 105                 110

Gly Gly Ala Val Ala Lys Pro Phe Ile Thr Tyr His Asn Glu Leu Asp
                115                 120                 125

Met Asn Leu Tyr Met Arg Ile Ala Pro Glu Leu Tyr His Lys Met Leu
        130                 135                 140

Val Val Gly Gly Ile Asp Arg Val Tyr Glu Ile Gly Arg Gln Phe Arg
145                 150                 155                 160

Asn Glu Gly Ile Asp Leu Thr His Asn Pro Glu Phe Thr Thr Cys Glu
                165                 170                 175

Phe Tyr Met Ala Tyr Ala Asp Tyr His Asp Leu Met Glu Ile Thr Glu
        180                 185                 190

Lys Met Val Ser Gly Met Val Lys His Ile Thr Gly Ser Tyr Lys Val
        195                 200                 205

Thr Tyr His Pro Asp Gly Pro Glu Gly Gln Ala Tyr Asp Val Asp Phe
    210                 215                 220

Thr Pro Pro Phe Arg Arg Ile Asn Met Val Glu Leu Glu Lys Ala
225                 230                 235                 240

Leu Gly Met Lys Leu Pro Glu Thr Asn Leu Phe Glu Thr Glu Glu Thr
                245                 250                 255

Arg Lys Ile Leu Asp Asp Ile Cys Val Ala Lys Ala Val Glu Cys Pro
        260                 265                 270

Pro Pro Arg Thr Thr Ala Arg Leu Leu Asp Lys Leu Val Gly Glu Phe
        275                 280                 285

Leu Glu Val Thr Cys Ile Asn Pro Thr Phe Ile Cys Asp His Pro Gln
        290                 295                 300

Ile Met Ser Pro Leu Ala Lys Trp His Arg Ser Lys Glu Gly Leu Thr
305                 310                 315                 320

Glu Arg Phe Glu Leu Phe Val Met Lys Lys Glu Ile Cys Asn Ala Tyr
                325                 330                 335

Thr Glu Leu Asn Asp Pro Met Arg Gln Arg Gln Leu Phe Glu Glu Gln
                340                 345                 350

Ala Lys Ala Lys Ala Ala Gly Asp Asp Glu Ala Met Phe Ile Asp Glu
                355                 360                 365

Asn Phe Cys Thr Ala Leu Glu Tyr Gly Leu Pro Pro Thr Ala Gly Trp
        370                 375                 380

Gly Met Gly Ile Asp Arg Val Ala Met Phe Leu Thr Asp Ser Asn Asn
385                 390                 395                 400

Ile Lys Glu Val Leu Leu Phe Pro Ala Met Lys Pro Glu Asp Lys Lys
                405                 410                 415

Glu Asn Val Ala Thr Thr Asp Thr Leu Glu Ser Thr Thr Val Gly Thr
                420                 425                 430

Ser Val
```

-continued

<210> SEQ ID NO 155
<211> LENGTH: 1305
<212> TYPE: DNA
<213> ORGANISM: Homo sapiens

<400> SEQUENCE: 155

| | | | | | |
|---|---|---|---|---|---|
| atgttgacgc | aagctgctgt | aaggcttgtt | aggggggtccc | tgcgcaaaac | ctcctgggca | 60 |
| gagtggggtc | acagggaact | gcgactgggt | caacttgctc | ctttcacagc | gcctcacaag | 120 |
| gacaagtcat | tttctgatca | agaagtgag | ctgaagagac | gcctgaaagc | tgagaagaaa | 180 |
| gtagcagaga | aggaggccaa | acagaaagag | ctcagtgaga | aacagctaag | ccaagccact | 240 |
| gctgctgcca | ccaaccacac | cactgataat | ggtgtgggtc | ctgaggaaga | gagcgtggac | 300 |
| ccaaatattg | aaactcccat | gatgaacatc | atcccagggg | gagccgtggc | caagcctttc | 360 |
| atcacttatc | acaacgagct | ggacatgaac | ttatatatga | aattgctcc | agaactctat | 420 |
| cataagatgc | ttgtggttgg | tggcatcgac | cgggtttatg | aaattggacg | ccagttccgg | 480 |
| aatgagggga | ttgatttgac | gcacaatcct | gagttcacca | cctgtgagtt | ctacatggcc | 540 |
| tatgcagact | atcacgatct | catggaaatc | acggagaaga | tggtttcagg | gatggtgaag | 600 |
| catattacag | gcagttacaa | ggtcacctac | cacccagatg | gcccagaggg | ccaagcctac | 660 |
| gatgttgact | tcaccccacc | cttccggcga | atcaacatgg | tagaagagct | tgagaaagcc | 720 |
| ctggggatga | agctgccaga | aacgaacctc | tttgaaactg | aagaaactcg | caaaattctt | 780 |
| gatgatatct | gtgtggcaaa | agctgttgaa | tgccctccac | ctcggaccac | agccaggctc | 840 |
| cttgacaagc | ttgttgggga | gttcctggaa | gtgacttgca | tcaatcctac | attcatctgt | 900 |
| gatcacccac | agataatgag | cccctttggct | aaatggcacc | gctctaaaga | gggtctgact | 960 |
| gagcgctttg | agctgtttgt | catgaagaaa | gagatatgca | atgcgtatac | tgagctgaat | 1020 |
| gatcccatgc | ggcagcggca | gcttttttgaa | gaacaggcca | aggccaaggc | tgcaggtgat | 1080 |
| gatgaggcca | tgttcataga | tgaaaaactttc | tgtactgccc | tggaatatgg | gctgccccccc | 1140 |
| acagctggct | ggggcatggg | cattgatcga | gtcgccatgt | ttctcacgga | ctccaacaac | 1200 |
| atcaaggaag | tacttctgtt | tcctgccatg | aaacccgaag | acaagaagga | gaatgtagca | 1260 |
| accactgata | cactggaaag | cacaacagtt | ggcacttctg | tctag | | 1305 |

<210> SEQ ID NO 156
<211> LENGTH: 413
<212> TYPE: PRT
<213> ORGANISM: Homo sapiens

<400> SEQUENCE: 156

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
            85                  90                  95

Glu Ser Val Asp Pro Asn Gln Tyr Tyr Lys Ile Arg Ser Gln Ala Ile
            100                 105                 110

His Gln Leu Lys Val Asn Gly Glu Asp Pro Tyr Pro His Lys Phe His
            115                 120                 125

Val Asp Ile Ser Leu Thr Asp Phe Ile Gln Lys Tyr Ser His Leu Gln
130                 135                 140

Pro Gly Asp His Leu Thr Asp Ile Thr Leu Lys Val Ala Gly Arg Ile
145                 150                 155                 160

His Ala Lys Arg Ala Ser Gly Gly Lys Leu Ile Phe Tyr Asp Leu Arg
                165                 170                 175

Gly Glu Gly Val Lys Leu Gln Val Met Ala Asn Ser Arg Asn Tyr Lys
            180                 185                 190

Ser Glu Glu Phe Ile His Ile Asn Asn Lys Leu Arg Arg Gly Asp
        195                 200                 205

Ile Ile Gly Val Gln Gly Asn Pro Gly Lys Thr Lys Lys Gly Glu Leu
    210                 215                 220

Ser Ile Ile Pro Tyr Glu Ile Thr Leu Leu Ser Pro Cys Leu His Met
225                 230                 235                 240

Leu Pro His Leu His Phe Gly Leu Lys Asp Lys Glu Thr Arg Tyr Arg
                245                 250                 255

Gln Arg Tyr Leu Asp Leu Ile Leu Asn Asp Phe Val Arg Gln Lys Phe
            260                 265                 270

Ile Ile Arg Ser Lys Ile Ile Thr Tyr Ile Arg Ser Phe Leu Asp Glu
        275                 280                 285

Leu Gly Phe Leu Glu Ile Glu Thr Pro Met Met Asn Ile Ile Pro Gly
    290                 295                 300

Gly Ala Val Ala Lys Pro Phe Ile Thr Tyr His Asn Glu Leu Asp Met
305                 310                 315                 320

Asn Leu Tyr Met Arg Ile Ala Pro Glu Leu Tyr His Lys Ala Lys Ala
                325                 330                 335

Ala Gly Asp Asp Glu Ala Met Phe Ile Asp Glu Asn Phe Cys Thr Ala
            340                 345                 350

Leu Glu Tyr Gly Leu Pro Pro Thr Ala Gly Trp Gly Met Gly Ile Asp
        355                 360                 365

Arg Val Ala Met Phe Leu Thr Asp Ser Asn Asn Ile Lys Glu Val Leu
    370                 375                 380

Leu Phe Pro Ala Met Lys Pro Glu Asp Lys Lys Glu Asn Val Ala Thr
385                 390                 395                 400

Thr Asp Thr Leu Glu Ser Thr Thr Val Gly Thr Ser Val
                405                 410

<210> SEQ ID NO 157
<211> LENGTH: 1242
<212> TYPE: DNA
<213> ORGANISM: Homo sapiens

<400> SEQUENCE: 157
atgttgacgc aagctgctgt aaggcttgtt aggggtccc tgcgcaaaac ctcctgggca    60
gagtggggtc acagggaact gcgactgggt caacttgctc ctttcacagc gcctcacaag   120
gacaagtcat tttctgatca agaagtgag ctgaagagac gcctgaaagc tgagaagaaa    180
gtagcagaga aggaggccaa acagaaagag ctcagtgaga aacagctaag ccaagccact    240
gctgctgcca ccaaccacac cactgataat ggtgtgggtc tgaggaaga gagcgtggac    300 ccaaatcaat actacaaaat ccgcagtcaa gcaattcatc agctgaaggt caatggggaa    360
gacccatacc cacacaagtt ccatgtagac atctcactca ctgacttcat ccaaaaatat    420

```
agtcacctgc agcctgggga tcacctgact gacatcacct taaaggtggc aggtaggatc    480
catgccaaaa gagcttctgg gggaaagctc atcttctatg atcttcgagg agagggggtg    540
aagttgcaag tcatggccaa ttccagaaat tataaatcag aagaagaatt tattcatatt    600
aataacaaac tgcgtcgggg agacataatt ggagttcagg ggaatcctgg taaaaccaag    660
aagggtgagc tgagcatcat tccgtatgag atcacactgc tgtctccctg tttgcatatg    720
ttacctcatc ttcactttgg cctcaaagac aaggaaacaa ggtatcgcca gagatacttg    780
gacttgatcc tgaatgactt tgtgaggcag aaatttatca tccgctctaa gatcatcaca    840
tatataagaa gtttcttaga tgagctggga ttcctagaga ttgaaactcc catgatgaac    900
atcatcccag ggggagccgt ggccaagcct ttcatcactt atcacaacga gctggacatg    960
aacttatata tgagaattgc tccagaactc tatcataagg ccaaggctgc aggtgatgat   1020
gaggccatgt tcatagatga aaacttctgt actgccctgg aatatgggct gccccccaca   1080
gctggctggg gcatgggcat tgatcgagtc gccatgtttc tcacggactc caacaacatc   1140
aaggaagtac ttctgtttcc tgccatgaaa cccgaagaca agaaggagaa tgtagcaacc   1200
actgatacac tggaaagcac aacagttggc acttctgtct ag                     1242

<210> SEQ ID NO 158
<211> LENGTH: 104
<212> TYPE: PRT
<213> ORGANISM: Homo sapiens

<400> SEQUENCE: 158

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Lys Leu
            100

<210> SEQ ID NO 159
<211> LENGTH: 315
<212> TYPE: DNA
<213> ORGANISM: Homo sapiens

<400> SEQUENCE: 159
atgttgacgc aagctgctgt aaggcttgtt aggggtccc tgcgcaaaac ctcctgggca     60
gagtggggtc acagggaact gcgactgggt caacttgctc ctttcacagc gcctcacaag    120
gacaagtcat tttctgatca agaagtgag ctgaagagac gcctgaaagc tgagaagaaa    180
gtagcagaga aggaggccaa acagaaagag ctcagtgaga aacagctaag ccaagccact    240
gctgctgcca ccaaccacac cactgataat ggtgtgggtc ctgaggaaga gagcgtggac    300
ccaaataaat ataa                                                     315
```

```
<210> SEQ ID NO 160
<211> LENGTH: 49
<212> TYPE: PRT
<213> ORGANISM: Homo sapiens

<400> SEQUENCE: 160

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Arg

<210> SEQ ID NO 161
<211> LENGTH: 150
<212> TYPE: DNA
<213> ORGANISM: Homo sapiens

<400> SEQUENCE: 161
atgttgacgc aagctgctgt aaggcttgtt aggggggtccc tgcgcaaaac ctcctgggca      60
gagtggggtc acagggaact gcgactgggt caacttgctc ctttcacagc gcctcacaag     120
gacaagtcat tttctgatca agaaggtag                                       150

<210> SEQ ID NO 162
<211> LENGTH: 177
<212> TYPE: PRT
<213> ORGANISM: Homo sapiens

<400> SEQUENCE: 162

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Gln Tyr Tyr Lys Ile Arg Ser Gln Ala Ile
            100                 105                 110

His Gln Leu Lys Val Asn Gly Glu Asp Pro Tyr Pro His Lys Phe His
        115                 120                 125

Val Asp Ile Ser Leu Thr Asp Phe Ile Gln Lys Tyr Ser His Leu Gln
    130                 135                 140

Pro Gly Asp His Leu Thr Asp Ile Thr Leu Lys Val Ala Glu Ile Ile
145                 150                 155                 160

Asn Gln Lys Lys Asn Leu Phe Ile Leu Ile Thr Asn Cys Val Gly Glu
                165                 170                 175

Thr

<210> SEQ ID NO 163
<211> LENGTH: 534
<212> TYPE: DNA
```

<213> ORGANISM: Homo sapiens

<400> SEQUENCE: 163

```
atgttgacgc aagctgctgt aaggcttgtt aggggggtccc tgcgcaaaac ctcctgggca      60
gagtggggtc acagggaact gcgactgggt caacttgctc ctttcacagc gcctcacaag     120
gacaagtcat tttctgatca agaagtgag ctgaagagac gcctgaaagc tgagaagaaa      180
gtagcagaga aggaggccaa acagaaagag ctcagtgaga aacagctaag ccaagccact     240
gctgctgcca ccaaccacac cactgataat ggtgtgggtc ctgaggaaga gagcgtggac     300
ccaaatcaat actacaaaat ccgcagtcaa gcaattcatc agctgaaggt caatggggaa     360
gacccatacc cacacaagtt ccatgtagac atctcactca ctgacttcat ccaaaaatat     420
agtcacctgc agcctgggga tcacctgact gacatcacct taaaggtggc agaaattata     480
aatcagaaga gaatttatt catattaata acaaactgcg tcggggagac ataa            534
```

<210> SEQ ID NO 164
<211> LENGTH: 287
<212> TYPE: PRT
<213> ORGANISM: Homo sapiens

<400> SEQUENCE: 164

```
Met Leu Thr Gln Ala Ala Val Arg Leu Val Arg Gly Ser Leu Arg Lys
1               5                   10                  15
Thr Ser Trp Ala Glu Trp Gly His Arg Glu Leu Arg Leu Gly Gln Leu
                20                  25                  30
Ala Pro Phe Thr Ala Pro His Lys Asp Lys Ser Phe Ser Asp Gln Arg
            35                  40                  45
Ser Glu Leu Lys Arg Arg Leu Lys Ala Glu Lys Val Ala Glu Lys
        50                  55                  60
Glu Ala Lys Gln Lys Glu Leu Ser Glu Lys Gln Leu Ser Gln Ala Thr
65                  70                  75                  80
Ala Ala Ala Thr Asn His Thr Thr Asp Asn Gly Val Gly Pro Glu Glu
                85                  90                  95
Glu Ser Val Asp Pro Asn Gln Tyr Tyr Lys Ile Arg Ser Gln Ala Ile
            100                 105                 110
His Gln Leu Lys Val Asn Gly Glu Asp Pro Tyr Pro His Lys Phe His
        115                 120                 125
Val Asp Ile Ser Leu Thr Asp Phe Ile Gln Lys Tyr Ser His Leu Gln
130                 135                 140
Pro Gly Asp His Leu Thr Asp Ile Thr Leu Lys Val Ala Gly Arg Ile
145                 150                 155                 160
His Ala Lys Arg Ala Ser Gly Gly Lys Leu Ile Phe Tyr Asp Leu Arg
                165                 170                 175
Gly Glu Gly Val Lys Leu Gln Val Met Ala Asn Ser Arg Asn Tyr Lys
            180                 185                 190
Ser Glu Glu Glu Phe Ile His Ile Asn Asn Lys Leu Arg Arg Gly Asp
        195                 200                 205
Ile Ile Gly Val Gln Gly Asn Pro Gly Lys Thr Lys Lys Gly Glu Leu
    210                 215                 220
Ser Ile Ile Pro Tyr Glu Ile Thr Leu Leu Ser Pro Cys Leu His Met
225                 230                 235                 240
Leu Pro His Leu His Phe Gly Leu Lys Asp Lys Leu Ala Lys Phe
                245                 250                 255
Leu Met Ile Ser Val Trp Gln Lys Leu Leu Asn Ala Leu His Leu Gly
```

Pro Gln Pro Gly Ser Leu Thr Ser Leu Leu Gly Ser Ser Trp Lys
    260             265             270
            275             280             285

<210> SEQ ID NO 165
<211> LENGTH: 864
<212> TYPE: DNA
<213> ORGANISM: Homo sapiens

<400> SEQUENCE: 165
atgttgacgc aagctgctgt aaggcttgtt aggggggtccc tgcgcaaaac ctcctgggca      60
gagtggggtc acagggaact gcgactgggt caacttgctc ctttcacagc gcctcacaag     120
gacaagtcat tttctgatca agaagtgag ctgaagagac gcctgaaagc tgagaagaaa      180
gtagcagaga aggaggccaa acagaaagag ctcagtgaga acagctaag ccaagccact      240 gctgctgcca ccaaccacac cactgataat ggtgtgggtc ctgaggaaga gagcgtggac     300
ccaaatcaat actacaaaat ccgcagtcaa gcaattcatc agctgaaggt caatggggaa     360
gacccatacc cacacaagtt ccatgtagac atctcactca ctgacttcat ccaaaaatat     420
agtcacctgc agcctgggga tcacctgact gacatcacct taaaggtggc aggtaggatc     480
catgccaaaa gagcttctgg gggaaagctc atcttctatg atcttcgagg agaggggggtg      540 aagttgcaag tcatggccaa ttccagaaat tataaatcag aagaagaatt tattcatatt     600
aataacaaac tgcgtcgggg agacataatt ggagttcagg ggaatcctgg taaaaccaag     660
aagggtgagc tgagcatcat tccgtatgag atcacactgc tgtctccctg tttgcatatg     720
ttacctcatc ttcactttgg cctcaaagac aagaaactcg caaaattctt gatgatatct     780
gtgtggcaaa agctgttgaa tgccctccac ctcggaccac agccaggctc cttgacaagc     840
ttgttgggga gttcctggaa gtga                                            864

<210> SEQ ID NO 166
<211> LENGTH: 50
<212> TYPE: DNA
<213> ORGANISM: Homo sapiens

<400> SEQUENCE: 166
acaagtcatt ttctgatcaa agaagcaata ctacaaaatc cgcagtcaag                  50

<210> SEQ ID NO 167
<211> LENGTH: 16
<212> TYPE: PRT
<213> ORGANISM: Homo sapiens

<400> SEQUENCE: 167

Lys Ser Phe Ser Asp Gln Arg Ser Asn Thr Thr Lys Ser Ala Val Lys
1               5                   10                  15

<210> SEQ ID NO 168
<211> LENGTH: 50
<212> TYPE: DNA
<213> ORGANISM: Homo sapiens

<400> SEQUENCE: 168
tgaggaagag agcgtggacc caaatgtagg atccatgcca aaagagcttc                  50

<210> SEQ ID NO 169
<211> LENGTH: 16
<212> TYPE: PRT
<213> ORGANISM: Homo sapiens

<400> SEQUENCE: 169

Glu Glu Glu Ser Val Asp Pro Asn Val Gly Ser Met Pro Lys Glu Leu
1               5                   10                  15

<210> SEQ ID NO 170
<211> LENGTH: 50
<212> TYPE: DNA
<213> ORGANISM: Homo sapiens

<400> SEQUENCE: 170
cttagatgag ctgggattcc tagagatgct tgtggttggt ggcatcgacc           50

<210> SEQ ID NO 171
<211> LENGTH: 16
<212> TYPE: PRT
<213> ORGANISM: Homo sapiens

<400> SEQUENCE: 171

Leu Asp Glu Leu Gly Phe Leu Glu Met Leu Val Val Gly Gly Ile Asp
1               5                   10                  15

<210> SEQ ID NO 172
<211> LENGTH: 49
<212> TYPE: DNA
<213> ORGANISM: Homo sapiens

<400> SEQUENCE: 172
tgaggaagag agcgtggacc caaatattga aactcccatg atgaacatc             49

<210> SEQ ID NO 173
<211> LENGTH: 16
<212> TYPE: PRT
<213> ORGANISM: Homo sapiens

<400> SEQUENCE: 173

Glu Glu Glu Ser Val Asp Pro Asn Ile Glu Thr Pro Met Met Asn Ile
1               5                   10                  15

<210> SEQ ID NO 174
<211> LENGTH: 50
<212> TYPE: DNA
<213> ORGANISM: Homo sapiens

<400> SEQUENCE: 174
aattgctcca gaactctatc ataaggccaa ggctgcaggt gatgatgagg           50

<210> SEQ ID NO 175
<211> LENGTH: 16
<212> TYPE: PRT
<213> ORGANISM: Homo sapiens

<400> SEQUENCE: 175

Ile Ala Pro Glu Leu Tyr His Lys Ala Lys Ala Ala Gly Asp Asp Glu
1               5                   10                  15

<210> SEQ ID NO 176
<211> LENGTH: 50
<212> TYPE: DNA
<213> ORGANISM: Homo sapiens

<400> SEQUENCE: 176
tgaggaagag agcgtggacc caaataaatt ataaatcaga agaagaattt           50

<210> SEQ ID NO 177
<211> LENGTH: 10
<212> TYPE: PRT
<213> ORGANISM: Homo sapiens

<400> SEQUENCE: 177

Glu Glu Glu Ser Val Asp Pro Asn Lys Leu
1               5                   10

<210> SEQ ID NO 178
<211> LENGTH: 50
<212> TYPE: DNA
<213> ORGANISM: Homo sapiens

<400> SEQUENCE: 178
acaagtcatt ttctgatcaa agaaggtagg atccatgcca aaagagcttc          50

<210> SEQ ID NO 179
<211> LENGTH: 8
<212> TYPE: PRT
<213> ORGANISM: Homo sapiens

<400> SEQUENCE: 179

Lys Ser Phe Ser Asp Gln Arg Arg
1               5

<210> SEQ ID NO 180
<211> LENGTH: 50
<212> TYPE: DNA
<213> ORGANISM: Homo sapiens

<400> SEQUENCE: 180
actgacatca ccttaaaggt ggcagaaatt ataaatcaga agaagaattt          50

<210> SEQ ID NO 181
<211> LENGTH: 16
<212> TYPE: PRT
<213> ORGANISM: Homo sapiens

<400> SEQUENCE: 181

Thr Asp Ile Thr Leu Lys Val Ala Glu Ile Ile Asn Gln Lys Lys Asn
1               5                   10                  15

<210> SEQ ID NO 182
<211> LENGTH: 50
<212> TYPE: DNA
<213> ORGANISM: Homo sapiens

<400> SEQUENCE: 182
tcttcacttt ggcctcaaag acaagaaact cgcaaaattc ttgatgatat          50

<210> SEQ ID NO 183
<211> LENGTH: 16
<212> TYPE: PRT
<213> ORGANISM: Homo sapiens

<400> SEQUENCE: 183

Leu His Phe Gly Leu Lys Asp Lys Lys Leu Ala Lys Phe Leu Met Ile
1               5                   10                  15

<210> SEQ ID NO 184
<211> LENGTH: 104
<212> TYPE: PRT
<213> ORGANISM: Homo sapiens

<400> SEQUENCE: 184

| Met | Leu | Thr | Gln | Ala | Ala | Val | Arg | Leu | Val | Arg | Gly | Ser | Leu | Arg | Lys |
|---|---|---|---|---|---|---|---|---|---|---|---|---|---|---|---|
| 1 | | | | 5 | | | | | 10 | | | | | 15 | |

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
            35                  40                  45

Ser Glu Leu Lys Arg Arg Leu Lys Ala Glu Lys Lys Val Ala Glu Lys
        50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Gln Tyr
            100

<210> SEQ ID NO 185
<211> LENGTH: 312
<212> TYPE: DNA
<213> ORGANISM: Homo sapiens

<400> SEQUENCE: 185

```
atgttgacgc aagctgctgt aaggcttgtt aggggggtccc tgcgcaaaac ctcctgggca    60
gagtggggtc acagggaact gcgactgggt caacttgctc ctttcacagc gcctcacaag   120
gacaagtcat tttctgatca agaagtgag ctgaagagac gcctgaaagc tgagaagaaa   180
gtagcagaga aggaggccaa acagaaagag ctcagtgaga acagctaag ccaagccact   240
gctgctgcca ccaaccacac cactgataat ggtgtgggtc ctgaggaaga gagcgtggac   300
ccaaatcaat ac                                                      312
```

<210> SEQ ID NO 186
<211> LENGTH: 222
<212> TYPE: PRT
<213> ORGANISM: Homo sapiens

<400> SEQUENCE: 186

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Gln Tyr Tyr Lys Ile Arg Ser Gln Ala Ile
            100                 105                 110

His Gln Leu Lys Val Asn Gly Glu Asp Pro Tyr Pro His Lys Phe His
        115                 120                 125

Val Asp Ile Ser Leu Thr Asp Phe Ile Gln Lys Tyr Ser His Leu Gln
    130                 135                 140

Pro Gly Asp His Leu Thr Asp Ile Thr Leu Lys Val Ala Gly Arg Ile
145                 150                 155                 160

His Ala Lys Arg Ala Ser Gly Gly Lys Leu Ile Phe Tyr Asp Leu Arg
            165                 170                 175

Gly Glu Gly Val Lys Leu Gln Val Met Ala Asn Ser Arg Asn Tyr Lys
        180                 185                 190

Ser Glu Glu Glu Phe Ile His Ile Asn Asn Lys Leu Arg Arg Gly Asp
    195                 200                 205

Ile Ile Gly Val Gln Gly Asn Pro Gly Lys Thr Lys Lys Gly
    210                 215                 220

```
<210> SEQ ID NO 187
<211> LENGTH: 666
<212> TYPE: DNA
<213> ORGANISM: Homo sapiens

<400> SEQUENCE: 187
atgttgacgc aagctgctgt aaggcttgtt aggggtccc tgcgcaaaac ctcctgggca    60
gagtggggtc acagggaact gcgactgggt caacttgctc ctttcacagc gcctcacaag   120
gacaagtcat tttctgatca agaagtgag ctgaagagac gcctgaaagc tgagaagaaa   180
gtagcagaga aggaggccaa acagaaagag ctcagtgaga acagctaag ccaagccact   240 gctgctgcca ccaaccacac cactgataat ggtgtgggtc ctgaggaaga gagcgtggac   300
ccaaatcaat actacaaaat ccgcagtcaa gcaattcatc agctgaaggt caatggggaa   360
gacccatacc cacacaagtt ccatgtagac atctcactca ctgacttcat ccaaaaatat   420
agtcacctgc agcctgggga tcacctgact gacatcacct taaaggtggc aggtaggatc   480
catgccaaaa gagcttctgg gggaaagctc atcttctatg atcttcgagg agaggggtg   540 aagttgcaag tcatggccaa ttccagaaat tataaatcag aagaagaatt tattcatatt   600
aataacaaac tgcgtcgggg agacataatt ggagttcagg ggaatcctgg taaaaccaag   660
aagggt                                                              666

<210> SEQ ID NO 188
<211> LENGTH: 93
<212> TYPE: PRT
<213> ORGANISM: Homo sapiens

<400> SEQUENCE: 188
```

Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly
                85                  90

```
<210> SEQ ID NO 189
<211> LENGTH: 279
<212> TYPE: DNA
<213> ORGANISM: Homo sapiens
```

<400> SEQUENCE: 189

```
atgttgacgc aagctgctgt aaggcttgtt aggggggtccc tgcgcaaaac ctcctgggca    60
gagtggggtc acagggaact gcgactgggt caacttgctc ctttcacagc gcctcacaag   120
gacaagtcat tttctgatca agaagtgag ctgaagagac gcctgaaagc tgagaagaaa   180
gtagcagaga aggaggccaa acagaaagag ctcagtgaga aacagctaag ccaagccact   240
gctgctgcca ccaaccacac cactgataat ggtgtgggt                          279
```

<210> SEQ ID NO 190
<211> LENGTH: 242
<212> TYPE: PRT
<213> ORGANISM: Homo sapiens

<400> SEQUENCE: 190

```
Met Leu Thr Gln Ala Ala Val Arg Leu Val Arg Gly Ser Leu Arg Lys
1               5                   10                  15

Thr Ser Trp Ala Glu Trp Gly His Arg Glu Leu Arg Leu Gly Gln Leu
            20                  25                  30

Ala Pro Phe Thr Ala Pro His Lys Asp Lys Ser Phe Ser Asp Gln Arg
        35                  40                  45

Ser Glu Leu Lys Arg Arg Leu Lys Ala Glu Lys Val Ala Glu Lys
    50                  55                  60

Glu Ala Lys Gln Lys Glu Leu Ser Glu Lys Gln Leu Ser Gln Ala Thr
65                  70                  75                  80

Ala Ala Ala Thr Asn His Thr Thr Asp Asn Gly Val Gly Pro Glu Glu
                85                  90                  95

Glu Ser Val Asp Pro Asn Gln Tyr Tyr Lys Ile Arg Ser Gln Ala Ile
            100                 105                 110

His Gln Leu Lys Val Asn Gly Glu Asp Pro Tyr Pro His Lys Phe His
        115                 120                 125

Val Asp Ile Ser Leu Thr Asp Phe Ile Gln Lys Tyr Ser His Leu Gln
    130                 135                 140

Pro Gly Asp His Leu Thr Asp Ile Thr Leu Lys Val Ala Gly Arg Ile
145                 150                 155                 160

His Ala Lys Arg Ala Ser Gly Gly Lys Leu Ile Phe Tyr Asp Leu Arg
                165                 170                 175

Gly Glu Gly Val Lys Leu Gln Val Met Ala Asn Ser Arg Asn Tyr Lys
            180                 185                 190

Ser Glu Glu Glu Phe Ile His Ile Asn Asn Lys Leu Arg Arg Gly Asp
        195                 200                 205

Ile Ile Gly Val Gln Gly Asn Pro Gly Lys Thr Lys Lys Gly Glu Leu
    210                 215                 220

Ser Ile Ile Pro Tyr Glu Ile Thr Leu Leu Ser Pro Cys Leu His Met
225                 230                 235                 240

Leu Pro
```

<210> SEQ ID NO 191
<211> LENGTH: 726
<212> TYPE: DNA
<213> ORGANISM: Homo sapiens

<400> SEQUENCE: 191

```
atgttgacgc aagctgctgt aaggcttgtt aggggggtccc tgcgcaaaac ctcctgggca    60
gagtggggtc acagggaact gcgactgggt caacttgctc ctttcacagc gcctcacaag   120
```

-continued

```
gacaagtcat tttctgatca agaagtgag ctgaagagac gcctgaaagc tgagaagaaa    180
gtagcagaga aggaggccaa acagaaagag ctcagtgaga aacagctaag ccaagccact    240
gctgctgcca ccaaccacac cactgataat ggtgtgggtc ctgaggaaga gagcgtggac    300
ccaaatcaat actacaaaat ccgcagtcaa gcaattcatc agctgaaggt caatggggaa    360
gacccatacc cacacaagtt ccatgtagac atctcactca ctgacttcat ccaaaaatat    420
agtcacctgc agcctgggga tcacctgact gacatcacct aaaggtggc aggtaggatc     480 catgccaaaa gagcttctgg gggaaagctc atcttctatg atcttcgagg agaggggtg     540 aagttgcaag tcatggccaa ttccagaaat tataaatcag aagaagaatt tattcatatt    600
aataacaaac tgcgtcgggg agacataatt ggagttcagg ggaatcctgg taaaaccaag    660
aagggtgagc tgagcatcat tccgtatgag atcacactgc tgtctccctg tttgcatatg    720
ttacct                                                                726
```

<210> SEQ ID NO 192
<211> LENGTH: 418
<212> TYPE: PRT
<213> ORGANISM: Artificial Sequence
<220> FEATURE:
<223> OTHER INFORMATION: Lysyl tRNA Synthetase polypeptide with
    N-terminal 6xHis affinity tag

<400> SEQUENCE: 192

```
Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Arg Leu Lys Ala Glu
65                  70                  75                  80

Lys Lys Val Ala Glu Lys Glu Ala Lys Gln Lys Glu Leu Ser Glu Lys
                85                  90                  95

Gln Leu Ser Gln Ala Thr Ala Ala Thr Asn His Thr Thr Asp Asn
            100                 105                 110

Gly Val Gly Pro Glu Glu Glu Ser Val Asp Pro Asn Gln Tyr Tyr Lys
        115                 120                 125

Ile Arg Ser Gln Ala Ile His Gln Leu Lys Val Asn Gly Glu Asp Pro
    130                 135                 140

Tyr Pro His Lys Phe His Val Asp Ile Ser Leu Thr Asp Phe Ile Gln
145                 150                 155                 160

Lys Tyr Ser His Leu Gln Pro Gly Asp His Leu Thr Asp Ile Thr Leu
                165                 170                 175

Lys Val Ala Gly Arg Ile His Ala Lys Arg Ala Ser Gly Gly Lys Leu
            180                 185                 190

Ile Phe Tyr Asp Leu Arg Gly Glu Gly Val Lys Leu Gln Val Met Ala
        195                 200                 205

Asn Ser Arg Asn Tyr Lys Ser Glu Glu Glu Phe Ile His Ile Asn Asn
    210                 215                 220

Lys Leu Arg Arg Gly Asp Ile Ile Gly Val Gln Gly Asn Pro Gly Lys
225                 230                 235                 240

Thr Lys Lys Gly Glu Leu Ser Ile Ile Pro Tyr Glu Ile Thr Leu Leu
```

```
                245                 250                 255
Ser Pro Cys Leu His Met Leu Pro His Leu His Phe Gly Leu Lys Asp
            260                 265                 270

Lys Glu Thr Arg Tyr Arg Gln Arg Tyr Leu Asp Leu Ile Leu Asn Asp
        275                 280                 285

Phe Val Arg Gln Lys Phe Ile Ile Arg Ser Lys Ile Ile Thr Tyr Ile
    290                 295                 300

Arg Ser Phe Leu Asp Glu Leu Gly Phe Leu Glu Ile Glu Thr Pro Met
305                 310                 315                 320

Met Asn Ile Ile Pro Gly Gly Ala Val Ala Lys Pro Phe Ile Thr Tyr
                325                 330                 335

His Asn Glu Leu Asp Met Asn Leu Tyr Met Arg Ile Ala Pro Glu Leu
            340                 345                 350

Tyr His Lys Met Leu Val Val Gly Gly Ile Asp Arg Val Tyr Glu Ile
        355                 360                 365

Gly Arg Gln Phe Arg Asn Glu Gly Ile Asp Leu Thr His Asn Pro Glu
    370                 375                 380

Phe Thr Thr Cys Glu Phe Tyr Met Ala Tyr Ala Asp Tyr His Asp Leu
385                 390                 395                 400

Met Glu Ile Thr Glu Lys Met Val Ser Gly Met Val Lys His Ile Thr
                405                 410                 415

Leu Glu

<210> SEQ ID NO 193
<211> LENGTH: 418
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 193

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
        35                  40                  45

Gln Arg Ser Glu Leu Lys Arg Leu Lys Ala Glu Lys Lys Val Ala
    50                  55                  60

Glu Lys Glu Ala Lys Gln Lys Glu Leu Ser Lys Gln Leu Ser Gln
65                  70                  75                  80

Ala Thr Ala Ala Thr Asn His Thr Thr Asp Asn Gly Val Gly Pro
                85                  90                  95

Glu Glu Glu Ser Val Asp Pro Asn Gln Tyr Tyr Lys Ile Arg Ser Gln
            100                 105                 110

Ala Ile His Gln Leu Lys Val Asn Gly Glu Asp Pro Tyr Pro His Lys
        115                 120                 125

Phe His Val Asp Ile Ser Leu Thr Asp Phe Ile Gln Lys Tyr Ser His
    130                 135                 140

Leu Gln Pro Gly Asp His Leu Thr Asp Ile Thr Leu Lys Val Ala Gly
145                 150                 155                 160

Arg Ile His Ala Lys Arg Ala Ser Gly Gly Lys Leu Ile Phe Tyr Asp
                165                 170                 175

Leu Arg Gly Glu Gly Val Lys Leu Gln Val Met Ala Asn Ser Arg Asn
```

```
                180                 185                 190
Tyr Lys Ser Glu Glu Phe Ile His Ile Asn Asn Lys Leu Arg Arg
            195                 200                 205

Gly Asp Ile Ile Gly Val Gln Gly Asn Pro Gly Lys Thr Lys Lys Gly
            210                 215                 220

Glu Leu Ser Ile Ile Pro Tyr Glu Ile Thr Leu Leu Ser Pro Cys Leu
225                 230                 235                 240

His Met Leu Pro His Leu His Phe Gly Leu Lys Asp Lys Glu Thr Arg
                245                 250                 255

Tyr Arg Gln Arg Tyr Leu Asp Leu Ile Leu Asn Asp Phe Val Arg Gln
            260                 265                 270

Lys Phe Ile Ile Arg Ser Lys Ile Ile Thr Tyr Ile Arg Ser Phe Leu
            275                 280                 285

Asp Glu Leu Gly Phe Leu Glu Ile Glu Thr Pro Met Met Asn Ile Ile
            290                 295                 300

Pro Gly Gly Ala Val Ala Lys Pro Phe Ile Thr Tyr His Asn Glu Leu
305                 310                 315                 320

Asp Met Asn Leu Tyr Met Arg Ile Ala Pro Glu Leu Tyr His Lys Met
                325                 330                 335

Leu Val Val Gly Gly Ile Asp Arg Val Tyr Glu Ile Gly Arg Gln Phe
            340                 345                 350

Arg Asn Glu Gly Ile Asp Leu Thr His Asn Pro Glu Phe Thr Thr Cys
            355                 360                 365

Glu Phe Tyr Met Ala Tyr Ala Asp Tyr His Asp Leu Met Glu Ile Thr
            370                 375                 380

Glu Lys Met Val Ser Gly Met Val Lys His Ile Thr Leu Glu Gly Lys
385                 390                 395                 400

Pro Ile Pro Asn Pro Leu Leu Gly Leu Asp Ser Thr His His His
                405                 410                 415

His His

<210> SEQ ID NO 194
<211> LENGTH: 128
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 194

Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Arg Leu Lys Ala Glu
65                  70                  75                  80

Lys Lys Val Ala Glu Lys Ala Lys Gln Lys Glu Leu Ser Glu Lys
                85                  90                  95

Gln Leu Ser Gln Ala Thr Ala Ala Ala Thr Asn His Thr Thr Asp Asn
            100                 105                 110

Gly Val Gly Pro Glu Glu Glu Ser Val Asp Pro Asn Gln Tyr Leu Glu
```

<210> SEQ ID NO 195
<211> LENGTH: 128
<212> TYPE: PRT
<213> ORGANISM: Artificial Sequence
<220> FEATURE:
<223> OTHER INFORMATION: Lysyl tRNA Synthetase polypeptide with C-terminal 6xHis affinity tag

<400> SEQUENCE: 195

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
        35                  40                  45

Gln Arg Ser Glu Leu Lys Arg Arg Leu Lys Ala Glu Lys Lys Val Ala
    50                  55                  60

Glu Lys Glu Ala Lys Gln Lys Glu Leu Ser Glu Lys Gln Leu Ser Gln
65                  70                  75                  80

Ala Thr Ala Ala Thr Asn His Thr Thr Asp Asn Gly Val Gly Pro
                85                  90                  95

Glu Glu Glu Ser Val Asp Pro Asn Gln Tyr Leu Glu Gly Lys Pro Ile
            100                 105                 110

Pro Asn Pro Leu Leu Gly Leu Asp Ser Thr His His His His His
        115                 120                 125

<210> SEQ ID NO 196
<211> LENGTH: 246
<212> TYPE: PRT
<213> ORGANISM: Artificial Sequence
<220> FEATURE:
<223> OTHER INFORMATION: Lysyl tRNA Synthetase polypeptide with N-terminal 6xHis affinity tag

<400> SEQUENCE: 196

Met His His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Arg Leu Lys Ala Glu
65                  70                  75                  80

Lys Lys Val Ala Glu Lys Glu Ala Lys Gln Lys Glu Leu Ser Glu Lys
                85                  90                  95

Gln Leu Ser Gln Ala Thr Ala Ala Thr Asn His Thr Thr Asp Asn
            100                 105                 110

Gly Val Gly Pro Glu Glu Glu Ser Val Asp Pro Asn Gln Tyr Tyr Lys
        115                 120                 125

Ile Arg Ser Gln Ala Ile His Gln Leu Lys Val Asn Gly Glu Asp Pro
    130                 135                 140

Tyr Pro His Lys Phe His Val Asp Ile Ser Leu Thr Asp Phe Ile Gln
145                 150                 155                 160

Lys Tyr Ser His Leu Gln Pro Gly Asp His Leu Thr Asp Ile Thr Leu

```
                165                 170                 175
Lys Val Ala Gly Arg Ile His Ala Lys Arg Ala Ser Gly Gly Lys Leu
            180                 185                 190

Ile Phe Tyr Asp Leu Arg Gly Glu Gly Val Lys Leu Gln Val Met Ala
            195                 200                 205

Asn Ser Arg Asn Tyr Lys Ser Glu Glu Glu Phe Ile His Ile Asn Asn
210                 215                 220

Lys Leu Arg Arg Gly Asp Ile Ile Gly Val Gln Gly Asn Pro Gly Lys
225                 230                 235                 240

Thr Lys Lys Gly Leu Glu
            245

<210> SEQ ID NO 197
<211> LENGTH: 246
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 197

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
            35                  40                  45

Gln Arg Ser Glu Leu Lys Arg Arg Leu Lys Ala Glu Lys Lys Val Ala
        50                  55                  60

Glu Lys Glu Ala Lys Gln Lys Glu Leu Ser Glu Lys Gln Leu Ser Gln
65                  70                  75                  80

Ala Thr Ala Ala Ala Thr Asn His Thr Thr Asp Asn Gly Val Gly Pro
                85                  90                  95

Glu Glu Glu Ser Val Asp Pro Asn Gln Tyr Tyr Lys Ile Arg Ser Gln
            100                 105                 110

Ala Ile His Gln Leu Lys Val Asn Gly Glu Asp Pro Tyr Pro His Lys
        115                 120                 125

Phe His Val Asp Ile Ser Leu Thr Asp Phe Ile Gln Lys Tyr Ser His
    130                 135                 140

Leu Gln Pro Gly Asp His Leu Thr Asp Ile Thr Leu Lys Val Ala Gly
145                 150                 155                 160

Arg Ile His Ala Lys Arg Ala Ser Gly Gly Lys Leu Ile Phe Tyr Asp
                165                 170                 175

Leu Arg Gly Glu Gly Val Lys Leu Gln Val Met Ala Asn Ser Arg Asn
            180                 185                 190

Tyr Lys Ser Glu Glu Glu Phe Ile His Ile Asn Asn Lys Leu Arg Arg
        195                 200                 205

Gly Asp Ile Ile Gly Val Gln Gly Asn Pro Gly Lys Thr Lys Lys Gly
    210                 215                 220

Leu Glu Gly Lys Pro Ile Pro Asn Pro Leu Leu Gly Leu Asp Ser Thr
225                 230                 235                 240

His His His His His His
            245

<210> SEQ ID NO 198
<211> LENGTH: 117
```

```
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 198
```

| Met | His | His | His | His | His | His | Gly | Lys | Pro | Ile | Pro | Asn | Pro | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Leu | Asp | Ser | Thr | Gly | Ser | Leu | Thr | Gln | Ala | Ala | Val | Arg | Leu | Val |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Gly | Ser | Leu | Arg | Lys | Thr | Ser | Trp | Ala | Glu | Trp | Gly | His | Arg | Glu |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Leu | Arg | Leu | Gly | Gln | Leu | Ala | Pro | Phe | Thr | Ala | Pro | His | Lys | Asp | Lys |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Ser | Phe | Ser | Asp | Gln | Arg | Ser | Glu | Leu | Lys | Arg | Arg | Leu | Lys | Ala | Glu |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Lys | Lys | Val | Ala | Glu | Lys | Glu | Ala | Lys | Gln | Lys | Glu | Leu | Ser | Glu | Lys |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Gln | Leu | Ser | Gln | Ala | Thr | Ala | Ala | Thr | Asn | His | Thr | Thr | Asp | Asn |
|-----|-----|-----|-----|-----|-----|-----|-----|-----|-----|-----|-----|-----|-----|-----|
|     |     |     | 100 |     |     |     |     | 105 |     |     |     |     | 110 |     |

| Gly | Val | Gly | Leu | Glu |
|-----|-----|-----|-----|-----|
|     |     |     | 115 |     |

```
<210> SEQ ID NO 199
<211> LENGTH: 117
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 199
```

| Met | Gly | Ser | Leu | Thr | Gln | Ala | Ala | Val | Arg | Leu | Val | Arg | Gly | Ser | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Lys | Thr | Ser | Trp | Ala | Glu | Trp | Gly | His | Arg | Glu | Leu | Arg | Leu | Gly |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Gln | Leu | Ala | Pro | Phe | Thr | Ala | Pro | His | Lys | Asp | Lys | Ser | Phe | Ser | Asp |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Gln | Arg | Ser | Glu | Leu | Lys | Arg | Arg | Leu | Lys | Ala | Glu | Lys | Lys | Val | Ala |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Glu | Lys | Glu | Ala | Lys | Gln | Lys | Glu | Leu | Ser | Glu | Lys | Gln | Leu | Ser | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Thr | Ala | Ala | Thr | Asn | His | Thr | Thr | Asp | Asn | Gly | Val | Gly | Leu |
|-----|-----|-----|-----|-----|-----|-----|-----|-----|-----|-----|-----|-----|-----|-----|
|     |     |     |     | 85  |     |     |     |     | 90  |     |     |     |     | 95  |

| Glu | Gly | Lys | Pro | Ile | Pro | Asn | Pro | Leu | Leu | Gly | Leu | Asp | Ser | Thr | His |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| His | His | His | His | His |
|-----|-----|-----|-----|-----|
|     |     |     | 115 |     |

```
<210> SEQ ID NO 200
<211> LENGTH: 266
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 200
```

| Met | His | His | His | His | His | His | Gly | Lys | Pro | Ile | Pro | Asn | Pro | Leu | Leu |
|-----|-----|-----|-----|-----|-----|-----|-----|-----|-----|-----|-----|-----|-----|-----|-----|

```
            1               5                  10                 15
         Gly Leu Asp Ser Thr Gly Ser Leu Thr Gln Ala Ala Val Arg Leu Val
                       20                  25                 30

Arg Gly Ser Leu Arg Lys Thr Ser Trp Ala Glu Trp Gly His Arg Glu
                       35                  40                 45

Leu Arg Leu Gly Gln Leu Ala Pro Phe Thr Ala Pro His Lys Asp Lys
                  50                  55                 60

Ser Phe Ser Asp Gln Arg Ser Glu Leu Lys Arg Arg Leu Lys Ala Glu
         65                  70                  75                 80

Lys Lys Val Ala Glu Lys Glu Ala Lys Gln Lys Glu Leu Ser Glu Lys
                            85                  90                 95

Gln Leu Ser Gln Ala Thr Ala Ala Thr Asn His Thr Thr Asp Asn
                        100                 105                110

Gly Val Gly Pro Glu Glu Ser Val Asp Pro Asn Gln Tyr Tyr Lys
                        115                 120                125

Ile Arg Ser Gln Ala Ile His Gln Leu Lys Val Asn Gly Glu Asp Pro
                    130                 135                140

Tyr Pro His Lys Phe His Val Asp Ile Ser Leu Thr Asp Phe Ile Gln
         145                 150                 155                160

Lys Tyr Ser His Leu Gln Pro Gly Asp His Leu Thr Asp Ile Thr Leu
                         165                 170                175

Lys Val Ala Gly Arg Ile His Ala Lys Arg Ala Ser Gly Gly Lys Leu
                     180                 185                190

Ile Phe Tyr Asp Leu Arg Gly Glu Gly Val Lys Leu Gln Val Met Ala
                     195                 200                205

Asn Ser Arg Asn Tyr Lys Ser Glu Glu Glu Phe Ile His Ile Asn Asn
                     210                 215                220

Lys Leu Arg Arg Gly Asp Ile Ile Gly Val Gln Gly Asn Pro Gly Lys
         225                 230                 235                240

Thr Lys Lys Gly Glu Leu Ser Ile Ile Pro Tyr Glu Ile Thr Leu Leu
                         245                 250                255

Ser Pro Cys Leu His Met Leu Pro Leu Glu
                         260                 265

<210> SEQ ID NO 201
<211> LENGTH: 266
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 201

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
                20                  25                  30

Gln Leu Ala Pro Phe Thr Ala Pro His Lys Asp Lys Ser Phe Ser Asp
            35                  40                  45

Gln Arg Ser Glu Leu Lys Arg Arg Leu Lys Ala Glu Lys Lys Val Ala
        50                  55                  60

Glu Lys Glu Ala Lys Gln Lys Glu Leu Ser Glu Lys Gln Leu Ser Gln
65                  70                  75                  80

Ala Thr Ala Ala Thr Asn His Thr Thr Asp Asn Gly Val Gly Pro
                85                  90                  95
```

Glu Glu Glu Ser Val Asp Pro Asn Gln Tyr Tyr Lys Ile Arg Ser Gln
            100                 105                 110

Ala Ile His Gln Leu Lys Val Asn Gly Glu Asp Pro Tyr Pro His Lys
        115                 120                 125

Phe His Val Asp Ile Ser Leu Thr Asp Phe Ile Gln Lys Tyr Ser His
    130                 135                 140

Leu Gln Pro Gly Asp His Leu Thr Asp Ile Thr Leu Lys Val Ala Gly
145                 150                 155                 160

Arg Ile His Ala Lys Arg Ala Ser Gly Gly Lys Leu Ile Phe Tyr Asp
                165                 170                 175

Leu Arg Gly Glu Gly Val Lys Leu Gln Val Met Ala Asn Ser Arg Asn
            180                 185                 190

Tyr Lys Ser Glu Glu Glu Phe Ile His Ile Asn Asn Lys Leu Arg Arg
        195                 200                 205

Gly Asp Ile Ile Gly Val Gln Gly Asn Pro Gly Lys Thr Lys Lys Gly
    210                 215                 220

Glu Leu Ser Ile Ile Pro Tyr Glu Ile Thr Leu Ser Pro Cys Leu
225                 230                 235                 240

His Met Leu Pro Leu Glu Gly Lys Pro Ile Pro Asn Pro Leu Leu Gly
                245                 250                 255

Leu Asp Ser Thr His His His His His
            260                 265

<210> SEQ ID NO 202
<211> LENGTH: 85
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 202

Met His His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Asn Thr Thr Lys Ser Ala Val Lys Gln
65                  70                  75                  80

Phe Ile Ser Leu Glu
            85

<210> SEQ ID NO 203
<211> LENGTH: 85
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 203

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

```
Gln Leu Ala Pro Phe Thr Ala Pro His Lys Asp Lys Ser Phe Ser Asp
            35                  40                  45

Gln Arg Ser Asn Thr Thr Lys Ser Ala Val Lys Gln Phe Ile Ser Leu
        50                  55                  60

Glu Gly Lys Pro Ile Pro Asn Pro Leu Leu Gly Leu Asp Ser Thr His
65                  70                  75                  80

His His His His His
                85
```

```
<210> SEQ ID NO 204
<211> LENGTH: 148
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 204

Met His His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Leu Lys Ala Glu
65                  70                  75                  80

Lys Lys Val Ala Glu Lys Ala Lys Gln Lys Glu Leu Ser Glu Lys
                85                  90                  95

Gln Leu Ser Gln Ala Thr Ala Ala Thr Asn His Thr Thr Asp Asn
            100                 105                 110

Gly Val Gly Pro Glu Glu Glu Ser Val Asp Pro Asn Val Gly Ser Met
        115                 120                 125

Pro Lys Glu Leu Leu Gly Glu Ser Ser Ser Ser Met Ile Phe Glu Glu
    130                 135                 140

Arg Gly Leu Glu
145
```

```
<210> SEQ ID NO 205
<211> LENGTH: 148
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 205

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
        35                  40                  45

Gln Arg Ser Glu Leu Lys Arg Arg Leu Lys Ala Glu Lys Lys Val Ala
    50                  55                  60

Glu Lys Glu Ala Lys Gln Lys Glu Leu Ser Glu Lys Gln Leu Ser Gln
65                  70                  75                  80
```

```
Ala Thr Ala Ala Ala Thr Asn His Thr Thr Asp Asn Gly Val Gly Pro
                85                  90                  95

Glu Glu Glu Ser Val Asp Pro Asn Val Gly Ser Met Pro Lys Glu Leu
            100                 105                 110

Leu Gly Glu Ser Ser Ser Met Ile Phe Glu Glu Arg Gly Leu Glu
        115                 120                 125

Gly Lys Pro Ile Pro Asn Pro Leu Leu Gly Leu Asp Ser Thr His His
    130                 135                 140

His His His His
145

<210> SEQ ID NO 206
<211> LENGTH: 458
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 206

Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Arg Leu Lys Ala Glu
65                  70                  75                  80

Lys Lys Val Ala Glu Lys Glu Ala Lys Gln Lys Glu Leu Ser Glu Lys
                85                  90                  95

Gln Leu Ser Gln Ala Thr Ala Ala Thr Asn His Thr Thr Asp Asn
            100                 105                 110

Gly Val Gly Pro Glu Glu Ser Val Asp Pro Asn Ile Glu Thr Pro
        115                 120                 125

Met Met Asn Ile Ile Pro Gly Gly Ala Val Ala Lys Pro Phe Ile Thr
    130                 135                 140

Tyr His Asn Glu Leu Asp Met Asn Leu Tyr Met Arg Ile Ala Pro Glu
145                 150                 155                 160

Leu Tyr His Lys Met Leu Val Val Gly Gly Ile Asp Arg Val Tyr Glu
                165                 170                 175

Ile Gly Arg Gln Phe Arg Asn Glu Gly Ile Asp Leu Thr His Asn Pro
            180                 185                 190

Glu Phe Thr Thr Cys Glu Phe Tyr Met Ala Tyr Ala Asp Tyr His Asp
        195                 200                 205

Leu Met Glu Ile Thr Glu Lys Met Val Ser Gly Met Val Lys His Ile
    210                 215                 220

Thr Gly Ser Tyr Lys Val Thr Tyr His Pro Asp Gly Pro Glu Gly Gln
225                 230                 235                 240

Ala Tyr Asp Val Asp Phe Thr Pro Pro Phe Arg Arg Ile Asn Met Val
                245                 250                 255

Glu Glu Leu Glu Lys Ala Leu Gly Met Lys Leu Pro Glu Thr Asn Leu
            260                 265                 270

Phe Glu Thr Glu Glu Thr Arg Lys Ile Leu Asp Asp Ile Cys Val Ala
        275                 280                 285
```

```
Lys Ala Val Glu Cys Pro Pro Arg Thr Thr Ala Arg Leu Leu Asp
    290                 295                 300

Lys Leu Val Gly Glu Phe Leu Glu Val Thr Cys Ile Asn Pro Thr Phe
305                 310                 315                 320

Ile Cys Asp His Pro Gln Ile Met Ser Pro Leu Ala Lys Trp His Arg
                325                 330                 335

Ser Lys Glu Gly Leu Thr Glu Arg Phe Glu Leu Phe Val Met Lys Lys
            340                 345                 350

Glu Ile Cys Asn Ala Tyr Thr Glu Leu Asn Asp Pro Met Arg Gln Arg
        355                 360                 365

Gln Leu Phe Glu Glu Gln Ala Lys Ala Lys Ala Gly Asp Asp Glu
    370                 375                 380

Ala Met Phe Ile Asp Glu Asn Phe Cys Thr Ala Leu Glu Tyr Gly Leu
385                 390                 395                 400

Pro Pro Thr Ala Gly Trp Gly Met Gly Ile Asp Arg Val Ala Met Phe
                405                 410                 415

Leu Thr Asp Ser Asn Asn Ile Lys Glu Val Leu Leu Phe Pro Ala Met
            420                 425                 430

Lys Pro Glu Asp Lys Lys Glu Asn Val Ala Thr Thr Asp Thr Leu Glu
        435                 440                 445

Ser Thr Thr Val Gly Thr Ser Val Leu Glu
    450                 455
```

<210> SEQ ID NO 207
<211> LENGTH: 458
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 207

```
Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
        35                  40                  45

Gln Arg Ser Glu Leu Lys Arg Leu Lys Ala Glu Lys Lys Val Ala
    50                  55                  60

Glu Lys Glu Ala Lys Gln Lys Glu Leu Ser Lys Gln Leu Ser Gln
65                  70                  75                  80

Ala Thr Ala Ala Ala Thr Asn His Thr Thr Asp Asn Gly Val Gly Pro
                85                  90                  95

Glu Glu Glu Ser Val Asp Pro Asn Ile Glu Thr Pro Met Met Asn Ile
            100                 105                 110

Ile Pro Gly Gly Ala Val Ala Lys Pro Phe Ile Thr Tyr His Asn Glu
        115                 120                 125

Leu Asp Met Asn Leu Tyr Met Arg Ile Ala Pro Glu Leu Tyr His Lys
    130                 135                 140

Met Leu Val Val Gly Gly Ile Asp Arg Val Tyr Glu Ile Gly Arg Gln
145                 150                 155                 160

Phe Arg Asn Glu Gly Ile Asp Leu Thr His Asn Pro Glu Phe Thr Thr
                165                 170                 175

Cys Glu Phe Tyr Met Ala Tyr Ala Asp Tyr His Asp Leu Met Glu Ile
```

-continued

```
                180                 185                 190
Thr Glu Lys Met Val Ser Gly Met Val Lys His Ile Thr Gly Ser Tyr
                    195                 200                 205
Lys Val Thr Tyr His Pro Asp Gly Pro Glu Gly Gln Ala Tyr Asp Val
                210                 215                 220
Asp Phe Thr Pro Pro Phe Arg Arg Ile Asn Met Val Glu Glu Leu Glu
225                 230                 235                 240
Lys Ala Leu Gly Met Lys Leu Pro Glu Thr Asn Leu Phe Glu Thr Glu
                    245                 250                 255
Glu Thr Arg Lys Ile Leu Asp Asp Ile Cys Val Ala Lys Ala Val Glu
                260                 265                 270
Cys Pro Pro Arg Thr Thr Ala Arg Leu Leu Asp Lys Leu Val Gly
                275                 280                 285
Glu Phe Leu Glu Val Thr Cys Ile Asn Pro Thr Phe Ile Cys Asp His
                290                 295                 300
Pro Gln Ile Met Ser Pro Leu Ala Lys Trp His Arg Ser Lys Glu Gly
305                 310                 315                 320
Leu Thr Glu Arg Phe Glu Leu Phe Val Met Lys Lys Glu Ile Cys Asn
                    325                 330                 335
Ala Tyr Thr Glu Leu Asn Asp Pro Met Arg Gln Arg Gln Leu Phe Glu
                340                 345                 350
Glu Gln Ala Lys Ala Lys Ala Ala Gly Asp Asp Glu Ala Met Phe Ile
                355                 360                 365
Asp Glu Asn Phe Cys Thr Ala Leu Glu Tyr Gly Leu Pro Pro Thr Ala
                370                 375                 380
Gly Trp Gly Met Gly Ile Asp Arg Val Ala Met Phe Leu Thr Asp Ser
385                 390                 395                 400
Asn Asn Ile Lys Glu Val Leu Leu Phe Pro Ala Met Lys Pro Glu Asp
                    405                 410                 415
Lys Lys Glu Asn Val Ala Thr Thr Asp Thr Leu Glu Ser Thr Thr Val
                420                 425                 430
Gly Thr Ser Val Leu Glu Gly Lys Pro Ile Pro Asn Pro Leu Leu Gly
                435                 440                 445
Leu Asp Ser Thr His His His His His His
                450                 455
```

```
<210> SEQ ID NO 208
<211> LENGTH: 437
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 208
```

```
Met His His His His His Gly Lys Pro Ile Pro Asn Pro Leu Leu
1               5                   10                  15
Gly Leu Asp Ser Thr Gly Ser Leu Thr Gln Ala Ala Val Arg Leu Val
                    20                  25                  30
Arg Gly Ser Leu Arg Lys Thr Ser Trp Ala Glu Trp Gly His Arg Glu
                35                  40                  45
Leu Arg Leu Gly Gln Leu Ala Pro Phe Thr Ala Pro His Lys Asp Lys
            50                  55                  60
Ser Phe Ser Asp Gln Arg Ser Glu Leu Lys Arg Arg Leu Lys Ala Glu
65                  70                  75                  80
```

```
Lys Lys Val Ala Glu Lys Glu Ala Lys Gln Lys Glu Leu Ser Glu Lys
                 85                  90                  95

Gln Leu Ser Gln Ala Thr Ala Ala Thr Asn His Thr Thr Asp Asn
            100                 105                 110

Gly Val Gly Pro Glu Glu Ser Val Asp Pro Asn Gln Tyr Tyr Lys
            115                 120                 125

Ile Arg Ser Gln Ala Ile His Gln Leu Lys Val Asn Gly Glu Asp Pro
        130                 135                 140

Tyr Pro His Lys Phe His Val Asp Ile Ser Leu Thr Asp Phe Ile Gln
145                 150                 155                 160

Lys Tyr Ser His Leu Gln Pro Gly Asp His Leu Thr Asp Ile Thr Leu
                165                 170                 175

Lys Val Ala Gly Arg Ile His Ala Lys Arg Ala Ser Gly Gly Lys Leu
            180                 185                 190

Ile Phe Tyr Asp Leu Arg Gly Glu Gly Val Lys Leu Gln Val Met Ala
        195                 200                 205

Asn Ser Arg Asn Tyr Lys Ser Glu Glu Phe Ile His Ile Asn Asn
210                 215                 220

Lys Leu Arg Arg Gly Asp Ile Ile Gly Val Gln Gly Asn Pro Gly Lys
225                 230                 235                 240

Thr Lys Lys Gly Glu Leu Ser Ile Ile Pro Tyr Glu Ile Thr Leu Leu
                245                 250                 255

Ser Pro Cys Leu His Met Leu Pro His Leu His Phe Gly Leu Lys Asp
            260                 265                 270

Lys Glu Thr Arg Tyr Arg Gln Arg Tyr Leu Asp Leu Ile Leu Asn Asp
                275                 280                 285

Phe Val Arg Gln Lys Phe Ile Ile Arg Ser Lys Ile Ile Thr Tyr Ile
290                 295                 300

Arg Ser Phe Leu Asp Glu Leu Gly Phe Leu Glu Ile Glu Thr Pro Met
305                 310                 315                 320

Met Asn Ile Ile Pro Gly Gly Ala Val Ala Lys Pro Phe Ile Thr Tyr
                325                 330                 335

His Asn Glu Leu Asp Met Asn Leu Tyr Met Arg Ile Ala Pro Glu Leu
            340                 345                 350

Tyr His Lys Ala Lys Ala Ala Gly Asp Asp Glu Ala Met Phe Ile Asp
        355                 360                 365

Glu Asn Phe Cys Thr Ala Leu Glu Tyr Gly Leu Pro Pro Thr Ala Gly
        370                 375                 380

Trp Gly Met Gly Ile Asp Arg Val Ala Met Phe Leu Thr Asp Ser Asn
385                 390                 395                 400

Asn Ile Lys Glu Val Leu Leu Phe Pro Ala Met Lys Pro Glu Asp Lys
                405                 410                 415

Lys Glu Asn Val Ala Thr Thr Asp Thr Leu Glu Ser Thr Thr Val Gly
                420                 425                 430

Thr Ser Val Leu Glu
            435

<210> SEQ ID NO 209
<211> LENGTH: 437
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 209
```

```
Met Gly Ser Leu Thr Gln Ala Ala Val Arg Leu Val Arg Gly Ser Leu
 1               5                  10                  15

Arg Lys Thr Ser Trp Ala Glu Trp Gly His Arg Glu Leu Arg Leu Gly
             20                  25                  30

Gln Leu Ala Pro Phe Thr Ala Pro His Lys Asp Lys Ser Phe Ser Asp
             35                  40                  45

Gln Arg Ser Glu Leu Lys Arg Arg Leu Lys Ala Glu Lys Lys Val Ala
 50                  55                  60

Glu Lys Glu Ala Lys Gln Lys Glu Leu Ser Glu Lys Gln Leu Ser Gln
 65                  70                  75                  80

Ala Thr Ala Ala Ala Thr Asn His Thr Thr Asp Asn Gly Val Gly Pro
                 85                  90                  95

Glu Glu Glu Ser Val Asp Pro Asn Gln Tyr Tyr Lys Ile Arg Ser Gln
                100                 105                 110

Ala Ile His Gln Leu Lys Val Asn Gly Glu Asp Pro Tyr Pro His Lys
            115                 120                 125

Phe His Val Asp Ile Ser Leu Thr Asp Phe Ile Gln Lys Tyr Ser His
            130                 135                 140

Leu Gln Pro Gly Asp His Leu Thr Asp Ile Thr Leu Lys Val Ala Gly
145                 150                 155                 160

Arg Ile His Ala Lys Arg Ala Ser Gly Gly Lys Leu Ile Phe Tyr Asp
                165                 170                 175

Leu Arg Gly Glu Gly Val Lys Leu Gln Val Met Ala Asn Ser Arg Asn
            180                 185                 190

Tyr Lys Ser Glu Glu Phe Ile His Ile Asn Asn Lys Leu Arg Arg
            195                 200                 205

Gly Asp Ile Ile Gly Val Gln Gly Asn Pro Gly Lys Thr Lys Lys Gly
210                 215                 220

Glu Leu Ser Ile Ile Pro Tyr Glu Ile Thr Leu Leu Ser Pro Cys Leu
225                 230                 235                 240

His Met Leu Pro His Leu His Phe Gly Leu Lys Asp Lys Glu Thr Arg
                245                 250                 255

Tyr Arg Gln Arg Tyr Leu Asp Leu Ile Leu Asn Asp Phe Val Arg Gln
            260                 265                 270

Lys Phe Ile Ile Arg Ser Lys Ile Ile Thr Tyr Ile Arg Ser Phe Leu
275                 280                 285

Asp Glu Leu Gly Phe Leu Glu Ile Glu Thr Pro Met Met Asn Ile Ile
290                 295                 300

Pro Gly Gly Ala Val Ala Lys Pro Phe Ile Thr Tyr His Asn Glu Leu
305                 310                 315                 320

Asp Met Asn Leu Tyr Met Arg Ile Ala Pro Glu Leu Tyr His Lys Ala
            325                 330                 335

Lys Ala Ala Gly Asp Asp Glu Ala Met Phe Ile Asp Glu Asn Phe Cys
            340                 345                 350

Thr Ala Leu Glu Tyr Gly Leu Pro Pro Thr Ala Gly Trp Gly Met Gly
            355                 360                 365

Ile Asp Arg Val Ala Met Phe Leu Thr Asp Ser Asn Asn Ile Lys Glu
370                 375                 380

Val Leu Leu Phe Pro Ala Met Lys Pro Glu Asp Lys Lys Glu Asn Val
385                 390                 395                 400

Ala Thr Thr Asp Thr Leu Glu Ser Thr Thr Val Gly Thr Ser Val Leu
                405                 410                 415
```

```
Glu Gly Lys Pro Ile Pro Asn Pro Leu Leu Gly Leu Asp Ser Thr His
            420                 425                 430
His His His His His
        435

<210> SEQ ID NO 210
<211> LENGTH: 128
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 210

Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Arg Leu Lys Ala Glu
65                  70                  75                  80

Lys Lys Val Ala Glu Lys Glu Ala Lys Gln Lys Glu Leu Ser Glu Lys
                85                  90                  95

Gln Leu Ser Gln Ala Thr Ala Ala Ala Thr Asn His Thr Thr Asp Asn
            100                 105                 110

Gly Val Gly Pro Glu Glu Glu Ser Val Asp Pro Asn Lys Leu Leu Glu
        115                 120                 125

<210> SEQ ID NO 211
<211> LENGTH: 128
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 211

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
        35                  40                  45

Gln Arg Ser Glu Leu Lys Arg Arg Leu Lys Ala Glu Lys Lys Val Ala
    50                  55                  60

Glu Lys Glu Ala Lys Gln Lys Glu Leu Ser Glu Lys Gln Leu Ser Gln
65                  70                  75                  80

Ala Thr Ala Ala Ala Thr Asn His Thr Thr Asp Asn Gly Val Gly Pro
                85                  90                  95

Glu Glu Glu Ser Val Asp Pro Asn Lys Leu Leu Glu Gly Lys Pro Ile
            100                 105                 110

Pro Asn Pro Leu Leu Gly Leu Asp Ser Thr His His His His His His
        115                 120                 125

<210> SEQ ID NO 212
<211> LENGTH: 73
```

```
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 212

Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
                20                  25                  30

Arg Gly Ser Leu Arg Lys Thr Ser Trp Ala Glu Trp Gly His Arg Glu
            35                  40                  45

Leu Arg Leu Gly Gln Leu Ala Pro Phe Thr Ala Pro His Lys Asp Lys
    50                  55                  60

Ser Phe Ser Asp Gln Arg Arg Leu Glu
65                  70

<210> SEQ ID NO 213
<211> LENGTH: 73
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 213

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
                20                  25                  30

Gln Leu Ala Pro Phe Thr Ala Pro His Lys Asp Lys Ser Phe Ser Asp
            35                  40                  45

Gln Arg Arg Leu Glu Gly Lys Pro Ile Pro Asn Pro Leu Leu Gly Leu
    50                  55                  60

Asp Ser Thr His His His His His His
65                  70

<210> SEQ ID NO 214
<211> LENGTH: 201
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag

<400> SEQUENCE: 214

Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
                20                  25                  30

Arg Gly Ser Leu Arg Lys Thr Ser Trp Ala Glu Trp Gly His Arg Glu
            35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Leu Lys Ala Glu
65                  70                  75                  80

Lys Lys Val Ala Glu Lys Glu Ala Lys Gln Lys Glu Leu Ser Glu Lys
                85                  90                  95

Gln Leu Ser Gln Ala Thr Ala Ala Ala Thr Asn His Thr Thr Asp Asn
```

```
                    100                 105                 110
Gly Val Gly Pro Glu Glu Ser Val Asp Pro Asn Gln Tyr Tyr Lys
            115                 120                 125

Ile Arg Ser Gln Ala Ile His Gln Leu Lys Val Asn Gly Glu Asp Pro
        130                 135                 140

Tyr Pro His Lys Phe His Val Asp Ile Ser Leu Thr Asp Phe Ile Gln
145                 150                 155                 160

Lys Tyr Ser His Leu Gln Pro Gly Asp His Leu Thr Asp Ile Thr Leu
                165                 170                 175

Lys Val Ala Glu Ile Ile Asn Gln Lys Lys Asn Leu Phe Ile Leu Ile
            180                 185                 190

Thr Asn Cys Val Gly Glu Thr Leu Glu
            195                 200

<210> SEQ ID NO 215
<211> LENGTH: 201
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 215

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

Gln Leu Ala Pro Phe Thr Ala Pro His Lys Asp Lys Ser Phe Ser Asp
        35                  40                  45

Gln Arg Ser Glu Leu Lys Arg Arg Leu Lys Ala Glu Lys Lys Val Ala
    50                  55                  60

Glu Lys Glu Ala Lys Gln Lys Glu Leu Ser Glu Lys Gln Leu Ser Gln
65                  70                  75                  80

Ala Thr Ala Ala Ala Thr Asn His Thr Thr Asp Asn Gly Val Gly Pro
                85                  90                  95

Glu Glu Glu Ser Val Asp Pro Asn Gln Tyr Tyr Lys Ile Arg Ser Gln
            100                 105                 110

Ala Ile His Gln Leu Lys Val Asn Gly Glu Asp Pro Tyr Pro His Lys
        115                 120                 125

Phe His Val Asp Ile Ser Leu Thr Asp Phe Ile Gln Lys Tyr Ser His
    130                 135                 140

Leu Gln Pro Gly Asp His Leu Thr Asp Ile Thr Leu Lys Val Ala Glu
145                 150                 155                 160

Ile Ile Asn Gln Lys Lys Asn Leu Phe Ile Leu Ile Thr Asn Cys Val
                165                 170                 175

Gly Glu Thr Leu Glu Gly Lys Pro Ile Pro Asn Pro Leu Leu Gly Leu
            180                 185                 190

Asp Ser Thr His His His His His His
        195                 200

<210> SEQ ID NO 216
<211> LENGTH: 311
<212> TYPE: PRT
<213> ORGANISM: Artificial Sequence
<220> FEATURE:
<223> OTHER INFORMATION: Lysyl tRNA Synthetase polypeptide with
      N-terminal 6xHis affinity tag
```

<400> SEQUENCE: 216

Met His His His His His Gly Lys Pro Ile Pro Asn Pro Leu Leu
1               5                   10                  15

Gly Leu Asp Ser Thr Gly Ser Leu Thr Gln Ala Ala Val Arg Leu Val
            20                  25                  30

Arg Gly Ser Leu Arg Lys Thr Ser Trp Ala Glu Trp Gly His Arg Glu
        35                  40                  45

Leu Arg Leu Gly Gln Leu Ala Pro Phe Thr Ala Pro His Lys Asp Lys
    50                  55                  60

Ser Phe Ser Asp Gln Arg Ser Glu Leu Lys Arg Leu Lys Ala Glu
65                  70                  75                  80

Lys Lys Val Ala Glu Lys Glu Ala Lys Gln Lys Glu Leu Ser Glu Lys
                85                  90                  95

Gln Leu Ser Gln Ala Thr Ala Ala Thr Asn His Thr Thr Asp Asn
            100                 105                 110

Gly Val Gly Pro Glu Glu Glu Ser Val Asp Pro Asn Gln Tyr Tyr Lys
        115                 120                 125

Ile Arg Ser Gln Ala Ile His Gln Leu Lys Val Asn Gly Glu Asp Pro
    130                 135                 140

Tyr Pro His Lys Phe His Val Asp Ile Ser Leu Thr Asp Phe Ile Gln
145                 150                 155                 160

Lys Tyr Ser His Leu Gln Pro Gly Asp His Leu Thr Asp Ile Thr Leu
                165                 170                 175

Lys Val Ala Gly Arg Ile His Ala Lys Arg Ala Ser Gly Gly Lys Leu
            180                 185                 190

Ile Phe Tyr Asp Leu Arg Gly Glu Gly Val Lys Leu Gln Val Met Ala
        195                 200                 205

Asn Ser Arg Asn Tyr Lys Ser Glu Glu Phe Ile His Ile Asn Asn
    210                 215                 220

Lys Leu Arg Arg Gly Asp Ile Ile Gly Val Gln Gly Asn Pro Gly Lys
225                 230                 235                 240

Thr Lys Lys Gly Glu Leu Ser Ile Ile Pro Tyr Glu Ile Thr Leu Leu
                245                 250                 255

Ser Pro Cys Leu His Met Leu Pro His Leu His Phe Gly Leu Lys Asp
            260                 265                 270

Lys Lys Leu Ala Lys Phe Leu Met Ile Ser Val Trp Gln Lys Leu Leu
        275                 280                 285

Asn Ala Leu His Leu Gly Pro Gln Pro Gly Ser Leu Thr Ser Leu Leu
    290                 295                 300

Gly Ser Ser Trp Lys Leu Glu
305                 310

<210> SEQ ID NO 217
<211> LENGTH: 311
<212> TYPE: PRT
<213> ORGANISM: Artificial Sequence
<220> FEATURE:
<223> OTHER INFORMATION: Lysyl tRNA Synthetase polypeptide with
      C-terminal 6xHis affinity tag

<400> SEQUENCE: 217

Met Gly Ser Leu Thr Gln Ala Ala Val Arg Leu Val Arg Gly Ser Leu
1               5                   10                  15

Arg Lys Thr Ser Trp Ala Glu Trp Gly His Arg Glu Leu Arg Leu Gly
            20                  25                  30

```
Gln Leu Ala Pro Phe Thr Ala Pro His Lys Asp Lys Ser Phe Ser Asp
             35                  40                  45

Gln Arg Ser Glu Leu Lys Arg Leu Lys Ala Glu Lys Lys Val Ala
 50                  55                  60

Glu Lys Glu Ala Lys Gln Lys Glu Leu Ser Glu Lys Gln Leu Ser Gln
 65                  70                  75                  80

Ala Thr Ala Ala Ala Thr Asn His Thr Thr Asp Asn Gly Val Gly Pro
                 85                  90                  95

Glu Glu Glu Ser Val Asp Pro Asn Gln Tyr Tyr Lys Ile Arg Ser Gln
            100                 105                 110

Ala Ile His Gln Leu Lys Val Asn Gly Glu Asp Pro Tyr Pro His Lys
            115                 120                 125

Phe His Val Asp Ile Ser Leu Thr Asp Phe Ile Gln Lys Tyr Ser His
    130                 135                 140

Leu Gln Pro Gly Asp His Leu Thr Asp Ile Thr Leu Lys Val Ala Gly
145                 150                 155                 160

Arg Ile His Ala Lys Arg Ala Ser Gly Gly Lys Leu Ile Phe Tyr Asp
                165                 170                 175

Leu Arg Gly Glu Gly Val Lys Leu Gln Val Met Ala Asn Ser Arg Asn
            180                 185                 190

Tyr Lys Ser Glu Glu Glu Phe Ile His Ile Asn Asn Lys Leu Arg Arg
        195                 200                 205

Gly Asp Ile Ile Gly Val Gln Gly Asn Pro Gly Lys Thr Lys Lys Gly
210                 215                 220

Glu Leu Ser Ile Ile Pro Tyr Glu Ile Thr Leu Leu Ser Pro Cys Leu
225                 230                 235                 240

His Met Leu Pro His Leu His Phe Gly Leu Lys Asp Lys Lys Leu Ala
                245                 250                 255

Lys Phe Leu Met Ile Ser Val Trp Gln Lys Leu Leu Asn Ala Leu His
            260                 265                 270

Leu Gly Pro Gln Pro Gly Ser Leu Thr Ser Leu Leu Gly Ser Ser Trp
        275                 280                 285

Lys Leu Glu Gly Lys Pro Ile Pro Asn Pro Leu Leu Gly Leu Asp Ser
    290                 295                 300

Thr His His His His His
305                 310

<210> SEQ ID NO 218
<211> LENGTH: 1191
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 218
ggatccctga cacaagcggc agttcgtctg gttcgtggtt ctctgcgtaa aacctcttgg     60
gctgaatggg gtcatcgtga ctgcgcctg ggacaactgg caccgtttac agcacctcat    120
aaagacaaat ccttctccga tcaacgctcc gagctgaaac gtcgcctgaa agccgagaaa    180
aaagtggcgg aaaagaagc caaacagaaa gagctgtcgg aaaaacaact gagccaagca    240
acagcagcag caaccaatca taccaccgat aatggtgttg gtccggagga agaatcagtc    300
gatcctaatc aatattataa aattcgttca caggccatcc atcaactgaa agtgaatggc    360
gaagatccgt atcctcacaa attccacgtg gacattagcc tgaccgattt catccagaaa    420
```

```
tatagccacc tgcagccagg agatcatctg acagacatca ctctgaaagt tgccggccgt    480
attcatgcca acgtgctag cggcggaaaa ctgatcttct atgacctgcg tggtgaaggt    540
gttaaactgc aagtcatggc caattcccgt aactataaaa gtgaagagga gttcatccac   600
atcaacaaca aactgcgtcg cggtgatatc atcggggttc agggaaatcc tggtaaaacg   660
aaaaaaggcg agctgtccat cattccgtat gagattacac tgctgagtcc gtgcctgcat   720
atgctgcctc atctgcattt tggtctgaaa gacaaagaaa cccgctatcg tcagcgttat   780
ctggacctga tcctgaatga ctttgttcgc caaaaattca tcatccgctc gaaaatcatc   840
acgtatatcc gttcatttct ggacgagctg ggtttcctgg aaattgaaac accaatgatg   900
aacatcatcc cgggtggagc agttgctaaa cctttcatca cctatcacaa cgagctggac   960
atgaacctgt atatgcgcat tgccccagaa ctgtatcata aaatgctggt tgtgggcggt  1020
attgatcgtg tgtatgaaat cggtcgtcag ttccgtaatg agggtattga cctgacccat  1080
aatccggaat tcaccacctg tgagttctat atggcctatg ccgactatca tgatctgatg  1140
gaaatcacgg agaaaatggt ttctggcatg gtaaaacaca tcaccctcga g           1191

<210> SEQ ID NO 219
<211> LENGTH: 321
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 219
ggatccctga cacaagcggc agttcgtctg gttcgtggtt ctctgcgtaa aacctcttgg    60
gctgaatggg gtcatcgtga gctgcgcctg gacaactgg caccgtttac agcacctcat   120
aaagacaaat ccttctccga tcaacgctcc gagctgaaac gtcgcctgaa agccgagaaa   180
aaagtggcgg aaaagaagc caaacagaaa gagctgtcgg aaaaacaact gagccaagca   240
acagcagcag caaccaatca taccaccgat aatggtgttg gtccggagga gaatcagtc   300
gatcctaatc aatatctcga g                                            321

<210> SEQ ID NO 220
<211> LENGTH: 675
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 220
ggatccctga cacaagcggc agttcgtctg gttcgtggtt ctctgcgtaa aacctcttgg    60
gctgaatggg gtcatcgtga gctgcgcctg gacaactgg caccgtttac agcacctcat   120
aaagacaaat ccttctccga tcaacgctcc gagctgaaac gtcgcctgaa agccgagaaa   180
aaagtggcgg aaaagaagc caaacagaaa gagctgtcgg aaaaacaact gagccaagca   240
acagcagcag caaccaatca taccaccgat aatggtgttg gtccggagga gaatcagtc   300
gatcctaatc aatattataa aattcgttca caggccatcc atcaactgaa agtgaatggc   360
gaagatccgt atcctcacaa attccacgtg acattagcc tgaccgattt catccagaaa   420
tatagccacc tgcagccagg agatcatctg acagacatca ctctgaaagt tgccggccgt   480
attcatgcca acgtgctag cggcggaaaa ctgatcttct atgacctgcg tggtgaaggt   540
gttaaactgc aagtcatggc caattcccgt aactataaaa gtgaagagga gttcatccac   600
```

```
atcaacaaca aactgcgtcg cggtgatatc atcggggttc agggaaatcc tggtaaaacg    660
aaaaaaggcc tcgag                                                     675
```

<210> SEQ ID NO 221
<211> LENGTH: 288
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 221

```
ggatccctga cacaagcggc agttcgtctg gttcgtggtt ctctgcgtaa aacctcttgg    60
gctgaatggg gtcatcgtga gctgcgcctg ggacaactgg caccgtttac agcacctcat   120
aaagacaaat ccttctccga tcaacgctcc gagctgaaac gtcgcctgaa agccgagaaa   180
aaagtggcgg aaaagaagc caaacagaaa gagctgtcgg aaaaacaact gagccaagca   240
acagcagcag caaccaatca taccaccgat aatggtgttg gtctcgag               288
```

<210> SEQ ID NO 222
<211> LENGTH: 735
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 222

```
ggatccctga cacaagcggc agttcgtctg gttcgtggtt ctctgcgtaa aacctcttgg    60
gctgaatggg gtcatcgtga gctgcgcctg ggacaactgg caccgtttac agcacctcat   120
aaagacaaat ccttctccga tcaacgctcc gagctgaaac gtcgcctgaa agccgagaaa   180
aaagtggcgg aaaagaagc caaacagaaa gagctgtcgg aaaaacaact gagccaagca   240
acagcagcag caaccaatca taccaccgat aatggtgttg gtccggagga agaatcagtc   300
gatcctaatc aatattataa aattcgttca caggccatcc atcaactgaa agtgaatggc   360
gaagatccgt atcctcacaa attccacgtg acattagcc tgaccgattt catccagaaa   420
tatagccacc tgcagccagg agatcatctg acagacatca ctctgaaagt tgccggccgt   480
attcatgcca acgtgctag cggcggaaaa ctgatcttct atgacctgcg tggtgaaggt   540
gttaaactgc aagtcatggc caattcccgt aactataaaa gtgaagagga gttcatccac   600
atcaacaaca aactgcgtcg cggtgatatc atcggggttc agggaaatcc tggtaaaacg   660
aaaaaaggcg agctgtccat cattccgtat gagattacac tgctgagtcc gtgcctgcat   720
atgctgcctc tcgag                                                    735
```

<210> SEQ ID NO 223
<211> LENGTH: 192
<212> TYPE: DNA
<213> ORGANISM: Artificial Sequence
<220> FEATURE:
<223> OTHER INFORMATION: Codon optimized lysyl tRNA Synthetase
      polynucleotide

<400> SEQUENCE: 223

```
ggatccctga cacaagcggc agttcgtctg gttcgtggtt ctctgcgtaa aacctcttgg    60
gctgaatggg gtcatcgtga gctgcgcctg ggacaactgg caccgtttac agcacctcat   120
aaagacaaat ccttctccga tcaacgctcc aacaccacga atcagcagt aaaacagttc   180
```

<210> SEQ ID NO 224
<211> LENGTH: 381
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 224

| | |
|---|---|
| ggatccctga cacaagcggc agttcgtctg gttcgtggtt ctctgcgtaa aacctcttgg | 60 |
| gctgaatggg gtcatcgtga gctgcgcctg ggacaactgg caccgtttac agcacctcat | 120 |
| aaagacaaat ccttctccga tcaacgctcc gagctgaaac gtcgcctgaa agccgagaaa | 180 |
| aaagtggcgg aaaagaagc caaacagaaa gagctgtcgg aaaaacaact gagccaagca | 240 |
| acagcagcag caaccaatca taccaccgat aatggtgttg gtccggagga agaatcagtc | 300 |
| gatcctaatg tgggaagcat gccgaaagag ctgctgggag aatcttctag cagtatgatc | 360 |
| ttcgaagagc gtggtctcga g | 381 |

<210> SEQ ID NO 225
<211> LENGTH: 1311
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 225

| | |
|---|---|
| ggatccctga cacaagcggc agttcgtctg gttcgtggtt ctctgcgtaa aacctcttgg | 60 |
| gctgaatggg gtcatcgtga gctgcgcctg ggacaactgg caccgtttac agcacctcat | 120 |
| aaagacaaat ccttctccga tcaacgctcc gagctgaaac gtcgcctgaa agccgagaaa | 180 |
| aaagtggcgg aaaagaagc caaacagaaa gagctgtcgg aaaaacaact gagccaagca | 240 |
| acagcagcag caaccaatca taccaccgat aatggtgttg gtccggagga agaatcagtc | 300 |
| gatcctaata tcgaaacccc tatgatgaat atcattccgg tggtgctgt tgctaaaccg | 360 |
| tttatcacct atcacaacga gctggacatg aacctgtata tgcgcattgc ccctgagctg | 420 |
| tatcacaaaa tgctggtagt gggtggcatt gatcgtgtgt atgagattgg tcgccagttc | 480 |
| cgtaacgagg gtattgacct gacccataat ccggagttta cgacgtgtga gttctatatg | 540 |
| gcctatgccg actatcatga cctgatggaa atcaccgaga aatggtgag tggtatggtg | 600 |
| aaacacatta ccggctccta taaagtgacg tatcatcctg acggtcctga aggacaggct | 660 |
| tatgacgtgg acttcactcc tccttttcgc cgtattaaca tggtggaaga gctggaaaaa | 720 |
| gcactgggca tgaaactgcc tgaaaccaac ctgttcgaga cagaagaaac ccgtaaaatt | 780 |
| ctggacgaca tctgtgtggc taaagccgtc gagtgtccgc tcctcgtac aactgctcgt | 840 |
| ctgctggaca aactggtggg tgaatttctg gaagtgacgt gtattaatcc gacgttcatc | 900 |
| tgtgatcatc ctcaaatcat gagccctctg gcaaaatggc atcgttccaa gaaggtctg | 960 |
| accgaacgct tcgagctgtt tgttatgaaa aaagagatct gtaacgccta taccgagctg | 1020 |
| aatgacccta tgcgtcaacg ccagctgttt gaagaacaag ccaaagccaa agcagcgggt | 1080 |
| gacgatgaag caatgttcat tgacgaaaac ttttgtaccg ccctggaata tggactgccg | 1140 |
| cctacagcgg gatggggtat gggaatcgac cgtgttgcca tgtttctgac ggattccaac | 1200 |

```
aacatcaaag aggtgctgct gttccctgct atgaaacctg aggacaaaaa agaaaacgtg    1260
gccacgaccg atactctgga aagcacgaca gtgggtacta gtgtactcga g             1311
```

<210> SEQ ID NO 226
<211> LENGTH: 1248
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 226

```
ggatccctga cacaagcggc agttcgtctg gttcgtggtt ctctgcgtaa aacctcttgg    60
gctgaatggg gtcatcgtga gctgcgcctg ggacaactgg caccgtttac agcacctcat   120
aaagacaaat ccttctccga tcaacgctcc gagctgaaac gtcgcctgaa agccgagaaa   180
aaagtggcgg aaaagaagc caaacagaaa gagctgtcgg aaaaacaact gagccaagca   240
acagcagcag caaccaatca taccaccgat aatggtgttg gtccggagga agaatcagtc   300
gatcctaatc aatattataa aattcgttca caggccatcc atcaactgaa agtgaatggc   360
gaagatccgt atcctcacaa attccacgtg acattagcc tgaccgattt catccagaaa   420
tatagccacc tgcagccagg agatcatctg acagacatca ctctgaaagt tgccggccgt   480
attcatgcca acgtgctag cggcggaaaa ctgatcttct atgacctgcg tggtgaaggt   540
gttaaactgc aagtcatggc caattcccgt aactataaaa gtgaagagga gttcatccac   600
atcaacaaca aactgcgtcg cggtgatatc atcggggttc agggaaatcc tggtaaaacg   660
aaaaaaggcg agctgtccat cattccgtat gagattacac tgctgagtcc gtgcctgcat   720
atgctgcctc atctgcattt tggtctgaaa gacaaagaaa cccgctatcg tcagcgttat   780
ctggacctga tcctgaatga ctttgttcgc caaaaattca tcatccgctc gaaaatcatc   840
acgtatatcc gttcatttct ggacgagctg ggtttcctgg aaattgaaac accaatgatg   900
aacatcatcc cgggtggagc agttgctaaa cctttcatca cctatcacaa cgagctggac   960
atgaacctgt atatgcgcat tgccccagaa ctgtatcata agccaaagc agcaggcgac  1020 gatgaagcta tgtttatcga cgagaacttc tgtacagcac tggagtatgg tctgccacca  1080
acagctggat ggggaatggg tattgatcgt gtcgccatgt ttctgactga tagcaacaac  1140
atcaaagagg ttctgctgtt cccagcaatg aaaccgagg acaaaaaga aaatgtggcc  1200 acgactgaca cactggaatc aaccacagtt ggcaccagcg ttctcgag                1248
```

<210> SEQ ID NO 227
<211> LENGTH: 321
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 227

```
ggatccctga cacaagcggc agttcgtctg gttcgtggtt ctctgcgtaa aacctcttgg    60
gctgaatggg gtcatcgtga gctgcgcctg ggacaactgg caccgtttac agcacctcat   120
aaagacaaat ccttctccga tcaacgctcc gagctgaaac gtcgcctgaa agccgagaaa   180
aaagtggcgg aaaagaagc caaacagaaa gagctgtcgg aaaaacaact gagccaagca   240
acagcagcag caaccaatca taccaccgat aatggtgttg gtccggagga agaatcagtc   300
gatcctaata aactgctcga g                                              321
```

<210> SEQ ID NO 228
<211> LENGTH: 156
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 228

```
ggatccctga cacaagcggc agttcgtctg gttcgtggtt ctctgcgtaa aacctcttgg      60
gctgaatggg gtcatcgtga gctgcgcctg ggacaactgg caccgtttac agcacctcat     120
aaagacaaat ccttctccga tcaacgccgc ctcgag                               156
```

<210> SEQ ID NO 229
<211> LENGTH: 540
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 229

```
ggatccctga cacaagcggc agttcgtctg gttcgtggtt ctctgcgtaa aacctcttgg      60
gctgaatggg gtcatcgtga gctgcgcctg ggacaactgg caccgtttac agcacctcat     120
aaagacaaat ccttctccga tcaacgctcc gagctgaaac gtcgcctgaa agccgagaaa     180
aaagtggcgg aaaagaagc caaacagaaa gagctgtcgg aaaaacaact gagccaagca     240
acagcagcag caaccaatca taccaccgat aatggtgttg gtccggagga agaatcagtc     300
gatcctaatc aatattataa aattcgttca caggccatcc atcaactgaa agtgaatggc     360
gaagatccgt atcctcacaa attccacgtg acattagcc tgaccgattt catccagaaa     420
tatagccacc tgcagccagg agatcatctg acagacatca ctctgaaagt tgccgagatc     480
attaaccaga aaaaaaacct gttcatcctg attaccaact gtgtgggcga gacactcgag     540
```

<210> SEQ ID NO 230
<211> LENGTH: 870
<212> TYPE: DNA
<213> ORGANISM: Artificial Sequence
<220> FEATURE:
<223> OTHER INFORMATION: Codon optimized lysyl tRNA Synthetase polynucleotide

<400> SEQUENCE: 230

```
ggatccctga cacaagcggc agttcgtctg gttcgtggtt ctctgcgtaa aacctcttgg      60
gctgaatggg gtcatcgtga gctgcgcctg ggacaactgg caccgtttac agcacctcat     120
aaagacaaat ccttctccga tcaacgctcc gagctgaaac gtcgcctgaa agccgagaaa     180
aaagtggcgg aaaagaagc caaacagaaa gagctgtcgg aaaaacaact gagccaagca     240
acagcagcag caaccaatca taccaccgat aatggtgttg gtccggagga agaatcagtc     300
gatcctaatc aatattataa aattcgttca caggccatcc atcaactgaa agtgaatggc     360
gaagatccgt atcctcacaa attccacgtg acattagcc tgaccgattt catccagaaa     420
tatagccacc tgcagccagg agatcatctg acagacatca ctctgaaagt tgccggccgt     480
attcatgcca acgtgctag cggcggaaaa ctgatcttct atgacctgcg tggtgaaggt     540
gttaaactgc aagtcatggc caattcccgt aactataaaa gtgaagagga gttcatccac     600
atcaacaaca aactgcgtcg cggtgatatc atcgggttc agggaaatcc tggtaaaacg     660
aaaaaaggcg agctgtccat cattccgtat gagattacac tgctgagtcc gtgcctgcat     720
```

-continued

```
atgctgcctc atctgcattt tggtctgaaa gacaaaaaac tggccaaatt cctgatgatt        780
agcgtgtggc agaaactgct gaatgccctg cacctgggtc ctcaaccggg ttctctgact        840
agcctgctgg gttcgtcttg gaaactcgag                                        870
```

US 9,322,009 B2

INNOVATIVE DISCOVERY OF THERAPEUTIC, DIAGNOSTIC, AND ANTIBODY COMPOSITIONS RELATED TO PROTEIN FRAGMENTS OF LYSYL-TRNA SYNTHETASES

CROSS-REFERENCE TO RELATED APPLICATIONS

This application is a Continuation of U.S. application Ser. No. 13/700,998, filed on Apr. 29, 2013, now U.S. Pat. No. 8,962,560, which is a U.S. National Phase Application of International Patent Application No. PCT/US2011/038813, filed Jun. 1, 2011, which claims the benefit under 35 U.S.C. §119(e) of U.S. provisional patent application No. 61/350, 407 filed on Jun. 1, 2010; U.S. provisional patent application No. 61/350,409 filed on Jun. 1, 2010; U.S. provisional patent application No. 61/350,411 filed on Jun. 1, 2010; U.S. provisional patent application No. 61/350,242 filed on Jun. 1, 2010; U.S. provisional patent application No. 61/488,528 filed on May 20, 2011; U.S. provisional patent application No. 61/488,514 filed on May 20, 2011; U.S. provisional patent application No. 61/488,503 filed on May 20, 2011; and U.S. provisional patent application No. 61/488,619 filed on May 20, 2011, the entire contents of each of which, are incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ATYR_059_03US_ST25.txt. The text file is about 291 KB, was created on Jan. 8, 2015, and is being submitted electronically via EFS-Web.

TECHNICAL FIELD

The present invention relates generally to compositions comprising newly identified protein fragments of aminoacyl-tRNA synthetases and other proteins, polynucleotides that encode them and complements thereof, related agents, and methods of use thereof in diagnostic, drug discovery, research, and therapeutic applications.

BACKGROUND

For over four decades, aminoacyl-tRNA synthetases (AARSs) were thought of as essential housekeeping proteins that catalyze the aminoacylation of tRNA molecules as part of the decoding of genetic information during the process of protein translation. AARSs have been extensively studied in this respect, and many of their full-length sequences were cloned for sequence analysis and to provide a rich source of biochemical experimentation. Some fragments of AARSs, and other proteins, however, possess unexpected activities not associated with aminoacylation, including extracellular signaling activities that modulate pathways beyond protein translation. Generally, these unexpected activities are not observed in the context of the full-length or parental protein sequences; instead, they are observed following removal or resection of AARS protein fragments from their parental sequences, or by expressing and sufficiently purifying fragment AARS sequences and then testing for novel, non-synthetase related activities.

While the full-length sequences of AARS have been known for some time, no systematic experimental analysis has been conducted to elucidate such AARS protein fragments, or protein fragments from related or associated proteins, or to evaluate the potential role of the full length AARS proteins for novel biological activities outside of the context of amino acid synthesis. In portions of this specification, such AARS protein fragments, AARS domains, or AARS alternative splice variants are referred to herein as "resectins". In its broadest context, the term "resectin" refers to a portion of a protein which has been excised or restricted (either by means of proteolysis, alternative splicing, mutagenesis, or recombinant genetic engineering) from the context of its native full-length or parental protein sequence, which often otherwise masks its novel biological activities. Likewise, no systematic experimental analysis has been conducted to explore the use of such resectins as biotherapeutic agents, diagnostic agents, or drug targets in the treatment of various medical conditions, or their potential association with human diseases. As essential housekeeping genes with a known function in mammals that is critical to life, AARSs were neither considered as drug targets in mammals, nor were they parsed out by standard genomic sequencing, bioinformatic, or similar efforts to identify resectins having non-synthetase activities. Standard biochemical research efforts have similarly been directed away from characterizing the biological properties of AARS resectins and their potential therapeutic and diagnostic relevance, mainly due to the previously understood role of their corresponding full-length parental AARSs.

BRIEF DESCRIPTION OF THE DRAWINGS

FIG. 1A representing fragments identified from mass spectrometry analysis, FIG. 1B representing the fragments identified from deep sequencing of transcriptomes, and FIG. 1C representing fragments identified from bioinformatics analysis.

FIG. 2A representing fragments identified from mass spectrometry analysis, FIG. 2B representing fragments identified from deep sequencing of transcriptomes.

FIG. 4A representing fragments identified from mass spectrometry analysis, FIG. 4B representing the fragments identified from deep sequencing of transcriptomes, and FIG. 4C representing fragments identified from bioinformatics analysis.

BRIEF SUMMARY OF THE INVENTION

Figure 1A:
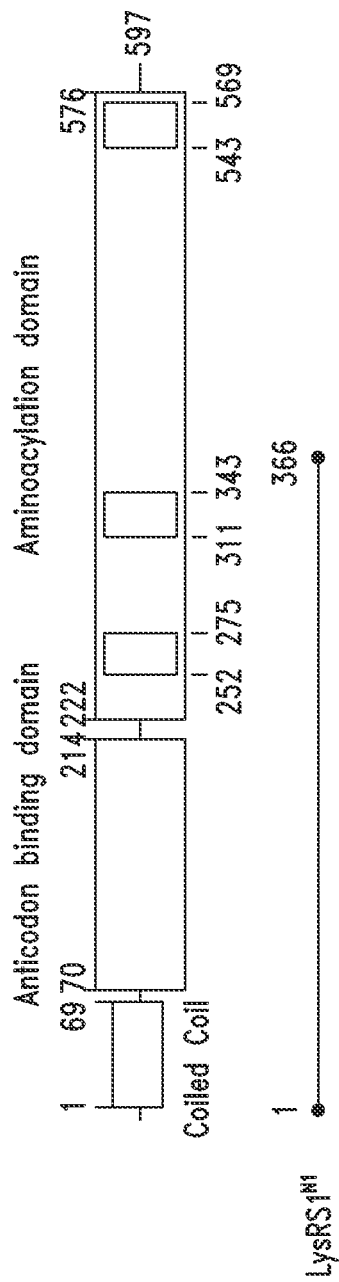
FIGS. 1A-1C show the domain structure of the Lysyl RS1 aminoacyl tRNA synthetase overlaid with the relative positions and sizes of N-terminal AARS polypeptides identified shown schematically.
Figure 1B:
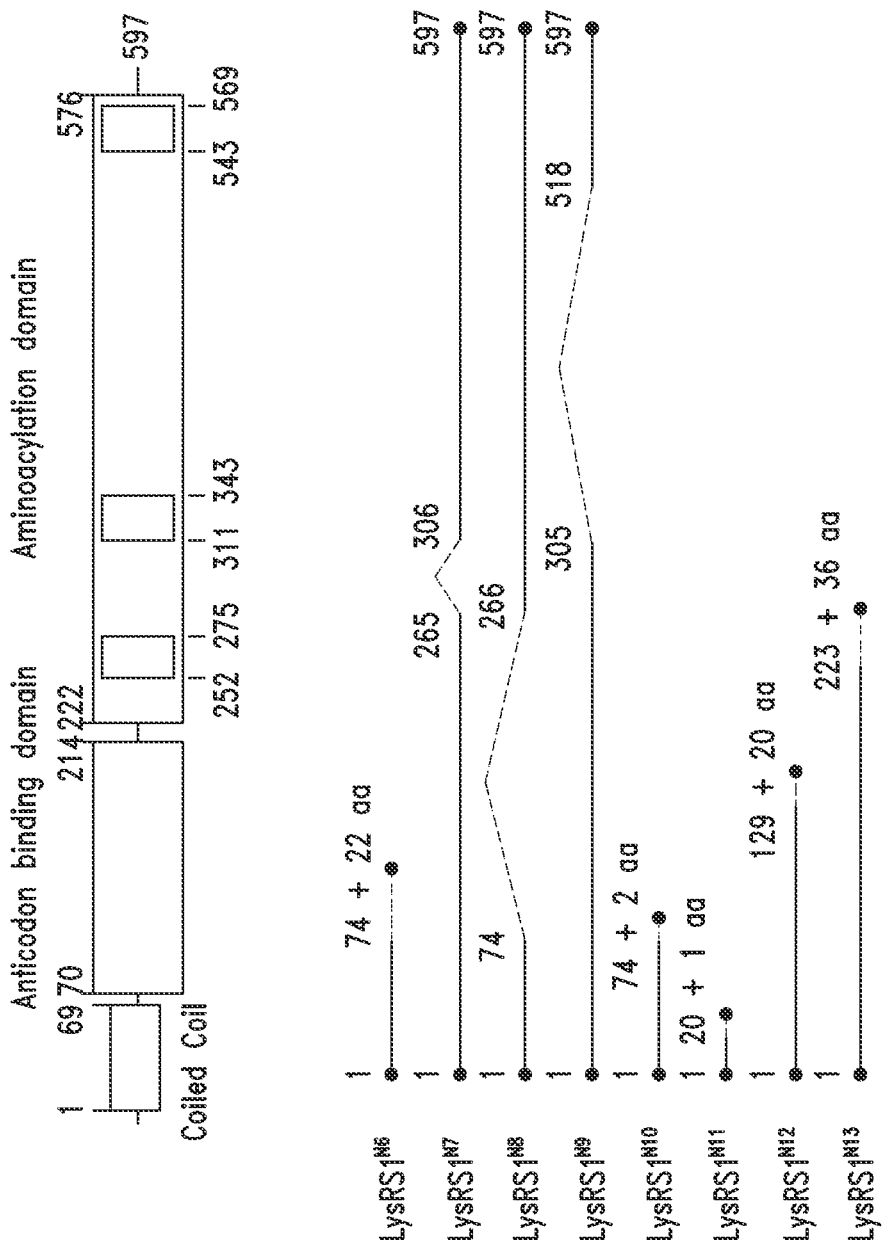
Figure 1C:
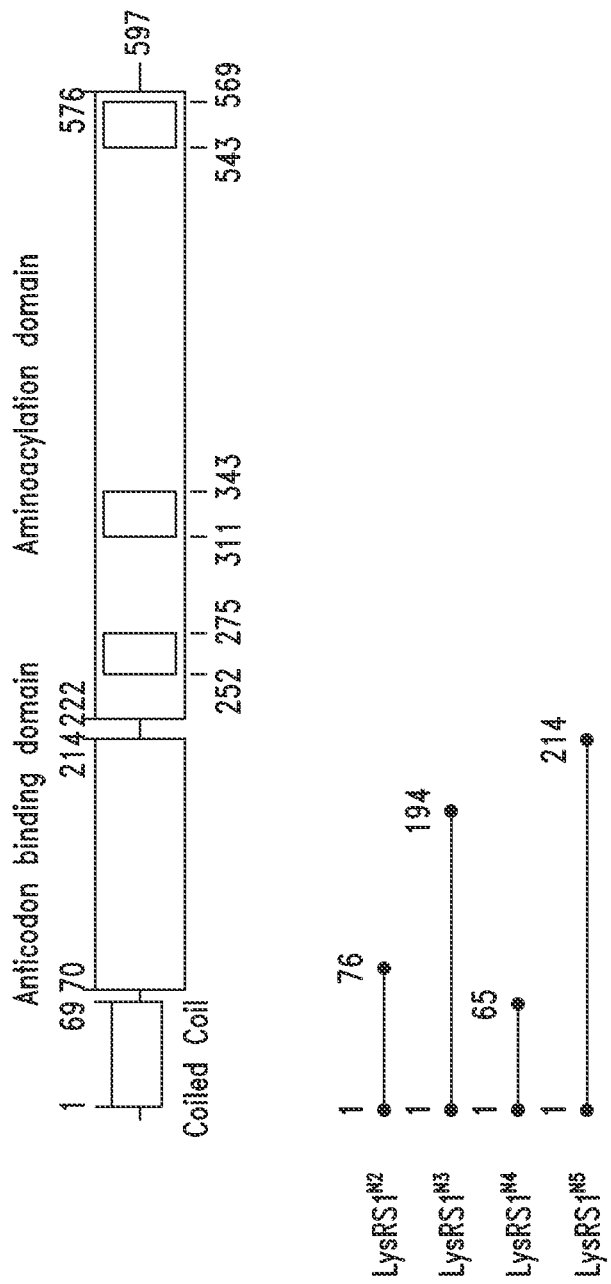
Figure 2A:
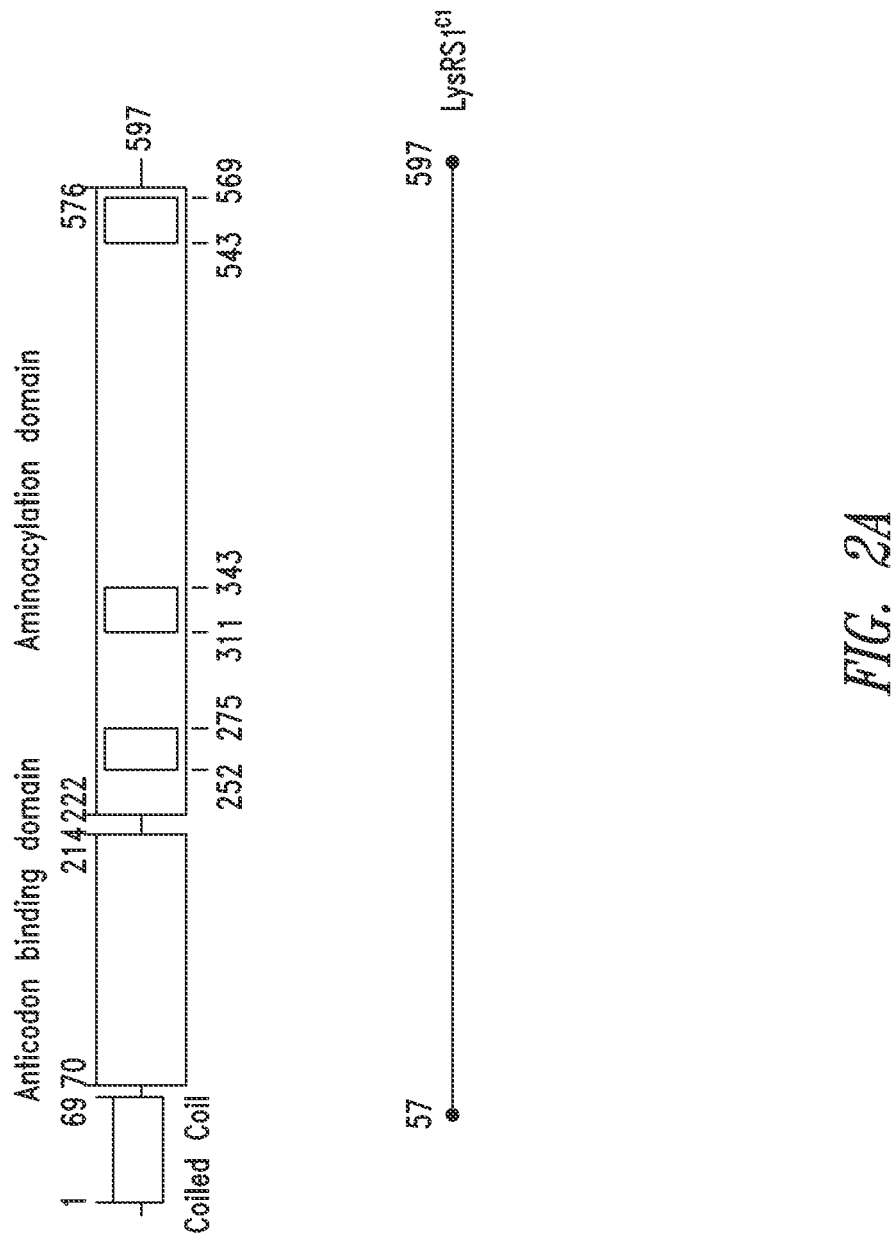
FIGS. 2A-2B show the domain structure of the Lysyl RS1 aminoacyl tRNA synthetase overlaid with the relative positions and sizes of C-terminal AARS polypeptides identified shown schematically.
Figure 2B:
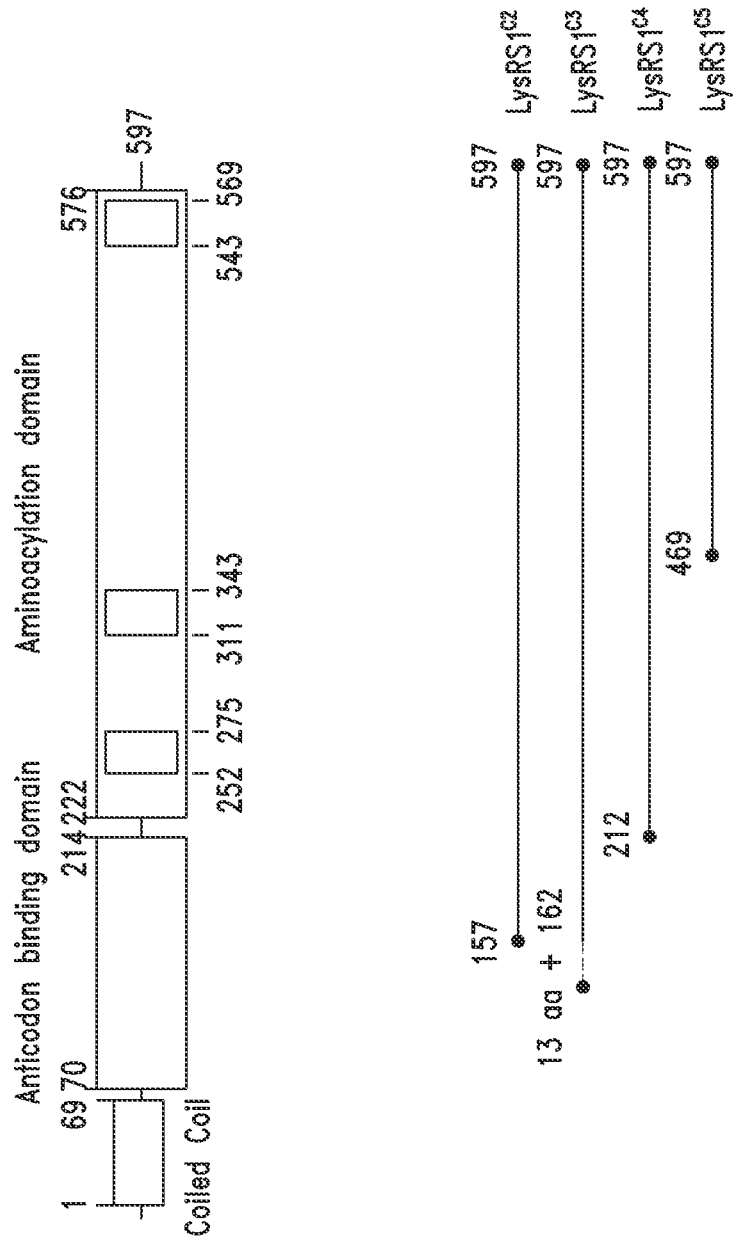
Figure 3:
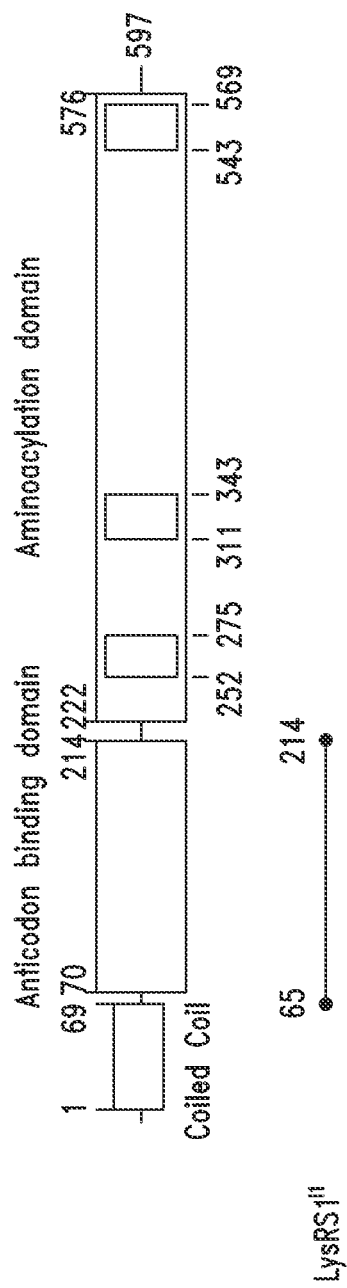
FIG. 3 shows the domain structure of the Lysyl RS1 aminoacyl tRNA synthetase overlaid with the relative positions and sizes of the Internal AARS polypeptides identified from bioinformatics analysis shown schematically.
Figure 4A:
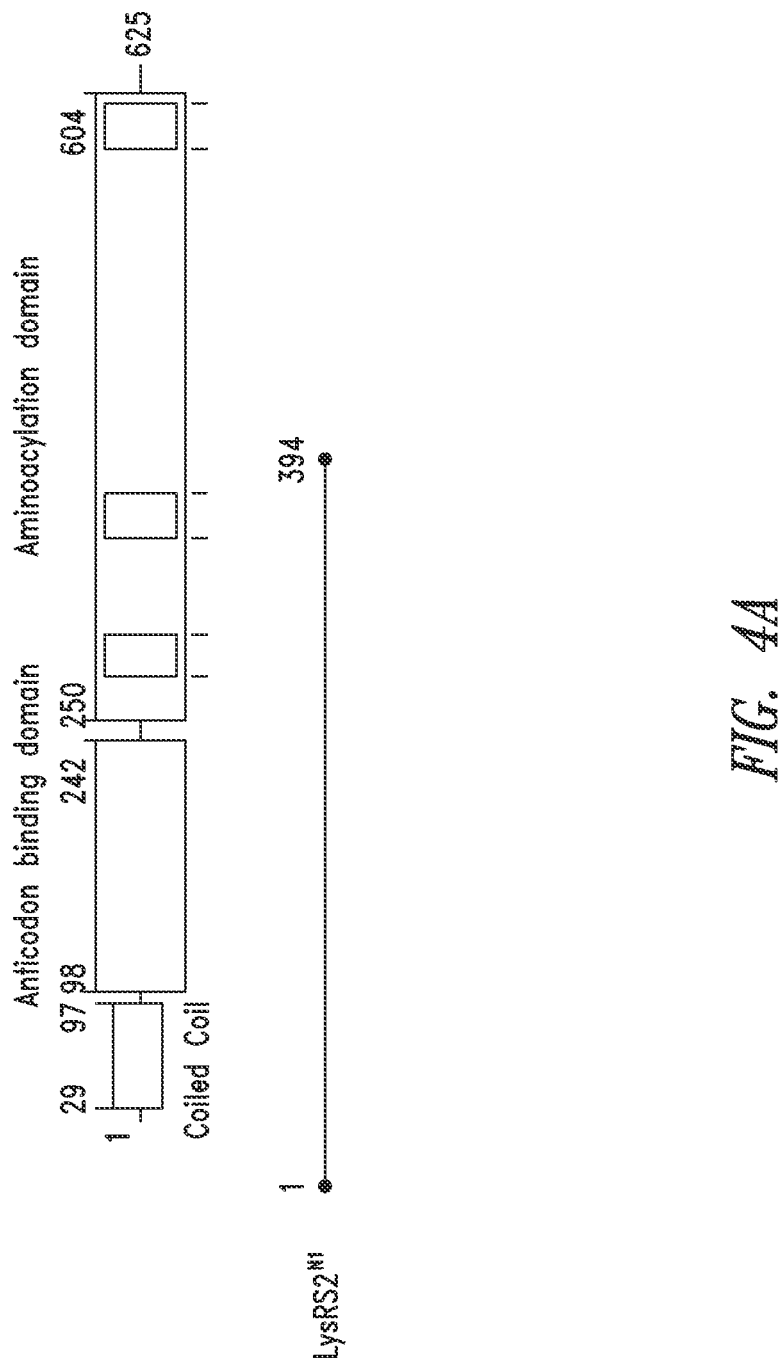
FIGS. 4A-4C show the domain structure of the Lysyl RS2 (mitochondrial) aminoacyl tRNA synthetase overlaid with the relative positions and sizes of N-terminal AARS polypeptides identified shown schematically.
Figure 4B:
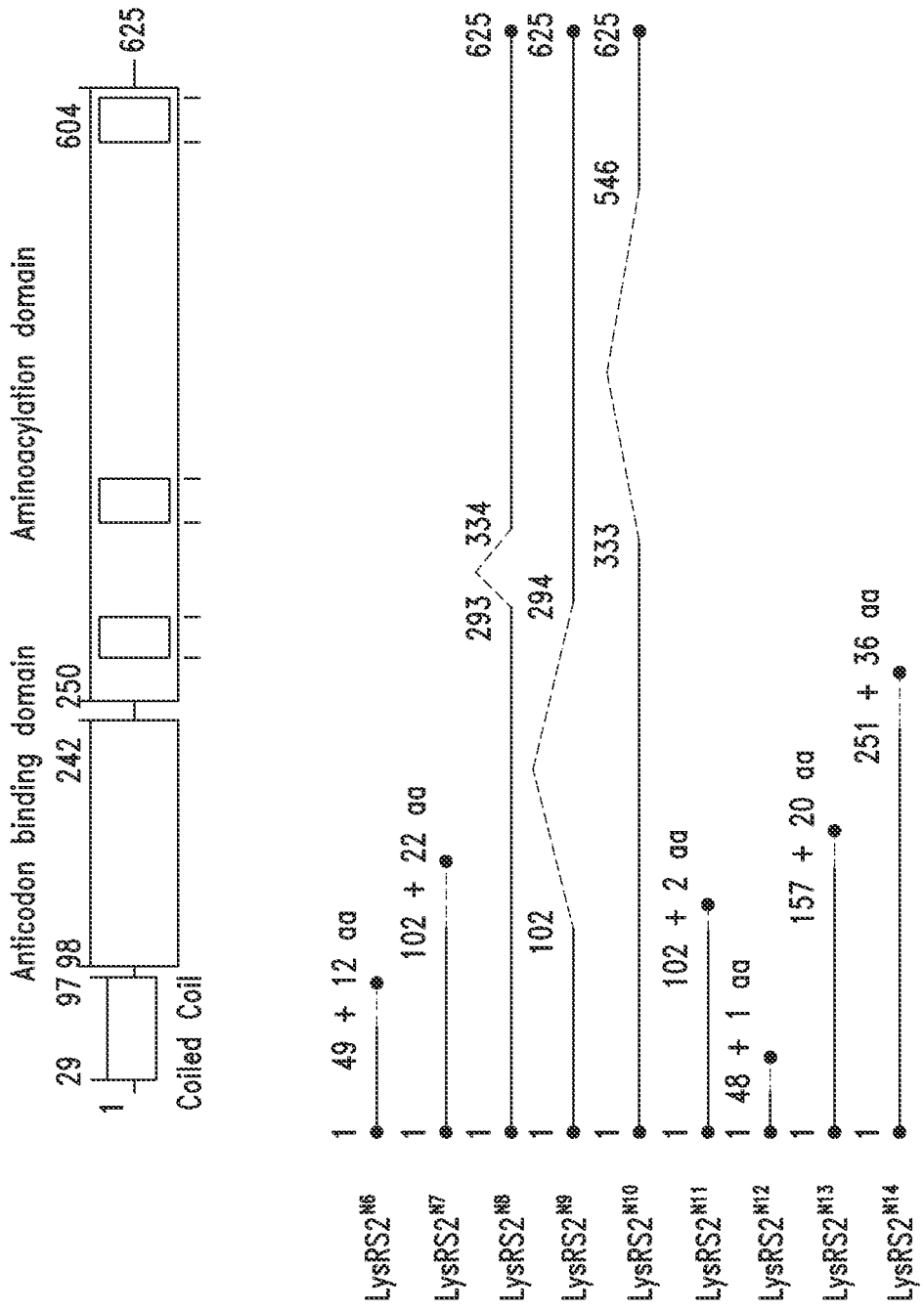
Figure 4C:
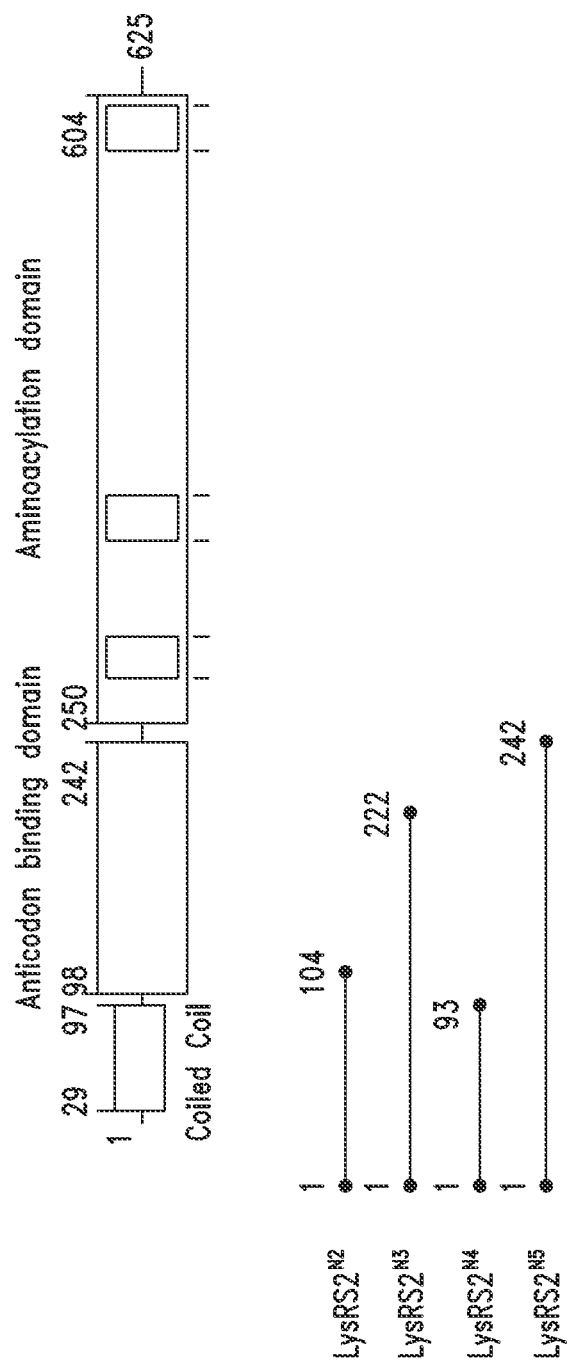

Embodiments of the present invention relate generally to the discovery of protein fragments of aminoacyl-tRNA synthetases (AARSs), which possess non-canonical biological activities, such as extracellular signaling activities, and/or other characteristics of therapeutic and diagnostic relevance.

The AARSs are universal and essential elements of the protein synthesis machinery found in all organisms, but human AARSs and their associated proteins have naturally-occurring resected variants, with potent cell signaling activities that contribute to normal functioning of humans. The activities of these protein fragments are distinct from the protein synthesis activities commonly known for AARSs, and the present invention includes the discovery and development of these resected proteins as new biotherapeutic agents, new discovery research reagents, and as new antigens/targets for directed biologics and diagnostic agents that can be used to potentially treat or diagnose a wide variety of human diseases, such as inflammatory, hematological, neurodegenerative, autoimmune, hematopoietic, cardiovascular, and metabolic diseases or disorders.

The AARS protein fragment(s) of the present invention may therefore be referred to as "resectins," or alternatively as "appendacrines." As noted above, the term "resectin" derives from the process of excising or resecting a given AARS protein fragment from the context of its full-length parent AARS sequence, which typically masks its non-canonical activities. In certain instances, the AARS protein fragments and polynucleotides of the present invention were identified through the occurrence of this resection process, whether naturally-occurring (e.g., proteolytic, splice variant), artificially-induced, or predicted. The term "appendacrine" derives from a combination of "append" (from Latin—appender) and to "separate" or "discern" (from Greek—crines)," and also reflects the separation of one or more appended domains of the AARS protein fragments from their corresponding full-length or parent AARS sequences.

Although a few AARS fragments have been previously shown to have non-synthetase activities, the expression, isolation, purification, and characterization of such fragments for biotherapeutic, discovery, or diagnostic utility is limited, and persons skilled in the art would not have readily appreciated such activities to associate with each member of the entire family of AARSs, or with alternative fragments. Here, a methodical approach was utilized to discover and verify AARS protein fragments for the 20 mitochondrial and 20 cytosolic AARSs (and associated proteins) for biotherapeutic discovery and diagnostic utility. For instance, certain of the present AARS protein fragment(s) and polynucleotides that encode them are identified from biological samples using mass spectrometry (MS), mainly to identify proteolytic fragments, and others were identified by deep sequencing techniques, mainly to identify splice variants. Other AARS protein fragment(s) are identified using in silico predictions of amino acid sequences, such as by computationally comparing synthetases from humans and lower organisms along with key demarcations (e.g., protease sites); this approach utilized sequence analysis of the full-length AARS based on specific criteria to discern proteolytic fragments and functional domains possessing non-canonical biological activities.

Novel resectins of the AARSs are unexpected, and their differential expression is also unexpected. Specific resections are typically seen under different treatments (e.g., from cells grown in media with or without serum), at different stages of growth (e.g., adult brain vs. fetal brain) and for different tissue types (e.g., pancreas vs. liver). The pattern of expression is not the same for all aminoacyl tRNA synthetases despite the fact that the canonical functions for all aminoacyl tRNA synthetases are needed in the same cell locations and in relatively proportional amounts. One would not expect the levels of an aminoacyl tRNA synthetase activity to increase without an increase in the amounts of other aminoacyl tRNA synthetase activities at the same time. The mass spectrometry and deep sequencing data indicates that aminoacyl tRNA synthetase resectins do have varying levels and do occur in different sites and at different stages.

In addition, AARS protein fragments can be expressed and purified to sufficiently high purity to discern their biological properties. Previously, fragments were often not of sufficient purity, folding, and stability to enable proper biological characterization of non-synthetase activities. Cell based assays, for instance, are used in conjunction with sufficiently pure, stable, soluble and folded resectins to reveal their important biotherapeutic, discovery or diagnostic activities.

In particular, embodiments of the present invention relate to protein fragments of Lysyl tRNA synthetases, related agents and compositions of biotherapeutic, discovery, or diagnostic utility, and methods of use thereof. The compositions of the present invention are useful in a variety of diagnostic, drug discovery, and therapeutic applications, as described herein. Preferably, the AARS proteins and fragments are purified and stored in suitable condition to the extent required for such biotherapeutic, discovery, or diagnostic uses.

Certain embodiments include compositions, comprising an isolated aminoacyl-tRNA synthetase (AARS) protein fragment of at least about 100, 90, 80, 70, 60, 50 or 40 amino acids that comprises an amino acid sequence as set forth in Table(s) 1-3, or Table(s) 4-6, or Table(s) 7-9, or Table(s) 10-12, and has a solubility of at least about 5 mg/ml, and wherein the composition has a purity of at least about 95% on a protein basis, and less than about 10 EU/mg protein endotoxin. In one aspect, the composition is a therapeutic composition. In specific embodiments, the composition is substantially serum free. In some embodiments the AARS protein fragment comprises a non-canonical activity. In some embodiments, the non-canonical biological activity is selected from modulation of extracellular signaling, modulation of cell proliferation, modulation of cell differentiation, modulation of gene transcription, modulation of cytokine production or activity, modulation of cytokine receptor activity, and modulation of inflammation. In some embodiments, the AARS protein fragment has an $EC_{50}$ of less than about 1 nM, about 5 nM, about 10 nM, about 50 nM, about 100 nM or about 200 nM for a cell-based non-canonical biological activity.

In certain embodiments the AARS protein fragment is fused to a heterologous polypeptide. In some embodiments, the AARS fusion protein substantially retains a non-canonical activity of the AARS protein fragment. In some embodiments, the AARS fusion protein suppresses a non-canonical activity of the AARS protein fragment. In some embodiments, the heterologous polypeptide is attached to the N-terminus of the AARS protein fragment. In some embodiments, the heterologous polypeptide is attached to the C-terminus of the AARS protein fragment. In one aspect of any of these embodiments the heterologous polypeptide is selected from the group consisting of purification tags, epitope tags, targeting sequences, signal peptides, membrane translocating sequences, and PK modifiers.

In certain embodiments, the composition comprises an AARS protein fragment at a concentration of at least about 10 mg/mL. In certain embodiments the composition comprises an AARS protein fragment which is at least 90% monodisperse. In certain embodiments the composition comprises less than about 3% high molecular weight aggregated proteins. In certain embodiments the composition exhibits less than 3% aggregation when stored at a concentration of at least 10 mg/mL in PBS for one week at 4° C. In certain embodiments the composition exhibits less than 3% aggregation when stored at a concentration of at least 10 mg/mL in PBS for one week at room temperature.

Various assays for measuring such features of resectins are described herein and may be used to define aspects of the invention. In certain aspects, these features will be preferable for biotherapeutic utility of the AARS protein fragments described herein.

Certain embodiments include compositions, comprising an isolated aminoacyl-tRNA synthetase (AARS) protein fragment of at least 40 amino acids that differs from an amino acid sequence set forth in Table(s) 1-3, or Table(s) 4-6, or Table(s) 7-9, or Table(s) 10-12, or Table E2 by substitution, deletion, and/or addition of about 1, 2, 3, 4, 5, 6, 7, 8, 9, 10, 11, 12, 13, 14, 15, 16, 17, 18, 19, or 20 amino acids, wherein the altered protein fragment substantially retains a non-canonical activity of the unaltered protein, or has a dominant negative phenotype in relation to the non-canonical activity, wherein the protein fragment has a solubility of at least about 5 mg/ml, and wherein the composition has a purity of at least about 95% on a protein basis and less than about 10 EU/mg protein endotoxin. In specific embodiments, the composition is substantially serum free.

Other embodiments include compositions, comprising an isolated antibody that specifically binds to an isolated aminoacyl-tRNA synthetase (AARS) protein fragment as set forth in Table(s) 1-3, or Table(s) 4-6, or Table(s) 7-9, or Table(s) 10-12, or Table E2, wherein affinity of the antibody for the AARS protein fragment is about 10× stronger than its affinity for a corresponding full-length AARS polypeptide. One of the surprising aspects of the present invention includes certain resectins possessing "new" surfaces accessible to antibody or other directed biologics, whereas the full length AARS "hides" or covers these surfaces with other sequences or adjacent domains. The process of resecting can also create greater aqueous accessibility for revealing previously unidentified biological activities. Some embodiments include compositions, comprising an isolated antibody that specifically binds to an isolated aminoacyl-tRNA synthetase (AARS) protein fragment as set forth in Table(s) 1-3, or Table(s) 4-6, or Table(s) 7-9, or Table(s) 10-12, or Table E2, wherein the antibody has an affinity of at least about 10 nM for the AARS protein fragment, and an affinity of at least about 100 nM for a corresponding full-length AARS polypeptide. In some embodiments, the antibody binds to an epitope located within an AARS polypeptide unique splice junction as set forth in any of Table(s) 1-3, or Table(s) 4-6, or Table(s) 7-9, or Table(s) 10-12, or Table E2, or to an amino acid sequence C-terminal of this splice site. In certain embodiments, the antibody antagonizes the non-canonical activity of the AARS protein fragment. Such antagonists may optionally bind the corresponding parental or full-length AARS.

Other aspects relate to bioassay systems, comprising a substantially pure aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12, or Table E2, and a binding partner that binds to the AARS protein fragment. In one aspect, the binding partner is selected from the group consisting of a cellular surface receptor protein, nucleic acid, lipid membrane, cell regulatory protein, enzyme, and transcription factor. Optionally, such a receptor may be part of a cell, preferably a cell relevant to the revealed biology of the resectin.

Certain embodiments include cellular compositions, comprising an isolated aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12, or Table E2, and an engineered population of cells in which at least one cell comprises a polynucleotide encoding said AARS protein fragment. In one aspect, the cells are capable of growing in a serum free medium.

Also included are detection systems, comprising a substantially pure aminoacyl-tRNA synthetase (AARS) protein fragment of at least 50 or 100 amino acids that comprises an amino acid sequence as set forth in Table(s) 1-3, or Table(s) 4-6, or Table(s) 7-9, or Table(s) 10-12, or Table E2, a cell that comprises a cell-surface receptor or an extracellular portion thereof that binds to the protein fragment, and a molecule of less than about 2000 daltons, or a second polypeptide, which modulates binding or interaction between the AARS protein fragment and the extracellular receptor.

Particular embodiments include diagnostic systems, comprising a substantially pure aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12, or Table E2, and a cell that comprises a cell-surface receptor or an extracellular portion thereof that binds to the AARS protein fragment, wherein the system or cell comprises an indicator molecule that allows detection of a change in the levels or activity of the cell-surface receptor or extracellular portion thereof.

Certain embodiments include cellular growth devices, comprising an isolated aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12, or Table E2, an engineered population of cells in which at least one cell comprises a polynucleotide encoding said AARS protein fragment, at least about 10 liters of serum-free cell media, and a sterile container. In specific embodiments, the cells utilized for any of the methods or compositions described herein are capable of growing in serum-free media, optionally with an antibiotic and an inducer.

Some embodiments relate to antisense or RNA interference (RNAi) agents, comprising a sequence that is targeted against a unique splice junction of an AARS splice variant as set forth in Table(s) 1-3, or Table(s) 4-6, or Table(s) 7-9, or Table(s) 10-12, or Table E2.

Also included are therapeutic compositions, comprising an isolated aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12, or Table E2, wherein the protein fragment specifically binds to a binding partner and has a solubility of at least about 5 mg/ml, and wherein the composition has a purity of at least about 95% on a protein basis. In some aspects, the composition may have less than 10 EU endotoxin/mg protein.

Also included are compositions, comprising an isolated aminoacyl-tRNA synthetase (AARS) protein fragment of at least 40 amino acids that is at least 80%, 85%, 90%, 95%, 98%, or 100% identical to an amino acid sequence set forth in Table(s) 1-3, or Table(s) 4-6, or Table(s) 7-9, or Table(s) 10-12, or Table E2, wherein the protein fragment has a solubility of at least about 5 mg/ml, and wherein the composition has a purity of at least about 95% on a protein basis and less than 10 EU endotoxin/mg protein. In any of these embodiments, the compositions may comprise an AARS protein fragment that is at least about 50%, about 60%, about 70%, about 80%, about 90% or about 95% monodisperse with respect to its apparent molecular mass. In another aspect of any of these embodiments, the compositions comprise less than about 10% (on a protein basis) high molecular weight aggregated proteins, or less than about 5% high molecular weight aggregated proteins, or less than about 4% high molecular weight aggregated proteins, or less than about 3% high molecular weight aggregated proteins, or less than about 2% high molecular weight aggregated proteins, or less than about 1% high molecular weight aggregated proteins.

In another aspect of any of these embodiments, the compositions exhibits less than about 10% aggregation when stored at a concentration of at least 10 mg/mL in PBS for one week at 4° C., or less than about 5% aggregation when stored at a concentration of at least 10 mg/mL in PBS for one week at 4° C., or less than about 3% aggregation when stored at a concentration of at least 10 mg/mL in PBS for one week at 4° C., or less than about 2% aggregation when stored at a concentration of at least 10 mg/mL in PBS for one week at 4° C., or less than about 1% aggregation when stored at a concentration of at least 10 mg/mL in PBS for one week at 4° C.

Certain embodiments include compositions, comprising a substantially pure aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12, or Table E2, and at least one covalently or noncovalently moiety attached thereto. In some embodiments, the moiety is a detectable label. In some embodiments, the moiety is a water soluble polymer. In some embodiments, the moiety is PEG. In one aspect of any of these embodiments, the moiety is attached to the N-terminus of the protein fragment. In one aspect of any of these embodiments, the moiety is attached to the C-terminus of the protein fragment.

Particular embodiments include compositions, comprising a solid substrate attached to an isolated aminoacyl-tRNA synthetase (AARS) protein fragment of at least 40 amino acids that comprises an amino acid sequence as set forth in Table(s) 1-3, or Table(s) 4-6, or Table(s) 7-9, or Table(s) 10-12 or Table E2, or a biologically active fragment or variant thereof, wherein the protein fragment has a solubility of at least about 5 mg/ml, and the composition has a purity of at least about 95% on a protein basis.

Also included are compositions, comprising a binding agent that specifically binds to an isolated aminoacyl-tRNA synthetase (AARS) protein fragment as set forth in Table(s) 1-3, or Table(s) 4-6, or Table(s) 7-9, or Table(s) 10-12, wherein the binding agent has an affinity of at least about 1 nM for the protein fragment. In one aspect, the binding agent binds to an epitope located within an AARS polypeptide unique splice junction as set forth in any of Table(s) 1-3, or Table(s) 4-6, or Table(s) 7-9, or Table(s) 10-12, or to an amino acid sequence C-terminal of this splice site. In some embodiments, the binding agent antagonizes a non-canonical activity of the AARS polypeptide.

Certain embodiments include isolated aminoacyl-tRNA synthetase (AARS) polypeptides, comprising an amino acid sequence of an AARS protein fragment as described herein, an amino acid sequence encoded by an AARS polynucleotide as described herein, or a variant or fragment thereof. Certain AARS polypeptides comprise an amino acid sequence that is at least 80%, 85%, 90%, 95%, 98%, or 100% identical to an AARS reference sequence as disclosed in Table(s) 1-3, or Table(s) 4-6, or Table(s) 7-9, or Table(s) 10-12, or Table E2. Certain AARS polypeptides consist essentially of an amino acid sequence that is at least 80%, 85%, 90%, 95%, 98%, or 100% identical to an AARS reference sequence as disclosed in Table(s) 1-3, or Table(s) 4-6, or Table(s) 7-9, or Table(s) 10-12, or Table E2. In certain embodiments, the polypeptide comprises a non-canonical biological activity. In specific embodiments, the non-canonical biological activity is selected from modulation of cell signaling (e.g., extracellular signaling), modulation of cell proliferation, modulation of cell migration, modulation of cell differentiation, modulation of apoptosis or cell death, modulation of angiogenesis, modulation of cell binding, modulation of cellular metabolism, modulation of cellular uptake, modulation of gene transcription, or secretion, modulation of cytokine production or activity, modulation of cytokine receptor activity, and modulation of inflammation.

Other aspects include antibodies and other binding agents that exhibit binding specificity for an isolated AARS polypeptide as described herein, a binding partner of the AARS polypeptide, or the complex of both. In some embodiments, the affinity of the antibody or binding agent for the AARS polypeptide is about 10× stronger than its affinity for a corresponding full-length AARS polypeptide. In specific embodiments, the binding agent is selected from a peptide, peptide mimetic, an adnectin, an aptamer, and a small molecule. In certain embodiments, the antibody or binding agent antagonizes a non-canonical activity of the AARS polypeptide. In other embodiments, the antibody or binding agent agonizes a non-canonical activity of the AARS polypeptide.

Certain embodiments include isolated aminoacyl-tRNA synthetase (AARS) polynucleotides, comprising a nucleotide sequence of an AARS polynucleotide as described herein, a nucleotide sequence that encodes an AARS protein fragment as described herein, or a variant, a fragment, or a complement thereof. Certain AARS polynucleotides comprise a nucleotide sequence that is at least 80%, 85%, 90%, 95%, 98%, or 100% identical to an AARS reference polynucleotide, or a complement thereof, as disclosed in Table(s) 1-3, or Table(s) 4-6, or Table(s) 7-9, or Table(s) 10-12, or Table E2. In some embodiments, the nucleotide sequence is codon optimized for bacterial expression. In one aspect, the nucleotide sequence is at least 80% identical a polynucleotide sequence disclosed in Table E2.

Specific AARS polynucleotides consist essentially of a nucleotide sequence that is at least 80%, 85%, 90%, 95%, 98%, or 100% identical to an AARS reference polynucleotide, or a complement thereof, as disclosed in Table(s) 1-3, or Table(s) 4-6, or Table(s) 7-9, or Table(s) 10-12, or Table E2. Other AARS polynucleotides comprise or consist essentially of a nucleotide sequence that specifically hybridizes to an AARS reference polynucleotide, as disclosed in Table(s) 1-3, or Table(s) 4-6, or Table(s) 7-9, or Table(s) 10-12, or Table E2. In certain embodiments, the polynucleotide is selected from a primer, a probe, and an antisense oligonucleotide. In specific embodiments, the primer, probe, or antisense oligonucleotide is targeted to a specific or unique splice junction, and/or sequence 3' of this splice site within an AARS polynucleotide.

Certain embodiments include methods of determining presence or levels of an AARS protein fragment in a sample, comprising contacting the sample with one or more binding agents that specifically bind to an AARS protein fragment as described herein, detecting the presence or absence of the binding agent, and thereby determining the presence or levels of the AARS protein fragment. Other embodiments include methods of determining presence or levels of an AARS protein fragment in a sample, comprising analyzing the sample with a detector that is capable of specifically identifying a protein fragment as described herein, and thereby determining the presence or levels of the AARS protein fragment. In specific embodiments, the detector is a mass spectrometer (MS), a flow cytometer, a protein imaging device, an enzyme-linked immunosorbent assays (ELISA), or a protein microarray. Certain embodiments comprise comparing the presence or levels of the AARS protein fragment to a control sample or a predetermined value. Certain embodiments comprise characterizing the state of the sample to distinguish it from the control. In specific embodiments, the sample and control comprise a cell or tissue, and the method comprises distinguishing between cells or tissues of different species, cells of different tissues or organs, cells at different cellular developmental states, cells at different cellular differentiation states, cells at different physiological states, or healthy and diseased cells. For instance, selected resectins may be more abundant under conditions such as stress or insult.

Certain embodiments include discovery methods of, and related compositions for, identifying a compound that specifically binds to an aminoacyl-tRNA synthetase (AARS) polypeptide as described herein, or one or more of its cellular binding partners, comprising a) combining the AARS polypeptide or its cellular binding partner or both with at least one test compound under suitable conditions, and b) detecting binding of the AARS polypeptide or its cellular binding partner or both to the test compound, thereby identifying a compound that specifically binds to the AARS polypeptide or its cellular binding partner or both. In certain embodiments, the test compound is a polypeptide or peptide, an antibody or antigen-binding fragment thereof, a peptide mimetic, or a small molecule. In certain embodiments, the test compound agonizes a non-canonical biological activity of the AARS polypeptide or its cellular binding partner. In other embodiments, the test compound antagonizes a non-canonical biological activity of the AARS polypeptide or its cellular binding partner. Certain embodiments include a compound identified by the above-method, such as an agonist (e.g., small molecule, peptide).

Certain embodiments include methods of determining presence or levels of a polynucleotide sequence of an AARS splice variant in a sample, comprising contacting the sample with one or more oligonucleotides that specifically hybridize to an AARS polynucleotide as described herein, detecting the presence or absence of the oligonucleotides in the sample, and thereby determining the presence or levels of the polynucleotide sequence of the AARS splice variant. Other embodiments include methods of determining presence or levels of a polynucleotide sequence of an AARS splice variant in a sample, comprising contacting the sample with at least two oligonucleotides that specifically amplify an AARS polynucleotide as described herein, performing an amplification reaction, detecting the presence or absence of an amplified product, and thereby determining presence or levels of the polynucleotide sequence of the AARS splice variant. In specific embodiments, the oligonucleotide(s) specifically hybridize to or specifically amplify a splice junction that is unique to the AARS splice variant. Certain embodiments include comparing the presence or levels of the AARS protein fragment or splice variant to a control sample or a predetermined value. Certain embodiments include characterizing the state of the sample to distinguish it from the control. In specific embodiments, the sample and control comprise a cell or tissue, and the method comprises distinguishing between cells or tissues of different species, cells of different tissues or organs, cells at different cellular developmental states, cells at different cellular differentiation states, or healthy and diseased cells.

Some embodiments include pharmaceutical compositions, comprising an AARS polynucleotide described herein, an AARS polypeptide described herein, a binding agent as described herein, or a compound identified by the above-method or described herein, and a pharmaceutically acceptable excipient or carrier.

Certain embodiments include methods of modulating a cellular activity of a cell, comprising contacting the cell with an AARS polynucleotide described herein, an AARS polypeptide described herein, a binding agent described herein, a compound of the above-method or described herein, or a pharmaceutical composition described herein. In specific embodiments, the cellular activity is selected from cell proliferation, cell migration, cell differentiation, apoptosis or cell death, cell signaling, angiogenesis, cell binding, cellular uptake, cell secretion, metabolism, cytokine production or activity, cytokine receptor activity, gene transcription, and inflammation. In one aspect, the cell is selected from the group consisting of pre-adipocytes, bone marrow, neutrophils, blood cells, hepatocytes, astrocytes, mesenchymal stem cells, and skeletal muscle cells.

In certain embodiments, the cell is in a subject. Certain embodiments comprise treating the subject, wherein the subject has a condition associated with a neoplastic disease, an immune system disease or condition, an infectious disease, a metabolic disease, an inflammatory disorder, neuronal/neurological disease, a muscular/cardiovascular disease, a disease associated with aberrant hematopoiesis, a disease associated with aberrant angiogenesis, or a disease associated with aberrant cell survival.

Also included are processes for manufacturing a pharmaceutical compound, comprising: a) performing an in vitro screen of one or more candidate compounds in the presence an AARS protein fragment of at least 40 amino acids that comprises an amino acid sequence as set forth in Table(s) 1-3, or Table(s) 4-6, or Table(s) 7-9, or Table(s) 10-12, to identify a compound that specifically binds to the AARS protein fragment; b) performing a cell-based or biochemical or receptor assay with the compound identified in step a), to identify a compound that modulates one or more non-canonical activities of the AARS protein fragment; c) optionally assessing the structure-activity relationship (SAR) of the compound identified in step b), to correlate its structure with modulation of the non-canonical activity, and optionally derivatizing the compound to alter its ability to modulate the non-canonical activity; and d) producing sufficient amounts of the compound identified in step b), or the derivatized compound in step c), for use in humans, thereby manufacturing the pharmaceutical compound.

Other embodiments include processes for manufacturing a pharmaceutical compound, comprising: a) performing an in vitro screen of one or more candidate compounds in the presence a cell-surface receptor or an extracellular portion thereof that specifically binds to an AARS protein fragment of Table(s) 1-3, or Table(s) 4-6, or Table(s) 7-9, or Table(s) 10-12, to identify a compound that specifically binds to the cell-surface receptor or extracellular portion thereof; b) performing a cell-based or biochemical or receptor assay with the compound identified in step a), to identify a compound that modulates one or more non-canonical activities of the AARS protein fragment; c) optionally assessing the structure-activity relationship (SAR) of the compound identified in step b), to correlate its structure with modulation of the non-canonical activity, and optionally derivatizing the compound to alter its ability to modulate the non-canonical activity; and d) producing sufficient amounts of the compound identified in step b), or the derivatized compound in step c), for use in humans, thereby manufacturing the pharmaceutical compound.

Some embodiments include a cellular composition, comprising an engineered population of cells in which at least one cell comprises a polynucleotide encoding a heterologous full length aminoacyl-tRNA synthetase (AARS) protein, wherein the cells are capable of growing in a serum-free medium. In one aspect, the full length aminoacyl-tRNA synthetase (AARS) protein comprises a heterologous purification or epitope tag to facilitate purification of an AARS protein fragment. In another aspect, the full length aminoacyl-tRNA synthetase (AARS) protein comprises a heterologous proteolysis site to enable production of the AARS protein fragment upon cleavage.

Some embodiments include a method for producing an AARS polypeptide as set forth in Table(s) 1-3, or Table(s) 4-6, or Table(s) 7-9, or Table(s) 10-12, or Table E2 in situ within a cell, comprising; i) expressing a heterologous full length aminoacyl-tRNA synthetase (AARS) protein within the cell, wherein the cell comprises a protease capable of cleaving the heterologous full length aminoacyl-tRNA synthetase (AARS) protein to produce the AARS polypeptide.

Some embodiments include a method for producing an AARS polypeptide as set forth in Table(s) 1-3, or Table(s) 4-6, or Table(s) 7-9, or Table(s) 10-12, or Table E2 comprising contacting an isolated full length aminoacyl-tRNA synthetase (AARS) protein with a protease that is capable of cleaving the full length aminoacyl-tRNA synthetase (AARS) protein and producing an AARS polypeptide.

Some embodiments include an engineered full length aminoacyl-tRNA synthetase (AARS) protein comprising a heterologous proteolysis site to enable the proteolytic generation of an AARS protein fragment as set forth in any of Table(s) 1-3, or Table(s) 4-6, or Table(s) 7-9, or Table(s) 10-12 or Table E2.

Some embodiments include a composition, comprising an isolated full length aminoacyl-tRNA synthetase protein, wherein the composition has a purity of at least about 95% on a protein basis, less than about 10 EU endotoxin/mg protein, and is substantially serum free. In one aspect, the full length aminoacyl-tRNA synthetase protein is present at a concentration of at least 10 mg/mL, and is at least 90% monodisperse.

A further embodiment includes a method of reducing or ameliorating at least one symptom of a disease mediated by a mutation, or inappropriate subcellular association, or over expression, or subcellular distribution of Lysyl-tRNA synthetase (LysRS), comprising administering to a subject an isolated aminoacyl-tRNA synthetase (AARS) protein fragment that consists essentially of an amino acid sequence as set forth in any of Table(s) 1-3, or Table(s) 4-6, or Table(s) 7-9, or Table(s) 10-12, or Table E2.

In some embodiments the AARS protein fragment has at least 40 amino acids. In some embodiments the AARS protein fragment has a non canonical activity. In some embodiments the AARS protein fragment is fused to a heterologous fusion partner.

In some embodiments the disease is Charcot-Marie-Tooth Disease Type 2D (CMT2D) or Distal Spinal Muscular Atrophy Type V (dSMA-V). In some embodiments the disease is CMT2D. In some embodiments the at least one symptom is reduced nerve conduction velocity. In some embodiments the disease is dSMA-V. In some embodiments the at least one symptom is muscle weakness.

In some embodiments the AARS fusion protein substantially retains a non-canonical activity of the AARS protein fragment. In some embodiments the AARS fusion protein suppresses a non-canonical activity of the AARS protein fragment. In some embodiments the heterologous polypeptide is attached to the N-terminus of the AARS protein fragment. In some embodiments the heterologous polypeptide is attached to the C-terminus of the AARS protein fragment. In some embodiments the heterologous polypeptide is selected from the group consisting of purification tags, epitope tags, targeting sequences, signal peptides, membrane translocating sequences, and PK modifiers.

A further embodiment includes a method of reducing or ameliorating a symptom of a disease mediated by a mutation, or inappropriate subcellular association, or over expression, or subcellular distribution of Lysyl-tRNA synthetase (LysRS), comprising administering to a subject an isolated antibody or binding agent that specifically binds to an isolated aminoacyl-tRNA synthetase (AARS) protein fragment as set forth in any of Table(s) 1-3, or Table(s) 4-6, or Table(s) 7-9, or Table(s) 10-12, or Table E2, wherein affinity of the antibody for the AARS protein fragment is about 10× stronger than its affinity for a corresponding full-length AARS polypeptide. In some embodiments the antibody, or binding agent antagonizes a non-canonical activity of the AARS polypeptide.

DETAILED DESCRIPTION OF THE INVENTION

| TABLE OF CONTENTS | |
|---|---|
| I. OVERVIEW | 16 |
| II. DEFINITIONS | 17 |
| III. PURIFIED AARS PROTEIN FRAGMENTS AND VARIANTS | 30 |
| IV. AARS POLYNUCLEOTIDES | 85 |
| V. ANTIBODIES | 98 |
| VI. ANTIBODY ALTERNATIVES AND OTHER BINDING AGENTS | 103 |
| VII. BIOASSAYS AND ANALYTICAL ASSAYS | 107 |
| VIII. EXPRESSION AND PURIFICATION SYSTEMS | 110 |
| IX. DIAGNOSTIC METHODS AND COMPOSITIONS | 122 |
| X. ANTISENSE AND RNAI AGENTS | 138 |
|    A. ANTISENSE AGENTS | 139 |
|    B. RNA INTERFERENCE AGENTS | 147 |
| XI. DRUG DISCOVERY | 154 |
| XII. METHODS OF USE | 163 |
| XIII. PHARMACEUTICAL FORMULATIONS, ADMINISTRATION AND KITS | 170 |
| XIV. EXAMPLES | 178 |

I. Overview

The current invention is directed, at least in part, to the discovery of novel AARS polypeptides, and methods for their preparation and use, which represent the transformation of native wild type proteins into new forms that exhibit markedly different characteristics compared to the naturally occurring full length Lysyl tRNA synthetase genes. Such AARS polypeptides were identified based on extensive sequence, and mass spectrum analysis of expressed Lysyl tRNA synthetases in different tissues, followed by the systematic production and testing of each potential AARS polypeptide to identify protein sequences that represent stable and soluble protein domains which exhibit novel biological activities, and favorable therapeutic drug characteristics.

Based on this analysis several novel families of AARS polypeptides derived from both the cytosolic and mitochondrial Lysyl tRNA synthetases have been identified.

In one aspect, such Lysyl tRNA synthetase derived AARS polypeptides comprise polypeptide sequences comprising approximately amino acids 1-74 of cytosolic Lysyl tRNA synthetase.

In one aspect, such Lysyl tRNA synthetase derived AARS polypeptides comprise polypeptide sequences comprising approximately amino acids 1-214 of cytosolic Lysyl tRNA synthetase.

In one aspect, such Lysyl tRNA synthetase derived AARS polypeptides comprise polypeptide sequences comprising approximately amino acids 157-597 of cytosolic Lysyl tRNA synthetase.

In one aspect, such Lysyl tRNA synthetase derived AARS polypeptides comprise polypeptide sequences comprising approximately amino acids 469-597 of cytosolic Lysyl tRNA synthetase.

In one aspect, such Lysyl tRNA synthetase derived AARS polypeptides comprise polypeptide sequences comprising approximately amino acids 65-214 of cytosolic Lysyl tRNA synthetase.

In a further aspect, such Lysyl tRNA synthetase derived AARS polypeptides comprise alternatively spliced mitochondrial Lysyl tRNA synthetase transcripts encoding AARS polypeptides comprising either i) amino acids 1 to 49 of mitochondrial Lysyl tRNA synthetase plus 12 amino acids, or ii) amino acids 1 to 102 of mitochondrial Lysyl tRNA synthetase plus 22 amino acids, or iii) amino acids 1 to 102 of mitochondrial Lysyl tRNA synthetase plus 2 amino acids, or iv) amino acids 1 to 48 of mitochondrial Lysyl tRNA synthetase, plus one amino acid or v) amino acids 1 to 333 plus amino acids 546-625 of mitochondrial Lysyl tRNA synthetase.

In further aspects, such Lysyl tRNA synthetase derived AARS polypeptides comprise polypeptide sequences comprising approximately amino acids 1-104 of the mitochondrial Lysyl tRNA synthetase.

In one aspect, such Lysyl tRNA synthetase derived AARS polypeptides comprise polypeptide sequences comprising approximately amino acids 1-242 of the mitochondrial Lysyl tRNA synthetase.

These new AARS polypeptide families represent novel, previously unknown protein products which exhibit inter alia i) novel biological activity, ii) favorable protein stability and aggregation characteristics, and iii) the ability to be expressed and produced at high level in prokaryotic expression systems, which are materially different characteristics not found in the intact wild type protein.

II. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length.

An "agonist" refers to a molecule that intensifies or mimics an activity. For example, a non-canonical biological activity of an AARS, or another protein. Agonists may include proteins, nucleic acids, carbohydrates, small molecules, or any other compound or composition that modulates the activity of an AARS either by directly interacting with the AARS or its binding partner, or by acting on components of the biological pathway in which the AARS participates. Included are partial and full agonists.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivitization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

In certain aspects, the use of non-natural amino acids can be utilized to modify (e.g., increase) a selected non-canonical activity of an AARS protein fragment, or to alter the in vivo or in vitro half-life of the protein. Non-natural amino acids can also be used to facilitate (selective) chemical modifications (e.g., pegylation) of an AARS protein. For instance, certain non-natural amino acids allow selective attachment of polymers such as PEG to a given protein, and thereby improve their pharmacokinetic properties.

Specific examples of amino acid analogs and mimetics can be found described in, for example, Roberts and Vellaccio, The Peptides: Analysis, Synthesis, Biology, Eds. Gross and Meinhofer, Vol. 5, p. 341, Academic Press, Inc., New York, N.Y. (1983), the entire volume of which is incorporated herein by reference. Other examples include peralkylated amino acids, particularly permethylated amino acids. See, for example, Combinatorial Chemistry, Eds. Wilson and Czarnik, Ch. 11, p. 235, John Wiley & Sons Inc., New York, N.Y. (1997), the entire book of which is incorporated herein by reference. Yet other examples include amino acids whose amide portion (and, therefore, the amide backbone of the resulting peptide) has been replaced, for example, by a sugar ring, steroid, benzodiazepine or carbo cycle. See, for instance, Burger's Medicinal Chemistry and Drug Discovery, Ed. Manfred E. Wolff, Ch. 15, pp. 619-620, John Wiley & Sons Inc., New York, N.Y. (1995), the entire book of which is incorporated herein by reference. Methods for synthesizing peptides, polypeptides, peptidomimetics and proteins are well known in the art (see, for example, U.S. Pat. No. 5,420, 109; M. Bodanzsky, Principles of Peptide Synthesis (1st ed. & 2d rev. ed.), Springer-Verlag, New York, N.Y. (1984 & 1993), see Chapter 7; Stewart and Young, Solid Phase Peptide Synthesis, (2d ed.), Pierce Chemical Co., Rockford, Ill. (1984), each of which is incorporated herein by reference). Accordingly, the AARS polypeptides of the present invention may be composed of naturally occurring and non-naturally occurring amino acids as well as amino acid analogs and mimetics.

The term "antagonist" refers to a molecule that reduces or attenuates an activity. For example, a non-canonical biological activity of an AARS, or another protein. Antagonists may include proteins such as antibodies, nucleic acids, carbohydrates, small molecules, or any other compound or composition that modulates the activity of an AARS or its binding partner, either by directly interacting with the AARS or its binding partner or by acting on components of the biological pathway in which the AARS participates. Included are partial and full antagonists.

The term "aminoacyl-tRNA synthetase" (AARS) refers generally to enzymes that in their natural or wild-type form are capable of catalyzing the esterification of a specific amino acid or its precursor to one of all its compatible cognate tRNAs to form an aminoacyl-tRNA. In this "canonical" activity, aminoacyl-tRNA synthetases catalyze a two-step reaction: first, they activate their respective amino acid by forming an aminoacyl-adenylate, in which the carboxyl of the amino acid is linked in to the alpha-phosphate of ATP by displacing pyrophosphate, and then, when the correct tRNA is bound, the aminoacyl group of the aminoacyl-adenylate is transferred to the 2' or 3' terminal OH of the tRNA.

Class I aminoacyl-tRNA synthetases typically have two highly conserved sequence motifs. These enzymes aminoacylate at the 2'-OH of an adenosine nucleotide, and are usually monomeric or dimeric. Class II aminoacyl-tRNA synthetases typically have three highly conserved sequence motifs. These enzymes aminoacylate at the 3'-OH of the same adenosine, and are usually dimeric or tetrameric. The active sites of class II enzymes are mainly made up of a seven-stranded anti-parallel β-sheet flanked by α-helices. Although phenylalanine-tRNA synthetase is class II, it aminoacylates at the 2'-OH.

AARS polypeptides include sources of mitochondrial and cytoplasmic forms of tyrosyl-tRNA synthetase (TyrRS), a tryptophanyl-tRNA synthetase (TrpRS), a glutaminyl-tRNA synthetase (GlnRS), a glycyl-tRNA synthetase (GlyRS), a histidyl-tRNA synthetase (HisRS), a seryl-tRNA synthetase (SerRS), a phenylalanyl-tRNA synthetase (PheRS), an alanyl-tRNA synthetase (AlaRS), an asparaginyl-tRNA synthetase (AsnRS), an aspartyl-tRNA synthetase (AspRS), a cysteinyl-tRNA synthetase (CysRS), a glutamyl-tRNA synthetase (GluRS), a prolyl-tRNA synthetase (ProRS), an arginyl-tRNA synthetase (ArgRS), an isoleucyl-tRNA synthetase (IleRS), a leucyl-tRNA synthetase (LeuRS), a lysyl-tRNA synthetase (LysRS), a threonyl-tRNA synthetase (ThrRS), a methionyl-tRNA synthetases (MetRS), or a valyl-tRNA synthetase (ValRS). The wild-type or parental sequences of these AARS polypeptides are known in the art.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The recitation "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production of AARS polypeptides, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art. Also included are methods of producing AARS polypeptides in and isolating them from eukaryotic cells such as mammalian cells to reduce, if not eliminate, the risk of endotoxins being present in a composition of the invention. Preferred are methods of producing AARS polypeptides in and isolating them from serum free cells. Such compositions comprising AARS polypeptides represent new formulations which exhibit novel and new biological and therapeutic characteristics not found in AARS polypeptide compositions contaminated with serum or endotoxin which have the potential to bind to and alter the novel biological properties of the AARS polypeptides.

Endotoxins can be detected using routine techniques known in the art. For example, the *Limulus* Ameobocyte Lysate assay, which utilizes blood from the horseshoe crab, is a very sensitive assay for detecting presence of endotoxin, and reagents, kits and instrumentation for the detection of endotoxin based on this assay are commercially available, for example from the Lonza Group. In this test, very low levels of LPS can cause detectable coagulation of the *limulus* lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of protein. Typically, 1 ng lipopolysaccharide (LPS) corresponds to about 1-10 EU.

In certain embodiments, the "purity" of any given agent (e.g., AARS protein fragment) in a composition may be specifically defined. For instance, certain compositions may comprise an agent that is at least 80, 85, 90, 91, 92, 93, 94, 95, 96, 97, 98, 99, or 100% pure, including all decimals in between, as measured, for example and by no means limiting, by high pressure liquid chromatography (HPLC), a well-known form of column chromatography used frequently in biochemistry and analytical chemistry to separate, identify, and quantify compounds.

As used herein, the terms "function" and "functional" and the like refer to a biological, enzymatic, or therapeutic function.

By "gene" is meant a unit of inheritance that may occupy a specific locus on a chromosome and consists of transcriptional and/or translational regulatory sequences and/or a coding region and/or non-translated sequences (i.e., introns, 5' and 3' untranslated sequences).

"Homology" refers to the percentage number of amino acids that are identical or constitute conservative substitutions. Homology may be determined using sequence comparison programs such as GAP (Deveraux et al., 1984, Nucleic Acids Research 12, 387-395), which is incorporated herein by reference. In this way sequences of a similar or substantially different length to those cited herein could be compared by insertion of gaps into the alignment, such gaps being determined, for example, by the comparison algorithm used by GAP.

The term "host cell" includes an individual cell or cell culture that can be or has been a recipient of any recombinant vector(s), isolated polynucleotide, or polypeptide of the invention. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention is a recombinant host cell.

By "isolated" is meant material that is substantially or essentially free from components that normally accompany it in its native state. For example, an "isolated polynucleotide," as used herein, includes a polynucleotide that has been purified from the sequences that flank it in its naturally-occurring state, e.g., a DNA fragment which has been removed from the sequences that are normally adjacent to the fragment. Alternatively, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances.

The term "mRNA" or sometimes refer by "mRNA transcripts" as used herein, include, but not limited to pre-mRNA transcript(s), transcript processing intermediates, mature mRNA(s) ready for translation and transcripts of the gene or genes, or nucleic acids derived from the mRNA transcript(s). Transcript processing may include splicing, editing and degradation. As used herein, a nucleic acid derived from an mRNA transcript refers to a nucleic acid for whose synthesis the mRNA transcript or a subsequence thereof has ultimately served as a template. A cDNA reverse transcribed from an mRNA, an RNA transcribed from that cDNA, a DNA amplified from the cDNA, an RNA transcribed from the amplified DNA, etc., are all derived from the mRNA transcript and detection of such derived products is indicative of the presence and/or abundance of the original transcript in a sample. Thus, mRNA derived samples include, but are not limited to, mRNA transcripts of the gene or genes, cDNA reverse transcribed from the mRNA, cRNA transcribed from the cDNA, DNA amplified from the genes, RNA transcribed from amplified DNA, and the like.

"Non-canonical" activity as used herein, refers generally to either i) a new activity possessed by an AARS polypeptide of the invention that is not possessed to any significant degree by the intact native full length parental protein, or ii) an activity that was possessed by the by the intact native full length parental protein, where the AARS polypeptide either exhibits a significantly higher (i.e., at least 20% greater) specific activity compared to the intact native full length parental protein, or exhibits the activity in a new context; for example by isolating the activity from other activities possessed by the intact native full length parental protein. In the case of AARS polypeptides, non-limiting examples of non-canonical activities include extracellular signaling, RNA-binding, amino acid-binding, modulation of cell proliferation, modulation of cell migration, modulation of cell differentiation (e.g., hematopoiesis, neurogenesis, myogenesis, osteogenesis, and adipogenesis), modulation of gene transcription, modulation of apoptosis or other forms of cell death, modulation of cell signaling, modulation of cellular uptake, or secretion, modulation of angiogenesis, modulation of cell binding, modulation of cellular metabolism, modulation of cytokine production or activity, modulation of cytokine receptor activity, modulation of inflammation, and the like.

The term "half maximal effective concentration" or "$EC_{50}$" refers to the concentration of an AARS protein fragment, antibody or other agent described herein at which it induces a response halfway between the baseline and maximum after some specified exposure time; the $EC_{50}$ of a graded dose response curve therefore represents the concentration of a compound at which 50% of its maximal effect is observed. In certain embodiments, the $EC_{50}$ of an agent provided herein is indicated in relation to a "non-canonical" activity, as noted above. $EC_{50}$ also represents the plasma concentration required for obtaining 50% of a maximum effect in vivo. Similarly, the "$EC_{90}$" refers to the concentration of an agent or composition at which 90% of its maximal effect is observed. The "$EC_{90}$" can be calculated from the "$EC_{50}$" and the Hill slope, or it can be determined from the data directly, using routine knowledge in the art. In some embodiments, the $EC_{50}$ of an AARS protein fragment, antibody, or other agent is less than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, or 100 nM. Preferably, biotherapeutic composition will have an $EC_{50}$ value of about 1 nM or less.

The term "modulating" includes "increasing" or "stimulating," as well as "decreasing" or "reducing," typically in a statistically significant or a physiologically significant amount as compared to a control. Accordingly a "modulator" may be an agonist, an antagonist, or any mixture thereof depending upon the conditions used. An "increased" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the amount produced by no composition (the absence of an agent or compound) or a control composition. A "decreased" or reduced amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease in the amount produced by no composition (the absence of an agent or compound) or a control composition, including all integers in between. As one non-limiting example, a control in comparing canonical and non-canonical activities could include the AARS protein fragment of interest compared to its corresponding full-length AARS, or a fragment AARS having comparable canonical activity to its corresponding full-length AARS. Other examples of "statistically significant" amounts are described herein.

By "obtained from" is meant that a sample such as, for example, a polynucleotide extract or polypeptide extract is isolated from, or derived from, a particular source of the subject. For example, the extract can be obtained from a tissue or a biological fluid isolated directly from the subject. "Derived" or "obtained from" can also refer to the source of a polypeptide or polynucleotide sequence. For instance, an AARS sequence of the present invention may be "derived" from the sequence information of an AARS proteolytic fragment or AARS splice variant, or a portion thereof, whether naturally-occurring or artificially generated, and may thus comprise, consist essentially of, or consist of that sequence The terms "polypeptide" and "protein" are used interchangeably herein to refer to a polymer of amino acid residues and to variants and synthetic and naturally occurring analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers and naturally occurring chemical derivatives thereof. Such derivatives include, for example, post-translational modifications and degradation products including pyroglutamyl, iso-aspartyl, proteolytic, phosphorylated, glycosylated, oxidatized, isomerized, and deaminated variants of the AARS reference fragment.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity" and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, *J. Mol. Biol.* 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frame shift gap penalty of 5.

The percent identity between two amino acid or nucleotide sequences can be determined using the algorithm of E. Meyers and W. Miller (1989, *Cabios,* 4: 11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol*, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997, *Nucleic Acids Res*, 25: 3389-3402). When utilizing BLAST and Gapped BLAST programs, the default parameters of the respective programs (e.g., XBLAST and NBLAST) can be used.

The term "solubility" refers to the property of an agent provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH. In certain embodiments, solubility is measured in water or a physiological buffer such as PBS. In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent such as an AARS protein fragment has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/ml at room temperature or at 37° C.

A "splice junction" as used herein includes the region in a mature mRNA transcript or the encoded polypeptide where the 3' end of a first exon joins with the 5' end of a second exon. The size of the region may vary, and may include 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more (including all integers in between) nucleotide or amino acid residues on either side of the exact residues where the 3' end of one exon joins with the 5' end of another exon. An "exon" refers to a nucleic acid sequence that is represented in the mature form of an RNA molecule after either portions of a precursor RNA (introns) have been removed by cis-splicing or two or more precursor RNA molecules have been ligated by trans-splicing. The mature RNA molecule can be a messenger RNA or a functional form of a non-coding RNA such as rRNA or tRNA. Depending on the context, an exon can refer to the sequence in the DNA or its RNA transcript. An "intron" refers to a non-coding nucleic acid region within a gene, which is not translated into a protein. Non-coding intronic sections are transcribed to precursor mRNA (pre-mRNA) and some other RNAs (such as long noncoding RNAs), and subsequently removed by splicing during the processing to mature RNA.

A "splice variant" refers to a mature mRNA and its encoded protein that are produced by alternative splicing, a process by which the exons of the RNA (a primary gene transcript or pre-mRNA) are reconnected in multiple ways during RNA splicing. The resulting different mRNAs may be translated into different protein isoforms, allowing a single gene to code for multiple proteins.

A "subject," as used herein, includes any animal that exhibits a symptom, or is at risk for exhibiting a symptom, which can be treated or diagnosed with an AARS polynucleotide or polypeptide of the invention. Also included are subjects for which it is desirable to profile levels of AARS polypeptides and/or polynucleotides of the invention, for diagnostic or other purposes. Suitable subjects (patients) include laboratory animals (such as mouse, rat, rabbit, or guinea pig), farm animals, and domestic animals or pets (such as a cat or dog). Non-human primates and, preferably, human patients, are included.

"Treatment" or "treating," as used herein, includes any desirable effect on the symptoms or pathology of a disease or condition that can be effected by the non-canonical activities of an AARS polynucleotide or polypeptide, as described herein, and may include even minimal changes or improvements in one or more measurable markers of the disease or condition being treated. Also included are treatments that relate to non-AARS therapies, in which an AARS sequence described herein provides a clinical marker of treatment. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The practice of the present invention will employ, unless indicated specifically to the contrary, conventional methods of molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* ($3^{rd}$ Edition, 2000); *DNA Cloning: A Practical Approach*, vol. I & II (D. Glover, ed.); *Oligonucleotide Synthesis* (N. Gait, ed., 1984); *Oligonucleotide Synthesis: Methods and Applications* (P. Herdewijn, ed., 2004); *Nucleic Acid Hybridization* (B. Hames & S. Higgins, eds., 1985); *Nucleic Acid Hybridization: Modern Applications* (Buzdin and Lukyanov, eds., 2009); *Transcription and Translation* (B. Hames & S. Higgins, eds., 1984); *Animal Cell Culture* (R. Freshney, ed., 1986); Freshney, R. I. (2005) *Culture of Animal Cells, a Manual of Basic Technique*, $5^{th}$ Ed. Hoboken N.J., John Wiley & Sons; B. Perbal, *A Practical Guide to Molecular Cloning* ($3^{rd}$ Edition 2010); Farrell, R., *RNA Methodologies: A Laboratory Guide for Isolation and Characterization* ($3^{rd}$ Edition 2005), *Methods of Enzymology: DNA Structure Part A: Synthesis and Physical Analysis of DNA* Methods in Enzymology, Academic Press; *Using Antibodies: A Laboratory Manual: Portable Protocol NO. I* by Edward Harlow, David Lane, Ed Harlow (1999, Cold Spring Harbor Laboratory Press, ISBN 0-87969-544-7); *Antibodies: A Laboratory Manual* by Ed Harlow (Editor), David Lane (Editor) (1988, Cold Spring Harbor Laboratory Press, ISBN 0-87969-3, 4-2), 1855. *Handbook of Drug Screening*, edited by Ramakrishna Seethala, Prabhavathi B. Fernandes (2001, New York, N.Y., Marcel Dekker, ISBN 0-8247-0562-9); and *Lab Ref A Handbook of Recipes, Reagents, and Other Reference Tools for Use at the Bench*, Edited Jane Roskams and Linda Rodgers, (2002, Cold Spring Harbor Laboratory, ISBN 0-87969-630-3).

All publications, patents and patent applications cited herein are hereby incorporated by reference in their entirety.

III. Purified AARS Protein Fragments and Variants for Therapeutics and Other Applications Surprisingly, and unlike their full-length parental sequences that are known only for their aminoacylation-activities, it has been found that AARS fragments possess biological activities important for biotherapeutic, discovery and diagnostic applications. Embodiments of the present invention therefore include full length proteins, mature protein isoforms and protein fragments of aminoacyl-tRNA synthetases (AARS), in addition to biologically active variants and fragments thereof. In certain embodiments, the proteins and fragments may arise through endogenous proteolysis, in vitro proteolysis, splice variation, or in silico prediction, among other mechanisms.

The AARS protein fragments described herein, and variants thereof, may possess at least one "non-canonical" biological activity. The AARS protein fragment(s) of the present invention are also referred to herein as "AARS polypeptides" or "AARS reference polypeptides." In certain embodiments, the AARS polypeptides provided herein comprise or consist essentially of all or a portion of the AARS polypeptide "reference sequence(s)" as set forth in Table(s) 1-3, or Table(s) 4-6, or Table(s) 7-9, or Table(s) 10-12 below, which represent the amino acid sequence(s) of various fragments of Lysyl tRNA synthetases. Mouse and human AARS protein sequences are highly related, typically differing by no more than a few amino acids within an entire sequence, a particular domain, or a particular protein fragment.

N-terminal AARS Polypeptides: (Tables 1, 2 & 3)

Table 1A
AARS polypeptides identified by MS

| Name | Type/species/ Residues | Amino acid and Nucleic Acid Sequences | SEQ. ID. NO. |
|---|---|---|---|
| LysRS1$^{N1}$ | Protein/ Human/1-366 | MAAVQAAEVKVDGSEPKLSKNELKRR LKAEKKVAEKEAKQKELSEKQLSQAT AAATNHTTDNGVGPEEESVDPNQYYK IRSQAIHQLKVNGEDPYPHKFHVDISLT DFIQKYSHLQPGDHLTDITLKVAGRIH AKRASGGKLIFYDLRGEGVKLQVMAN SRNYKSEEEFIHINNKLRRGDIIGVQGN PGKTKKGELSIIPYEITLLSPCLHMLPHL HFGLKDKETRYRQRYLDLILNDFVRQ KFIIRSKIITYIRSFLDELGFLEIETPMMN IIPGGAVAKPFITYHNELDMNLYMRIAP ELYHKMLVVGGIDRVYEIGRQFRNEGI DLTHNPEFTTCEFYMAYADYHDLMEI TEKMVSGMVKHIT | SEQ. ID. NO. 12 |
| LysRS1$^{N1}$ | DNA/ Human/ | ATGGCGGCCGTGCAGGCGGCCGAGG TGAAAGTGGATGGCAGCGAGCCGAA ACTGAGCAAGAATGAGCTGAAGAGA CGCCTGAAAGCTGAGAAGAAAGTAG CAGAGAAGGAGGCCAAACAGAAAGA GCTCAGTGAGAAACAGCTAAGCCAA GCCACTGCTGCTGCCACCAACCACAC CACTGATAATGGTGTGGGTCCTGAGG AAGAGAGCGTGGACCCAAATCAATA CTACAAAATCCGCAGTCAAGCAATTC ATCAGCTGAAGGTCAATGGGGAAGA CCCATACCCACACAAGTTCCATGTAG ACATCTCACTCACTGACTTCATCCAA AAATATAGTCACCTGCAGCCTGGGG ATCACCTGACTGACATCACCTTAAAG GTGGCAGGTAGGATCCATGCCAAAA GAGCTTCTGGGGGAAAGCTCATCTTC TATGATCTTCGAGGAGAGGGGGTGA AGTTGCAAGTCATGGCCAATTCCAGA AATTATAAATCAGAAGAAGAATTTAT TCATATTAATAACAAACTGCGTCGGG GAGACATAATTGGAGTTCAGGGGAA TCCTGGTAAAACCAAGAAGGGTGAG CTGAGCATCATTCCGTATGAGATCAC ACTGCTGTCTCCCTGTTTGCATATGTT ACCTCATCTTCACTTTGGCCTCAAAG ACAAGGAAACAAGGTATCGCCAGAG ATACTTGGACTTGATCCTGAATGACT TTGTGAGGCAGAAATTTATCATCCGC TCTAAGATCATCACATATATAAGAAG TTTCTTAGATGAGCTGGGATTCCTAG AGATTGAAACTCCCATGATGAACATC ATCCCAGGGGGAGCCGTGGCCAAGC CTTTCATCACTTATCACAACGAGCTG GACATGAACTTATATATGAGAATTGC TCCAGAACTCTATCATAAGATGCTTG TGGTTGGTGGCATCGACCGGGTTTAT | SEQ. ID. NO. 13 |

```
GAAATTGGACGCCAGTTCCGGAATG
AGGGGATTGATTTGACGCACAATCCT
GAGTTCACCACCTGTGAGTTCTACAT
GGCCTATGCAGACTATCACGATCTCA
TGGAAATCACGGAGAAGATGGTTTC
AGGGATGGTGAAGCATATTACA
```

Table 1B
LysRS1$^{N1}$
Mass spec peptides detected and inferred linking peptides

| Type/species | Sequence | SEQ. ID. NO. |
| --- | --- | --- |
| Protein/mouse | RGDIIGVEGNPGK | SEQ. ID. NO. 14 |
| Protein/mouse | TKKGELSIIPQEITLLSPCLHMLPHLHFGLKDKETRYRQR | SEQ. ID. NO. 15 |
| Protein/mouse | YLDLILNDFVR | SEQ. ID. NO. 16 |

Table 1C
LysRS1$^{N1}$
Concatenated sequences based on mass spec peptides detected

| Type/species | Sequence | SEQ. ID. NO. |
| --- | --- | --- |
| Protein/mouse | RGDIIGVEGNPGKTKKGELSIIPQEITLLSPCLHMLPHLHFGLKDKETRYRQRYLDLILNDFVR | SEQ. ID. NO. 17 |

Table 2
AARS polypeptides and alternative transcripts identified by Deep Sequencing

| Name | Type/species/Residues | Amino acid and Nucleic Acid Sequences | SEQ. ID. NO. |
| --- | --- | --- | --- |
| LysRS1$^{N6}$ | Protein/Human/1-74 + 22 aa | MAAVQAAEVKVDGSEPKLSKNELKRRL KAEKKVAEKEAKQKELSEKQLSQATAA ATNHTTDNGVGPEEESVDPNVGSMPKEL LGESSSSMIFEERG | SEQ. ID. NO. 18 |
| LysRS1$^{N6}$ | DNA/Human | ATGGCGGCCGTGCAGGCGGCCGAGGT GAAAGTGGATGGCAGCGAGCCGAAAC TGAGCAAGAATGAGCTGAAGAGACGC CTGAAAGCTGAGAAGAAAGTAGCAGA GAAGGAGGCCAAACAGAAAGAGCTCA GTGAGAAACAGCTAAGCCAAGCCACTG CTGCTGCCACCAACCACACCACTGATA ATGGTGTGGGTCCTGAGGAAGAGAGC GTGGACCCAAATGTAGGATCCATGCCA AAAGAGCTTCTGGGGGAAAGCTCATCT TCTATGATCTTCGAGGAGAGGGGGTGA | SEQ. ID. NO. 19 |
| LysRS1$^{N7}$ | Protein/Human/1-265 + 306-597 | MAAVQAAEVKVDGSEPKLSKNELKRRL KAEKKVAEKEAKQKELSEKQLSQATAA ATNHTTDNGVGPEEESVDPNQYYKIRSQ AIHQLKVNGEDPYPHKFHVDISLTDFIQK YSHLQPGDHLTDITLKVAGRIHAKRASG GKLIFYDLRGEGVKLQVMANSRNYKSEE EFIHINNKLRRGDIIGVQGNPGKTKKGEL SIIPYEITLLSPCLHMLPHLHFGLKDKET RYRQRYLDLILNDFVRQKFIIRSKIITYIR SFLDELGFLEMLVVGGIDRVYEIGRQFR NEGIDLTHNPEFTTCEFYMAYADYHDLM EITEKMVSGMVKHITGSYKVTYHPDGPE GQAYDVDFTPPFRRINMVEELEKALGM KLPETNLFETEETRKILDDICVAKAVECP PPRTTARLLDKLVGEFLEVTCINPTFICD HPQIMSPLAKWHRSKEGLTERFELFVM KKEICNAYTELNDPMRQRQLFEEQAKA KAAGDDEAMFIDENFCTALEYGLPPTAG | SEQ. ID. NO. 20 |

-continued

| | | WGMGIDRVAMFLTDSNNIKEVLLFPAM<br>KPEDKKENVATTDTLESTTVGTSV | |
|---|---|---|---|
| LysRS1[N7] | DNA/<br>Human | ATGGCGGCCGTGCAGGCGGCCGAGGT<br>GAAAGTGGATGGCAGCGAGCCGAAAC<br>TGAGCAAGAATGAGCTGAAGAGACGC<br>CTGAAAGCTGAGAAGAAAGTAGCAGA<br>GAAGGAGGCCAAACAGAAAGAGCTCA<br>GTGAGAAACAGCTAAGCCAAGCCACTG<br>CTGCTGCCACCAACCACACCACTGATA<br>ATGGTGTGGGTCCTGAGGAAGAGAGC<br>GTGGACCCAAATCAATACTACAAAATC<br>CGCAGTCAAGCAATTCATCAGCTGAAG<br>GTCAATGGGGAAGACCCATACCCACAC<br>AAGTTCCATGTAGACATCTCACTCACT<br>GACTTCATCCAAAAATATAGTCACCTG<br>CAGCCTGGGGATCACCTGACTGACATC<br>ACCTTAAAGGTGGCAGGTAGGATCCAT<br>GCCAAAAGAGCTTCTGGGGGAAAGCT<br>CATCTTCTATGATCTTCGAGGAGAGGG<br>GGTGAAGTTGCAAGTCATGGCCAATTC<br>CAGAAATTATAAATCAGAAGAAGAATT<br>TATTCATATTAATAACAAACTGCGTCG<br>GGGGAGACATAATTGGAGTTCAGGGGA<br>ATCCTGGTAAAACCAAGAAGGGTGAGC<br>TGAGCATCATTCCGTATGAGATCACAC<br>TGCTGTCTCCCTGTTTGCATATGTTAC<br>CTCATCTTCACTTTGGCCTCAAAGACA<br>AGGAAACAAGGTATCGCCAGAGATACT<br>TGGACTTGATCCTGAATGACTTTGTGA<br>GGCAGAAATTTATCATCCGCTCTAAGA<br>TCATCACATATATAAGAAGTTTCTTAG<br>ATGAGCTGGGATTCCTAGAGATGCTTG<br>TGGTTGGTGGCATCGACCGGGTTTATG<br>AAATTGGACGCCAGTTCCGGAATGAGG<br>GGATTGATTTGACGCACAATCCTGAGT<br>TCACCACCTGTGAGTTCTACATGGCCT<br>ATGCAGACTATCACGATCTCATGGAAA<br>TCACGGAGAAGATGGTTTCAGGGATG<br>GTGAAGCATATTACAGGCAGTTACAAG<br>GTCACCTACCACCCAGATGGCCCAGAG<br>GGCCAAGCCTACGATGTTGACTTCACC<br>CCACCCTTCCGGCGAATCAACATGGTA<br>GAAGAGCTTGAGAAAGCCCTGGGGAT<br>GAAGCTGCCAGAAACGAACCTCTTTGA<br>AACTGAAGAAACTCGCAAAATTCTTGA<br>TGATATCTGTGTGGCAAAAGCTGTTGA<br>ATGCCCTCCACCTCGGACCACAGCCAG<br>GCTCCTTGACAAGCTTGTTGGGGAGTT<br>CCTGGAAGTGACTTGCATCAATCCTAC<br>ATTCATCTGTGATCACCCACAGATAAT<br>GAGCCCTTTGGCTAAATGGCACCGCTC<br>TAAAGAGGGTCTGACTGAGCGCTTTGA<br>GCTGTTTGTCATGAAGAAAGAGATATG<br>CAATGCGTATACTGAGCTGAATGATCC<br>CATGCGGCAGCGGCAGCTTTTTGAAGA<br>ACAGGCCAAGGCCAAGGCTGCAGGTG<br>ATGATGAGGCCATGTTCATAGATGAAA<br>ACTTCTGTACTGCCCTGGAATATGGGC<br>TGCCCCCCACAGCTGGCTGGGGCATG<br>GGCATTGATCGAGTCGCCATGTTTCTC<br>ACGGACTCCAACAACATCAAGGAAGTA<br>CTTCTGTTTCCTGCCATGAAACCCGAA<br>GACAAGAAGGAGAATGTAGCAACCACT<br>GATACACTGGAAAGCACAACAGTTGGC<br>ACTTCTGTCTAG | SEQ. ID.<br>NO. 21 |
| LysRS1[N8] | Protein/<br>Human/<br>1-74 +<br>266-597 | MAAVQAAEVKVDGSEPKLSKNELKRRLK<br>AEKKVAEKEAKQKELSEKQLSQATAAATN<br>HTTDNGVGPEEESVDPNIETPMMNIIPGGA<br>VAKPFITYHNELDMNLYMRIAPELYHKML<br>VVGGIDRVYEIGRQFRNEGIDLTHNPEFTTC<br>EFYMAYADYHDLMEITEKMVSGMVKHIT<br>GSYKVTYHPDGPEGQAYDVDFTPPFRRIN<br>MVEELEKALGMKLPETNLFETEETRKILDD<br>ICVAKAVECPPPRTTARLLDKLVGEFLEVT<br>CINPTFICDHPQIMSPLAKWHRSKEGLTERF<br>ELFVMKKEICNAYTELNDPMRQRQLFEEQ<br>AKAKAAGDDEAMFIDENFCTALEYGLPPT | SEQ. ID.<br>NO. 22 |

| | | | |
|---|---|---|---|
| | | AGWGMGIDRVAMFLTDSNNIKEVLLFPAM<br>KPEDKKENVATTDTLESTTVGTSV | |
| LysRS1^N8 | DNA/<br>Human | ATGGCGGCCGTGCAGGCGGCCGAGGTGA<br>AAGTGGATGGCAGCGAGCCGAAACTGAG<br>CAAGAATGAGCTGAAGAGACGCCTGAAA<br>GCTGAGAAGAAAGTAGCAGAGAAGGAG<br>GCCAAACAGAAAGAGCTCAGTGAGAAAC<br>AGCTAAGCCAAGCCACTGCTGCTGCCAC<br>CAACCACACCACTGATAATGGTGTGGGT<br>CCTGAGGAAGAGAGCGTGGACCCAAATA<br>TTGAAACTCCCATGATGAACATCATCCCA<br>GGGGGAGCCGTGGCCAAGCCTTTCATCA<br>CTTATCACAACGAGCTGGACATGAACTT<br>ATATATGAGAATTGCTCCAGAACTCTATC<br>ATAAGATGCTTGTGGTTGGTGGCATCGAC<br>CGGGTTTATGAAATTGGACGCCAGTTCCG<br>GAATGAGGGGATTGATTTGACGCACAAT<br>CCTGAGTTCACCACCTGTGAGTTCTACAT<br>GGCCTATGCAGACTATCACGATCTCATGG<br>AAATCACGGAGAAGATGGTTTCAGGGAT<br>GGTGAAGCATATTACAGGCAGTTACAAG<br>GTCACCTACCACCCAGATGGCCCAGAGG<br>GCCAAGCCTACGATGTTGACTTCACCCCA<br>CCCTTCCGGCAATCAACATGGTAGAAG<br>AGCTTGAGAAAGCCCTGGGGATGAAGCT<br>GCCAGAAACGAACCTCTTTGAAACTGAA<br>GAAACTCGCAAAATTCTTGATGATATCTG<br>TGTGGCAAAAGCTGTTGAATGCCCTCCAC<br>CTCGGACCACAGCCAGGCTCCTTGACAA<br>GCTTGTTGGGGAGTTCCTGGAAGTGACTT<br>GCATCAATCCTACATTCATCTGTGATCAC<br>CCACAGATAATGAGCCCTTTGGCTAAAT<br>GGCACCGCTCTAAAGAGGGTCTGACTGA<br>GCGCTTTGAGCTGTTTGTCATGAAGAAAG<br>AGATATGCAATGCGTATACTGAGCTGAA<br>TGATCCCATGCGGCAGCGGCAGCTTTTTG<br>AAGAACAGGCCAAGGCCAAGGCTGCAGG<br>TGATGATGAGGCCATGTTCATAGATGAA<br>AACTTCTGTACTGCCCTGGAATATGGGCT<br>GCCCCCCACAGCTGGCTGGGGCATGGGC<br>ATTGATCGAGTCGCCATGTTTCTCACGGA<br>CTCCAACAACATCAAGGAAGTACTTCTGT<br>TTCCTGCCATGAAACCCGAAGACAAGAA<br>GGAGAATGTAGCAACCACTGATACACTG<br>GAAAGCACAACAGTTGGCACTTCTGTCT<br>AG | SEQ. ID.<br>NO. 23 |
| LysRS1^N9 | Protein/<br>Human/1-305<br>+ 518-597 | MAAVQAAEVKVDGSEPKLSKNELKRRLK<br>AEKKVAEKEAKQKELSEKQLSQATAAATN<br>HTTDNGVGPEEESVDPNQYYKIRSQAIHQL<br>KVNGEDPYPHKFHVDISLTDFIQKYSHLQP<br>GDHLTDITLKVAGRIHAKRASGGKLIFYDL<br>RGEGVKLQVMANSRNYKSEEEFIHINNKLR<br>RGDIIGVQGNPGKTKKGELSIIPYEITLLSPC<br>LHMLPHLHFGLKDKETRYRQRYLDLILND<br>FVRQKFIIRSKIITYIRSFLDELGFLEIETPMM<br>NIIPGGAVAKPFITYHNELDMNLYMRIAPE<br>LYHKAKAAGDDEAMFIDENFCTALEYGLP<br>PTAGWGMGIDRVAMFLTDSNNIKEVLLFP<br>AMKPEDKKENVATTDTLESTTVGTSV | SEQ. ID.<br>NO. 24 |
| LysRS1^N9 | DNA/<br>Human | ATGGCGGCCGTGCAGGCGGCCGAGGTGA<br>AAGTGGATGGCAGCGAGCCGAAACTGAG<br>CAAGAATGAGCTGAAGAGACGCCTGAAA<br>GCTGAGAAGAAAGTAGCAGAGAAGGAG<br>GCCAAACAGAAAGAGCTCAGTGAGAAAC<br>AGCTAAGCCAAGCCACTGCTGCTGCCAC<br>CAACCACACCACTGATAATGGTGTGGGT<br>CCTGAGGAAGAGAGCGTGGACCCAAATC<br>AATACTACAAAATCCGCAGTCAAGCAAT<br>TCATCAGCTGAAGGTCAATGGGGAAGAC<br>CCATACCCACACAAGTTCCATGTAGACAT<br>CTCACTCACTGACTTCATCCAAAAATATA<br>GTCACCTGCAGCCTGGGGATCACCTGACT<br>GACATCACCTTAAAGGTGGCAGGTAGGA<br>TCCATGCCAAAAGAGCTTCTGGGGGAAA<br>GCTCATCTTCTATGATCTTCGAGGAGAGG<br>GGGTGAAGTTGCAAGTCATGGCCAATTC | SEQ. ID.<br>NO. 25 |

-continued

```
                    CAGAAATTATAAATCAGAAGAAGAATTT
                    ATTCATATTAATAACAAACTGCGTCGGG
                    GAGACATAATTGGAGTTCAGGGGAATCC
                    TGGTAAAACCAAGAAGGGTGAGCTGAGC
                    ATCATTCCGTATGAGATCACACTGCTGTC
                    TCCCTGTTTGCATATGTTACCTCATCTTCA
                    CTTTGGCCTCAAAGACAAGGAAACAAGG
                    TATCGCCAGAGATACTTGGACTTGATCCT
                    GAATGACTTTGTGAGGCAGAAATTTATC
                    ATCCGCTCTAAGATCATCACATATATAAG
                    AAGTTTCTTAGATGAGCTGGGATTCCTAG
                    AGATTGAAACTCCCATGATGAACATCAT
                    CCCAGGGGGAGCCGTGGCCAAGCCTTTC
                    ATCACTTATCACAACGAGCTGGACATGA
                    ACTTATATATGAGAATTGCTCCAGAACTC
                    TATCATAAGGCCAAGGCTGCAGGTGATG
                    ATGAGGCCATGTTCATAGATGAAAACTT
                    CTGTACTGCCCTGGAATATGGGCTGCCCC
                    CCACAGCTGGCTGGGCATGGGCATTGA
                    TCGAGTCGCCATGTTTCTCACGGACTCCA
                    ACAACATCAAGGAAGTACTTCTGTTTCCT
                    GCCATGAAACCCGAAGACAAGAAGGAG
                    AATGTAGCAACCACTGATACACTGGAAA
                    GCACAACAGTTGGCACTTCTGTCTAG
```

| LysRS1<sup>N10</sup> | Protein/<br>Human/1-74 +<br>2 aa | MAAVQAAEVKVDGSEPKLSKNELKRRL<br>KAEKKVAEKEAKQKELSEKQLSQATAA<br>ATNHTTDNGVGPEEESVDPNKL | SEQ. ID.<br>NO. 26 |
|---|---|---|---|
| LysRS1<sup>N10</sup> | DNA/<br>Human | ATGGCGGCCGTGCAGGCGGCCGAGGT<br>GAAAGTGGATGGCAGCGAGCCGAAAC<br>TGAGCAAGAATGAGCTGAAGAGACGC<br>CTGAAAGCTGAGAAGAAAGTAGCAGA<br>GAAGGAGGCCAAACAGAAAGAGCTCA<br>GTGAGAAACAGCTAAGCCAAGCCACTG<br>CTGCTGCCACCAACCACACCACTGATA<br>ATGGTGTGGGTCCTGAGGAAGAGAGC<br>GTGGACCCAAATAAATTATAA | SEQ. ID.<br>NO. 27 |
| LysRS1<sup>N11</sup> | Protein/<br>Human/1-20 +<br>1 aa | MAAVQAAEVKVDGSEPKLSKK | SEQ. ID.<br>NO. 28 |
| LysRS1<sup>N11</sup> | DNA/<br>Human | ATGGCGGCCGTGCAGGCGGCCGAGGTGA<br>AAGTGGATGGCAGCGAGCCGAAACTGAG<br>CAAGAAGTAG | SEQ. ID.<br>NO. 29 |
| LysRS1<sup>N12</sup> | Protein/<br>Human/1-129 +<br>20 aa | MAAVQAAEVKVDGSEPKLSKNELKRRLK<br>AEKKVAEKEAKQKELSEKQLSQATAAATN<br>HTTDNGVGPEEESVDPNQYYKIRSQAIHQL<br>KVNGEDPYPHKFHVDISLTDFIQKYSHLQP<br>GDHLTDITLKVAEIINQKKNLFILITNCVGET | SEQ. ID.<br>NO. 30 |
| LysRS1<sup>N12</sup> | DNA/<br>Human | ATGGCGGCCGTGCAGGCGGCCGAGGTGA<br>AAGTGGATGGCAGCGAGCCGAAACTGAG<br>CAAGAATGAGCTGAAGAGACGCCTGAAA<br>GCTGAGAAGAAAGTAGCAGAGAAGGAG<br>GCCAAACAGAAAGAGCTCAGTGAGAAAC<br>AGCTAAGCCAAGCCACTGCTGCTGCCAC<br>CAACCACACCACTGATAATGGTGTGGGT<br>CCTGAGGAAGAGAGCGTGGACCCAAATC<br>AATACTACAAAATCCGCAGTCAAGCAAT<br>TCATCAGCTGAAGGTCAATGGGGAAGAC<br>CCATACCCACACAAGTTCCATGTAGACAT<br>CTCACTCACTGACTTCATCCAAAAATATA<br>GTCACCTGCAGCCTGGGGATCACCTGACT<br>GACATCACCTTAAAGGTGGCAGAAATTA<br>TAAATCAGAAGAAGAATTTATTCATATTA<br>ATAACAAACTGCGTCGGGGAGACATAA | SEQ. ID.<br>NO. 31 |
| LysRS1<sup>N13</sup> | Protein/<br>Human/1-223 +<br>36 aa | MAAVQAAEVKVDGSEPKLSKNELKRRLK<br>AEKKVAEKEAKQKELSEKQLSQATAAATN<br>HTTDNGVGPEEESVDPNQYYKIRSQAIHQL<br>KVNGEDPYPHKFHVDISLTDFIQKYSHLQP<br>GDHLTDITLKVAGRIHAKRASGGKLIFYDL<br>RGEGVKLQVMANSRNYKSEEEFIHINNKLR<br>RGDIIGVQGNPGKTKKGELSIIPYEITLLSPC<br>LHMLPHLHFGLKDKKLAKFLMISVWQKLL<br>NALHLGPQPGSLTSLLGSSWK | SEQ. ID.<br>NO. 32 |

-continued

| | | | |
|---|---|---|---|
| LysRS1<sup>N13</sup> | DNA/<br>Human | ATGGCGGCCGTGCAGGCGGCCGAGGTGA<br>AAGTGGATGGCAGCGAGCCGAAACTGAG<br>CAAGAATGAGCTGAAGAGACGCCTGAAA<br>GCTGAGAAGAAAGTAGCAGAGAAGGAG<br>GCCAAACAGAAAGAGCTCAGTGAGAAAC<br>AGCTAAGCCAAGCCACTGCTGCTGCCAC<br>CAACCACACCACTGATAATGGTGTGGGT<br>CCTGAGGAAGAGAGCGTGGACCCAAATC<br>AATACTACAAAATCCGCAGTCAAGCAAT<br>TCATCAGCTGAAGGTCAATGGGGAAGAC<br>CCATACCCACACAAGTTCCATGTAGACAT<br>CTCACTCACTGACTTCATCCAAAAATATA<br>GTCACCTGCAGCCTGGGGATCACCTGACT<br>GACATCACCTTAAAGGTGGCAGGTAGGA<br>TCCATGCCAAAAGAGCTTCTGGGGGAAA<br>GCTCATCTTCTATGATCTTCGAGGAGAGG<br>GGGTGAAGTTGCAAGTCATGGCCAATTC<br>CAGAAATTATAAATCAGAAGAAGAATTT<br>ATTCATATTAATAACAAACTGCGTCGGG<br>GAGACATAATTGGAGTTCAGGGGAATCC<br>TGGTAAAACCAAGAAGGGTGAGCTGAGC<br>ATCATTCCGTATGAGATCACACTGCTGTC<br>TCCCTGTTTGCATATGTTACCTCATCTTCA<br>CTTTGGCCTCAAAGACAAGAAACTCGCA<br>AAATTCTTGATGATATCTGTGTGGCAAAA<br>GCTGTTGAATGCCCTCCACCTCGGACCAC<br>AGCCAGGCTCCTTGACAAGCTTGTTGGG<br>GAGTTCCTGGAAGTGA | SEQ. ID.<br>NO. 33 |

Table 2B
AARS polypeptides unique splice junctions

| Name | Type/<br>species | Amino acid and Nucleic Acid Sequences in<br>the vicinity of the unique splice junction | SEQ. ID.<br>NO. |
|---|---|---|---|
| K1-SV04 | DNA/<br>Human/<br>Protein/<br>Human | TGAGGAAGAGAGCGTGGACCCAAAT\|GT<br>AGGATCCATGCCAAAAGAGCTTC<br>EEESVDPNVGSMPKEL | SEQ. ID.<br>NO. 34<br>SEQ. ID.<br>NO. 35 |
| K1-SV06 | DNA/<br>Human/<br>Protein/<br>Human | CTTAGATGAGCTGGGATTCCTAGAG\|ATG<br>CTTGTGGTTGGTGGCATCGACC<br>LDELGFLEMLVVGGID | SEQ. ID.<br>NO. 36<br>SEQ. ID.<br>NO. 37 |
| K1-SV07 | DNA/<br>Human/<br>Protein/<br>Human | TGAGGAAGAGAGCGTGGACCCAAAT\|ATT<br>GAAACTCCCATGATGAACATCA<br>EEESVDPNIETPMMNI | SEQ. ID.<br>NO. 38<br>SEQ. ID.<br>NO. 39 |
| K1-SV08 | DNA/<br>Human/<br>Protein/<br>Human | AATTGCTCCAGAACTCTATCATAAG\|GCC<br>AAGGCTGCAGGTGATGATGAGG<br>IAPELYHKAKAAGDDE | SEQ. ID.<br>NO. 40<br>SEQ. ID.<br>NO. 41 |
| K1-SV10 | DNA/<br>Human/<br>Protein/<br>Human | TGAGGAAGAGAGCGTGGACCCAAAT\|AA<br>ATTATAAATCAGAAGAAGAATTT<br>EEESVDPNKL | SEQ. ID.<br>NO. 42<br>SEQ. ID.<br>NO. 43 |
| K1-AS02 | DNA/<br>Human/<br>Protein/<br>Human | GCAGCGAGCCGAAACTGAGCAAGANGT<br>AGGATCCATGCCAAAAGAGCTTC<br>SEPKLSKK | SEQ. ID.<br>NO. 44<br>SEQ. ID.<br>NO. 45 |
| K1-AS04 | DNA/<br>Human/<br>Protein/<br>Human | ACTGACATCACCTTAAAGGTGGCAG\|AAA<br>TTATAAATCAGAAGAAGAATTT<br>TDITLKVAEIINQKKN | SEQ. ID.<br>NO. 46<br>SEQ. ID.<br>NO. 47 |
| K1-AS05 | DNA/<br>Human/<br>Protein/<br>Human | TCTTCACTTTGGCCTCAAAGACAAG\|AAA<br>CTCGCAAAATTCTTGATGATAT<br>LHFGLKDKKLAKFLMI | SEQ. ID.<br>NO. 48<br>SEQ. ID.<br>NO. 49 |

TABLE 3

AARS polypeptides and nucleic acids identified by Bioinformatics

| Name | Type/ species/ Residues | Amino acid and Nucleic Acid Sequences | SEQ. ID. NO. |
|---|---|---|---|
| LysRS1$^{N2}$ | Protein/ Human/1-76 | MAAVQAAEVKVDGSEPKLSKNELKRRLK AEKKVAEKEAKQKELSEKQLSQATAAATN HTTDNGVGPEEESVDPNQY | SEQ. ID. NO. 50 |
| LysRS1$^{N2}$ | DNA/ Human | ATGGCGGCCGTGCAGGCGGCCGAGGTGA AGTGGATGGCAGCGAGCCGAAACTGAG CAAGAATGAGCTGAAGAGACGCCTGAAA GCTGAGAAGAAAGTAGCAGAGAAGGAG GCCAAACAGAAAGAGCTCAGTGAGAAC AGCTAAGCCAAGCCACTGCTGCTGCCAC CAACCACACCACTGATAATGGTGTGGGT CCTGAGGAAGAGAGCGTGGACCCAAATC AATAC | SEQ. ID. NO. 51 |
| LysRS1$^{N3}$ | Protein/ Human/1-194 | MAAVQAAEVKVDGSEPKLSKNELKRRLK AEKKVAEKEAKQKELSEKQLSQATAAATN HTTDNGVGPEEESVDPNQYYKIRSQAIHQL KVNGEDPYPHKFHVDISLTDFIQKYSHLQP GDHLTDITLKVAGRIHAKRASGGKLIFYDL RGEGVKLQVMANSRNYKSEEEFIHINNKLR RGDIIGVQGNPGKTKKG | SEQ. ID. NO. 52 |
| LysRS1$^{N3}$ | DNA/ Human | ATGGCGGCCGTGCAGGCGGCCGAGGTGA AGTGGATGGCAGCGAGCCGAAACTGAG CAAGAATGAGCTGAAGAGACGCCTGAAA GCTGAGAAGAAAGTAGCAGAGAAGGAG GCCAAACAGAAAGAGCTCAGTGAGAAAC AGCTAAGCCAAGCCACTGCTGCTGCCAC CAACCACACCACTGATAATGGTGTGGGT CCTGAGGAAGAGAGCGTGGACCCAAATC AATACTACAAAATCCGCAGTCAAGCAAT TCATCAGCTGAAGGTCAATGGGGAAGAC CCATACCCACACAAGTTCCATGTAGACAT CTCACTCACTGACTTCATCCAAAAATATA GTCACCTGCAGCCTGGGGATCACCTGACT GACATCACCTTAAAGGTGGCAGGTAGGA TCCATGCCAAAAGAGCTTCTGGGGGAAA GCTCATCTTCTATGATCTTCGAGGAGAGG GGGTGAAGTTGCAAGTCATGGCCAATTC CAGAAATTATAAATCAGAAGAAGAATTT ATTCATATTAATAACAAACTGCGTCGGG GAGACATAATTGGAGTTCAGGGGAATCC TGGTAAAACCAAGAAGGGT | SEQ. ID. NO. 53 |
| LysRS1$^{N4}$ | Protein/ Human/1-65 | MAAVQAAEVKVDGSEPKLSKNELKRRLK AEKKVAEKEAKQKELSEKQLSQATAAATN HTTDNGVG | SEQ. ID. NO. 54 |
| LysRS1$^{N4}$ | DNA/ Human | ATGGCGGCCGTGCAGGCGGCCGAGGTGA AGTGGATGGCAGCGAGCCGAAACTGAG CAAGAATGAGCTGAAGAGACGCCTGAAA GCTGAGAAGAAAGTAGCAGAGAAGGAG GCCAAACAGAAAGAGCTCAGTGAGAAAC AGCTAAGCCAAGCCACTGCTGCTGCCAC CAACCACACCACTGATAATGGTGTGGGT | SEQ. ID. NO. 55 |
| LysRS1$^{N5}$ | Protein/ Human/1-214 | MAAVQAAEVKVDGSEPKLSKNELKRRLK AEKKVAEKEAKQKELSEKQLSQATAAATN HTTDNGVGPEEESVDPNQYYKIRSQAIHQL KVNGEDPYPHKFHVDISLTDFIQKYSHLQP GDHLTDITLKVAGRIHAKRASGGKLIFYDL RGEGVKLQVMANSRNYKSEEEFIHINNKLR RGDIIGVQGNPGKTKKGELSIIPYEITLLSPC LHMLP | SEQ. ID. NO. 56 |
| LysRS1$^{N5}$ | DNA/ Human | ATGGCGGCCGTGCAGGCGGCCGAGGTGA AGTGGATGGCAGCGAGCCGAAACTGAG CAAGAATGAGCTGAAGAGACGCCTGAAA GCTGAGAAGAAAGTAGCAGAGAAGGAG GCCAAACAGAAAGAGCTCAGTGAGAAAC AGCTAAGCCAAGCCACTGCTGCTGCCAC CAACCACACCACTGATAATGGTGTGGGT CCTGAGGAAGAGAGCGTGGACCCAAATC | SEQ. ID. NO. 57 |

TABLE 3-continued

AARS polypeptides and nucleic acids identified by Bioinformatics

| Name | Type/ species/ Residues | Amino acid and Nucleic Acid Sequences | SEQ. ID. NO. |
|---|---|---|---|
| | | AATACTACAAAATCCGCAGTCAAGCAAT TCATCAGCTGAAGGTCAATGGGGAAGAC CCATACCCACACAAGTTCCATGTAGACAT CTCACTCACTGACTTCATCCAAAAATATA GTCACCTGCAGCCTGGGGATCACCTGACT GACATCACCTTAAAGGTGGCAGGTAGGA TCCATGCCAAAAGAGCTTCTGGGGGAAA GCTCATCTTCTATGATCTTCGAGGAGAGG GGGTGAAGTTGCAAGTCATGGCCAATTC CAGAAATTATAAATCAGAAGAAGAATTT ATTCATATTAATAACAAACTGCGTCGGG GAGACATAATTGGAGTTCAGGGGAATCC TGGTAAAACCAAGAAGGGTGAGCTGAGC ATCATTCCGTATGAGATCACACTGCTGTC TCCCTGTTTGCATATGTTACCT | |

C-Terminal AARS Polypeptides: (Tables 4, 5 & 6)

Table 4A
AARS polypeptides identified by MS

| Name | Type/ species/ Residues | Amino acid and Nucleic Acid Sequences | SEQ. ID. NO. |
|---|---|---|---|
| LysRS1<sup>C1</sup> | Protein/ Human/ 57-597 | NHTTDNGVGPEEESVDPNQYYKIRSQAIHQ LKVNGEDPYPHKFHVDISLTDFIQKYSHLQ PGDHLTDITLKVAGRIHAKRASGGKLIFYD LRGEGVKLQVMANSRNYKSEEEFIHINNKL RRGDIIGVQGNPGKTKKGELSIIPYEITLLSP CLHMLPHLHFGLKDKETRYRQRYLDLILN DFVRQKFIIRSKIITYIRSFLDELGFLEIETPM MNIIPGGAVAKPFITYHNELDMNLYMRIAP ELYHKMLVVGGIDRVYEIGRQFRNEGIDLT HNPEFTTCEFYMAYADYHDLMEITEKMVS GMVKHITGSYKVTYHPDGPEGQAYDVDFT PPFRRINMVEELEKALGMKLPETNLFETEE TRKILDDICVAKAVECPPPRTTARLLDKLV GEFLEVTCINPTFICDHPQIMSPLAKWHRSK EGLTERFELFVMKKEICNAYTELNDPMRQ RQLFEEQAKAKAAGDDEAMFIDENFCTAL EYGLPPTAGWGMGIDRVAMFLTDSNNIKE VLLFPAMKPEDKKENVATTDTLESTTVGTSV | SEQ. ID. NO. 94 |
| LysRS1<sup>C1</sup> | DNA/ Human/ | AACCACACCACTGATAATGGTGTGGGTC CTGAGGAAGAGAGCGTGGACCCAAATCA ATACTACAAAATCCGCAGTCAAGCAATT CATCAGCTGAAGGTCAATGGGGAAGACC CATACCCACACAAGTTCCATGTAGACATC TCACTCACTGACTTCATCCAAAAATATAG TCACCTGCAGCCTGGGGATCACCTGACTG ACATCACCTTAAAGGTGGCAGGTAGGAT CCATGCCAAAAGAGCTTCTGGGGGAAAG CTCATCTTCTATGATCTTCGAGGAGAGGG GGTGAAGTTGCAAGTCATGGCCAATTCC AGAAATTATAAATCAGAAGAAGAATTTA TTCATATTAATAACAAACTGCGTCGGGG AGACATAATTGGAGTTCAGGGGAATCCT GGTAAAACCAAGAAGGGTGAGCTGAGCA TCATTCCGTATGAGATCACACTGCTGTCT CCCTGTTTGCATATGTTACCTCATCTTCA CTTTGGCCTCAAAGACAAGGAAACAAGG TATCGCCAGAGATACTTGGACTTGATCCT GAATGACTTTGTGAGGCAGAAATTTATC ATCCGCTCTAAGATCATCACATATATAAG AAGTTTCTTAGATGAGCTGGGATTCCTAG AGATTGAAACTCCCATGATGAACATCAT CCCAGGGGGAGCCGTGGCCAAGCCTTTC ATCACTTATCACAACGAGCTGGACATGA ACTTATATATGAGAATTGCTCCAGAACTC | SEQ. ID. NO. 95 |

-continued

```
TATCATAAGATGCTTGTGGTTGGTGGCAT
CGACCGGGTTTATGAAATTGGACGCCAG
TTCCGGAATGAGGGGATTGATTTGACGC
ACAATCCTGAGTTCACCACCTGTGAGTTC
TACATGGCCTATGCAGACTATCACGATCT
CATGGAAATCACGGAGAAGATGGTTTCA
GGGATGGTGAAGCATATTACAGGCAGTT
ACAAGGTCACCTACCACCCAGATGGCCC
AGAGGGCCAAGCCTACGATGTTGACTTC
ACCCCACCCTTCCGGCGAATCAACATGGT
AGAAGAGCTTGAGAAAGCCCTGGGGATG
AAGCTGCCAGAAACGAACCTCTTTGAAA
CTGAAGAAACTCGCAAAATTCTTGATGA
TATCTGTGTGGCAAAAGCTGTTGAATGCC
CTCCACCTCGGACCACAGCCAGGCTCCTT
GACAAGCTTGTTGGGGAGTTCCTGGAAG
TGACTTGCATCAATCCTACATTCATCTGT
GATCACCCACAGATAATGAGCCCTTTGG
CTAAATGGCACCGCTCTAAAGAGGGTCT
GACTGAGCGCTTTGAGCTGTTTGTCATGA
AGAAAGAGATATGCAATGCGTATACTGA
GCTGAATGATCCCATGCGGCAGCGGCAG
CTTTTTGAAGAACAGGCCAAGGCCAAGG
CTGCAGGTGATGATGAGGCCATGTTCAT
AGATGAAAACTTCTGTACTGCCCTGGAAT
ATGGGCTGCCCCCCACAGCTGGCTGGGG
CATGGGCATTGATCGAGTCGCCATGTTTC
TCACGGACTCCAACAACATCAAGGAAGT
ACTTCTGTTTCCTGCCATGAAACCCGAAG
ACAAGAAGGAGAATGTAGCAACCACTGA
TACACTGGAAAGCACAACAGTTGGCACT
TCTGTCTAG
```

Table 4B
LysRS1$^{C1}$
Mass spec peptides detected and inferred linking peptides

| Type/<br>species | Sequence | SEQ. ID.<br>NO. |
| --- | --- | --- |
| Protein/<br>mouse | GVGAEEETLDPNQYYK | SEQ. ID.<br>NO. 96 |
| Protein/<br>mouse | IRSQAVQQLK | SEQ. ID.<br>NO. 97 |
| Protein/<br>mouse | VTGEDPYPHK | SEQ. ID.<br>NO. 98 |
| Protein/<br>mouse | FHVDISLTQFIQEYSHLQPGDHLTDVTLKVAGRIHAKRA<br>SGGKLIFYDLRGEGVKLQVMANSRNYKSEEEFVHINNK<br>LRRGDIIGVEGNPGKTKKGELSIIPQEITLLSPCLHMLPHL<br>HFGLKDKETRYRQR | SEQ. ID.<br>NO. 99 |
| Protein/<br>mouse | YLDLILNDFVR | SEQ. ID.<br>NO. 100 |
| Protein/<br>mouse | QKFIVRSKIITYIRSFLDELGFLEIETPMMNIIPGGAVAKP<br>FITYHNELDMNLYMRIAPELYHKMLVVGGIDRVYEIGR<br>QFRNEGIDLTHNPEFTTCEFYMAYADYHDLMEITEKML<br>SGMVKSITGSYKITYHPDGPEGQAYEVDFTPPFRRISMV<br>EELEKALGVK | SEQ. ID.<br>NO. 101 |
| Protein/<br>mouse | LPETSLFETEETR | SEQ. ID.<br>NO. 102 |
| Protein/<br>mouse | KILDDICVAKAVECPPPRTTARLLDK | SEQ. ID.<br>NO. 103 |
| Protein/<br>mouse | LVGEFLEVTCISPTFICDHPQIMSPLAK | SEQ. ID.<br>NO. 104 |
| Protein/<br>mouse | WHRSKEGLTERFELFVMKK | SEQ. ID.<br>NO. 105 |
| Protein/<br>mouse | EICNAYTELNDPVR | SEQ. ID.<br>NO. 106 |

-continued

| Protein/mouse | QRQLFEEQAKAKAAGDDEAMFIDENFCTALEYGLPPTAGWGMGIDR | SEQ. ID. NO. 107 |
| Protein/mouse | LTMFLTDSNNIK | SEQ. ID. NO. 108 |
| Protein/mouse | EVLLFPAMKPEDK | SEQ. ID. NO. 109 |
| Protein/mouse | KETAATTETPESTEASPSV | SEQ. ID. NO. 110 |

TABLE 4C
LysRS1$^{C1}$
Concatenated sequences based on mass spec peptides detected

| Type/species | Sequence | SEQ. ID. NO. |
| Protein/mouse | GVGAEEETLDPNQYYKIRSQAVQQLKVTGEDPYPHKFHVDISLTQFIQEYSHLQPGDHLTDVTLKVAGRIHAKRASGGKLIFYDLRGEGVKLQVMANSRNYKSEEEFVHINNKLRRGDIIGVEGNPGKTKKGELSIIPQEITLLSPCLHMLPHLHFGLKDKETRYRQRYLDLILNDFVRQKFIVRSKIITYIRSFLDELGFLEIETPMMNIIPGGAVAKPFITYHNELDMNLYMRIAPELYHKMLVVGGIDRVYEIGRQFRNEGIDLTHNPEFTTCEFYMAYADYHDLMEITEKMLSGMVKSITGSYKITYHPDGPEGQAYEVDFTPPFRRISMVEELEKALGVKLPETSLFETEETRKILDDICVAKAVECPPPRTTARLLDKLVGEFLEVTCISPTFICDHPQIMSPLAKWHRSKEGLTERFELFVMKKEICNAYTELNDPVRQRQLFEEQAKAKAAGDDEAMFIDENFCTALEYGLPPTAGWGMGIDRLTMFLTDSNNIKEVLLFPAMKPEDKKETAATTETPESTEASPSV | SEQ. ID. NO. 111 |

Table 5
AARS polypeptides and alternative transcripts identified by Deep Sequencing

| Name | Type/species/Residues | Amino acid and Nucleic Acid Sequences | SEQ. ID. NO. |
| LysRS1$^{C2}$ | Protein/Human/157-597 | MANSRNYKSEEEFIHINNKLRRGDIIGVQGNPGKTKKGELSIIPYEITLLSPCLHMLPHLHFGLKDKETRYRQRYLDLILNDFVRQKFIIRSKIITYIRSFLDELGFLEIETPMMNIIPGGAVAKPFITYHNELDMNLYMRIAPELYHKMLVVGGIDRVYEIGRQFRNEGIDLTHNPEFTTCEFYMAYADYHDLMEITEKMVSGMVKHITGSYKVTYHPDGPEGQAYDVDFTPPFRRINMVEELEKALGMKLPETNLFETEETRKILDDICVAKAVECPPPRTTARLLDKLVGEFLEVTCINPTFICDHPQIMSPLAKWHRSKEGLTERFELFVMKKEICNAYTELNDPMRQRQLFEEQAKAKAAGDDEAMFIDENFCTALEYGLPPTAGWGMGIDRVAMFLTDSNNIKEVLLFPAMKPEDKKENVATTDTLESTTVGTSV | SEQ. ID. NO. 112 |
| LysRS1$^{C2}$ | DNA/Human/ | ATGGCCAATTCCAGAAATTATAAATCAGAAGAAGAATTTATTCATATTAATAACAAACTGCGTCGGGGAGACATAATTGGAGTTCAGGGGAATCCTGGTAAAACCAAGAAGGGTGAGCTGAGCATCATTCCGTATGAGATCACACTGCTGTCTCCCTGTTTGCATATGTTACCTCATCTTCACTTTGGCCTCAAAGACAAGGAAACAAGGTATCGCCAGAGATACTTGGACTTGATCCTGAATGACTTTGTGAGGCAGAAATTTATCATCCGCTCTAAGATCATCACATATATAAGAAGTTTCTTAGATGAGCTGGGATTCCTAGAGATTGAAACTCCCATGATGAACATCATCCCAGGGGGAGCCGTGGCCAAGCCTTTCATCACTTATCACAACGAGCTGGACATGAACTTATATATGAGAATTGCTCCAGAACTCTATCATAAGATGCTTGTGGTTGGTGGCATCGACCGGGTTTATGAAATTGGACGCCAGTTCCGGAATGAGGGGATTG | SEQ. ID. NO. 113 |

| | | |
|---|---|---|
| | ATTTGACGCACAATCCTGAGTTCACCACC<br>TGTGAGTTCTACATGGCCTATGCAGACTA<br>TCACGATCTCATGGAAATCACGGAGAAG<br>ATGGTTTCAGGGATGGTGAAGCATATTA<br>CAGGCAGTTACAAGGTCACCTACCACCC<br>AGATGGCCCAGAGGGCCAAGCCTACGAT<br>GTTGACTTCACCCCACCCTTCCGGCGAAT<br>CAACATGGTAGAAGAGCTTGAGAAAGCC<br>CTGGGGATGAAGCTGCCAGAAACGAACC<br>TCTTTGAAACTGAAGAAACTCGCAAAAT<br>TCTTGATGATATCTGTGTGGCAAAAGCTG<br>TTGAATGCCCTCCACCTCGGACCACAGCC<br>AGGCTCCTTGACAAGCTTGTTGGGGAGTT<br>CCTGGAAGTGACTTGCATCAATCCTACAT<br>TCATCTGTGATCACCCACAGATAATGAGC<br>CCTTTGGCTAAATGGCACCGCTCTAAAGA<br>GGGTCTGACTGAGCGCTTTGAGCTGTTTG<br>TCATGAAGAAAGAGATATGCAATGCGTA<br>TACTGAGCTGAATGATCCCATGCGGCAG<br>CGGCAGCTTTTTGAAGAACAGGCCAAGG<br>CCAAGGCTGCAGGTGATGATGAGGCCAT<br>GTTCATAGATGAAAACTTCTGTACTGCCC<br>TGGAATATGGGCTGCCCCCCACAGCTGG<br>CTGGGGCATGGGCATTGATCGAGTCGCC<br>ATGTTTCTCACGGACTCCAACAACATCAA<br>GGAAGTACTTCTGTTTCCTGCCATGAAAC<br>CCGAAGACAAGAAGGAGAATGTAGCAAC<br>CACTGATACACTGGAAAGCACAACAGTT<br>GGCACTTCTGTCTAG | |
| LysRS1$^{C3}$ Protein/<br>Human/13<br>aa + 162-597 | MVWVLRKRAWTQINYKSEEEFIHINNKLR<br>RGDIIGVQGNPGKTKKGELSIIPYEITLLSPC<br>LHMLPHLHFGLKDKETRYRQRYLDLILND<br>FVRQKFIIRSKIITYIRSFLDELGFLEIETPMM<br>NIIPGGAVAKPFITYHNELDMNLYMRIAPE<br>LYHKMLVVGGIDRVYEIGRQFRNEGIDLTH<br>NPEFTTCEFYMAYADYHDLMEITEKMVSG<br>MVKHITGSYKVTYHPDGPEGQAYDVDFTP<br>PFRRINMVEELEKALGMKLPETNLFETEET<br>RKILDDICVAKAVECPPPRTTARLLDKLVG<br>EFLEVTCINPTFICDHPQIMSPLAKWHRSKE<br>GLTERFELFVMKKEICNAYTELNDPMRQR<br>QLFEEQAKAKAAGDDEAMFIDENFCTALE<br>YGLPPTAGWGMGIDRVAMFLTDSNNIKEV<br>LLFPAMKPEDKKENVATTDTLESTTVGTSV | SEQ. ID.<br>NO. 114 |
| LysRS1$^{C3}$ DNA/<br>Human/ | ATGGTGTGGGTCCTGAGGAAGAGAGCGT<br>GGACCCCAAATAAATTATAAATCAGAAGA<br>AGAATTTATTCATATTAATAACAAACTGC<br>GTCGGGGAGACATAATTGGAGTTCAGGG<br>GAATCCTGGTAAAACCAAGAAGGGTGAG<br>CTGAGCATCATTCCGTATGAGATCACACT<br>GCTGTCTCCCTGTTTGCATATGTTACCTC<br>ATCTTCACTTTGGCCTCAAAGACAAGGA<br>AACAAGGTATCGCCAGAGATACTTGGAC<br>TTGATCCTGAATGACTTTGTGAGGCAGAA<br>ATTTATCATCCGCTCTAAGATCATCACAT<br>ATATAAGAAGTTTCTTAGATGAGCTGGG<br>ATTCCTAGAGATTGAAACTCCCATGATGA<br>ACATCATCCCAGGGGGAGCCGTGGCCAA<br>GCCTTTCATCACTTATCACAACGAGCTGG<br>ACATGAACTTATATATGAGAATTGCTCCA<br>GAACTCTATCATAAGATGCTTGTGGTTGG<br>TGGCATCGACCGGGTTTATGAAATTGGA<br>CGCCAGTTCCGGAATGAGGGGATTGATT<br>TGACGCACAATCCTGAGTTCACCACCTGT<br>GAGTTCTACATGGCCTATGCAGACTATCA<br>CGATCTCATGGAAATCACGGAGAAGATG<br>GTTTCAGGGATGGTGAAGCATATTACAG<br>GCAGTTACAAGGTCACCTACCACCCAGA<br>TGGCCCAGAGGGCCAAGCCTACGATGTT<br>GACTTCACCCCACCCTTCCGGCGAATCAA<br>CATGGTAGAAGAGCTTGAGAAAGCCCTG<br>GGGATGAAGCTGCCAGAAACGAACCTCT<br>TTGAAACTGAAGAAACTCGCAAAATTCT<br>TGATGATATCTGTGTGGCAAAAGCTGTTG<br>AATGCCCTCCACCTCGGACCACAGCCAG<br>GCTCCTTGACAAGCTTGTTGGGGAGTTCC<br>TGGAAGTGACTTGCATCAATCCTACATTC | SEQ. ID.<br>NO. 115 |

-continued

|  |  |  |
|---|---|---|
|  | ATCTGTGATCACCCACAGATAATGAGCC<br>CTTTGGCTAAATGGCACCGCTCTAAAGA<br>GGGTCTGACTGAGCGCTTTGAGCTGTTTG<br>TCATGAAGAAAGAGATATGCAATGCGTA<br>TACTGAGCTGAATGATCCCATGCGGCAG<br>CGGCAGCTTTTTGAAGAACAGGCCAAGG<br>CCAAGGCTGCAGGTGATGATGAGGCCAT<br>GTTCATAGATGAAAACTTCTGTACTGCCC<br>TGGAATATGGGCTGCCCCCCACAGCTGG<br>CTGGGGCATGGGCATTGATCGAGTCGCC<br>ATGTTTCTCACGGACTCCAACAACATCAA<br>GGAAGTACTTCTGTTTCCTGCCATGAAAC<br>CCGAAGACAAGAAGGAGAATGTAGCAAC<br>CACTGATACACTGGAAAGCACAACAGTT<br>GGCACTTCTGTCTAG |  |
| LysRS1<sup>C4</sup> Protein/<br>Human/<br>212-597 | MLPHLHFGLKDKETRYRQRYLDLILNDFV<br>RQKFIIRSKIITYIRSFLDELGFLEIETPMMNII<br>PGGAVAKPPITYHNELDMNLYMRIAPELY<br>HKMLVVGGIDRVYEIGRQFRNEGIDLTHNP<br>EFTTCEFYMAYADYHDLMEITEKMVSGM<br>VKHITGSYKVTYHPDGPEGQAYDVDFTPPF<br>RRINMVEELEKALGMKLPETNLFETEETRK<br>ILDDICVAKAVECPPPRTTARLLDKLVGEFL<br>EVTCINPTFICDHPQIMSPLAKWHRSKEGLT<br>ERFELFVMKKEICNAYTELNDPMRQRQLFE<br>EQAKAKAAGDDEAMFIDENFCTALEYGLP<br>PTAGWGMGIDRVAMFLTDSNNIKEVLLFP<br>AMKPEDKKENVATTDTLESTTVGTSV | SEQ. ID.<br>NO. 116 |
| LysRS1<sup>C4</sup> DNA/<br>Human/ | ATGTTACCTCATCTTCACTTTGGCCTCAA<br>AGACAAGGAAACAAGGTATCGCCAGAGA<br>TACTTGGACTTGATCCTGAATGACTTTGT<br>GAGGCAGAAATTTATCATCCGCTCTAAG<br>ATCATCACATATATAAGAAGTTTCTTAGA<br>TGAGCTGGGATTCCTAGAGATTGAAACT<br>CCCATGATGAACATCATCCCAGGGGGAG<br>CCGTGGCCAAGCCTTTCATCACTTATCAC<br>AACGAGCTGGACATGAACTTATATATGA<br>GAATTGCTCCAGAACTCTATCATAAGATG<br>CTTGTGGTTGGTGGCATCGACCGGGTTTA<br>TGAAATTGGACGCCAGTTCCGGAATGAG<br>GGGATTGATTTGACGCACAATCCTGAGTT<br>CACCACCTGTGAGTTCTACATGGCCTATG<br>CAGACTATCACGATCTCATGGAAATCAC<br>GGAGAAGATGGTTTCAGGGATGGTGAAG<br>CATATTACAGGCAGTTACAAGGTCACCT<br>ACCACCCAGATGGCCCAGAGGGCCAAGC<br>CTACGATGTTGACTTCACCCCACCCTTCC<br>GGCGAATCAACATGGTAGAAGAGCTTGA<br>GAAAGCCCTGGGGATGAAGCTGCCAGAA<br>ACGAACCTCTTTGAAACTGAAGAAACTC<br>GCAAAATTCTTGATGATATCTGTGTGGCA<br>AAAGCTGTTGAATGCCCTCCACCTCGGAC<br>CACAGCCAGGCTCCTTGACAAGCTTGTTG<br>GGGAGTTCCTGGAAGTGACTTGCATCAA<br>TCCTACATTCATCTGTGATCACCCACAGA<br>TAATGAGCCCTTTGGCTAAATGGCACCGC<br>TCTAAAGAGGGTCTGACTGAGCGCTTTG<br>AGCTGTTTGTCATGAAGAAAGAGATATG<br>CAATGCGTATACTGAGCTGAATGATCCC<br>ATGCGGCAGCGGCAGCTTTTTGAAGAAC<br>AGGCCAAGGCCAAGGCTGCAGGTGATGA<br>TGAGGCCATGTTCATAGATGAAAACTTCT<br>GTACTGCCCTGGAATATGGGCTGCCCCCC<br>ACAGCTGGCTGGGGCATGGGCATTGATC<br>GAGTCGCCATGTTTCTCACGGACTCCAAC<br>AACATCAAGGAAGTACTTCTGTTTCCTGC<br>CATGAAACCCGAAGACAAGAAGGAGAAT<br>GTAGCAACCACTGATACACTGGAAAGCA<br>CAACAGTTGGCACTTCTGTCTAG | SEQ. ID.<br>NO. 117 |
| LysRS1<sup>C5</sup> Protein/<br>Human/<br>469-597 | MSPLAKWHRSKEGLTERFELFVMKKEICN<br>AYTELNDPMRQRQLFEEQAKAKAAGDDE<br>AMFIDENFCTALEYGLPPTAGWGMGIDRV<br>AMFLTDSNNIKEVLLFPAMKPEDKKENVA<br>TTDTLESTTVGTSV | SEQ. ID.<br>NO. 118 |

-continued

| | | | |
|---|---|---|---|
| LysRS1^C5 | DNA/<br>Human/ | ATGAGCCCTTTGGCTAAATGGCACCGCTC<br>TAAAGAGGGTCTGACTGAGCGCTTTGAG<br>CTGTTTGTCATGAAGAAAGAGATATGCA<br>ATGCGTATACTGAGCTGAATGATCCCATG<br>CGGCAGCGGCAGCTTTTTGAAGAACAGG<br>CCAAGGCCAAGGCTGCAGGTGATGATGA<br>GGCCATGTTCATAGATGAAACTTCTGTA<br>CTGCCCTGGAATATGGGCTGCCCCCCACA<br>GCTGGCTGGGGCATGGGCATTGATCGAG<br>TCGCCATGTTTCTCACGGACTCCAACAAC<br>ATCAAGGAAGTACTTCTGTTTCCTGCCAT<br>GAAACCCGAAGACAAGAAGGAGAATGT<br>AGCAACCACTGATACACTGGAAAGCACA<br>ACAGTTGGCACTTCTGTCTAG | SEQ. ID.<br>NO. 119 |

Table 5B
AARS polypeptides unique splice junctions

| Name | Type/<br>species | Amino acid and Nucleic Acid Sequences in the<br>vicinity of the unique splice junction | SEQ. ID.<br>NO. |
|---|---|---|---|
| K1-AS01 | DNA/<br>Human/<br>Protein/<br>Human | ACAAGTCATTTTCTGATCAAAGAAG\|CAAT<br>ACTACAAAATCCGCAGTCAAG<br>N/A | SEQ. ID.<br>NO. 120 |
| K1-SV10 | DNA/<br>Human/<br>Protein/<br>Human | TGAGGAAGAGAGCGTGGACCCAAAT\|AAA<br>TTATAAATCAGAAGAAGAATTT<br>RKRAWTQINYKSEEEF | SEQ. ID.<br>NO. 121<br>SEQ. ID.<br>NO. 122 |
| K1-AS04 | DNA/<br>Human/<br>Protein/<br>Human | ACTGACATCACCTTAAAGGTGGCAG\|AAAT<br>TATAAATCAGAAGAAGAATTT<br>N/A | SEQ. ID.<br>NO. 123 |
| K1-AS05 | DNA/<br>Human/<br>Protein/<br>Human | TCTTCACTTTGGCCTCAAAGACAAG\|AAAC<br>TCGCAAAATTCTTGATGATAT<br>N/A | SEQ. ID.<br>NO. 124 |

TABLE 6

AARS polypeptides and nucleic acids identified by Bioinformatics

| Name | Type/<br>species/<br>Residues | Amino<br>acid and Nucleic Acid Sequences | SEQ. ID.<br>NO. |
|---|---|---|---|

Internal AARS Polypeptides: (Tables 7, 8 & 9)

TABLE 7A

AARS polypeptides identified by MS

| Name | Type/<br>species/<br>Residues | Amino<br>acid and Nucleic Acid Sequences | SEQ. ID.<br>NO. |
|---|---|---|---|

TABLE 7B

Mass spec peptides detected and inferred linking peptides

| Name | Type/<br>species | Sequence | SEQ. ID.<br>NO. |
|---|---|---|---|

TABLE 7C

Concatenated sequences based on mass spec peptides detected

| Name | Type/<br>species | Sequence | SEQ. ID.<br>NO. |
|---|---|---|---|

TABLE 8

AARS polypeptides and alternative
transcripts identified by Deep Sequencing

| Name | Type/<br>species/<br>Residues | Amino acid and<br>Nucleic Acid Sequences | SEQ. ID.<br>NO. |
|---|---|---|---|

TABLE 8B

AARS polypeptides unique splice junctions

| Name | Type/<br>species | Amino acid and Nucleic<br>Acid Sequences in the vicinity<br>of the unique splice junction | SEQ. ID.<br>NO. |
|---|---|---|---|

TABLE 9

AARS polypeptides and nucleic acids identified by Bioinformatics

| Name | Type/ species/ Residues | Amino acid and Nucleic Acid Sequences | SEQ. ID. NO. |
|---|---|---|---|
| LysRS1[I1] | Protein/ Human/ 65-214 | GPEEESVDPNQYYKIRSQAIHQLKVNGEDP YPHKFHVDISLTDFIQKYSHLQPGDHLTDIT LKVAGRIHAKRASGGKLIFYDLRGEGVKL QVMANSRNYKSEEEFIHINNKLRRGDIIGV QGNPGKTKKGELSIIPYEITLLSPCLHMLP | SEQ. ID. NO. 137 |
| LysRS1[I1] | DNA/ Human | GGTCCTGAGGAAGAGAGCGTGGACCCAA ATCAATACTACAAAATCCGCAGTCAAGC AATTCATCAGCTGAAGGTCAATGGGGAA GACCCATACCCACACAAGTTCCATGTAG ACATCTCACTCACTGACTTCATCCAAAAA TATAGTCACCTGCAGCCTGGGGATCACCT GACTGACATCACCTTAAAGGTGGCAGGT AGGATCCATGCCAAAAGAGCTTCTGGGG GAAAGCTCATCTTCTATGATCTTCGAGGA GAGGGGGTGAAGTTGCAAGTCATGGCCA ATTCCAGAAATTATAAATCAGAAGAAGA ATTTATTCATATTAATAACAAACTGCGTC GGGGAGACATAATTGGAGTTCAGGGGAA TCCTGGTAAAACCAAGAAGGGTGAGCTG AGCATCATTCCGTATGAGATCACACTGCT GTCTCCCTGTTTGCATATGTTACCT | SEQ. ID. NO. 138 |

N-Terminal Mitochondrial AARS Polypeptides: (Tables 10, 11 & 12)

Table 10A
AARS polypeptides identified by MS

| Name | Type/ species/ Residues | Amino acid and Nucleic Acid Sequences | SEQ. ID. NO. |
|---|---|---|---|
| LysRS2[N1] | Protein/ Human/ 1-394 | MLTQAAVRLVRGSLRKTSWAEWGHRELR LGQLAPFTAPHKDKSFSDQRSELKRRLKAE KKVAEKEAKQKELSEKQLSQATAAATNHT TDNGVGPEEESVDPNQYYKIRSQAIHQLKV NGEDPYPHKFHVDISLTDFIQKYSHLQPGD HLTDITLKVAGRIHAKRASGGKLIFYDLRG EGVKLQVMANSRNYKSEEEFIHINNKLRRG DIIGVQGNPGKTKKGELSIIPYEITLLSPCLH MLPHLHFGLKDKETRYRQRYLDLILNDFV RQKFIIRSKIITYIRSFLDELGFLEIETPMMNII PGGAVAKPFITYHNELDMNLYMRIAPELY HKMLVVGGIDRVYEIGRQFRNEGIDLTHNP EFTTCEFYMAYADYHDLMEITEKMVSGM VKHIT | SEQ. ID. NO. 142 |
| LysRS2[N1] | DNA/ Human/ | ATGTTGACGCAAGCTGCTGTAAGGCTTGT TAGGGGGTCCCTGCGCAAAACCTCCTGG GCAGAGTGGGGTCACAGGGAACTGCGAC TGGGTCAACTTGCTCCTTTCACAGCGCCT CACAAGGACAAGTCATTTTCTGATCAAA GAAGTGAGCTGAAGAGACGCCTGAAAGC TGAGAAGAAAGTAGCAGAGAAGGAGGC CAAACAGAAAGAGCTCAGTGAGAAACAG CTAAGCCAAGCCACTGCTGCTGCCACCA ACCACACCACTGATAATGGTGTGGGTCCT GAGGAAGAGAGCGTGGACCCAAATCAAT ACTACAAAATCCGCAGTCAAGCAATTCA TCAGCTGAAGGTCAATGGGGAAGACCCA TACCCACACAAGTTCCATGTAGACATCTC ACTCACTGACTTCATCCAAAAATATAGTC ACCTGCAGCCTGGGGATCACCTGACTGA CATCACCTTAAAGGTGGCAGGTAGGATC CATGCCAAAAGAGCTTCTGGGGGAAAGC TCATCTTCTATGATCTTCGAGGAGAGGGG GTGAAGTTGCAAGTCATGGCCAATTCCA GAAATTATAAATCAGAAGAAGAATTTAT | SEQ. ID. NO. 143 |

```
            TCATATTAATAACAAACTGCGTCGGGGA
            GACATAATTGGAGTTCAGGGGAATCCTG
            GTAAAACCAAGAAGGGTGAGCTGAGCAT
            CATTCCGTATGAGATCACACTGCTGTCTC
            CCTGTTTGCATATGTTACCTCATCTTCACT
            TTGGCCTCAAAGACAAGGAAACAAGGTA
            TCGCCAGAGATACTTGGACTTGATCCTGA
            ATGACTTTGTGAGGCAGAAATTTATCATC
            CGCTCTAAGATCATCACATATATAAGAA
            GTTTCTTAGATGAGCTGGGATTCCTAGAG
            ATTGAAACTCCCATGATGAACATCATCCC
            AGGGGGAGCCGTGGCCAAGCCTTTCATC
            ACTTATCACAACGAGCTGGACATGAACT
            TATATATGAGAATTGCTCCAGAACTCTAT
            CATAAGATGCTTGTGGTTGGTGGCATCG
            ACCGGGTTTATGAAATTGGACGCCAGTTC
            CGGAATGAGGGGATTGATTTGACGCACA
            ATCCTGAGTTCACCACCTGTGAGTTCTAC
            ATGGCCTATGCAGACTATCACGATCTCAT
            GGAAATCACGGAGAAGATGGTTTCAGGG
            ATGGTGAAGCATATTACA
```

Table 10B
LysRS2[N1]
Mass spec peptides detected and inferred linking peptides

| Type/species | Sequence | SEQ. ID. NO. |
|---|---|---|
| Protein/mouse | RGDIIGVEGNPGK | SEQ. ID. NO. 144 |
| Protein/mouse | TKKGELSIIPQEITLLSPCLHMLPHLHFGLKDKETRYRQR | SEQ. ID. NO. 145 |
| Protein/mouse | YLDLILNDFVR | SEQ. ID. NO. 146 |

Table 10C
LysRS2[N1]
Concatenated sequences based on mass spec peptides detected

| Type/species | Sequence | SEQ. ID. NO. |
|---|---|---|
| Protein/mouse | RGDIIGVEGNPGKTKKGELSIIPQEITLLSPCLHMLPHLHFGLKDKETRYRQRYLDLILNDFVR | SEQ. ID. NO. 147 |

Table 11
AARS polypeptides and alternative transcripts identified by Deep Sequencing

| Name | Type/species/Residues | Amino acid and Nucleic Acid Sequences | SEQ. ID. NO. |
|---|---|---|---|
| LysRS2[N6] | Protein/Human/1-49 + 12 aa | MLTQAAVRLVRGSLRKTSWAEWGHRELRLGQLAPFTAPHKDKSFSDQRSNTTKSAVKQFIS | SEQ. ID. NO. 148 |
| LysRS2[N6] | DNA/Human | ATGTTGACGCAAGCTGCTGTAAGGCTTGTTAGGGGGTCCCTGCGCAAAACCTCCTGGGCAGAGTGGGGTCACAGGGAACTGCGACTGGGTCAACTTGCTCCTTTCACAGCGCCTCACAAGGACAAGTCATTTTCTGATCAAAGAAGCAATACTACAAAATCCGCAGTCAAGCAATTCATCAGCTGA | SEQ. ID. NO. 149 |
| LysRS2[N7] | Protein/Human/1-102 + 22 aa | MLTQAAVRLVRGSLRKTSWAEWGHRELRLGQLAPFTAPHKDKSFSDQRSELKRRLKAEKKVAEKEAKQKELSEKQLSQATAAATNHTTDNGVGPEEESVDPNVGSMPKELLGESSSSMIFEERG | SEQ. ID. NO. 150 |

| | | | |
|---|---|---|---|
| LysRS2[N7] | DNA/ Human | ATGTTGACGCAAGCTGCTGTAAGGCTTGT TAGGGGGTCCCTGCGCAAAACCTCCTGGG CAGAGTGGGGTCACAGGGAACTGCGACT GGGTCAACTTGCTCCTTTCACAGCGCCTC ACAAGGACAAGTCATTTTCTGATCAAAGA AGTGAGCTGAAGAGACGCCTGAAAGCTG AGAAGAAAGTAGCAGAGAAGGAGGCCAA ACAGAAAGAGCTCAGTGAGAAACAGCTA AGCCAAGCCACTGCTGCTGCCACCAACCA CACCACTGATAATGGTGTGGGTCCTGAGG AAGAGAGCGTGGACCCAAATGTAGGATC CATGCCAAAAGAGCTTCTGGGGGAAAGCT CATCTTCTATGATCTTCGAGGAGAGGGGG TGA | SEQ. ID. NO. 151 |
| LysRS2[N8] | Protein/ Human/ 1-293 + 334-625 | MLTQAAVRLVRGSLRKTSWAEWGHRELRL GQLAPFTAPHKDKSFSDQRSELKRRLKAEK KVAEKEAKQKELSEKQLSQATAAATNHTT DNGVGPEEESVDPNQYYKIRSQAIHQLKVN GEDPYPHKFHVDISLTDFIQKYSHLQPGDHL TDITLKVAGRIHAKRASGGKLIFYDLRGEGV KLQVMANSRNYKSEEEFIHINNKLRRGDIIG VQGNPGKTKKGELSIIPYEITLLSPCLHMLPH LHFGLKDKETRYRQRYLDLILNDFVRQKFII RSKIITYIRSFLDELGFLEMLVVGGIDRVYEI GRQFRNEGIDLTHNPEFTTCEFYMAYADYH DLMEITEKMVSGMVKHITGSYKVTYHPDGP EGQAYDVDFTPPFRRINMVEELEKALGMKL PETNLFETEETRKILDDICVAKAVECPPPRTT ARLLDKLVGEFLEVTCINPTFICDHPQIMSPL AKWHRSKEGLTERFELFVMKKEICNAYTEL NDPMRQRQLFEEQAKAKAAGDDEAMFIDE NFCTALEYGLPPTAGWGMGIDRVAMFLTD SNNIKEVLLFPAMKPEDKKENVATTDTLES TTVGTSV | SEQ. ID. NO. 152 |
| LysRS2[N8] | DNA/ Human | ATGTTGACGCAAGCTGCTGTAAGGCTTGT TAGGGGGTCCCTGCGCAAAACCTCCTGGG CAGAGTGGGGTCACAGGGAACTGCGACT GGGTCAACTTGCTCCTTTCACAGCGCCTC ACAAGGACAAGTCATTTTCTGATCAAAGA AGTGAGCTGAAGAGACGCCTGAAAGCTG AGAAGAAAGTAGCAGAGAAGGAGGCCAA ACAGAAAGAGCTCAGTGAGAAACAGCTA AGCCAAGCCACTGCTGCTGCCACCAACCA CACCACTGATAATGGTGTGGGTCCTGAGG AAGAGAGCGTGGACCCAAATCAATACTA CAAAATCCGCAGTCAAGCAATTCATCAGC TGAAGGTCAATGGGGAAGACCCATACCC ACACAAGTTCCATGTAGACATCTCACTCA CTGACTTCATCCAAAATATAGTCACCTG CAGCCTGGGGATCACCTGACTGACATCAC CTTAAAGGTGGCAGGTAGGATCCATGCCA AAAGAGCTTCTGGGGGAAAGCTCATCTTC TATGATCTTCGAGGAGAGGGGGTGAAGTT GCAAGTCATGGCCAATTCCAGAAATTATA AATCAGAAGAAGAATTTATTCATATTAAT AACAAACTGCGTCGGGGAGACATAATTG GAGTTCAGGGGAATCCTGGTAAAACCAA GAAGGGTGAGCTGAGCATCATTCCGTATG AGATCACACTGCTGTCTCCCTGTTTGCATA TGTTACCTCATCTTCACTTTGGCCTCAAAG ACAAGGAAACAAGGTATCGCCAGAGATA CTTGGACTTGATCCTGAATGACTTTGTGA GGCAGAAATTTATCATCCGCTCTAAGATC ATCACATATATAAGAAGTTTCTTAGATGA GCTGGGATTCCTAGAGATGCTTGTGGTTG GTGGCATCGACCGGGTTTATGAAATTGGA CGCCAGTTCCGGAATGAGGGGATTGATTT GACGCACAATCCTGAGTTCACCACCTGTG AGTTCTACATGGCCTATGCAGACTATCAC GATCTCATGGAAATCACGGAGAAGATGGT TTCAGGGATGGTGAAGCATATTACAGGCA GTTACAAGGTCACCTACCACCCAGATGGC CCAGAGGGCCAAGCCTACGATGTTGACTT CACCCCACCCTTCCGGCGAATCAACATGG TAGAAGAGCTTGAGAAAGCCCTGGGGAT GAAGCTGCCAGAAACGAACCTCTTTGAAA CTGAAGAAACTCGCAAAATTCTTGATGAT | SEQ. ID. NO. 153 |

| | | | |
|---|---|---|---|
| | | ATCTGTGTGGCAAAAGCTGTTGAATGCCC<br>TCCACCTCGGACCACAGCCAGGCTCCTTG<br>ACAAGCTTGTTGGGGAGTTCCTGGAAGTG<br>ACTTGCATCAATCCTACATTCATCTGTGAT<br>CACCCACAGATAATGAGCCCTTTGGCTAA<br>ATGGCACCGCTCTAAAGAGGGTCTGACTG<br>AGCGCTTTGAGCTGTTTGTCATGAAGAAA<br>GAGATATGCAATGCGTATACTGAGCTGAA<br>TGATCCCATGCGGCAGCGGCAGCTTTTTG<br>AAGAACAGGCCAAGGCCAAGGCTGCAGG<br>TGATGATGAGGCCATGTTCATAGATGAAA<br>ACTTCTGTACTGCCCTGGAATATGGGCTG<br>CCCCCCACAGCTGGCTGGGGCATGGGCAT<br>TGATCGAGTCGCCATGTTTCTCACGGACT<br>CCAACAACATCAAGGAAGTACTTCTGTTT<br>CCTGCCATGAAACCCGAAGACAAGAAGG<br>AGAATGTAGCAACCACTGATACACTGGAA<br>AGCACAACAGTTGGCACTTCTGTCTAG | |
| LysRS2$^{N9}$ | Protein/<br>Human/<br>1-102 +<br>294-625 | MLTQAAVRLVRGSLRKTSWAEWGHRELRL<br>GQLAPFTAPHKDKSFSDQRSELKRRLKAEK<br>KVAEKEAKQKELSEKQLSQATAAATNHTT<br>DNGVGPEEESVDPNIETPMMNIIPGGAVAKP<br>FITYHNELDMNLYMRIAPELYHKMLVVGGI<br>DRVYEIGRQFRNEGIDLTHNPEFTTCEFYMA<br>YADYHDLMEITEKMVSGMVKHITGSYKVT<br>YHPDGPEGQAYDVDFTPPFRRINMVEELEK<br>ALGMKLPETNLFETEETRKILDDICVAKAVE<br>CPPPRTTARLLDKLVGEFLEVTCINPTFICDH<br>PQIMSPLAKWHRSKEGLTERFELFVMKKEI<br>CNAYTELNDPMRQRQLFEEQAKAKAAGDD<br>EAMFIDENFCTALEYGLPPTAGWGMGIDRV<br>AMFLTDSNNIKEVLLFPAMKPEDKKENVAT<br>TDTLESTTVGTSV | SEQ. ID.<br>NO. 154 |
| LysRS2$^{N9}$ | DNA/<br>Human | ATGTTGACGCAAGCTGCTGTAAGGCTTGT<br>TAGGGGGTCCCTGCGCAAAACCTCCTGGG<br>CAGAGTGGGGTCACAGGGAACTGCGACT<br>GGGTCAACTTGCTCCTTTCACAGCGCCTC<br>ACAAGGACAAGTCATTTTCTGATCAAAGA<br>AGTGAGCTGAAGAGACGCCTGAAAGCTG<br>AGAAGAAAGTAGCAGAGAAGGAGGCCAA<br>ACAGAAAGAGCTCAGTGAGAAACAGCTA<br>AGCCAAGCCACTGCTGCTGCCACCAACCA<br>CACCACTGATAATGGTGTGGGTCCTGAGG<br>AAGAGAGCGTGGACCCAAATATTGAAAC<br>TCCCATGATGAACATCATCCCAGGGGGAG<br>CCGTGGCCAAGCCTTTCATCACTTATCAC<br>AACGAGCTGGACATGAACTTATATATGAG<br>AATTGCTCCAGAACTCTATCATAAGATGC<br>TTGTGGTTGGTGGCATCGACCGGGTTTAT<br>GAAATTGGACGCCAGTTCCGGAATGAGG<br>GGATTGATTTGACGCACAATCCTGAGTTC<br>ACCACCTGTGAGTTCTACATGGCCTATGC<br>AGACTATCACGATCTCATGGAAATCACGG<br>AGAAGATGGTTTCAGGGATGGTGAAGCAT<br>ATTACAGGCAGTTACAAGGTCACCTACCA<br>CCCAGATGGCCCAGAGGGCCAAGCCTAC<br>GATGTTGACTTCACCCCACCCTTCCGGCG<br>AATCAACATGGTAGAAGAGCTTGAGAAA<br>GCCCTGGGGATGAAGCTGCCAGAAACGA<br>ACCTCTTTGAAACTGAAGAAACTCGCAAA<br>ATTCTTGATGATATCTGTGTGGCAAAAGC<br>TGTTGAATGCCCTCCACCTCGGACCACAG<br>CCAGGCTCCTTGACAAGCTTGTTGGGGAG<br>TTCCTGGAAGTGACTTGCATCAATCCTAC<br>ATTCATCTGTGATCACCCACAGATAATGA<br>GCCCTTTGGCTAAATGGCACCGCTCTAAA<br>GAGGGTCTGACTGAGCGCTTTGAGCTGTT<br>TGTCATGAAGAAAGAGATATGCAATGCGT<br>ATACTGAGCTGAATGATCCCATGCGGCAG<br>CGGCAGCTTTTTGAAGAACAGGCCAAGGC<br>CAAGGCTGCAGGTGATGATGAGGCCATGT<br>TCATAGATGAAAACTTCTGTACTGCCCTG<br>GAATATGGGCTGCCCCCCACAGCTGGCTG<br>GGCATGGGCATTGATCGAGTCGCCATGT<br>TTCTCACGGACTCCAACAACATCAAGGAA<br>GTACTTCTGTTTCCTGCCATGAAACCCGA<br>AGACAAGAAGGAGAATGTAGCAACCACT | SEQ. ID.<br>NO. 155 |

| | | | |
|---|---|---|---|
| | | GATACACTGGAAAGCACAACAGTTGGCA<br>CTTCTGTCTAG | |
| LysRS2<sup>N10</sup> | Protein/<br>Human/<br>1-333 +<br>546-625 | MLTQAAVRLVRGSLRKTSWAEWGHRELRL<br>GQLAPFTAPHKDKSFSDQRSELKRRLKAEK<br>KVAEKEAKQKELSEKQLSQATAAATNHTT<br>DNGVGPEEESVDPNQYYKIRSQAIHQLKVN<br>GEDPYPHKFHVDISLTDFIQKYSHLQPGDHL<br>TDITLKVAGRIHAKRASGGKLIFYDLRGEGV<br>KLQVMANSRNYKSEEEFIHINNKLRRGDIIG<br>VQGNPGKTKKGELSIIPYEITLLSPCLHMLPH<br>LHFGLKDKETRYRQRYLDLILNDFVRQKFII<br>RSKIITYIRSFLDELGFLEIETPMMNIIPGGAV<br>AKPFITYHNELDMNLYMRIAPELYHKAKAA<br>GDDEAMFIDENFCTALEYGLPPTAGWGMGI<br>DRVAMFLTDSNNIKEVLLFPAMKPEDKKEN<br>VATTDTLESTTVGTSV | SEQ. ID.<br>NO. 156 |
| LysRS2<sup>N10</sup> | DNA/<br>Human | ATGTTGACGCAAGCTGCTGTAAGGCTTGT<br>TAGGGGGTCCCTGCGCAAAACCTCCTGGG<br>CAGAGTGGGGTCACAGGGAACTGCGACT<br>GGGTCAACTTGCTCCTTTCACAGCGCCTC<br>ACAAGGACAAGTCATTTTCTGATCAAAGA<br>AGTGAGCTGAAGAGACGCCTGAAAGCTG<br>AGAAGAAAGTAGCAGAGAAGGAGGCCAA<br>ACAGAAAGAGCTCAGTGAGAAACAGCTA<br>AGCCAAGCCACTGCTGCTGCCACCAACCA<br>CACCACTGATAATGGTGTGGGTCCTGAGG<br>AAGAGAGCGTGGACCCAAATCAATACTA<br>CAAAATCCGCAGTCAAGCAATTCATCAGC<br>TGAAGGTCAATGGGGAAGACCCATACCC<br>ACACAAGTTCCATGTAGACATCTCACTCA<br>CTGACTTCATCCAAAAATATAGTCACCTG<br>CAGCCTGGGGATCACCTGACTGACATCAC<br>CTTAAAGGTGGCAGGTAGGATCCATGCCA<br>AAAGAGCTTCTGGGGGAAAGCTCATCTTC<br>TATGATCTTCGAGGAGAGGGGGTGAAGTT<br>GCAAGTCATGGCCAATTCCAGAAATTATA<br>AATCAGAAGAAGAATTTATTCATATATTAAT<br>AACAAACTGCGTCGGGGAGACATAATTG<br>GAGTTCAGGGGAATCCTGGTAAAACCAA<br>GAAGGGTGAGCTGAGCATCATTCCGTATG<br>AGATCACACTGCTGTCTCCCTGTTTGCATA<br>TGTTACCTCATCTTCACTTTGGCCTCAAAG<br>ACAAGGAAACAAGGTATCGCCAGAGATA<br>CTTGGACTTGATCCTGAATGACTTTGTGA<br>GGCAGAAATTTATCATCCGCTCTAAGATC<br>ATCACATATATAAGAAGTTTCTTAGATGA<br>GCTGGGATTCCTAGAGATTGAAACTCCCA<br>TGATGAACATCATCCCAGGGGAGCCGTG<br>GCCAAGCCTTTCATCACTTATCACAACGA<br>GCTGGACATGAACTTATATATGAGAATTG<br>CTCCAGAACTCTATCATAAGGCCAAGGCT<br>GCAGGTGATGATGAGGCCATGTTCATAGA<br>TGAAAACTTCTGTACTGCCCTGGAATATG<br>GGCTGCCCCCCACAGCTGGCTGGGGCATG<br>GGCATTGATCGAGTCGCCATGTTTCTCAC<br>GGACTCCAACAACATCAAGGAAGTACTTC<br>TGTTTCCTGCCATGAAACCCGAAGACAAG<br>AAGGAGAATGTAGCAACCACTGATACACT<br>GGAAAGCACAACAGTTGGCACTTCTGTCT<br>AG | SEQ. ID.<br>NO. 157 |
| LysRS2<sup>N11</sup> | Protein/<br>Human/<br>1-102 + 2<br>aa | MLTQAAVRLVRGSLRKTSWAEWGHRELRL<br>GQLAPFTAPHKDKSFSDQRSELKRRLKAEK<br>KVAEKEAKQKELSEKQLSQATAAATNHTT<br>DNGVGPEEESVDPNKL | SEQ. ID.<br>NO. 158 |
| LysRS2<sup>N11</sup> | DNA/<br>Human | ATGTTGACGCAAGCTGCTGTAAGGCTTGT<br>TAGGGGGTCCCTGCGCAAAACCTCCTGGG<br>CAGAGTGGGGTCACAGGGAACTGCGACT<br>GGGTCAACTTGCTCCTTTCACAGCGCCTC<br>ACAAGGACAAGTCATTTTCTGATCAAAGA<br>AGTGAGCTGAAGAGACGCCTGAAAGCTG<br>AGAAGAAAGTAGCAGAGAAGGAGGCCAA<br>ACAGAAAGAGCTCAGTGAGAAACAGCTA<br>AGCCAAGCCACTGCTGCTGCCACCAACCA<br>CACCACTGATAATGGTGTGGGTCCTGAGG<br>AAGAGAGCGTGGACCCAAATAAATTATAA | SEQ. ID.<br>NO. 159 |

| | | | |
|---|---|---|---|
| LysRS2^N12 | Protein/<br>Human/<br>1-48 + 1<br>aa | MLTQAAVRLVRGSLRKTSWAEWGHRELRL<br>GQLAPFTAPHKDKSFSDQRR | SEQ. ID.<br>NO. 160 |
| LysRS2^N12 | DNA/<br>Human | ATGTTGACGCAAGCTGCTGTAAGGCTTGT<br>TAGGGGGTCCCTGCGCAAAACCTCCTGGG<br>CAGAGTGGGGTCACAGGGAACTGCGACT<br>GGGTCAACTTGCTCCTTTCACAGCGCCTC<br>ACAAGGACAAGTCATTTTCTGATCAAAGA<br>AGGTAG | SEQ. ID.<br>NO. 161 |
| LysRS2^N13 | Protein/<br>Human/<br>1-157 +<br>20 aa | MLTQAAVRLVRGSLRKTSWAEWGHRELRL<br>GQLAPFTAPHKDKSFSDQRSELKRRLKAEK<br>KVAEKEAKQKELSEKQLSQATAAATNHTT<br>DNGVGPEEESVDPNQYYKIRSQAIHQLKVN<br>GEDPYPHKFHVDISLTDFIQKYSHLQPGDHL<br>TDITLKVAEIINQKKNLFILITNCVGET | SEQ. ID.<br>NO. 162 |
| LysRS2^N13 | DNA/<br>Human | ATGTTGACGCAAGCTGCTGTAAGGCTTGT<br>TAGGGGGTCCCTGCGCAAAACCTCCTGGG<br>CAGAGTGGGGTCACAGGGAACTGCGACT<br>GGGTCAACTTGCTCCTTTCACAGCGCCTC<br>ACAAGGACAAGTCATTTTCTGATCAAAGA<br>AGTGAGCTGAAGAGACGCCTGAAAGCTG<br>AGAAGAAAGTAGCAGAGAAGGAGGCCAA<br>ACAGAAAGAGCTCAGTGAGAAACAGCTA<br>AGCCAAGCCACTGCTGCTGCCACCAACCA<br>CACCACTGATAATGGTGTGGGTCCTGAGG<br>AAGAGAGCGTGGACCCAAATCAATACTA<br>CAAAATCCGCAGTCAAGCAATTCATCAGC<br>TGAAGGTCAATGGGGAAGACCCATACCC<br>ACACAAGTTCCATGTAGACATCTCACTCA<br>CTGACTTCATCCAAAAATATAGTCACCTG<br>CAGCCTGGGGATCACCTGACTGACATCAC<br>CTTAAAGGTGGCAGAAATTATAAATCAGA<br>AGAAGAATTTATTCATATTAATAACAAAC<br>TGCGTCGGGGAGACATAA | SEQ. ID.<br>NO. 163 |
| LysRS2^N14 | Protein/<br>Human/<br>1-251 +<br>36 aa | MLTQAAVRLVRGSLRKTSWAEWGHRELRL<br>GQLAPFTAPHKDKSFSDQRSELKRRLKAEK<br>KVAEKEAKQKELSEKQLSQATAAATNHTT<br>DNGVGPEEESVDPNQYYKIRSQAIHQLKVN<br>GEDPYPHKFHVDISLTDFIQKYSHLQPGDHL<br>TDITLKVAGRIHAKRASGGKLIFYDLRGEGV<br>KLQVMANSRNYKSEEEFIHINNKLRRGDIIG<br>VQGNPGKTKKGELSIIPYEITLLSPCLHMLPH<br>LHFGLKDKKLAKFLMISVWQKLLNALHLG<br>PQPGSLTSLLGSSWK | SEQ. ID.<br>NO. 164 |
| LysRS2^N14 | DNA/<br>Human | ATGTTGACGCAAGCTGCTGTAAGGCTTGT<br>TAGGGGGTCCCTGCGCAAAACCTCCTGGG<br>CAGAGTGGGGTCACAGGGAACTGCGACT<br>GGGTCAACTTGCTCCTTTCACAGCGCCTC<br>ACAAGGACAAGTCATTTTCTGATCAAAGA<br>AGTGAGCTGAAGAGACGCCTGAAAGCTG<br>AGAAGAAAGTAGCAGAGAAGGAGGCCAA<br>ACAGAAAGAGCTCAGTGAGAAACAGCTA<br>AGCCAAGCCACTGCTGCTGCCACCAACCA<br>CACCACTGATAATGGTGTGGGTCCTGAGG<br>AAGAGAGCGTGGACCCAAATCAATACTA<br>CAAAATCCGCAGTCAAGCAATTCATCAGC<br>TGAAGGTCAATGGGGAAGACCCATACCC<br>ACACAAGTTCCATGTAGACATCTCACTCA<br>CTGACTTCATCCAAAAATATAGTCACCTG<br>CAGCCTGGGGATCACCTGACTGACATCAC<br>CTTAAAGGTGGCAGGTAGGATCCATGCCA<br>AAAGAGCTTCTGGGGAAAGCTCATCTTC<br>TATGATCTTCGAGGAGAGGGGTGAAGTT<br>GCAAGTCATGGCCAATTCCAGAAATTATA<br>AATCAGAAGAAGAATTTATTCATATTAAT<br>AACAAACTGCGTCGGGGAGACATAATTG<br>GAGTTCAGGGGAATCCTGGTAAAACCAA<br>GAAGGGTGAGCTGAGCATCATTCCGTATG<br>AGATCACACTGCTGTCTCCCTGTTTGCATA<br>TGTTACCTCATCTTCACTTTGGCCTCAAAG<br>ACAAGAAACTCGCAAAATTCTTGATGATA | SEQ. ID.<br>NO. 165 |

-continued

```
TCTGTGTGGCAAAAGCTGTTGAATGCCCT
CCACCTCGGACCACAGCCAGGCTCCTTGA
CAAGCTTGTTGGGGAGTTCCTGGAAGTGA
```

Table 11B
AARS polypeptides unique splice junctions

| Name | Type/ species | Amino acid and Nucleic Acid Sequences in the vicinity of the unique splice junction | SEQ. ID. NO. |
|---|---|---|---|
| K1-AS01 | DNA/ Human/ Protein/ Human | ACAAGTCATTTTCTGATCAAAGAAG\|CAAT ACTACAAAATCCGCAGTCAAG KSFSDQRSNTTKSAVK | SEQ. ID. NO. 166 SEQ. ID. NO. 167 |
| K1-SV04 | DNA/ Human/ Protein/ Human | TGAGGAAGAGAGCGTGGACCCAAAT\|GTA GGATCCATGCCAAAAGAGCTTC EEESVDPNVGSMPKEL | SEQ. ID. NO. 168 SEQ. ID. NO. 169 |
| K1-SV06 | DNA/ Human/ Protein/ Human | CTTAGATGAGCTGGGATTCCTAGAG\|ATGC TTGTGGTTGGTGGCATCGACC LDELGFLEMLVVGGID | SEQ. ID. NO. 170 SEQ. ID. NO. 171 |
| K1-SV07 | DNA/ Human/ Protein/ Human | TGAGGAAGAGAGCGTGGACCCAAAT\|ATT GAAACTCCCATGATGAACATC EEESVDPNIETPMMNI | SEQ. ID. NO. 172 SEQ. ID. NO. 173 |
| K1-SV08 | DNA/ Human/ Protein/ Human | AATTGCTCCAGAACTCTATCATAAG\|GCCA AGGCTGCAGGTGATGATGAGG IAPELYHKAKAAGDDE | SEQ. ID. NO. 174 SEQ. ID. NO. 175 |
| K1-SV10 | DNA/ Human/ Protein/ Human | TGAGGAAGAGAGCGTGGACCCAAAT\|AAA TTATAAATCAGAAGAAGAATTT EEESVDPNKL | SEQ. ID. NO. 176 SEQ. ID. NO. 177 |
| K1-AS03 | DNA/ Human/ Protein/ Human | ACAAGTCATTTTCTGATCAAAGAAG\|GTAG GATCCATGCCAAAAGAGCTTC KSFSDQRR | SEQ. ID. NO. 178 SEQ. ID. NO. 179 |
| K1-AS04 | DNA/ Human/ Protein/ Human | ACTGACATCACCTTAAAGGTGGCAG\|AAA TTATAAATCAGAAGAAGAATTT TDITLKVAEIINQKKN | SEQ. ID. NO. 180 SEQ. ID. NO. 181 |
| K1-AS05 | DNA/ Human/ Protein/ Human | TCTTCACTTTGGCCTCAAAGACAAG\|AAAC TCGCAAAATTCTTGATGATAT LHFGLKDKKLAKFLMI | SEQ. ID. NO. 182 SEQ. ID. NO. 183 |

TABLE 12
AARS polypeptides and nucleic acids identified by Bioinformatics

| Name | Type/ species/ Residues | Amino acid and Nucleic Acid Sequences | SEQ. ID. NO. |
|---|---|---|---|
| LysRS2$^{N2}$ | Protein/ Human/ 1-104 | MLTQAAVRLVRGSLRKTSWAEWGHRELRL GQLAPFTAPHKDKSFSDQRSELKRRLKAEK KVAEKEAKQKELSEKQLSQATAAATNHTT DNGVGPEEESVDPNQY | SEQ. ID. NO. 184 |
| LysRS2$^{N2}$ | DNA/ Human/ | ATGTTGACGCAAGCTGCTGTAAGGCTTGT TAGGGGGTCCCTGCGCAAAACCTCCTGGG CAGAGTGGGGTCACAGGGAACTGCGACT GGGTCAACTTGCTCCTTTCACAGCGCCTC ACAAGGACAAGTCATTTTCTGATCAAAGA AGTGAGCTGAAGAGACGCCTGAAAGCTG AGAAGAAAGTAGCAGAGAAGGAGGCCAA ACAGAAAGAGCTCAGTGAGAAACAGCTA | SEQ. ID. NO. 185 |

TABLE 12-continued

AARS polypeptides and nucleic acids identified by Bioinformatics

| Name | Type/species/Residues | Amino acid and Nucleic Acid Sequences | SEQ. ID. NO. |
|---|---|---|---|
| | | AGCCAAGCCACTGCTGCTGCCACCAACCA CACCACTGATAATGGTGTGGGTCCTGAGG AAGAGAGCGTGGACCCAAATCAATAC | |
| LysRS2$^{N3}$ | Protein/Human/1-222 | MLTQAAVRLVRGSLRKTSWAEWGHRELRL GQLAPFTAPHKDKSFSDQRSELKRRLKAEK KVAEKEAKQKELSEKQLSQATAAATNHTT DNGVGPEEESVDPNQYYKIRSQAIHQLKVN GEDPYPHKFHVDISLTDFIQKYSHLQPGDHL TDITLKVAGRIHAKRASGGKLIFYDLRGEGV KLQVMANSRNYKSEEEFIHINNKLRRGDIIG VQGNPGKTKKG | SEQ. ID. NO. 186 |
| LysRS2$^{N3}$ | DNA/Human/ | ATGTTGACGCAAGCTGCTGTAAGGCTTGT TAGGGGGTCCCTGCGCAAAACCTCCTGGG CAGAGTGGGGTCACAGGGAACTGCGACT GGGTCAACTTGCTCCTTTCACAGCGCCTC ACAAGGACAAGTCATTTTCTGATCAAAGA AGTGAGCTGAAGAGACGCCTGAAAGCTG AGAAGAAAGTAGCAGAGAAGGAGGCCAA ACAGAAAGAGCTCAGTGAGAAACAGCTA AGCCAAGCCACTGCTGCTGCCACCAACCA CACCACTGATAATGGTGTGGGTCCTGAGG AAGAGAGCGTGGACCCAAATCAATACTA CAAAATCCGCAGTCAAGCAATTCATCAGC TGAAGGTCAATGGGGAAGACCCATACCC ACACAAGTTCCATGTAGACATCTCACTCA CTGACTTCATCCAAAATATAGTCACCTG CAGCCTGGGGATCACCTGACTGACATCAC CTTAAAGGTGGCAGGTAGGATCCATGCCA AAAGAGCTTCTGGGGGAAAGCTCATCTTC TATGATCTTCGAGGAGAGGGGGTGAAGTT GCAAGTCATGGCCAATTCCAGAAATTATA AATCAGAAGAAGAATTTATTCATATTAAT AACAAACTGCGTCGGGGAGACATAATTG GAGTTCAGGGGAATCCTGGTAAAACCAA GAAGGGT | SEQ. ID. NO. 187 |
| LysRS2$^{N4}$ | Protein/Human/1-93 | MLTQAAVRLVRGSLRKTSWAEWGHRELRL GQLAPFTAPHKDKSFSDQRSELKRRLKAEK KVAEKEAKQKELSEKQLSQATAAATNHTT DNGVG | SEQ. ID. NO. 188 |
| LysRS2$^{N4}$ | DNA/Human/ | ATGTTGACGCAAGCTGCTGTAAGGCTTGT TAGGGGGTCCCTGCGCAAAACCTCCTGGG CAGAGTGGGGTCACAGGGAACTGCGACT GGGTCAACTTGCTCCTTTCACAGCGCCTC ACAAGGACAAGTCATTTTCTGATCAAAGA AGTGAGCTGAAGAGACGCCTGAAAGCTG AGAAGAAAGTAGCAGAGAAGGAGGCCAA ACAGAAAGAGCTCAGTGAGAAACAGCTA AGCCAAGCCACTGCTGCTGCCACCAACCA CACCACTGATAATGGTGTGGGT | SEQ. ID. NO. 189 |
| LysRS2$^{N5}$ | Protein/Human/1-242 | MLTQAAVRLVRGSLRKTSWAEWGHRELRL GQLAPFTAPHKDKSFSDQRSELKRRLKAEK KVAEKEAKQKELSEKQLSQATAAATNHTT DNGVGPEEESVDPNQYYKIRSQAIHQLKVN GEDPYPHKFHVDISLTDFIQKYSHLQPGDHL TDITLKVAGRIHAKRASGGKLIFYDLRGEGV KLQVMANSRNYKSEEEFIHINNKLRRGDIIG VQGNPGKTKKGELSIIPYEITLLSPCLHMLP | SEQ. ID. NO. 190 |
| LysRS2$^{N5}$ | DNA/Human/ | ATGTTGACGCAAGCTGCTGTAAGGCTTGT TAGGGGGTCCCTGCGCAAAACCTCCTGGG CAGAGTGGGGTCACAGGGAACTGCGACT GGGTCAACTTGCTCCTTTCACAGCGCCTC ACAAGGACAAGTCATTTTCTGATCAAAGA AGTGAGCTGAAGAGACGCCTGAAAGCTG AGAAGAAAGTAGCAGAGAAGGAGGCCAA ACAGAAAGAGCTCAGTGAGAAACAGCTA AGCCAAGCCACTGCTGCTGCCACCAACCA CACCACTGATAATGGTGTGGGTCCTGAGG | SEQ. ID. NO. 191 |

TABLE 12-continued

AARS polypeptides and nucleic acids identified by Bioinformatics

| Name | Type/species/Residues | Amino acid and Nucleic Acid Sequences | SEQ. ID. NO. |
|---|---|---|---|
| | | AAGAGAGCGTGGACCCAAATCAATACTA<br>CAAAATCCGCAGTCAAGCAATTCATCAGC<br>TGAAGGTCAATGGGGAAGACCCATACCC<br>ACACAAGTTCCATGTAGACATCTCACTCA<br>CTGACTTCATCCAAAAATATAGTCACCTG<br>CAGCCTGGGGATCACCTGACTGACATCAC<br>CTTAAAGGTGGCAGGTAGGATCCATGCCA<br>AAAGAGCTTCTGGGGGAAAGCTCATCTTC<br>TATGATCTTCGAGGAGAGGGGGTGAAGTT<br>GCAAGTCATGGCCAATTCCAGAAATTATA<br>AATCAGAAGAAGAATTTATTCATATTAAT<br>AACAAACTGCGTCGGGGAGACATAATTG<br>GAGTTCAGGGGAATCCTGGTAAAACCAA<br>GAAGGGTGAGCTGAGCATCATTCCGTATG<br>AGATCACACTGCTGTCTCCCTGTTTGCATA<br>TGTTACCT | |

"Protein fragments," or the amino acid sequence of protein fragments, such as proteolytic fragments or splice variant fragments, can be characterized, identified, or derived according to a variety of techniques. For instance, splice variants can be identified by techniques such as deep sequencing (see, e.g., Xing et al., *RNA.* 14:1470-1479, 2008; and Zhang et al., *Genome Research.* 17:503-509, 2007). As a further example, protein fragments such as proteolytic fragments can be identified in vitro, such as by incubating full-length or other AARS polypeptides with selected proteases, or they can be identified endogenously (e.g., in vivo). In certain embodiments, protein fragments such as endogenous proteolytic fragments can be generated or identified, for instance, by recombinantly expressing full-length or other AARS polypeptides in a selected microorganism or eukaryotic cell that has been either modified to contain one or more selected proteases, or that naturally contains one or more proteases that are capable of acting on a selected AARS polypeptide, and isolating and characterizing the endogenously produced protein fragments therefrom.

In certain embodiments, protein fragments such as endogenous (e.g., naturally-occurring) proteolytic fragments can be generated or identified, for instance, from various cellular fractions (e.g., cytosolic, membrane, nuclear) and/or growth medium of various cell-types, including, for example, immune cells such as monocytes, dendritic cells, macrophages (e.g., RAW 264.7 macrophages), neutrophils, eosinophils, basophils, and lymphocytes, such as B-cells and T-cells (e.g., CD4+ helper and CD8+ killer cells), including primary T-cells and T-cell lines such as Jurkat T-cells, as well as natural killer (NK) cells.

In certain embodiments, protein fragments such as endogenous proteolytic fragments, however generated, can be identified by techniques such as mass-spectrometry, or equivalent techniques. Once an in vitro or endogenously identified protein fragment has been generated or identified, it can be mapped or sequenced, and, for example, cloned into an expression vector for recombinant production, or produced synthetically.

A wide variety of proteases can be used to produce, identify, derive, or characterize the sequence of AARS protein fragments such as proteolytic fragments. Generally, proteases are usually classified according to three major criteria: (i) the reaction catalyzed, (ii) the chemical nature of the catalytic site, and (iii) the evolutionary relationship, as revealed by the structure. General examples of proteases or proteinases, as classified by mechanism of catalysis, include aspartic proteases, serine proteases, cysteine proteases, and metalloproteases.

Most aspartic proteases belong to the pepsin family. This family includes digestive enzymes, such as pepsin and chymosin, as well as lysosomal cathepsins D and processing enzymes such as renin, and certain fungal proteases (e.g., penicillopepsin, rhizopuspepsin, endothiapepsin). A second family of aspartic proteases includes viral proteinases such as the protease from the AIDS virus (HIV), also called retropepsin.

Serine proteases include two distinct families. First, the chymotrypsin family, which includes the mammalian enzymes such as chymotrypsin, trypsin, elastase, and kallikrein, and second, the substilisin family, which includes the bacterial enzymes such as subtilisin. The general 3D structure between these two families is different, but they have the same active site geometry, and catalysis proceeds via the same mechanism. The serine proteases exhibit different substrate specificities, differences which relate mainly to amino acid substitutions in the various enzyme subsites (substrate residue interacting sites). Some serine proteases have an extended interaction site with the substrate whereas others have a specificity that is restricted to the P1 substrate residue.

The cysteine protease family includes the plant proteases such as papain, actinidin, and bromelain, several mammalian lysosomal cathepsins, the cytosolic calpains (calcium-activated), as well as several parasitic proteases (e.g., *Trypanosoma, Schistosoma*). Papain is the archetype and the best studied member of the family. Recent elucidation of the X-ray structure of the Interleukin-1-beta Converting Enzyme has revealed a novel type of fold for cysteine proteinases.

The metalloproteases are one of the older classes of proteases, found in bacteria, fungi, and higher organisms. They differ widely in their sequences and their 3D structures, but the great majority of enzymes contain a zinc atom that is catalytically active. In some cases, zinc may be replaced by another metal such as cobalt or nickel without loss of proteolytic activity. Bacterial thermolysin has been well characterized and its crystallographic structure indicates that zinc is bound by two histidines and one glutamic acid. Many metalloproteases contain the sequence motif HEXXH, which provides two histidine ligands for the zinc. The third ligand is either a glutamic acid (thermolysin, neprilysin, alanyl aminopeptidase) or a histidine (astacin, serralysin).

Illustrative proteases include, for example, achromopeptidase, aminopeptidase, ancrod, angiotensin converting enzyme, bromelain, calpain, calpain I, calpain II, carboxypeptidase A, carboxypeptidase B, carboxypeptidase G, carboxypeptidase P, carboxypeptidase W, carboxypeptidase Y, caspase 1, caspase 2, caspase 3, caspase 4, caspase 5, caspase 6, caspase 7, caspase 8, caspase 9, caspase 10, caspase 11, caspase 12, caspase 13, cathepsin B, cathepsin C, cathepsin D, cathepsin E, cathepsin G, cathepsin H, cathepsin L, chymopapain, chymase, chymotrypsin, clostripain, collagenase, complement C1r, complement C1s, complement Factor D, complement factor I, cucumisin, dipeptidyl peptidase IV, elastase (leukocyte), elastase (pancreatic), endoproteinase Arg-C, endoproteinase Asp-N, endoproteinase Glu-C, endoproteinase Lys-C, enterokinase, factor Xa, ficin, furin, granzyme A, granzyme B, HIV Protease, IGase, kallikrein tissue, leucine aminopeptidase (general), leucine aminopeptidase (cytosol), leucine aminopeptidase (microsomal), matrix metalloprotease, methionine aminopeptidase, neutrase, papain, pepsin, plasmin, prolidase, pronase E, prostate specific antigen, protease alkalophilic from *Streptomyces griseus*, protease from *Aspergillus*, protease from *Aspergillus saitoi*, protease from *Aspergillus sojae*, protease (*B. licheniformis*) (alkaline or alcalase), protease from *Bacillus polymyxa*, protease from *Bacillus* sp, protease from *Rhizopus* sp., protease S, proteasomes, proteinase from *Aspergillus oryzae*, proteinase 3, proteinase A, proteinase K, protein C, pyroglutamate aminopeptidase, rennin, rennin, streptokinase, subtilisin, thermolysin, thrombin, tissue plasminogen activator, trypsin, tryptase and urokinase.

Certain embodiments relate to isolated AARS polypeptides, comprising, consisting essentially of, or consisting of amino acid sequences that have been derived from endogenous, naturally-occurring AARS polypeptide fragments, and pharmaceutical compositions comprising said fragments, and methods of use thereof. These and related embodiments can be generated or identified in vivo, ex vivo, and/or in vitro. In certain preferred in vitro embodiments, AARS proteolytic fragments are generated or identified by incubating an AARS polypeptide, such as a full-length AARS polypeptide, with one or more isolated human proteases, mainly those proteases that are endogenous or natural to humans, such as elastase and others described herein and known in the art. Other embodiments relate to isolated AARS polypeptides, comprising, consisting essentially of, or consisting of amino acid sequences that have been derived from endogenous, naturally-occurring AARS splice variants, and pharmaceutical compositions comprising said fragments, and methods of use thereof. Essentially, AARS protein fragment can be isolated from samples that have been exposed to proteases, whether in vivo or in vitro.

In certain embodiments, AARS protein fragments can be identified by techniques such as mass-spectrometry, or equivalent techniques. Merely by way of illustration and not limitation, in certain embodiments the proteomes from various cell types, tissues, or body fluids from a variety of physiological states (e.g., hypoxia, diet, age, disease) or fractions thereof may be separated by 1D SDS-PAGE and the gel lanes cut into bands at fixed intervals; after which the bands may be optionally digested with an appropriate protease, such as trypsin, to release the peptides, which may then be analyzed by 1D reverse phase LC-MS/MS. The resulting proteomic data may be integrated into so-called peptographs, which plot, in the left panel, sequence coverage for a given protein in the horizontal dimension (N to C terminus, left to right) versus SDS-PAGE migration in the vertical dimension (high to low molecular weight, top to bottom). The specific peptide fragments can then be sequenced or mapped. In certain embodiments, the AARS reference fragment may be characterized by its unique molecular weight, as compared, for example, to the molecular weight of the corresponding full-length AARS.

As noted above, embodiments of the present invention include the AARS polypeptides set forth in Table(s) 1-3, or Table(s) 4-6, or Table(s) 7-9, or Table(s) 10-12. Also included are "variants" of the AARS reference polypeptides. The recitation polypeptide "variant" refers to polypeptides that are distinguished from a reference AARS polypeptide by the addition, deletion, and/or substitution of at least one amino acid residue, and which typically retain (e.g., mimic) or modulate (e.g., antagonize) one or more non-canonical activities of a reference AARS polypeptide.

Moreover human Lysyl tRNA synthetases include several hundred highly related polymorphic forms, and these are known in the art to be at least partially functionally interchangeable. It would thus be a routine matter to select a naturally occurring variant of Lysyl tRNA synthetase, including, for example the single nucleotide polymorphic forms listed in Table A to create an AARS polypeptide containing one or more amino acid changes based on the sequence of any of the homologues, orthologs, and naturally-occurring isoforms of human as well as other species of Lysyl tRNA synthetase.

TABLE A

Human Lysyl tRNA synthetase SNPs

| Gene Bank Accession Number | Nucleotide Change | Gene Bank Accession Number | Nucleotide Change |
|---|---|---|---|
| rs117946205 | G/T | rs11557665 | C/G |
| rs117872527 | A/T | rs11557664 | C/T |
| rs117585187 | C/G | rs11556640 | A/C |
| rs117561624 | G/T | rs11556639 | C/G |
| rs117472224 | C/G | rs11556638 | C/G |
| rs117457640 | C/T | rs11386229 | —/A |
| rs117188693 | A/C | rs11363202 | —/A |

TABLE A-continued

Human Lysyl tRNA synthetase SNPs

| Gene Bank Accession Number | Nucleotide Change | Gene Bank Accession Number | Nucleotide Change |
|---|---|---|---|
| rs117100154 | C/T | rs9938305 | C/G |
| rs117041419 | C/T | rs8057723 | C/T |
| rs117013282 | G/T | rs8053257 | A/G |
| rs116989849 | A/T | rs8051771 | C/T |
| rs116928063 | C/T | rs8051113 | A/C |
| rs116811812 | C/G | rs8047430 | C/T |
| rs116801062 | C/G | rs7195338 | A/G |
| rs116635879 | C/T | rs7193257 | C/G |
| rs116584059 | G/T | rs7189895 | A/G |
| rs116531622 | A/G | rs7187847 | A/G |
| rs116468372 | C/T | rs7186504 | G/T |
| rs116318609 | C/G | rs6564271 | C/T |
| rs116129958 | A/G | rs6564270 | C/T |
| rs116069782 | C/T | rs5817958 | —/A |
| rs115957689 | A/T | rs5817957 | —/G |
| rs115912670 | C/T | rs5030748 | A/G |
| rs115518873 | C/T | rs4888442 | A/G |
| rs115450297 | C/T | rs4888441 | C/G |
| rs115134738 | C/G | rs4888440 | A/G |
| rs115082322 | A/T | rs3837756 | —/T |
| rs114768348 | C/T | rs3784931 | A/G |
| rs113993881 | A/G | rs3784930 | A/G |
| rs113909347 | A/T | rs3784929 | C/T |
| rs113846451 | A/C | rs3784928 | A/G |
| rs113813120 | C/T | rs3214635 | —/G |
| rs113577360 | C/T | rs3211301 | A/G |
| rs113570860 | C/T | rs2289064 | A/C |
| rs113531576 | A/G | rs2289063 | C/T |
| rs113335212 | A/G | rs2233810 | A/C |
| rs113272137 | C/T | rs2233809 | G/T |
| rs113001454 | A/C | rs2233808 | A/G |
| rs112982343 | C/G | rs2233807 | C/T |
| rs112934609 | A/G | rs34610510 | —/C |
| rs112878760 | A/C | rs34570398 | —/A |
| rs112834496 | C/T | rs34367936 | —/T |
| rs112783308 | C/T | rs34160918 | —/T |
| rs112603638 | C/T | rs34084576 | C/T |

TABLE A-continued

Human Lysyl tRNA synthetase SNPs

| Gene Bank Accession Number | Nucleotide Change | Gene Bank Accession Number | Nucleotide Change |
|---|---|---|---|
| rs112599651 | C/T | rs28615806 | A/T |
| rs112389955 | —/A | rs28609444 | A/T |
| rs112370895 | A/G | rs28376768 | A/T |
| rs112319505 | G/T | rs28365852 | A/G |
| rs112268246 | —/G | rs17764797 | C/T |
| rs112225278 | A/G | rs17697211 | C/T |
| rs112121151 | A/G | rs17607381 | A/T |
| rs112063795 | A/C | rs16941533 | C/T |
| rs111883921 | C/T | rs16941516 | A/G |
| rs111836109 | A/G | rs16941409 | C/T |
| rs111806827 | A/G | rs16941400 | A/G |
| rs111772248 | C/T | rs16941301 | A/G |
| rs111679674 | C/G | rs16941296 | —/C |
| rs111676921 | A/C | rs16941287 | C/T |
| rs111330594 | A/G | rs16941282 | C/G |
| rs111323143 | G/T | rs13380501 | A/G |
| rs111236795 | A/G | rs13333731 | C/T |
| rs80328717 | C/G | rs12934451 | C/T |
| rs80288252 | A/G | rs12932643 | A/C |
| rs80287344 | A/G | rs12919013 | C/T |
| rs80068681 | C/G | rs12599809 | G/T |
| rs79964843 | G/T | rs12596816 | G/T |
| rs79612807 | A/G | rs12596033 | A/C |
| rs79367972 | A/G | rs12447289 | A/G |
| rs79309890 | C/T | rs11866252 | C/T |
| rs79256828 | C/T | rs11649494 | C/G |
| rs79248873 | A/G | rs11649491 | C/G |
| rs79158843 | A/C | rs11649388 | A/G |
| rs78908884 | A/T | rs11647615 | C/G |
| rs78798046 | A/G | rs11639582 | A/C |
| rs78654839 | C/G | rs11639581 | C/T |
| rs78496415 | A/G | rs11557669 | C/G |
| rs78279493 | A/C | rs11557668 | A/G |
| rs78198545 | C/T | rs11557667 | A/C |
| rs78028405 | C/G | rs71763095 | —/T |
| rs77917474 | A/G | rs71394230 | G/T |
| rs77909125 | —/G | rs71394229 | A/T |

TABLE A-continued

Human Lysyl tRNA synthetase SNPs

| Gene Bank Accession Number | Nucleotide Change | Gene Bank Accession Number | Nucleotide Change |
|---|---|---|---|
| rs77573084 | A/G | rs71394228 | A/G |
| rs77547020 | C/T | rs71272462 | –/T |
| rs77405224 | A/G | rs67862594 | –/A |
| rs77039575 | C/T | rs67793208 | –/AA |
| rs76950867 | C/T | rs66921889 | –/A |
| rs76937292 | C/T | rs66866136 | –/A |
| rs76742560 | G/T | rs62058713 | G/T |
| rs76645676 | C/T | rs61588474 | G/T |
| rs76583709 | A/C | rs60487109 | G/T |
| rs76407110 | G/T | rs60376290 | A/C |
| rs76274703 | A/G | rs59297469 | G/T |
| rs76197636 | A/C | rs59116766 | G/T |
| rs76151791 | C/T | rs58996069 | G/T |
| rs76083304 | A/G | rs58780202 | G/T |
| rs76000432 | A/T | rs58657577 | C/T |
| rs75909814 | C/T | rs58508930 | A/G |
| rs75636445 | G/T | rs58000098 | C/G |
| rs75584151 | A/G | rs57551067 | –/T |
| rs75374652 | A/C | rs57228113 | –/A |
| rs75260215 | G/T | rs57060791 | –/T |
| rs75134162 | C/T | rs56951212 | –/A |
| rs75096057 | A/C | rs56140205 | A/G |
| rs74830021 | A/T | rs41505349 | C/T |
| rs74250915 | G/T | rs36101987 | C/T |
| rs74024804 | A/T | rs36091972 | C/T |
| rs73615082 | C/T | rs35638876 | –/A |
| rs73615080 | C/T | rs35501069 | –/C |
| rs72789443 | A/G | rs35494814 | –/T |
| rs72563119 | C/G | rs35478599 | –/C |
| rs72563118 | C/G | rs35321652 | A/G |
| rs72563117 | C/G | rs35197449 | –/A |
| rs72526055 | –/A | rs35143320 | C/G |
| rs72500765 | –/A | rs35021757 | –/A |
| rs72465966 | –/A | rs34920043 | –/C |
| rs72092434 | –/TT | rs34838148 | A/C |
| rs71945664 | –/T | rs34729412 | –/A |

TABLE A-continued

Human Lysyl tRNA synthetase SNPs

| Gene Bank Accession Number | Nucleotide Change | Gene Bank Accession Number | Nucleotide Change |
|---|---|---|---|
| rs2233806 | C/G | rs35311324 | -/T/TTTTTTTTTTTTTTTT |
| rs2233805 | C/T | rs67860096 | -/TTTTTTTTTTTTTTTTT |
| rs2233804 | C/T | rs71378624 | CTA/GTG |
| rs2233803 | C/T | rs10556967 | -/TAT |
| rs1865493 | C/G | rs57952495 | -/AATA |
| rs1865492 | A/G | rs16941276 | -/TAA |
| rs1836547 | C/G | rs111735733 | -/TTG |
| rs1802511 | C/T | rs66905258 | -/ATT |
| rs1802510 | C/T | rs71883952 | -/TTA |
| rs920037 | G/T | rs71839384 | -/TTA |
| rs11505 | GTCTTTGCATTTCTGCGAAAGATCAA | rs80330368 | -/AAA |
| rs6834 | TACACTGGAAAGCACAACAGTTGGCA | rs35993558 | CT/GC |
| | | rs35903494 | -/G |
| | | rs35903075 | C/G |
| | | rs35806222 | -/T/TG |
| | | rs59378310 | -/ATT |
| | | rs72129089 | -/TAT |

In certain embodiments, a polypeptide variant is distinguished from a reference polypeptide by one or more substitutions, which may be conservative or non-conservative, as described herein and known in the art. In certain embodiments, the polypeptide variant comprises conservative substitutions and, in this regard, it is well understood in the art that some amino acids may be changed to others with broadly similar properties without changing the nature of the activity of the polypeptide.

In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98% or more sequence identity or similarity to a corresponding sequence of an AARS reference polypeptide, as described herein, and substantially retains the non-canonical activity of that reference polypeptide. Also included are sequences differing from the reference AARS sequences by the addition, deletion, or substitution of 1, 2, 3, 4, 5, 6, 7, 8, 9, 10, 11, 12, 13, 14, 15, 16, 17, 18, 19, 20, 30, 40, 50, 60, 70, 80, 90, 100, 110, 120, 130, 140, 150 or more amino acids but which retain the properties of the reference AARS polypeptide. In certain embodiments, the amino acid additions or deletions occur at the C-terminal end and/or the N-terminal end of the AARS reference polypeptide. In certain embodiments, the amino acid additions include 1, 2, 3, 4, 5, 6, 7, 8, 9, 10, 11, 12, 13, 14, 15, 16, 17, 18, 19, 20, 30, 40, 50 or more wild-type residues (i.e., from the corresponding full-length AARS polypeptide) that are proximal to the C-terminal end and/or the N-terminal end of the AARS reference polypeptide.

In certain embodiments, variant polypeptides differ from the corresponding AARS reference sequences by at least 1% but less than 20%, 15%, 10% or 5% of the residues. (If this comparison requires alignment, the sequences should be aligned for maximum similarity. "Looped" out sequences from deletions or insertions, or mismatches, are considered differences.) The differences are, suitably, differences or changes at a non-essential residue or a conservative substitution. In certain embodiments, the molecular weight of a variant AARS polypeptide differs from that of the AARS reference polypeptide by about 1%, 2%, 3%, 4%, 5%, 6%, 7%, 8%, 9%, 10%, 11%, 12%, 13%, 14%, 15%, 16%, 17%, 18%, 19%, 20%, or more.

Also included are biologically active "fragments" of the AARS reference polypeptides, i.e., biologically active fragments of the AARS protein fragments. Representative biologically active fragments generally participate in an interaction, e.g., an intramolecular or an inter-molecular interaction. An inter-molecular interaction can be a specific binding interaction or an enzymatic interaction. An inter-molecular interaction can be between an AARS polypeptide and a cellular binding partner, such as a cellular receptor or other host molecule that participates in the non-canonical activity of the AARS polypeptide. In some embodiments, AARS proteins, variants, and biologically active fragments thereof, bind to one or more cellular binding partners with an affinity of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. The binding affinity of an AARS protein fragment for a selected cellular binding partner, particularly a binding partner that participates in a non-canonical activity, is typically stronger than that of the AARS protein fragment's corresponding full-length AARS polypeptide, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between). The binding affinity of an AARS protein fragment for a binding partner that participates in at least one canonical activity of an AARS is typically weaker than that of the AARS protein fragment's corresponding full-length AARS polypeptide, by at least about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more.

Typically, biologically active fragments comprise a domain or motif with at least one activity of an AARS reference polypeptide and may include one or more (and in some cases all) of the various active domains, and include fragments having a non-canonical activity. In some cases, biologically active fragments of an AARS polypeptide have a biological activity that is unique to the particular, truncated fragment, such that the full-length AARS polypeptide may not have that activity. In certain cases, the biological activity may be revealed by separating the biologically active AARS polypeptide fragment from the other full-length AARS polypeptide sequences, or by altering certain residues of the full-length AARS wild-type polypeptide sequence to unmask the biologically active domains.

A biologically active fragment of an AARS reference polypeptide can be a polypeptide fragment which is, for example, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 450, 500, 550, 600, 650, 700, 750 or more contiguous or non-contiguous amino acids, including all integers (e.g., 101, 102, 103) and ranges (e.g., 50-100, 50-150, 50-200) in between, of the amino acid sequences set forth in any one of the AARS reference polypeptides described herein, but typically exclude the full-length AARS. In certain embodiments, a biologically active fragment comprises a non-canonical activity-related sequence, domain, or motif. In certain embodiments, the C-terminal or N-terminal region of any AARS reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, or 700 or more amino acids, or by about 10-50, 20-50, 50-100, 100-150, 150-200, 200-250, 250-300, 300-350, 350-400, 400-450, 450-500, 500-550, 550-600, 600-650, 650-700 or more amino acids, including all integers and ranges in between (e.g., 101, 102, 103, 104, 105), so long as the truncated AARS polypeptide retains the non-canonical activity of the reference polypeptide. Typically, the biologically-active fragment has no less than about 1%, about 5%, about 10%, about 25%, or about 50% of an activity of the biologically-active (i.e., non-canonical activity) AARS reference polypeptide from which it is derived. Exemplary methods for measuring such non-canonical activities are described in the Examples.

As noted above, an AARS polypeptide may be altered in various ways including amino acid substitutions, deletions, truncations, and insertions. Methods for such manipulations are generally known in the art. For example, amino acid sequence variants of an AARS reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., ("Molecular Biology of the Gene", Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Similarly it is within the skill in the art to address and/or mitigate immunogenicity concerns if they arise using an AARS polypeptide, e.g., by the use of automated computer recognition programs to identify potential T cell epitopes, and directed evolution approaches to identify less immunogenic forms.

Methods for screening gene products of combinatorial libraries made by point mutations or truncation, and for screening cDNA libraries for gene products having a selected property are known in the art. Such methods are adaptable for rapid screening of the gene libraries generated by combinatorial mutagenesis of AARS polypeptides. Recursive ensemble mutagenesis (REM), a technique which enhances the frequency of functional mutants in the libraries, can be used in combination with the screening assays to identify AARS polypeptide variants (Arkin and Yourvan (1992) *Proc. Natl. Acad. Sci. USA* 89: 7811-7815; Delgrave et al., (1993) *Protein Engineering,* 6: 327-331). Conservative substitutions, such as exchanging one amino acid with another having similar properties, may be desirable as discussed in more detail below.

Biologically active truncated and/or variant AARS polypeptides may contain conservative amino acid substitutions at various locations along their sequence, as compared to a reference AARS amino acid residue. Additionally, naturally occurring variants of AARS proteins have been sequenced, and are known in the art to be at least partially functionally interchangeable. It would thus be a routine matter to select an amino acid position to introduce a conservative, or non conservative mutation into an AARS polypeptide based on naturally occurring sequence variation among the known AARS protein homologues, orthologs, and naturally-occurring isoforms of human as well as other species of an AARS protein.

A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH Amino acids having an acidic side chain include glutamic acid and aspartic acid.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e., glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not Amino acids having a small side chain include glycine, serine, alanine and threonine. The gene-encoded secondary amino acid proline is a special case due to its known effects on the secondary conformation of peptide chains. The structure of proline differs from all the other naturally-occurring amino acids in that its side chain is bonded to the nitrogen of the α-amino group, as well as the α-carbon. Several amino acid similarity matrices are known in the art (see e.g., PAM120 matrix and PAM250 matrix as disclosed for example by Dayhoff et al., 1978, A model of evolutionary change in proteins). Matrices for determining distance relationships In M. O. Dayhoff, (ed.), Atlas of protein sequence and structure, Vol. 5, pp. 345-358, National Biomedical Research Foundation, Washington D.C.; and by Gonnet et al., (Science, 256: 14430-1445, 1992), however, include proline in the same group as glycine, serine, alanine and threonine. Accordingly, for the purposes of the present invention, proline is classified as a "small" amino acid.

The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes. For the naturally-occurring protein amino acids, sub-classification according to this scheme is presented in Table B.

TABLE B

Amino acid sub-classification

| Sub-classes | Amino acids |
| --- | --- |
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional truncated and/or variant AARS polypeptide can readily be determined by assaying its non-canonical activity, as described herein. Conservative substitutions are shown in Table C under the heading of exemplary substitutions. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, (c) the bulk of the side chain, or (d) the biological function. After the substitutions are introduced, the variants are screened for biological activity.

TABLE C

Exemplary Amino Acid Substitutions

| Original Residue | Exemplary Substitutions | Preferred Substitutions |
| --- | --- | --- |
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |

TABLE C-continued

Exemplary Amino Acid Substitutions

| Original Residue | Exemplary Substitutions | Preferred Substitutions |
|---|---|---|
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay, G., *Biochemistry*, third edition, Wm. C. Brown Publishers (1993).

Thus, a predicted non-essential amino acid residue in a truncated and/or variant AARS polypeptide is typically replaced with another amino acid residue from the same side chain family. Alternatively, mutations can be introduced randomly along all or part of an AARS coding sequence, such as by saturation mutagenesis, and the resultant mutants can be screened for an activity of the parent polypeptide to identify mutants which retain that activity. Following mutagenesis of the coding sequences, the encoded peptide can be expressed recombinantly and the activity of the peptide can be determined. A "non-essential" amino acid residue is a residue that can be altered from the reference sequence of an embodiment polypeptide without abolishing or substantially altering one or more of its activities. Suitably, the alteration does not substantially abolish one of these activities, for example, the activity is at least 20%, 40%, 60%, 70% or 80% 100%, 500%, 1000% or more of the reference AARS sequence. An "essential" amino acid residue is a residue that, when altered from the reference sequence of an AARS polypeptide, results in abolition of an activity of the parent molecule such that less than 20% of the reference activity is present. For example, such essential amino acid residues include those that are conserved in AARS polypeptides across different species, including those sequences that are conserved in the active binding site(s) or motif(s) of AARS polypeptides from various sources.

In general, polypeptides and fusion polypeptides (as well as their encoding polynucleotides) are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Certain embodiments also encompass dimers of AARS polypeptides. Dimers may include, for example, homodimers between two identical AARS polypeptides, heterodimers between two different AARS polypeptides (e.g., a full-length YRS polypeptide and a truncated YRS polypeptide; a truncated YRS polypeptide and a truncated WRS polypeptide), and/or heterodimers between an AARS polypeptide and a heterologous polypeptide. Certain heterodimers, such as those between an AARS polypeptide and a heterologous polypeptide, may be bi-functional, as described herein.

Also included are monomers of AARS polypeptides, including isolated AARS polypeptides monomers that do not substantially dimerize with a second AARS polypeptide, whether due to one or more substitutions, truncations, deletions, additions, chemical modifications, or a combination of these alterations. In certain embodiments, monomeric AARS polypeptides possess biological activities, including non-canonical activities, which are not possessed by dimeric or multimeric AARS polypeptide complexes.

Certain embodiments of the present invention also contemplate the use of modified AARS polypeptides, including modifications that improved the desired characteristics of an AARS polypeptide, as described herein. Modifications of AARS polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Exemplary modifications also include pegylation of an AARS polypeptide (see, e.g., Veronese and Harris, *Advanced Drug Delivery Reviews* 54: 453-456, 2002; and Pasut et al., *Expert Opinion. Ther. Patents* 14(6) 859-894 2004, both herein incorporated by reference).

PEG is a well-known polymer having the properties of solubility in water and in many organic solvents, lack of toxicity, and lack of immunogenicity. It is also clear, colorless, odorless, and chemically stable. For these reasons and others, PEG has been selected as the preferred polymer for attachment, but it has been employed solely for purposes of illustration and not limitation. Similar products may be obtained with other water-soluble polymers, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

In particular a wide variety of PEG derivatives are both available and suitable for use in the preparation of PEG-conjugates. For example, NOF Corp.'s PEG reagents sold under the trademark SUNBRIGHT® Series provides numerous PEG derivatives, including methoxypolyethylene glycols and activated PEG derivatives such as methoxy-PEG amines, maleimides, N-hydroxysuccinimide esters, and carboxylic acids, for coupling by various methods to the N-terminal, C-terminal or any internal amino acid of the AARS polypeptide. Nektar Therapeutics' Advanced PEGylation technology also offers diverse PEG-coupling technologies to potentially improve the safety and efficacy of an AARS polypeptide based therapeutic.

A search of patents, published patent applications, and related publications will also provide those skilled in the art reading this disclosure with significant possible PEG-coupling technologies and PEG-derivatives. For example, U.S. Pat. Nos. 6,436,386; 5,932,462; 5,900,461; 5,824,784; and 4,904,584; the contents of which are incorporated by reference in their entirety, describe such technologies and derivatives, and methods for their manufacture.

In certain aspects, chemoselective ligation technology may be utilized to modify AARS polypeptides of the invention, such as by attaching polymers in a site-specific and controlled manner. Such technology typically relies on the incorporation of chemoselective anchors into the protein backbone by either chemical, or recombinant means, and subsequent modification with a polymer carrying a complementary linker. As a result, the assembly process and the covalent structure of the resulting protein-polymer conjugate may be controlled, enabling the rational optimization of drug properties, such as efficacy and pharmacokinetic properties (see, e.g., Kochendoerfer, *Current Opinion in Chemical Biology* 9:555-560, 2005).

In other embodiments, fusion proteins of AARS polypeptide to other proteins are also included, and these fusion proteins may increase the AARS polypeptide's biological activity, secretion, targeting, biological life, ability to penetrate cellular membranes, or the blood brain barrier, or pharmacokinetic properties. Examples of fusion proteins that improve pharmacokinetic properties ("PK modifiers") include without limitation, fusions to human albumin (Osborn et al.: *Eur. J. Pharmacol.* 456(1-3): 149-158, (2002)), antibody Fc domains, poly Glu or poly Asp sequences, and transferrin. Additionally, fusion with conformationally disordered polypeptide sequences composed of the amino acids Pro, Ala, and Ser ('PASylation') or hydroxyethyl starch (sold under the trademark HESYLATION®) provides a simple way to increase the hydrodynamic volume of the AARS polypeptide. This additional extension adopts a bulky random structure, which significantly increases the size of the resulting fusion protein. By this means the typically rapid clearance of smaller AARS polypeptides via kidney filtration is retarded by several orders of magnitude. Additionally use of Ig G fusion proteins has also been shown to enable some fusion protein proteins to penetrate the blood brain barrier (Fu et al., (2010) Brain Res. 1352:208-13).

Examples of fusion proteins that improve penetration across cellular membranes include fusions to membrane translocating sequences. In this context, the term "membrane translocating sequences" refers to naturally occurring and synthetic amino acid sequences that are capable of membrane translocation across a cellular membrane. Representative membrane translocating sequences include those based on the naturally occurring membrane translocating sequences derived from the Tat protein, and homeotic transcription protein Antennapedia, as well as synthetic membrane translocating sequences based in whole or part on poly Arginine and Lysine resides. Representative membrane translocating sequences include for example those disclosed in the following patents, U.S. Pat. No. 5,652,122; U.S. Pat. No. 5,670,617; U.S. Pat. No. 5,674,980; U.S. Pat. No. 5,747,641; U.S. Pat. No. 5,804,604; U.S. Pat. No. 6,316,003; U.S. Pat. No. 7,585,834; U.S. Pat. No. 7,312,244; U.S. Pat. No. 7,279,502; U.S. Pat. No. 7,229,961; U.S. Pat. No. 7,169,814; U.S. Pat. No. 7,453,011; U.S. Pat. No. 7,235,695; U.S. Pat. No. 6,982,351; U.S. Pat. No. 6,605,115; U.S. Pat. No. 7,306,784; U.S. Pat. No. 7,306,783; U.S. Pat. No. 6,589,503; U.S. Pat. No. 6,348,185; U.S. Pat. No. 6,881,825; U.S. Pat. No. 7,431,915; WO0074701A2; WO2007111993A2; WO2007106554A2; WO02069930A1; WO03049772A2; WO03106491A2; and WO2008063113A1.

It will be appreciated that a flexible molecular linker (or spacer) optionally may be interposed between, and covalently join, the AARS polypeptide and any of the fusion proteins disclosed herein.

Additionally in some embodiments, the AARS polypeptide can include synthetic, or naturally occurring secretion signal sequences, derived from other well characterized secreted proteins. In some embodiments such proteins, may be processed by proteolytic cleavage to form the AARS polypeptide in situ. Such fusions proteins include for example fusions of AARS polypeptide to ubiquitin to provide a new N-terminal amino acid, or the use of a secretion signal to mediate high level secretion of the AARS polypeptide into the extracellular medium, or N, or C-terminal epitope tags to improve purification or detection.

The AARS polypeptides described herein may be prepared by any suitable procedure known to those of skill in the art, such as by recombinant techniques. In addition to recombinant production methods, polypeptides of the invention may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the desired molecule.

IV. AARS Polynucleotides

Embodiments of the present invention include polynucleotides that encode one or more newly identified protein fragments of an aminoacyl-tRNA synthetase (AARS), in addition to complements, variants, and fragments thereof. In certain embodiments, an AARS polynucleotide encodes all or a portion of the AARS polypeptide reference sequence(s) as set forth in Table(s) 1-3, or Table(s) 4-6, or Table(s) 7-9, or Table(s) 10-12, which represent splice variants, proteolytic fragments, or other type of fragments of Lysyl tRNA synthetase. Certain embodiments include polynucleotides, encoding polypeptides or proteins that comprise the sequence of one or more splice junctions of those splice variants, in addition to complements, variants, and fragments thereof. In certain embodiments, typically due to the singular nature of a selected AARS splice variant, which combines exons in a new or exceptional way, the AARS polynucleotide references sequences comprise a unique or exceptional splice junction. Certain embodiments exclude a corresponding full-length AARS polynucleotide.

Also included within the AARS polynucleotides of the present invention are primers, probes, antisense oligonucleotides, and RNA interference agents that comprise all or a portion of these reference polynucleotides, which are complementary to all or a portion of these reference polynucleotides, or which specifically hybridize to these reference polynucleotides, as described herein.

The term "polynucleotide" or "nucleic acid" as used herein designates mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA. The terms "DNA" and "polynucleotide" and "nucleic acid" refer to a DNA molecule that has been isolated free of total genomic DNA of a particular species. Therefore, an isolated DNA segment encoding a polypeptide refers to a DNA segment that contains one or more coding sequences yet is substantially isolated away from, or purified free from, total genomic DNA of the species from which the DNA segment is obtained. Also included are non-coding polynucleotides (e.g., primers, probes, oligonucleotides), which do not encode an AARS polypeptide. Included within the terms "DNA segment" and "polynucleotide" are DNA segments and smaller fragments of such segments, and also recombinant vectors, including, for example, plasmids, cosmids, phagemids, phage, viruses, and the like.

Additional coding or non-coding sequences may, but need not, be present within a polynucleotide of the present invention, and a polynucleotide may, but need not, be linked to other molecules and/or support materials. Hence, the polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

It is therefore contemplated that a polynucleotide fragment of almost any length may be employed; with the total length preferably being limited by the ease of preparation and use in the intended recombinant DNA protocol. Included are polynucleotides of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100, 110, 120, 130, 140, 150, 160, 170, 180, 190, 200, 220, 240, 260, 270, 280, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or more (including all integers in between) bases in length, including any portion or fragment (e.g., greater than about 6, 7, 8, 9, or 10 nucleotides in length) of an AARS reference polynucleotide (e.g., base number X-Y, in which X is about 1-3000 or more and Y is about 10-3000 or more), or its complement.

Embodiments of the present invention also include "variants" of the AARS reference polynucleotide sequences. Polynucleotide "variants" may contain one or more substitutions, additions, deletions and/or insertions in relation to a reference polynucleotide. Generally, variants of an AARS reference polynucleotide sequence may have at least about 30%, 40% 50%, 55%, 60%, 65%, 70%, generally at least about 75%, 80%, 85%, desirably about 90% to 95% or more, and more suitably about 98% or more sequence identity to that particular nucleotide sequence as determined by sequence alignment programs described elsewhere herein using default parameters. In certain embodiments, variants may differ from a reference sequence by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 41, 43, 44, 45, 46, 47, 48, 49, 50, 60, 70, 80, 90, 100 (including all integers in between) or more bases. In certain embodiments, such as when the polynucleotide variant encodes an AARS polypeptide having a non-canonical activity, the desired activity of the encoded AARS polypeptide is not substantially diminished relative to the unmodified polypeptide. The effect on the activity of the encoded polypeptide may generally be assessed as described herein.

Certain embodiments include polynucleotides that hybridize to a reference AARS polynucleotide sequence, or to their complements, under stringency conditions described below. As used herein, the term "hybridizes under low stringency, medium stringency, high stringency, or very high stringency conditions" describes conditions for hybridization and washing. Guidance for performing hybridization reactions can be found in Ausubel et al., (1998, supra), Sections 6.3.1-6.3.6. Aqueous and non-aqueous methods are described in that reference and either can be used.

Reference herein to low stringency conditions include and encompass from at least about 1% v/v to at least about 15% v/v formamide and from at least about 1 M to at least about 2 M salt for hybridization at 42° C., and at least about 1 M to at least about 2 M salt for washing at 42° C. Low stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at room temperature. One embodiment of low stringency conditions includes hybridization in 6× sodium chloride/sodium citrate (SSC) at about 45° C., followed by two washes in 0.2×SSC, 0.1% SDS at least at 50° C. (the temperature of the washes can be increased to 55° C. for low stringency conditions).

Medium stringency conditions include and encompass from at least about 16% v/v to at least about 30% v/v formamide and from at least about 0.5 M to at least about 0.9 M salt for hybridization at 42° C., and at least about 0.1 M to at least about 0.2 M salt for washing at 55° C. Medium stringency conditions also may include 1% Bovine Serum Albumin (BSA), 1 mM EDTA, 0.5 M NaHPO$_4$ (pH 7.2), 7% SDS for hybridization at 65° C., and (i) 2×SSC, 0.1% SDS; or (ii) 0.5% BSA, 1 mM EDTA, 40 mM NaHPO$_4$ (pH 7.2), 5% SDS for washing at 60-65° C. One embodiment of medium stringency conditions includes hybridizing in 6×SSC at about 45° C., followed by one or more washes in 0.2×SSC, 0.1% SDS at 60° C. High stringency conditions include and encompass from at least about 31% v/v to at least about 50% v/v formamide and from about 0.01 M to about 0.15 M salt for hybridization at 42° C., and about 0.01 M to about 0.02 M salt for washing at 55° C.

High stringency conditions also may include 1% BSA, 1 mM EDTA, 0.5 M NaHPO$_4$ (pH 7.2), 7% SDS for hybridization at 65° C., and (i) 0.2×SSC, 0.1% SDS; or (ii) 0.5% BSA, 1 mM EDTA, 40 mM NaHPO$_4$ (pH 7.2), 1% SDS for washing at a temperature in excess of 65° C. One embodiment of high stringency conditions includes hybridizing in 6×SSC at about 45° C., followed by one or more washes in 0.2×SSC, 0.1% SDS at 65° C. One embodiment of very high stringency conditions includes hybridizing in 0.5 M sodium phosphate, 7% SDS at 65° C., followed by one or more washes in 0.2× SSC, 1% SDS at 65° C.

Other stringency conditions are well known in the art and a skilled artisan will recognize that various factors can be manipulated to optimize the specificity of the hybridization. Optimization of the stringency of the final washes can serve to ensure a high degree of hybridization. For detailed examples, see Ausubel et al., supra at pages 2.10.1 to 2.10.16 and Sambrook et al. (1989, supra) at sections 1.101 to 1.104.

While stringent washes are typically carried out at temperatures from about 42° C. to 68° C., one skilled in the art will appreciate that other temperatures may be suitable for stringent conditions. Maximum hybridization rate typically occurs at about 20° C. to 25° C. below the $T_m$ for formation of a DNA-DNA hybrid. It is well known in the art that the $T_m$ is the melting temperature, or temperature at which two complementary polynucleotide sequences dissociate. Methods for estimating $T_m$ are well known in the art (see Ausubel et al., supra at page 2.10.8).

In general, the $T_m$ of a perfectly matched duplex of DNA may be predicted as an approximation by the formula: $T_m = 81.5 + 16.6 \ (\log_{10} M) + 0.41 \ (\% \ G+C) - 0.63 \ (\% \ \text{formamide}) - (600/\text{length})$ wherein: M is the concentration of Na$^+$, preferably in the range of 0.01 molar to 0.4 molar; % G+C is the sum of guanosine and cytosine bases as a percentage of the total number of bases, within the range between 30% and 75% G+C; % formamide is the percent formamide concentration by volume; length is the number of base pairs in the DNA duplex. The $T_m$ of a duplex DNA decreases by approximately 1° C. with every increase of 1% in the number of randomly mismatched base pairs. Washing is generally carried out at $T_m$—15° C. for high stringency, or $T_m$—30° C. for moderate stringency.

In one example of a hybridization procedure, a membrane (e.g., a nitrocellulose membrane or a nylon membrane) containing immobilized DNA is hybridized overnight at 42° C. in a hybridization buffer (50% deionized formamide, 5×SSC, 5×Denhardt's solution (0.1% ficoll, 0.1% polyvinylpyrollidone and 0.1% bovine serum albumin), 0.1% SDS and 200 mg/mL denatured salmon sperm DNA) containing a labeled probe. The membrane is then subjected to two sequential medium stringency washes (i.e., 2×SSC, 0.1% SDS for 15 min at 45° C., followed by 2×SSC, 0.1% SDS for 15 min at 50° C.), followed by two sequential higher stringency washes (i.e., 0.2×SSC, 0.1% SDS for 12 min at 55° C. followed by 0.2×SSC and 0.1% SDS solution for 12 min at 65-68° C.

As noted above, certain embodiments relate to AARS polynucleotides that encode an AARS polypeptide. Among other uses, these embodiments may be utilized to recombinantly produce a desired AARS polypeptide or variant thereof, or to express the AARS polypeptide in a selected cell or subject. It will be appreciated by those of ordinary skill in the art that, as a result of the degeneracy of the genetic code, there are many nucleotide sequences that encode a polypeptide as described herein. Some of these polynucleotides may bear minimal homology to the nucleotide sequence of any native gene. Nonetheless, polynucleotides that vary due to differences in codon usage are specifically contemplated by the present invention, for example polynucleotides that are optimized for human and/or primate codon selection.

Therefore, multiple polynucleotides can encode the AARS polypeptides of the invention. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. (2000) 28 (1): 292). In addition, silent mutations can be incorporated in order to introduce, or eliminate restriction sites, decrease the density of CpG dinucleotide motifs (see for example, Kameda et al., Biochem. Biophys. Res. Commun (2006) 349(4): 1269-1277) or reduce the ability of single stranded sequences to form stem-loop structures: (see, e.g., Zuker M., Nucl. Acid Res. (2003); 31(13): 3406-3415). In addition, mammalian expression can be further optimized by including a Kozak consensus sequence [i.e., (a/g)cc(a/g) ccATGg] at the start codon. Kozak consensus sequences useful for this purpose are known in the art (Mantyh et al. PNAS 92: 2662-2666 (1995); Mantyh et al. Prot. Exp. & Purif. 6,124 (1995)).

The polynucleotides of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Polynucleotides and fusions thereof may be prepared, manipulated and/or expressed using any of a variety of well established techniques known and available in the art. For example, polynucleotide sequences which encode polypeptides of the invention, or fusion proteins or functional equivalents thereof, may be used in recombinant DNA molecules to direct expression of an AARS polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as *E. coli* or yeast such as *S. cerevisiae* (see, e.g., Burgess-Brown et al., *Protein Expr Purif.* 59:94-102, 2008; Ermolaeva M D (2001) *Curr. Iss. Mol. Biol.* 3 (4) 91-7; Welch et al., *PLoS ONE* 4(9): e7007 doi:10.1371/journal.pone.0007002).

Moreover, the polynucleotide sequences of the present invention can be engineered using methods generally known in the art in order to alter polypeptide encoding sequences for a variety of reasons, including but not limited to, alterations which modify the cloning, processing, expression and/or activity of the gene product.

According to another aspect of the invention, polynucleotides encoding polypeptides of the invention may be delivered to a subject in vivo, e.g., using gene therapy techniques. Gene therapy refers generally to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced.

Various viral vectors that can be utilized for gene therapy as taught herein include adenovirus, herpes virus, vaccinia, adeno-associated virus (AAV), or, preferably, an RNA virus such as a retrovirus. Preferably, the retroviral vector is a derivative of a murine or avian retrovirus, or is a lentiviral vector. The preferred retroviral vector is a lentiviral vector. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. All of these vectors can transfer or incorporate a gene for a selectable marker so that transduced cells can be identified and generated. By inserting a zinc finger derived-DNA binding polypeptide sequence of interest into the viral vector, along with another gene that encodes the ligand for a receptor on a specific target cell, for example, the vector may be made target specific. Retroviral vectors can be made target specific by inserting, for example, a polynucleotide encoding a protein (dimer). Illustrative targeting may be accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the zinc finger-nucleotide binding protein polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include but are not limited to PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

"Non-viral" delivery techniques for gene therapy can also be used including, for example, DNA-ligand complexes, adenovirus-ligand-DNA complexes, direct injection of DNA, $CaPO_4$ precipitation, gene gun techniques, electroporation, liposomes, lipofection, and the like. Any of these methods are widely available to one skilled in the art and would be suitable for use in the present invention. Other suitable methods are available to one skilled in the art, and it is to be understood that the present invention can be accomplished using any of the available methods of transfection. Lipofection can be accomplished by encapsulating an isolated DNA molecule within a liposomal particle and contacting the liposomal particle with the cell membrane of the target cell. Liposomes are self-assembling, colloidal particles in which a lipid bilayer, composed of amphiphilic molecules such as phosphatidyl serine or phosphatidyl choline, encapsulates a portion of the surrounding media such that the lipid bilayer surrounds a hydrophilic interior. Unilammellar or multilammellar liposomes can be constructed such that the interior contains a desired chemical, drug, or, as in the instant invention, an isolated DNA molecule.

In another aspect, polynucleotides encoding polypeptides of the invention may be used to express and delivery an AARS polypeptide via cell therapy. Accordingly in another aspect, the current invention includes a cell therapy for treating a disease or disorder, comprising administering a host cell expressing, or capable of expressing, an AARS polypeptide.

Cell therapy involves the administration of cells which have been selected, multiplied and pharmacologically treated or altered (i.e., genetically modified) outside of the body (Bordignon, C. et al, *Cell Therapy: Achievements and Perspectives* (1999), Haematologica, 84, pp. 1110-1149). Such host cells include for example, primary cells, including macrophages, and stem cells which have been genetically modified to express an AARS polypeptide. The aim of cell therapy is to replace, repair or enhance the biological function of damaged tissues or organs.

The use of transplanted cells has been investigated for the treatment of numerous endocrine disorders such as anemia and dwarfism, hematological disorders, kidney and liver failure, pituitary and CNS deficiencies and diabetes mellitus (Uludag et al., *Technology of Mammalian Cell Encapsulation* (2000), *Advanced Drug Delivery Reviews*, 42, pp. 29-64). Transplanted cells may function by releasing bioactive compounds such as an AARS polypeptide of the invention, to replace endogenous AARS polypeptides which are absent or produced in insufficient quantities in an effected system.

Embodiments of the present invention also include oligonucleotides, whether for detection, amplification, antisense therapies, or other purpose. For these and related purposes, the term "oligonucleotide" or "oligo" or "oligomer" is intended to encompass a singular "oligonucleotide" as well as plural "oligonucleotides," and refers to any polymer of two or more of nucleotides, nucleosides, nucleobases or related compounds used as a reagent in the amplification methods of the present invention, as well as subsequent detection methods. The oligonucleotide may be DNA and/or RNA and/or analogs thereof.

The term oligonucleotide does not necessarily denote any particular function to the reagent, rather, it is used generically to cover all such reagents described herein. An oligonucleotide may serve various different functions, e.g., it may function as a primer if it is capable of hybridizing to a complementary strand and can further be extended in the presence of a nucleic acid polymerase, it may provide a promoter if it contains a sequence recognized by an RNA polymerase and allows for transcription, and it may function to prevent hybridization or impede primer extension if appropriately situated and/or modified. An oligonucleotide may also function as a probe, or an antisense agent. An oligonucleotide can be virtually any length, limited only by its specific function, e.g., in an amplification reaction, in detecting an amplification product of the amplification reaction, or in an antisense or RNA interference application. Any of the oligonucleotides described herein can be used as a primer, a probe, an antisense oligomer, or an RNA interference agent.

The term "primer" as used herein refers to a single-stranded oligonucleotide capable of acting as a point of initiation for template-directed DNA synthesis under suitable conditions defined, for example, by buffer and temperature, in the presence of four different nucleoside triphosphates and an agent for polymerization, such as a DNA or RNA polymerase or reverse transcriptase. The length of the primer, in any given case, depends on, for example, the intended use of the primer, and generally ranges from about 15 to 30 nucleotides, although shorter and longer primers may be used. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein includes a surface-immobilized or soluble but capable of being immobilized molecule that can be recognized by a particular target. See, e.g., U.S. Pat. No. 6,582,908 for an example of arrays having all possible combinations of probes with 10, 12, and more bases. Probes and primers as used herein typically comprise at least 10-15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 nucleotides of an AARS reference sequence or its complement. Probes and primers may be considerably longer than these examples, and it is understood that any length supported by the knowledge in the art and the specification, including the tables, figures, and Sequence Listing, may be used.

Methods for preparing and using probes and primers are described in the references, for example Sambrook, J. et al. (1989) Molecular Cloning: A Laboratory Manual, 2.sup.nd ed., vol. 1-3, Cold Spring Harbor Press, Plainview N.Y.; Ausubel, F. M. et al. (1987) Current Protocols in Molecular Biology, Greene Publ. Assoc. & Wiley-Intersciences, New York N.Y.; Innis, M. et al. (1990) PCR Protocols. A Guide to Methods and Applications, Academic Press, San Diego Calif.

PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers or probes may be selected using software known in the art. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope.

The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described herein.

In certain embodiments, oligonucleotides can be prepared by stepwise solid-phase synthesis, employing methods detailed in the references cited above, and below with respect to the synthesis of oligonucleotides having a mixture of uncharged and cationic backbone linkages. In some cases, it may be desirable to add additional chemical moieties to the oligonucleotide, e.g., to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake.

A variety of detectable molecules may be used to render an oligonucleotide, or protein detectable, such as a radioisotopes, fluorochromes, dyes, enzymes, nanoparticles, chemiluminescent markers, biotin, or other monomer known in the art that can be detected directly (e.g., by light emission) or indirectly (e.g., by binding of a fluorescently-labeled antibody).

Radioisotopes provide examples of detectable molecules that can be utilized in certain aspects of the present invention. Several radioisotopes can be used as detectable molecules for labeling nucleotides or proteins, including, for example, $^{32}P$, $^{33}P$, $^{35}S$, $^{3}H$, and $^{125}I$. These radioisotopes have different half-lives, types of decay, and levels of energy which can be tailored to match the needs of a particular protocol. For example, $^{3}H$ is a low energy emitter which results in low background levels, however this low energy also results in long time periods for autoradiography. Radioactively labeled ribonucleotides, deoxyribonucleotides and amino acids are commercially available. Nucleotides are available that are radioactively labeled at the first, or a, phosphate group, or the third, or γ, phosphate group. For example, both $[\alpha-^{32}P]dATP$ and $[\gamma-^{32}P]dATP$ are commercially available. In addition, different specific activities for radioactively labeled nucleotides are also available commercially and can be tailored for different protocols.

Other examples of detectable molecules that can be utilized to detect an oligonucleotide include fluorophores. Several fluorophores can be used for labeling nucleotides including, for example, fluorescein, tetramethylrhodamine, Texas Red, and a number of others (e.g., Haugland, *Handbook of Fluorescent Probes*—9th Ed., 2002, Molec. Probes, Inc., Eugene Oreg.; Haugland, *The Handbook: A Guide to Fluorescent Probes and Labeling Technologies*—10th Ed., 2005, Invitrogen, Carlsbad, Calif.).

As one example, oligonucleotides may be fluorescently labeled during chemical synthesis, since incorporation of amines or thiols during nucleotide synthesis permit addition of fluorophores. Fluorescently labeled nucleotides are commercially available. For example, uridine and deoxyuridine triphosphates are available that are conjugated to ten different fluorophores that cover the spectrum. Fluorescent dyes that can be bound directly to nucleotides can also be utilized as detectable molecules. For example, FAM, JOE, TAMRA, and ROX are amine reactive fluorescent dyes that have been attached to nucleotides and are used in automated DNA sequencing. These fluorescently labeled nucleotides, for example, ROX-ddATP, ROX-ddCTP, ROX-ddGTP and ROX-ddUTP, are commercially available.

Non-radioactive and non-fluorescent detectable molecules are also available. As noted above, biotin can be attached directly to nucleotides and detected by specific and high affinity binding to avidin or streptavidin which has been chemically coupled to an enzyme catalyzing a colorimetric reaction (such as phosphatase, luciferase, or peroxidase). Digoxigenin labeled nucleotides can also similarly be used for non-isotopic detection of nucleic acids. Biotinylated and digoxigenin-labeled nucleotides are commercially available.

Very small particles, termed nanoparticles, also can be used to label oligonucleotide probes. These particles range from 1-1000 nm in size and include diverse chemical structures such as gold and silver particles and quantum dots. When irradiated with angled incident white light, silver or gold nanoparticles ranging from 40-120 nm will scatter monochromatic light with high intensity. The wavelength of the scattered light is dependent on the size of the particle. Four to five different particles in close proximity will each scatter monochromatic light, which when superimposed will give a specific, unique color. The particles are being manufactured by companies such as Genicon Sciences (Carlsbad, Calif.). Derivatized silver or gold particles can be attached to a broad array of molecules including, proteins, antibodies, small molecules, receptor ligands, and nucleic acids. For example, the surface of the particle can be chemically derivatized to allow attachment to a nucleotide.

Other types of nanoparticles that can be used for detection of a detectable molecule include quantum dots. Quantum dots are fluorescing crystals 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Many dozens of classes of particles can be created according to the number of size classes of the quantum dot crystals. The size classes of the crystals are created either 1) by tight control of crystal formation parameters to create each desired size class of particle, or 2) by creation of batches of crystals under loosely controlled crystal formation parameters, followed by sorting according to desired size and/or emission wavelengths. Two examples of references in which quantum dots are embedded within intrinsic silicon epitaxial layers of semiconductor light emitting/detecting devices are U.S. Pat. Nos. 5,293,050 and 5,354,707 to Chapple Sokol, et al.

In certain embodiments, oligonucleotide primers or probes may be labeled with one or more light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(ε-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhodamine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

The AARS polynucleotides and oligonucleotides of the present invention can be used in any of the therapeutic, diagnostic, research, or drug discovery compositions and methods described herein.

V. Antibodies

According to another aspect, the present invention further provides antibodies that exhibit binding specificity for an AARS polypeptide, or its native cellular binding partner (i.e., cellular receptor, lipid, carbohydrate, protein, or nucleic acid binding partner), or complex thereof, and methods of using the same. The term antibody includes the various variations of the same, such as FABs, human antibodies, modified human antibodies, single chains, nonhuman antibodies, and other derivatives of the immunoglobulin fold that underlie immune system ligands for antigens, as described herein and known in the art. Antibodies can be used in any of the therapeutic, diagnostic, drug discovery, or protein expression/purification methods and compositions provided herein.

Certain antibodies of the present invention differ from certain previously made antibodies because they can distinguish between the AARS protein fragments of Table(s) 1-3, or Table(s) 4-6, or Table(s) 7-9, or Table(s) 10-12 and their corresponding full-length AARS, typically by binding with greater affinity to the AARS protein fragments than to the corresponding full-length AARS. Generally, such antibodies may bind to unique sequences or structures generated or revealed by splice variations, proteolysis, or other cellular processing that generates an AARS protein fragment of the invention (e.g., post translational processing, including but not limited to phosphorylation and other modifications that change protein structure). In some aspects the antibodies may bind to sequences around a unique splice junction (for example to one or more regions of at least 5 contiguous amino acids selected from the splice junction sequences listed in Tables 2B, 5B, 8B, or 11B or alternatively to any amino acid sequence C-terminal of this splice site, for example as listed in Tables 2B, 5B, 8B, or 11B. For example, such antibodies may have binding specificity to one or more non-solvent exposed faces that are exposed in the AARS protein fragment but not in the full-length AARS, or sequences that are not found or are otherwise inaccessible in the full-length AARS. Antibodies may also bind to unique three-dimensional structures that result from differences in folding between the AARS protein fragment and the full-length AARS. Such differences in folding may be localized (e.g., to a specific domain or region) or globalized. As one example, folding of AARS protein fragments may generate unique continuous or discontinuous epitopes that are not found in the corresponding or parent AARS. Examples also include antibodies that specifically bind to N- or C-termini generated by splice variations, proteolysis, or other cellular processing; such termini may be unique compared to the full-length AARS or may not be exposed for antibody binding in the full-length versions due to their termini being completely or partially buried in the overall structure of the larger AARS parent molecule.

In some embodiments, antibodies provided herein do not form aggregates, have a desired solubility, and/or have an immunogenicity profile that is suitable for use in humans, as described herein and known in the art. Also included are antibodies that are suitable for production work, such as to purify the AARS protein fragments described herein. Preferably, active antibodies can be concentrated to at least about 10 mg/ml and optional formulated for biotherapeutic uses.

In certain embodiments, antibodies are effective for modulating one or more of the non-canonical activities mediated by an AARS polypeptide of the invention. In certain embodiments, for example, the antibody is one that binds to an AARS polypeptide and/or its binding partner, inhibits their ability to interact with each other, and/or antagonizes the non-canonical activity of the AARS polypeptide. In certain embodiments, for example, the antibody binds to the cellular binding partner of an AARS polypeptide, and mimics the AARS polypeptide activity, such as by increasing or agonizing the non-canonical activity mediated by the AARS polypeptide. Accordingly, antibodies may be used to diagnose, treat, or prevent diseases, disorders or other conditions that are mediated by an AARS polypeptide of the invention, such as by antagonizing or agonizing its activity partially or fully.

An antibody, or antigen-binding fragment thereof, is said to "specifically bind," "immunologically bind," and/or is "immunologically reactive" to a polypeptide of the invention if it reacts at a detectable level (within, for example, an ELISA assay) with the polypeptide, and does not react detectably in a statistically significant manner with unrelated polypeptides under similar conditions. In certain instances, a binding agent does not significantly interact with a full-length version of the AARS polypeptide.

Immunological binding, as used in this context, generally refers to the non-covalent interactions of the type which occur between an immunoglobulin molecule and an antigen for which the immunoglobulin is specific. The strength, or affinity of binding such as immunological binding interactions can be expressed in terms of the dissociation constant ($K_d$) of the interaction, wherein a smaller $K_d$ represents a greater affinity. Immunological binding properties of selected polypeptides can be quantified using methods well known in the art. See, e.g., Davies et al. (1990) Annual Rev. Biochem. 59:439-473. In certain illustrative embodiments, an antibody has an affinity for an AARS protein fragment of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments, the affinity of the antibody for an AARS protein fragment is stronger than its affinity for a corresponding full-length AARS polypeptide, typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between). In certain embodiments, an antibody as an affinity for a corresponding full-length AARS protein of at least about 0.05, 0.1, 0.25, 0.5, 0.75, 1, 2, 3, 4, 5, 6, 7, 8, 9, 10, 11, 12, 13, 14, 15, 16, 17, 18, 19, or 20 µM. In certain embodiments, an antibody binds weakly or substantially undetectably to a full-length AARS protein.

An "antigen-binding site," or "binding portion" of an antibody, refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Antibodies may be prepared by any of a variety of techniques known to those of ordinary skill in the art. See, e.g., Harlow and Lane, *Antibodies: A Laboratory Manual*, Cold Spring Harbor Laboratory, 1988. Monoclonal antibodies specific for a polypeptide of interest may be prepared, for example, using the technique of Kohler and Milstein, *Eur. J. Immunol.* 6:511-519, 1976, and improvements thereto. Also included are methods that utilize transgenic animals such as mice to express human antibodies. See, e.g., Neuberger et al., *Nature Biotechnology* 14:826, 1996; Lonberg et al., *Handbook of Experimental Pharmacology* 113:49-101, 1994; and Lonberg et al., *Internal Review of Immunology* 13:65-93, 1995. Particular examples include the VELOCIMMUNE® platform by REGERNEREX® (see, e.g., U.S. Pat. No. 6,596,541). Antibodies can also be generated or identified by the use of phage display or yeast display libraries (see, e.g., U.S. Pat. No. 7,244,592; Chao et al., *Nature Protocols.* 1:755-768, 2006). Non-limiting examples of available libraries include cloned or synthetic libraries, such as the Human Combinatorial Antibody Library (HuCAL), in which the structural diversity of the human antibody repertoire is represented by seven heavy chain and seven light chain variable region genes. The combination of these genes gives rise to 49 frameworks in the master library. By superimposing highly variable genetic cassettes (CDRs=complementarity determining regions) on these frameworks, the vast human antibody repertoire can be reproduced. Also included are human libraries designed with human-donor-sourced fragments encoding a light-chain variable region, a heavy-chain CDR-3, synthetic DNA encoding diversity in heavy-chain CDR-1, and synthetic DNA encoding diversity in heavy-chain CDR-2. Other libraries suitable for use will be apparent to persons skilled in the art. The polypeptides of this invention may be used in the purification process in, for example, an affinity chromatography step.

An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. See, e.g., Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *PNAS USA.* 85(16):5879-5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

Certain embodiments include single domain antibody (sd-Abs or "nanobodies"), which refer to an antibody fragment consisting of a single monomeric variable antibody domain (see, e.g., U.S. Pat. Nos. 5,840,526; 5,874,541; 6,005,079, 6,765,087, 5,800,988; 5,874,541; and 6,015,695). Such sdABs typically have a molecular weight of about 12-15 kDa. In certain aspects, sdABs and other antibody molecules can be derived or isolated from the unique heavy-chain antibodies of immunized camels and llamas, often referred to as camelids. See, e.g., Conrath et al., *JBC.* 276:7346-7350, 2001.

A number of "humanized" antibody molecules comprising an antigen-binding site derived from a non-human immunoglobulin have been described, including chimeric antibodies having rodent V regions and their associated CDRs fused to human constant domains (Winter et al. (1991) Nature 349: 293-299; Lobuglio et al. (1989) *Proc. Nat. Acad. Sci. USA* 86:4220-4224; Shaw et al. (1987) *J Immunol.* 138:4534-4538; and Brown et al. (1987) Cancer Res. 47:3577-3583), rodent CDRs grafted into a human supporting FR prior to fusion with an appropriate human antibody constant domain (Riechmann et al. (1988) *Nature* 332:323-327; Verhoeyen et al. (1988) *Science* 239:1534-1536; and Jones et al. (1986) *Nature* 321:522-525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients. See, e.g., U.S. Pat. Nos. 5,530,101; 5,585,089; 5,693,762; 6,180,370; and 7,022,500.

The antibodies of the present invention can be used in any of the therapeutic, diagnostic, drug discovery, protein purification, and analytical methods and compositions described herein.

VI. Antibody Alternatives and Other Binding Agents

According to another aspect, the present invention further provides antibody alternatives or other binding agents, such as soluble receptors, adnectins, peptides, peptide mimetics, small molecules, aptamers, etc., that exhibit binding specificity for an AARS polypeptide or its cellular binding partner as disclosed herein, or to a portion, variant or derivative thereof, and compositions and methods of using same. Binding agents can be used in any of the therapeutic, diagnostic, drug discovery, or protein expression/purification, and analytical methods and compositions described herein. Biologic-based binding agents such as adnectins, soluble receptors, avimers, and trinectins are particularly useful.

In certain embodiments, such binding agents are effective for modulating one or more of the non-canonical activities mediated by an AARS polypeptide of the invention. In some embodiments, for example, the binding agent is one that binds to an AARS polypeptide and/or its binding partner, inhibits their ability to interact with each other, and/or antagonizes the non-canonical activity of the AARS polypeptide. In certain embodiments, for example, the binding agent binds to the cellular binding partner of an AARS polypeptide, and mimics the AARS polypeptide activity, such as by increasing or agonizing the non-canonical activity mediated by the AARS polypeptide. Accordingly, such binding agents may be used to diagnose, treat, or prevent diseases, disorders or other conditions that are mediated by an AARS polypeptide of the invention, such as by antagonizing or agonizing its activity partially or fully.

A binding agent is said to "specifically bind" to an AARS polypeptide of the invention, or its cellular binding partner, if it reacts at a detectable level (within, for example, an ELISA assay) with the polypeptide or its cellular binding partner, and does not react detectably in a statistically significant manner with unrelated polypeptides under similar conditions. In certain instances, a binding agent does not significantly interact with a full-length version of the AARS polypeptide. In certain illustrative embodiments, a binding agent has an affinity for an AARS protein fragment or its cellular binding partner of at least about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM. In certain embodiments, the affinity of the binding agent for an AARS protein fragment is stronger than its affinity for a corresponding full-length AARS polypeptide, typically by about 1.5×, 2×, 2.5×, 3×, 3.5×, 4×, 4.5×, 5×, 6×, 7×, 8×, 9×, 10×, 15×, 20×, 25×, 30×, 40×, 50×, 60×, 70×, 80×, 90×, 100×, 200×, 300×, 400×, 500×, 600×, 700×, 800×, 900×, 1000× or more (including all integers in between). In certain embodiments, a binding agent has an affinity for a corresponding full-length AARS protein of at least about 0.5, 1, 2, 3, 4, 5, 6, 7, 8, 9, 10, 11, 12, 13, 14, 15, 16, 17, 18, 19, or 20 μM.

As noted above, "peptides" are included as binding agents. The term peptide typically refers to a polymer of amino acid residues and to variants and synthetic analogues of the same. In certain embodiments, the term "peptide" refers to relatively short polypeptides, including peptides that consist of about 2, 3, 4, 5, 6, 7, 8, 9, 10, 11, 12, 13, 14, 15, 16, 17, 18, 19, 20, 25, 30, 35, 40, 45, or 50 amino acids, including all integers and ranges (e.g., 5-10, 8-12, 10-15) in between, and interact with an AARS polypeptide, its cellular binding partner, or both. Peptides can be composed of naturally-occurring amino acids and/or non-naturally occurring amino acids, as described herein.

In addition to peptides consisting only of naturally-occurring amino acids, peptidomimetics or peptide analogs are also provided. Peptide analogs are commonly used in the pharmaceutical industry as non-peptide drugs with properties analogous to those of the template peptide. These types of non-peptide compound are termed "peptide mimetics" or "peptidomimetics" (Luthman, et al., *A Textbook of Drug Design and Development,* 14:386-406, 2nd Ed., Harwood Academic Publishers (1996); Joachim Grante, *Angew. Chem. Int. Ed. Engl.,* 33:1699-1720 (1994); Fauchere, J., *Adv. Drug Res.,* 15:29 (1986); Veber and Freidinger TINS, p. 392 (1985); and Evans, et al., *J. Med. Chem.* 30:229 (1987)). A peptidomimetic is a molecule that mimics the biological activity of a peptide but is no longer peptidic in chemical nature. Peptidomimetic compounds are known in the art and are described, for example, in U.S. Pat. No. 6,245,886.

The present invention also includes peptoids. Peptoid derivatives of peptides represent another form of modified peptides that retain the important structural determinants for biological activity, yet eliminate the peptide bonds, thereby conferring resistance to proteolysis (Simon, et al., *PNAS USA.* 89:9367-9371, 1992). Peptoids are oligomers of N-substituted glycines. A number of N-alkyl groups have been described, each corresponding to the side chain of a natural amino acid. The peptidomimetics of the present invention include compounds in which at least one amino acid, a few amino acids or all amino acid residues are replaced by the corresponding N-substituted glycines. Peptoid libraries are described, for example, in U.S. Pat. No. 5,811,387.

A binding agent may also include one or more small molecules. A "small molecule" refers to an organic compound that is of synthetic or biological origin (biomolecule), but is typically not a polymer. Organic compounds refer to a large class of chemical compounds whose molecules contain carbon, typically excluding those that contain only carbonates, simple oxides of carbon, or cyanides. A "biomolecule" refers generally to an organic molecule that is produced by a living organism, including large polymeric molecules (biopolymers) such as peptides, polysaccharides, and nucleic acids as well, and small molecules such as primary secondary metabolites, lipids, phospholipids, glycolipids, sterols, glycerolipids, vitamins, and hormones. A "polymer" refers generally to a large molecule or macromolecule composed of repeating structural units, which are typically connected by covalent chemical bond.

In certain embodiments, a small molecule has a molecular weight of less than 1000-2000 Daltons, typically between about 300 and 700 Daltons, and including about 50, 100, 150, 200, 250, 300, 350, 400, 450, 500, 550, 500, 650, 600, 750, 700, 850, 800, 950, 1000 or 2000 Daltons. Small molecule libraries are described elsewhere herein.

Aptamers are also included as binding agents (see, e.g., Ellington et al., *Nature*. 346, 818-22, 1990; and Tuerk et al., *Science*. 249, 505-10, 1990). Examples of aptamers included nucleic acid aptamers (e.g., DNA aptamers, RNA aptamers) and peptide aptamers. Nucleic acid aptamers refer generally to nucleic acid species that have been engineered through repeated rounds of in vitro selection or equivalent method, such as SELEX (systematic evolution of ligands by exponential enrichment), to bind to various molecular targets such as small molecules, proteins, nucleic acids, and even cells, tissues and organisms. See, e.g., U.S. Pat. Nos. 6,376,190; and 6,387,620. Hence, included are nucleic acid aptamers that bind to the AARS polypeptides described herein and/or their cellular binding partners.

Peptide aptamers typically include a variable peptide loop attached at both ends to a protein scaffold, a double structural constraint that typically increases the binding affinity of the peptide aptamer to levels comparable to that of an antibody's (e.g., in the nanomolar range). In certain embodiments, the variable loop length may be composed of about 10-20 amino acids (including all integers in between), and the scaffold may include any protein that has good solubility and compacity properties. Certain exemplary embodiments may utilize the bacterial protein Thioredoxin-A as a scaffold protein, the variable loop being inserted within the reducing active site (-Cys-Gly-Pro-Cys-loop in the wild protein), with the two cysteines lateral chains being able to form a disulfide bridge. Methods for identifying peptide aptamers are described, for example, in U.S. Application No. 2003/0108532. Hence, included are peptide aptamers that bind to the AARS polypeptides described herein and/or their cellular binding partners. Peptide aptamer selection can be performed using different systems known in the art, including the yeast two-hybrid system.

Also included are ADNECTINS™, AVIMERS™, anaphones and anticalins that specifically bind to an AARS protein fragment of the invention. ADNECTINS™ refer to a class of targeted biologics derived from human fibronectin, an abundant extracellular protein that naturally binds to other proteins. See, e.g., U.S. Application Nos. 2007/0082365; 2008/0139791; and 2008/0220049. ADNECTINS™ typically consists of a natural fibronectin backbone, as well as the multiple targeting domains of a specific portion of human fibronectin. The targeting domains can be engineered to enable an ADNECTIN™ to specifically recognize a therapeutic target of interest, such as an AARS protein fragment of the invention.

AVIMERS™ refer to multimeric binding proteins or peptides engineered using in vitro exon shuffling and phage display. Multiple binding domains are linked, resulting in greater affinity and specificity compared to single epitope immunoglobulin domains. See, e.g., Silverman et al., *Nature Biotechnology*. 23:1556-1561, 2005; U.S. Pat. No. 7,166, 697; and U.S. Application Nos. 2004/0175756, 2005/0048512, 2005/0053973, 2005/0089932 and 2005/0221384.

Also included are designed ankyrin repeat proteins (DARPins), which include a class of non-immunoglobulin proteins that can offer advantages over antibodies for target binding in drug discovery and drug development. Among other uses, DARPins are ideally suited for in vivo imaging or delivery of toxins or other therapeutic payloads because of their favorable molecular properties, including small size and high stability. The low-cost production in bacteria and the rapid generation of many target-specific DARPins make the DARPin approach useful for drug discovery. Additionally, DARPins can be easily generated in multispecific formats, offering the potential to target an effector DARPin to a specific organ or to target multiple receptors with one molecule composed of several DARPins. See, e.g., Stumpp et al., *Curr Opin Drug Discov Devel*. 10:153-159, 2007; U.S. Application No. 2009/0082274; and PCT/EP2001/10454.

Certain embodiments include "monobodies," which typically utilize the 10th fibronectin type III domain of human fibronectin (FNfn10) as a scaffold to display multiple surface loops for target binding. FNfn10 is a small (94 residues) protein with a β-sandwich structure similar to the immunoglobulin fold. It is highly stable without disulfide bonds or metal ions, and it can be expressed in the correctly folded form at a high level in bacteria. The FNfn10 scaffold is compatible with virtually any display technologies. See, e.g., Batori et al., *Protein Eng*. 15:1015-20, 2002; and Wojcik et al., *Nat Struct Mol Biol.*, 2010; and U.S. Pat. No. 6,673,901.

Anticalins refer to a class of antibody mimetics, which are typically synthesized from human lipocalins, a family of binding proteins with a hypervariable loop region supported by a structurally rigid framework. See, e.g., U.S. Application No. 2006/0058510. Anticalins typically have a size of about 20 kDa. Anticalins can be characterized by a barrel structure formed by eight antiparallel β-strands (a stable β-barrel scaffold) that are pairwise connected by four peptide loops and an attached α-helix. In certain aspects, conformational deviations to achieve specific binding are made in the hypervariable loop region(s). See, e.g., Skerra, *FEBS J*. 275:2677-83, 2008, herein incorporated by reference.

VII. Bioassays and Analytical Assays for Drug Release Assays and Product Specifications, Diagnostics, and Reagents Also included are bioassays that relate to the AARS protein fragments and related agents as therapeutic and diagnostic reagents. Examples include bioassays and analytical assays that measure purity, biological activity, affinity, solubility, pH, endotoxin levels, among others, many of which are described herein. Also included are assays that establish dose response curves and/or provide one or more bases for comparison between different batches of agents. Batch comparisons can be based on any one or more of chemical characterization, biological characterization, and clinical characterization. For protein agents, also included are methods of evaluating the potency, stability, pharmacokinetics, and immunogenicity of a selected agent. Among other uses, these and other methods can be used for lot releasing testing of biologic or chemical agents, including the AARS protein fragments, antibodies, binding agents, polynucleotides such as antisense agents and vectors, and others described herein.

Certain embodiments include the use of bioaffinity assays. Such assays can be used to assess the binding affinity, for example, between an AARS protein fragment and a cellular binding partner, or between an AARS protein fragment and an antibody. Binding affinity can also be measured between an AARS protein fragment and an alternate binding agent such as a candidate or lead test compound (e.g., small molecule modulator of an AARS), or between an AARS cellular binding partner and a candidate or lead test compound. Certain exemplary binding affinity assays may utilize ELISA assays, as described herein and known in the art. Certain assays utilize high-performance receptor binding chromatography (see, e.g., Roswall et al., *Biologicals.* 24:25-39, 1996). Other exemplary binding affinity assays may utilize surface plasmon resonance (SPR)-based technologies. Examples include BIACore technologies, certain of which integrate SPR technology with a microfluidics system to monitor molecular interactions in real time at concentrations ranging from pM to mM. Also included are KINEXA™ assays, which provide accurate measurements of binding specificity, binding affinity, and binding kinetics/rate constants.

Certain embodiments relate to immunoassays for evaluating or optimizing the immunogenicity of protein agents. Examples include ex vivo human cellular assays and in vitro immuno-enzymatic assays to provide useful information on the immunogenic potential of a therapeutic protein. Ex vivo cell-response assays can be used, for example, to reproduce the cellular co-operation between antigen-presenting cells (APCs) and T-cells, and thereby measure T-cells activation after contact with a protein of interest. Certain in vitro enzymatic assays may utilize a collection of recombinant HLA-DR molecules that cover a significant portion of a relevant human population, and may include automated immuno-enzymatic assays for testing the binding of peptides (stemming from the fragmentation of the therapeutic protein) with the HLA-DR molecules. Also included are methods of reducing the immunogenicity of a selected protein, such as by using these and related methods to identify and then remove or alter one or more T-cell epitopes from a protein agent.

Also included are biological release assays (e.g., cell-based assays) for measuring parameters such as specific biological activities, including non-canonical biological activities, and cytotoxicity. Certain specific biological assays include, for example, cell-based assays that utilize a cellular binding partner (e.g., cell-surface receptor) of a selected AARS protein fragment, which is functionally coupled to a readout, such as a fluorescent or luminescent indicator of a non-canonical biological activity, as described herein. For instance, specific embodiments include a cell that comprises a cell-surface receptor or an extracellular portion thereof that binds to an AARS protein fragment, wherein the cell comprises a detector or readout. Also included are in vivo biological assays to characterize the pharmacokinetics of an agent, such as an AARS polypeptide or antibody, typically utilizing engineered mice or other mammal (see, e.g., Lee et al., *The Journal of Pharmacology.* 281:1431-1439, 1997). Examples of cytotoxicity-based biological assays include release assays (e.g., chromium or europium release assays to measure apoptosis; see, e.g., von Zons et al., *Clin Diagn Lab Immunol.* 4:202-207, 1997), among others, which can assess the cytotoxicity of AARS protein fragments, whether for establishing dose response curves, batch testing, or other properties related to approval by various regulatory agencies, such as the Food and Drug Administration (FDA).

Such assays can be used, for example, to develop a dose response curve for a selected AARS protein fragment or other agent, and/or to compare the dose response curve of different batches of proteins or other agents. A dose-response curve is an X-Y graph that relates the magnitude of a stressor to the response of a receptor; the response may be a physiological or biochemical response, such as a non-canonical biological activity in a cell in vitro or in a cell or tissue in vivo, a therapeutically effective amount as measured in vivo (e.g., as measured by $EC_{50}$), or death, whether measured in vitro or in vivo (e.g., cell death, organismal death). Death is usually indicated as an $LD_{50}$, a statistically-derived dose that is lethal to 50% of a modeled population, though it can be indicated by $LC_{01}$ (lethal dose for 1% of the animal test population), $LC_{100}$ (lethal dose for 100% of the animal test population), or $LC_{LO}$ (lowest dose causing lethality). Almost any desired effect or endpoint can be characterized in this manner.

The measured dose of a response curve is typically plotted on the X axis and the response is plotted on the Y axis. More typically, the logarithm of the dose is plotted on the X axis, most often generating a sigmoidal curve with the steepest portion in the middle. The No Observable Effect Level (NOEL) refers to the lowest experimental dose for which no measurable effect is observed, and the threshold dose refers to the first point along the graph that indicates a response above zero. As a general rule, stronger drugs generate steeper dose response curves. For many drugs, the desired effects are found at doses slightly greater than the threshold dose, often because lower doses are relatively ineffective and higher doses lead to undesired side effects. For in vivo generated dose response curves, a curve can be characterized by values such as µg/kg, mg/kg, or g/kg of body-weight, if desired.

For batch comparisons, it can be useful to calculate the coefficient of variation (CV) between different dose response curves of different batches (e.g., between different batches of AARS protein fragments, antibodies, or other agents), in part because the CV allows comparison between data sets with different units or different means. For instance, in certain exemplary embodiments, two or three or more different batches of AARS protein fragments or other agents have a CV between them of less than about 15%, 14%, 13%, 12%, 11%, 10%, 9%, 8%, 7%, 6%, 5%, 4%, 3%, 2%, or 1% for a 4, 5, 6, 7, or 8 point dose curve. In certain embodiments, the dose response curve is measured in a cell-based assay, and its readout relates to an increase or a decrease in a selected non-canonical activity of the AARS protein fragment. In certain embodiments, the dose response curve is measured in a cell release assay or animal model (e.g., mouse model), and its readout relates to cell death or animal death. Other variations will be apparent to persons skilled in the art.

VIII. Expression and Purification Systems

Embodiments of the present invention include methods and related compositions for expressing and purifying the AARS protein fragments or other polypeptide-based agents of the invention. Such recombinant AARS polypeptides can be conveniently prepared using standard protocols as described for example in Sambrook, et al., (1989, supra), in particular Sections 16 and 17; Ausubel et al., (1994, supra), in particular Chapters 10 and 16; and Coligan et al., Current Protocols in Protein Science (John Wiley & Sons, Inc. 1995-1997), in particular Chapters 1, 5 and 6. As one general example, AARS polypeptides may be prepared by a procedure including one or more of the steps of: (a) preparing a construct comprising a polynucleotide sequence that encodes a AARS polypeptide and that is operably linked to a regulatory element; (b) introducing the construct into a host cell; (c) culturing the host cell to express the AARS polypeptide; and (d) isolating the AARS polypeptide from the host cell.

AARS polynucleotides are described elsewhere herein. In order to express a desired polypeptide, a nucleotide sequence encoding the polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (1989), and Ausubel et al., Current Protocols in Molecular Biology (1989).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

Certain embodiments may employ *E. coli*-based expression systems (see, e.g., Structural Genomics Consortium et al., *Nature Methods.* 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG. Particular embodiments employ hexahistidine tags (such as those sold under the trademark HIS.TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

Also included are high-density bacterial fermentation systems. For example, high cell density cultivation of *Ralstonia eutropha* allows protein production at cell densities of over 150 g/L, and the expression of recombinant proteins at titers exceeding 10 g/L.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987). Also included are *Pichia pandoris* expression systems (see, e.g., Li et al., *Nature Biotechnology.* 24, 210-215, 2006; and Hamilton et al., *Science,* 301:1244, 2003). Certain embodiments include yeast systems that are engineered to selectively glycosylate proteins, including yeast that have humanized N-glycosylation pathways, among others (see, e.g., Hamilton et al., *Science.* 313:1441-1443, 2006; Wildt et al., *Nature Reviews Microbiol.* 3:119-28, 2005; and Gerngross et al., *Nature-Biotechnology.* 22:1409-1414, 2004; U.S. Pat. Nos. 7,629,163; 7,326,681; and 7,029,872).

Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in McGraw Hill, *Yearbook of Science and Technology*, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., *Proc. Natl. Acad. Sci. U.S.A.* 91:3224-3227 (1994)). Also included are baculovirus expression systems, including those that utilize SF9, SF21, and *T. ni* cells (see, e.g., Murphy and Piwnica-Worms, *Curr Protoc Protein Sci.* Chapter 5:Unit5.4, 2001). Insect systems can provide post-translation modifications that are similar to mammalian systems.

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *PNAS USA* 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

Also included is cell-free expression of proteins. These and related embodiments typically utilize purified RNA polymerase, ribosomes, tRNA and ribonucleotides; these reagents may be produced by extraction from cells or from a cell-based expression system.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 and CHO-based systems.

Any number of selection systems may be used to recover transformed or transduced cell lines. These include, but are not limited to, the herpes simplex virus thymidine kinase (Wigler et al., *Cell* 11:223-232 (1977)) and adenine phosphoribosyltransferase (Lowy et al., *Cell* 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). The use of visible markers has gained popularity with such markers as green fluorescent protein (GFP) and other fluorescent proteins (e.g., RFP, YFP), anthocyanins, β-glucuronidase and its substrate GUS, and luciferase and its substrate luciferin, being widely used not only to identify transformants, but also to quantify the amount of transient or stable protein expression attributable to a specific vector system (see, e.g., Rhodes et al., *Methods Mol. Biol.* 55:121-131 (1995)).

Embodiments of the present invention also include high-throughput protein production systems, or micro-production systems. Certain aspects may utilize, for example, hexa-histidine fusion tags for protein expression and purification on metal chelate-modified slide surfaces or MagneHis Ni-Particles (see, e.g., Kwon et al., *BMC Biotechnol.* 9:72, 2009; and Lin et al., *Methods Mol Biol.* 498:129-41, 2009)). Also included are high-throughput cell-free protein expression systems (see, e.g., Sitaraman et al., *Methods Mol Biol.* 498: 229-44, 2009). These and related embodiments can be used, for example, to generate microarrays of AARS protein fragment(s), which can then be used for screening libraries to identify agents that interact with the AARS protein fragment(s).

A variety of protocols for detecting and measuring the expression of polynucleotide-encoded products, using binding agents or antibodies such as polyclonal or monoclonal antibodies specific for the product, are known in the art. Examples include enzyme-linked immunosorbent assay (ELISA), western immunoblots, radioimmunoassays (RIA), and fluorescence activated cell sorting (FACS). These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grown on serum free medium (see, e.g., Rosser et al., *Protein Expr. Purif.* 40:237-43, 2005; and U.S. Pat. No. 6,210,922).

The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification and/or detection of soluble proteins. Examples of such domains include cleavable and non-cleavable affinity purification and epitope tags such as avidin, FLAG tags, poly-histidine tags (e.g., 6×His), cMyc tags, V5-tags, glutathione S-transferase (GST) tags, and others.

The protein produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-pressure liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating AARS protein fragments, and composition comprising concentrated soluble proteins. In different aspects such concentrated solutions of AARS polypeptides may comprise proteins at a concentration of about 5 mg/mL; or about 8 mg/mL; or about 10 mg/mL; about 15 mg/mL; or about 20 mg/mL.

In one aspect such compositions may be substantially monodisperse, meaning that the AARS polypeptide compositions exist primarily (i.e., at least about 90%, or greater) in one apparent molecular weight form when assessed for example, by size exclusion chromatography, dynamic light scattering, or analytical ultracentrifugation.

In another aspect, such compositions have a purity (on a protein basis) of at least about 90%, or in some aspects at least about 95% purity, or in some embodiments, at least 98% purity. Purity may be determined via any routine analytical method as known in the art.

In another aspect, such compositions have a high molecular weight aggregate content of less than about 10%, compared to the total amount of protein present, or in some embodiments such compositions have a high molecular weight aggregate content of less than about 5%, or in some aspects such compositions have a high molecular weight aggregate content of less than about 3%, or in some embodiments a high molecular weight aggregate content of less than about 1%. High molecular weight aggregate content may be determined via a variety of analytical techniques including for example, by size exclusion chromatography, dynamic light scattering, or analytical ultracentrifugation.

In certain embodiments, as noted herein, the AARS polypeptide compositions have an endotoxin content of less than about 10 EU/mg of AARS polypeptide, or less than about 5 EU/mg of AARS polypeptide, less than about 3 EU/mg of AARS polypeptide, or less than about 1 EU/mg of AARS polypeptide.

Examples of concentration approaches contemplated herein include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the reagents, AARS protein fragments, or related agents (e.g., antibodies) have a purity of at least about 90%, as measured according to routine techniques in the art. In certain embodiments, such as diagnostic compositions or certain therapeutic compositions, the AARS compositions of the present invention have a purity of at least about 95%. In specific embodiments, such as therapeutic or pharmaceutical compositions, the AARS compositions of the present invention have a purity of at least about 97% or 98% or 99%. In other embodiments, such as when being used as reference or research reagents, AARS protein fragments can be of lesser purity, and may have a purity of at least about 50%, 60%, 70%, or 80%. Purity can be measured overall or in relation to selected components, such as other proteins, e.g., purity on a protein basis.

Purified AARS protein fragments can also be characterized according to their biological characteristics. Examples include binding affinity or binding kinetics to a selected ligand (e.g., a cellular binding partner of the AARS protein fragment such as a cell-surface receptor or an extracellular domain thereof), and the presence or levels of one or more canonical or non-canonical biological activity, as described herein. Binding affinity and binding kinetics can be measured according to a variety of techniques known in the art, such as Biacore® and related technologies that utilize surface plasmon resonance (SPR), an optical phenomenon that enables detection of unlabeled interactants in real time. SPR-based biosensors can be used in determination of active concentration, screening and characterization in terms of both affinity and kinetics. The presence or levels of one or more canonical or non-canonical biological activities can be measured according to cell-based assays, including those that utilize a cellular binding partner (e.g., cell-surface receptor) of a selected AARS protein fragment, which is functionally coupled to a readout or indicator, such as a fluorescent or luminescent indicator of a non-canonical biological activity, as described herein.

In certain embodiments, as noted above, the AARS polypeptide compositions are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the AARS compositions are made from a eukaryotic cell such as a mammalian or human cell in substantially serum free media.

In certain embodiments, the AARS polypeptide compositions comprise less than about 10% wt/wt high molecular weight aggregates, or less than about 5% wt/wt high molecular weight aggregates, or less than about 2% wt/wt high molecular weight aggregates, or less than about or less than about 1% wt/wt high molecular weight aggregates.

Also included are protein-based analytical assays and methods, which can be used to assess, for example, protein purity, size, solubility, and degree of aggregation, among other characteristics. Protein purity can be assessed a number of ways. For instance, purity can be assessed based on primary structure, higher order structure, size, charge, hydrophobicity, and glycosylation. Examples of methods for assessing primary structure include N- and C-terminal sequencing and peptide-mapping (see, e.g., Allen et al., *Biologicals*. 24:255-275, 1996)). Examples of methods for assessing higher order structure include circular dichroism (see, e.g., Kelly et al., *Biochim Biophys Acta*. 1751:119-139, 2005), fluorescent spectroscopy (see, e.g., Meagher et al., *J. Biol. Chem.* 273:23283-89, 1998), FT-IR, amide hydrogen-deuterium exchange kinetics, differential scanning calorimetry, NMR spectroscopy, immunoreactivity with conformationally sensitive antibodies. Higher order structure can also be assessed as a function of a variety of parameters such as pH, temperature, or added salts. Examples of methods for assessing protein characteristics such as size include analytical ultracentrifugation and size exclusion HPLC (SEC-HPLC), and exemplary methods for measuring charge include ion-exchange chromatography and isoelectric focusing. Hydrophobicity can be assessed, for example, by reverse-phase HPLC and hydrophobic interaction chromatography HPLC. Glycosylation can affect pharmacokinetics (e.g., clearance), conformation or stability, receptor binding, and protein function, and can be assessed, for example, by mass spectrometry and nuclear magnetic resonance (NMR) spectroscopy.

As noted above, certain embodiments include the use of SEC-HPLC to assess protein characteristics such as purity, size (e.g., size homogeneity) or degree of aggregation, and/or to purify proteins, among other uses. SEC, also including gel-filtration chromatography (GFC) and gel-permeation chromatography (GPC), refers to a chromatographic method in which molecules in solution are separated in a porous material based on their size, or more specifically their hydrodynamic volume, diffusion coefficient, and/or surface properties. The process is generally used to separate biological molecules, and to determine molecular weights and molecular weight distributions of polymers. Typically, a biological or protein sample (such as a protein extract produced according to the protein expression methods provided herein and known in the art) is loaded into a selected size-exclusion column with a defined stationary phase (the porous material), preferably a phase that does not interact with the proteins in the sample. In certain aspects, the stationary phase is composed of inert particles packed into a dense three-dimensional matrix within a glass or steel column. The mobile phase can be pure water, an aqueous buffer, an organic solvent, or a mixture thereof. The stationary-phase particles typically have small pores and/or channels which only allow molecules below a certain size to enter. Large particles are therefore excluded from these pores and channels, and their limited interaction with the stationary phase leads them to elute as a "totally-excluded" peak at the beginning of the experiment. Smaller molecules, which can fit into the pores, are removed from the flowing mobile phase, and the time they spend immobilized in the stationary-phase pores depends, in part, on how far into the pores they penetrate. Their removal from the mobile phase flow causes them to take longer to elute from the column and results in a separation between the particles based on differences in their size. A given size exclusion column has a range of molecular weights that can be separated. Overall, molecules larger than the upper limit will not be trapped by the stationary phase, molecules smaller than the lower limit will completely enter the solid phase and elute as a single band, and molecules within the range will elute at different rates, defined by their properties such as hydrodynamic volume. For examples of these methods in practice with pharmaceutical proteins, see Bruner et al., *Journal of Pharmaceutical and Biomedical Analysis.* 15: 1929-1935, 1997.

Protein purity for clinical applications is also discussed, for example, by Anicetti et al. (*Trends in Biotechnology.* 7:342-349, 1989). More recent techniques for analyzing protein purity include, without limitation, the LabChip GXII, an automated platform for rapid analysis of proteins and nucleic acids, which provides high throughput analysis of titer, sizing, and purity analysis of proteins. In certain non-limiting embodiments, clinical grade proteins such as protein fragments and antibodies can be obtained by utilizing a combination of chromatographic materials in at least two orthogonal steps, among other methods (see, e.g., Therapeutic Proteins: Methods and Protocols. Vol. 308, Eds., Smales and James, Humana Press Inc., 2005). Typically, protein agents (e.g., AARS protein fragments, antibodies, binding agents) and other agents (e.g., antisense, RNAi, small molecules) are substantially endotoxin-free, as measured according to techniques known in the art and described herein.

Protein solubility assays are also included. Such assays can be utilized, for example, to determine optimal growth and purification conditions for recombinant production, to optimize the choice of buffer(s), and to optimize the choice of AARS protein fragments or variants thereof. Solubility or aggregation can be evaluated according to a variety of parameters, including temperature, pH, salts, and the presence or absence of other additives. Examples of solubility screening assays include, without limitation, microplate-based methods of measuring protein solubility using turbidity or other measure as an end point, high-throughput assays for analysis of the solubility of purified recombinant proteins (see, e.g., Stenvall et al., *Biochim Biophys Acta.* 1752:6-10, 2005), assays that use structural complementation of a genetic marker protein to monitor and measure protein folding and solubility in vivo (see, e.g., Wigley et al., *Nature Biotechnology.* 19:131-136, 2001), and electrochemical screening of recombinant protein solubility in *Escherichia coli* using scanning electrochemical microscopy (SECM) (see, e.g., Nagamine et al., *Biotechnology and Bioengineering.* 96:1008-1013, 2006), among others. AARS protein fragments with increased solubility (or reduced aggregation) can be identified or selected for according to routine techniques in the art, including simple in vivo assays for protein solubility (see, e.g., Maxwell et al., *Protein Sci.* 8:1908-11, 1999).

Protein solubility and aggregation can also be measured by dynamic light scattering techniques. Aggregation is a general term that encompasses several types of interactions or characteristics, including soluble/insoluble, covalent/noncovalent, reversible/irreversible, and native/denatured interactions and characteristics. For protein therapeutics, the presence of aggregates is typically considered undesirable because of the concern that aggregates may cause an immunogenic reaction (e.g., small aggregates), or may cause adverse events on administration (e.g., particulates).

Dynamic light scattering refers to a technique that can be used to determine the size distribution profile of small particles in suspension or polymers such as proteins in solution. This technique, also referred to as photon correlation spectroscopy (PCS) or quasi-elastic light scattering (QELS), uses scattered light to measure the rate of diffusion of the protein particles. Fluctuations of the scattering intensity can be observed due to the Brownian motion of the molecules and particles in solution. This motion data can be conventionally processed to derive a size distribution for the sample, wherein the size is given by the Stokes radius or hydrodynamic radius of the protein particle. The hydrodynamic size depends on both mass and shape (conformation). Dynamic scattering can detect the presence of very small amounts of aggregated protein (<0.01% by weight), even in samples that contain a large range of masses. It can also be used to compare the stability of different formulations, including, for example, applications that rely on real-time monitoring of changes at elevated temperatures. Accordingly, certain embodiments include the use of dynamic light scattering to analyze the solubility and/or presence of aggregates in a sample that contains an AARS protein fragment, antibody, or other agent of the invention.

IX. Diagnostic Methods and Compositions

AARS agents such as AARS protein fragments, AARS polynucleotides, and antibodies and other binding agents described herein can be used in diagnostic assays and diagnostic compositions. Included are biochemical, histological, and cell-based methods and compositions, among others.

These and related embodiments include the detection of the AARS polynucleotide sequence(s) or corresponding AARS polypeptide sequence(s) or portions thereof of one or more newly identified AARS protein fragments, also referred to as AARS polypeptides. For instance, certain aspects include detection of the AARS polynucleotide sequence(s) or corresponding polypeptide sequence(s) or portions thereof of one or more newly identified AARS splice variants, and/or one or more splice junctions of those splice variants. In certain embodiments, the polynucleotide or corresponding polypeptide sequence(s) of at least one of the splice junctions is unique to that particular AARS splice variant.

Also included is the direct detection of AARS protein fragments, including splice variants, proteolytic fragments, and others. In certain embodiments, the presence or levels of one or more newly identified AARS protein fragments associate or correlate with one or more cellular types or cellular states. Hence, the presence or levels of an AARS polypeptide or polynucleotide can be used to distinguish between different cellular types or different cellular states. The presence or levels of AARS protein fragments or their related polynucleotides can be detected according to polynucleotide and/or polypeptide-based diagnostic techniques, as described herein and known in the art.

Certain aspects can employ the AARS protein fragments, antibody, or AARS polynucleotides as part of a companion diagnostic method, typically to assess whether a subject or population subjects will respond favorably to a specific medical treatment. For instance, a given AARS therapeutic agent (e.g., protein fragment, antisense, RNAi, antibody, binding agent) could be identified as suitable for a subject or certain populations of subjects based on whether the subject(s) have one or more selected biomarkers for a given disease or condition. Examples of biomarkers include serum/tissue markers as well as markers that can be identified by medical imaging techniques. In certain embodiments, a naturally-occurring AARS protein fragment (or its corresponding polynucleotide) may itself provide a serum and/or tissue biomarker that can be utilized to measure drug outcome or assess the desirability of drug use in a specific subject or a specific population of subjects. In certain aspects, the identification of an AARS polypeptide or polynucleotide reference sequence may include characterizing the differential expression of that sequence, whether in a selected subject, selected tissue, or otherwise, as described herein and known in the art.

Certain of the methods provided herein rely on the differential expression of an AARS polypeptide or polynucleotide to characterize the condition or state of a cell, tissue, or subject, and to distinguish it from another cell, tissue, or subject. Non-limiting examples include methods of detecting the presence or levels of an AARS polypeptide or polynucleotide in a biological sample to distinguish between cells or tissues of different species, cells of different tissues or organs, cellular developmental states such as neonatal and adult, cellular differentiation states, conditions such as healthy, diseased and treated, intracellular and extracellular fractions, in addition to primary cell cultures and other cell cultures, such as immortalized cell cultures.

Differential expression includes a statistically significant difference in one or more gene expression levels of an AARS polynucleotide or polypeptide reference sequence compared to the expression levels of the same sequence in an appropriate control. The statistically significant difference may relate to either an increase or a decrease in expression levels, as measured by RNA levels, protein levels, protein function, or any other relevant measure of gene expression such as those described herein. Also included is a comparison between an AARS polynucleotide or polypeptide of the invention and a full-length or wild-type cytosolic or mitochondrial AARS sequence, typically of the same or corresponding type. Differential expression can be detected by a variety of techniques in the art and described herein, including polynucleotide and polypeptide based techniques, such as real-time PCR, subtractive hybridization, polynucleotide and polypeptide arrays, and others.

A result is typically referred to as statistically significant if it is unlikely to have occurred by chance. The significance level of a test or result relates traditionally to a frequentist statistical hypothesis testing concept. In simple cases, statistical significance may be defined as the probability of making a decision to reject the null hypothesis when the null hypothesis is actually true (a decision known as a Type I error, or "false positive determination"). This decision is often made using the p-value: if the p-value is less than the significance level, then the null hypothesis is rejected. The smaller the p-value, the more significant the result. Bayes factors may also be utilized to determine statistical significance (see, e.g., Goodman S., *Ann Intern Med* 130:1005-13, 1999).

In more complicated, but practically important cases, the significance level of a test or result may reflect an analysis in which the probability of making a decision to reject the null hypothesis when the null hypothesis is actually true is no more than the stated probability. This type of analysis allows for those applications in which the probability of deciding to reject may be much smaller than the significance level for some sets of assumptions encompassed within the null hypothesis.

In certain exemplary embodiments, statistically significant differential expression may include situations wherein the expression level of a given AARS sequence provides at least about a 1.2×, 1.3×, 1.4×, 1.5×, 1.6×, 1.7×, 1.8×, 1.9×, 2.0×, 2.2×, 2.4×, 2.6×, 2.8×, 3.0×, 4.0×, 5.0×, 6.0×, 7.0×, 8.0×, 9.0×, 10.0×, 15.0×, 20.0×, 50.0×, 100.0×, or greater difference in expression (i.e., differential expression that may be higher or lower expression) in a suspected biological sample as compared to an appropriate control, including all integers and decimal points in between (e.g., 1.24×, 1.25×, 2.1×, 2.5×, 60.0×, 75.0×, etc.). In certain embodiments, statistically significant differential expression may include situations wherein the expression level of a given AARS sequence provides at least about 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900, 1000 percent (%) or greater difference in expression (i.e., differential expression that may be higher or lower) in a suspected biological sample as compared to an appropriate control, including all integers and decimal points in between.

As an additional example, differential expression may also be determined by performing Z-testing, i.e., calculating an absolute Z score, as described herein and known in the art (see Example 1). Z-testing is typically utilized to identify significant differences between a sample mean and a population mean. For example, as compared to a standard normal table (e.g., a control tissue), at a 95% confidence interval (i.e., at the 5% significance level), a Z-score with an absolute value greater than 1.96 indicates non-randomness. For a 99% confidence interval, if the absolute Z is greater than 2.58, it means that $p<0.01$, and the difference is even more significant—the null hypothesis can be rejected with greater confidence. In these and related embodiments, an absolute Z-score of 1.96, 2, 2.58, 3, 4, 5, 6, 7, 8, 9, 10, 11, 12, 13, 14, 15, 16, 17, 18, 19, 20 or more, including all decimal points in between (e.g., 10.1, 10.6, 11.2, etc.), may provide a strong measure of statistical significance. In certain embodiments, an absolute Z-score of greater than 6 may provide exceptionally high statistical significance.

Substantial similarly relates generally to the lack of a statistically significant difference in the expression levels between the biological sample and the reference control. Examples of substantially similar expression levels may include situations wherein the expression level of a given SSCIGS provides less than about a 0.05×, 0.1×, 0.2×, 0.3×, 0.4×, 0.5×, 0.6×, 0.7×, 0.8×, 0.9×, 1.0×, 1.1×, 1.2×, 1.3×, or 1.4× difference in expression (i.e., differential expression that may be higher or lower expression) in a suspected biological sample as compared to a reference sample, including all decimal points in between (e.g., 0.15×, 0.25×, 0.35×, etc.). In certain embodiments, differential expression may include situations wherein the expression level of a given AARS sequence provides less than about 0.25, 0.5, 1, 2, 3, 4, 5, 6, 7, 8, 9, 10, 11, 12, 13, 14, 15, 16, 17, 18, 19, 20, 30, 40, 50 percent (%) difference in expression (i.e., differential expression that may be higher or lower) in a suspected biological sample as compared to a reference sample, including all decimal points in between.

In certain embodiments, such as when using an Affymetrix Microarray to measure the expression levels of an AARS polynucleotide or polypeptide reference sequence, differential expression may also be determined by the mean expression value summarized by Affymetrix Microarray Suite 5 software (Affymetrix, Santa Clara, Calif.), or other similar software, typically with a scaled mean expression value of 1000.

Embodiments of the present invention include methods of detecting the presence or levels of an AARS polynucleotide or polypeptide reference sequence or a portion thereof to distinguish between cells or tissues or other biological sample of a different organism or species, wherein the presence or levels of that sequence associates with a selected organism or species. General examples include methods of distinguishing between humans and any combination of bacteria, fungi, plants, and other non-human animals. Included within animals are methods of distinguishing between humans and any combination of vertebrates and invertebrates, including vertebrates such as fish, amphibians, reptiles, birds, and non-human mammals, and invertebrates such as insects, mollusks, crustaceans, and corals. Included within non-human mammals are methods of distinguishing between humans and any combination of non-human mammals from the Order Afrosoricida, Macroscelidea, Tubulidentata, Hyracoidea, Proboscidea, Sirenia, Cingulata, Pilosa, Scandentia, Dermoptera, Primates, Rodentia, Lagomorpha, Erinaceomorpha, Soricomorpha, Chiroptera, Pholidota, Cetacea, Carnivora, Perissodactyla, or Artiodactyla. Included within the Primate Order are monkeys, apes, gorillas, and chimpanzees, among others known in the art. Accordingly, the presence or levels of an AARS polynucleotide or polypeptide reference sequence or variant, as described herein, may be used to identify the source of a given biological sample, such as a cell, tissue, or organ, by distinguishing between any combination of these organisms, or by distinguishing between humans and any one or more of these organisms, such as a panel of organisms. In certain embodiments, the source of a given biological sample may also be determined by comparing the presence or levels of an AARS sequence or a portion thereof to a pre-determined value.

Embodiments of the present invention include methods of detecting the presence or levels of an AARS polynucleotide or polypeptide reference sequence or a portion thereof to distinguish between cells or other biological samples that originate from different tissues or organs. Non-limiting examples include methods of distinguishing between a cell or other biological sample that originates from any combination of skin (e.g., dermis, epidermis, subcutaneous layer), hair follicles, nervous system (e.g., brain, spinal cord, peripheral nerves), auditory system or balance organs (e.g., inner ear, middle ear, outer ear), respiratory system (e.g., nose, trachea, lungs), gastroesophogeal tissues, the gastrointestinal system (e.g., mouth, esophagus, stomach, small intestines, large intestines, rectum), vascular system (e.g., heart, blood vessels and arteries), liver, gallbladder, lymphatic/immune system (e.g., lymph nodes, lymphoid follicles, spleen, thymus, bone marrow), uro-genital system (e.g., kidneys, ureter, bladder, urethra, cervix, Fallopian tubes, ovaries, uterus, vulva, prostate, bulbourethral glands, epididymis, prostate, seminal vesicles, testicles), musculoskeletal system (e.g., skeletal muscles, smooth muscles, bone, cartilage, tendons, ligaments), adipose tissue, mammary tissue, and the endocrine system (e.g., hypothalamus, pituitary, thyroid, pancreas, adrenal glands). Hence, based on the association of an AARS polynucleotide or polypeptide sequence as described herein, these methods may be used to identify or characterize the tissue or organ from which a cell or other biological sample is derived.

Embodiments of the present invention include methods of detecting the presence or levels of an AARS polynucleotide or polypeptide reference sequence or a portion thereof to distinguish between or characterize the developmental or differentiation state of the cell. Also included are methods of differentiating between germ cells, stem cells, and somatic cells. Examples of developmental states include neonatal and adult. Examples of cellular differentiation states include all of the discreet and identifiable stages between a totipotent cell, a pluripotent cell, a multipotent progenitor stem cell and a mature, fully differentiated cell.

A totipotent cell has total potential, typically arises during sexual and asexual reproduction, and includes and spores and zygotes, though in certain instances cells can dedifferentiate and regain totipotency. A pluripotent cell includes a stem cell that has the potential to differentiate into any of the three germ layers, including the endoderm (interior stomach lining, gastrointestinal tract, the lungs), the mesoderm (muscle, bone, blood, urogenital), and the ectoderm (epidermal tissues and nervous system). Multipotent progenitor cells are typically capable of differentiating into a limited number of tissue types. Examples of multipotent cells include, without limitation, hematopoietic stem cells (adult stem cells) from the bone marrow that give rise to immune cells such as red blood cells, white blood cells, and platelets, mesenchymal stem cells (adult stem cells) from the bone marrow that give rise to stromal cells, fat cells, and various types of bone cells, epithelial stem cells (progenitor cells) that give rise to the various types of skin cells, and muscle satellite cells (progenitor cells) that contribute to differentiated muscle tissue. Accordingly, the presence or levels of particular AARS polynucleotide or polypeptide sequence (e.g., splice junction of an AARS splice variant, AARS proteolytic fragment), can be used to distinguish between or characterize the above-noted cellular differentiation states, as compared to a control or a predetermined level.

Embodiments of the present invention include methods of detecting the presence or levels of an AARS polynucleotide or polypeptide reference sequence to characterize or diagnose the condition or a cell, tissue, organ, or subject, in which that condition may be characterized as healthy, diseased, at risk for being diseased, or treated. For such diagnostic purposes, the term "diagnostic" or "diagnosed" includes identifying the presence or nature of a pathologic condition, characterizing the risk of developing such a condition, and/or measuring the change (or no change) of a pathologic condition in response to therapy. Diagnostic methods may differ in their sensitivity and specificity. In certain embodiments, the "sensitivity" of a diagnostic assay refers to the percentage of diseased cells, tissues or subjects which test positive (percent of "true positives"). Diseased cells, tissues or subjects not detected by the assay are typically referred to as "false negatives." Cells, tissues or subjects that are not diseased and which test negative in the assay may be termed "true negatives." In certain embodiments, the "specificity" of a diagnostic assay may be defined as one (1) minus the false positive rate, where the "false positive" rate is defined as the proportion of those samples or subjects without the disease and which test positive. While a particular diagnostic method may not provide a definitive diagnosis of a condition, it suffices if the method provides a positive indication that aids in diagnosis.

In certain instances, the presence or risk of developing a pathologic condition can be diagnosed by comparing the presence or levels of one or more selected AARS polynucleotide or polypeptide reference sequences or portions thereof that correlate with the condition, whether by increased or decreased levels, as compared to a suitable control. A "suitable control" or "appropriate control" includes a value, level, feature, characteristic, or property determined in a cell or other biological sample of a tissue or organism, e.g., a control or normal cell, tissue or organism, exhibiting, for example, normal traits, such as the absence of the condition. In certain embodiments, a "suitable control" or "appropriate control" is a predefined value, level, feature, characteristic, or property. Other suitable controls will be apparent to persons skilled in the art. Examples of diseases and conditions are described elsewhere herein.

Embodiments of the present invention include AARS polynucleotide or nucleic acid-based detection techniques, which offer certain advantages due to sensitivity of detection.

Hence, certain embodiments relate to the use or detection of AARS polynucleotides as part of a diagnostic method or assay. The presence and/or levels of AARS polynucleotides may be measured by any method known in the art, including hybridization assays such as Northern blot, quantitative or qualitative polymerase chain reaction (PCR), quantitative or qualitative reverse transcriptase PCR (RT-PCR), microarray, dot or slot blots, or in situ hybridization such as fluorescent in situ hybridization (FISH), among others. Certain of these methods are described in greater detail below.

AARS polynucleotides such as DNA and RNA can be collected and/or generated from blood, biological fluids, tissues, organs, cell lines, or other relevant sample using techniques known in the art, such as those described in Kingston. (2002 *Current Protocols in Molecular Biology*, Greene Publ. Assoc. Inc. & John Wiley & Sons, Inc., NY, N.Y. (see, e.g., as described by Nelson et al. *Proc Natl Acad Sci USA*, 99: 11890-11895, 2002) and elsewhere. Further, a variety of commercially available kits for constructing RNA are useful for making the RNA to be used in the present invention. RNA may be constructed from organs/tissues/cells procured from normal healthy subjects; however, this invention also contemplates construction of RNA from diseased subjects. Certain embodiments contemplate using any type of organ from any type of subject or animal. For test samples RNA may be procured from an individual (e.g., any animal, including mammals) with or without visible disease and from tissue samples, biological fluids (e.g., whole blood) or the like.

In certain embodiments, amplification or construction of cDNA sequences may be helpful to increase detection capabilities. The instant disclosure, as well as the art, provides the requisite level of detail to perform such tasks. In one exemplary embodiment, whole blood is used as the source of RNA and accordingly, RNA stabilizing reagents are optionally used, such as PAX tubes, as described, for example, in Thach et al., *J. Immunol. Methods*. December 283(1-2):269-279, 2003 and Chai et al., *J. Clin. Lab Anal.* 19(5):182-188, 2005 (both of which are incorporated by reference). Complementary DNA (cDNA) libraries can be generated using techniques known in the art, such as those described in Ausubel et al. (2001 *Current Protocols in Molecular Biology*, Greene Publ. Assoc. Inc. & John Wiley & Sons, Inc., NY, NY); Sambrook et al. (1989 *Molecular Cloning*, Second Ed., Cold Spring Harbor Laboratory, Plainview, N.Y.); Maniatis et al. (1982 *Molecular Cloning*, Cold Spring Harbor Laboratory, Plainview, N.Y.) and elsewhere. Further, a variety of commercially available kits for constructing cDNA libraries are useful for making the cDNA libraries of the present invention. Libraries can be constructed from organs/tissues/cells procured from normal, healthy subjects.

Certain embodiments may employ hybridization methods for detecting AARS polynucleotide sequences. Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, *PNAS.* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference Certain embodiments may employ nucleic acid amplification methods for detecting AARS polynucleotide sequences. The term "amplification" or "nucleic acid amplification" refers to the production of multiple copies of a target nucleic acid that contains at least a portion of the intended specific target nucleic acid sequence. The multiple copies may be referred to as amplicons or amplification products. In certain embodiments, the amplified target contains less than the complete target gene sequence (introns and exons) or an expressed target gene sequence (spliced transcript of exons and flanking untranslated sequences). For example, specific amplicons may be produced by amplifying a portion of the target polynucleotide by using amplification primers that hybridize to, and initiate polymerization from, internal positions of the target polynucleotide. Preferably, the amplified portion contains a detectable target sequence that may be detected using any of a variety of well-known methods.

"Selective amplification" or "specific amplification," as used herein, refers to the amplification of a target nucleic acid sequence according to the present invention wherein detectable amplification of the target sequence is substantially limited to amplification of target sequence contributed by a nucleic acid sample of interest that is being tested and is not contributed by target nucleic acid sequence contributed by some other sample source, e.g., contamination present in reagents used during amplification reactions or in the environment in which amplification reactions are performed.

The term "amplification conditions" refers to conditions permitting nucleic acid amplification according to the present invention. Amplification conditions may, in some embodiments, be less stringent than "stringent hybridization conditions" as described herein. Oligonucleotides used in the amplification reactions of the present invention hybridize to their intended targets under amplification conditions, but may or may not hybridize under stringent hybridization conditions. On the other hand, detection probes of the present invention typically hybridize under stringent hybridization conditions. Acceptable conditions to carry out nucleic acid amplifications according to the present invention can be easily ascertained by someone having ordinary skill in the art depending on the particular method of amplification employed.

Many well-known methods of nucleic acid amplification require thermocycling to alternately denature double-stranded nucleic acids and hybridize primers; however, other well-known methods of nucleic acid amplification are isothermal. The polymerase chain reaction (U.S. Pat. Nos. 4,683,195; 4,683,202; 4,800,159; 4,965,188), commonly referred to as PCR, uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

As noted above, the term "PCR" refers to multiple amplification cycles that selectively amplify a target nucleic acid species. Included are quantitative PCR (qPCR), real-time PCR), reverse transcription PCR (RT-PCR) and quantitative reverse transcription PCR (qRT-PCR) is well described in the art. The term "pPCR" refers to quantitative polymerase chain reaction, and the term "qRT-PCR" refers to quantitative reverse transcription polymerase chain reaction. qPCR and qRT-PCR may be used to amplify and simultaneously quantify a targeted cDNA molecule. It enables both detection and quantification of a specific sequence in a cDNA pool, such as a selected AARS gene or transcript.

The term "real-time PCR" may use DNA-binding dye to bind to all double-stranded (ds) DNA in PCR, causing fluorescence of the dye. An increase in DNA product during PCR therefore leads to an increase in fluorescence intensity and is measured at each cycle, thus allowing DNA concentrations to be quantified. However, dsDNA dyes such as SYBR Green will bind to all dsDNA PCR products. Fluorescence is detected and measured in the real-time PCR thermocycler, and its geometric increase corresponding to exponential increase of the product is used to determine the threshold cycle ("Ct") in each reaction.

The term "Ct Score" refers to the threshold cycle number, which is the cycle at which PCR amplification has surpassed a threshold level. If there is a higher quantity of mRNA for a particular gene in a sample, it will cross the threshold earlier than a lowly expressed gene since there is more starting RNA to amplify. Therefore, a low Ct score indicates high gene expression in a sample and a high Ct score is indicative of low gene expression.

Certain embodiments may employ the ligase chain reaction (Weiss, Science. 254: 1292, 1991), commonly referred to as LCR, which uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Another method is strand displacement amplification (Walker, G. et al., 1992, Proc. Natl. Acad. Sci. USA 89:392-396; U.S. Pat. Nos. 5,270,184 and 5,455,166), commonly referred to as SDA, which uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (European Pat. No. 0 684 315).

Other amplification methods include, for example: nucleic acid sequence based amplification (U.S. Pat. No. 5,130,238), commonly referred to as NASBA; one that uses an RNA replicase to amplify the probe molecule itself (Lizardi, P. et al., 1988, BioTechnol. 6: 1197-1202), commonly referred to as Qβ replicase; a transcription based amplification method (Kwoh, D. et al., 1989, Proc. Natl. Acad. Sci. USA 86:1173-1177); self-sustained sequence replication (Guatelli, J. et al., 1990, Proc. Natl. Acad. Sci. USA 87: 1874-1878); and, transcription mediated amplification (U.S. Pat. Nos. 5,480,784 and 5,399,491), commonly referred to as TMA. For further discussion of known amplification methods see Persing, David H., 1993, "In Vitro Nucleic Acid Amplification Techniques" in Diagnostic Medical Microbiology: Principles and Applications (Persing et al., Eds.), pp. 51-87 (American Society for Microbiology, Washington, D.C.).

Illustrative transcription-based amplification systems of the present invention include TMA, which employs an RNA polymerase to produce multiple RNA transcripts of a target region (U.S. Pat. Nos. 5,480,784 and 5,399,491). TMA uses a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In an illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a subpopulation of such promoter-primers, may be modified to block or reduce primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer." From this second amplification primer, reverse transcriptase creates another DNA strand, resulting in a double-stranded DNA with a functional promoter at one end. When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

In certain embodiments, other techniques may be used to evaluate RNA transcripts of the transcripts from a particular cDNA library, including microarray analysis (Han, M., et al., Nat Biotechnol, 19: 631-635, 2001; Bao, P., et al., Anal Chem, 74: 1792-1797, 2002; Schena et al., Proc. Natl. Acad. Sci. USA 93:10614-19, 1996; and Heller et al., Proc. Natl. Acad. Sci. USA 94:2150-55, 1997) and SAGE (serial analysis of gene expression). Like MPSS, SAGE is digital and can generate a large number of signature sequences. (see e.g., Velculescu, V. E., et al., Trends Genet, 16: 423-425., 2000; Tuteja R. and Tuteja N. Bioessays. 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), DNA Microarrays: A Practical Approach (Practical Approach Series), Oxford University Press (1999); Nature Genet. 21(1) (suppl.): 1-60 (1999); Schena (ed.), Microarray Biochip: Tools and Technology, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., *Proc. Natl. Acad. Sci. USA* 97(4): 1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, and 5,405,783, the disclosures of which are incorporated by reference.

Additional examples include nucleic acid arrays that are commercially available from Affymetrix (Santa Clara, Calif.) under the brand name GENECHIP™. Further exemplary methods of manufacturing and using arrays are provided in, for example, U.S. Pat. Nos. 7,028,629; 7,011,949; 7,011,945; 6,936,419; 6,927,032; 6,924,103; 6,921,642; and 6,818,394.

The present invention as related to arrays and microarrays also contemplates many uses for polymers attached to solid substrates. These uses include gene expression monitoring, profiling, library screening, genotyping and diagnostics. Gene expression monitoring and profiling methods and methods useful for gene expression monitoring and profiling are shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 10/442,021, 10/013,598 (U.S. Application No. 2003/0036069), and U.S. Pat. Nos. 5,925,525, 6,268,141, 5,856,092, 6,267,152, 6,300, 063, 6,525,185, 6,632,611, 5,858,659, 6,284,460, 6,361,947, 6,368,799, 6,673,579 and 6,333,179. Other methods of nucleic acid amplification, labeling and analysis that may be used in combination with the methods disclosed herein are embodied in U.S. Pat. Nos. 5,871,928, 5,902,723, 6,045,996, 5,541,061, and 6,197,506.

As will be apparent to persons skilled in the art, certain embodiments may employ oligonucleotides, such as primers or probes, for amplification or detection, as described herein. Oligonucleotides of a defined sequence and chemical structure may be produced by techniques known to those of ordinary skill in the art, such as by chemical or biochemical synthesis, and by in vitro or in vivo expression from recombinant nucleic acid molecules, e.g., bacterial or viral vectors. In certain embodiments, an oligonucleotide does not consist solely of wild-type chromosomal DNA or the in vivo transcription products thereof.

Oligonucleotides or primers may be modified in any way, as long as a given modification is compatible with the desired function of a given oligonucleotide. One of ordinary skill in the art can easily determine whether a given modification is suitable or desired for any given oligonucleotide of the present invention. Relevant AARS oligonucleotides are described in greater detail elsewhere herein.

While the design and sequence of oligonucleotides depends on their function as described herein, several variables are generally taken into account. Among the most relevant are: length, melting temperature (Tm), specificity, complementarity with other oligonucleotides in the system, G/C content, polypyrimidine (T, C) or polypurine (A, G) stretches, and the 3'-end sequence. Controlling for these and other variables is a standard and well known aspect of oligonucleotide design, and various computer programs are readily available to screen large numbers of potential oligonucleotides for optimal ones.

Certain embodiments therefore include methods for detecting a target AARS polynucleotide in a sample, the polynucleotide comprising the sequence of a reference AARS polynucleotide, as described herein, comprising a) hybridizing the sample with a probe comprising a sequence complementary to the target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. Also included are methods for detecting a target AARS polynucleotide in a sample, the polynucleotide comprising the sequence of a reference AARS polynucleotide, as described herein, comprising a) amplifying the target polynucleotide or fragment thereof, and b) detecting the presence or absence of said amplified target polynucleotide or fragment thereof, and, optionally, if present, the amount thereof. Specific embodiments relate to the detection of AARS splice variants, such as by detecting a unique splice junction of the splice variant, whether by hybridization, amplification, or other detection method.

Embodiments of the present invention include a variety of AARS polypeptide-based detection techniques, including antibody-based detection techniques. Included in these embodiments are the use of AARS polypeptides to generate antibodies or other binders, which may then be used in diagnostic methods and compositions to detect or quantitate selected AARS polypeptides in a cell or other biological sample, typically from a subject.

Certain embodiments may employ standard methodologies and detectors such as western blotting and immunoprecipitation, enzyme-linked immunosorbent assays (ELISA), flow cytometry, and immunofluorescence assays (IFA), which utilize an imaging device. These well-known methods typically utilize one or more monoclonal or polyclonal antibodies as described herein that specifically bind to a selected AARS polypeptide of the invention, or a unique region of that AARS polypeptide, and generally do not bind significantly to other AARS polypeptides, such as a full-length AARS polypeptide. In certain embodiments, the unique region of the AARS polypeptide may represent a unique three-dimensional structure that is possessed by a newly identified protein fragment of an AARS.

Certain embodiments may employ "arrays," such as "microarrays." In certain embodiments, a "microarray" may also refer to a "peptide microarray" or "protein microarray" having a substrate-bound collection or plurality of polypeptides, the binding to each of the plurality of bound polypeptides being separately detectable. Alternatively, the peptide microarray may have a plurality of binders, including but not limited to monoclonal antibodies, polyclonal antibodies, phage display binders, yeast 2 hybrid binders, and aptamers, which can specifically detect the binding of the AARS polypeptides described herein. The array may be based on autoantibody detection of these AARS polypeptides, as described, for example, in Robinson et al., *Nature Medicine* 8(3):295-301 (2002). Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, and WO 97/42507 and U.S. Pat. Nos. 6,268,210, 5,766,960, and 5,143,854, each of which are incorporated by reference.

Certain embodiments may employ MS or other molecular weight-based methods for diagnostically detecting AARS polypeptide sequences. Mass spectrometry (MS) refers generally to an analytical technique for determining the elemental composition of a sample or molecule. MS may also be used for determining the chemical structures of molecules, such as peptides and other chemical compounds.

Generally, the MS principle consists of ionizing chemical compounds to generate charged molecules or molecule fragments, and then measuring their mass-to-charge ratios. In an illustrative MS procedure: a sample is loaded onto the MS instrument, and undergoes vaporization, the components of the sample are ionized by one of a variety of methods (e.g., by impacting them with an electron beam), which results in the formation of positively charged particles, the positive ions are then accelerated by a magnetic field, computations are performed on the mass-to-charge ratio (m/z) of the particles based on the details of motion of the ions as they transit through electromagnetic fields, and, detection of the ions, which in step prior were sorted according to m/z.

An illustrative MS instruments has three modules: an ion source, which converts gas phase sample molecules into ions (or, in the case of electrospray ionization, move ions that exist in solution into the gas phase); a mass analyzer, which sorts the ions by their masses by applying electromagnetic fields; and a detector, which measures the value of an indicator quantity and thus provides data for calculating the abundances of each ion present.

The MS technique has both qualitative and quantitative uses, including identifying unknown compounds, determining the isotopic composition of elements in a molecule, and determining the structure of a compound by observing its fragmentation. Other uses include quantifying the amount of a compound in a sample or studying the fundamentals of gas phase ion chemistry (the chemistry of ions and neutrals in a vacuum). Included are gas chromatography-mass spectrometry (GC/MS or GC-MS), liquid chromatography mass spectrometry (LC/MS or LC-MS), and ion mobility spectrometry/mass spectrometry (IMS/MS or IMMS) Accordingly, MS techniques may be used according to any of the methods provided herein to measure the presence or levels of an AARS polypeptide of the invention in a biological sample, and to compare those levels to a control sample or a pre-determined value.

Certain embodiments may employ cell-sorting or cell visualization or imaging devices/techniques to detect or quantitate the presence or levels of AARS polynucleotides or polypeptides. Examples include flow cytometry or FACS, immunofluorescence analysis (IFA), and in situ hybridization techniques, such as fluorescent in situ hybridization (FISH).

Certain embodiments may employ conventional biology methods, software and systems for diagnostic purposes. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). See U.S. Pat. No. 6,420,108.

Certain embodiments may employ various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

The whole genome sampling assay (WGSA) is described, for example in Kennedy et al., Nat. Biotech. 21, 1233-1237 (2003), Matsuzaki et al., Gen. Res. 14: 414-425, (2004), and Matsuzaki, et al., Nature Methods 1:109-111 (2004). Algorithms for use with mapping assays are described, for example, in Liu et al., Bioinformatics. 19: 2397-2403 (2003) and Di et al. Bioinformatics. 21:1958 (2005). Additional methods related to WGSA and arrays useful for WGSA and applications of WGSA are disclosed, for example, in U.S. Patent Application Nos. 60/676,058 filed Apr. 29, 2005, 60/616,273 filed Oct. 5, 2004, Ser. No. 10/912,445, 11/044, 831, 10/442,021, 10/650,332 and 10/463,991. Genome wide association studies using mapping assays are described in, for example, Hu et al., Cancer Res.; 65(7):2542-6 (2005), Mitra et al., Cancer Res., 64(21):8116-25 (2004), Butcher et al., Hum Mol Genet., 14(10):1315-25 (2005), and Klein et al., Science. 308(5720):385-9 (2005).

Additionally, certain embodiments may include methods for providing genetic information over networks such as the Internet as shown, for example, in U.S. application Ser. Nos. 10/197,621, 10/063,559 (United States Publication Number 2002/0183936), 10/065,856, 10/065,868, 10/328,818, 10/328,872, 10/423,403, and 60/482,389.

X. Antisense and RNAi Agents

Embodiments of the present invention also include antisense oligonucleotides and RNAi agents that target the AARS polynucleotide sequences, and methods of use thereof to reduce expression of a selected AARS transcript and/or protein fragment. Certain embodiments relate to targeting one or more splice junctions (often unique) that generate a splice variant, AARS protein fragment of instant invention. Also included are methods of antisense or RNAi inhibition that target certain splice forms, either to encourage or discourage splicing of a selected protein fragment. In certain preferred embodiments, the splice junctions that generate the AARS protein fragments are over-expressed with respect to particular tissues, and are unique to that splice variant. In these and related embodiments, such splice variants are not the only source of cytosolic AARS activity in the targeted cell type. For instance, certain splice variants to be targeted may represent about 10% to 50% of the total copy number of the AARS RNA splice variants in a given cell or tissue, and preferably about 1-10% of the total copy number of the AARS RNA splice variants in a given cell or tissue. Splice variants that are about <1% of the total copy number of the AARS RNA splice variants in a given cell or tissue may also be targeted.

In certain embodiments, the antisense or RNAi agent does not target the full-length protein, because such full-length proteins are responsible for a key step in protein synthesis, and thereby avoids lethality that often results from wild-type AARS knockouts. Certain of the methods described herein can therefore by used to avoid undesired effects such as toxicities in both chronic and acute treatments, and to selectively modulate the non-canonical activities of the AARS protein fragment. However, certain embodiments may generically target AARS sequences, including full-length AARS sequences, such as to kill or substantially derange the cell physiology of a target cell or tissue.

In certain embodiments, the AARS splice variant to be targeted possesses a non-canonical biological activity. In some embodiments, the AARS splice variant has reduced or undetectable canonical AARS activity, and the antisense or RNAi-related method more specifically modulates its non-canonical activity. In certain embodiments, the antisense or RNAi-related agents can be combined with a targeted or local delivery approach to lessen systemic undesired effects to non-targeted cells or tissues. Among others described herein, exemplary cells or tissues that could be targeted this way include cancer cells, and cells to tissues that lend themselves to localized targeting, such as tumors or epithelia via topical application.

A. Antisense Agents

The terms "antisense oligomer" or "antisense compound" or "antisense oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence, and typically thereby prevent translation of that RNA. Also included are methods of use thereof to modulate expression of a selected AARS transcript, such as a splice variant or proteolytic fragment, and/or its corresponding polypeptide.

Antisense oligonucleotides may contain between about 8 and 40 subunits, typically about 8-25 subunits, and preferably about 12 to 25 subunits. In certain embodiments, oligonucleotides may have exact sequence complementarity to the target sequence or near complementarity, as defined below. In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, or 12-25 bases, including all integers in between these ranges. An antisense oligomer of about 14-15 bases is generally long enough to have a unique complementary sequence in targeting the selected AARS gene. In certain embodiments, a minimum length of complementary bases may be required to achieve the requisite binding Tm, as discussed herein.

In certain embodiments, antisense oligomers as long as 40 bases may be suitable, where at least a minimum number of bases, e.g., 10-12 bases, are complementary to the target sequence. In general, however, facilitated or active uptake in cells is optimized at oligomer lengths less than about 30. For certain oligomers, described further below, an optimum balance of binding stability and uptake generally occurs at lengths of 18-25 bases. Included are antisense oligomers (e.g., PNAs, LNAs, 2'-OMe, MOE) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous or non-contiguous bases are complementary to their AARS target sequence, or variants thereof.

In certain embodiments, antisense oligomers may be 100% complementary to an AARS nucleic acid target sequence, or it may include mismatches, e.g., to accommodate variants, as long as a heteroduplex formed between the oligomer and AARS nucleic acid target sequence is sufficiently stable to withstand the action of cellular nucleases and other modes of degradation which may occur in vivo. The term "target sequence" refers to a portion of the target RNA against which the oligonucleotide is directed, that is, the sequence to which the oligonucleotide will hybridize by Watson-Crick base pairing of a complementary sequence. In certain embodiments, the target sequence may be a contiguous region of an AARS mRNA (e.g., a unique splice junction of an AARS mRNA), or may be composed of non-contiguous regions of the mRNA.

Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the AARS nucleic acid target sequence, it is effective to stably and specifically bind to the target sequence, such that a biological activity of the nucleic acid target, e.g., expression of AARS protein(s), is modulated.

The stability of the duplex formed between an oligomer and a target sequence is a function of the binding Tm and the susceptibility of the duplex to cellular enzymatic cleavage. The Tm of an antisense oligonucleotide with respect to complementary-sequence RNA may be measured by conventional methods, such as those described by Hames et al., *Nucleic Acid Hybridization*, IRL Press, 1985, pp. 107-108 or as described in Miyada C. G. and Wallace R. B., 1987, Oligonucleotide hybridization techniques, *Methods Enzymol.* Vol. 154 pp. 94-107. In certain embodiments, antisense oligomer may have a binding Tm, with respect to a complementary-sequence RNA, of greater than body temperature and preferably greater than 50° C. Tm's in the range 60-80° C. or greater are preferred. According to well known principles, the Tm of an oligomer compound, with respect to a complementary-based RNA hybrid, can be increased by increasing the ratio of C:G paired bases in the duplex, and/or by increasing the length (in base pairs) of the heteroduplex. At the same time, for purposes of optimizing cellular uptake, it may be advantageous to limit the size of the antisense oligomer. For this reason, compounds that show high Tm (50° C. or greater) at a length of 25 bases or less are generally preferred over those requiring greater than 25 bases for high Tm values.

Antisense oligomers can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence may include any coding or non-coding sequence of an AARS mRNA transcript, and may thus by within an exon or within an intron. In certain embodiments, the target sequence is relatively unique or exceptional among AARSs (e.g., a full-length AARS) and is selective for reducing expression of a selected AARS protein fragment, such as a proteolytic fragment or splice variant. In certain embodiments, the target site includes a 3' or 5' splice site of a pre-processed mRNA, or a branch point. The target sequence for a splice site may include an mRNA sequence having its 5' end 1 to about 25 to about 50 base pairs downstream of a splice acceptor junction or upstream of a splice donor junction in a preprocessed mRNA. In certain embodiments, a target sequence may include a splice junction of an alternatively splice AARS mRNA, such as a splice junction that does not occur in the full-length AARS, or is unique or exceptional to that transcript, in that it either does not occur or only seldom occurs in other AARS splice variants. An oligomer is more generally said to be "targeted against" a biologically relevant target, such as reference AARS polynucleotide, when it is targeted against the nucleic acid of the target in the manner described herein.

An oligonucleotide is typically complementary to a target sequence, such as a target DNA or RNA. The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity (100%) between the nucleic acids. The degree of complementarity between nucleic acid strands has significant effects on the efficiency and strength of hybridization between nucleic acid strands. While perfect complementarity is often desired, some embodiments can include one or more but preferably 20, 19, 18, 17, 16, 15, 14, 13, 12, 11, 10, 9, 8, 7, 6, 5, 4, 3, 2, or 1 mismatches with respect to the target sequence. Variations at any location within the oligomer are included. In certain embodiments, variations in sequence near the termini of an oligomer are generally preferable to variations in the interior, and if present are typically within about 10, 9, 8, 7, 6, 5, 4, 3, 2, or 1 nucleotides of the 5' and/or 3' terminus.

The term "targeting sequence" or in certain embodiments "antisense targeting sequence" refers to the sequence in an oligonucleotide that is complementary (meaning, in addition, substantially complementary) to the target sequence in the DNA or RNA target molecule. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present invention, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least about 80%, 85%, 90% sequence homology, and preferably at least 95% sequence homology, with an AARS reference polynucleotide sequence described herein, or its complement.

An oligonucleotide "specifically hybridizes" to a target polynucleotide if the oligomer hybridizes to a target (e.g., an AARS reference polynucleotide or its complement) under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

The terms specifically binds or specifically hybridizes refer generally to an oligonucleotide probe or polynucleotide sequence that not only binds to its intended target gene sequence in a sample under selected hybridization conditions, but does not bind significantly to other target sequences in the sample, and thereby discriminates between its intended target and all other targets in the target pool. A probe that specifically hybridizes to its intended target sequence may also detect concentration differences under the selected hybridization conditions, as described herein.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

A "heteroduplex" refers to a duplex between an oligonucleotide and the complementary portion of a target polynucleotide, such as a target DNA or RNA. A "nuclease-resistant heteroduplex" refers to a heteroduplex formed by the binding of an oligomer to its complementary target, such that the heteroduplex is substantially resistant to in vivo degradation by intracellular and extracellular nucleases, such as RNaseH, which are capable of cutting double-stranded RNA/RNA or RNA/DNA complex es.

A "subunit" of an oligonucleotide refers to one nucleotide (or nucleotide analog) unit. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The cyclic subunits of an oligonucleotide may be based on ribose or another pentose sugar or, in certain embodiments, alternate or modified groups. Examples of modified oligonucleotide backbones include, without limitation, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphoramidates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Also contemplated are peptide nucleic acids (PNAs), locked nucleic acids (LNAs), 2'-O-Methyl oligonucleotides (2'-OMe), 2'-methoxyethoxy oligonucleotides (MOE), among other oligonucleotides known in the art.

The purine or pyrimidine base pairing moiety is typically adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, 3-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U.

As noted above, certain oligonucleotides provided herein include peptide nucleic acids (PNAs). Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligonucleotides obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases.

PNAs may be produced synthetically using any technique known in the art. PNA is a DNA analog in which a polyamide backbone replaces the traditional phosphate ribose ring of DNA. Despite a radical structural change to the natural structure, PNA is capable of sequence-specific binding in a helix form to DNA or RNA. Characteristics of PNA include a high binding affinity to complementary DNA or RNA, a destabilizing effect caused by single-base mismatch, resistance to nucleases and proteases, hybridization with DNA or RNA independent of salt concentration and triplex formation with homopurine DNA. Panagene™ has developed its proprietary Bts PNA monomers (Bts; benzothiazole-2-sulfonyl group) and proprietary oligomerisation process. The PNA oligomerisation using Bts PNA monomers is composed of repetitive cycles of deprotection, coupling and capping. Panagene's patents to this technology include U.S. Pat. No. 6,969,766, U.S. Pat. No. 7,211,668, U.S. Pat. No. 7,022,851, U.S. Pat. No. 7,125,994, U.S. Pat. No. 7,145,006 and U.S. Pat. No. 7,179,896. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

Also included are "locked nucleic acid" subunits (LNAs). The structures of LNAs are known in the art: for example, Wengel, et al., Chemical Communications (1998) 455; Tetrahedron (1998) 54, 3607, and Accounts of Chem. Research (1999) 32, 301); Obika, et al., Tetrahedron Letters (1997) 38, 8735; (1998) 39, 5401, and Bioorganic Medicinal Chemistry (2008) 16, 9230.

Oligonucleotides may incorporate one or more LNAs; in some cases, the compounds may be entirely composed of LNAs. Methods for the synthesis of individual LNA nucleoside subunits and their incorporation into oligonucleotides are known in the art: U.S. Pat. Nos. 7,572,582; 7,569,575; 7,084,125; 7,060,809; 7,053,207; 7,034,133; 6,794,499; and 6,670,461. Typical intersubunit linkers include phosphodiester and phosphorothioate moieties; alternatively, non-phosphorous containing linkers may be employed. A preferred embodiment is an LNA containing compound where each LNA subunit is separated by a DNA subunit (i.e., a deoxyribose nucleotide). Further preferred compounds are composed of alternating LNA and DNA subunits where the intersubunit linker is phosphorothioate.

Certain oligonucleotides may comprise morpholino-based subunits bearing base-pairing moieties, joined by uncharged or substantially uncharged linkages. The terms "morpholino oligomer" or "PMO" (phosphoramidate- or phosphorodiamidate morpholino oligomer) refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine or an equivalent base-pairing moiety effective to bind, by base specific hydrogen bonding, to a base in a polynucleotide.

Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. The purine or pyrimidine base pairing moiety is typically adenine, cytosine, guanine, uracil, thymine or inosine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337, and PCT Appn. Nos. PCT/US07/11435 (cationic linkages) and U.S. Ser. No. 08/012,804 (improved synthesis), all of which are incorporated herein by reference.

The morpholino subunits may also be linked by non-phosphorus-based intersubunit linkages, as described further below, where at least one linkage is modified with a pendant cationic group as described above. Other oligonucleotide analog linkages which are uncharged in their unmodified state but which could also bear a pendant amine substituent could be used. For example, a 5'nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above Certain embodiments include substantially uncharged morpholino oligomers, such as a substantially uncharged phosphorodiamidate-linked morpholino oligomer. A substantially uncharged, phosphorus containing backbone in an oligonucleotide analog is one in which a majority of the subunit linkages, e.g., between 50-100%, typically at least 60% to 100% or 75% or 80% of its linkages, are uncharged at physiological pH, and contain a single phosphorous atom. Examples of morpholino oligonucleotides having phosphorus-containing backbone linkages include phosphoroamidate and phosphorodiamidate-linked morpholino oligonucleotides. Certain embodiments may contain positively charged groups at preferably about 10%-50% of their backbone linkages.

Properties of the morpholino-based subunits include, for example, the ability to be linked in a oligomeric form by stable, uncharged or positively charged backbone linkages, the ability to support a nucleotide base (e.g., adenine, cytosine, guanine, thymidine, uracil and hypoxanthine) such that the polymer formed can hybridize with a complementary-base target nucleic acid, including target RNA, Tm values above about 45° C. in relatively short oligonucleotides (e.g., 10-15 bases), the ability of the oligonucleotide to be actively or passively transported into mammalian cells, and the ability of the antisense oligonucleotide:RNA heteroduplex to resist RNase and RNaseH degradation, respectively.

In certain embodiments, a substantially uncharged oligonucleotide may be modified to include charged linkages, e.g., up to about 1 per every 2-5 uncharged linkages, such as about 4-5 per every 10 uncharged linkages. In certain embodiments, optimal improvement in antisense activity may be seen when about 25% of the backbone linkages are cationic. In certain embodiments, enhancement may be seen with a small number e.g., 10-20% cationic linkages, or where the number of cationic linkages are in the range 50-80%, such as about 60%. In certain embodiments the cationic backbone charges may be further enhanced by distributing the bulk of the charges close of the "center-region" backbone linkages of the antisense oligonucleotide, e.g., in a 20-mer oligonucleotide with 8 cationic backbone linkages, having at least 70% of these charged linkages localized in the 10 centermost linkages.

Oligonucleotides that target one or more portions of an AARS polynucleotide reference sequence or its complement may be used in any of the therapeutic, diagnostic, or drug screening methods described herein and apparent to persons skilled in the art.

B. RNA Interference Agents

Certain embodiments relate to RNA interference (RNAi) agents that target one or more mRNA transcripts of an aminoacyl-tRNA synthetase (AARS) reference polynucleotide, including fragments and splice variants thereof. Also included are methods of use thereof to modulate the levels of a selected AARS transcript, such as an AARS splice variant or endogenous proteolytic fragment.

The term "double-stranded" means two separate nucleic acid strands comprising a region in which at least a portion of the strands are sufficiently complementary to hydrogen bond and form a duplex structure. The term "duplex" or "duplex structure" refers to the region of a double stranded molecule wherein the two separate strands are substantially complementary, and thus hybridize to each other. "dsRNA" refers to a ribonucleic acid molecule having a duplex structure comprising two complementary and anti-parallel nucleic acid strands (i.e., the sense and antisense strands). Not all nucleotides of a dsRNA must exhibit Watson-Crick base pairs; the two RNA strands may be substantially complementary. The RNA strands may have the same or a different number of nucleotides.

In certain embodiments, a dsRNA is or includes a region which is at least partially complementary to the target RNA. In certain embodiments, the dsRNA is fully complementary to the target RNA. It is not necessary that there be perfect complementarity between the dsRNA and the target, but the correspondence must be sufficient to enable the dsRNA, or a cleavage product thereof, to direct sequence specific silencing, such as by RNAi cleavage of the target RNA. Complementarity, or degree of homology with the target strand, is typically most critical in the antisense strand. While perfect complementarity, particularly in the antisense strand, is often desired some embodiments can include one or more but preferably 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be substantially complementary with the antisense strand to maintain the overall double-strand character of the molecule.

As used herein, "modified dsRNA" refers to a dsRNA molecule that comprises at least one alteration that renders it more resistant to nucleases (e.g., protein kinase) than an identical dsRNA molecule that recognizes the same target RNA. Modified dsRNAs may include a single-stranded nucleotide overhang and/or at least one substituted nucleotide.

As used herein, a "nucleotide overhang" refers to the unpaired nucleotide or nucleotides that protrude from the duplex structure when a 3'-end of one RNA strand extends beyond the 5'-end of the other complementary strand, or vice versa. "Blunt" or "blunt end" means that there are no unpaired nucleotides at that end of the dsRNA, i.e., no nucleotide overhang. A "blunt ended" dsRNA is a dsRNA that is double stranded over its entire length, i.e., no nucleotide overhang at either end of the molecule.

The term "terminal base pair," as used herein, refers to the last nucleotide base pair on one end of the duplex region of a double-stranded molecule. For example, if a dsRNA or other molecule is blunt ended (i.e., has no nucleotide overhangs), the last nucleotide base pairs at both ends of the molecule are terminal base pairs. Where a dsRNA or other molecule has a nucleotide overhang at one or both ends of the duplex structure, the last nucleotide base pair(s) immediately adjacent the nucleotide overhang(s) is the terminal base pair at that end(s) of the molecule.

In certain embodiments, the methods provided herein may utilize double-stranded ribonucleic acid (dsRNA) molecules as modulating agents, for reducing expression of an AARS transcript such as a selected fragment or splice variant. dsRNAs generally comprise two single strands. One strand of the dsRNA comprises a nucleotide sequence that is substantially identical to a portion of the target gene or target region (the "sense" strand), and the other strand (the "complementary" or "antisense" strand) comprises a sequence that is substantially complementary to a portion of the target region. The strands are sufficiently complementary to hybridize to form a duplex structure. In certain embodiments, the complementary RNA strand may be less than 30 nucleotides, less than 25 nucleotides in length, or even 19 to 24 nucleotides in length. In certain aspects, the complementary nucleotide sequence may be 20-23 nucleotides in length, or 22 nucleotides in length.

In certain embodiments, at least one of the RNA strands comprises a nucleotide overhang of 1 to 4 nucleotides in length. In other embodiments, the dsRNA may further comprise at least one chemically modified nucleotide. In certain aspects, a dsRNA comprising a single-stranded overhang of 1 to 4 nucleotides may comprise a molecule wherein the unpaired nucleotide of the single-stranded overhang that is directly adjacent to the terminal nucleotide pair contains a purine base. In other aspects, the last complementary nucleotide pairs on both ends of a dsRNA are a G-C pair, or, at least two of the last four terminal nucleotide pairs are G-C pairs.

Certain embodiments of the present invention may comprise microRNAs. Micro-RNAs represent a large group of small RNAs produced naturally in organisms, some of which regulate the expression of target genes. Micro-RNAs are formed from an approximately 70 nucleotide single-stranded hairpin precursor transcript by Dicer. (V. Ambros et al. Current Biology 13:807, 2003). Certain micro-RNAs may be transcribed as hairpin RNA precursors, which are then processed to their mature forms by Dicer enzyme.

Certain embodiments may also employ short-interfering RNAs (siRNA). In certain embodiments, the first strand of the double-stranded oligonucleotide contains two more nucleoside residues than the second strand. In other embodiments, the first strand and the second strand have the same number of nucleosides; however, the first and second strands may be offset such that the two terminal nucleosides on the first and second strands are not paired with a residue on the complimentary strand. In certain instances, the two nucleosides that are not paired are thymidine resides.

Also included are short hairpin RNAs (shRNAs) and micro RNAs (miRNAs). A double-stranded structure of an shRNA is formed by a single self-complementary RNA strand, and RNA duplex formation may be initiated either inside or outside the cell. MicroRNAs (miRNAs) are small non-coding RNAs of 20-22 nucleotides, typically excised from ~70 nucleotide foldback RNA precursor structures known as pre-miRNAs.

In instances when the modulating agent comprises siRNA, the agent should include a region of sufficient homology to the target region, and be of sufficient length in terms of nucleotides, such that the siRNA agent, or a fragment thereof, can mediate down regulation of the target RNA. It will be understood that the term "ribonucleotide" or "nucleotide" can, in the case of a modified RNA or nucleotide surrogate, also refer to a modified nucleotide, or surrogate replacement moiety at one or more positions. Thus, an siRNA agent is or includes a region which is at least partially complementary to the target RNA, as described herein.

In addition, an siRNA modulating agent may be modified or include nucleoside surrogates. Single stranded regions of an siRNA agent may be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA agent, e.g., against exonucleases, or to favor the antisense siRNA agent to enter into RISC are also useful. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents may include, for example, molecules that are long enough to trigger the interferon response (which can be cleaved by Dicer (Bernstein et al. 2001. Nature, 409:363-366) and enter a RISC (RNAi-induced silencing complex)), in addition to molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. An siRNA modulating agent, or a cleavage product thereof, can down regulate a target gene, e.g., by inducing RNAi with respect to a target RNA, preferably an AARS target such as a selected splice variant.

Each strand of an siRNA agent can be equal to or less than 35, 30, 25, 24, 23, 22, 21, 20, 19, 18, 17, 16, or 15 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA agent may have one or more of the following properties: it may, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA; it may, despite modifications, even to a very large number, or all of the nucleosides, still have "RNA-like" properties, i.e., it may possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_3'$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide.

A "single strand RNAi agent" as used herein, is an RNAi agent which is made up of a single molecule. It may include a duplexed region, formed by intra-strand pairing, e.g., it may be, or include, a hairpin or pan-handle structure. Single strand RNAi modulating agents are preferably antisense with regard to the target molecule. A single strand RNAi agent should be sufficiently long that it can enter the RISC and participate in RISC mediated cleavage of a target mRNA. A single strand RNAi agent is at least 14, and more preferably at least 15, 20, 25, 29, 35, 40, or 50 nucleotides in length. It is preferably less than 200, 100, or 60 nucleotides in length.

Hairpin RNAi modulating agents may have a duplex region equal to or at least 17, 18, 19, 29, 21, 22, 23, 24, or 25 nucleotide pairs. The duplex region may preferably be equal to or less than 200, 100, or 50, in length. Certain ranges for the duplex region are 15-30, 17 to 23, 19 to 23, and 19 to 21 nucleotides pairs in length. The hairpin may have a single strand overhang or terminal unpaired region, preferably the 3', and preferably of the antisense side of the hairpin. In certain embodiments, overhangs are 2-3 nucleotides in length.

Certain modulating agents utilized according to the methods provided herein may comprise RNAi oligonucleotides such as chimeric oligonucleotides, or "chimeras," which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides may be formed as composite structures of two or more oligonucleotides, modified oligonucleotides, oligonucleotides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

In one aspect of the invention RNAi agents relate to an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl. A wide variety of ligands are known in the art and are amenable to the present invention. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In other embodiments, the RNAi agent is an oligonucleotide tethered to a ligand for the purposes of improving cellular targeting and uptake. For example, an RNAi agent may be tethered to an antibody, or antigen binding fragment thereof. As an additional example, an RNAi agent may be tethered to a specific ligand binding molecule, such as a polypeptide or polypeptide fragment that specifically binds a particular cell-surface receptor.

In other embodiments, the modulating agent comprises a non-natural nucleobase, as described herein. In certain instances, the ribose sugar moiety that naturally occurs in nucleosides is replaced with a hexose sugar. In certain aspects, the hexose sugar is an allose, altrose, glucose, mannose, gulose, idose, galactose, talose, or a derivative thereof. In a preferred embodiment, the hexose is a D-hexose. In certain instances, the ribose sugar moiety that naturally occurs in nucleosides is replaced with a polycyclic heteroalkyl ring or cyclohexenyl group. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1] octane, or a bicyclo[3.3.1]nonane. Examples of modified RNAi agents also include oligonucleotides containing modified backbones or non-natural internucleoside linkages, as described herein.

The present invention further encompasses oligonucleotides employing ribozymes. Synthetic RNA molecules and derivatives thereof that catalyze highly specific endoribonuclease activities are known as ribozymes. (see, e.g., U.S. Pat. No. 5,543,508 to Haseloff et al., and U.S. Pat. No. 5,545,729 to Goodchild et al.) The cleavage reactions are catalyzed by the RNA molecules themselves. In naturally occurring RNA molecules, the sites of self-catalyzed cleavage are located within highly conserved regions of RNA secondary structure (Buzayan et al., Proc. Natl. Acad. Sci. U.S.A., 1986, 83, 8859; Forster et al., Cell, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness.

In certain instances, the RNAi agents or antisense oligonucleotides for use with the methods provided herein may be modified by non-ligand group. A number of non-ligand molecules have been conjugated to oligonucleotides in order to enhance the activity, cellular distribution, cellular targeting, or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA*, 1989, 86:6553), arginine-rich peptides, cholic acid (Manoharan et al., *Bioorg. Med. Chem. Lett.*, 1994, 4:1053), a thioether, e.g., hexyl-5-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Ex p. Ther.*, 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Additional examples of RNAi agents may be found in U.S. Application Publication Nos. 2007/0275465, 2007/0054279, 2006/0287260, 2006/0035254, 2006/0008822, which are incorporated by reference. Also included are vector delivery systems that are capable of expressing the AARS-targeting sequences described herein. Included are vectors that express siRNA or other duplex-forming RNA interference molecules.

A vector or nucleic acid construct system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector or nucleic acid construct is preferably one which is operably functional in a mammalian cell, such as a muscle cell. The vector can also include a selection marker such as an antibiotic or drug resistance gene, or a reporter gene (i.e., green fluorescent protein, luciferase), that can be used for selection or identification of suitable transformants or transfectants. Exemplary delivery systems may include viral vector systems (i.e., viral-mediated transduction) including, but not limited to, retroviral (e.g., lentiviral) vectors, adenoviral vectors, adeno-associated viral vectors, and herpes viral vectors, among others known in the art.

XI. Drug Discovery

Certain embodiments relate to the use of AARS polypeptides, antibodies, or polynucleotides in drug discovery, typically to identify agents that modulate one or more of the non-canonical activities of the reference AARS polypeptide, e.g., the AARS protein fragment. For example, certain embodiments include methods of identifying one or more "cellular binding partners" of an AARS reference polypeptide, such as a cellular protein, lipid, nucleic acid or other host molecule that directly or physically interacts with the AARS polypeptide. Particular examples include for example cell-surface receptors, such as GPCRs, protein-protein interaction domains, and extracellular or intracellular domains thereof.

Also included are methods of identifying host molecules that participate in one or more non-canonical activities of the AARS polypeptide, including molecules that directly or indirectly interact with the cellular binding partner, and either regulate its role in a non-canonical activity, or are regulated by the binding partner. Such host molecules include both upstream and downstream components of the non-canonical pathway, typically related by about 1, 2, 3, 4, 5 or more identifiable steps in the pathway, relative to the cellular binding partner/AARS protein interaction.

Certain aspects include methods of identifying a compound (e.g., polypeptide) or other agent that agonizes or antagonizes the non-canonical activity of an AARS reference polypeptide or active variant thereof, such as by interacting with the AARS polypeptide and/or one or more of its cellular binding partners. Also included are methods of identifying agents that modulate the expression (e.g., splicing) of AARS splice variants, or modulate the activity of proteases that otherwise regulate the production of endogenous AARS protein fragments (resectins) at the protein level.

Certain embodiments therefore include methods of identifying a binding partner of an AARS reference polypeptide, comprising a) combining the AARS polypeptide with a biological sample under suitable conditions, and b) detecting specific binding of the AARS polypeptide to a binding partner, thereby identifying a binding partner that specifically binds to the AARS reference polypeptide. Also included are methods of screening for a compound that specifically binds to an AARS reference polypeptide or a binding partner of the AARS polypeptide, comprising a) combining the polypeptide or the binding partner with at least one test compound under suitable conditions, and b) detecting binding of the polypeptide or the binding partner to the test compound, thereby identifying a compound that specifically binds to the polypeptide or its binding partner. In certain embodiments, the compound is a polypeptide or peptide. In certain embodiments, the compound is a small molecule or other (e.g., non-biological) chemical compound. In certain embodiments, the compound is a peptide mimetic.

Any method suitable for detecting protein-protein interactions may be employed for identifying cellular proteins that interact with an AARS reference polypeptide, interact with one or more of its cellular binding partners, or both. Examples of traditional methods that may be employed include co-immunoprecipitation, cross-linking, and co-purification through gradients or chromatographic columns of cell lysates or proteins obtained from cell lysates, mainly to identify proteins in the lysate that interact with the AARS polypeptide.

In these and related embodiments, at least a portion of the amino acid sequence of a protein that interacts with an AARS polypeptide or its binding partner can be ascertained using techniques well known to those of skill in the art, such as via the Edman degradation technique. See, e.g., Creighton Proteins: Structures and Molecular Principles, W. H. Freeman & Co., N.Y., pp. 34 49, 1983. The amino acid sequence obtained may be used as a guide for the generation of oligonucleotide mixtures that can be used to screen for gene sequences encoding such proteins. Screening may be accomplished, for example, by standard hybridization or PCR techniques, as described herein and known in the art. Techniques for the generation of oligonucleotide mixtures and the screening are well known. See, e.g., Ausubel et al. Current Protocols in Molecular Biology Green Publishing Associates and Wiley Interscience, N.Y., 1989; and Innis et al., eds. PCR Protocols: A Guide to Methods and Applications Academic Press, Inc., New York, 1990.

Additionally, methods may be employed in the simultaneous identification of genes that encode the binding partner or other polypeptide. These methods include, for example, probing expression libraries, in a manner similar to the well known technique of antibody probing of lambda-gt11 libraries, using labeled AARS protein, or another polypeptide, peptide or fusion protein, e.g., a variant AARS polypeptide or AARS domain fused to a marker (e.g., an enzyme, fluor, luminescent protein, or dye), or an Ig-Fc domain.

One method that detects protein interactions in vivo, the two-hybrid system, is described in detail for illustration only and not by way of limitation. One example of this system has been described (Chien et al., *PNAS USA* 88:9578 9582, 1991) and is commercially available from Clontech (Palo Alto, Calif.).

Briefly, utilizing such a system, plasmids may be constructed that encode two hybrid proteins: one plasmid consists of nucleotides encoding the DNA-binding domain of a transcription activator protein fused to an AARS reference nucleotide sequence (or, in certain embodiments, its binding partner), or a variant thereof, and the other plasmid consists of nucleotides encoding the transcription activator protein's activation domain fused to a cDNA (or collection of cDNAs) encoding an unknown protein(s) that has been recombined into the plasmid as part of a cDNA library. The DNA-binding domain fusion plasmid and the activator cDNA library may be transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or other such methodology may be used to screen activation domain libraries for proteins that interact with the "bait" gene product. By way of example, and not by way of limitation, an AARS reference polypeptide or variant may be used as the bait gene product. An AARS binding partner may also be used as a "bait" gene product. Total genomic or cDNA sequences are fused to the DNA encoding an activation domain. This library and a plasmid encoding a hybrid of a bait AARS gene product fused to the DNA-binding domain are co-transformed into a yeast reporter strain, and the resulting transformants are screened for those that express the reporter gene.

A cDNA library of the cell line from which proteins that interact with bait AARS gene products are to be detected can be made using methods routinely practiced in the art. For example, the cDNA fragments can be inserted into a vector such that they are translationally fused to the transcriptional activation domain of GAL4. This library can be co-transformed along with the bait gene-GAL4 fusion plasmid into a yeast strain, which contains a lacZ gene driven by a promoter that contains GAL4 activation sequence. A cDNA encoded protein, fused to GAL4 transcriptional activation domain, that interacts with bait gene product will reconstitute an active GAL4 protein and thereby drive expression of the HIS3 gene. Colonies, which express HIS3, can be detected by their growth on Petri dishes containing semi-solid agar based media lacking histidine. The cDNA can then be purified from these strains, and used to produce and isolate the bait AARS gene-interacting protein using techniques routinely practiced in the art.

Also included are three-hybrid systems, which allow the detection of RNA-protein interactions in yeast. See, e.g., Hook et al., RNA. 11:227-233, 2005. Accordingly, these and related methods can be used to identify a cellular binding partner of an AARS polypeptide, and to identify other proteins or nucleic acids that interact with the AARS polypeptide, the cellular binding partner, or both.

Certain embodiments relate to the use of interactome screening approaches. Particular examples include protein domain-based screening (see, e.g., Boxem et al., *Cell.* 134: 534-545, 2008; and Yu et al., *Science.* 322:10-110, 2008).

As noted above, once isolated, binding partners can be identified and can, in turn, be used in conjunction with standard techniques to identify proteins or other compounds with which it interacts. Certain embodiments thus relate to methods of screening for a compound that specifically binds to the binding partner of an AARS reference polypeptide, comprising a) combining the binding partner with at least one test compound under suitable conditions, and b) detecting binding of the binding partner to the test compound, thereby identifying a compound that specifically binds to the binding partner. In certain embodiments, the test compound is a polypeptide. In certain embodiments, the test compound is a chemical compound, such as a small molecule compound or peptide mimetic.

Certain embodiments include methods of screening for a compound that modulates the activity of an AARS reference polypeptide, comprising a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide. Certain embodiments include methods of screening for a compound that modulates the activity of a binding partner of an AARS reference polypeptide, comprising a) combining the polypeptide with at least one test compound under conditions permissive for the activity of the binding partner, b) assessing the activity of the binding partner in the presence of the test compound, and c) comparing the activity of the binding partner in the presence of the test compound with the activity of the binding partner in the absence of the test compound, wherein a change in the activity of the binding partner in the presence of the test compound is indicative of a compound that modulates the activity of the binding partner. Typically, these and related embodiments include assessing a selected non-canonical activity that is associated with the AARS polypeptide or its binding partner. Included are in vitro and in vivo conditions, such as cell culture conditions.

Certain embodiments include methods of screening a compound for effectiveness as a full or partial agonist of an AARS reference polypeptide or an active fragment or variant thereof, comprising a) exposing a sample comprising the polypeptide to a compound, and b) detecting agonist activity in the sample, typically by measuring an increase in the non-canonical activity of the AARS polypeptide. Certain methods include a) exposing a sample comprising a binding partner of the AARS polypeptide to a compound, and b) detecting agonist activity in the sample, typically by measuring an increase in the selected non-canonical activity of the AARS polypeptide. Certain embodiments include compositions that comprise an agonist compound identified by the method and a pharmaceutically acceptable carrier or excipient.

Also included are methods of screening a compound for effectiveness as a full or partial antagonist of an AARS reference polypeptide, comprising a) exposing a sample comprising the polypeptide to a compound, and b) detecting antagonist activity in the sample, typically by measuring a decrease in the non-canonical activity of the AARS polypeptide. Certain methods include a) exposing a sample comprising a binding partner of the AARS polypeptide to a compound, and b) detecting antagonist activity in the sample, typically by measuring a decrease in the selected non-canonical activity of the AARS polypeptide. Certain embodiments include compositions that comprise an antagonist compound identified by the method and a pharmaceutically acceptable carrier or excipient.

In certain embodiments, in vitro systems may be designed to identify compounds capable of interacting with or modulating an AARS reference sequence or its binding partner. Certain of the compounds identified by such systems may be useful, for example, in modulating the activity of the pathway, and in elaborating components of the pathway itself. They may also be used in screens for identifying compounds that disrupt interactions between components of the pathway; or may disrupt such interactions directly. One exemplary approach involves preparing a reaction mixture of the AARS polypeptide and a test compound under conditions and for a time sufficient to allow the two to interact and bind, thus forming a complex that can be removed from and/or detected in the reaction mixture In vitro screening assays can be conducted in a variety of ways. For example, an AARS polypeptide, a cellular binding partner, or test compound(s) can be anchored onto a solid phase. In these and related embodiments, the resulting complex es may be captured and detected on the solid phase at the end of the reaction. In one example of such a method, the AARS polypeptide and/or its binding partner are anchored onto a solid surface, and the test compound(s), which are not anchored, may be labeled, either directly or indirectly, so that their capture by the component on the solid surface can be detected. In other examples, the test compound(s) are anchored to the solid surface, and the AARS polypeptide and/or its binding partner, which are not anchored, are labeled or in some way detectable. In certain embodiments, microtiter plates may conveniently be utilized as the solid phase. The anchored component (or test compound) may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

To conduct an exemplary assay, the non-immobilized component is typically added to the coated surface containing the anchored component. After the reaction is complete, un-reacted components are removed (e.g., by washing) under conditions such that any specific complex es formed will remain immobilized on the solid surface. The detection of complex es anchored on the solid surface can be accomplished in a number of ways. For instance, where the previously non-immobilized component is pre-labeled, the detection of label immobilized on the surface indicates that complex es were formed. Where the previously non-immobilized component is not pre-labeled, an indirect label can be used to detect complex es anchored on the surface; e.g., using a labeled antibody specific for the previously non-immobilized component (the antibody, in turn, may be directly labeled or indirectly labeled with a labeled anti-Ig antibody).

Alternatively, the presence or absence of binding of a test compound can be determined, for example, using surface plasmon resonance (SPR) and the change in the resonance angle as an index, wherein an AARS polypeptide or a cellular binding partner is immobilized onto the surface of a commercially available sensorchip (e.g., manufactured by BIA-CORE™) according to a conventional method, the test compound is contacted therewith, and the sensorchip is illuminated with a light of a particular wavelength from a particular angle. The binding of a test compound can also be measured by detecting the appearance of a peak corresponding to the test compound by a method wherein an AARS polypeptide or a cellular binding partner is immobilized onto the surface of a protein chip adaptable to a mass spectrometer, a test compound is contacted therewith, and an ionization method such as MALDI-MS, ESI-MS, FAB-MS and the like is combined with a mass spectrometer (e.g., double-focusing mass spectrometer, quadrupole mass spectrometer, time-of-flight mass spectrometer, Fourier transformation mass spectrometer, ion cyclotron mass spectrometer and the like).

In certain embodiments, cell-based assays, membrane vesicle-based assays, or membrane fraction-based assays can be used to identify compounds that modulate interactions in the non-canonical pathway of the selected AARS polypeptide. To this end, cell lines that express an AARS polypeptide and/or a binding partner, or a fusion protein containing a domain or fragment of such proteins (or a combination thereof), or cell lines (e.g., COS cells, CHO cells, HEK293 cells, Hela cells etc.) that have been genetically engineered to express such protein(s) or fusion protein(s) can be used. Test compound(s) that influence the non-canonical activity can be identified by monitoring a change (e.g., a statistically significant change) in that activity as compared to a control or a predetermined amount.

For embodiments that relate to antisense and RNAi agents, for example, also included are methods of screening a compound for effectiveness in altering expression of an AARS reference polynucleotide, comprising a) exposing a sample comprising the AARS reference polynucleotide to a compound such as a potential antisense oligonucleotide, and b) detecting altered expression of the AARS polynucleotide. In certain non-limiting examples, these and related embodiments can be employed in cell-based assays or in cell-free translation assays, according to routine techniques in the art. Also included are the antisense and RNAi agents identified by such methods.

Antibodies to AARS protein fragments can also be used in screening assays, such as to identify an agent that specifically binds to an AARS, confirm the specificity or affinity of an agent that binds to an AARS protein fragment, or identify the site of interaction between the agent and the AARS protein fragment. Included are assays in which the antibody is used as a competitive inhibitor of the agent. For instance, an antibody that specifically binds to an AARS protein fragment with a known affinity can act as a competitive inhibitor of a selected agent, and be used to calculate the affinity of the agent for the AARS protein fragment. Also, one or more antibodies that specifically bind to known epitopes or sites of an AARS protein fragment can be used as a competitive inhibitor to confirm whether or not the agent binds at that same site. Other variations will be apparent to persons skilled in the art.

Also included are any of the above methods, or other screening methods known in the art, which are adapted for high-throughput screening (HTS). HTS typically uses automation to run a screen of an assay against a library of candidate compounds, for instance, an assay that measures an increase or a decrease in a non-canonical activity, as described herein.

Any of the screening methods provided herein may utilize small molecule libraries or libraries generated by combinatorial chemistry. Libraries of chemical and/or biological mixtures, such as fungal, bacterial, or algal extracts, are known in the art and can be screened with any of the assays of the invention. Examples of methods for the synthesis of molecular libraries can be found in: (Carell et al., 1994a; Carell et al., 1994b; Cho et al., 1993; DeWitt et al., 1993; Gallop et al., 1994; Zuckermann et al., 1994).

Libraries of compounds may be presented in solution (Houghten et al., 1992) or on beads (Lam et al., 1991), on chips (Fodor et al., 1993), bacteria, spores (Ladner et al., U.S. Pat. No. 5,223,409, 1993), plasmids (Cull et al., 1992) or on phage (Cwirla et al., 1990; Devlin et al., 1990; Felici et al., 1991; Ladner et al., U.S. Pat. No. 5,223,409, 1993; Scott and Smith, 1990). Embodiments of the present invention encompass the use of different libraries for the identification of small molecule modulators of one or more AARS protein fragments, their cellular binding partners, and/or their related non-canonical activities. Libraries useful for the purposes of the invention include, but are not limited to, (1) chemical libraries, (2) natural product libraries, and (3) combinatorial libraries comprised of random peptides, oligonucleotides and/or organic molecules.

Chemical libraries consist of structural analogs of known compounds or compounds that are identified as "hits" or "leads" via natural product screening. Natural product libraries are derived from collections of microorganisms, animals, plants, or marine organisms which are used to create mixtures for screening by: (1) fermentation and extraction of broths from soil, plant or marine microorganisms or (2) extraction of plants or marine organisms. Natural product libraries include polyketides, non-ribosomal peptides, and variants (non-naturally occurring) thereof. See, e.g., Cane et al., *Science* 282: 63-68, 1998. Combinatorial libraries may be composed of large numbers of peptides, oligonucleotides or organic compounds as a mixture. They are relatively easy to prepare by traditional automated synthesis methods, PCR, cloning or proprietary synthetic methods.

More specifically, a combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

For a review of combinatorial chemistry and libraries created therefrom, see, e.g., Huc, I. and Nguyen, R. (2001) Comb. Chem. High Throughput Screen 4:53-74; Lepre, C A. (2001) Drug Discov. Today 6:133-140; Peng, S. X. (2000) Biomed. Chromatogr. 14:430-441; Bohm, H. J. and Stahl, M. (2000) Curr. Opin. Chem. Biol. 4:283-286; Barnes, C and Balasubramanian, S. (2000) Curr. Opin. Chem. Biol. 4:346-350; Lepre, Enjalbal, C, et al., (2000) Mass Septrom Rev. 19:139-161; Hall, D. G., (2000) Nat. Biotechnol. 18:262-262; Lazo, J. S., and Wipf, P. (2000) J. Pharmacol. Ex p. Ther. 293:705-709; Houghten, R. A., (2000) Ann. Rev. Pharmacol. Toxicol. 40:273-282; Kobayashi, S. (2000) Curr. Opin. Chem. Biol. (2000) 4:338-345; Kopylov, A. M. and Spiridonova, V. A. (2000) Mol. Biol. (Mosk) 34:1097-1113; Weber, L. (2000) Curr. Opin. Chem. Biol. 4:295-302; Dolle, R. E. (2000) J. Comb. Chem. 2:383-433; Floyd, C D., et al., (1999) Prog. Med. Chem. 36:91-168; Kundu, B., et al., (1999) Prog. Drug Res. 53:89-156; Cabilly, S. (1999) Mol. Biotechnol. 12:143-148; Lowe, G. (1999) Nat. Prod. Rep. 16:641-651; Dolle, R. E. and Nelson, K. H. (1999) J. Comb. Chem. 1:235-282; Czarnick, A. W. and Keene, J. D. (1998) Curr. Biol. 8:R705-R707; Dolle, R. E. (1998) Mol. Divers. 4:233-256; Myers, P. L., (1997) Curr. Opin. Biotechnol. 8:701-707; and Pluckthun, A. and Cortese, R. (1997) Biol. Chem. 378: 443.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Biosciences, Columbia, Md., etc.).

XII. Methods of Use

Embodiments of the present invention include therapeutic methods of treatment. Accordingly, the AARS agents described herein, including AARS polypeptides, AARS polynucleotides, AARS polynucleotide-based vectors, AARS expressing host cells, antisense oligonucleotides, RNAi agents, as well as binding agents such as peptides, antibodies and antigen-binding fragments, peptide mimetics and other small molecules, can be used to treat a variety of non-limiting diseases or conditions associated with the non-canonical activities of a reference AARS. Examples of such non-canonical activities include modulation of extracellular signaling, modulation of cell proliferation, modulation of cell migration, modulation of cell differentiation (e.g., hematopoiesis, neurogenesis, myogenesis, osteogenesis, and adipogenesis), modulation of apoptosis or other forms of cell death, modulation of angiogenesis, modulation of cell binding, modulation of cellular metabolism, modulation of cytokine production or activity, modulation of cytokine receptor activity, modulation of cellular uptake, or secretion, immunomodulation, modulation of inflammation, modulation of metabolic processes such as glucose control, and the like.

Included are polynucleotide-based therapies, such as antisense therapies and RNAi interference therapies, which typically relate to reducing the expression of a target molecule, such as an endogenous fragment of an AARS, or a cellular binding partner of an AARS polypeptide, which otherwise contributes to its non-canonical activity. Antisense or RNAi therapies typically antagonize the non-canonical activity, such as by reducing expression of the AARS reference polypeptide. Also included are polypeptides or peptides, antibodies or antigen-binding fragment, peptide mimetics, or other small molecule-based therapies, which either agonize or antagonize the non-canonical activity of an AARS reference polypeptide, such as by interacting directly with the AARS polypeptide, its cellular binding partner(s), or both.

These and related embodiments include methods of using the AARS agents or compositions of the present invention for treating a cell, tissue or subject. The cells or tissues that may be treated or modulated by the present invention are preferably mammalian cells or tissues, or more preferably human cells or tissues. Such cells or tissues can be of a healthy state or of a diseased state.

In certain embodiments, for example, methods are provided for modulating therapeutically relevant cellular activities including, but not limited to, cellular metabolism, cell differentiation, cell proliferation, cellular uptake, cell secretion, cell death, cell mobilization, cell migration, gene transcription, mRNA translation, cell impedance, immune responses, inflammatory responses, and the like, comprising contacting a cell with an AARS agent or composition as described herein. In certain embodiments, the cell is in a subject. Accordingly, the AARS compositions may be employed in treating essentially any cell or tissue or subject that would benefit from modulation of one or more such activities.

The AARS agents and compositions may also be used in any of a number of therapeutic contexts including, for example, those relating to the treatment or prevention of neoplastic diseases, immune system diseases or conditions (e.g., autoimmune diseases and inflammation), infectious diseases, metabolic diseases, neuronal/neurological diseases, muscular/cardiovascular diseases, diseases associated with aberrant hematopoiesis, diseases associated with aberrant myogenesis, diseases associated with aberrant neurogenesis, diseases associated with aberrant adipogenesis, diseases associated with aberrant osteogenesis, diseases associated with aberrant angiogenesis, diseases associated with aberrant cell survival, diseases associated with aberrant lipid uptake, diseases associated with aging (e.g., hearing loss, peripheral or autonomic neuropathies, senile dementia, retinopathy) and others.

For example, in certain illustrative embodiments, the AARS compositions of the invention may be used to modulate angiogenesis, e.g., via modulation of endothelial cell proliferation and/or signaling. Endothelial cell proliferation and/or signaling may be monitored using an appropriate cell line (e.g., human microvascular endothelial lung cells (HM-VEC-L) and human umbilical vein endothelial cells (HU-VEC)), and using an appropriate assay (e.g., endothelial cell migration assays, endothelial cell proliferation assays, tube-forming assays, matrigel plug assays, etc.), many of which are known and available in the art.

Therefore, in related embodiments, the compositions of the invention may be employed in the treatment of essentially any cell or tissue or subject that would benefit from modulation of angiogenesis. For example, in some embodiments, a cell or tissue or subject experiencing or susceptible to angiogenesis (e.g., an angiogenic condition) may be contacted with a suitable composition of the invention to inhibit an angiogenic condition. In other embodiments, a cell or tissue experiencing or susceptible to insufficient angiogenesis (e.g., an angiostatic condition) may be contacted with an appropriate composition of the invention in order to interfere with angiostatic activity and/or promote angiogenesis.

Also included are methods of modulating hematopoiesis and related conditions. Examples of hematopoietic processes that may be modulated by the AARS polypeptides of the invention include, without limitation, the formation of myeloid cells (e.g., erythroid cells, mast cells monocytes/macrophages, myeloid dendritic cells, granulocytes such as basophils, neutrophils, and eosinophils, megakaryocytes, platelets) and lymphoid cells (e.g., natural killer cells, lymphoid dendritic cells, B-cells, and T-cells). Certain specific hematopoietic processes include erythropoiesis, granulopoiesis, lymphopoiesis, megakaryopoiesis, thrombopoiesis, and others. Also included are methods of modulating the trafficking or mobilization of hematopoietic cells, including hematopoietic stem cells, progenitor cells, erythrocytes, granulocytes, lymphocytes, megakaryocytes, and thrombocytes.

The methods of modulating hematopoiesis may be practiced in vivo, in vitro, ex vivo, or in any combination thereof. These methods can be practiced on any biological sample, cell culture, or tissue that contains hematopoietic stem cells, hematopoietic progenitor cells, or other stem or progenitor cells that are capable of differentiating along the hematopoietic lineage (e.g., adipose tissue derived stem cells). For in vitro and ex vivo methods, stem cells and progenitor cells, whether of hematopoietic origin or otherwise, can be isolated and/or identified according to the techniques and characteristics described herein and known in the art.

The compositions of the invention may also be useful as immunomodulators for treating anti- or pro-inflammatory indications by modulating the cells that mediate, either directly or indirectly, autoimmune and/or inflammatory diseases, conditions and disorders. The utility of the compositions of the invention as immunomodulators or modulators of inflammation can be monitored using any of a number of known and available techniques in the art including, for example, migration assays (e.g., using leukocytes or lymphocytes) or cell viability assays (e.g., using B-cells, T-cells, monocytes or NK cells).

"Inflammation" refers generally to the biological response of tissues to harmful stimuli, such as pathogens, damaged cells (e.g., wounds), and irritants. The term "inflammatory response" refers to the specific mechanisms by which inflammation is achieved and regulated, including, merely by way of illustration, immune cell activation or migration, cytokine production, vasodilation, including kinin release, fibrinolysis, and coagulation, among others described herein and known in the art.

Clinical signs of chronic inflammation are dependent upon duration of the illness, inflammatory lesions, cause and anatomical area affected. (see, e.g., Kumar et al., Robbins Basic Pathology—$8^{th}$ Ed., 2009 Elsevier, London; Miller, L M, Pathology Lecture Notes, Atlantic Veterinary College, Charlottetown, PEI, Canada). Chronic inflammation is associated with a variety of pathological conditions or diseases, including, for example, allergies, Alzheimer's disease, anemia, aortic valve stenosis, arthritis such as rheumatoid arthritis and osteoarthritis, cancer, congestive heart failure, fibromyalgia, fibrosis, heart attack, kidney failure, lupus, pancreatitis, stroke, surgical complications, inflammatory lung disease, inflammatory bowel disease, atherosclerosis, neurological disorders, diabetes, metabolic disorders, obesity, and psoriasis, among others described herein and known in the art. Hence, AARS compositions may be used to treat or manage chronic inflammation, modulate any of one or more of the individual chronic inflammatory responses, or treat any one or more diseases or conditions associated with chronic inflammation.

Criteria for assessing the signs and symptoms of inflammatory and other conditions, including for purposes of making differential diagnosis and also for monitoring treatments such as determining whether a therapeutically effective dose has been administered in the course of treatment, e.g., by determining improvement according to accepted clinical criteria, will be apparent to those skilled in the art and are exemplified by the teachings of e.g., Berkow et al., eds., The Merck Manual, $16^{th}$ edition, Merck and Co., Rahway, N.J., 1992; Goodman et al., eds., Goodman and Gilman's The Pharmacological Basis of Therapeutics, $10^{th}$ edition, Pergamon Press, Inc., Elmsford, N.Y., (2001); Avery's Drug Treatment: Principles and Practice of Clinical Pharmacology and Therapeutics, 3rd edition, ADIS Press, Ltd., Williams and Wilkins, Baltimore, Md. (1987); Ebadi, Pharmacology, Little, Brown and Co., Boston, (1985); Osolci al., eds., Remington's Pharmaceutical Sciences, $18^{th}$ edition, Mack Publishing Co., Easton, Pa. (1990); Katzung, Basic and Clinical Pharmacology, Appleton and Lange, Norwalk, Conn. (1992).

In other embodiments, the AARS compositions of the invention may be used to modulate cellular proliferation and/or survival and, accordingly, for treating or preventing diseases, disorders or conditions characterized by abnormalities in cellular proliferation and/or survival. For example, in certain embodiments, the AARS compositions may be used to modulate apoptosis and/or to treat diseases or conditions associated with abnormal apoptosis. Apoptosis can be monitored by any of a number of available techniques known and available in the art including, for example, assays that measure fragmentation of DNA, alterations in membrane asymmetry, activation of apoptotic caspases and/or release of cytochrome C and AIF.

Embodiments of the present invention include methods of treating and preventing diseases associated with the mutation, in appropriate subcellular association, over expression, or subcellular distribution of the parental aminoacyl-tRNA synthetase (See generally Park et al., (2008) PNAS 105 (32) 11043-11049).

Examples of diseases associated with the mutation of aminoacyl-tRNA synthetases include for example Charcot-Marie-Tooth Disease and Distal Spinal Muscular Atrophy Type V which are caused by mutations in Glycyl tRNA synthetase, Lysyl tRNA synthetase and Tyrosyl tRNA synthetase, as well as other aminoacyl-tRNA synthetases, diabetic nephropathy associated with mutations in Cysteinyl tRNA synthetase (Pezzolesi et al., (2009) Diabetes 58 1403-1410) and leukoenchalopathy associated with mutations in mitochrondrial Aspartyl tRNA synthetase. Examples of diseases caused by inappropriate subcellular association of aminoacyl-tRNA synthetases include for example, the interaction of Lysyl tRNA synthetase with superoxide dismutase 1 in Amyotrophic Lateral Sclerosis (ALS) (Banks et al., (2009) PLOSone 4(7)e6218 1-12), and the interaction of AIMP2 (p38) with Parkin in Parkinson's disease (Choi et al., (2011) 7(3)e1001351 1-13). Examples of diseases caused by, or associated with, the over expression of tRNA synthetases, include for example, the association of various aminoacyl-tRNA synthetases, including methionyl, cysteinyl, isoleucyl, glutamyl-prolyl, phenylalanyl, glycyl, lysyl, tyrosyl and tryptophanyl tRNA synthetases in cancer development and progression (Kushner et al., (1976) Proc. Soc. Ex p. Biol. Med. 153 273-276; Wasenius et al., (2003) Clin. Cancer. Res. 9 68-75; Scandurro et al., (2001) Int. J. Oncol. 19 129-135; Park (2005) PNAS 102 6356-6361; Park et al., (2008) PNAS 105 (32) 11043-11049).

Thus in certain embodiments, the present invention provides soluble AARS protein fragments, that exhibit favorable protein stability and aggregation characteristics, and the ability to be expressed and produced at high level in prokaryotic expression systems, which can be used to complement, or suppress the activity of a parental tRNA synthetase associated with a disease.

Accordingly the present invention also includes therapeutic methods for the use of such AARS protein fragments for the treatment and prevention of diseases associated with aminoacyl-tRNA synthetases. Without being bound by any particular theory of operation, it is believed that such AARS protein fragments may act to complement a lost function of a mutant aminoacyl-tRNA synthetase, or suppress a change in the conformation, rigidity, or dimerization state of a mutant AARS, or act as a decoy to a second molecule which would otherwise inappropriately interact with the wild type or mutant AARS.

In certain embodiments, such therapeutic methods include the administration of one or more of the Lysyl AARS protein fragments as set forth in any of Table(s) 1-3, or Table(s) 4-6, or Table(s) 7-9, or Table(s) 10-12, or Table E2, to a subject which has, or is at risk of developing, a disease which is characterized by the mutation, inappropriate subcellular association, over expression, or subcellular distribution of a Lysyl tRNA synthetase.

In certain embodiments, such AARS protein fragments may be used to develop antibodies and binding agents which enable the development of antibodies and binding agents to novel cryptic epitopes which may also act to suppress a disease phenotype associated with the parental aminoacyl-tRNA synthetase. Accordingly certain embodiments, include the administration of one or more antibodies or binding agents to the Lysyl AARS polypeptides as set forth in any of Table(s) 1-3, or Table(s) 4-6, or Table(s) 7-9, or Table(s) 10-12, or Table E2, to a subject which has, or is at risk of developing a disease which is characterized by the mutation, inappropriate subcellular association, over expression, or subcellular distribution of a Lysyl tRNA synthetase.

Specific Examples of diseases associated with the mutation of Lysyl tRNA synthetase that can be treated with the AARS polypeptides of the present invention include for example, distal spinal muscular atrophies (dSMA) and distal hereditary motor neuropathies (dHMN), such as Charcot-Marie-Tooth Disease Type 2D (CMT2D) and Distal Spinal Muscular Atrophy Type V (dSMA-V), among others described herein and known in the art. See, e.g., Sivakamur et al., Brain. 128:2304-2314, 2005; and Antonellis et al., Am. J. Hum. Genet. 72:1293-1299, 2003.

Distal spinal muscular atrophies (dSMA) and distal hereditary motor neuropathies (dHMNs) such as CMT represent a group of inherited disorders that affect the peripheral nerves (i.e., the nerves outside the brain and spine). These diseases can be characterized by slowly progressive muscle weakness and atrophy in the distal parts of the limbs caused, for example, by progressive anterior horn cell degeneration, among other processes. CMT Type 1 (CMT1) is a peripheral motor and sensory demyelinating neuropathy caused, for example, by degeneration of Schwann cells, and CMT Type 2 (CMT2) is typically characterized by primary axonal degeneration. CMT2 is often characterized by distal muscular atrophy, reduced compound motor action potentials, and/or reduced sensory nerve action potentials, but normal or mildly slowed motor nerve conduction velocity.

CMT disease is also known as known also as Morbus Charcot-Marie-Tooth, Charcot-Marie-Tooth neuropathy, hereditary motor and sensory neuropathy (HMSN), hereditary motor neuropathy type V (dHMN-V), hereditary sensor and motor neuropathy (HSMN), and peroneal muscular atrophy. Currently incurable, this family of diseases is one of the most common inherited neurological disorders, with an estimated 1 in 2500 individuals affected (see, e.g., Krajewski et al., Brain. 123:1516-27, 2000; and Skre, Clin. Genet. 6:98-118, 1974).

In certain embodiments, the invention includes a method of treating a subject which has, or is at risk of developing, a CMT disease such as CMT1 or CMT2 (including CMT2D), or dSMA-V, which is characterized by one or more mutations in Lysyl tRNA synthetase, comprising the step of administering one or more of the Lysyl AARS protein fragments as set forth in any of Table(s) 1-3, or Table(s) 4-6, or Table(s) 7-9, or Table(s) 10-12, or Table E2, or an antibody, or binding agent directed to any of the Lysyl AARS protein fragments as set forth in any of Table(s) 1-3, or Table(s) 4-6, or Table(s) 7-9, or Table(s) 10-12, or Table E2, which treats, or reduces the risk of developing, one or more symptoms of that disease.

Further to the characteristics described above, exemplary clinical symptoms of neuronal diseases such as CMT include, without limitation, foot deformity (very high arch to feet), foot drop (inability to hold foot horizontal), loss of lower leg muscle, leading to skinny calves, numbness in the foot or leg, "slapping" gait (feet hit the floor hard when walking), and weakness of the hips, legs, or feet. These symptoms often present between mid-childhood and early adulthood. Later, similar symptoms may appear in the arms and hands, including, for example, claw-like hand deformities. Also included are complications such as a progressive inability to walk, a progressive weakness, and injury to areas of the body that have decreased sensation. Accordingly, the Lysyl polypeptides, antibodies, binding agents, and other compounds described herein may reduce or ameliorate any one or more of these characteristics, symptoms or complications of neuronal diseases such as dSMA and dHMN, including CMT disease such as CMT1 and CMT2 (including CMT2D).

Neuronal diseases such as CMT can be diagnosed according to routine techniques in the art. For example, physical examination may be used to observe signs such as difficulty lifting up the foot and making toe-out movements, lack of stretch reflexes in the legs, loss of muscle control and atrophy (shrinking of the muscles) in the foot or leg, and thickened nerve bundles under the skin of the legs. Muscle biopsies and/or nerve biopsies may be used to confirm a diagnosis, and nerve conduction tests can be used to tell the difference between different forms of the disease.

In certain embodiments, the invention includes a method of treating a subject which has, or is at risk of developing a cancer which is characterized by the over expression of Lysyl tRNA synthetase, comprising the step of administering one or more of the Lysyl AARS protein fragments as set forth in any of Table(s) 1-3, or Table(s) 4-6, or Table(s) 7-9, or Table(s) 10-12, or Table E2, or an antibody, or binding agent directed to any of the Lysyl AARS protein fragments as set forth in any of Table(s) 1-3, or Table(s) 4-6, or Table(s) 7-9, or Table(s) 10-12, or Table E2, which treats, or reduces the risk of developing, or the recurrence of cancer. In certain embodiments, the cancer is breast cancer.

In certain embodiments, the invention includes a method of treating a subject which has, or is at risk of developing ALS which is characterized by the interaction of Lysyl tRNA synthetase with superoxide dismutase 1, comprising the step of administering one or more of the Lysyl AARS protein fragments as set forth in any of Table(s) 1-3, or Table(s) 4-6, or Table(s) 7-9, or Table(s) 10-12, or Table E2, or an antibody, or binding agent directed to any of the Lysyl AARS protein fragments as set forth in any of Table(s) 1-3, or Table(s) 4-6, or Table(s) 7-9, or Table(s) 10-12, or Table E2, which treats, or reduces the risk of developing, or the recurrence of ALS.

The progress of these and other therapies (e.g., ex vivo therapies) can be readily monitored by conventional methods and assays and based on criteria known to the physician or other persons of skill in the art.

XIII. Pharmaceutical Formulations, Administration and Kits

Embodiments of the present invention include AARS polynucleotides, AARS polypeptides, host cells expressing AARS polypeptides, binding agents, modulatory agents, or other compounds described herein, formulated in pharmaceutically-acceptable or physiologically-acceptable solutions for administration to a cell or an animal, either alone, or in combination with one or more other modalities of therapy. It will also be understood that, if desired, the compositions of the invention may be administered in combination with other agents as well, such as, e.g., other proteins or polypeptides or various pharmaceutically-active agents. There is virtually no limit to other components that may also be included in the compositions, provided that the additional agents do not adversely affect the modulatory or other effects desired to be achieved.

In the pharmaceutical compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, subcutaneous, and intramuscular administration and formulation.

In certain applications, the pharmaceutical or therapeutic compositions of the invention do not stimulate an immune reaction. In other embodiments, the pharmaceutical or therapeutic compositions of the invention, typically comprising one or more AARS polypeptides or polynucleotides, stimulate an immune reaction, such as by serving as an adjuvant in a vaccine or related composition, or being present in a composition together with a separate adjuvant or agent stimulates an immune response.

In certain embodiments, the AARS agents such as AARS polypeptides, AARS polynucleotides, and antibodies have a solubility that is desirable for the particular mode of administration, such intravenous administration. Examples of desirable solubilities include at least about 1 mg/ml, at least about 10 mg/ml, at least about 25 mg/ml, and at least about 50 mg/ml.

In certain applications, the pharmaceutical compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the pharmaceutical compositions disclosed herein parenterally, subcutaneously, intravenously, intramuscularly, intra-arterially, intrathecally, intraparenchymally, intracisternally, intraventricularlly, intraurethrally, intrasternally, intracranially, intrasynovially, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Suitable devices for parenteral administration include needle (including microneedle) injectors, needle-free injectors, and infusion techniques.

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences*, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions can be prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the pharmaceutical compositions may be delivered by intranasal sprays, inhalation, and/or other aerosol delivery vehicles. Methods for delivering genes, polynucleotides, and peptide compositions directly to the lungs via nasal aerosol sprays have been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The pharmaceutical compositions may be formulated to be immediate and/or sustained release. Sustained release compositions include delayed, modified, pulsed, controlled, targeted and programmed release. Thus the compositions may be formulated as a suspension or as a solid, semi-solid, or thixotropic liquid for administration as an implanted depot providing sustained release of the AARS polynucleotides, AARS polypeptides, binding agents, modulatory agents and other active agents. Examples of such formulations include without limitation, drug-coated stents and semi-solids and suspensions comprising drug-loaded poly(DL-lactic-co-glycolic)acid (PGLA), poly(DL-lactide-co-glycolide) (PLG) or poly(lactide) (PLA) lamellar vesicles or microparticles, hydrogels (Hoffman A S: Ann. N.Y. Acad. Sci. 944: 62-73 (2001)), poly-amino acid nanoparticles systems, sold under the trademark MEDUSA® developed by Flamel Technologies Inc., non aqueous gel systems sold under the trademark ATRIGEL® developed by Atrix, Inc., and Sucrose Acetate Isobutyrate Extended Release formulations sold under the trademark SABER® developed by Durect Corporation, and lipid-based systems developed by SkyePharma and sold under the trademark DEPOFOAM®.

Sustained release devices capable of delivering desired doses of the pharmaceutical compositions over extended periods of time are known in the art. For example, U.S. Pat. Nos. 5,034,229; 5,557,318; 5,110,596; 5,728,396; 5,985,305; 6,113,938; 6,156,331; 6,375,978; and 6,395,292; teach osmotically-driven devices capable of delivering an active agent formulation, such as a solution or a suspension, at a desired rate over an extended period of time (i.e., a period ranging from more than one week up to one year or more). Other exemplary sustained release devices include regulator-type pumps that provide constant flow, adjustable flow, or programmable flow of beneficial agent formulations, which are available from Medtronic including the Intrathecal pumps sold under the trademark SYNCHROMED INFUSION SYSTEM®, the Johnson and Johnson systems sold under the trademark CODMAN® division pumps, and INSET® technologies pumps. Further examples of devices are described in U.S. Pat. Nos. 6,283,949; 5,976,109; 5,836,935; and 5,511,355.

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

In certain embodiments, the agents provided herein may be attached to a pharmaceutically acceptable solid substrate, including biocompatible and biodegradable substrates such as polymers and matrices. Examples of such solid substrates include, without limitation, polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as poly(lactic-co-glycolic acid) (PLGA) and the LUPRON DEPOT™ (injectable microspheres composed of lactic acid-glycolic acid copolymer and leuprolide acetate), poly-D-(−)-3-hydroxybutyric acid, collagen, metal, hydroxyapatite, bioglass, aluminate, bioceramic materials, and purified proteins.

In one particular embodiment, the solid substrate comprises biodegradable polymers sold under the trademark ATRIGEL™ (QLT, Inc., Vancouver, B.C.). The ATRIGEL® drug delivery system consists of biodegradable polymers dissolved in biocompatible carriers. Pharmaceuticals may be blended into this liquid delivery system at the time of manufacturing or, depending upon the product, may be added later by the physician at the time of use. When the liquid product is injected into the subcutaneous space through a small gauge needle or placed into accessible tissue sites through a cannula, water in the tissue fluids causes the polymer to precipitate and trap the drug in a solid implant. The drug encapsulated within the implant is then released in a controlled manner as the polymer matrix biodegrades with time.

Pharmaceutical compositions for use in the present invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages, and microemulsions. Liposomes may also be used. Typical carriers include alcohol, water, mineral oil, liquid petrolatum, white petrolatum, glycerin, polyethylene glycol, and propylene glycol. Penetration enhancers may be incorporated—see, e.g., Finnin and Morgan: J. Pharm. Sci. 88(10): 955-958, (1999). Other means of topical administration include delivery by electroporation, iontophoresis, phonophoresis, sonophoresis, and microneedle or needle-free injection for example using the systems sold under the trademarks POWDERJECT™, and BIOJECT™.

Methods of formulation are well known in the art and are disclosed, for example, in Remington: The Science and Practice of Pharmacy, Mack Publishing Company, Easton, Pa., 20th edition, ISBN: 0683306472 (2000). The compositions and agents provided herein may be administered according to the methods of the present invention in any therapeutically effective dosing regimen. The dosage amount and frequency are selected to create an effective level of the agent without harmful effects. The effective amount of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

In particular embodiments, the amount of a composition or agent administered will generally range from a dosage of from about 0.1 to about 100 mg/kg/day, and typically from about 0.1 to 10 mg/kg where administered orally or intravenously. In particular embodiments, a dosage is 5 mg/kg or 7.5 mg/kg. In various embodiments, the dosage is about 50-2500 mg per day, 100-2500 mg/day, 300-1800 mg/day, or 500-1800 mg/day. In one embodiment, the dosage is between about 100 to 600 mg/day. In another embodiment, the dosage is between about 300 and 1200 mg/day. In particular embodiments, the composition or agent is administered at a dosage of 100 mg/day, 240 mg/day 300 mg/day, 600 mg/day, 1000 mg/day, 1200 mg/day, or 1800 mg/day, in one or more doses per day (i.e., where the combined doses achieve the desired daily dosage). In related embodiments, a dosage is 100 mg bid, 150 mg bid, 240 mg bid, 300 mg bid, 500 mg bid, or 600 mg bid. In various embodiments, the composition or agent is administered in single or repeat dosing. The initial dosage and subsequent dosages may be the same or different.

In certain embodiments, a composition or agent is administered in a single dosage of 0.1 to 10 mg/kg or 0.5 to 5 mg/kg. In other embodiments, a composition or agent is administered in a dosage of 0.1 to 50 mg/kg/day, 0.5 to 20 mg/kg/day, or 5 to 20 mg/kg/day.

In certain embodiments, a composition or agent is administered orally or intravenously, e.g., by infusion over a period of time of about, e.g., 10 minutes to 90 minutes. In other related embodiments, a composition or agent is administered by continuous infusion, e.g., at a dosage of between about 0.1 to about 10 mg/kg/hr over a time period. While the time period can vary, in certain embodiments the time period may be between about 10 minutes to about 24 hours or between about 10 minutes to about three days.

In particular embodiments, an effective amount or therapeutically effective amount is an amount sufficient to achieve a total concentration of the composition or agent in the blood plasma of a subject with a $C_{max}$ of between about 0.1 µg/ml and about 20 µg/ml or between about 0.3 µg/ml and about 20 µg/ml. In certain embodiments, an oral dosage is an amount sufficient to achieve a blood plasma concentration ($C_{max}$) of between about 0.1 µg/ml to about 5 µg/ml or between about 0.3 µg/ml to about 3 µg/ml. In certain embodiments, an intravenous dosage is an amount sufficient to achieve a blood plasma concentration ($C_{max}$) of between about 1 µg/ml to about 10 µg/ml or between about 2 µg/ml and about 6 µg/ml. In a related embodiment, the total concentration of an agent in the blood plasma of the subject has a mean trough concentration of less than about 20 µg/ml and/or a steady state concentration of less than about 20 µg/ml. In a further embodiment, the total concentration of an agent in the blood plasma of the subject has a mean trough concentration of less than about 10 µg/ml and/or a steady state concentration of less than about 10 µg/ml.

In yet another embodiment, the total concentration of an agent in the blood plasma of the subject has a mean trough concentration of between about 1 ng/ml and about 10 µg/ml and/or a steady state concentration of between about 1 ng/ml and about 10 µg/ml. In one embodiment, the total concentration of an agent in the blood plasma of the subject has a mean trough concentration of between about 0.3 µg/ml and about 3 µg/ml and/or a steady state concentration of between about 0.3 µg/ml and about 3 µg/ml.

In particular embodiments, a composition or agent is administered in an amount sufficient to achieve in the mammal a blood plasma concentration having a mean trough concentration of between about 1 ng/ml and about 10 µg/ml and/or a steady state concentration of between about 1 ng/ml and about 10 µg/ml. In related embodiments, the total concentration of the agent in the blood plasma of the mammal has a mean trough concentration of between about 0.3 µg/ml and about 3 µg/ml and/or a steady state concentration of between about 0.3 µg/ml and about 3 µg/ml.

In particular embodiments of the present invention, the effective amount of a composition or agent, or the blood plasma concentration of composition or agent is achieved or maintained, e.g., for at least 15 minutes, at least 30 minutes, at least 45 minutes, at least 60 minutes, at least 90 minutes, at least 2 hours, at least 3 hours, at least 4 hours, at least 8 hours, at least 12 hours, at least 24 hours, at least 48 hours, at least 3 days, at least 4 days, at least 5 days, at least 6 days, at least one week, at least 2 weeks, at least one month, at least 2 months, at least 4 months, at least 6 months, at least one year, at least 2 years, or greater than 2 years.

In certain polypeptide-based embodiments, the amount of polypeptide administered will typically be in the range of about 0.1 µg/kg to about 0.1 mg/kg to about 50 mg/kg of patient body weight. Depending on the type and severity of the disease, about 0.1 µg/kg to about 0.1 mg/kg to about 50 mg/kg body weight (e.g., about 0.1-15 mg/kg/dose) of polypeptide can be an initial candidate dosage for administration to the patient, whether, for example, by one or more separate administrations, or by continuous infusion. For example, a dosing regimen may comprise administering an initial loading dose of about 4 mg/kg, followed by a weekly maintenance dose of about 2 mg/kg of the polypeptide, or about half of the loading dose. However, other dosage regimens may be useful. A typical daily dosage might range from about 0.1 µg/kg to about 1 µg/kg to 100 mg/kg or more, depending on the factors mentioned above. For repeated administrations over several days or longer, depending on the condition, the treatment is sustained until a desired suppression of disease symptoms occurs.

In particular embodiments, the effective dosage achieves the blood plasma levels or mean trough concentration of a composition or agent described herein. These may be readily determined using routine procedures.

Embodiments of the present invention, in other aspects, provide kits comprising one or more containers filled with one or more of the polypeptides, polynucleotides, antibodies, multiunit complex es, compositions thereof, etc., of the invention, as described herein. The kits can include written instructions on how to use such compositions (e.g., to modulate cellular signaling, angiogenesis, cancer, inflammatory conditions, diagnosis etc.).

The kits herein may also include a one or more additional therapeutic agents or other components suitable or desired for the indication being treated, or for the desired diagnostic application. An additional therapeutic agent may be contained in a second container, if desired. Examples of additional therapeutic agents include, but are not limited to anti-neoplastic agents, anti-inflammatory agents, antibacterial agents, antiviral agents, angiogenic agents, etc.

The kits herein can also include one or more syringes or other components necessary or desired to facilitate an intended mode of delivery (e.g., stents, implantable depots, etc.).

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

XIV. Examples

General Methods

Unless indicated otherwise in the examples below, the following general methods for gene optimization, small and large scale protein expression, protein purification, transcriptional profiling and screening were used to make and characterize the AARS polypeptides described in the Examples below.

Gene Synthesis and Cloning into Expression Vectors

Polynucleotide sequences encoding epitope tagged versions of the AARS polypeptides were codon optimized and cloned into bacterial expression vectors using the methods listed below.

In method (1), E. coli codon-optimized DNA (Welch et al., PLoS ONE 4(9): e7007 doi:10.1371/journal.pone.0007002) encoding each AARS polypeptide is synthesized by DNA 2.0 (Menlo Park, Calif.), and two versions of each AARS polypeptide are synthesized, containing either an N-terminal, or C-terminal combined epitope tag comprising both a six histidine tag and V5 epitope tag.

DNA encoding the N-terminally tagged AARS polypeptides is synthesized with a 5' extension encoding in 5' to 3' orientation, a ribosome binding site (rbs (underlined below)), NdeI restriction site, six histidine tag, and a V5 epitope tag, (AGGAGGTAAAACATATGCATCATCATCATCATCACGGTAAGCCTATCCCTAACCCTTTGCTCGGTCTCGATTCTACG) (SEQ. ID. No. 1), which is fused in frame to the predicted AARS polypeptide open reading frame. In cases where the AARS polypeptide comprises a predicted native initiation methionine (ATG) residue, or the first amino acid residue of the predicted AARS polypeptide is Met, this was deleted. At the end of the predicted AARS polypeptide open reading frame, two stop codons and a XhoI site (TAATGACTCGAG) (SEQ. ID. No. 2) are added.

DNA encoding the C-terminally tagged AARS polypeptides is synthesized with a 5' extension encoding a rbs (underlined below) and NdeI restriction site that either recapitulates the predicted native start codon for the AARS polypeptide, or inserts an ATG in frame with the predicted AARS polypeptide open reading frame, (AGGAGATAAAACATATG) (SEQ. ID. No. 3). In different embodiments, the ribosome binding site can comprise the sequences "AGGAGGTAAAACAT" (SEQ. ID. No. 4), "AGGAGATAAAACAT" (SEQ. ID. No. 5), or GAAGGAGATATACAT (SEQ. ID. No. 6). At the 3' end of the predicted AARS polypeptide open reading frame, a 3' extension is synthesized which encodes in 5' to 3' order, a V5 epitope tag, six histidine tag, two stop codons and a XhoI site, (GGTAAGCCTATCCCTAACCCTCTCCTCGGTCTCGATTCTACGCACCACCATC ATCACCATTAATGACTCGAG) (SEQ. ID. No. 7), which is fused in frame to the predicted AARS polypeptide open reading frame. If the AARS polypeptide included a predicted native stop codon, this was deleted.

Synthesized DNA sequences encoding the AARS polypeptides are subcloned into pJExpress411 vector (DNA 2.0). After sequencing to confirm synthesis of the correct product, expression vectors are transformed into bacteria for protein expression as described more fully below.

In method (2), E. coli codon-optimized DNA (Ermolaeva M D (2001) Curr. Iss. Mol. Biol. 3 (4) 91-7) encoding each AARS polypeptide is synthesized by GENEWIZ (South Plainfield, N.J.). Each polynucleotide sequence encoding the AARS polypeptide was synthesized with short 5' and 3' extensions comprising unique restriction sites for subsequent cloning.

Specifically a BamHI restriction site was inserted at the 5' end of the predicted open reading frame. In cases where the AARS polypeptide comprises a predicted native initiation methionine residue (ATG), or the first amino acid residue of the predicted AARS polypeptide is Met, this was deleted. Additionally a XhoI restriction site was inserted at the 3' end of the predicted open reading frame. In cases where the AARS polypeptide comprises a predicted native stop codon, this was deleted.

After restriction digestion, the resulting DNA sequences are subcloned into modified pET-24b vectors (EMD, Gibbstown, N.J.) containing either an N-terminal (pET24b_N-6×His/V5), or C-terminal (pET24b_C-V5/6×His) combined epitope tag comprising both a six histidine and V5 epitope tag (vector modification by GENEWIZ, (South Plainfield, N.J.).

After restriction digestion, and cloning, the DNA encoding the N-tagged AARS polypeptide is cloned into the N-tagged vector (pET24b_N-6×His/V5), which comprises a 5' DNA sequence encoding six histidines and a V5 epitope tag, (CATATGCATCATCATCATCATCACGGTAAGCCTATCCCTAACCCTCTCCTCGGTCTCGATTCTACGGGATCC) (SEQ. ID. No. 8), in frame with an initiation codon (ATG) embedded within the NdeI restriction site. This 5' extension is fused to the predicted AARS polypeptide open reading frame through a short 2 amino acid linker (GS).

At the 3' end of the predicted open reading frame, the DNA encoding the N-tagged AARS polypeptide comprises a DNA sequence encoding a 2 amino acid extension (LE) followed by two termination codons (CTCGAGTAATGA) (SEQ. ID. No. 9).

After restriction digestion, and cloning, the DNA encoding the C-tagged AARS polypeptide cloned into the C-tagged vector (pET24b_C-V5/6×His), comprises a 5' sequence encoding an initiation codon (ATG) embedded within the NdeI restriction site which is fused to the predicted AARS polypeptide open reading frame through a short 2 amino acid linker (GS), (CATATGGGATCC) (SEQ. ID. No. 10).

At the 3' end of the predicted open reading frame, the DNA encoding the C-tagged AARS polypeptide comprises a 3' DNA sequence encoding a short linker 2 amino acid linker (LE) followed by a V5 epitope tag followed by six histidines, and two stop codons, CTCGAGGGTAAGCCTATC-CCTAACCCTCTCCTCGGTCTCGATTCTACGCACC ACCACCACCACCACTAATGA (SEQ. ID. No. 11).

AARS Polypeptide Expression, Purification and Biophysical Characterization

6×His-tagged AARS polypeptides are expressed in bacteria in a medium-throughput format and/or in larger scale flask cultures depending upon the amount of protein required. AARS polypeptides are purified using affinity and ion exchange chromatography as described below, and as specified for specific experiments.

Bacterial Cultures:

100 ng of expression vector comprising codon optimized DNA encoding each AARS polypeptide (as described above) is transformed into BL21(DE3) (EMD chemicals, cat. no. 69450) competent E. coli bacteria at 42° C. for 30 seconds in PCR plates. C41(DE3) (Lucigen, cat. no. 60442), HMS174 (DE3) (EMD chemicals, cat. no. 69453) and Origami2(DE3) (EMD chemicals, cat. no. 71345) strains are also evaluated. The plates are placed on ice for 2 minutes and 100 µL of SOC medium is added, followed by a 1-hour incubation at 37° C. 5 mL of auto-induction medium (EMD chemicals, cat. no. 71491) supplemented with kanamycin (100 µg/mL) is added into each well of a 24-well block (Qiagen, cat. no. 19583). The transformation reactions are added to the individual wells, the block is sealed with adhesive film (VWR, cat. no 60941-078) and incubated overnight at 250 rpm in a 37° C. shaker. When low temperature (25° C.) conditions are used, incubation is carried out for 48 hours instead.

For larger scale expression, 200 mL of auto-induction medium supplemented with kanamycin (100 µg/mL) is added into 500-mL Erlenmeyer flasks with vent caps (Corning, cat. no. 431401). The transformation reactions are added to the individual flasks and incubated for 30 hours at 250 rpm in a 37° C. shaker.

Protein Isolation:

After the culture reached stationary phase (typical $OD_{600}$ of 3-6), the blocks are centrifuged at 3600×g for 10 minutes. The medium is carefully aspirated and the blocks are frozen at −80° C. or −20° C. for 10 minutes. The blocks are then allowed to thaw at room temperature and 1 mL lysis buffer (100 mL Bugbuster supplemented with 200 µL lysonase (EMD chemicals, cat. no 71370) and protease inhibitors "complete mini EDTA-free" (Roche, cat. no. 11 836 170 001)) is added into each well. The pellets are resuspended by repeat pipetting until no clump is visible and transferred to eppendorf tubes, followed by a 10-20 minute incubation on a shaker at room temperature. After centrifugation at 16,000 g for 10 minutes at 4° C., the lysates are loaded onto a Turbo-Filter 96 Plate included in the Ni-NTA Superflow 96 BioRobot Kit (Qiagen, cat. no. 969261) and centrifuged at 500 g for 5-10 minutes.

For larger scale expression, the stationary phase culture is transferred into 500-mL bottles and centrifuged at 6,000 g for 10 minutes. The medium is decanted and the pellet is stored at −80° C. or −20° C. before further processing. The pellet is then allowed to thaw at room temperature and 20 mL lysis buffer is added into each bottle. The pellets are resuspended by repeat pipetting until no clump is visible, followed by 20 minute incubation on a shaker at room temperature. After centrifugation at 10,000 g for 30 minutes at 4° C., the lysates are transferred to clean tubes or bottles. If trace amounts of debris are carried over during the transfer, the sample is centrifuged again or passed through a 0.45 µm cellulose acetate membrane (Corning, cat. no. 430314) for further clarification.

Affinity Purification:

A QIAFilter 96 Plate is loaded with 200 µL Ni-NTA Superflow slurry included in the Ni-NTA Superflow 96 BioRobot Kit and the resin is equilibrated by adding 600 µL binding buffer (20 mM sodium phosphate, 500 mM sodium chloride and 10 mM imidazole, pH 7.5). A vacuum of −15 in. Hg is applied until all the buffer has passed through the resin. The clarified cell lysates from the previous step are then loaded onto the QIAFilter® 96 Plate and allowed to bind for 5 minutes. A vacuum of −3 in. Hg is applied for approximately 5 minutes until all the samples have passed through the resin. The resin is then washed with 1 mL binding buffer, followed by two washes with 1 mL binding buffer containing 0.1% Triton X-100. The resin is then washed 10 times with 1 mL binding buffer without Triton X-100. The bound 6×His-tagged AARS polypeptides are eluted with 450 µL elution buffer (20 mM sodium phosphate, 500 mM sodium chloride and 500 mM imidazole, pH 7.5) and stored at 4° C.

For larger scale expression, an empty disposable column "Poly-Prep" (Bio-Rad, cat. no. 731-1550) is loaded with 1 mL Ni-NTA Superflow slurry (Qiagen, cat. no. 30450) and the 0.5 mL resin is equilibrated by adding 5 mL binding buffer. The clarified cell lysate from the previous step is then loaded onto the column and allowed to pass through by gravity. The resin is first washed with 50 mL binding buffer plus 0.1% Triton X-100, then washed with 50 mL binding buffer without Triton X-100. The bound 6×His-tagged AARS polypeptides are eluted with 2 mL elution buffer and stored at 4° C.

Desalting and Polishing Steps:

For AARS polypeptides with a molecular mass of >10 kDa, the Omega 10K membrane of an AcroPrep 96 filter plate (Pall, cat. no. 5034) is rinsed with 20 µL 1×PBS and the plate is placed onto a vacuum manifold (>10 in Hg) until all the liquid passes through. The eluates from the previous step (Ni-NTA) are dispensed into each well and the vacuum applied until all the liquid passes through. These steps are repeated until the total eluate volume (450 µL) has been processed. AARS polypeptides are recovered by adding 180 µL of 1×PBS pH 7.4 to each well, pipetting up and down 10 times carefully and then transferred to a clean block. This step is repeated to yield a total volume of 360 µL per well and the block is stored at 4° C. For AARS polypeptides with a molecular mass of <10 kDa, the eluates from Ni-NTA are loaded onto an Amicon Ultra-15 Centrifugal Filter Unit with Ultracel-3 membrane (Millipore, cat. no. UFC900308), followed by the addition of 10 mL 1×PBS and a centrifugation at 3,600 g for 10-30 minutes until the volume is less than 360 µL. The samples are recovered and 1×PBS is added to a final volume of 360 µL.

In order to remove endotoxins, an AcroPrep Advance filter plate with Mustang Q membrane (Pall, cat. no. 8171) is rinsed with 300 µL of 1×PBS and centrifuged at 1,000 g for 5 minutes to remove the buffer. The desalted AARS polypeptides (360 µL/well) are added to the filter plate and incubated on a shaker for 5-10 minutes. The plate is then centrifuged at 1,000 g for 5-10 minutes and the flow through fractions containing the AARS polypeptides are collected and stored at 4° C.

For larger scale expression, the eluates from Ni-NTA are loaded onto an Amicon Ultra-15 Centrifugal Filter Unit with Ultracel-3 or Ultracel-10 membrane (Millipore, cat. no. UFC900308 or UFC901008) depending on the molecular weight of the AARS polypeptide and then centrifuged at 3,600 g for 10-30 minutes until the volume is reduced to 250 µL. The samples are mixed in 10 mL 1×PBS, pH7.4 and centrifuged again at 3,600 g for 10-30 minutes until the volume is about 250 μL. This step is repeated one more time, the supernatants are recovered and 1×PBS is added to a final volume of 1.5 mL.

In order to remove endotoxins, a Sartobind Q 5 strong anion exchanger membrane (Sartorius, cat. no. Q5F) is flushed with 1 mL 1×PBS and the AARS polypeptides are slowly passed through the membrane using a plastic syringe. The flow through fraction containing the AARS polypeptides is collected in a 96-deep well block that is sealed and stored at 4° C.

6×His-tagged AARS polypeptides expressed in bacteria and found in inclusion bodies are purified using affinity chromatography and a series of refolding steps, as described below.

Bacterial Cultures:

100 ng of plasmid encoding each AARS polypeptide is transformed into BL21(DE3) (EMD chemicals, cat. no. 69450) or C41(DE3) (Lucigen, cat. no. 60442) competent E. coli bacteria at 42° C. for 30 seconds in PCR plates. The plates are placed on ice for 2 minutes and 100 μL of SOC medium is added, followed by a 1-hour incubation at 37° C. 5 mL of auto-induction medium (EMD chemicals, cat. no. 71491) supplemented with kanamycin (100 μg/mL) is added into each well of a 24-well block (Qiagen, cat. no. 19583). The transformation reactions are added to the individual wells, the block is sealed with adhesive film (VWR, cat. no 60941-078) and incubated overnight at 250 rpm in a 37° C. shaker.

For larger scale expression, 200 mL of auto-induction medium supplemented with kanamycin (100 μg/mL) is added into 500-mL Erlenmeyer flasks with vent caps (Corning, cat. no. 431401). The transformation reactions are added to the individual flasks and incubated for 30 hours at 250 rpm in a 37° C. shaker.

Isolation:

After the cultures reach stationary phase (typical $OD_{600}$ of 3-6), the blocks are centrifuged at 3,600×g for 10 minutes. The medium is carefully aspirated and the blocks are frozen at −80° C. or −20° C. for 10 minutes. The blocks are then allowed to thaw at room temperature and 1 mL lysis buffer (100 mL Bugbuster supplemented with 200 μl lysonase (EMD chemicals, cat. no 71370) and protease inhibitor "complete mini EDTA-free" (Roche, cat. no. 11 836 170 001)) is added into each well. The pellets are resuspended by repeat pipetting until no clump is visible and transferred to eppendorf tubes, followed by a 10-20 minute incubation on a shaker at room temperature. After centrifugation at 16,000×g for 10 minutes at 4° C., the soluble lysates are discarded and the inclusion bodies are thoroughly resuspended in denaturing binding buffer (20 mM sodium phosphate, 500 mM sodium chloride, 6 M guanidine hydrochloride, 10 mM imidazole, pH 7.5). The samples are centrifuged at 16,000 g for 10 minutes and the supernatants loaded onto a TurboFilter 96 Plate included in the Ni-NTA Superflow 96 BioRobot Kit (Qiagen, cat. no. 969261) followed by centrifugation at 500 g for 5-10 minutes. The filtrates are collected in a clean 96-well block (Greiner, cat. no. 780286).

For larger scale expression, the stationary phase culture is transferred into 500-mL bottles and centrifuged at 6,000 g for 10 minutes. The medium is decanted and the pellet is stored at −80° C. or −20° C. before further processing. The pellet is then allowed to thaw at room temperature and 20 mL lysis buffer is added into each bottle. The pellets are resuspended by repeat pipetting until no clump is visible, followed by 20 minute incubation on a shaker at room temperature. After centrifugation at 10,000 g for 30 minutes at 4° C., the soluble lysates are discarded and the insoluble inclusion bodies thoroughly resuspended in denaturing binding buffer.

Affinity Purification:

A QIAFilter 96 Plate is loaded with 200 μL Ni-NTA Superflow slurry included in the Ni-NTA Superflow 96 BioRobot Kit and the resin is equilibrated by adding 600 μL denaturing binding buffer (see above). A vacuum of −15 in. Hg is applied until all of the buffer passes through the resin. The clarified denatured samples from the previous step are then loaded onto the QIAFilter® 96 Plate and allowed to bind for 5 minutes. A vacuum of approximately 3 inches of mercury is applied for approximately 5 minutes until all the samples pass through the resin. The resin is then washed with 1 mL denaturing binding buffer, followed by five washes with 1 mL denaturing binding buffer containing 0.1% Triton X-100. The resin is then washed 15 times with 1 mL denaturing binding buffer without Triton X-100. The bound 6×His-tagged AARS polypeptides are then eluted with 450 μL denaturing elution buffer (20 mM sodium phosphate, 500 mM sodium chloride, 6 M guanidine hydrochloride and 500 mM imidazole, pH 7.5) and stored at 4° C.

For larger scale expression, an empty disposable column "Poly-Prep" (Bio-Rad, cat. no. 731-1550) is loaded with 1 mL Ni-NTA Superflow slurry (Qiagen, cat. no. 30450) and the 0.5 mL resin is equilibrated by adding 5 mL denaturing binding buffer (see above). The denatured inclusion bodies from the previous step are then loaded onto the column and allowed to pass through by gravity. The resin is first washed with 50 mL denaturing binding buffer plus 0.1% Triton X-100, then washed with 50 mL denaturing binding buffer without Triton X-100. The bound 6×His-tagged AARS polypeptides are eluted with 2 mL denaturing elution buffer and stored at 4° C.

Refolding:

For AARS polypeptides>10 kDa, the Omega 10K membrane of an AcroPrep 96 filter plate (Pall, cat. no. 5034) is rinsed with 20 μL, 1×PBS and the plate is placed onto a vacuum manifold (>10 in. Hg) until all the liquid passes through. The eluates from the previous step (Ni-NTA) are dispensed into each well and the vacuum applied until all the liquid passes through. These steps are repeated until the total eluate volume (450 μL) has been processed. AARS polypeptides are recovered by adding 200 μL, of refolding buffer containing 50 mM Tris, 250 mM sodium chloride, 10 mM potassium chloride, 2 mM magnesium chloride, 2 mM calcium chloride, 400 mM sucrose, 500 mM arginine, 1 mM DTT and 0.01% polysorbate 80, pH 7.4) to each well, pipetting up and down 10 times carefully, and then transferred to a clean block. This step is repeated to yield a total volume of 400 μL, per well and the block is placed on the shaker overnight at 4° C. For AARS polypeptides<10 kDa, the eluates from Ni-NTA are loaded onto an Amicon Ultra-15 Centrifugal Filter Unit with Ultracel-3 membrane (Millipore, cat. no. UFC900308), followed by the addition of 10 mL refolding buffer and a centrifugation at 3,600 g for 10-30 minutes until the volume is less than 400 μL. The samples are recovered and extra refolding buffer is added to a final volume of 400 μL. The samples are transferred to a 96-well block, sealed with film and placed on a shaker overnight at 4° C.

For larger scale cultures, the eluates from Ni-NTA are loaded onto an Amicon Ultra-15 centrifugal filter unit with Ultracel-3 or Ultracel-10 membrane (Millipore, cat. no. UFC900308 or UFC901008 depending on the molecular weight of the AARS polypeptide) and then centrifuged at 3,600 g for 10-30 minutes until the volume is reduced to about 500 μL. For AARS polypeptides with pI>7, the samples are diluted 20-fold in the following buffer: 50 mM sodium acetate, 10 mM sodium chloride, 0.4 mM potassium chloride, 1 mM EDTA, 400 mM sucrose, 500 mM arginine, 1 mM DTT and 0.01% polysorbate 80, pH 6.0. For AARS polypeptides with pI<7, the samples are diluted 20-fold in the following buffer: 50 mM Tris, 250 mM sodium chloride, 10 mM potassium chloride, 2 mM magnesium chloride, 2 mM calcium chloride, 400 mM sucrose, 500 mM arginine, 1 mM DTT and 0.01% polysorbate 80, pH 8.0. The samples are incubated on a shaker at 4° C. overnight.

Desalting and Polishing Steps:

After overnight incubation, the 96-well block is centrifuged at 3,600 g to remove any potential aggregates. The supernatants are then subjected to buffer exchange with 1×PBS (Invitrogen, cat. no. 10010). For AARS polypeptides>10 kDa, the Omega 10K membrane of an AcroPrep 96 filter plate is rinsed with 20 μL, 1×PBS and the plate is placed onto a vacuum manifold (>10 in. Hg) until all the liquid passes through. The samples in the refolding buffer are dispensed into each well and the vacuum applied until all the liquid passes through. These steps are repeated until the total sample volume (400 μL) has been processed. AARS polypeptides are recovered by adding 180 μL, of 1×PBS pH 7.4 to each well, pipetting up and down 10 times carefully, and then transferred to a clean block. This step is repeated to yield a total volume of 360 μL, per well and the block is stored at 4° C. For AARS polypeptides<10 kDa, the refolded samples are loaded onto an Amicon Ultra-15 Centrifugal Filter Unit with Ultracel-3 membrane (Millipore, cat. no. UFC900308) followed by the addition of 10 mL 1×PBS and centrifugation at 3,600 g for 10-30 minutes until the volume is less than 360 μL. The samples are recovered and 1×PBS is added to a final volume of 360 μL.

In order to remove endotoxins, an AcroPrep Advance filter plate with Mustang Q membrane (Pall, cat. no. 8171) is rinsed with 300 μL of 1×PBS and centrifuged at 1,000 g for 5 minutes to remove the buffer. The AARS polypeptides (360 μL/well) are added to the filter plate and incubated on a shaker for 5-10 minutes. The plate is then centrifuged at 1,000 g for 5-10 minutes and the flow through fractions containing the AARS polypeptides are collected and stored at 4° C.

For larger scale cultures, after overnight incubation, the refolded samples are centrifuged at 10,000 g for 10 minutes to remove any insoluble aggregates. The supernatant is loaded onto an Amicon Ultra-15 Centrifugal Filter Unit and centrifuged at 3,600 g until the volume is reduced to 250 μL. The samples are mixed in 10 mL 1×PBS and centrifuged again at 3,600 g for 10-30 minutes until the volume is about 250 μL. Note that the pH of 1×PBS is adjusted to match the pH of the refolding buffer, either pH 6.0 or pH 8.0. This step is repeated one more time, the supernatants are recovered and 1×PBS is added to a final volume of 1.5 mL.

In order to remove endotoxins, a Sartobind Q 5 strong anion exchanger membrane (Sartorius, cat. no. Q5F) is flushed with 1 mL 1×PBS and the AARS polypeptides are slowly passed through the membrane using a plastic syringe. The flow through fraction containing the AARS polypeptides is collected in a 96-deep well block that is sealed and stored at 4° C.

Biophysical Characterization:

All purified AARS polypeptides are analyzed by SDS-PAGE, their concentration determined based on $A_{280}$ and calculated extinction coefficient (ProtParam on ExPASy server). Endotoxin levels are measured by the QCL-1000 Endpoint Chromogenic LAL assay (Lonza, cat. no. 50-648U) according to the manufacturer's instructions.

Dynamic Light Scattering:

A Wyatt Technology DynaPro 99 instrument and the temperature controller (20° C.) are warmed up for 15 minutes before the experiment followed by connection of the Dynamics software to the instrument. The acquisition time is set to 10 seconds for multiple acquisitions and the laser power is set to 100%. The quartz cuvette is washed thoroughly with deionized water and methanol before the addition of the protein sample (15 μL at a concentration of approximately 1 mg/mL in PBS). Air bubbles are removed by tapping the cuvette before it is inserted into the holder with the frosted side to the left. If the intensity is too high (warning message shown on the screen), the sample is further diluted with PBS until the intensity is decreased to a normal range. The data collected include hydrodynamic radius, polydispersity, predicted average molecular weight, percentage of intensity and percentage of mass.

Size Exclusion Chromatography:

The protein sample is diluted to a concentration of about 5-10 mg/mL in PBS before being loaded into a 100 μL sample loop on the General Electric AKTA FPLC. The Superdex 200 10/300 GL size exclusion column (General Electric, cat. no. 17-5175-01) is used for separation. The column is first equilibrated with 1.5 column volume (CV) of 1×PBS buffer, followed by sample injection. The column is run in 1 CV of 1×PBS buffer (isocratic flow) with absorbance at 280 nm monitoring. The peak area is integrated and the percentage calculated with the Unicorn software. The elution volume is used to estimate the molecular weight based on comparison with gel filtration calibration kits (General Electric, cat. no. 28-4038-41 and 28-4038-42).

Protein Recovery Upon Storage at High Concentration:

10 μL of the AARS polypeptides concentrated to >10 mg/mL using an Amicon Ultra-15 filter unit (Millipore, cat. no. UFC901024 or UFC900324 depending on molecular weight) are transferred to a clean microcentrifuge tube. The sample is stored at room temperature for one week followed by centrifugation at 16,000 g for 10 minutes to pellet any precipitates. The concentration of the supernatant is determined by a Bradford protein assay and compared to the concentration measured prior to the week-long exposure to room temperature. The recovery is expressed as percentage of the starting concentration.

Characterization of AARS Polypeptides by LC-MS:

Purified AARS polypeptides (1 mg/mL) are diluted 1:10 into 0.1% formic acid and 0.6 mg protein is loaded with a Dionex autosampler onto a C4 capillary column. The capillary column is prepared by cutting 150 mm of fused silica tubing (0.36 mm OD by 0.1 mm ID, Polymicro Technologies, cat. no. 2000023). The capillary is pulled at one end with a Suter Instrument Laser Fiber Puller and cut with a fused silica cutter to generate a 5 μm tip. The capillary is packed to the length of 75 mm with C4 resin (5 μm, 300 Å, Michrom, cat. no. PM5/64300/00) using pressure bomb. The LC-MS analysis is performed on an ThermoFisher LTQ ion trap mass spectrometer coupled to a Dionex Ultimate3000 HPLC system. The analyte is eluted from the column using a 35-minute gradient of 5-70% acetonitrile in 0.1% formic acid at a flow rate of 0.9 μL/min. The LTQ is operated on a full MS scan mode (300-2,000 m/z) with a spray voltage of 2.5 kV.

Data collection and analysis: raw mass spectrometry data are stored in RAW files generated by XCalibur running on the LTQ XL mass spectrometer. The MS spectra of the major peaks on the chromatograph are further analyzed with ThermoFisher deconvoluting algorithm ProMass to obtain the AARS polypeptide molecular weights.

Functional Analysis of AARS Polypeptides
Transcriptional Profiling

Background and Therapeutic Relevance:

In addition to traditional target identification techniques, genomic tools have recently emerged as important approaches to aid in elucidating the mechanism of action of AARS polypeptides and can provide direct insight into therapeutic relevance early in the drug discovery process. To facilitate an understanding of potential therapeutic utility, primary human cell types are cultured with AARS polypeptides and transcriptional profiling is assessed at two separate time points following incubation with AARS polypeptides.

The cell types chosen for transcriptional profiling are based on the pluripotent capabilities of the cells in question and potential to identify AARS polypeptides of direct therapeutic value. For example, Mesenchymal stem cells (MSCs) can differentiate into osteogenic, adipogenic, chondrogenic, myocardial, or neural lineages when exposed to specific stimuli, making them attractive for understanding the potential relevance of the AARS polypeptides to a broad range of cell types, and diseases.

In addition to supporting hematopoietic cells, marrow stromal cells can also be induced to differentiate into cells of different connective tissue lineage, such as bone, cartilage, and fat. The potential of Human Mesenchymal stem cells (hMSCs) to maintain multipotency and proliferate extensively in vitro provides new avenues for cell-based therapy in the restoration of damaged or diseased tissue. Recent reports also indicate that HMSCs are capable of cell fate crossing germ layer boundaries. In addition to differentiating into multi-lineages of the mesoderm, these cells can also differentiate into neurons of ectodermal origin and hepatocyte-like cells of endodermal origin. During the process of differentiation, these cells may modify expression patterns of certain lineage specific transcripts.

Accordingly the ability of specific AARS polypeptides to modulate specific patterns of genes in HMSCs in a time dependent manner demonstrates that these proteins play potentially significant roles in a broad array of differentiation pathways, as well as diseases and disorders resulting from the dysfunction, or deterioration of these processes, or the corresponding cell types. Moreover AARS polypeptides with the ability to modulate gene transcription in MSCs have significant therapeutic utility to enable the in vitro or in vivo modulation of hematopoiesis, neurogenesis, myogenesis, osteogenesis, and adipogenesis, as well as in a broad range of disorders and diseases, including for example inflammatory responses, autoimmunity, cancer, neuronal degeneration, muscular dystrophy, osteoporosis, and lipodystrophy.

Human Skeletal Muscle Cells (HSkMC) can undergo differentiation to exhibit actin and myosin myofilaments, and have been used in the study of genetic muscular diseases such as Malignant Hyperthermial. HSkMC also have the potential to act as a cardiac graft, mending damage to the heart. Recently, cultured Human Skeletal Muscle cells have been used in micro gravity experiments to study the effects of low gravity environments on Human Skeletal Muscle.

Accordingly the ability of specific AARS polypeptides to modulate specific patterns of genes in HSkMC in a time dependent manner demonstrates that these proteins play potentially significant roles in the processes of myogenesis, as well as diseases and disorders resulting from the dysfunction, or deterioration of these processes as well as muscle cell development or metabolism. Accordingly AARS polypeptides with the ability to modulate gene transcription in muscle cells have therapeutic utility in a broad range of diseases including for example, the treatment of metabolic disease, cachexia, various muscle wasting conditions, as well as musculoskeletal diseases.

Methods:

The ability of AARS polypeptides to modulate gene expression is assessed using a high-throughput microfluidic real-time quantitative PCR (RT-qPCR) approach (Fluidigm Corporation). (See Petriv et al., (2010) PNAS (doi/10.1073/pnas.1009320107) in Human Marrow Stromal Cells (HMSC) and Human Skeletal Muscle Cells (HSkMC). In the experiments reported here, Human HSkMC (Cat #150-05f) and HMSC (Cat #492-05f) were purchased from Cell Applications. HMSC cells are cryopreserved at second passage and can be cultured and propagated to 10 population doublings. Here HMSC in the $6^{th}$ Passage are used. Human Skeletal Muscle Cells (HSkMC) are cryopreserved at second passage and can be cultured and propagated for at least 15 population doublings. In the experiments reported here HSkMC at passage 6 post harvest from normal human donor are used.

In both cases, cells are plated at 50000 cells/mL in 100 μL volume of growth media and exposed to AARS polypeptides at a concentration of 250 nM, or as otherwise indicated below, for 24 hours and 72 hours. Controls include Differentiation media with a standard cocktail to promote (1) Adipogenesis, (2) Osteogenesis, (3) Chondrogenesis and (4) Skeletal muscle myotube formation. Additional controls include untreated wells containing only growth media. Two wells were run for each Differentiation control. Controls: all media was made utilizing DMEM as the basal media. Standard literature was followed and Differentiation media was purchased from Cell Applications. Per the vendor, differentiation media contained the following additives: Skeletal muscle differentiation cocktail: FBS, insulin, glutamine, FGF, EGF; Adipogenesis cocktail: insulin, dexamethasone and IBMX; Osteogenesis cocktail: FBS, dexamethasone, ascorbate 2 phosphate, beta-glycerophosphate; Chondrogenesis cocktail: insulin, ascorbate-2-phosphate, and TGF-β1.

Standard protocols for using an ABI (Applied Biosystems, Item # AM1728) TAQMAN® Gene Expression Cells-to-CT™ Kit are utilized to lyse cells and harvest genomic material. An ABI Pre-Amp Mix (Applied Biosystems, Item#4391128) is used to initiate pre-amplification. Gene specific primers are created using a Primer 3 program and purchased from IDT technologies. Fluidigm profiling arrays (Item # BMK-M-96.96) were used for actual quantitative PCR with standard Fluidigm loading reagents and pipetting devices. Table E1 below lists the genes profiled.

TABLE E1

List of genes assessed in transcriptional profiling

| Compiled Unique List | refseq_nt | Full_name_ | Synonyms |
|---|---|---|---|
| ABCA1 | NM_005502 | ATP-binding cassette, sub-family A (ABC1), member 1 | ABC-1\|ABC1\|CERP\|FLJ14958\|HDLDT1\|MGC164864\|MGC165011\|TGD |

TABLE E1-continued

List of genes assessed in transcriptional profiling

| Compiled Unique List | refseq_nt | Full_name | Synonyms |
|---|---|---|---|
| ACTB | NM_001101 | actin, beta | PS1TP5BP1 |
| ACTG1 | NM_001614 | actin, gamma 1 | ACT\|ACTG\|DFNA20\|DFNA26 |
| ACVR2B | NM_001106 | activin A receptor, type IIB | ACTRIIB\|ActR-IIB\|MGC116908 |
| APOA1 | NM_000039 | apolipoprotein A-I | MGC117399 |
| ARNT | NM_178427 | aryl hydrocarbon receptor nuclear translocator | HIF-1beta\|HIF1B\|HIF1BETA\|TANGO\|bHLHe2 |
| BAD | NM_032989 | BCL2-associated agonist of cell death | BBC2\|BCL2L8 |
| BCL2 | NM_000657 | B-cell CLL/lymphoma 2 | Bcl-2 |
| BMP2 | NM_001200 | bone morphogenetic protein 2 | BMP2A |
| BMP4 | NM_130851 | bone morphogenetic protein 4 | BMP2B\|BMP2B1\|MCOPS6\|OFC11\|ZYME |
| C3AR1 | NM_004054 | complement component 3a receptor 1 | AZ3B\|C3AR\|HNFAG09 |
| CASP3 | NM_032991 | caspase 3, apoptosis-related cysteine peptidase | CPP32\|CPP32B\|SCA-1 |
| CAV1 | NM_001753 | caveolin 1, caveolae protein, 22 kDa | BSCL3\|CGL3\|MSTP085\|VIP21 |
| CDH5 | NM_001795 | cadherin 5, type 2 (vascular endothelium) | 7B4\|CD144\|FLJ17376 |
| CFLAR | NM_003879 | CASP8 and FADD-like apoptosis regulator | CASH\|CASP8AP1\|CLARP\|Casper\|FLAME\|FLAME-1\|FLAME1\|FLIP\|I-FLICE\|MRIT\|c-FLIP\|c-FLIPL\|c-FLIPR\|c-FLIPS |
| COMP | NM_000095 | cartilage oligomeric matrix protein | EDM1\|EPD1\|MED\|MGC131819\|MGC149768\|PSACH\|THBS5 |
| CSF1 | NM_172212 | colony stimulating factor 1 (macrophage) | MCSF\|MGC31930 |
| CTGF | NM_001901 | connective tissue growth factor | CCN2\|HCS24\|IGFBP8\|MGC102839\|NOV2 |
| CTNNB1 | NM_001904 | catenin (cadherin-associated protein), beta 1, 88 kDa | CTNNB\|DKFZp686D02253\|FLJ25606\|FLJ37923 |
| DAAM1 | NM_014992 | dishevelled associated activator of morphogenesis 1 | FLJ41657\|KIAA0666 |
| ELN | NM_001081755 | elastin | FLJ38671\|FLJ43523\|SVAS\|WBS\|WS |
| ENO1 | NM_001428 | enolase 1, (alpha) | ENO1L1\|MPB1\|NNE\|PPH |
| FABP3 | NM_004102 | fatty acid binding protein 3, muscle and heart (mammary-derived growth inhibitor) | FABP11\|H-FABP\|MDGI\|O-FABP |
| FAK | NM_001199649 | focal adhesion kinase | fak1 |
| FGF4 | NM_002007 | fibroblast growth factor 4 | HBGF-4\|HST\|HST-1\|HSTF1\|K-FGF\|KFGF |
| FIGF | NM_004469 | c-fos induced growth factor (vascular endothelial growth factor D) | VEGF-D\|VEGFD |
| FLT1 | NM_002019 | fms-related tyrosine kinase 1 (vascular endothelial growth factor/vascular permeability factor receptor) | FLT\|VEGFR1 |
| FOXA1 | NM_004496 | forkhead box A1 | HNF3A\|MGC33105\|TCF3A |

TABLE E1-continued

List of genes assessed in transcriptional profiling

| Compiled Unique List | refseq_nt | Full_name | Synonyms |
|---|---|---|---|
| GAPDH | NM_002046 | glyceraldehyde-3-phosphate dehydrogenase | G3PD\|GAPD\|MGC88685 |
| GFAP | NM_002055 | glial fibrillary acidic protein | FLJ45472 |
| SLC2A4 | NM_001042 | solute carrier family 2 (facilitated glucose transporter), member 4 | GLUT4 |
| HAND1 | NM_004821 | heart and neural crest derivatives expressed 1 | Hxt\|Thing1\|bHLHa27\|eHand |
| HIF1A | NM_181054 | hypoxia inducible factor 1, alpha subunit (basic helix-loop-helix transcription factor) | HIF-1alpha\|HIF1\|HIF1-ALPHA\|MOP1\|PASD8\|bHLHe78 |
| HK2 | NM_000189 | hexokinase 2 | DKFZp686M1669\|HKII\|HXK2 |
| HMGB1 | NM_002128 | high-mobility group box 1 | DKFZp686A04236\|HMG1\|HMG3\|SBP-1 |
| HNF4A | NM_178850 | hepatocyte nuclear factor 4, alpha | FLJ39654\|HNF4\|HNF4a7\|HNF4a8\|HNF4a9\|HNF4alpha\|MODY\|MODY1\|NR2A1\|NR2A21\|TCF\|TCF14 |
| HPRT1 | NM_000194 | hypoxanthine phosphoribosyltransferase 1 | HGPRT\|HPRT |
| HSPB1 | NM_001540 | heat shock 27 kDa protein 1 | CMT2F\|DKFZp586P1322\|HMN2B\|HS.76067\|HSP27\|HSP28\|HsP25\|SRP27 |
| ICAM1 | NM_000201 | intercellular adhesion molecule 1 | BB2\|CD54\|P3.58 |
| IFNG | NM_000619 | interferon, gamma | IFG\|IFI |
| IGF1 | NM_001111285 | insulin-like growth factor 1 (somatomedin C) | IGF-I\|IGF1A1\|GFI |
| IGF2 | NM_001127598 | insulin-like growth factor 2 (somatomedin A) | C11orf43\|FLJ22066\|FLJ44734\|INSIGF\|pp9974 |
| IGFBP3 | NM_001013398 | insulin-like growth factor binding protein 3 | BP-53\|IBP3 |
| IGFBP5 | NM_000599 | insulin-like growth factor binding protein 5 | IBP5 |
| IKBKB | NM_001556 | inhibitor of kappa light polypeptide gene enhancer in B-cells, kinase beta | FLJ33771\|FLJ36218\|FLJ38368\|FLJ40509\|IKK-beta\|IKK2\|IKKB\|MGC131801\|NFKBIKB |
| IL10 | NM_000572 | interleukin 10 | CSIF\|IL-10\|IL10A\|MGC126450\|MGC126451\|TGIF |
| IL1B | NM_000576 | interleukin 1, beta | IL-1\|IL1-BETA\|IL1F2 |
| IL3 | NM_000588 | interleukin 3 (colony-stimulating factor, multiple) | IL-3\|MCGF\|MGC79398\|MGC79399\|MULTI-CSF |
| IL4 | NM_172348 | interleukin 4 | BCGF-1\|BCGF1\|BSF1\|IL-4\|MGC79402 |
| IL5 | NM_000879 | interleukin 5 (colony-stimulating | EDF\|IL-5\|TRF factor, eosinophil) |
| IL6R | NM_181359 | interleukin 6 receptor | CD126\|IL-6R-1\|IL-6R-alpha\|IL6RA\|MGC104991 |

TABLE E1-continued

List of genes assessed in transcriptional profiling

| Compiled Unique List | refseq_nt | Full_name_ | Synonyms |
|---|---|---|---|
| IL8 | NM_000584 | interleukin 8 | CXCL8|GCP-1|GCP1|LECT|LUCT|LYNAP|MDNCF|MONAP|NAF|NAP-1|NAP1 |
| ITGA5 | NM_002205 | integrin, alpha 5 (fibronectin receptor, alpha polypeptide) | CD49e|FNRA|VLA5A |
| KDR | NM_002253 | kinase insert domain receptor (a type III receptor tyrosine kinase) | CD309|FLK1|VEGFR|VEGFR2 |
| LEP | NM_000230 | leptin | FLJ94114|OB|OBS |
| LPL | NM_000237 | lipoprotein lipase | HDLCQ11|LIPD |
| MAPK11 | NM_002751 | mitogen-activated protein kinase 11 | P38B|1338BETA2|PRKM11|SAPK2|SAPK2B|p38-2|p38Beta |
| MMP1 | NM_002421 | matrix metallopeptidase 1 (interstitial collagenase) | CLG|CLGN |
| MMP3 | NM_002422 | matrix metallopeptidase 3 (stromelysin 1, progelatinase) | CHDS6|MGC126102|MGC126103|MGC126104|MMP-3|SL-1|STMY|STMY1|STR1 |
| MYH1 | NM_005963 | myosin, heavy chain 1, skeletal muscle, adult | MGC133384|MYHSA1|MYHa|MyHC-2X/D|MyHC-2x |
| MYH11 | NM_022844 | myosin, heavy chain 11, smooth muscle | AAT4|DKFZp686D10126|DKFZp686D19237|FAA4|FLJ35232|MGC126726|MGC32963|SMHC|SMMHC |
| MYH7 | NM_000257 | myosin, heavy chain 7, cardiac muscle, beta | CMD1S|CMH1|DKFZp451F047|MGC138376|MGC138378IMPD1|MYHCB|SPMD|SPMM |
| MYOD1 | NM_002478 | myogenic differentiation 1 | MYF3|MYOD|PUM|bHLHc1 |
| NFATC1 | NM_172390 | nuclear factor of activated T-cells, cytoplasmic, calcineurin-dependent 1 | MGC138448|NF-ATC|NFAT2|NFATc |
| NFATC2 | NM_173091 | nuclear factor of activated T-cells, cytoplasmic, calcineurin-dependent 2 | NFAT1|NFATP |
| NFKB1 | NM_003998 | nuclear factor of kappa light polypeptide gene enhancer in B-cells 1 | DKFZp686C01211|EBP-1|KBF1|MGC5415|NF-kappa-B|NF-kappaB|NFKB-p105|NFKB-p50|p105|p50 |
| NOS2 | NM_000625 | nitric oxide synthase 2, inducible | HEP-NOS|INOS|NOS|NOS2A |
| NOTCH1 | NM_017617 | notch 1 | TAN1|hN1 |
| NR3C1 | NM_001024094 | nuclear receptor subfamily 3, group C, member 1 (glucocorticoid receptor) | GCCR|GCR|GR|GRL |
| NRP2 | NM_201279 | neuropilin 2 | MGC126574|NP2|NPN2|PRO2714|VEGF165R2 |
| PAX7 | NM_013945 | paired box 7 | FLJ37460|HUP1|PAX7B|RMS2 |

TABLE E1-continued

List of genes assessed in transcriptional profiling

| Compiled Unique List | refseq_nt | Full_name_ | Synonyms |
|---|---|---|---|
| PDGFB | NM_033016 | platelet-derived growth factor beta polypeptide (simian sarcoma viral (v-sis) oncogene homolog) | FLJ12858\|PDGF2\|SIS\|SSV\|c-sis |
| PDK4 | NM_002612 | pyruvate dehydrogenase kinase, isozyme 4 | FLJ40832 |
| PLA2G1B | NM_000928 | phospholipase A2, group IB (pancreas) | MGC119834\|MGC119835\|PLA2\|PLA2A\|PPLA2 |
| PLIN1 | NM_002666 | lipid droplet associated protein | perilipin |
| PPARG | NM_138712 | peroxisome proliferator-activated receptor gamma | CIMT1\|GLM1\|NR1C3\|PPARG1\|PPARG2\|PPARgamma |
| QARS | NM_005051 | Glutaminyl-tRNA synthetase | GLNRS\|PRO2195 |
| RHOA | NM_001664 | ras homolog gene family, member A | ARH12\|ARHA\|RHO12\|RHOH12 |
| RUNX1 | NM_001754 | runt-related transcription factor 1 | AML1\|AML1-EVI-1\|AMLCR1\|CBFA2\|EVI-1\|PEBP2aB |
| RXRA | NM_002957 | retinoid X receptor, alpha | FLJ00280\|FLJ00318\|FLJ16020\|FLJ16733\|MGC102720\|NR2B1 |
| SERPINE1 | NM_001165413 | serpin peptidase inhibitor, Glade E (nexin, plasminogen activator inhibitor type 1), member 1 | PAI\|PAI-1\|PAI1\|PLANH1 |
| SMAD2 | NM_005901 | SMAD family member 2 | JV18\|JV18-1\|MADH2\|MADR2\|MGC22139\|MGC34440\|hMAD-2\|hSMAD2 |
| SMAD4 | NM_005359 | SMAD family member 4 | DPC4\|JIP\|MADH4 |
| TERT | NM_198255 | telomerase reverse transcriptase | EST2\|TCS1\|TP2\|TRT\|hEST2 |
| TGFB1 | NM_000660 | transforming growth factor, beta 1 | CED\|DPD1\|LAP\|TGFB\|TGFbeta |
| TGFB3 | NM_003239 | transforming growth factor, beta 3 | ARVD\|FLJ16571\|TGF-beta3 |
| THBS4 | NM_003248 | thrombospondin 4 | TSP4 |
| TNF | NM_000594 | tumor necrosis factor | DIF\|TNF-alpha\|TNFA\|TNFSF2 |
| TUBB | NM_178014 | tubulin, beta | M40\|MGC117247\|MGC16435\|OK/SW-cl.56\|TUBB1\|TUBB5 |
| TUBB1 | NM_030773 | tubulin, beta 1 | tubulin isoform beta (1) |
| TUBG1 | NM_001070 | tubulin, gamma 1 | GCP-1\|TUBG\|TUBGCP1 |
| VCAM1 | NM_080682 | vascular cell adhesion molecule 1 | CD106\|DKFZp779G2333\|INCAM-100\|MGC99561 |
| VEGFA | NM_003376 | vascular endothelial growth factor A | MGC70609\|MVCD1\|VEGF\|VPF |
| VIM | NM_003380 | vimentin | FLJ36605 |
| WISP1 | NM_080838 | WNT1 inducible signaling pathway protein 1 | CCN4\|WISP1c\|WISP1i\|WISP1tc |
| WNT1 | NM_005430 | wingless-type MMTV integration site family, member 1 | INT1 |

Bioinformatics Analysis:

Data retrieved in .csv format from the Biomark machine by Fluidigm is converted to a tabular format including sample, mRNA, and replicate information along with the raw fluorescence value. PCR reactions that failed are marked as missing. Multiple experiments are combined after normalizing to total expression of mRNA species. All measured mRNA expression is filtered based on the requirement of detection in at least 2 of all of the biological replicates tested in the control samples. We assessed technical, biological and set deviation from the mean in entire dataset.

The Fluidigm Biomark software is utilized for the analysis of the transcriptional profiling. For data analysis Ct values for all genes of interest are first normalized to the averaged Ct values for housekeeping genes from the corresponding sample to obtain $\Delta$Ct values ($\Delta$Ct=Ct gene−Ct average housekeeping genes). Genes from each protein treated sample are then normalized to the same gene in a vehicle treated (PBS) sample to obtain $\Delta\Delta$Ct values ($\Delta\Delta$Ct=$\Delta$Ct control sample−$\Delta$Ct treated sample). All measured mRNA expression is filtered based on the requirement of detection in at least 2 of all of the biological replicates of the control samples.

The Fluidigm Biomark software package is used to automatically obtain fold change values based on control normalized sample and gene Ct values. Analysis was performed in the same way for each unique data set analyzed. For up-regulated genes, fold Change is equivalent to $2^{\wedge}\Delta\Delta Ct$. For down-regulated genes (i.e., $\Delta\Delta$Cts less than 0): Fold Change=$-(2^{\wedge}|\Delta\Delta Ct|)$.

Cellular Proliferation Assays (Assays A1-A1 in the Data Tables Below)

Background and Therapeutic Relevance:

The ability to modulate the rate of cellular proliferation and apoptosis of different cell types represents a fundamental property of many therapeutic compounds, and is of direct relevance to the treatment and prevention of a broad range of diseases and disorders.

Accordingly AARS polypeptides with the ability to modulate the rate of cellular proliferation and or apoptosis have significant therapeutic utility in a broad range of diseases including, as growth factors, and differentiation factors for stem cells, and in treatment regimens to enhance or suppress the proliferation of specific cell types of interest in vivo or in vitro, including for example, haemopoietic cells, immunomodulatory cells, cancer, and for the treatment and prevention of diseases associated with aging, including for example neurodegeneration, peripheral neuropathy, and loss of muscular and soft tissue tone.

Methods:

Effects of the AARS polypeptides on cellular proliferation is assessed using one or more of the methods listed below, and as more specifically elaborated in the methods below.

Hoechst 33432.

Standard cell counts to assess proliferation are performed using Hoechst 33432, which is a cell-permeant nuclear counterstain that emits blue fluorescence when bound to dsDNA. It is available as a solution (Invitrogen Cat # H-3570) that is used at a final concentration of 1 ug/mL in either media or PBS. Cells are grown in 96 well plates in the presence of AARS polypeptides for a standard growth time of 48 hours, or longer depending on cell type and as described in the examples below.

ATP-Lite.

Cellular ATP levels correlate with cellular health and can be readily determined using a variety of commercially available kits. ATP-lite (Perkin-Elmer, Cat #6016947 Boston, Mass. 02481) which is a homogenous mixture of lysis solution and ATP-detection reagent. is pre-mixed before use and is used 1:1 v:v ratio with cultured cells. Plates are incubated for 5 minutes to promote lysis and plates are measured using a luminescent plate reader. Cells are grown in 96 well plates in the presence of AARS polypeptides for a standard growth time of 48 hours, or longer depending on cell type and as described in the examples below.

ALAMARBLUE® (Resazurin) is a cell viability indicator which is based on the redox state of the cells. Resazurin, the active ingredient, is a nontoxic, cell permeable compound that is blue in color and virtually nonfluorescent when present in its oxidized form. However upon entering normal viable cells, resazurin is rapidly reduced to resorufin, which produces a red fluorescence signal. Viable cells continuously convert resazurin to resorufin, thereby generating a quantitative measure of viability—and cytotoxicity. The lack of toxicity allows long-term exposure of cells to resazurin without negative impact; cells grown in the presence of resazurin were found to produce similar numbers of viable cells as control cells, as determined by flow cytometric analysis.

Measurements are made by adding a solution of Resazurin/ALAMARBLUE® to cells, incubating them for 1-4 hours, and reading the fluorescence or absorbance. The amount of fluorescence or absorbance is proportional to the number of living cells and corresponds to the cells metabolic activity. Damaged and nonviable cells have lower innate metabolic activity and thus generate a proportionally lower signal than healthy cells. After incubation with ALAMARBLUE®, samples can readily be measured on fluorescence and absorbance instrumentation. For fluorescence readings: 530 nm excitation and 590 nm emission filter settings are used.

Cells are grown in 96 well plates in the presence of AARS polypeptides for a standard growth time of 48 hours, or longer depending on cell type and as described in the examples below.

Acetylated LDL Uptake in HepG2C3a Human Hepatocyte Cells. (Assay B1 in the Data Tables Below)

Background and Therapeutic Relevance:

LDL is the major carrier of cholesterol in the blood, accounting for more than 60% of the cholesterol in plasma. In humans, the hepatic LDL receptor is responsible for clearing around 70% of plasma LDL from circulation. Internalized LDL is degraded to free cholesterol and amino acids in the lysosome. The liver is the most important organ for LDL catabolism and LDL receptor activity in humans. LDL that is not internalized and remains in circulation can be transported by endothelial cells into the vessel wall, resulting in the formation of atherosclerotic plaques. Circulating LDL can also be taken up by macrophages and this can also contribute to the formation of plaques. Increasing LDL uptake into hepatic tissue is thought to be beneficial to human health and finding safe and efficacious therapeutics that may the positively regulate this process may provide new therapies for cardiovascular and metabolic diseases. To investigate whether the unique properties of AARS polypeptides can regulate uptake of acetylated LDL, a standard assay for measuring acetylated LDL uptake is employed in HepG2C3a cells.

Accordingly AARS polypeptides with the ability to modulate LDL uptake have significant therapeutic utility in a broad range of diseases including for example, the treatment of hypercholesteremia, hyperlipidemia, type 1 and 2 diabetes, metabolic syndrome, and vascular diseases including atherosclerosis Methods:

HEPG2C3a cells (ATCC# CRL-10741) are maintained in Eagles Minimal Essential (EMEM) medium supplemented with 10% FBS (HyClone Cat#SH30910.03), 50 u/mL penicillin/50 µg/mL streptomycin, (Invitrogen) in 15 mL medium in 75 mL flasks. Cells are grown at 37° C., 5% $CO_2$, in a humidified environment and utilized in BSL2 certified tissue culture hoods using sterile technique and appropriate personal protective equipment including goggles, gloves and lab coats. HEPG2C3a express the LDL-receptor and are competent for acetylated LDL uptake when grown on clear bottom collagen coated plates. A 100 µL volume of cells is plated on collagen coated plates (Invitrogen Cat#A11428) overnight in complete medium (above) at a cell density of 50,000 cells/mL. Cells are washed once with PBS (Invitrogen Cat#10010) and 80 µL of serum free EMEM is added to each well. AARS polypeptides at a final concentration of 250 nM per well are added in a consistent volume in sterile PBS to each well. A unique AARS polypeptide is placed in each well. Cells are serum starved and exposed to the AARS polypeptides for 16 hours. Following the 16 hour incubation, the, supernatant is collected and soluble ICAM is measured using a standard ELISA kit from RND Systems (Cat #DY643), and serum free media supplemented with 5 µg/mL ac-LDL (Alexa Fluor 488 labeled Cat # L23380, Invitrogen) is added to each well. Following a 2 hour incubation at 37° C. 5% $CO_2$, cells are washed twice with sterile PBS before 100 µL PBS is added to each well for quantification. Plates were analyzed for total fluorescent intensity using a bottom read on a Victor X5 fluorescent plate reader (Perkin Elmer) at an excitation wavelength centered around 485 nm, and an emission wavelength centered around 535 nm. Cells are stained with Hoechst dye and fluorescent intensity 405 nm Excitation/450 nM Emission is read to confirm total cell number is consistent across the plate.

Regulation of Human Neutrophil Oxidative Burst and Elastase Production (Assays C1-C3 in the Data Tables Below)

Neutrophil Oxidative Burst

Background and Therapeutic Relevance:

Phagocytosis by polymorphonuclear neutrophils and monocytes constitutes an essential arm of host defense against infections by microorganisms including bacteria and fungi. The phagocytic process can be separated into several major stages: chemotaxis (migration of phagocytes to inflammatory sites), attachment of particles to the cell surface of phagocytes, ingestion (phagocytosis) and intracellular killing by oxygen-dependent (oxidative burst) and oxygen-independent mechanisms. Reduced or missing burst activity is observed in inborne defects like the chronic granulomatous disease (CGD). CGD is a heterogeneous group of inherited disorders that usually manifests itself during the first two years of life. The disease is characterized by repeated and life-threatening infections caused by bacterial and fungal organisms. These infections typically consist of pneumonia, lymphadenitis, or abscesses that involve lymph nodes, lungs, and liver. The NADPH oxidase is the enzyme system responsible for producing superoxide anion, which is quickly converted to hydrogen peroxide and hydroxyl radicals. Abnormalities in the constituent peptides of the NADPH oxidase enzyme system lead to the dysfunctions characteristic of CGD. Neutrophils from CGD patients fail to produce a significant oxidative burst following stimulation. Different forms of CGD are described (classical X-linked CGD and autosomal recessive patterns). The oxidative burst of granulocytes is impaired in transplantation, later stages of HIV infection, and in the elderly, making these populations more susceptible to secondary infection and exacerbations of inflammatory disease. Various immunomodulators (e.g., cytokines (GM-CSF, G-CSF, TNF) or drugs) also seem to have effects on the oxidative burst. There is the potential for proteins with the ability to up-regulate or down-regulate oxidative burst in a therapeutic fashion to be useful for a variety of different disease states.

Methods:

The protein kinase C ligand phorbol 12-myristate 13-acetate (PMA) can be utilized in this assay as an agonist of the oxidative burst process. Heparinized whole blood is mixed with sterile dextran (0.6% final concentration) for 1 hour and allowed to separate into layers. The lower layer contains neutrophil, monocytes and red blood cells. An ammonium chloride lysis step is utilized to remove all RBCs and a 97% pure population of neutrophils with approximately 3% monocyte contamination remains following lysis step. Upon stimulation, granulocytes and monocytes produce reactive oxygen metabolites (superoxide anion, hydrogen peroxide, hypochlorous acid) which destroy bacteria inside the phagosome. Formation of the reactive oxidants during the oxidative burst can be monitored by the addition and oxidation of Amplex Red. The percentage of cells having produced reactive oxygen radicals are then analyzed as well as their mean fluorescence intensity using a fluorescent plate reader. The typical time course for this reaction is 10 minutes, with obvious burst being seen by 2 minutes and a drop off of signal being seen by 20 minutes. This assay can be run in agonist mode in the absence of PMA or in antagonist mode, with concomitant administration of AARS polypeptides and PMA at a concentration that is below the EC50 for this compound.

Regulation of Human Neutrophil Elastase Production

Background and Therapeutic Relevance:

Neutrophil elastase is a serine protease that has been implicated as having a specific role in the development of a wide range of human diseases, including inflammatory disorders of the lung and cardiovascular system. Although its key physiologic role is in innate host defense, it can also participate in tissue remodeling and possesses secretagogue actions that are now recognized as important to local inflammatory signals. Neutrophil elastase activity has been implicated in the development of emphysema for several decades, however only relatively recently has a pathogenetic function been ascribed to this serine proteinase in situations where excessive extracellular matrix deposition occurs. The use of genetically manipulated animal models is starting to uncover the potential ways in which its actions might influence fibrotic lung repair. Emerging evidence suggests that the engagement of cellular pathways with more direct effects on fibrogenic mediator generation and collagen synthesis appears to underpin the actions of neutrophil elastase in promoting lung matrix accumulation. Human neutrophil elastase is also present within atherosclerotic plaques where it contributes to matrix degradation and weakening of the vessel wall associated with the complications of aneurysm formation and plaque rupture. It is joined by other extracellular proteases in these actions but the broad range of substrates and potency of this enzyme coupled with activity associated with neutrophil degranulation single this disruptive protease out as therapeutic target in atherosclerotic disease.

Methods:

This assay uses the ENZCHEK® Elastase Assay Kit (Invitrogen Catalog # E-12056). Neutrophils are prepared from fresh human blood using a 6% dextran solution and red blood cells are lysed before plating cells in RPMI media (media should be un-supplemented with no serum, no antibiotics). A 1.0 mg/mL stock solution of the DQ elastin substrate is prepared by adding 1.0 mL of deionized water (dH2O) directly to one of the three vials containing the lyophilized substrate and mixing to dissolve. 1× Reaction Buffer is prepared by diluting 6 mL of the 10× Reaction Buffer in 54 mL dH2O. A 100

μg/mL working solution of the DQ elastin substrate is prepared by diluting the DQ elastin stock solution tenfold in 1× Reaction Buffer. Porcine pancreatic elastase stock solution is prepared by making a 100 U/mL stock solution in dH2O. To assay for elastase activity, 50 μL of 1× Reaction Buffer is pipette into each assay well containing 500,000 neutrophils/mL in a 30 μL volume. 8 μL of each AARS polypeptide is added per well, and the sample incubated for 20 minutes at 37° C. 50 μL of 100 μg/mL DQ elastin working solution is added to each well and mixed. Samples are incubated at room temperature, protected from light, for 30 minutes. Fluorescence intensity in a fluorescence microplate reader equipped with standard fluorescein filters (ex 485/Em 535) fluorescence may be measured over multiple time points.

Binding to Toll-Like Receptors and Activation of NFκB (Assays D1-D4 in the Data Tables Below)

Background and Therapeutic Relevance:

Macrophages are major players in the innate immune system and express a large repertoire of different classes of pattern recognition receptors (PRRs), including the family of Toll-like receptors (TLRs) which are powerful regulators and controllers of the immune response.

Stimulation of TLRs by microbial pathogens and endogenous ligands initiates signaling cascades that induce the secretion of pro-inflammatory cytokines and effector cytokines that direct downstream adaptive immune responses. Endogenous ligands, as well as microbial components, are recognized by and can activate TLRs, raising the possibility that these receptors may be critical targets for the development of new therapies for multiple diseases.

Accordingly AARS polypeptides that modulate TLR receptor activity, have therapeutic utility in a broad range of diseases and disorders including for example, inflammatory diseases and disorders, autoimmune diseases, tissue transplantation/organ rejection, cancer prevention or treatment, the modulation of haematopoiesis and infection.

Measurement of TLR Activation in RAW-BLUE Cells

Mouse macrophages sold under the trademark RAW-BLUE™ cells (Invivogen, Catalog code: raw-sp) express all TLRs except TLR5 and include a secreted embryonic alkaline phosphatase (SEAP) gene which is inducible by NF-kB and AP-1 transcription factors. Upon TLR stimulation, RAW-BLUE™ cells activate NF-kB and/or AP-1 leading to the secretion of SEAP which is measurable when using SEAP detection medium.

Methods:

RAW-BLUE™ cells are washed twice with PBS, trypsinized and resuspended in fresh Growth Medium (Growth Medium: DMEM, 4.5 g/1 glucose, 10% heat-inactivated fetal bovine serum (30 minutes at 56° C.), 100 mg/mL ZEOCIN™, 2 mM L-glutamine). Cells are plated at a concentration of 50,000 cells/well in a 96 well plate in a total volume of 100 μL, and AARS polypeptides, controls, or AARS polypeptides (+LPS) are added to each well at the concentrations shown in the experiments outlined below. Cells are incubated at 37° C. in a 5% CO2 incubator for 18 hours. On experimental day 2, SEAP detection medium (QUANTI-BLUE™) (Invivogen Catalog code: rep-qbl) is prepared following the instructions and 120 μL is added per well to a clear flat-bottom 96-well plate, and cell supernatant is added (20 μL). Samples are incubated at 37° C. for about 30 minutes to up to 2 hours. SEAP levels are determined using a spectrophotometer and reading absorbance at 650 nM.

To detect AARS polypeptides that specifically block TLR activation this assay can be modified to identify potential TLR antagonists. In this case AARS polypeptides are added to the cells at a final concentration of about 250 nM per well, (or as otherwise specified in the Examples below) 1 hour prior to adding 50 ng/mL LPS. Cells are incubated and SEAP detected as described above. PBS control wells with no LPS or AARS polypeptide alone added are used to find the basal level of TLR stimulation at the time of the measurement. Control wells are pretreated with PBS and known TLR agonists and antagonists. The ratio of the background subtracted [PBS plus LPS signal] to [AARS polypeptide plus LPS signal] is used to determine percent antagonism.

Human TLR Screening in Hek293 Cells

Human HEK293 cells are genetically modified and sold under the trademark HEK-Blue™ TLR cells (Invivogen). The TLR2 and TLR4 versions of this cell type selectively express all TLR2 or TLR4 and include a secreted embryonic alkaline phosphatase (SEAP) reporter gene under the control of an IFN-beta minimal promoter which is fused to five NF-kB and AP-1 transcription factors binding sites. With the use of specific TLR 2 or 4 agonists (respectively), HEK-BLUE™ TLR2 and HEK-BLUE™ TLR4 cells activate NF-kB and/or AP-1 leading to the secretion of SEAP which is measurable when using SEAP detection reagent. The HEK-BLUE™ TLR2 cells are co-transfected with the LPS co-receptor protein CD14 to enhance TLR2 responsiveness and improve signal quality. The parent cell expresses endogenous levels of TLR1, 3, 5, 6 and also NOD1.

Methods:

HEK-BLUE™-TLR2 or HEK-BLUE™-TLR4 cells are washed twice with PBS, trypsinized and resuspended in fresh Growth Medium (Growth Medium: DMEM, 4.5 g/L glucose, 10% heat-inactivated fetal bovine serum (30 minutes at 56° C.), 100 mg/mL ZEOCIN™, 2 mM L-glutamine). Cells are plated at a concentration of 50,000 cells/well in a 96 well plate in a total volume of 100 μL, and AARS polypeptides, controls, or AARS polypeptides (+LPS) are added to each well at the concentrations shown in the experiments outlined below. Cells are incubated at 37° C. in a 5% CO2 incubator for 18 hours. On experimental day 2, SEAP detection medium (QUANTI-BLUE™) (Invivogen Catalog code: rep-qbl) is prepared following the instructions and 120 μL is added per well to a clear flat-bottom 96-well plate, and cell supernatant is added (20 μL). Samples are incubated at 37° C. for about 30 minutes to up to 2 hours. SEAP levels are determined using a spectrophotometer and reading absorbance at 650 nM. Control wells are pretreated with PBS and known TLR agonists such as UltraPure LPS (TLR-4) or PAM3CSK4 (TLR-2). The ratio of the background subtracted [PBS plus LPS signal] to [AARS polypeptide plus LPS signal] is used to determine percent agonism.

Cytokine Release (Assays E1-E16 in the Data Tables Below)

Background and Therapeutic Relevance:

Cytokines are a diverse set of small cell signaling protein molecules that are used extensively for intercellular communication, and play significant roles in normal body homeostasis, including immunomodulation and regulation. Accordingly AARS polypeptides that modulate the release, or biological activities of cytokines, have therapeutic utility in a broad range of diseases and disorders including for example, inflammatory diseases and disorders, autoimmune diseases, tissue transplantation/organ rejection, cancer prevention or treatment, the modulation of haematopoiesis and infection.

Cytokine Release from Cells in Culture

Methods:

Test cells are seeded into a 24-well plate at density of about 1 million cells/well in 1 mL of growth media. Cells are treated with either AARS polypeptide (at the concentrations shown in the examples below) or an equal volume of PBS and incubated overnight at 37° with 5% CO2. Following cell treatment, samples are centrifuged at 4° C. in a swinging bucket centrifuge at 2,000×g for 5 minutes. Media is carefully removed so as to not disturb the cell pellet and transferred to a new tube. Samples are assayed immediately or snap frozen in liquid nitrogen for subsequent analysis. Cytokine release (including the cytokines MIF, IL-8, IL-10, Serpin E1, GM-CSF, GIRO, IL-1 alpha, IL-1beta, IL-1ra, IL-6, MCP-1, MIP-1, RANTES and TNFalpha) is determined using commercially available kits (R&D Systems, Inc, MN, USA) or via a contract research organization (MD Biosciences (St. Paul, Minn.).

Cytokine Release from Human Whole Blood

Methods:

Human whole blood is obtained from normal human donors and collected with heparin in standard collection tubes. Blood is used on the same day as it is collected to ensure adequate cell health. Blood is mixed gently and plated in an 100 µL volume into 96 well polycarbonate V bottom plates. AARS polypeptides are added and slowly mixed into blood 2× using a multichannel pipet set on 50 µL. Filter tips are used for all experimentation and full PPE is worn. All experimentation occurs in a dedicated biosafety hood that is suitable for experimentation with human blood. Blood is incubated overnight at 37° C. with 5% $CO_2$. Following cell treatment, samples are centrifuged in a swinging bucket centrifuge at 2,000×g for 5 minutes. Supernatant is collected for cytokine ELISAs ELISA are performed as described previously.

Cytokine Release from PBMCs

Methods:

To isolate peripheral blood mononuclear cells freshly isolated human whole blood is gently layered over Sigma HISTOPAQUE®-1077 at a ratio of 1:1 in 50 mL conical tubes at room temperature. Layered samples are centrifuged at 400×g in a swinging bucket clinical centrifuge for 30 minutes at room temperature with no brake. The white cellular layer at the interface between the plasma and density gradient is then removed by pipet. These peripheral blood mononuclear cells are washed twice with RPMI-1640 (Invitrogen #22400-105) by dilution and centrifugation for 10 minutes at 250×g. The washed PBMC were resuspended in RPMI-1640+10% FBS and plated at $1 \times 10^6$ cells/mL.

Cytokine Release from Human Synoviocytes

Background and Therapeutic Relevance:

A large number of studies have demonstrated that IL-6 and IL-8 are overproduced in several diseases, and thus may play a fundamental role in the pathogenesis of inflammatory disease. IL-6 activates endothelial cell production, leading to the release of IL-8 and monocyte chemoattractant protein, expression of adhesion molecules, and recruitment of leukocytes to inflammatory sites. These cytokines are expressed in cell types associated with inflammatory disease, including cells involved in the pathogenesis of systemic juvenile arthritis, systemic lupus erythematosus, Crohn's disease, and rheumatoid arthritis. One of the most important systemic actions of cytokine production is the induction of the acute phase response. Acute phase proteins are produced primarily by the liver and include proteins that promote the immune response through activation of complement, induction of proinflammatory cytokines, and stimulation of neutrophil chemotaxis. Alternatively, the acute phase response can be helpful, and acute-phase proteins, such as proteinase antagonists, opsonins, and procoagulants, help limit tissue destruction by resolving inflammation. In particular, IL-6 can stimulate synoviocyte proliferation and osteoclast activation, leading to synovial pannus formation and repair. IL-6 acts with IL-1 to increase production of matrix metalloproteinases, which may contribute to joint and cartilage destruction. However, IL-6 may also have protective effects in the joint, as suggested by the finding that this cytokine induces the expression of the tissue inhibitor of metalloproteinase and stimulates proteoglycan synthesis when injected into the joints of mice with antigen-induced arthritis. Human Fibroblast-Like Synoviocytes-Rheumatoid Arthritis (HFLS-RA) are isolated from synovial tissues obtained from patients with Rheumatoid Arthritis (RA). They are cryopreserved at second passage and can be cultured and propagated at least 5 population doublings. HFLS are long known for their role in joint destruction by producing cytokines and metalloproteinases that contribute to cartilage degradation.

Accordingly AARS polypeptides with the ability to modulate the growth, differentiation, or cytokine release profile of fibroblast-like synoviocytes-rheumatoid arthritis (HFLS-RA) have therapeutic utility in a broad range of diseases including for example, the treatment of inflammatory diseases and disorders including systemic juvenile arthritis, systemic lupus erythematosus, Crohn's disease, and rheumatoid arthritis.

Methods:

HFLS-RA, adult cells (Cell Applications Cat #408RA-05a) are maintained in Synoviocyte Growth Medium (Cell Applications Cat #415-50) in 15 mL medium in 125 mL flasks for 1 passage before use. Cells are maintained at 37° C., 5% $CO_2$, in a humidified environment and utilized in BSL2 certified tissue culture hoods using sterile technique and appropriate personal protective equipment including goggles, gloves and lab coats. An 80 µL volume of cells is plated overnight in growth medium at a cell density of about 50,000 cells/mL. AARS polypeptides at a final concentration of 250 nM per well (or as otherwise indicated in the examples below) are added in sterile PBS to each well following overnight adherence. Control wells contain untreated cells and are incubated with an equivalent volume of PBS. Cells are exposed to proteins or PBS in basal media (Cell Applications Cat #310-470) for 24 hours. Supernatant is removed and IL-8, IL-6 and TNFa ELISA assays are run according to manufacturer's instructions (RND Systems, Cat #DY206 and DY-208, DY-210 Duo-set kits). Proliferation is assessed with Resazurin as described previously by adding fresh media containing Resazurin to plates following supernatant removal and incubating for three hours at 37° C. Plates are read on a fluorescent plate reader and viability/proliferation is expressed as a function of resorufin associated fluorescence of AARS polypeptide treated wells divided by resorufin associated fluorescence of PBS only treated wells.

Human Astrocyte Proliferation and Inflammatory Cytokine Production

Background and Therapeutic Relevance:

Human astrocytes (HA) are derived from human cerebral cortex. They are cryopreserved at second passage and can be cultured and propagated 10 population doublings. HA are the most abundant cells in the central nervous system and they perform many functions such as provision of mechanical support and nutrients to neurons, and removal of wastes from neurons. In addition to playing a critical support role for optimal neuronal functioning, they also provide biochemical support of endothelial cells which form the blood-brain barrier. Recent studies have shown that astrocytes are capable of regulating neurogenesis by instructing the stem cells to adopt a neuronal fate and controlling the function of single synapses, participate actively in the transfer and storage of information in the brain. Recognition of the importance of astrocytes in nervous system functioning is increasing, HA can serve as useful in vitro model for exploring the diversity of astrocytes functions. Astrocytes have been shown to proliferate in response to IL6 and TNFalpha. In addition, these cells are capable of making their own IL6 and TNFalpha. Thus AARS polypeptides which modulate the proliferation and cytokine production in HA have therapeutic utility in a variety of neurological diseases including neuro-inflammation, neurodegeneration, tumorigenesis of the brain, and brain ischemia and repair.

Methods:

Human Astrocytes (HA) from Cell Applications (Cat #882K-05f) are maintained in Cell Applications HA Cell Growth Medium (Cat #821-500) according to manufacturer's instructions. Cells are maintained at 37° C., 5% $CO_2$, in a humidified environment and utilized in BSL2 certified tissue culture hoods using sterile technique and appropriate personal protective equipment including goggles, gloves and lab coats. An 80 μL volume of cells is plated on collagen coated plates overnight in complete medium (above) at a cell density of 50,000 cells/mL. Cells are washed once with PBS and 80 μL of serum free growth media is added to each well. AARS polypeptides at a final concentration of 250 nM per well (or as otherwise described in the examples below) are added in a consistent volume in sterile PBS to each well. Cells are exposed to AARS polypeptides for 48 hours and spent media is removed for cytokine assessment (as described previously). Cells are exposed to proteins or PBS in basal media (Cell Applications Cat #310-470) for 48 hours. Supernatant is removed and IL-8 and IL-6 ELISA assays are run according to manufacturer's instructions (RND Systems, Cat #DY206 and DY-208, DY-210 Duo-set kits). Proliferation is assessed with Resazurin as described previously by adding fresh media containing Resazurin to plates following supernatant removal and incubating for three hours at 37° C. Plates are read on a fluorescent plate reader and viability/proliferation is expressed as a function of resorufin associated fluorescence of AARS polypeptide treated wells divided by resorufin associated fluorescence of PBS only treated wells.

Human Lung Microvascular Endothelial Cell (HLMVEC) Proliferation and Inflammatory Cytokine Production.

Background and Therapeutic Relevance:

The pulmonary vasculature is of great physiological/pathological significance. It is now recognized to be a tissue composed of metabolically active, functionally responsive cells, that interact with circulating substrates and formed elements in ways that regulate the composition of systemic arterial blood, affect target organ functions, and contribute to thrombosis, hemostasis and immune reactions, as well as tumor metastasis. Human lung microvascular endothelial cells (HLMVEC) exhibit elevated expression of chemoattractant cytokines and cell adhesion molecules that provide critical cues for directed migration of leucocytes into the lung during acute lung injury. This primary cell type can be useful tool for studying various aspects of pathology and biology of the pulmonary microvasculature in vitro. Alteration in the structure and function of the microvasculature in response to inflammatory stimuli is believed to be a key factor in organ damage and under appropriate conditions, may provide a stimulus for repair. A significant cause of these vascular alterations is the induction of an inflammatory reaction involving leukocyte infiltration. A variety of studies focused on granulocyte adhesion to the endothelium have revealed that leukocyte recruitment and emigration involves a well-orchestrated adhesion cascade. The adhesion cascade begins when the granulocyte attaches to the endothelium and begins to roll in the direction of fluid flow at a low velocity. As the granulocyte rolls, it becomes activated, subsequently firmly adheres to the endothelium, and migrates across the endothelium into the extravascular space. These adhesion events are mediated, in part, by molecular interactions that occur between CAMs on the surface of the granulocytes and cognate glycoproteins present on the endothelium. A variety of studies have revealed that the endothelial cell adhesion molecule E-selectin can interact with SLex-type glycan presenting granulocyte ligands to mediate the attachment and rolling steps of the adhesion cascade. The downstream steps of the cascade involve the interaction of endothelial-expressed intercellular adhesion molecule with granulocyte-expressed CD18 integrins.

Thus AARS polypeptides which modulate proliferation and/or cytokine production of human lung microvascular endothelial cells have therapeutic utility in a variety of vascular and pulmonary diseases including inflammatory and obstructive lung diseases including for example, pulmonary hypertension, chronic obstructive pulmonary disease, idiopathic pulmonary fibrosis, and asthma.

Methods:

HLMVEC (Cell Applications, Catalog #540-05) are maintained in Cell Applications Microvascular Endothelial Cell Growth Medium (Cat #111-500), For appropriate growth, an Attachment Factor Solution containing collagen (Cell Applications, Catalog #123-100), is used to coat plates and flasks before plating cells. Cells are maintained at 37° C., 5% $CO_2$, in a humidified environment and utilized in BSL2 certified tissue culture hoods using sterile technique and appropriate personal protective equipment including goggles, gloves and lab coats. A 804, volume of cells is plated on collagen coated plates overnight in complete medium (above) at a cell density of 50,000 cells/mL. Cells are washed once with PBS and 80 μL of serum free growth media is added to each well. AARS polypeptides at a final concentration of 250 nM per well (or as otherwise described in the examples below) are added in a consistent volume in sterile PBS to each well. Cells are exposed to AARS polypeptides for 48 hours and spent media is removed for ELISA for cell adhesion molecules and cytokine assessment (as described previously). Cell adhesion molecules including soluble VCAM and/or ICAM are measured using a standard ELISA kit from RND Systems (Cat #DY643 and DY720 respectively). Proliferation is assessed with Resazurin as described previously by adding fresh media containing Resazurin to plates following supernatant removal and incubating for three hours at 37° C. Plates are read on a fluorescent plate reader and viability/proliferation is expressed as a function of resorufin associated fluorescence of AARS polypeptide treated wells divided by resorufin associated fluorescence of PBS only treated wells.

Cell Adhesion ((Assays F1-F7 in the Data Tables Below)

Background and Therapeutic Relevance:

Cell Adhesion Molecules (CAMs) are proteins located on the cell surface which are involved with the binding with other cells or with the extracellular matrix (ECM) in the process called cell adhesion. These proteins are typically transmembrane receptors and are composed of three domains: an intracellular domain that interacts with the cytoskeleton, a transmembrane domain, and an extracellular domain that interacts either with other CAMs of the same kind (homophilic binding) or with other CAMs or the extracellular matrix (heterophilic binding). Most of the CAMs belong to four protein families: Ig (immunoglobulin) superfamily (IgSF CAMs), the integrins, the cadherins, and the selectins. The immunoglobulin superfamily (IgSF) cell adhesion molecules are calcium-independent transmembrane glycoproteins, including: neural cell adhesion molecules (NCAMs), intercellular cell adhesion molecules (ICAMs), vascular cell adhesion molecule (VCAM), platelet-endothelial cell adhesion molecule (PECAM-1), endothelial cell-selective adhesion molecule (ESAM), junctional adhesion molecule (JAMs), nectins, and other cell adhesion molecules.

Cell adhesion molecules are cell surface glycoproteins that are critical for leukocyte adhesion to the sinusoidal endothelium and transmigration and cytotoxicity in a variety of inflammatory liver diseases. ICAM-1 plays an important role in inflammation, and the increased expression of ICAM-1 on endothelial cells is reflected in the activation of endothelial cells. ICAM-1 is of particular importance since it mediates firm endothelial adhesion and facilitates leukocyte transmigration. Studies have shown that there is an upregulation of ICAM-1 on both sinusoidal cells and hepatocytes in inflammatory liver conditions such as hepatitis B viral infection, autoimmune liver disorders, alcoholic hepatitis, and liver allograft rejection.

Thus AARS polypeptides which modulate cell adhesion molecule production and cell adhesion to endothelial cells have therapeutic utility in a variety of inflammatory diseases including for example, cardiovascular diseases, atherosclerosis, autoimmunity and pulmonary hypertension.

Methods:

Human umbilical vein cells (ATCC, Cat # CRL-2873) (HUVEC) are seeded at a concentration of about $1.2 \times 10^5$ cells/well in 12 well plates coated with human fibronectin attachment solution in the suggested ATCC media and supplements and grown according to manufacturer's instructions. Cells are stimulated with AARS polypeptides at the indicated concentrations, or PBS alone, and incubated overnight in growth media. Human acute monocytic leukemia (THP-1 (TIB-202)), cells are resuspended into 0.1% BSA/RPMI serum free medium with calcein AM (6 µL/mL; Invitrogen Cat # C1430) and incubated for 30 minutes. Labeled cells are collected and resuspended in RPMI medium containing 10% FBS, and the density adjusted to $2 \times 10^6$ cells/mL.

100 µL ($2 \times 10^5$) labeled THP-1 cells are placed into each well of the HUVEC monolayer in 1 mL of growth media and incubated for 15 minutes. The wells are washed twice with PBS to remove unbound cells, and then the cells are read by fluorescent plate reader with an Excitation wavelength of 488 nm and an Emission wavelength of 530 nm.

Cellular Differentiation (Assays G1-G4 in the Data Tables Below)

Adipocyte Differentiation and Proliferation in Primary Human Pre-Adipocyte Cells.

Background and Therapeutic Relevance:

Both obesity and lipodystrophy are commonly associated with pathologies including diabetes and cardiovascular diseases. It is now recognized that adipose tissue is an endocrine organ that secretes a wide variety of factors, and dysregulated secretion affects adipogenesis as well as whole-body glucose/insulin homeostasis. Excess adipose tissue leading to obesity has become a severe public health threat. Adipose tissue development can be affected by genetic background, hormonal balance, diet, and physical activity. Adipose tissue mass can increase when fat cells are increased in size due to higher triacylglycerol accumulation. In addition, an increase in fat cell number, arising from differentiation of precursor cells into adipocytes, can also occur even in adults as observed in severe human obesity and in rodents fed a high-carbohydrate or high-fat diet. Adipocytes specifically are thought to arise from mesenchymal cells that undergo the commitment and differentiation process, adipogenesis. Pre-adipocyte cell lines can undergo adipocyte differentiation upon treatment with adipogenic agents comprised of synthetic glucocorticoid, dexamethasone (DEX), isobutylmethylxanthine (IBMX), and insulin, have been valuable in these studies. Peroxisome proliferator-activated receptor γ (PPARγ) and CCAAT enhancer-binding protein (C/EBP) family of transcription factors have been firmly established to play critical roles in adipocyte differentiation. Early during adipocyte differentiation, C/EBPβ and C/EBPδ are induced by DEX and IBMX, respectively, which together then induce PPARγ and C/EBPα to activate various adipocyte markers that are required for adipocyte function. Other transcription factors have also been reported to either positive or negatively regulate adipogenesis and various growth factors and hormones can affect adipocyte differentiation by regulating expression of adipogenic transcription factors. In fact, in addition to being the main site for energy storage in mammals by storing triacyglycerol and releasing fatty acids in times of need, adipose tissue secretes a wide array of molecules that are involved in diverse physiological processes including immune response, vascular function, and energy homeostasis. Cytokines such as TNF-α and IL-6 are secreted from adipocytes. Some of these factors may also affect growth and development of adipose tissue by autocrine/paracrine action.

Thus AARS polypeptides which have the ability to modulate the differentiation and/or proliferation of normal human pre-adipocytes have therapeutic utility in a broad range of diseases including for example, the treatment and prevention of metabolic disease, cardiovascular diseases, obesity and lipodystrophies, as well as the long term complications of diabetes.

Methods:

HPAd (human pre-adipocytes) (Cell Application Cat #803sD) are maintained according to vendor instructions. For culturing, cells are thawed quickly, and transferred immediately into 15 mL of Adipocyte Growth Medium (Cell Application Cat #811M-250) and plated into a standard sterile tissue culture treated flask. Media is replaced with fresh Adipocyte Growth Medium every other day until cell is >60% confluent. Cells are grown at 37° C., 5% $CO_2$, in a humidified environment and utilized in BSL2 certified tissue culture hoods using sterile technique and appropriate personal protective equipment including goggles, gloves and lab coats. Cells are plated in clear bottom black walled 96 well tissue culture treated assay plates for differentiation at a concentration of about 50,000 cells/mL. AARS polypeptides at a final concentration of 250 nM per well (or as otherwise indicated in the Examples below) are added to each assay well. All cells are maintained in growth media for 2 days with the exception of the positive controls which are stimulated with adipogenic differentiation media (Cell Applications Cat #811D-250). Cells are exposed to AARS polypeptides for 48 hours. Cell adhesion molecules including soluble VCAM and/or ICAM are measured using a standard ELISA kit from RND Systems (Cat #DY643 and DY720 respectively). Proliferation is assessed with Resazurin as described previously by adding fresh media containing Resazurin to plates following supernatant removal and incubating for three hours at 37° C. Plates are read on a fluorescent plate reader and viability/proliferation is expressed as a function of resorufin associated fluorescence of AARS polypeptide treated wells divided by resorufin associated fluorescence of PBS only treated wells. Fresh media is added and differentiation is maintained for 16 days post initial media exchange, with fresh media exchanged every other day to maintain cell health. On day 15, cells are placed in serum free media. On day 16, differentiation to mature adipocytes is assessed with Nile Red (Invitrogen, concentration of 3 µM final) staining and quantified with a fluorescent plate reader with the appropriate wavelengths. To perform this assay cells are fixed with 10% paraformaldehyde, washed in PBS and permeabilized in PBS containing 0.5% BSA and 0.1% Triton X-100. Cell proliferation is assessed with an intensity measurement on a fluorescent reader with Hoechst dye 33432 at a concentration of 1 ug/mL final, as described previously. Adipogenesis is expressed as intensity of Nile Red signal. Hoechst dye signal is used to assess cellular number.

Human Skeletal Muscle Cell Differentiation and Proliferation.

Background and Therapeutic Relevance:

The development of skeletal muscle is a multistep process that involves the determination of pluripotential mesodermal cells to give rise to myoblasts, withdrawal of the myoblasts from the cell cycle and differentiation into muscle cells, and finally growth and maturation of skeletal muscle fibers. Skeletal muscle differentiation involves myoblast alignment, elongation, and fusion into multinucleate myotubes, together with the induction of regulatory and structural muscle-specific genes. At the molecular level, myogenic commitment and muscle-specific gene expression involve the skeletal muscle-specific helix-loop-helix (bHLH) MyoD family of proteins, which includes MyoD, myogenin, myf-5, and MRF4, and the myocyte enhancer-binding factor 2 (MEF2). The DNA binding activity of MyoD family proteins is attenuated by Id, which forms complex es with E2a gene products in proliferating cells and is down-regulated when they are induced to differentiate. The decision to differentiate into myotubes is influenced negatively by several factors. Treatment of myoblasts with fetal bovine serum, basic fibroblast growth factor 2, or transforming growth factor β1 is known to inhibit differentiation of myoblasts. Myogenesis is also regulated negatively by oncogenes such as c-myc, c-jun, c-fos, H-ras, and E1a. There is very little information regarding the signaling that is triggered in the myoblast upon serum withdrawal which leads to the induction of the MyoD family gene expression and to muscle differentiation. Myogenic differentiation appears to depend on the activation of integrins present on the plasma membrane of myoblasts suggesting the operation of an "outside-in" biochemical pathway in which integrin is the upstream molecular species. Interactions of insulin-like growth factor (IGF)-I and -II with their receptors are also positive regulators of skeletal muscle differentiation.

Accordingly AARS polypeptides with the ability to modulate muscle development have therapeutic utility in a broad range of diseases including for example, the treatment of metabolic disease, cachexia, various muscle wasting conditions, as well as musculoskeletal disease where muscle atrophy plays a key role in the pathogenesis and symptomology. Human Skeletal Muscle Cells (HSkMC) can undergo differentiation to exhibit actin and myosin myofilaments. HSkMC have been used in the study of genetic muscular diseases such as Malignant Hyperthermia. HSkMC also have the potential to act as a cardiac graft, mending damage to the heart, and thus AARS polypeptides with the ability to modulate muscle development also have utility as in vitro and in vivo regulators of myogenesis.

Methods:

To assess the potential role of AARS polypeptides in this process, a standard assay of skeletal muscle cell differentiation was employed. For this assay, Human Adult Skeletal Muscle Cells (HSkMC, Cell Application Cat #150-05f) are isolated from healthy human donors from limbal skeletal muscle. Cells are maintained in HSkMC Growth Medium (Cell Applications, Cat #151-500). These cells can be cultured and propagated for at least 15 population doublings. For differentiation, cells are maintained in growth media for one passage and then plated at 50,000 cells per mL media in to 96 well clear bottom black walled TC treated plates treated with collagen at 100 µL per well. Cells are allowed to adhere overnight. AARS polypeptides in PBS, or PBS alone, is added to each well at a final concentration of 250 nM protein (or as otherwise indicated in the examples below). Control wells received the same volume of Differentiation Media (Cell Applications Cat #151D-250) at this time. Cells are incubated with protein or differentiation media for 48 hours. At 48 hours, cell culture supernatant is collected from all wells and differentiation media is added at a volume of 150 µL to the entire plate with the exception of control wells which are maintained in growth media only. Supernatant is utilized to assess cytokine production including IL6 and IL8 as described previously. Proliferation is assessed with Resazurin as described previously by adding fresh media containing Resazurin to plates following supernatant removal and incubating for three hours at 37° C. Cells are monitored under the microscope and media is exchanged for fresh Differentiation media every 2 days. On Day 10, media is removed and cells are fixed with 10% paraformaldehyde for 30 minutes. Cells are permeabilized with 0.1% Triton X-100 in PBS for 15 minutes and cells are stained with TR-Labeled phalloidin and Hoechst 33432 (as described previously) to define actin and nuclei respectively. Nuclear intensity is used to determine cell proliferation in each well and phalloidin intensity is used to determine total actin content. Cells are also stained with alpha actin skeletal muscle antibody (GenTex Cat #GTX101362). Digital photos using a fluorescent microscope as well as visual inspections and scoring are made of all wells.

Human Bone Marrow Mesenchymal Stem Differentiation and Proliferation.

Background and Therapeutic Relevance:

Mesenchymal stem cells (MSCs) are multipotent stem cells that can differentiate into a variety of cell types, including osteoblasts, chondrocytes, myocytes, adipocytes, beta-pancreatic islets cells, and potentially, neuronal cells. Many different events contribute to the commitment of the MSC to other lineages including the coordination of a complex network of transcription factors, cofactors and signaling intermediates from numerous pathways. MSCs are of intense therapeutic interest because they represent a population of cells with the potential treat a wide range of acute and degenerative diseases.

Moreover AARS polypeptides with the ability to modulate the differentiation of MSCs into different developmental pathways have significant therapeutic utility to enable the in vitro or in vivo modulation of hematopoiesis, neurogenesis, myogenesis, osteogenesis, and adipogenesis, as well as in a broad range of disorders and diseases, including for example inflammatory responses, autoimmunity, cancer, neuronal degeneration, muscular dystrophy, osteoporosis, and lipodystrophy. Human MSCs are immuno-privileged, and represent an advantageous cell type for allogenic transplantation, reducing the risks of rejection and complications of transplantation. Recently, there have also been significant advances in the use of autologous mesenchymal stem cells to regenerate human tissues, including cartilage and meniscus, tendons, and bone fractures. Many studies have also investigated the use of MSCs for gene therapy, including transplantation of MSCs transfected with vascular endothelial growth factor for the improvement of heart function after MI in rats, MSCs as vehicles for interferon-β delivery into tumors in mice and gene therapy with MSCs expressing BMPs to promote bone formation. Accordingly due to the intense interest as MSCs as direct and modified therapeutics, as well as the potential of AARS polypeptides to act as therapeutic agents to regulate the differentiation of MSCs in vivo, AARS polypeptides were tested as potential inducers of MSC proliferation and differentiation.

Methods:

hMSC (human marrow stromal cells) (Cell Application Cat #492-050) are maintained according to vendor instructions. For culturing, cells are thawed quickly, and transferred immediately into 15 mL of Marrow Stromal cell Growth Medium (Cell Application Cat #419-500) and plated into a standard sterile tissue culture treated flask. Media is replaced with fresh Marrow Stromal cell Growth Medium every other day until cells are >60% confluent. Cells are grown at 37° C., 5% $CO_2$, in a humidified environment and utilized in BSL2 certified tissue culture hoods using sterile technique and appropriate personal protective equipment including goggles, gloves and lab coats. Cells are plated in clear bottom black walled 96 well tissue culture treated assay plates for differentiation at a concentration of 50,000 cells/mL. tRNA synthetase derived proteins at a final concentration of 250 nM per well (or as otherwise specified in the Examples below) are added to each assay well. All cells are maintained in growth media for 2 days with the exception of the positive controls, which was stimulated with osteogenic or chonodrogenic differentiation media (StemPro, Invitrogen, Cat # A10072-01 and A10071-01 respectively). Cells are exposed to AARS polypeptides for 48 hours. Soluble VCAM is measured using a standard ELISA kit from RND Systems (Cat #DY643). Proliferation is assessed with Resazurin as described previously by adding fresh media containing Resazurin to plates following supernatant removal and incubating for three hours at 37° C. Plates are read on a fluorescent plate reader and viability/proliferation is expressed as a function of resorufin associated fluorescence of AARS polypeptide treated wells divided by resorufin associated fluorescence of PBS only treated wells. Following an assessment of cell viability, resazurin is removed with two media exchanges and 0.5× differentiation media is added to all wells. Differentiation is monitored by visual inspections of all wells for 10 days post media exchange, with fresh media exchanged every other day to maintain cell health. Differentiation was assessed with alkaline phosphatase staining using ELF-97 stain (Invitrogen Cat# E6601) at day 10 post first differentiation exchange. (Yang et al, Nature Protocols (6) 187-213 (2011) doi: 10.1038/nprot.2010.189).

Human Pulmonary Artery Smooth Muscle Cell (hPASMC) Proliferation and Differentiation.

Background and Therapeutic Relevance:

Pulmonary artery smooth muscle cells (PASMCs) in normal human adult lung blood vessels are mostly quiescent, non-migratory and are largely committed to executing their contractile function in the lung. However, PASMCs are not terminally differentiated and possess the ability to modulate their phenotype and exit their quiescent state in response to changing local environmental cues. This differentiation state may occur in development, tissue injury, and vessel remodeling in response to changes in tissue demand. Pulmonary hypertension (PH) is associated with a variety of underlying conditions including an increase in peripheral pulmonary vascular resistance as a result of increased vascular tone and PASMC contractility and vascular remodeling. Vascular remodeling involves PASMC growth, synthesis of matrix material, and alterations in cell-cell and cell-matrix interactions in the walls of small pulmonary arteries (PAs), which lead to increased thickness of the smooth muscle component of the vessel wall and abnormal muscularization of the normally nonmuscularized, distal PAs. This process contributes to reduced lumen diameter and increased peripheral resistance. Although the precise role of the PASMCs in the initial cause of the disease is controversial, the changes that occur play a key role in the clinical consequences of the disease. A crucial step in studying cellular differentiation is identifying a set of cell-specific or cell-selective genes that contribute to the differentiated function(s) of the cell. A variety of smooth muscle cell (SMC) genes have been identified that serve as useful markers of the relative state of differentiation or maturation of the vascular SMCs, such as SM alpha-actin, SM MHC, hl-calponin, SM22-alpha, desmin, metavinculin, smoothelin and others. The most widely used marker is SM alpha-actin, partially because of the commercial availability of a number of very high-affinity and highly selective antibodies for this protein. Whether changes in PASMCs result from their inherent characteristics or from dysregulation of molecular events that govern PASMC growth remains an open question. However determining the regulatory cues and managing potential dis-regulation provides significant therapeutic insight to managing a variety of vascular and pulmonary diseases including pulmonary hypertension, vascular diseases.

Thus AARS polypeptides which have the ability to modulate the differentiation and/or proliferation of normal human PASMCs derived from adult humans have therapeutic utility in a variety of vascular and pulmonary diseases including inflammatory and obstructive lung diseases including for example, pulmonary hypertension, chronic obstructive pulmonary disease, idiopathic pulmonary fibrosis, and asthma.

Methods:

HPASMC (Cell Applications Cat #352-05a) are maintained in HPASMC growth media (Cell Applications Cat #352-05a) in 15 mL medium in 125 mL flasks for 1 passage before use. Cells are maintained at 37° C., 5% $CO_2$, in a humidified environment and utilized in BSL2 certified tissue culture hoods using sterile technique and appropriate personal protective equipment including goggles, gloves and lab coats. An 80 μL volume of cells is plated on collagen coated overnight in growth medium at a cell density of 50,000 cells/mL. AARS polypeptides were added in sterile PBS to each well at a final concentration of 250 nM (or as otherwise specified in the Examples below). Control wells held only an equivalent volume of PBS. Positive control samples were incubated with vendor supplied HPASMC differentiation media (Cell Applications Cat #311D-250). Cells are exposed to AARS polypeptides or PBS in basal media (Cell Applications Cat #310-470) for 48 hours followed by a media exchange to differentiation media for the entire plate. Supernatant is collected and utilized to assess cytokine production including IL6 and IL8 as described previously. Proliferation is assessed with Resazurin as described previously by adding fresh media containing Resazurin to plates following supernatant removal and incubating for three hours at 37° C. Cells are monitored for 10 days with a media exchange every other day. Differentiation is assessed after fixation as described above, and permeabilzation with 0.1% Triton X-100, by quantifying staining to smooth muscle actin-alpha staining using an anti-SMA-alpha antibody (GeneTex Cat #GTX101362) and an Alexa 405 conjugated secondary antibody. Proliferation is assessed with Hoechst staining after cell fixation in 10% formaldehyde for 30 minutes. Hoechst dye is read using a bottom reading fluorescent plate reader with an excitation wavelength (Ex) of 405 nm, and an emission wavelength (Em) of 450 nm. Total actin staining is assessed via the use of an Alexa-488 labeled phalloidin stain (Invitrogen Cat# A12379).

Analysis of the Binding of AARS Polypeptides to Cells (Assays H1-H10 in the Data Tables Below)

Background and Therapeutic Relevance:

The binding of AARS polypeptides to specific cell types demonstrates that the cell type in question expresses specific receptors for the AARS polypeptide in question. Depending upon the cell type in question, cell binding implies a potential role for the AARS polypeptide in regulating the activity or behavior of the cell, or similar types of cell, in vivo. Specific examples of such regulatory roles include for example, the binding and modulation of B-cells and T-cells (immunomodulation/chemotaxis/autoimmunity/inflammation); HepG2 cells (control of metabolism, cholesterol uptake or metabolism); THP-1, jurkat, Raji cells (immunomodulation/chemotaxis/autoimmunity/inflammation), platelets (thrombopoiesis), 3T3L1 adipocytes (lipogenesis/metabolism), and C2C12 mouse myoblasts (myogenesis, osteogenesis).

Binding to Blood Cells

Methods:

Blood is collected in EDTA tubes from healthy donors. 2 mL whole blood is placed into 5 mL Falcon FACS tube. 2 mL of staining buffer (PBS+2% FBS) is added, vortexed 3-5 seconds, centrifuged for 5 minutes at 300×g. The supernatant aspirated, the wash repeated, and the pellet resuspended in 2 mL of staining buffer.

100 µl of washed blood is transferred to clean 5 mL FACS sample tubes. His6- or V5-His6-tagged AARS polypeptides are added to tubes at the concentrations indicated in the specific experiments outlined below and incubated on ice for 45 minutes. After incubation, antibodies for the different cell type surface markers (BD Pharmigen Cat Nos. 560910, 555398, 555415, 340953, 560361), and FITC labeled anti-V5 tag antibody (V5-FITC, Invitrogen Cat # R96325) or FITC labeled anti-His6 antibody (AbCam Cat #ab1206) are added to tubes, incubated in the dark on ice 30 minutes. After incubation 2 mL of BD FACS Lysing Solution (cat #349202) was added to tubes. Samples are vortexed, and placed on ice for 15 minutes. Samples are washed with 1×2 mL PBS and resuspended in 2 mL of 2% formaldehyde in PBS prior to FACS analysis. AARS polypeptides that bind greater than 25% of a cellular population, where antibody alone has no significant signal, is deemed a hit.

Platelet Binding Assays:

50 µL of washed blood is transferred to clean 5 mL FACS sample tubes, His6- or V5-His6-tagged AARS polypeptides are added to tubes at the concentrations indicated in the specific experiments outlined below and tubes are placed on ice for 45 minutes. 20 µL CD61 pan platelet antibody (BD Pharmigen, Cat #555754) and 0.5 µL anti-V5-FITC labeled antibody (Invitrogen, R96325) or FITC labeled anti-His6 antibody (AbCam Cat #ab1206) are added to each tube. Tubes are placed on ice and protected from light for 30 minutes. Samples are brought up to a total volume in 2 mL of 1% formaldehyde in PBS and analyzed by flow cytometry within 24 hours. AARS polypeptides that bind greater than 25% of a cellular population, where antibody alone has no significant signal, is deemed a hit.

Binding to Cells in Culture:

Approximately $1 \times 10^6$ cells in 100 µL complete RPMI medium are placed into 5 mL FACS tubes. His6- or V5-His6-tagged AARS polypeptides are added to tubes at the concentrations indicated in the specific experiments outlined below and tubes are placed on ice for 45 minutes. Cell samples are washed twice with 1 mL staining buffer (PBS+2% FBS), and then 0.5 µL of anti-V5-FITC antibody (Invitrogen R96325) or FITC labeled anti-His6 antibody (AbCam Cat #ab1206) in staining buffer with 200 µg/mL human IgG, is added and the samples incubated on ice, protected from light, for 30 minutes. Samples are washed twice with 1 mL staining buffer, and then brought up to a total volume in 2 mL of 1% formaldehyde in PBS and analyzed by flow cytometry within 24 hours. AARS polypeptides that bind greater than 25% of a cellular population, where antibody alone has no significant signal, is deemed a hit.

Animal Studies: Modulation of Haematopoiesis and Circulating Cytokines

Background and Therapeutic Relevance:

Hematopoiesis (alternatively haemopoiesis or hemopoiesis) is the formation of blood cellular components. All cellular blood components are derived from haematopoietic stem cells (HSCs) which reside in the medulla of the bone (bone marrow) and have the unique ability to give rise to all of the different mature blood cell types. HSCs are self renewing: when they proliferate, at least some of their daughter cells remain as HSCs, so the pool of stem cells does not become depleted. The other daughters of HSCs (myeloid and lymphoid progenitor cells), however can each commit to any of the alternative differentiation pathways that lead to the production of one or more specific types of blood cells, but cannot themselves self-renew. A change in the blood components in response to exposure to an AARS polypeptide therefore suggests that the AARS polypeptide is capable of modulating hematopoiesis, and regulating the development of haematopoietic stem cells.

All blood cells can be divided into three lineages; Erythroid cells, lymphocytes and myelocytes.

Erythroid cells are the oxygen carrying red blood cells. Both reticulocytes and erythrocytes are functional and are released into the blood. Accordingly a reticulocyte count estimates the rate of erythropoiesis, and a change in red blood cell count suggests that an AARS polypeptide modulates erythropoiesis.

Lymphocytes are the cornerstone of the adaptive immune system. They are derived from common lymphoid progenitors. The lymphoid lineage is primarily composed of T-cells and B-cells (types of white blood cells). Accordingly a change in white blood cell count or composition in response to exposure to an AARS polypeptide suggests that that the AARS polypeptide modulates lymphopoiesis.

Myelocytes, which include granulocytes, megakaryocytes and macrophages, and are derived from common myeloid progenitors, are involved in a variety of roles, including innate immunity, adaptive immunity, and blood clotting. Accordingly a change in myeloid cell count or composition in response to exposure to an AARS polypeptide suggests that that the AARS polypeptide modulates myelopoiesis. The same rationale can be used to establish whether the AARS polypeptides modulate granulopoiesis, by measuring changes in granulocyte number in response to exposure to the AARS polypeptides. A role for the AARS polypeptide in modulating megakaryocytopoiesis may be inferred by a change in megakaryocyte or platelet composition or number in the blood.

Cytokine release in either wild type mice, or in various animal model systems of inflammation, provides an initial assessment of the potential ability of the AARS polypeptides to modulate inflammatory responses. The role of AARS polypeptides in modulating acute chronic inflammatory processes for example, can be readily assessed using a mouse model of diet induced obesity (DIO). The DIO model centers upon placing rodents on a high fat diet for several months leading to increased obesity, insulin resistance and immune system dysfunction. A particular consequence of this immune system dysregulation results in increased production of proinflammatory cytokines in DIO animals leading to a condition of chronic systemic inflammation. There is a growing body of evidence suggesting that low grade inflammation contributes to the development and maintenance of obesity and a diabetic phenotype that is similarly observed in the human condition termed metabolic syndrome. As such, the ability of AARS polypeptides to modulate the immune system and restore homeostatic balance towards a resolution of this chronic inflammatory state would be particularly beneficial in numerous diseases and disorders including but not limited to the treatment and prevention of the symptoms and side effects of metabolic disease, diabetes, cardiovascular diseases, atherosclerosis, obesity, as well as various autoimmune diseases and disorders, including for example, multiple sclerosis, vascular and allergic disorders.

Methods:

Male wild type control (C57BL/6) or diet induced obesity mice (C57BL/6NHsd) are purchased from Harlan (Indianapolis, Ind.) and housed individually. DIO mice are fed a high fat diet (Cat. #TD.06414-60% kcal from fat) and control mice are fed a normal diet (Cat. #2018S-18% kcal from fat). DIO mice are placed on the high fat diet starting at 6 weeks of age for a total of 10 weeks. Both DIO and control mice are allowed to feed and drink ad libitum. At 16 weeks of age, mice are sorted and randomized into groups of 5 animals based on weight. On day 2, mice are weighed and tail vein bled (100 µL) for pre-treatment complete blood count (CBC) analysis. On day 1, mice are weighed and intravenously injected via the tail vein with vehicle (PBS) or individual AARS polypeptides at 10 mg/kg. Four hours post-injection, mice are facial vein bled (150-200 µL) for subsequent cytokine analysis. On days 2, 3, & 4, mice are intravenously dosed as on day 1. On day 5, mice are weighed, terminated and blood are collected by heart puncture for Complete Blood Count (CBC analysis) (plasma-EDTA) and cytokine examination (serum).

CBC and Cytokine Analysis:

Complete blood counts are analyzed from blood draws preceding injections (day −2) and 24 hours after the final injection (day 5). CBC values are assessed for total white blood cell counts and overall red blood cell morphology. White blood cells are further characterized by total and fractional percentage of neutrophils, lymphocytes, monocytes, eosinophils, & basophils. Red blood cell breakdown included measurements of hemoglobin (dL), hematocrit (%), mean corpuscular volume (fL), mean corpuscular hemoglobin, mean corpuscular hemoglobin concentration (%), and total platelet count ($10^3/\mu L$). CBC analysis is performed by Antech Diagnostics (Fishers, Ind.).

Circulating cytokine levels are examined at 4 hours post-injection (day 1) and 24 hours after the final injection (day 5). Serum is isolated, snap frozen and sent to Rules Based Medicine (Austin, Tex.) for multi-analyte profiling. Serum samples are analyzed using the RodentMap panel encompassing 59 unique biomarkers including Apo A-1, CD40, CD40-L, CRP, ET-1, eotaxin, EGF, Factor VII, fibrinogen, FGF-9, FGF-basic, GST-α, GCP-2, GM-CSF, KC/GROα, haptoglobin, IgA, IFNγ, IP-10, IL-1α, IL-1β, IL-10, IL-11, IL-12p70, Il-17A, IL-18, IL-2, IL-3, IL-4, IL-5, IL-6, IL-7, LIF, lymphotactin, M-CSF-1, MIP-1α, MIP-1β, MIP-1γ, MIP-2, MIP-3β, MDC, MMP-9, MCP-1, MCP-3, MCP-5, MPO, myoglobin, SAP, SGOT, SCF, RANTES, TPO, tissue factor, TIMP-1, TNF-α, VCAM-1, VEGF-A, and vWF. A change in cytokine levels was counted as a hit if the cytokine increased by at least 2-fold or decreased by at least 50% compared to vehicle controls.

Example 1

Identification of Proteolytic Fragments and Products of Alternative Splicing from AARSs Using Protein Topography and Migration Analysis Platform To identify AARS fragments from cell lines, conditioned media and tissues, samples are prepared in the following ways:

Mouse Macrophage (RAW 264.7), Cytosol and Conditioned Media:

Cells are treated with serum free DMEM media at a density of $15 \times 10^6$ cells/flasks. After 48 hours conditioned media and cell pellets are collected and processed. 200 µg of protein from secreted and cytosolic proteomic fractions are separated by SDS-PAGE and gel slices are prepared for analysis by mass spectrometry.

Mouse Pancreas Tissue:

The pancreas from three mice are chopped, dounce homogenized, and sonicated in PBS with protease inhibitors. Cytosolic proteome is isolated by centrifugation and 200 µg of protein is separated by SDS-PAGE and gel slices are prepared for analysis by mass spectrometry.

Mouse Liver Tissue:

Three mouse livers are chopped, dounced homogenized, and sonicated in PBS with protease inhibitors. Cytosolic proteome is isolated by centrifugation and 200 µg of protein is separated by SDS-PAGE and gel slices are prepared for analysis by mass spectrometry.

In-gel digests are analyzed by LTQ XL ion trap mass spectrometer (ThermoFisher) equipped with ultimate 3000 µLC system (Dionex). The samples are first loaded on Pep-Trap (michrom) for 10 min with 5% Acetonitrile in 0.1% formic acid using Dionex autosampler. Then the samples are analyzed with a 100 µm (inner diameter) fused silica capillary column containing 10 cm of C18 resin (michrom). Peptides are eluted from the column into mass spectrometer with a flow rate of 0.45 µl/min using a linear gradient of 5-33.5% acetonitrile in 0.1% formic acid within 110 min.

LTQ is operated in data-dependent scanning mode such that one full MS scan is followed by seven MS/MS scans of the seven most abundant ions. Dynamic exclusion is enabled with repeat count equals to 1, repeat duration equals to 20 seconds, exclusion list size is 300 and exclusion duration is 60 seconds.

After LC-MS/MS analysis, the raw data is searched with BioWorks3.3.1(SEQUEST) using a concatenated target/decoy variant of the mouse IPI database. The SEQUEST data are filtered and sorted with DTASelect. Tables 1, 4 and 7 show sequences identified in this way.

Example 2

Identification of Splice Variants Using Deep Sequencing

Splice variants of the aminoacyl tRNA synthetase are identified using high throughput sequencing of cDNA libraries enriched for aminoacyl tRNA synthetase transcripts. The cDNA templates are prepared from total RNA extracts of tissues such as human adult and fetal brains and enriched for aminoacyl tRNA synthetase transcripts by using primer sequences specific for all annotated exons of all annotated human aminoacyl tRNA synthetases and their associated proteins.

Human Total RNAs are obtained from Clontech. For cell line and mouse tissue samples, total RNAs are extracted using RNA Extract II Kit (MN). Genomic DNA is digested in the total RNA samples by DNAase I. To obtain mature messenger RNAs (mRNAs), the RNA samples are enriched twice by binding polyA+RNA and digestion of RNA without 5'-cap by 5'-phosphate dependent exonuclease. Complementary DNA (cDNA) is synthesized from mature RNAs using primers that anneal to exon sequences of aminoacyl tRNA synthetase genes. A transcriptome enriched for aminoacyl tRNA synthetase genes is amplified by multiplex PCR using the aminoacyl tRNA synthetase-exon specific cDNA and different combinations of aminoacyl tRNA synthetase-exon primers. The double-stranded aminoacyl tRNA synthetase-enriched transcriptome PCR products are enzymatically repaired at both ends before adding A-overhangs to the 3' ends of the repaired fragments. Sequencing adaptors and index sequences are then added to the aminoacyl tRNA synthetase-enriched transcriptome PCRs products to generate cDNA libraries for deep sequencing with Illumina's Multiplex Sequencing Kit. In brief, the aminoacyl tRNA synthetase-enriched transcriptome PCR products with 3'-A overhangs are ligated to the InPE adaptor oligonucleotides provided in the kits. Index sequences are added to the PCR products with InPE adaptors. To obtain enough DNA fragments for deep sequencing, the PCR products with index sequences are further amplified by PCR. Aminoacyl tRNA synthetase-enriched cDNA libraries with different indexes are pooled and sequenced using an Illumina DNA sequencing machine to get 50 base pair end reads. Sequencing reads are mapped to human or mouse genome for identification of alternative splicing events. "Splicemap" software (available for public download) is used to identify splice junctions.

Deep sequencing of these cDNAs are performed to generate about 1 million sequencing reads of about 50 nucleotides in length. The sequences specific for exons of the aminoacyl tRNA synthetases are queried against annotated exon junctions and new exon junctions are identified as alternative splicing events.

The columns in Tables 2, 5, and 8 labeled "5' exon" and "3' exon" indicate, when present, which exons are fused together in the cDNA sequence. Tables 2, 5, and 8 show sequences that were identified for alternative splice events, transcripts containing such splice events, and the polypeptides expressed by those transcripts. Alternative splice variants identified by deep sequencing are identified in Tables 2, 5, and 8 as those ones in which there are numbers greater than zero in the columns labeled as "Sequencing reads" in the human adult or fetal brain.

Example 3

Identification of AARS Polypeptides Using Bioinformatics

AARS protein fragments (resectin or appendacrine peptides) are identified using bioinformatics Amino acid sequences of the full length human aminoacyl tRNA synthetase are aligned with the full length amino acid sequence of its ortholog from the bacterium *Escherichia coli* using a program such as FASTA or the BLASTP program from the NCBI. Resectin sequences from the human proteins are identified as sequences covering regions where there are gaps in the bacterial sequence in the alignment, or regions with low homology between the two species. The peptide, and corresponding DNA sequences in Tables 3, 6, and 9 include examples identified in this way.

Example 4

Differential Expression of AARS Polypeptides Identified by Mass Spectrometry

The PROTOMAP technique is used as described in Example 1 to compare the differential expression of Lysyl tRNA synthetases in different tissues/cell types (refer to Tables 1, 4, and 7 for sequences and comparisons): Aminoacyl-tRNA synthetase resectin expression is compared between mouse liver tissue and mouse pancreas tissue Aminoacyl-tRNA synthetase resectin expression is compared between cytosol of RAW264.7 and conditioned media from RAW264.7 cells harvested after 48 hours of serum starvation.

Example 5

Differential Expression of AARS Polypeptides Identified by Deep Sequencing

To test for differential expression of spice events, the deep sequencing is done for cDNAs prepared from different tissues.

Expression of specific alternative splice events for aminoacyl tRNA synthetases is unexpected and indicates biological importance. The variation in relative number of reads seen in the deep sequencing of different transcriptome samples indicates that alternative splice events of aminoacyl tRNA synthetases are differentially regulated and not just artifacts due to sample handling.

Example 6

Antibody Screening

To facilitate the discovery of antibodies displaying preferential binding to specific aminoacyl tRNA synthetase fragments (e.g., >10-fold higher affinity when compared to the parental full length enzyme), a human antibody phage display library is screened by AbD Serotec (a division of MORPHOSYS™, Martinsried/Planegg, Germany) using affinity enrichment techniques (panning). Antibodies enriched after multiple rounds of screening with the aminoacyl tRNA synthetase fragments are subsequently characterized by ELISA for reactivity to the fragments, and to the parental, full length enzyme. Clones demonstrating preferential binding (e.g., >10-fold higher affinity) to the aminoacyl tRNA synthetase fragments are further characterized.

If the necessary specificity is not achieved at the end of this process, subtraction strategies, such as pre-adsorption steps with the full length enzyme and/or counter-screening, are used to eliminate cross reacting antibodies and drive the selection process towards the unique epitope(s) on the aminoacyl tRNA synthetase fragments.

Example 7

Identification of Splice Variants Using Systematic PCR cDNA templates for PCR reactions are reverse transcribed from total RNA extracts of tissues or cells (e.g., human brain, IMR-32 and HEK293T). PCR reactions are performed using aminoacyl tRNA synthetase specific primers, pairing a forward primer (FP1) designed to anneal to the 5' untranslated region or exons in the 5' half of the gene with a reverse primer (RP1) designed to anneal to exons in the 3' half of the gene or the 3'UTR. Amplified DNA products are analyzed by agarose gel electrophoresis to identify PCR products that are a different size then the fragment amplified from the canonical transcripts. These different PCR products are excised and purified from the gel and ligated into a standard cloning vector for DNA sequence analysis. Alternative splicing variants are identified as different sequences from the canonical transcripts. Splice variants identified by this systematic PCR approach are shown in Tables 2, 5 and 8.

Example 8

Codon Optimization of Selected AARS Polynucleotides

Representative AARS polypeptides (summarized in Table E2) are selected for further biochemical, biophysical and functional characterization based on one or more of the following criteria, i) the identification of AARS polypeptide proteolytic fragments, ii) the identification of AARS polypeptide splice variants, iii) the identification of AARS polypeptides by bioinformatic analysis, iv) evidence of differential expression of specific AARS polypeptides, v) the domain structure of the AARS protein, vi) the size of the AARS polypeptide, and vii) the minimization of similar duplicative sequences.

TABLE E2

Summary of AARS Polypeptides Selected for Codon Optimization and Bacterial Expression

| AARS Polypeptide Name | SEQ. ID Nos. for Epitope Tagged AARS polypeptides | SEQ. ID. Nos. for AARS Polynucleotides | Residues of AARS protein | Location of epitope tag | Cloning/ synthesis method used |
|---|---|---|---|---|---|
| LysRS1$^{N1}$ | SEQ. ID. NO. 58 | SEQ. ID. NO. 82 | 1-366 | N-terminal | 2 |
| LysRS1$^{N1}$ | SEQ. ID. NO. 59 | SEQ. ID. NO. 82 | 1-366 | C-terminal | 2 |
| LysRS1$^{N2}$ | SEQ. ID. NO. 60 | SEQ. ID. NO. 83 | 1-76 | N-terminal | 2 |
| LysRS1$^{N2}$ | SEQ. ID. NO. 61 | SEQ. ID. NO. 83 | 1-76 | C-terminal | 2 |
| LysRS1$^{N3}$ | SEQ. ID. NO. 62 | SEQ. ID. NO. 84 | 1-194 | N-terminal | 2 |
| LysRS1$^{N3}$ | SEQ. ID. NO. 63 | SEQ. ID. NO. 84 | 1-194 | C-terminal | 2 |
| LysRS1$^{N4}$ | SEQ. ID. NO. 64 | SEQ. ID. NO. 85 | 1-65 | N-terminal | 2 |
| LysRS1$^{N4}$ | SEQ. ID. NO. 65 | SEQ. ID. NO. 85 | 1-65 | C-terminal | 2 |
| LysRS1$^{N5}$ | SEQ. ID. NO. 66 | SEQ. ID. NO. 86 | 1-214 | N-terminal | 2 |
| LysRS1$^{N5}$ | SEQ. ID. NO. 67 | SEQ. ID. NO. 86 | 1-214 | C-terminal | 2 |
| LysRS1$^{N6}$ | SEQ. ID. NO. 68 | SEQ. ID. NO. 87 | 1-74 + 22aa | N-terminal | 2 |
| LysRS1$^{N6}$ | SEQ. ID. NO. 69 | SEQ. ID. NO. 87 | 1-74 + 22aa | C-terminal | 2 |
| LysRS1$^{N8}$ | SEQ. ID. NO. 70 | SEQ. ID. NO. 88 | 1-74 + 266-597 | N-terminal | 2 |
| LysRS1$^{N8}$ | SEQ. ID. NO. 71 | SEQ. ID. NO. 88 | 1-74 + 266-597 | C-terminal | 2 |
| LysRS1$^{N9}$ | SEQ. ID. NO. 72 | SEQ. ID. NO. 89 | 1-305 + 518-597 | N-terminal | 2 |
| LysRS1$^{N9}$ | SEQ. ID. NO. 73 | SEQ. ID. NO. 89 | 1-305 + 518-597 | C-terminal | 2 |
| LysRS1$^{N10}$ | SEQ. ID. NO. 74 | SEQ. ID. NO. 90 | 1-74 + 2 aa | N-terminal | 2 |
| LysRS1$^{N10}$ | SEQ. ID. NO. 75 | SEQ. ID. NO. 90 | 1-74 + 2 aa | C-terminal | 2 |
| LysRS1$^{N11}$ | SEQ. ID. NO. 76 | SEQ. ID. NO. 91 | 1-20 + 1 aa | N-terminal | 2 |
| LysRS1$^{N11}$ | SEQ. ID. NO. 77 | SEQ. ID. NO. 91 | 1-20 + 1 aa | C-terminal | 2 |
| LysRS1$^{N12}$ | SEQ. ID. NO. 78 | SEQ. ID. NO. 92 | 1-129 + 20 aa | N-terminal | 2 |
| LysRS1$^{N12}$ | SEQ. ID. NO. 79 | SEQ. ID. NO. 92 | 1-129 + 20 aa | C-terminal | 2 |
| LysRS1$^{N13}$ | SEQ. ID. NO. 80 | SEQ. ID. NO. 93 | 1-223 + 36 aa | N-terminal | 2 |
| LysRS1$_{N13}$ | SEQ. ID. NO. 81 | SEQ. ID. NO. 93 | 1-223 + 36 aa | C-terminal | 2 |
| LysRS1$^{C2}$ | SEQ. ID. NO. 125 | SEQ. ID. NO. 133 | 157-597 | N-terminal | 2 |
| LysRS1$^{C2}$ | SEQ. ID. NO. 126 | SEQ. ID. NO. 133 | 157-597 | C-terminal | 2 |
| LysRS1$^{C3}$ | SEQ. ID. NO. 127 | SEQ. ID. NO. 134 | 13 aa + 162-597 | N-terminal | 2 |
| LysRS1$^{C3}$ | SEQ. ID. NO. 128 | SEQ. ID. NO. 134 | 13 aa + 162-597 | C-terminal | 2 |

TABLE E2-continued

Summary of AARS Polypeptides Selected for Codon Optimization and Bacterial Expression

| AARS Polypeptide Name | SEQ. ID Nos. for Epitope Tagged AARS polypeptides | SEQ. ID. Nos. for AARS Polynucleotides | Residues of AARS protein | Location of epitope tag | Cloning/ synthesis method used |
|---|---|---|---|---|---|
| LysRS1$^{C4}$ | SEQ. ID. NO. 129 | SEQ. ID. NO. 135 | 212-597 | N-terminal | 2 |
| LysRS1$^{C4}$ | SEQ. ID. NO. 130 | SEQ. ID. NO. 135 | 212-597 | C-terminal | 2 |
| LysRS1$^{C5}$ | SEQ. ID. NO. 131 | SEQ. ID. NO. 136 | 469-597 | N-terminal | 2 |
| LysRS1$^{C5}$ | SEQ. ID. NO. 132 | SEQ. ID. NO. 136 | 469-597 | C-terminal | 2 |
| LysRS1$^{I1}$ | SEQ. ID. NO. 139 | SEQ. ID. NO. 141 | 65-214 | N-terminal | 2 |
| LysRS1$^{I1}$ | SEQ. ID. NO. 140 | SEQ. ID. NO. 141 | 65-214 | C-terminal | 2 |
| LysRS2$^{N1}$ | SEQ. ID. NO. 192 | SEQ. ID. NO. 218 | 1-394 | N-terminal | 2 |
| LysRS2$^{N1}$ | SEQ. ID. NO. 193 | SEQ. ID. NO. 218 | 1-394 | C-terminal | 2 |
| LysRS2$^{N2}$ | SEQ. ID. NO. 194 | SEQ. ID. NO. 219 | 1-104 | N-terminal | 2 |
| LysRS2$^{N2}$ | SEQ. ID. NO. 195 | SEQ. ID. NO. 219 | 1-104 | C-terminal | 2 |
| LysRS2$^{N3}$ | SEQ. ID. NO. 196 | SEQ. ID. NO. 220 | 1-222 | N-terminal | 2 |
| LysRS2$^{N3}$ | SEQ. ID. NO. 197 | SEQ. ID. NO. 220 | 1-222 | C-terminal | 2 |
| LysRS2$^{N4}$ | SEQ. ID. NO. 198 | SEQ. ID. NO. 221 | 1-93 | N-terminal | 2 |
| LysRS2$^{N4}$ | SEQ. ID. NO. 199 | SEQ. ID. NO. 221 | 1-93 | C-terminal | 2 |
| LysRS2$^{N5}$ | SEQ. ID. NO. 200 | SEQ. ID. NO. 222 | 1-242 | N-terminal | 2 |
| LysRS2$^{N5}$ | SEQ. ID. NO. 201 | SEQ. ID. NO. 222 | 1-242 | C-terminal | 2 |
| LysRS2$^{N6}$ | SEQ. ID. NO. 202 | SEQ. ID. NO. 223 | 1-49 + 12 aa | N-terminal | 2 |
| LysRS2$^{N6}$ | SEQ. ID. NO. 203 | SEQ. ID. NO. 223 | 1-49 + 12 aa | C-terminal | 2 |
| LysRS2$^{N7}$ | SEQ. ID. NO. 204 | SEQ. ID. NO. 224 | 1-102 + 22 aa | N-terminal | 2 |
| LysRS2$^{N7}$ | SEQ. ID. NO. 205 | SEQ. ID. NO. 224 | 1-102 + 22 aa | C-terminal | 2 |
| LysRS2$^{N9}$ | SEQ. ID. NO. 206 | SEQ. ID. NO. 225 | 1-102 + 294-625 | N-terminal | 2 |
| LysRS2$^{N9}$ | SEQ. ID. NO. 207 | SEQ. ID. NO. 225 | 1-102 + 294-625 | C-terminal | 2 |
| LysRS2$^{N10}$ | SEQ. ID. NO. 208 | SEQ. ID. NO. 226 | 1-333 + 546-625 | N-terminal | 2 |
| LysRS2$^{N10}$ | SEQ. ID. NO. 209 | SEQ. ID. NO. 226 | 1-333 + 546-625 | C-terminal | 2 |
| LysRS2$^{N11}$ | SEQ. ID. NO. 210 | SEQ. ID. NO. 227 | 1-102 + 2 aa | N-terminal | 2 |
| LysRS2$^{N11}$ | SEQ. ID. NO. 211 | SEQ. ID. NO. 227 | 1-102 + 2 aa | C-terminal | 2 |
| LysRS2$^{N12}$ | SEQ. ID. NO. 212 | SEQ. ID. NO. 228 | 1-48 + 1 aa | N-terminal | 2 |
| LysRS2$^{N12}$ | SEQ. ID. NO. 213 | SEQ. ID. NO. 228 | 1-48 + 1 aa | C-terminal | 2 |
| LysRS2$^{N13}$ | SEQ. ID. NO. 214 | SEQ. ID. NO. 229 | 1-157 + 20 aa | N-terminal | 2 |
| LysRS2$^{N13}$ | SEQ. ID. NO. 215 | SEQ. ID. NO. 229 | 1-157 + 20 aa | C-terminal | 2 |
| LysRS2$^{N14}$ | SEQ. ID. NO. 216 | SEQ. ID. NO. 230 | 1-251 + 36 aa | N-terminal | 2 |
| LysRS2$^{N14}$ | SEQ. ID. NO. 217 | SEQ. ID. NO. 230 | 1-251 + 36 aa | C-terminal | 2 |

Polynucleotides encoding the selected AARS polypeptides listed in Table E2, along with the appropriate N or C-terminal epitope tag, are synthesized and cloned as described in the General Materials and Methods section using the gene synthesis methodology listed in Table E2.

Example 9

Small Scale Bacterial Expression and Purification

The AARS polypeptides listed in Table E2 are expressed in *E. coli*. as described in the General Materials and Methods section. The relative expression of soluble and inclusion body localized AARS polypeptides is summarized in Table E3 below.

TABLE E3

Summary of AARS Polypeptide Bacterial Expression Characteristics

| AARS Polypeptide | Location of Epitope Tag | Amount of Protein Recovered from Soluble Fraction | Amount of Protein Recovered from Inclusion Bodies |
|---|---|---|---|
| LysRS1$^{N1}$ | N-terminal | + | ND |
| LysRS1$^{N1}$ | C-terminal | + | ND |
| LysRS1$^{N2}$ | N-terminal | +++++ | ND |
| LysRS1$^{N2}$ | C-terminal | ++++ | ND |
| LysRS1$^{N3}$ | N-terminal | + | ND |
| LysRS1$^{N3}$ | C-terminal | + | ND |
| LysRS1$^{N4}$ | N-terminal | ++ | ND |
| LysRS1$^{N4}$ | C-terminal | ++ | ND |
| LysRS1$^{N5}$ | N-terminal | ++ | ND |
| LysRS1$^{N5}$ | C-terminal | ++ | ND |
| LysRS1$^{N6}$ | N-terminal | + | ND |
| LysRS1$^{N6}$ | C-terminal | ++ | ND |
| LysRS1$^{N8}$ | N-terminal | + | + |
| LysRS1$^{N8}$ | C-terminal | + | + |
| LysRS1$^{N9}$ | N-terminal | + | ND |
| LysRS1$^{N9}$ | C-terminal | + | ND |
| LysRS1$^{N10}$ | N-terminal | ++ | ND |
| LysRS1$^{N10}$ | C-terminal | ++ | ND |
| LysRS1$^{N11}$ | N-terminal | + | ND |
| LysRS1$^{N11}$ | C-terminal | + | ND |
| LysRS1$^{N12}$ | N-terminal | + | ND |
| LysRS1$^{N12}$ | C-terminal | + | ND |
| LysRS1$^{N13}$ | N-terminal | + | ND |
| LysRS1$^{N13}$ | C-terminal | + | ND |
| LysRS1$^{C2}$ | N-terminal | + | + |
| LysRS1$^{C2}$ | C-terminal | + | + |
| LysRS1$^{C3}$ | N-terminal | + | + |
| LysRS1$^{C3}$ | C-terminal | + | + |
| LysRS1$^{C4}$ | N-terminal | + | + |
| LysRS1$^{C4}$ | C-terminal | + | + |
| LysRS1$^{C5}$ | N-terminal | + | ++ |
| LysRS1$^{C5}$ | C-terminal | + | ++ |
| LysRS1$^{I1}$ | N-terminal | ++ | ND |
| LysRS1$^{I1}$ | C-terminal | ++ | ND |
| LysRS2$^{N1}$ | N-terminal | + | + |
| LysRS2$^{N1}$ | C-terminal | + | + |
| LysRS2$^{N2}$ | N-terminal | + | + |
| LysRS2$^{N2}$ | C-terminal | + | ++ |
| LysRS2$^{N3}$ | N-terminal | + | ++ |
| LysRS2$^{N3}$ | C-terminal | + | + |
| LysRS2$^{N4}$ | N-terminal | + | + |
| LysRS2$^{N4}$ | C-terminal | + | ++ |
| LysRS2$^{N5}$ | N-terminal | + | ++ |
| LysRS2$^{N5}$ | C-terminal | + | ++ |
| LysRS2$^{N6}$ | N-terminal | + | + |
| LysRS2$^{N6}$ | C-terminal | + | ++ |
| LysRS2$^{N7}$ | N-terminal | + | + |
| LysRS2$^{N7}$ | C-terminal | + | ++ |
| LysRS2$^{N9}$ | N-terminal | + | + |
| LysRS2$^{N9}$ | C-terminal | + | + |
| LysRS2$^{N10}$ | N-terminal | + | + |
| LysRS2$^{N10}$ | C-terminal | + | + |
| LysRS2$^{N11}$ | N-terminal | + | + |
| LysRS2$^{N11}$ | C-terminal | + | ++ |
| LysRS2$^{N12}$ | N-terminal | + | ++ |
| LysRS2$^{N12}$ | C-terminal | + | + |
| LysRS2$^{N13}$ | N-terminal | + | + |
| LysRS2$^{N13}$ | C-terminal | + | + |
| LysRS2$^{N14}$ | N-terminal | + | + |
| LysRS2$^{N14}$ | C-terminal | + | + |

"+" represents 0-1 mg/L AARS polypeptide expression

"++" represents 1-5 mg/L AARS polypeptide expression;

"+++" represents 5-10 mg/L AARS polypeptide expression;

"++++" represents 10-15 mg/L AARS polypeptide expression;

"+++++" represents ≥15 mg/L AARS polypeptide expression;

ND: not determined

Surprisingly, the protein expression data demonstrates the existence of several protein domain families of both the cytosolic and mitochondrial Lysyl tRNA synthetase that exhibit high level expression in *E. coli*. Specifically the data demonstrates that the AARS polypeptides LysRS1$^{N2}$, (amino acids 1-76), LysRS1$^{N4}$ (amino acids 1-65), and LysRS1$^{N10}$ (amino acids 1-74+2 aa), define the boundary of a novel N-terminal domain of the cytosolic Lysyl tRNA synthetase that is highly expressed in *E. coli*, while the AARS polypeptides LysRS2$^{N2}$ (amino acids 1-104), and LysRS2$^{N11}$ (amino acids 1-102+2 aa), define the boundary of a novel N-terminal domain of the mitochondrial Lysyl tRNA synthetase that is highly expressed in *E. coli*. Moreover the AARS polypeptides LysRS1$^{I1}$ (amino acids 65-214), and LysRS1$^{C5}$ (amino acids 469-597), define the boundaries of two further novel internal and C-terminal protein domains of the cytosolic Lysyl tRNA synthetase that are highly expressed in *E. coli*.

Example 10

Large Scale Production of AARS Polypeptides

Representative AARS polypeptides are prepared in larger amounts to enable further functional and biophysical characterization. The AARS polypeptides listed in Table E4 are expressed in *E. coli* in large scale culture as described in the General Materials and Methods section. The yields, and specified biophysical characteristics, for each expressed soluble protein are summarized below in Table E4.

TABLE E4

Summary of representative AARS Polypeptides yield and biophysical characterization

| AARS Polypeptide | Location of Epitope Tag | Yield [mg/L] (1) | Purity [%] | Endotox in [EU/mg] | Molecular Weight | Working stock concentration [mg/ml] | Stability [percent recovery] (2) | Aggregation [DLS] |
|---|---|---|---|---|---|---|---|---|
| LysRS1$^{N2}$ | N-terminal | 4.3 | 80 | 1.6 | ND | 1.1 | ND | ND |
| LysRS1$^{I1}$ | N-terminal | 6.7 | 85 | 2.6 | 19,745 (C) 19,778, 39,494 (D) | 19.2 | 72 | + |
| LysRS1$^{C5}$ | N-terminal | 5.1$^{(3)}$ | 80 | NA | ND | 12.4 | 74 | +++++ |
| LysRS2$^{N12}$ | N-terminal | 0.9$^{(3)}$ | 95 | NA | 17,156 (C) 17,155 (D) | 3.5 | ND | ND |

Notes
(1): Yield determined by measuring protein recovery after last purification step
(2): Determined as percent recovery of non aggregated material after 1 week at 25° C.
(3): Measured after final Amicon concentration step
(4): Likely to represent MW without N-terminal methionine
C: Calculated
D: Determined molecular weight(s)
Key:
"+" represents less than 1% high molecular protein aggregates
"++" represents less than 2% high molecular protein aggregates
"+++" represents less than 5% high molecular protein aggregates
"++++" represents less than 10% high molecular protein aggregates
"+++++" represents more than 10% high molecular protein aggregates
ND: Not Determined The results from these studies establish that representative AARS proteins from the cytosolic LysRS1$^{N2}$, LysRS1$^{I1}$, LysRS1$^{C5}$ and mitochondrial LysRS2$^{N12}$ families of AARS proteins, exhibit reasonable initial protein expression yields and solubility characteristics.

Example 11

Transcriptional Profiling of Representative AARS Polypeptides

To test for the ability of the AARS polypeptides to modulate gene expression, selected AARS polypeptides were incubated with Mesenchymal stems cells or human skeletal muscle cells for the times and at the concentrations shown in Table E5.

TABLE E5

Transcriptional profiling of representative AARS Polypeptides in Mesenchymal Stem Cells (MSC) or Human Skeletal Muscle Cells (HSkMC)

Test Sample Description

| AARS Polypeptides | Location of Epitope Tag | Concentration nM | MSC 24 hours | MSC 72 hours | HSkMC 24 hours | HSkMC 72 hours |
|---|---|---|---|---|---|---|
| LysRS1$^{N2}$ | N-terminal | 250 | 4 | 2 | 3 | 0 |
| LysRS1$^{N2}$ | C-terminal | 250 | 3 | 2 | 1 | 1 |
| LysRS1$^{N4}$ | N-terminal | 250 | 5 | 0 | 0 | 0 |
| LysRS1$^{N4}$ | C-terminal | 250 | 1 | 1 | 0 | 0 |
| LysRS1$^{N5}$ | N-terminal | 250 | 3 | 1 | 3 | 0 |
| LysRS1$^{N5}$ | C-terminal | 250 | 6 | 1 | 1 | 1 |
| LysRS1$^{N6}$ | C-terminal | 250 | 5 | 11 | 2 | 0 |
| LysRS1$^{N10}$ | C-terminal | 250 | 1 | 0 | 2 | 1 |
| LysRS1$^{N10}$ | N-terminal | 250 | 5 | 0 | 4 | 0 |
| LysRS1$^{C2}$ | C-terminal | 30 | 0 | 1 | 6 | 0 |
| LysRS1$^{C5}$ | N-terminal | 250 | 4 | 1 | 6 | 0 |
| LysRS1$^{C5}$ | C-terminal | 250 | 0 | 2 | 2 | 0 |
| LysRS1$^{I1}$ | N-terminal | 250 | 4 | 0 | 3 | 0 |
| LysRS1$^{I1}$ | C-terminal | 250 | 2 | 0 | 4 | 0 |

TABLE E5-continued

Transcriptional profiling of representative AARS Polypeptides in Mesenchymal Stem Cells (MSC) or Human Skeletal Muscle Cells (HSkMC)

Test Sample Description

| AARS Polypeptides | Location of Epitope Tag | Concentration nM | MSC 24 hours | MSC 72 hours | HSkMC 24 hours | HSkMC 72 hours |
|---|---|---|---|---|---|---|
| LysRS2$^{N2}$ | C-terminal | 250 | 3 | 0 | 1 | 1 |
| LysRS2$^{N3}$ | N-terminal | 136 | 5 | 0 | 2 | 0 |
| LysRS2$^{N4}$ | C-terminal | 250 | 2 | 0 | 3 | 0 |
| LysRS2$^{N5}$ | N-terminal | 250 | 4 | 5 | 1 | 0 |
| LysRS2$^{N5}$ | C-terminal | 250 | 0 | 0 | 3 | 0 |
| LysRS2$^{N6}$ | C-terminal | 250 | 4 | 0 | 3 | 0 |
| LysRS2$^{N7}$ | C-termina | 250 | 4 | 3 | 3 | 0 |
| LysRS2$^{N10}$ | N-terminal | 38 | 3 | 0 | 0 | 0 |
| LysRS2$^{N11}$ | C-terminal | 250 | 4 | 5 | 1 | 1 |
| LysRS2$^{N12}$ | C-terminal | 250 | 5 | 0 | 1 | 3 |
| Controls | | | | | | |
| Average across all AARS polypeptides screened | | | 3 | 2 | 2 | 1 |
| Osteogenesis cocktail | | | 11 | 49 | ND | ND |
| Chondrogenesis cocktail | | | 15 | 33 | ND | ND |
| Adipogenesis cocktail | | | 9 | 22 | ND | ND |
| SKMC Pos Ctrl | | | ND | ND | 36 | 29 |
| Untreated | | | 2 | 1 | 0 | 0 |

In Table E5, the numbers in each column represent the number of genes which were modulated, either positively or negatively by at least 3 fold compared to the control samples as described in the general methods section. The data shows that specific forms of the AARS polypeptides tested have the surprising ability to regulate the transcription, and hence potentially modulate the developmental fate or differentiation status when added to either Mesenchymal Stem Cells (MSC) and/or Human Skeletal Muscle Cells (HSkMC). Shaded cells with bolded numbers in the table represent examples where the AARS polypeptide exhibits a significant impact on the regulation of gene transcription in the cell lines and times indicated in the table.

It is concluded that the cytosolic LysRS1$^{N2}$, LysRS1$^{N4}$, LysRS1$^{N5}$, LysRS1$^{N6}$, LysRS1$^{N10}$, LysRS1$^{C2}$, LysRS1$^{C5}$, LysRS1$^{T1}$, and mitochondrial LysRS2$^{N3}$, LysRS2$^{N5}$, LysRS2$^{N11}$, and LysRS2$^{N12}$ appear to be regulators of Mesenchymal Stem Cell and/or human skeletal muscle cell gene expression.

Example 12

Functional Profiling of AARS Polypeptides

To test for the ability of the AARS polypeptides to modulate a range of phenotypic processes, selected AARS polypeptides were incubated with the cell types, and the conditions provided in the general methods section, and Tables E5 and E6.

TABLE E6

Key to Assays and criteria for indicating a hit

Proliferation assays

| Source and cell type | Assay Number |
|---|---|
| Human megakaryocytic leukemia cells/Mo7e | A1 |
| Human acute promyelocytic leukemia cells/HL60 | A2 |
| Human lymphoblast (cancer cell line)/RPMI8226 | A3 |
| Human mesenchymal stem cells/hMSC | A4 |
| Human astrocytes | A5 |
| Human bone marrow aspirate cells/Bone Marrow Cells | A6 |
| Human bone marrow aspirate cells/Bone Marrow Cells (Long Term Culture) | A7 |
| Human Synoviocyte/HFLS-SynRA | A8 |
| Human pre-adipocyte cells /hPAD | A9 |

TABLE E6-continued

| Key to Assays and criteria for indicating a hit | |
| --- | --- |
| Human pulmonary artery smooth muscle cell /hPASMC | A10 |
| Human skeletal muscle cell/hSKMC | A11 |

Data analysis for proliferation assays was performed by dividing the numerical value in the assay well by the average PBS value for the assay plate. AARS polypeptides were considered to be proliferative if the measured value was greater than 3 SD away from the PBS value in the positive direction. A tRNA synthetase derived AARS polypeptide was considered to be cytotoxic if the measured value was greater than greater than 3 SD away from the PBS value in the negative direction. A cytotoxic compound was utilized as a negative control and the average value for this was always greater than 3 SD away from PBS average value.

Cellular differentiation and phenotype assays

| Assay Description | Assay Number |
| --- | --- |
| Human hepatocyte (HepG2C3 a cells) acetylated LDL uptake | B1 |

Data analysis for ac-LDL uptake assay was performed by dividing the numerical value in the assay well by the average PBS value for the assay plate. AARS polypeptides were considered to be a modulator of ac-LDL uptake if the measured value was greater than 2 SD away from the PBS value in the positive or negative direction. A visual check to confirm plate reader results was made using a fluorescent microscope.

Human Neutrophil assays

| Assay Description | Assay Number |
| --- | --- |
| Neutrophil Elastase | C1 |
| Neutrophil oxidative burst (agonist) | C2 |
| Neutrophil oxidative burst (antagonist) | C3 |

Data analysis for neutrophil assays was performed by dividing the numerical value in the assay well by the average PBS value for the assay plate. AARS polypeptides were considered to be a modulator of neutrophil elastase production or oxidative burst biology if the measured value was greater than 2 SD away from the PBS value in the positive or negative direction.

Modulation of Toll-like receptors (TLR)

| Assay Description | Assay Number |
| --- | --- |
| TLE activation in RAW BLUE cells | D1 |
| TLR antagonism in RAW BLUE cells | D2 |
| Activation of hTLR2 | D3 |
| Activation of hTLR4 | D4 |

Data analysis for TLR modulation assays was performed by dividing the numerical value in the assay well by the average PBS value for the assay plate. AARS polypeptides were considered to be a modulator of TLR specific biology if the measured value was greater than 3 SD away from the PBS value in the positive or negative direction. Positive controls, including LPS and detection reagent were always significantly distinct and >3 SD from PBS average value.

Cytokine Release

| Assay Description | Assay Number |
| --- | --- |
| Human Synoviocyte cytokine production (IL6 release) | E1 |
| Human pulmonary artery smooth muscle cell (hPASMC) cytokine production (IL6 release) | E2 |
| Human skeletal muscle cell (hSKMC) cytokine production (IL6 release) | E3 |
| Human Astrocyte cytokine production (IL6 release) | E4 |
| Whole blood IL6 release | E5 |
| Human pulmonary artery smooth muscle cell (hPASMC) cytokine production (IL8release) 72 h Incubation IL8 production | E6 |
| Human Synoviocyte cytokine production (IL8 release) | E7 |
| Human pulmonary artery smooth muscle cell (hPASMC) cytokine production (IL8release) | E8 |
| Human skeletal muscle cell (hSKMC) cytokine production (IL8 release) | E9 |
| Human Astrocyte cytokine production (IL8 release) | E10 |
| Humanhepatocyte (HepG2C3a cells) IL8 release | E11 |
| Human acute promyelocytic leukemia cells/HL60 (IL8 release) | E12 |
| Human lymphoblast (cancer cell line)/RPMI8226 (IL8 Release) | E13 |

TABLE E6-continued

Key to Assays and criteria for indicating a hit

TNF alpha production

| | |
|---|---|
| Human Synoviocyte cytokine production (TNF alpha release) | E14 |
| Whole blood TNF alpha release | E15 |

IL10 Release

| | |
|---|---|
| Human acute promyelocytic leukemia cells/HL60 IL10 release | E16 |
| Human Primary Blood Mononuclear cells (IL10 Release) | E17 |

Data analysis for cytokine release assays was performed by dividing the numerical value in the assay well by the average PBS value for the assay plate. AARS polypeptides were considered to be a modulator of cytokine production or cytokine related biology if the measured value was greater than 2 SD away from the PBS value in the positive or negative direction. A protein standard (specific to each assay kit) was run on every plate to insure good assay quality. Only assays with protein standard curves that had an R2 value of >22 than 0.9 were chosen for data analysis.

Cell Adhesion and Chemotaxis

| Assay Description | Assay Number |
|---|---|
| Monocyte THP 1/Human umbilical vein endothelial cell (HUVEC) cell adhesion | F1 |
| Human hepatocyte (HepG2C3a cells) (ICAM release) | F2 |
| Human lung microvascular endothelial cell (HLMVEC) cell adhesion regulation (ICAM release) | F3 |
| Human umbilical vein endothelial cell (HUVEC) cell adhesion regulation (VCAM release) | F4 |
| Human mesenchymal stem cell (hMSC) cell adhesion regulation (VCAM release) | F5 |
| Human skeletal muscle cell (hSKMC) cell adhesion regulation (VCAM release) | F6 |
| Human pulmonary artery smooth muscle cell (hPASMC) cell adhesion regulation (VCAM release) | F7 |

Data analysis for cell adhesion regulation assays was performed by dividing the numerical value in the assay well by the average PBS value for the assay plate. AARS polypeptides were considered to be a modulator of cell adhesion or a regulator of biology related to cell adhesion if a value of greater than 2 SD away from the PBS value in the positive or negative direction was obtained. In the case of the ELISA assays, a protein standard (specific to each assay kit) was run on every plate to insure good assay quality. Only assays with protein standard curves that had an R2 value of > than 0.9 were chosen for data analysis.

Cellular Differentiation

| Assay Description | Assay Number |
|---|---|
| Human pre-adipocyte (hPAD) cell differentiation | G1 |
| Human skeletal muscle (hSKMC) cell differentiation | G2 |
| Human mesenchymal stem (hMSC) cell differentiation | G3 |
| Human pulmonary artery smooth muscle cell (hPASMC) differentiation | G4 |

Data analysis for cellular differentiation assays was performed by dividing the numerical value in the assay well by the average PBS value for the assay plate. Differentiation assays were scored based upon fluorescent intensity of particular antibodies as described in the methods section. AARS polypeptides were considered to be a modulator of cellular differentiation if an intensity value for a specific marker of differentiation was greater than 2 SD away from the PBS value in the positive or negative direction in a given treated well. For the hSKMC analysis, digital photos were taken of all wells and photos were scored in a blinded fashion by three people using a 4 point scoring system where a score of "4" indicated intense skeletal muscle actin staining and obvious myotube formation and a score of "1" indicated a lack of any differentiation or a suppression of differentiation. The average value from visual scoring was used and only wells with an average value of >3 were considered hits. Differentiation control treated wells in this assay typically scored >2, while PBS treated wells scored <2.

Cell Binding

| Assay Description | Assay Number |
|---|---|
| PBMC | H1 |
| Primary T cell | H2 |
| Primary B cell | H3 |
| Primary Monocyte | H4 |
| HepG2 | H5 |
| 3T3L1 | H6 |
| C2C12 | H7 |
| THP 1 | H8 |

TABLE E6-continued

Key to Assays and criteria for indicating a hit

| | |
|---|---|
| Jurkat | H9 |
| Raji | H10 |

AARS polypeptides were considered to be binding to a particular cell type if the mean cell bound fluorescence intensity was greater than 2 SD away from the reagent control values for that cell type.

TABLE E7

Results of Functional Profiling studies of AARS Polypeptides

| AARS Polypeptides | Location of Epitope Tag | Concentration [nM] | Assay Hits |
|---|---|---|---|
| LysRS1$^{N2}$ | N-terminal | 250 | |
| LysRS1$^{N2}$ | C-terminal | 250 | |
| LysRS1$^{N4}$ | N-terminal | 250 | F1 (Cell Adhesion and Chemotaxis) |
| LysRS1$^{N4}$ | C-terminal | 250 | B1 (Ac-LDL Uptake), E11 (Cytokine Release) G2 (SKMC Differentiation), F1 (Cell Adhesion and Chemotaxis) |
| LysRS1$^{N5}$ | N-terminal | 250 | B1 (Ac-LDL Uptake), F4 (Cell Adhesion and Chemotaxis) |
| LysRS1$^{N5}$ | C-terminal | 250 | B1 (Ac-LDL Uptake), E11 (Cytokine Release) F1 (Cell Adhesion and Chemotaxis) |
| LysRS1$^{N6}$ | C-terminal | 250 | G2, G3, G4 (Differentiation), F1 (Cell Adhesion and Chemotaxis) |
| LysRS1$^{N10}$ | C-terminal | 250 | B1 (Ac-LDL Uptake), G2, G3, G4 (Differentiation) F1 (Cell Adhesion and Chemotaxis) |
| LysRS1$^{N10}$ | N-terminal | 250 | B1 (Ac-LDL Uptake) |
| LysRS1$^{C2}$ | C-terminal | 30 | |
| LysRS1$^{C5}$ | N-terminal | 250 | |
| LysRS1$^{C5}$ | C-terminal | 250 | |
| LysRS1$^{I1}$ | N-terminal | 250 | A1 (Proliferation) B1 (Ac-LDL Uptake), F1, F4 (Cell Adhesion and Chemotaxis) |
| LysRS1$^{I1}$ | C-terminal | 250 | B1 (Ac-LDL Uptake), F1 (Cell Adhesion and Chemotaxis) |
| LysRS2$^{N2}$ | C-terminal | 250 | G2, G4 (Differentiation), E1 (Cytokine Release) |
| LysRS2$^{N3}$ | N-terminal | 136 | E1 (Cytokine Release) F2 (Cell Adhesion and Chemotaxis) |
| LysRS2$^{N4}$ | C-terminal | 250 | E1 (Syn-RA IL6 down-regulation) |
| LysRS2$^{N5}$ | N-terminal | 250 | A3, A7 (Proliferation) E1 (Cytokine Release) F2 (Cell Adhesion and Chemotaxis) |
| LysRS2$^{N5}$ | C-terminal | 250 | B1 (ac-LDL uptake), E1 (Cytokine Release) |
| LysRS2$^{N6}$ | C-terminal | 250 | A7 (Proliferation) B1 (ac-LDL uptake), E1, EIS (Cytokine Release) G2 (Differentiation) |
| LysRS2$^{N7}$ | C-terminal | 250 | AS (Proliferation) C2 (Oxidative burst agonist) |
| LysRS2$^{N10}$ | N-terminal | 38 | E1 (Cytokine Release) |
| LysRS2$^{N11}$ | C-terminal | 250 | |
| LysRS2$^{N12}$ | C-terminal | 250 | E15 (Cytokine Release) F4 (Cell Adhesion and Chemotaxis) |

It is concluded that the cytosolic AARS polypeptides LysRS1$^{N4}$, LysRS1$^{N5}$, LysRS1$^{N6}$, LysRS1$^{N10}$, LysRS1$^{I1}$, as well as the mitochondrial AARS polypeptides LysRS2$^{N2}$, LysRS2$^{N3}$, LysRS2$^{N4}$, LysRS2$^{N5}$, LysRS2$^{N6}$, LysRS2$^{N7}$, LysRS2$^{N10}$, LysRS2$^{N11}$, and LysRS2$^{N12}$ appear to be major regulators of proliferation, differentiation, acetylated LDL-uptake, cytokine release, neutrophil activation, cell adhesion and chemotaxis. Of note is that in many cases, the N and C-terminal fusion proteins have differential patterns of activity in both the transcriptional profiling experiments, as well as in the phenotypic screening experiments. This data is consistent with the hypothesis that for these AARS polypeptides, the novel biological activity is suppressed when the AARS polypeptide is part of the intact tRNA synthetase, or translationally fused at either terminus to another protein, but that this biological activity is revealed when the AARS polypeptides has a free amino or carboxy terminus.

When viewed in light of the transcriptional profiling data, the phenotypic screening data demonstrates that the AARS polypeptides LysRS1$^{N4}$, (amino acids 1-65), LysRS1$^{N6}$ (amino acids 1-74+22aa) and LysRS1$^{N10}$, (amino acids 1-74+2aa) define the boundaries of a novel protein domain that is highly active in a broad array of phenotypic and/or transcriptional screening assays.

Accordingly it is concluded that AARS polypeptides comprising amino acids 1 to 74 amino acids of Lysyl tRNA synthetase define the approximate boundaries of a novel, highly active AARS polypeptide domain, that is i) highly functionally active, ii) can be readily made and produced in E. coli, and iii) exhibits favorable protein stability and aggregation characteristics. It will be appreciated by those of skill in the art that any AARS polypeptides comprising as few as about the first 65 amino acids of the Lysyl tRNA synthetase, to as large as about the first 74 amino acids (+an optional extension of up to 22 amino acids) of Lysyl tRNA synthetase represent functional equivalents of the specific AARS polypeptides described.

Additionally the transcriptional and screening data demonstrates that the AARS polypeptides LysRS1$^{N5}$, (amino acids 1-214) define the boundaries of a second novel protein domain that is highly active in a broad array of phenotypic and/or transcriptional screening assays.

Accordingly it is concluded that AARS polypeptides comprising amino acids 1-214 amino acids of Lysyl tRNA synthetase define the approximate boundaries of a second novel, highly active AARS polypeptide domain, that is i) highly functionally active, ii) can be readily made and produced in E. coli, and iii) exhibits favorable protein stability and aggregation characteristics.

Additionally the transcriptional and screening data demonstrates that the AARS polypeptides LysRS1$^{C2}$, (amino acids 157-597) define the boundaries of a further novel protein domain that is highly active in a broad array of phenotypic and/or transcriptional screening assays.

Accordingly it is concluded that AARS polypeptides comprising amino acids 157-597amino acids of Lysyl tRNA synthetase define the approximate boundaries of a further novel, highly active AARS polypeptide domain, that is i) highly functionally active, ii) can be readily made and produced in E. coli, and iii) exhibits favorable protein stability and aggregation characteristics.

Additionally the transcriptional and screening data demonstrates that the AARS polypeptides LysRS1$^{C5}$, (amino acids 469-597) define the boundaries of a further novel protein domain that is highly active in a broad array of phenotypic and/or transcriptional screening assays.

Accordingly it is concluded that AARS polypeptides comprising amino acids 469-597 amino acids of Lysyl tRNA synthetase define the approximate boundaries of a further novel, highly active AARS polypeptide domain, that is i) highly functionally active, ii) can be readily made and produced in E. coli, and iii) exhibits favorable protein stability and aggregation characteristics.

Additionally the transcriptional and screening data demonstrates that the AARS polypeptides LysRS1$^{T1}$, (amino acids 65-214) define the boundaries of a further novel protein domain that is highly active in a broad array of phenotypic and/or transcriptional screening assays.

Accordingly it is concluded that AARS polypeptides comprising amino acids 65-214 amino acids of Lysyl tRNA synthetase define the approximate boundaries of a further novel, highly active AARS polypeptide domain, that is i) highly functionally active, ii) can be readily made and produced in E. coli, and iii) exhibits favorable protein stability and aggregation characteristics.

When viewed in the context of the transcriptional profiling studies, the phenotypic screening data also demonstrates that the AARS polypeptides LysRS2$^{N6}$, LysRS2$^{N7}$, LysRS2$^{N10}$, LysRS2$^{N11}$, LysRS2$^{N12}$, define the boundaries of various alternatively spliced mitochondrial Lysyl tRNA synthetase transcripts that are highly active in a broad array of phenotypic screening assays.

Accordingly it is concluded that AARS polypeptides comprising either i) amino acids 1 to 49 of mitochondrial Lysyl tRNA synthetase plus 12 amino acids, or ii) amino acids 1 to 102 of mitochondrial Lysyl tRNA synthetase plus 22 amino acids, or iii) amino acids 1 to 102 of mitochondrial Lysyl tRNA synthetase plus 2 amino acids, or iv) amino acids 1 to 48 of mitochondrial Lysyl tRNA synthetase, plus one amino acid or v) amino acids 1 to 333 plus amino acids 546-625 of mitochondrial Lysyl tRNA synthetase, define the approximate boundaries (i.e., within about +/−5 amino acids) of five novel, highly active alternatively spliced AARS polypeptides, that are i) highly functionally active, ii) can be readily made and produced in E. coli, and iii) exhibit favorable protein stability and aggregation characteristics.

The phenotypic screening data also demonstrates that the AARS polypeptides LysRS2$^{N2}$ (amino acids 1-104), and LysRS2$^{N4}$ (amino acids 1-93), define the boundaries of a further novel protein domain that is highly active in a broad array of phenotypic and/or transcriptional screening assays.

Accordingly it is concluded that AARS polypeptides comprising amino acids 1 to 104 amino acids of mitochondrial Lysyl tRNA synthetase define the approximate boundaries of a novel, highly active AARS polypeptide domain, that is i) highly functionally active, ii) can be readily made and produced in E. coli, and iii) exhibits favorable protein stability and aggregation characteristics. It will be appreciated by those of skill in the art that any AARS polypeptides comprising as few as about the first 93 amino acids of the Lysyl tRNA synthetase, to as large as about the first 104 amino acids of Lysyl tRNA synthetase represent functional equivalents of the specific AARS polypeptides described.

The phenotypic screening data also demonstrates that the AARS polypeptides LysRS2$^{N3}$ (amino acids 1-222), and LysRS2$^{N5}$ (amino acids 1-242), define the boundaries of a further novel protein domain that is highly active in a broad array of phenotypic and/or transcriptional screening assays.

Accordingly it is concluded that AARS polypeptides comprising amino acids 1 to 242 amino acids of mitochondrial Lysyl tRNA synthetase define the approximate boundaries of a novel, highly active AARS polypeptide domain, that is i) highly functionally active, ii) can be readily made and produced in E. coli, and iii) exhibits favorable protein stability and aggregation characteristics. It will be appreciated by those of skill in the art that any AARS polypeptides comprising as few as about the first 222 amino acids of the Lysyl tRNA synthetase, to as large as about the first 242 amino acids of Lysyl tRNA synthetase represent functional equivalents of the specific AARS polypeptides described.

We claim:

1. A pharmaceutical composition, comprising an isolated polynucleotide that encodes a lysyl-tRNA synthetase (KRS) polypeptide which consists of a sequence that is at least 95% identical to SEQ ID NO:50, 54, 26, or 18, or a fragment of SEQ ID NO:50, 54, 26, or 18 which is at least 60 contiguous amino acids of SEQ ID NO:50, 54, 26, or 18, wherein the polynucleotide is selected from (a) a cDNA polynucleotide and (b) a modified mRNA polynucleotide, and wherein the composition has less than about 10 EU endotoxin/mg protein.

2. The pharmaceutical composition of claim 1, wherein the KRS polypeptide consists of SEQ ID NO:50, 54, 26, or 18 or differs from SEQ ID NO:50, 54, 26, or 18 by substitution, deletion, and/or addition of 1, 2, or 3 amino acids.

3. The pharmaceutical composition of claim 1, wherein the KRS polypeptide is fused to a heterologous polypeptide.

4. The pharmaceutical composition of claim 3, wherein the heterologous polypeptide is selected from the group consisting of purification tags, epitope tags, targeting sequences, signal peptides, membrane translocating sequences, and pharmacokinetic (PK) property modifiers.

5. The pharmaceutical composition of claim 1, wherein the isolated polynucleotide is at least 95% identical to SEQ ID NO:51, 55, 27, or 19.

6. The pharmaceutical composition of claim 1, wherein the isolated polynucleotide comprises one or more transcriptional and/or translational control elements.

7. The pharmaceutical composition of claim 1, wherein the isolated polynucleotide is a modified mRNA polynucleotide that comprises at least one modified base.

8. The pharmaceutical composition of claim 1, wherein the isolated polynucleotide is formulated for delivery encapsulated in a lipid particle, a liposome, a vesicle, a nanosphere, or a nanoparticle.

9. The pharmaceutical composition of claim 1, which is suitable for intravenous administration.

* * * * *